(12) United States Patent
Patel et al.

(10) Patent No.: US 11,072,617 B2
(45) Date of Patent: Jul. 27, 2021

(54) BICYCLIC SULFONES AND SULFOXIDES AND METHODS OF USE THEREOF

(71) Applicant: Genentech, Inc., South San Francisco, CA (US)

(72) Inventors: Snahel Patel, South San Francisco, CA (US); Gregory Hamilton, South San Francisco, CA (US); Craig Stivala, South San Francisco, CA (US); Huifen Chen, South San Francisco, CA (US); Blake Daniels, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/175,206

(22) Filed: Oct. 30, 2018

(65) Prior Publication Data
US 2019/0127382 A1   May 2, 2019

Related U.S. Application Data

(60) Provisional application No. 62/579,392, filed on Oct. 31, 2017.

(51) Int. Cl.
| | | |
|---|---|---|
| *C07D 487/04* | (2006.01) | |
| *C07D 231/54* | (2006.01) | |
| *C07D 249/16* | (2006.01) | |
| *A61P 25/00* | (2006.01) | |

(52) U.S. Cl.
CPC ............ *C07D 487/04* (2013.01); *A61P 25/00* (2018.01); *C07D 231/54* (2013.01); *C07D 249/16* (2013.01)

(58) Field of Classification Search
CPC ... C07D 487/04; C07D 231/54; C07D 249/16
See application file for complete search history.

(56) References Cited

U.S. PATENT DOCUMENTS

| 3,948,903 | A | 4/1976 | Doub et al. | |
|---|---|---|---|---|
| 8,288,424 | B2 * | 10/2012 | Merla ................ | C07D 471/04 514/385 |
| 2018/0153831 | A1 | 6/2018 | Patel et al. | |
| 2018/0170927 | A1 | 6/2018 | Patel et al. | |
| 2019/0100530 | A1 | 4/2019 | Patel et al. | |
| 2020/0283446 | A1 | 9/2020 | Chen et al. | |

FOREIGN PATENT DOCUMENTS

| EP | 0244098 A2 | 11/1987 |
|---|---|---|
| FR | 94123 E | 7/1969 |
| WO | 98/27092 A1 | 6/1998 |
| WO | 98/56376 A1 | 12/1998 |
| WO | 01/58869 A2 | 8/2001 |
| WO | 2004/017908 A2 | 3/2004 |
| WO | 2004/098589 A1 | 11/2004 |
| WO | 2009/092565 A1 | 7/2009 |
| WO | 2010/100070 A1 | 9/2010 |
| WO | 2013/067260 A1 | 5/2013 |
| WO | 2014/125444 A1 | 8/2014 |
| WO | 2015/006280 A1 | 1/2015 |
| WO | 2015/144609 A1 | 10/2015 |
| WO | 2016/027253 A1 | 2/2016 |
| WO | 2017/004500 A1 | 1/2017 |
| WO | 2017/096301 A1 | 6/2017 |
| WO | 2017/109724 A1 | 6/2017 |
| WO | 2017/136727 A2 | 8/2017 |
| WO | 2018/100070 A1 | 6/2018 |
| WO | 2019/012063 A1 | 1/2019 |
| WO | 2019/072942 A1 | 4/2019 |

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784 (Year: 1995).*
Bertrand et al., "cIAP1 and cIAP2 facilitate cancer survival by functioning as E3 ligases that promote RIP1 ubiquitination" Mol Cell 30(6):689-700 (Jun. 2008).
CAS Registry Compounds, RN:1554480-89-5, 1554480-83-9, 1542201-50-2, 1540456-83-4, 1539697-89-6, 1536914-91-6, 1529444-36-7, 1528724-76-6, 1526961-09-0, 1515103-12-2, 1517186-33-2, 2092781-81-0, 1991193-96-4, 1989442-07-0, 1979877-21-8, 1979849-45-0, 1979849-27-8, 1554480-89-5 dated Aug. 25, 2016 through Apr. 20, 2017, pp. 1-7 ( Oct. 3, 2019).
Chen, "Ubiquitination in signaling to and activation of IKK" Immunol Rev. 246(1):95-106 (Mar. 1, 2012).
Cho et al., "Phosphorylation-driven assembly of the RIP1-RIP3 complex regulates programmed necrosis and virus-induced inflammation" Cell 137(6):1112-1123 (Jun. 12, 2009).
de Almagro, "Necroptosis: Pathway diversity and characteristics" Semin Cell Dev Biol. 39:56-62 (Mar. 2015).
Degterev et al., "Chemical inhibitor of nonapoptotic cell death with therapeutic potential for ischemic brain injury" Nat Chem Biol. 1(2):112-119 (Jul. 2005).
Degterev et al., "Identification of RIP1 kinase as a specific cellular target of necrostatins" Nat Chem Biol. 4(5):313-321 (May 1, 2008).
Feoktistova et al., "cIAPs block Ripoptosome formation, a RIP1/caspase-8 containing intracellular cell death complex differentially regulated by cFLIP isoforms" Mol Cell 43(3):449-463 (Aug. 5, 2011).
Harris et al., "Discovery of Small Molecule RIP1 Kinase Inhibitors for the Treatment of Pathologies Associated with Necroptosis" ACS Chem Lett 4(12):1238-1243 (Nov. 4, 2013).

(Continued)

*Primary Examiner* — Dennis Heyer
(74) *Attorney, Agent, or Firm* — Andre T. Krammer

(57) ABSTRACT

The invention provides novel compounds having the general formula I:

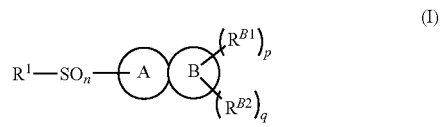

wherein $R^1$, $R^{B1}$, $R^{B2}$, n, p, q, the A ring and the B ring are as described herein, pharmaceutical compositions including the compounds, and methods of using the compounds.

35 Claims, No Drawings

(56) References Cited

OTHER PUBLICATIONS

Harris, P., et al., "Discovery of a First-in-Class Receptor Interacting Protein 1 (RIP1) Kinase Specific Clinical Candidate (GSK2982772) for the Treatment of Inflammatory Diseases" J Med Chem 60(4):1247-1261 (Feb. 7, 2017).
He et al., "Receptor interacting protein kinase-3 determines cellular necrotic response to TNF-alpha" Cell 137(6):1100-1111 (Jun. 12, 2009).
"International Preliminary Report on Patentability—PCT/EP2017/080996":pp. 1-10 (dated Jun. 13, 2019).
"International Search Report—PCT/EP2017/080996":pp. 1-4 (dated Feb. 2, 2018).
"International Search Report—PCT/EP2018/079772":pp. 1-25 (dated Dec. 17, 2018).
"International Search Report—PCT/EP2018/068998":pp. 1-4 (dated Aug. 27, 2018).
Jensen et al., "Biochemical characterization lysosomal localization of the mannose-6-phosphate protein p76 (hypothetical protein LOC196463)" Biochem J 402:449-463 ( 2007).
Kaiser et al., "Toll-like receptor 3-mediated necrosis via TRIF, RIP3, and MLKL" J Biol Chem. 288(43):31268-31279 (Oct. 25, 2013).
Linkermann et al., "Necroptosis" New Engl J Med 370(5):455-465 (Jan. 30, 2014).
Lipson et al., "Reactions of 3-amino-1,2,4-triazoles with cinnamic aldehydes" Russ Chem Bull 58(7):1441-1444 (May 27, 2010).
Najjar et al., "Structure Guided Design of Potent and Selective Ponatinib-Based Hybrid Inhibitors for RIPKI" Cell Rep. 10(11):1850-60 (Mar. 24, 2015).
Newton et al., "Activity of protein kinase RIPK3 determines whether cells die by necroptosis or apoptosis" Science 343(6177):1357-1360 (Mar. 21, 2014).
Newton, "RIPK1 and RIPK3: critical regulators of inflammation and cell death" Trends Cell Biol. 25(6):347-353 (Jun. 1, 2015).
O'Donnell et al., "Ubiquitination of RIP1 regulates an NF-kappaB-independent cell-death switch in TNF signaling" Curr Biol 17(5):418-424 (Mar. 6, 2007).
Ohta, et al., "Formation of pyridines by the reaction of isoxazoles with enamines" (with English Abstract), 9:1593-1600 (Jan. 1, 1989).
Sun et al., "Mixed lineage kinase domain-like protein mediates necrosis signaling downstream of RIP3 kinase" Cell 148(1-2):213-227 (Jan. 20, 2012).
Surase, Y., et al., "Identification and synthesis of novel inhibitors of *Mycobacterium* ATP synthase" Bioorg Med Chem Lett 27(15):3454-3459 (May 27, 2017).
Takahashi et al., "Necrostatin-1 analogues: critical issues on the specificity, activity and in vivo use in experimental disease models" Cell Death Dis. (Send to), 3:e43 (Nov. 2012).
"USPTO Non-Final Office Action, U.S. Appl. No. 15/828,271":1-13 (dated May 6, 2019).
"USPTO Non-Final Office Action, U.S. Appl. No. 16/034,307":1-9 (dated Oct. 10, 2019).
"USPTO Notice of Allowance, U.S. Appl. No. 15/828,271":1-7 (dated Aug. 22, 2019).
Van den Berghe et al., "Regulated necrosis: the expanding network of non-apoptotic cell death pathways" Nat Rev Mol Cell Bio 15:135-147 (Feb. 1, 2014).
Waly et al., "A novel Synthesis of Imidazo (4,5-d)azepine Ring System" Polish J Chem 70(3):296-301 ( 1996).
Wang et al., "TNF-alpha induces two distinct caspase-8 activation pathways" Cell 133(4):693-703 (May 2008).
Zhao et al., "Mixed lineage kinase domain-like is a key receptor interacting protein 3 downstream component of TNF-induced necrosis" PNAS 109(14):5322-5327 (Apr. 3, 2012).
International Search Report and Written Opinion for PCT/EP2017/076385 dated Dec. 7, 2019.
Notice of Allowance for U.S. Appl. No. 16/034,207 dated May 13, 2020.
Restriction Requirement for U.S. Appl. No. 16/034,207 dated Apr. 8, 2019.
CAS Registry Database, 1957920-91-0, p. 1, Jul 22, 2016.
CAS Registry Database, 1957970-02-3, p. 1, Jul 22, 2016.
CAS Registry Database, 2124968-54-1, p. 1, Sep 4, 2017.
CAS Registry Database, 2124990-56-1, p. 1, Sep 4, 2017.
CAS Registry Database, 2125071-93-2, p. 1, Sep 4, 2017.
CAS Registry Database, 2125192-86-9, p. 1, Sep 4, 2017.
International Preliminary Report on Patentability (IPRP) for PCT/EP2017/076385 dated Apr. 23, 2019.
International Search Report for PCT/EP2017/082851 dated Feb. 20, 2018.
Written Opinion of the International Searching Authority for PCT/EP2017/082851 dated Jun. 21, 2018, 8 pages.
Written Opinion of the International Searching Authority for PCT/EP2018/068998, dated Jan. 17, 2019, 5 pages.
Written Opinion of the International Searching Authority for PCT/EP2017/080996, dated Feb. 7, 2018, 8 pages.
https://pubchem.ncbi.nlm.nih.gov/compound/11845422; compound name: 6,7-Dihydro-4H-pyrazolo [5,1-c] [1,4]oxazine-2-carbaldehyde; created Nov. 6, 2006.
https://pubchem.ncbi.nlm.nih.gov/compound/20744102; compound name: 1-(5,6-Dihydro-4H-pyrrolo[1,2-b]pyrazol-2-yl)ethanone; created Dec. 5, 2007.
https://pubchem.ncbi.nlm.nih.gov/compound/82594726; compound name: 1-(6,7-Dihydro-5H-pyrrolo[1,2-a]imidazol-2-yl) ethanone; created Oct. 20, 2014.
https://pubchem.ncbi.nlm.nih.gov/compound/83875142; compound name: 1-(5-Methyl-5,6,7,8-tetrahydro-[1,2,4]triazolo[1,5-a]pyridin-2-yl)ethanone; created Oct. 20, 2014.
Rojas-Rivera, D. et al., "When PERK inhibitors turn out to be new potent RIPK1 inhibitors: critical issues on the specificity and use of GSK2606414 and GSK2656157" Cell Death Differ. 24(6):1100-1110 (2017).
https://pubchem.ncbi.nlm.nih.gov/compound/11845422;compound name: 6,7-Dihydro-4H-pyrazolo [5,1-c][1,4]oxazine-2-carbaldehyde; created Nov. 6, 2006; 14 pages.
https://pubchem.ncbi.nlm.nih.gov/compound/20744102; compound name: 1-(5,6-Dihydro-4H-pyrrolo[1,2-b]pyrazol-2-yl)ethanone; created Dec. 5, 2007; 10 pages.
yes Ihttps://pubchem.ncbi.nlm.nih.gov/compound/82594726; compound name: 1-(6,7-Dihydro-5H-pyrrolo[1,2-a]imidazol-2-yl)ethanone; created Oct. 20, 2014; 10 pages.
https://pubchem.ncbi.nlm.nih.gov/compound/83875142; compound name: 1-(5-Methyl-5,6,7,8-tetrahydro-[1,2,4]triazolo[1,5-a]pyridin-2-yl)ethanone; created Oct. 20, 2014, 8 pages.

* cited by examiner

BICYCLIC SULFONES AND SULFOXIDES AND METHODS OF USE THEREOF

CROSS REFERENCE TO RELATED APPLICATIONS

This application claims priority to U.S. Provisional Application No. 62/579,392 filed Oct. 31, 2017 which is hereby incorporated by reference in its entirety.

FIELD OF THE INVENTION

The present invention relates to organic compounds useful for therapy and/or prophylaxis in a mammal, and in particular to inhibitors of RIP1 kinase useful for treating diseases and disorders associated with inflammation, cell death and others.

BACKGROUND OF THE INVENTION

Receptor-interacting protein-1 ("RIP1") kinase is a serine/threonine protein kinase. RIP1 is a regulator of cell signaling that is involved, among other things, in the mediation of programmed cell death pathways, e.g., necroptosis. The best studied form of necroptotic cell death is initiated by TNFα (tumor necrosis factor), but necroptosis can also be induced by other members of the TNFα death ligand family (Fas and TRAIL/Apo2L), interferons, Toll-like receptors (TLRs) signaling and viral infection via the DNA sensor DAI (DNA-dependent activator of interferon regulatory factor) [1-3]. Binding of TNFα to the TNFR1 (TNF receptor 1) prompts TNFR1 trimerization and formation of an intracellular complex, Complex-I. TRADD (TNF receptor associated death domain protein) binds to the intracellular death domain of TNFR1 and recruits the protein kinase RIP1 (receptor-interacting protein 1) through the death domain present in both proteins [4]. Following initial recruitment into TNFR1-associated signaling complex, RIP1 translocates to a secondary cytoplasmatic complex, Complex-II [5-7]. Complex-II is formed by the death domain containing protein FADD (Fas-associated Protein), RIP1, caspase-8 and cFLIP. If caspase-8 is not fully activated or its activity is blocked, the protein kinase RIP3 gets recruited to the complex, forming a necrosome, which will lead to necroptotic cell death initiation [8-10]. Once the necrosome is formed, RIP1 and RIP3 engage in a series of auto and cross phosphorylation events that are essential for necroptotic cell death. Necroptosis can be completely blocked either by the kinase inactivating mutation in any of the two kinases, or chemically by RIP1 kinase inhibitors (necrostatins), or RIP3 kinase inhibitors [11-13]. Phosphorylation of RIP3 allows the binding and phosphorylation of pseudokinase MLKL (mixed lineage kinase domain-like), a key component of necroptotic cell death [14, 15].

Necroptosis has crucial pathophysiological relevance in myocardial infarction, stroke, atherosclerosis, ischemia-reperfusion injury, inflammatory bowel diseases, retinal degeneration and a number of other common clinical disorders [16]. Therefore, selective inhibitors of RIP1 kinase activity are therefore desired as a potential treatment of diseases mediated by this pathway and associated with inflammation and/or necroptotic cell death.

Inhibitors of RIP1 kinase have been previously described. The first published inhibitor of RIP1 kinase activity was necrostatin 1 (Nec-1) [17]. This initial discovery was followed by modified versions of Nec-1 with various abilities to block RIP1 kinase activity [11, 18]. Recently, additional RIP1 kinase inhibitors have been described that differ structurally from necrostatin class of compounds [19, 20, 21].

References cited above, each of which is hereby incorporated by reference in its entirety:
1) Vanden Berghe, T., Linkermann, A., Jouan-Lanhouet, S., Walczak, H. and Vandenabeele, P. (2014) Regulated necrosis: the expanding network of non-apoptotic cell death pathways. Nature reviews. Molecular cell biology. 15, 135-147.
2) Newton, K. (2015) RIPK1 and RIPK3: critical regulators of inflammation and cell death. Trends in cell biology. 25, 347-353.
3) de Almagro, M. C. and Vucic, D. (2015) Necroptosis: Pathway diversity and characteristics. Semin Cell Dev Biol. 39, 56-62.
4) Chen, Z. J. (2012) Ubiquitination in signaling to and activation of IKK. Immunological reviews. 246, 95-106.
5) O'Donnell, M. A., Legarda-Addison, D., Skountzos, P., Yeh, W. C. and Ting, A. T. (2007) Ubiquitination of RIP1 regulates an NF-kappaB-independent cell-death switch in TNF signaling. Curr Biol. 17, 418-424.
6) Feoktistova, M., Geserick, P., Kellert, B., Dimitrova, D. P., Langlais, C., Hupe, M., Cain, K., MacFarlane, M., Hacker, G. and Leverkus, M. (2011) cIAPs block Ripoptosome formation, a RIP1/caspase-8 containing intracellular cell death complex differentially regulated by cFLIP isoforms. Molecular cell. 43, 449-463.
7) Bertrand, M. J., Milutinovic, S., Dickson, K. M., Ho, W. C., Boudreault, A., Durkin, J., Gillard, J. W., Jaquith, J. B., Morris, S. J. and Barker, P. A. (2008) cIAP1 and cIAP2 facilitate cancer cell survival by functioning as E3 ligases that promote RIP1 ubiquitination. Mol Cell. 30, 689-700.
8) Wang, L., Du, F. and Wang, X. (2008) TNF-alpha induces two distinct caspase-8 activation pathways. Cell. 133, 693-703.
9) He, S., Wang, L., Miao, L., Wang, T., Du, F., Zhao, L. and Wang, X. (2009) Receptor interacting protein kinase-3 determines cellular necrotic response to TNF-alpha. Cell. 137, 1100-1111.
10) Cho, Y. S., Challa, S., Moquin, D., Genga, R., Ray, T. D., Guildford, M. and Chan, F. K. (2009) Phosphorylation-driven assembly of the RIP1-RIP3 complex regulates programmed necrosis and virus-induced inflammation. Cell. 137, 1112-1123.
11) Degterev, A., Hitomi, J., Germscheid, M., Ch'en, I. L., Korkina, O., Teng, X., Abbott, D., Cuny, G. D., Yuan, C., Wagner, G., Hedrick, S. M., Gerber, S. A., Lugovskoy, A. and Yuan, J. (2008) Identification of RIP1 kinase as a specific cellular target of necrostatins. Nat Chem Biol. 4, 313-321.
12) Newton, K., Dugger, D. L., Wickliffe, K. E., Kapoor, N., de Almagro, M. C., Vucic, D., Komuves, L., Ferrando, R. E., French, D. M., Webster, J., Roose-Girma, M., Warming, S. and Dixit, V. M. (2014) Activity of protein kinase RIPK3 determines whether cells die by necroptosis or apoptosis. Science. 343, 1357-1360.
13) Kaiser, W. J., Sridharan, H., Huang, C., Mandal, P., Upton, J. W., Gough, P. J., Sehon, C. A., Marquis, R. W., Bertin, J. and Mocarski, E. S. (2013) Toll-like receptor 3-mediated necrosis via TRIF, RIP3, and MLKL. The Journal of biological chemistry. 288, 31268-31279.
14) Zhao, J., Jitkaew, S., Cai, Z., Choksi, S., Li, Q., Luo, J. and Liu, Z. G. (2012) Mixed lineage kinase domain-like is a key receptor interacting protein 3 downstream component of TNF-induced necrosis. Proceedings of the National Academy of Sciences of the United States of America. 109, 5322-5327.

15) Sun, L., Wang, H., Wang, Z., He, S., Chen, S., Liao, D., Wang, L., Yan, J., Liu, W., Lei, X. and Wang, X. (2012) Mixed Lineage Kinase Domain-like Protein Mediates Necrosis Signaling Downstream of RIP3 Kinase. Cell. 148, 213-227.
16) Linkermann, A. and Green, D. R. (2014) Necroptosis. The New England journal of medicine. 370, 455-465.
17) Degterev, A., Huang, Z., Boyce, M., Li, Y., Jagtap, P., Mizushima, N., Cuny, G. D., Mitchison, T. J., Moskowitz, M. A. and Yuan, J. (2005) Chemical inhibitor of nonapoptotic cell death with therapeutic potential for ischemic brain injury. Nat Chem Biol. 1, 112-119.
18) Takahashi, N., Duprez, L., Grootjans, S., Cauwels, A., Nerinckx, W., DuHadaway, J. B., Goossens, V., Roelandt, R., Van Hauwermeiren, F., Libert, C., Declercq, W., Callewaert, N., Prendergast, G. C., Degterev, A., Yuan, J. and Vandenabeele, P. (2012) Necrostatin-1 analogues: critical issues on the specificity, activity and in vivo use in experimental disease models. Cell Death Dis. 3, e437.
19) Harris, P. A., Bandyopadhyay, D., Berger, S. B., Campobasso, N., Capriotti, C. A., Cox, J. A., Dare, L., Finger, J. N., Hoffman, S. J., Kahler, K. M., Lehr, R., Lich, J. D., Nagilla, R., Nolte, R. T., Ouellette, M. T., Pao, C. S., Schaeffer, M. C., Smallwood, A., Sun, H. H., Swift, B. A., Totoritis, R. D., Ward, P., Marquis, R. W., Bertin, J. and Gough, P. J. (2013) Discovery of Small Molecule RIP1 Kinase Inhibitors for the Treatment of Pathologies Associated with Necroptosis. ACS medicinal chemistry letters. 4, 1238-1243.
20) Najjar, M., Suebsuwong, C., Ray, S. S., Thapa, R. J., Maki, J. L., Nogusa, S., Shah, S., Saleh, D., Gough, P. J., Bertin, J., Yuan, J., Balachandran, S., Cuny, G. D. and Degterev, A. (2015) Structure Guided Design of Potent and Selective Ponatinib-Based Hybrid Inhibitors for RIPK1. Cell Rep.
21) International Patent Publication No. WO 2014/125444.
22) International Patent Publication No. WO 2017/004500.

SUMMARY OF THE INVENTION

Provided herein are compounds of formula I:

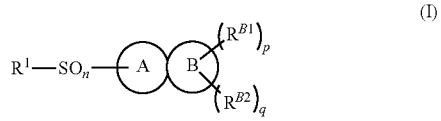

(I)

or a pharmaceutically acceptable salt thereof, wherein
$R^1$ is selected from the group consisting of $C_1$-$C_6$ alkyl, $C_3$-$C_6$ cycloalkyl, $CH_2$—($C_3$-$C_6$ cycloalkyl), $C_1$-$C_6$ alkoxy, $C_1$-$C_6$ haloalkyl, $C_1$-$C_6$ haloalkoxy, $C_1$-$C_6$ alkyl-$N(R^N)_2$, phenyl, benzyl, 4 to 8 membered heterocyclyl and 5 to 6 membered heteroaryl; and wherein $R^1$ is optionally substituted by one or two substituents selected from the group consisting of halogen, $C_1$-$C_6$ alkyl, $C_3$-$C_6$ cycloalkyl, $C_1$-$C_6$ alkoxy, $C_1$-$C_6$ haloalkyl, $C_1$-$C_6$ haloalkoxy, $C_1$-$C_6$ alkyl-$N(R^N)_2$, hydroxyl, $C_1$-$C_6$ hydroxyalkyl, cyano, $C_1$-$C_6$cyanoalkyl, $C(O)C_1$-$C_6$ alkyl, phenyl, benzyl, $CH_2$—($C_3$-$C_6$ cycloalkyl), 5 to 6 membered heteroaryl, and $CH_2$-(5 to 6 membered heteroaryl);
n is 0, 1 or 2;
each $R^2$ is independently selected from the group consisting of $C_1$-$C_6$ alkyl, $C_3$-$C_6$ cycloalkyl, $C_1$-$C_6$ alkoxy, and $C_1$-$C_6$ haloalkyl; or two $R^2$ together with the nitrogen atom to which they are both attached form a 4-6 membered heterocyclic ring;
the A ring and the B ring are fused to form a polycyclic ring system, wherein
the A ring is a 5 membered heteroaromatic ring having as its only heteroatoms, either (i) two or three nitrogen atoms, (ii) one nitrogen atom and one oxygen atom, or (iii) one nitrogen atom and one sulfur atom; wherein the A ring is optionally substituted at a carbon atom by one substituent selected from the group consisting of fluoro, chloro, methyl, and trifluoromethyl; and
the B ring is a 4 to 8 membered carbocyclic ring, or a 4 to 8 membered heterocyclic ring having 1 to 3 heteroatoms selected from the group consisting of nitrogen, oxygen, and sulfur;
p is 1 or 2, and q is 0 or 1; or p is 0, and q is 1;
wherein when p is 1, $R^{B1}$ is $R^{3a}$ and when p is 2, $R^{B1}$ is independently $R^{3a}$ and $R^{3b}$ and each $R^{3a}$ and $R^{3b}$, when present, is/are independently selected from the group consisting of halogen, deutero, hydroxyl, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-$N(R^2)_2$, and cyano; wherein two $C_1$-$C_6$ alkyl substituents may together form a bridged or spirocyclic ring; and wherein if a nitrogen atom in the B ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom; and
wherein when q is 1, $R^{B2}$ is $R^4$ and $R^4$ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-$N(R^2)_2$, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl);
wherein when $R^4$ is phenyl, heteroaryl or benzyl the phenyl or heteroaryl ring is optionally substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano.

Also provided herein are pharmaceutical compositions comprising a compound of formula I, or a pharmaceutically acceptable salt thereof, and one or more pharmaceutically acceptable carriers or excipients. Specific embodiments include pharmaceutical compositions suitable for oral delivery.

Also provided herein are oral formulations of a compound of formula I, or a pharmaceutically acceptable salt thereof, and one or more pharmaceutically acceptable carriers or excipients suitable for oral delivery.

Also provided herein are methods of treatment of diseases and disorders associated with inflammation, cell death, and others related to RIP1 kinase, as described further below.

Also provided herein are compounds or pharmaceutical compositions for use as therapeutically active substances.

Also provided herein are uses of compounds or pharmaceutical compositions for use in the treatment of diseases and disorders associated with inflammation, cell death, and others related to RIP1 kinase, as described further below.

Also provided herein are uses of compounds or pharmaceutical compositions for the preparation of a medicament for the treatment of diseases and disorders associated with inflammation, cell death, and others related to RIP1 kinase, as described further below.

Also provided herein are compounds or pharmaceutical compositions for use in the treatment of diseases and disorders associated with inflammation, cell death, and others related to RIP1 kinase, as described further below.

DETAILED DESCRIPTION OF THE INVENTION

Definitions

As provided herein, all chemical formulae and generic chemical structures should be interpreted to provide proper valence and chemically stable bonds between atoms as understood by one of ordinary skill in the art. Where appropriate, substituents may be bonded to more than one adjacent atom (e.g., alkyl includes methylene where two bonds are present).

In the chemical formulae provided herein, "halogen" or "halo' refers to flurorine, chlorine, and bromine (i.e., F, Cl, Br).

Alkyl, unless otherwise specifically defined, refers to an optionally substituted, straight-chain or branched $C_1$-$C_{12}$ alkyl group. In some embodiments, alkyl refers to a $C_1$-$C_6$ alkyl group. Exemplary alkyl groups include methyl, ethyl, propyl, iso-propyl, n-butyl, iso-butyl, tert-butyl, sec-butyl, n-pentyl, n-hexyl, n-heptyl, and n-oxtyl. Substituted alkyl groups provided herein are substituted by one or more substituents selected from the group consisting of halogen, cyano, trifluoromethyl, methoxy, ethoxy, difluoromethoxy, trifluoromethoxy, $C_3$-$C_6$ cycloalkyl, phenyl, OH, $CO_2H$, $CO_2(C_1$-$C_4$ alkyl), $NH_2$, $NH(C_1$-$C_4$ alkyl), $N(C_1$-$C_4$ alkyl)$_2$, $NH(C=O)C_1$-$C_4$ alkyl, $(C=O)NH(C_1$-$C_4$ alkyl), $(C=O)N(C_1$-$C_4$ alkyl)$_2$, $S(C_1$-$C_4$ alkyl), $SO(C_1$-$C_4$ alkyl), $SO_2(C_1$-$C_4$ alkyl), $SO_2NH(C_1$-$C_4$ alkyl), $SO_2N(C_1$-$C_4$ alkyl)$_2$, and $NHSO_2(C_1$-$C_4$ alkyl). In some embodiments, the substituted alkyl group has 1 or 2 substituents. In some embodiments, the alkyl group is unsubstituted.

Cycloalkyl, unless otherwise specifically defined, refers to an optionally substituted $C_3$-$C_{12}$ cycloalkyl group and includes fused, spirocyclic, and bridged bicyclic groups, wherein the substituents are selected from the group consisting of halogen, cyano, trifluoromethyl, methoxy, ethoxy, difluoromethoxy, trifluoromethoxy, $C_3$-$C_6$ cycloalkyl, phenyl, OH, $CO_2H$, $CO_2(C_1$-$C_4$ alkyl), $NH_2$, $NH(C_1$-$C_4$ alkyl), $N(C_1$-$C_4$ alkyl)$_2$, $NH(C=O)C_1$-$C_4$ alkyl, $(C=O)NH(C_1$-$C_4$ alkyl), $(C=O)N(C_1$-$C_4$ alkyl)$_2$, $S(C_1$-$C_4$ alkyl), $SO(C_1$-$C_4$ alkyl), $SO_2(C_1$-$C_4$ alkyl), $SO_2NH(C_1$-$C_4$ alkyl), $SO_2N(C_1$-$C_4$ alkyl)$_2$, and $NHSO_2(C_1$-$C_4$ alkyl). In some embodiments, cycloalkyl refers to a $C_3$-$C_6$ cycloalkyl group. In some embodiments, the $C_3$-$C_6$ cycloalkyl group is optionally substituted with 1 to three halogen atoms. In some embodiments, the $C_3$-$C_6$ cycloalkyl group is optionally substituted with 1 to three fluorine atoms. Exemplary $C_3$-$C_6$ cycloalkyl groups include cyclopropyl, cyclobutyl, cyclopentyl and cyclohexyl. Exemplary $C_3$-$C_{12}$ cycloalkyl groups further include bicyclo[3.1.0]hexyl, bicyclo[2.1.1]hexyl, cycloheptyl, bicycle[4.1.0]heptyl, spiro[4.2]heptyl, cyclooctyl, spiro[4.3]octyl, spiro[5.2]octyl, bicyclo[2.2.1]heptanyl, bicycle[2.2.2]octanyl, adamantanyl, decalinyl, and spiro[5.4]decanyl. Where appropriate, cycloalkyl groups may be fused to other groups such that more than one chemical bond exists between the cycloalkyl group and another ring system (e.g., the C ring of formula I). In some embodiments, the cycloalkyl group is unsubstituted.

Haloalkyl, unless otherwise specifically defined, refers to a straight-chain or branched $C_1$-$C_{12}$ alkyl group, wherein one or more hydrogen atoms are replaced by a halogen. In some embodiments, haloalkyl refers to a $C_1$-$C_6$ haloalkyl group. In some embodiments, 1 to 3 hydrogen atoms of the haloalkyl group are replaced by a halogen. In some embodiments, every hydrogen atom of the haloalkyl group is replaced by a halogen (e.g, trifluoromethyl). In some embodiments, the haloalkyl is as defined herein wherein the halogen in each instance is fluorine. Exemplary haloalkyl groups include fluoromethyl, difluoromethyl, trifluromethyl, trifluoroethyl, and pentafluoroethyl.

Alkoxy, unless otherwise specifically defined, refers to a straight-chain or branched $C_1$-$C_{12}$ alkyl group, wherein one or more oxygen atoms are present, in each instance between two carbon atoms. In some embodiments, alkoxy refers to a $C_1$-$C_6$ alkoxy group. In some embodiments, $C_1$-$C_6$ alkoxy groups provided herein have one oxygen atom. Exemplary alkoxy groups include methoxy, ethoxy, $CH_2OCH_3$, $CH_2CH_2OCH_3$, $CH_2OCH_2CH_3$, $CH_2CH_2OCH_2CH_3$, $CH_2OCH_2CH_2CH_3$, $CH_2CH_2CH_2OCH_3$, $CH_2OCH(CH_3)_2$, $CH_2OC(CH_3)_3$, $CH(CH_3)OCH_3$, $CH_2CH(CH_3)OCH_3$, $CH(CH_3)OCH_2CH_3$, $CH_2OCH_2OCH_3$, $CH_2CH_2OCH_2CH_2OCH_3$, and $CH_2OCH_2OCH_2OCH_3$.

Cycloalkoxy, unless otherwise specifically defined, refers to a $C_4$-$C_{10}$ or a $C_4$-$C_6$ alkoxy group as defined above wherein the group is cyclic and contains one oxygen atom. Exemplary cycloalkoxy groups include oxetanyl, tetrahydrofuranyl, and tetrahydropyranyl.

Haloalkoxy, unless otherwise specifically defined, refers to a $C_1$-$C_6$ haloalkyl group as defined above, wherein one or two oxygen atoms are present, in each instance between two carbon atoms. In some embodiments, $C_1$-$C_6$ haloalkoxy groups provided herein have one oxygen atom. Exemplary haloalkoxy groups include $OCF_3$, $OCHF_2$ and $CH_2OCF_3$.

Thioalkyl, unless otherwise specifically defined, refers to a $C_1$-$C_{12}$ or a $C_1$-$C_6$ alkoxy group as defined above wherein the oxygen atom is replaced by a sulfur atom. In some embodiments, thioalkyl groups may include sulfur atoms substituted by one or two oxygen atoms (i.e., alkylsulfones and alkylsulfoxides). Exemplary thioalkyl groups are those exemplified in the definition of alkoxy above, wherein each oxygen atom is replaced by a sulfur atom in each instance.

Thiocycloalkyl, unless otherwise specifically defined, refers to a $C_4$-$C_{10}$ or a $C_4$-$C_6$ thioalkyl group as defined above wherein the group is cyclic and contains one sulfur atom. In some embodiments, the sulfur atom of the thiocycloalkyl group is substituted by one or two oxygen atoms (i.e., a cyclic sulfone or sulfoxide). Exemplary thiocycloalkyl groups include thietanyl, thiolanyl, thianyl, 1,1-dioxothiolanyl, and 1,1-dioxothianyl.

Heterocyclyl, unless otherwise specifically defined, refers to a single saturated or partially unsaturated 4 to 8 membered ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems have from 7 to 12 atoms and are further described below. Thus, the term includes single saturated or partially unsaturated rings (e.g., 3, 4, 5, 6, 7 or 8 membered rings) from about 1 to 7 carbon atoms and from about 1 to 4 heteroatoms selected from the group consisting of oxygen, nitrogen and sulfur in the ring. The ring may be C-branched (i.e., substituted by $C_1$-$C_4$ alkyl). The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system. It is also to be understood that the point of attachment for a heterocycle or heterocycle multiple condensed ring system can be at any suitable atom of the heterocyclyl group including a carbon atom and a nitrogen atom. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidazolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrhydrothiophene, quinuclidine, tropane, 2-azaspiro[3.3]heptane, (1R,5S)-3-azabicyclo[3.2.1]octane, (1s,4s)-2-azabicyclo[2.2.2]octane, (1R,4R)-2-oxa-5-azabicyclo[2.2.2]octane and pyrrolidin-2-one.

In some embodiments, the heterocyclyl is a $C_4$-$C_{10}$ heterocyclyl having 1 to 3 heteroatoms selected from the group consisting of nitrogen, oxygen and sulfur. In some embodiments, the heterocyclyl group is neither bicyclic nor spirocyclic. In some embodiments, the heterocyclyl is a $C_5$-$C_6$ heterocylcyl having 1 to 3 heteroatoms, wherein at least 2 are nitrogen if 3 heteroatoms are present.

Aryl, unless otherwise specifically defined, refers to a single all carbon aromatic ring or a multiple condensed all carbon ring system wherein at least one of the rings is aromatic and wherein the aryl group has 6 to 20 carbon atoms, 6 to 14 carbon atoms, 6 to 12 carbon atoms, or 6 to 10 carbon atoms.

Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Exemplary aryl groups include phenyl, indenyl, naphthyl, 1, 2, 3, 4-tetrahydronaphthyl, anthracenyl, and the like.

Heteroaryl, unless otherwise specifically defined, refers to a 5 to 6 membered aromatic ring that has at least one atom other than carbon in the ring, wherein the atom is selected from the group consisting of oxygen, nitrogen and sulfur; "heteroaryl" also includes multiple condensed ring systems having 8 to 16 atoms that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2 or 3 rings) wherein a heteroaryl group, as defined above, is condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has 1 to 15 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclo-penta[1,2-c]pyrazole.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "⌇" that intersects a bond in a chemical structure indicates the point of attachment of the bond that the wavy bond intersects in the chemical structure to the remainder of a molecule.

As used herein, the term "C-linked" means that the group that the term describes is attached the remainder of the molecule through a ring carbon atom.

As used herein, the term "N-linked" means that the group that the term describes is attached to the remainder of the molecule through a ring nitrogen atom.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 97% the absolute stereoisomer depicted. In another embodiment, the compound may be at least 98% the absolute stereoisomer depicted. In another embodiment, the compound may be at least 99% the absolute stereoisomer depicted.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see P. G. M. Wuts and T. W. Greene, Greene's Protective Groups in Organic Synthesis 4$^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep.

As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_{1-6})$alkanoyloxymethyl, 1-(($C_{1-6}$)alkanoyloxy)ethyl, 1-methyl-1-(($C_{1-6}$)alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, alpha-amino$(C_{1-4})$alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

Inhibitors of RIP1 Kinase

All embodiments described herein can be combined.

The present invention provides novel compounds having the general formula I:

Provided herein are compounds of formula I:

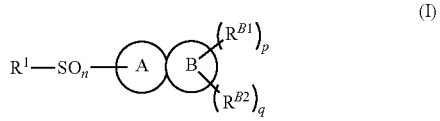

(I)

or pharmaceutically acceptable salts thereof, wherein
R$^1$ is selected from the group consisting of $C_1$-$C_6$ alkyl, $C_3$-$C_6$ cycloalkyl, $C_1$-$C_6$ alkoxy, $C_1$-$C_6$ haloalkyl, $C_1$-$C_6$ haloalkoxy, $C_1$-$C_6$ alkyl-N(R$^2$)$_2$, phenyl, benzyl, difluoro(phenyl)methyl, 4 to 6 membered heterocyclyl, 5 to 6 membered heteroaryl, and CH$_2$-(5 to 6 membered heteroaryl); wherein when R$^1$ is phenyl, benzyl, difluoro(phenyl)methyl, 5 to 6 membered heteroaryl or CH$_2$-(5 to 6 membered heteroaryl), the phenyl or aryl moiety of R$^1$ is optionally substituted by one or two substituents selected from the group consisting of fluoro, chloro, methyl, ethyl, hydroxyl, hydroxymethyl, methoxymethyl, cyano, trifluoromethyl, difluoromethoxy and trifluoromethoxy;
n is 1 or 2;
each R$^2$ is independently selected from the group consisting of $C_1$-$C_6$ alkyl, $C_3$-$C_6$ cycloalkyl, $C_1$-$C_6$ alkoxy, and $C_1$-$C_6$ haloalkyl; or two R$^2$ together with the nitrogen atom to which they are both attached form a 4-6 membered heterocyclic ring;
the A ring and the B ring are fused to form a polycyclic ring system, wherein
the A ring is a 5 membered heteroaromatic ring having as its only heteroatoms, either (i) two or three nitrogen atoms, (ii) one nitrogen atom and one oxygen atom, or (iii) one nitrogen atom and one sulfur atom; wherein the A ring is optionally substituted at a carbon atom by one substituent selected from the group consisting of fluoro, chloro, methyl, and trifluoromethyl; and
the B ring is a 4 to 8 membered carbocyclic ring, or a 4 to 8 membered heterocyclic ring having 1 to 3 heteroatoms selected from the group consisting of nitrogen, oxygen, and sulfur;
p is 1 or 2, and q is 0 or 1; or p is 0, and q is 1;
each R$^{B1}$ is independently selected from the group consisting of halogen, deutero, hydroxyl, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-N(R$^2$)$_2$, and cyano; wherein two $C_1$-$C_6$ alkyl substituents may together form a bridged or spirocyclic ring; and wherein if a nitrogen atom in the B ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom; and
R$^{B2}$ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-N(R$^2$)$_2$, phenyl, benzyl, CH$_2$—($C_3$-$C_6$ cycloalkyl), CH$_2$CH$_2$—($C_3$-$C_6$ cycloalkyl), CH$_2$-(4 to 6 membered heterocyclyl), CH$_2$CH$_2$-(4 to 6 membered heterocyclyl), 5 to 6 membered heteroaryl, and CH$_2$-(5 to 6 membered heteroaryl); wherein when R$^{B2}$ is phenyl or benzyl the phenyl ring is optionally substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano.

In some embodiments provided herein there is provided:
of formula I: or a pharmaceutically acceptable salt thereof, wherein
R$^1$ is selected from the group consisting of $C_1$-$C_6$ alkyl, $C_3$-$C_6$ cycloalkyl, $C_1$-$C_6$ alkoxy, $C_1$-$C_6$ haloalkyl, $C_1$-$C_6$ haloalkoxy, $C_1$-$C_6$ alkyl-N(R$^N$)$_2$, phenyl, benzyl, 4 to 8 membered heterocyclyl and 5 to 6 membered heteroaryl; wherein R$^1$ is bound to the adjacent —SO$_n$— by a carbon atom, and wherein R$^1$ is optionally substituted by one or two substituents selected from the group consisting of halogen, $C_1$-$C_6$ alkyl, $C_3$-$C_6$ cycloalkyl, $C_1$-$C_6$ alkoxy, $C_1$-$C_6$ haloalkyl, $C_1$-$C_6$ haloalkoxy, $C_1$-$C_6$ alkyl-N(R$^N$)$_2$, hydroxyl, $C_1$-$C_6$ hydroxyalkyl, cyano, $C_1$-$C_6$cyanoalkyl, C(O)$C_1$-$C_6$ alkyl, phenyl, benzyl, CH$_2$—($C_3$-$C_6$ cycloalkyl), 5 to 6 membered heteroaryl, and CH$_2$-(5 to 6 membered heteroaryl);
n is 1 or 2;
each R$^2$ is independently selected from the group consisting of $C_1$-$C_6$ alkyl, $C_3$-$C_6$ cycloalkyl, $C_1$-$C_6$ alkoxy, and $C_1$-$C_6$ haloalkyl; or two R$^2$ together with the nitrogen atom to which they are both attached form a 4-6 membered heterocyclic ring;
the A ring and the B ring are fused to form a polycyclic ring system, wherein
the A ring is a 5 membered heteroaromatic ring having as its only heteroatoms, either (i) two or three nitrogen atoms, (ii) one nitrogen atom and one oxygen atom, or (iii) one nitrogen atom and one sulfur atom; wherein the A ring is optionally substituted at a carbon atom by one substituent selected from the group consisting of fluoro, chloro, methyl, and trifluoromethyl; and the B ring is a 4 to 8 membered carbocyclic ring, or a 4 to 8 membered heterocyclic ring having 1 to 3 heteroatoms selected from the group consisting of nitrogen, oxygen, and sulfur;

p is 1 or 2, and q is 0 or 1; or p is 0, and q is 1;

wherein when p is 1, $R^{B1}$ is $R^{3a}$ and when p is 2, $R^{B1}$ is independently $R^{3a}$ and $R^{3b}$ and each $R^{3a}$ and $R^{3b}$, when present, is/are independently selected from the group consisting of halogen, deutero, hydroxyl, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-$N(R^2)_2$, and cyano; wherein two $C_1$-$C_6$ alkyl substituents may together form a bridged or spirocyclic ring; and wherein if a nitrogen atom in the B ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom; and wherein when q is 1, $R^{B2}$ is $R^4$ and $R^4$ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-$N(R^2)_2$, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl);

wherein when $R^4$ is phenyl, heteroaryl or benzyl the phenyl or heteroaryl ring is optionally substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano.

In some embodiments, provided herein is a compound of formula (I), or a pharmaceutically acceptable salt thereof, wherein the A ring and the B ring together (including substituents, p, q, $R^{B1}$ and $R^{B2}$) are selected from the group consisting of:

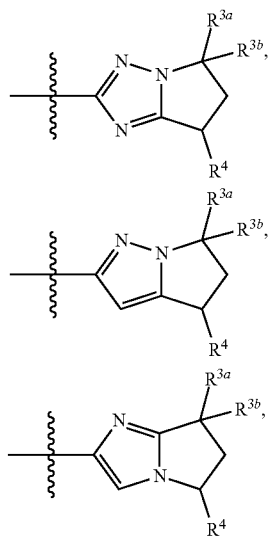
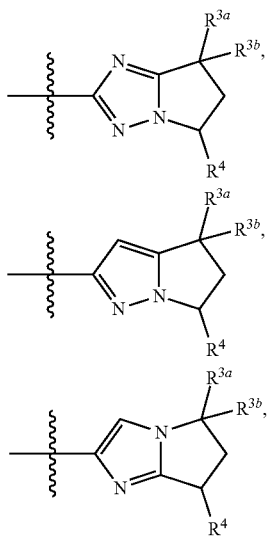
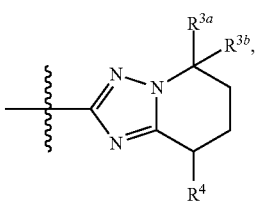
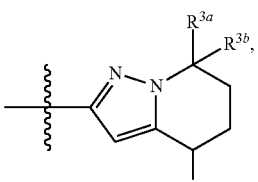
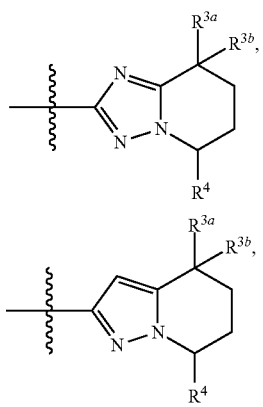
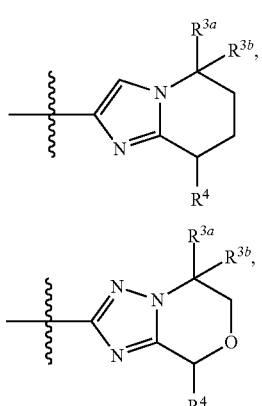
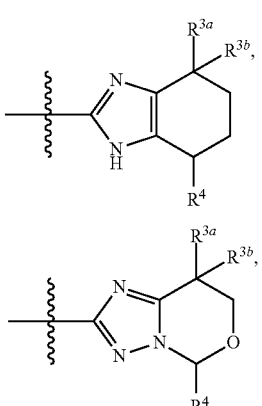
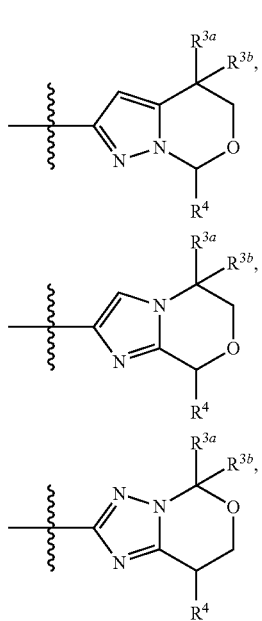

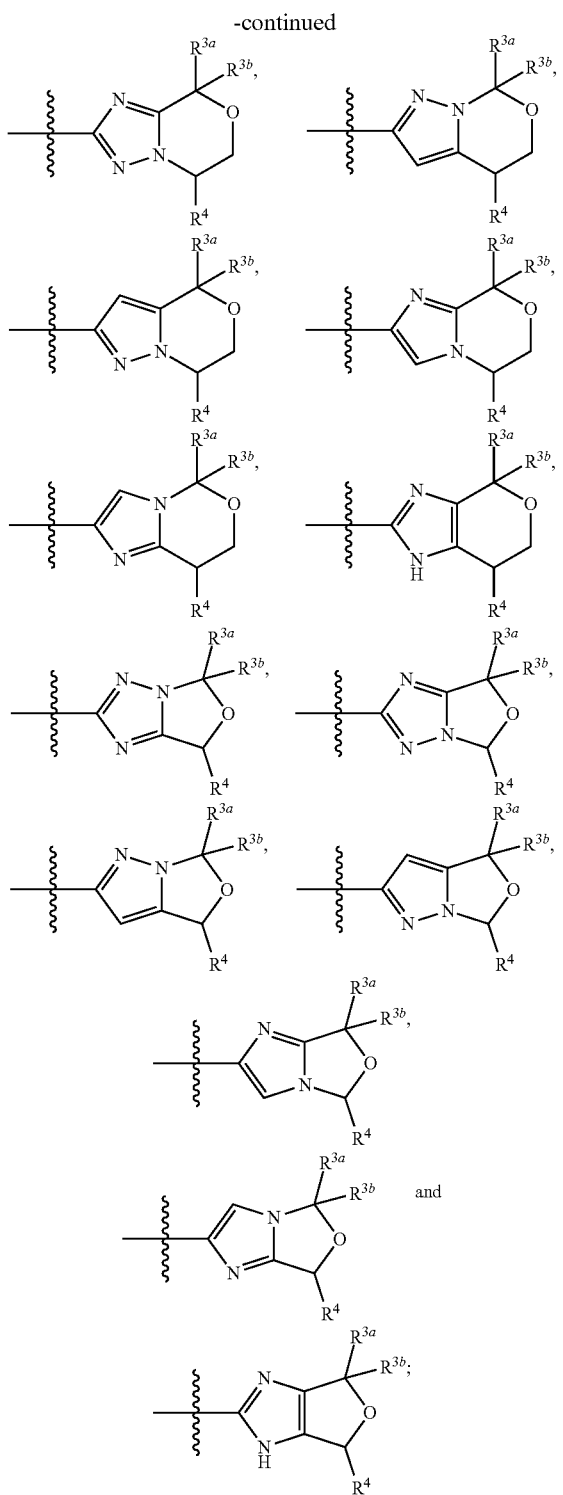

wherein
one of $R^{3a}$ and $R^{3b}$ is H, and the other is selected from the group consisting of hydrogen, deutero, fluoro, chloro, hydroxyl, cyano, $C_1$-$C_4$ alkyl, $C_1$-$C_4$ haloalkyl, cyclopropyl, $C_1$-$C_4$ alkoxy and $C_1$-$C_4$ haloalkoxy; or
each of $R^{3a}$ and $R^{3b}$ is independently selected from the group consisting of deutero, fluoro, chloro, hydroxyl, cyano, and methyl, provided that $R^{3a}$ and $R^{3b}$ cannot both be OH or CN; or $R^{3a}$ and $R^{3b}$, together with the carbon atom to which they are both attached, form 1,1-cyclopropylene; and
$R^4$ is selected from the group consisting of $C_1$-$C_6$ alkyl, $C_1$-$C_6$ haloalkyl, $C_{3-6}$ cycloalkyl, $C_1$-$C_6$ alkoxy, $C_1$-$C_6$ haloalkoxy, $C_1$-$C_6$ thioalkyl, phenyl, benzyl, $CH_2$—($C_3$-$C_6$cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl); wherein when a phenyl ring is present it may be substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano.

In another embodiment $R^1$, $R^2$, $R^{3a}$, $R^{3b}$ and $R^4$ are: or a pharmaceutically acceptable salt thereof, wherein:
$R^1$ is selected from the group consisting of $C_1$-$C_6$ alkyl, $C_3$-$C_6$ cycloalkyl, $C_1$-$C_6$ alkoxy, $C_1$-$C_6$ haloalkyl, $C_1$-$C_6$ haloalkoxy, $C_1$-$C_6$ hydroxyalkyl, $C_1$-$C_6$ cyanoalkyl, $C_3$-$C_6$ cycloalkyl-$C_1$-$C_3$ alkyl, $C_1$-$C_6$ alkyl-N($R^2$)$_2$, $C_1$-$C_6$ alkoxy-$C_1$-$C_6$ alkyl, $C_1$-$C_6$ haloalkoxy-$C_1$-$C_6$ alkyl, phenyl, benzyl, difluoro(phenyl)methyl, 4 to 6 membered heterocyclyl, 5 to 6 membered heteroaryl, and $CH_2$-(5 to 6 membered heteroaryl); wherein:
when $R^1$ is phenyl, benzyl, difluoro(phenyl)methyl, 5 to 6 membered heteroaryl or $CH_2$-(5 to 6 membered heteroaryl), the phenyl or heteroaryl moiety of $R^1$ is optionally substituted by one or two substituents independently selected from the group consisting of halogen, $C_1$-$C_6$ alkyl, hydroxyl, hydroxymethyl, methoxymethyl, cyano, trifluoromethyl, difluoromethoxy and trifluoromethoxy;
when $R^1$ is cycloalkyl the cycloalkyl is optionally substituted by one, two or three substituents independently selected from the group consisting of fluoro, $C_1$-$C_6$ alkyl, $C_1$-$C_6$ haloalkyl, $C_1$-$C_6$ haloalkoxy, hydroxyl, $C_1$-$C_6$ hydroxyalkyl or cyano;
n is 1 or 2;
each $R^2$ is independently selected from the group consisting of $C_1$-$C_6$ alkyl, $C_3$-$C_6$ cycloalkyl, $C_1$-$C_6$ alkoxy, and $C_1$-$C_6$ haloalkyl; or two $R^2$ together with the nitrogen atom to which they are both attached form a 4-6 membered heterocyclic ring;
$R^{3a}$ is hydrogen and $R^{3b}$, when p is 2, $R^{B1}$ is independently $R^{3a}$ and $R^{3b}$ and each $R^{3a}$ and $R^{3b}$, when present, is/are independently is selected from the group consisting of halogen, deutero, hydroxyl, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-N($R^2$)$_2$, and cyano; or
$R^{3a}$ and $R^{3b}$ are independently is selected from the group consisting of halogen, deutero, hydroxyl, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-N($R^2$)$_2$, and cyano; or $R^{3a}$ and $R^{3b}$ together with the atoms to which they are attached form a bridged or spirocyclic ring; and
wherein when q is 1, $R^{B2}$ is $R^4$ and $R^4$ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-N($R^2$)$_2$, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl);
wherein when $R^4$ is phenyl, heteroaryl or benzyl the phenyl or heteroaryl ring is optionally substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano.

In some embodiments, provided herein is a compound of formula (I), or a pharmaceutically acceptable salt thereof, wherein the A ring and the B ring together are:

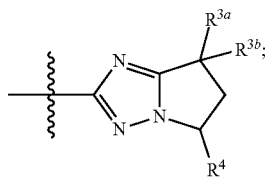

wherein
$R^{3a}$ and $R^{3b}$ are selected as follows:
one of $R^{3a}$ and $R^{3b}$ is H, and the other is selected from the group consisting of hydrogen, deutero, fluoro, chloro, hydroxyl, cyano, $C_1$-$C_4$ alkyl, $C_1$-$C_4$ haloalkyl, cyclopropyl, $C_1$-$C_4$ alkoxy and $C_1$-$C_4$ haloalkoxy; or
each of $R^{3a}$ and $R^{3b}$ is independently selected from the group consisting of deutero, fluoro, chloro, hydroxyl, cyano, and methyl, provided that $R^{3a}$ and $R^{3b}$ cannot both be OH or CN; or
$R^{3a}$ and $R^{3b}$, together with the carbon atom to which they are both attached, form 1,1-cyclopropylene; and
$R^4$ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, phenyl, benzyl, $CH_2$—($C_3$-$C_6$ cycloalkyl), $CH_2CH_2$—($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl); wherein when a phenyl ring is present it may be substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano.

In another embodiment $R^{3a}$ and $R^{3b}$ are selected as follows:
one of $R^{3a}$ and $R^{3b}$ is H, and the other is selected from the group consisting of hydrogen, deutero, fluoro, chloro, hydroxyl, cyano, $C_1$-$C_4$ alkyl, $C_1$-$C_4$ haloalkyl, cyclopropyl, $C_1$-$C_4$ alkoxy and $C_1$-$C_4$ haloalkoxy; or
each of $R^{3a}$ and $R^{3b}$ is independently selected from the group consisting of hydrogen, deutero, fluoro, chloro, hydroxyl, cyano, $C_1$-$C_4$ alkyl, $C_1$-$C_4$ haloalkyl, cyclopropyl, $C_1$-$C_4$ alkoxy and $C_1$-$C_4$ haloalkoxy; or, provided that $R^{3a}$ and $R^{3b}$ cannot both be OH or CN; or
$R^{3a}$ and $R^{3b}$, together with the carbon atom to which they are both attached, form 1,1-cyclopropylene.

In yet another embodiment $R^{3a}$ and $R^{3b}$ are selected as follows:
one of $R^{3a}$ and $R^{3b}$ is H, and the other is selected from the group consisting of hydrogen, deutero, fluoro, chloro, hydroxyl, cyano, $C_1$-$C_4$ alkyl, $C_1$-$C_4$ haloalkyl, cyclopropyl, $C_1$-$C_4$ alkoxy and $C_1$-$C_4$ haloalkoxy; or
each of $R^{3a}$ and $R^{3b}$ is independently selected from the group consisting of deutero, fluoro, chloro, hydroxyl, cyano, and methyl, provided that $R^{3a}$ and $R^{3b}$ cannot both be OH or CN; or
$R^{3a}$ and $R^{3b}$, together with the carbon atom to which they are both attached, form 1,1-cyclopropylene; and
$R^4$ is selected from the group consisting of $C_1$-$C_6$ alkyl, $C_1$-$C_6$ haloalkyl, phenyl or pyridinyl wherein the phenyl ring or pyridinyl ring is optionally substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano.

In some embodiments, provided herein is a compound of formula (I), or a pharmaceutically acceptable salt thereof, wherein the A ring and the B ring together are selected from the group consisting of:

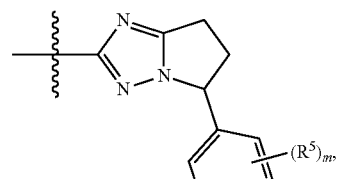

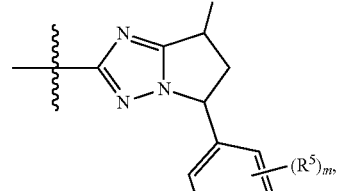

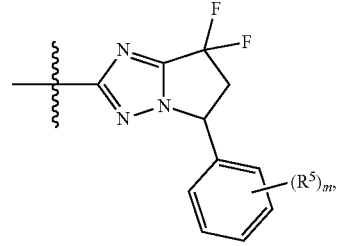

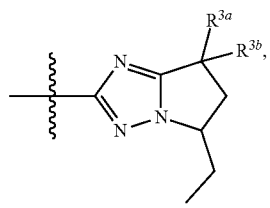 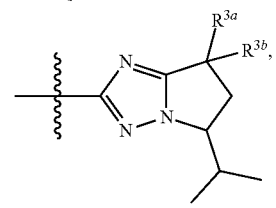

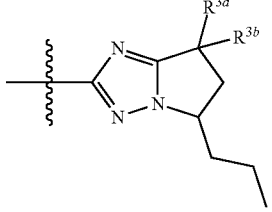 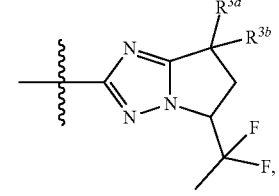

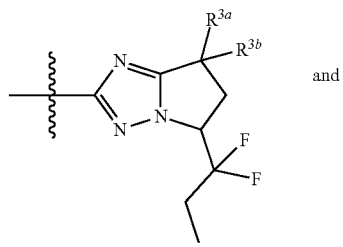

and

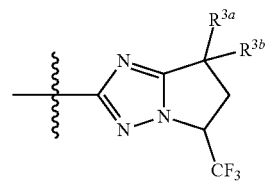

wherein
one of $R^{3a}$ and $R^{3b}$ is H, and the other is selected from the group consisting of hydrogen, deutero, fluoro, chloro, hydroxyl, cyano, $C_1$-$C_4$ alkyl, $C_1$-$C_4$ haloalkyl, cyclopropyl, $C_1$-$C_4$ alkoxy and $C_1$-$C_4$ haloalkoxy; or each of $R^{3a}$ and $R^{3b}$ is independently selected from the group consisting of deutero, fluoro, chloro, hydroxyl, cyano, and methyl, provided that $R^{3a}$ and $R^{3b}$ cannot both be OH or CN; or $R^{3a}$ and $R^{3b}$, together with the carbon atom to which they are both attached, form 1,1-cyclopropylene; and each $R^5$ is independently selected from the group consisting of H, F, Cl, $C_1$-$C_6$ alkyl, $C_1$-$C_6$ haloalkyl, $C_1$-$C_6$ alkoxy, and $C_1$-$C_6$ haloalkoxy; and m is 1, 2 or 3.

In some embodiments the A ring and the B ring together are selected from the group consisting of:

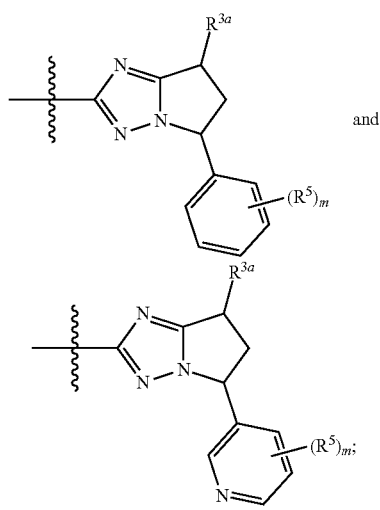

wherein
$R^{3a}$ is hydrogen or fluorine
each $R^5$ is selected from the group consisting of hydrogen, fluoro, chloro $C_1$-$C_6$ alkyl, $C_1$-$C_6$ haloalkyl, $C_1$-$C_6$ alkoxy, and $C_1$-$C_6$ haloalkoxy.

In s subembodiement $R^{3a}$ is fluoro.

In some embodiments, provided herein is a compound of formula (I), or a pharmaceutically acceptable salt thereof, wherein the A ring and the B ring together are selected from the group consisting of:

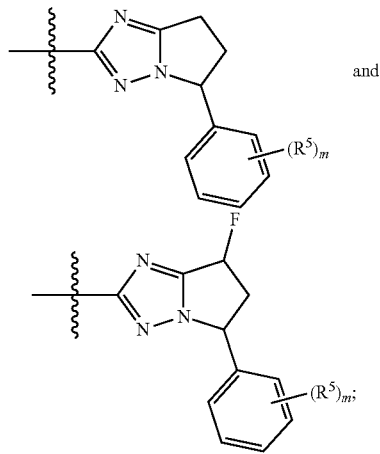

wherein
each $R^5$ is selected from the group consisting of hydrogen, fluoro, chloro $C_1$-$C_6$ alkyl, $C_1$-$C_6$ haloalkyl, $C_1$-$C_6$ alkoxy, and $C_1$-$C_6$ haloalkoxy; and
m is 1, 2 or 3.

In some embodiments, provided herein is a compound of formula (I), or a pharmaceutically acceptable salt thereof, wherein the A ring and the B ring together are:

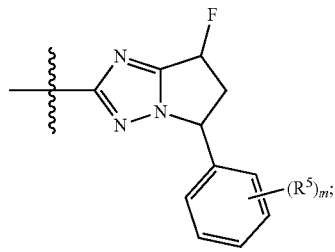

wherein
each $R^5$ is selected from the group consisting of hydrogen, fluoro, chloro $C_1$-$C_6$ alkyl, $C_1$-$C_6$ haloalkyl, $C_1$-$C_6$ alkoxy, and $C_1$-$C_6$ haloalkoxy; and
m is 1, 2 or 3.

In some embodiments $R^1$ is selected from the group consisting of $C_1$-$C_6$ alkyl, optionally substituted $C_3$-$C_6$ cycloalkyl, $C_3$-$C_6$ spirocycloalkyl. $C_1$-$C_6$ haloalkyl, $C_1$-$C_6$ alkoxy-$C_1$-$C_6$ alkyl, $C_1$-$C_6$ cyanoalkyl, $C_1$-$C_6$ hydroxyalkyl, phenyl, benzyl, and difluoro(phenyl)methyl, or, $R^1$ is selected from the group consisting of methyl, ethyl, tert-butyl, difluoromethyl, trifluoromethyl, cyclopropyl, fluorocyclopropyl, difluorocyclopropyl, phenyl, benzyl, and difluoro(phenyl)methyl. or, alternatively, $R^1$ is selected from the group consisting of ethyl, difluoromethyl, trifluoromethyl, cyclopropyl, fluorocyclopropyl or difluorocyclopropyl.

In some of the above embodiments, n is 1. In some embodiments, n is 2.

In some of the above embodiments, m is 1. In some embodiments, m is 2. In some of the above embodiments, m is 3.

In some embodiments $R^5$ is halo. In some embodiments each $R^5$ is independently selected from chloro and fluoro.

In some of the above embodiments, $R^1$ is selected from the group consisting of $C_1$-$C_6$ alkyl, $C_3$-$C_6$ cycloalkyl, $C_1$-$C_6$ haloalkyl, phenyl, benzyl, and difluoro(phenyl)methyl. In some embodiments, $R^1$ is selected from the group consisting of methyl, ethyl, tert-butyl, difluoromethyl, trifluoromethyl, cyclopropyl, phenyl, benzyl, and difluoro(phenyl)methyl. In some embodiments, $R^1$ is selected from the group consisting of ethyl, difluoromethyl, trifluoromethyl, benzyl, and difluoro(phenyl)methyl.

In some of the above embodiments, $R^{3a}$ and $R^{3b}$ are selected as follows:
one of $R^{3a}$ and $R^{3b}$ is H, and the other is selected from the group consisting of hydrogen, deutero, fluoro, chloro, hydroxyl, cyano, $C_1$-$C_4$ alkyl, $C_1$-$C_4$ haloalkyl, cyclopropyl, $C_1$-$C_4$ alkoxy and $C_1$-$C_4$ haloalkoxy; or each of $R^{3a}$ and $R^{3b}$ is independently selected from the group consisting of deutero, fluoro, chloro, hydroxyl, cyano, and methyl, provided that $R^{3a}$ and $R^{3b}$ cannot both be OH or CN.

In some of the above embodiments, $R^{3a}$ and $R^{3b}$ are each independently selected from the group consisting of hydrogen, deutero, fluoro, chloro, methyl and trifluoromethyl. In some embodiments, $R^{3a}$ and $R^{3b}$ are each independently selected from the group consisting of hydrogen, deutero, fluoro and chloro. In some embodiments, $R^{3a}$ and $R^{3b}$ are each independently selected from the group consisting of hydrogen, fluoro and chloro. In some embodiments, $R^{3a}$ and $R^{3b}$ are each fluoro. In some embodiments, $R^{3a}$ is hydrogen and $R^{3b}$ is fluoro.

In some of the above embodiments, $R^4$ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, phenyl, 5 to 6 membered heteroaryl, and $CH_2$-(5 to 6 membered heteroaryl); wherein when a phenyl ring is present it may be substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano.

In some of the above embodiments, $R^5$ is selected from the group consisting of H, $C_1$-$C_6$ alkyl, $C_1$-$C_6$ haloalkyl, $C_3$-$C_6$ cycloalkyl, $C_1$-$C_6$ alkoxy, and $C_1$-$C_6$ haloalkoxy. In some of the above embodiments, $R^5$ is selected from the group consisting of H, F, Cl, $CH_3$, $CH_2CH_3$, $OCH_3$, $CF_3$, $OCF_3$, $CF_2H$, and $OCF_2H$. In some of the above embodiments, $R^5$ is selected from the group consisting of H, F and Cl.

In another embodiment, provided herein is a compound selected from the compounds of Table 1 below or a pharmaceutically acceptable salt thereof. In another embodiment, provided herein is a compound of Table 1 having a $K_i$ of less than 100 nM in a RIP1K biochemical or cell-based assay, including as herein described. In another embodiment, the compound of Table 1 has a $K_i$ of less than 50 nM in a RIP1K biochemical or cell-based assay, including as herein described. In yet another embodiment, the compound of Table 1 has a K of less than 25 nM in a RIP1K biochemical or cell-based assay, including as herein described. In yet another embodiment, the compound of Table 1 has a K of less than 10 nM in a RIP1K biochemical or cell-based assay, including as herein described.

In some embodiments, provided herein is a single stereoisomer of a compound of Table 1, as characterized by reference to its chiral separation and isolation (e.g., as described in the Examples by chiral SFC).

In some embodiments, provided herein are pharmaceutical compositions comprising a compound of formula I as described in any one of the above embodiments, or a pharmaceutically acceptable salt thereof, and one or more pharmaceutically acceptable carriers or excipients. Specific embodiments include pharmaceutical compositions suitable for oral delivery.

Also provided herein are oral formulations of a compound of formula I as described in any one of the above embodiments, or a pharmaceutically acceptable salt thereof, and one or more pharmaceutically acceptable carriers or excipients suitable for oral delivery.

In some embodiments, provided herein are uses of a compound of formula I as described in any one of the above embodiments, or a pharmaceutically acceptable salt thereof, for the treatment of neurodegenerative diseases and disorders. In some embodiments, the diseases and disorders to be treated are synucleopathies such as Parkinson's Disease, Lewy body dementia, multiple system atrophy, Parkinson-plus syndromes. In some embodiments, the diseases and disorders to be treated are taupathies such as Alzheimer's Disease and frontotemporal dementia. In some embodiments, the diseases and disorders to be treated are demyelination diseases such as multiple sclerosis.

In some embodiments, the diseases and disorders to be treated are other neurodegenerative diseases such as amyotrophic lateral sclerosis, spinal muscular atrophy, primary lateral sclerosis, Huntington's disease, ischemia, and stroke. Additional exemplary neurodegenerative diseases to be treated as provided herein include, but are not limited to, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathies, progressive supranuclear palsy, corticobasal degeneration, and demyelinating diseases.

In some embodiments, the disease or disorder to be treated is Alzheimer's disease. In some embodiments, the disease or disorder to be treated is Parkinson's disease. In some embodiments, the disease or disorder to be treated is Huntington's disease. In some embodiments, the disease or disorder to be treated is multiple sclerosis. In some embodiments, the disease or disorder to be treated is amyotrophic lateral sclerosis (ALS). In some embodiments, the disease or disorder to be treated is spinal muscular atrophy (SMA).

In some embodiments, provided herein are uses of a compound of formula I as described in any one of the above embodiments, or a pharmaceutically acceptable salt thereof, for the treatment of inflammatory diseases and disorders. In some embodiments, the disease or disorder to be treated is selected from the group consisting of inflammatory bowel diseases (including Crohn's disease and ulcerative colitis), psoriasis, retinal detachment, retinitis pigmentosa, macular degeneration, pancreatitis, atopic dermatitis, arthritis (including rheumatoid arthritis, osteoarthritis, spondylarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, liver damage/diseases (non-alcohol steatohepatitis, alcohol steatohepatitis, autoimmune hepatitis autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI), Celiac disease, autoimmune idiopathic thrombocytopenic purpura, transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), spinal muscular atrophy (SMA), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), periodontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2, Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

In some embodiments, the disease or disorder to be treated is an inflammatory bowel disease. In some embodiments, the disease or disorder to be treated is Crohn's disease. In some embodiments, the disease or disorder to be treated is ulcerative colitis. In some embodiments, the disease or disorder to be treated is glaucoma. In some embodiments, the disease or disorder to be treated is psoriasis. In some embodiments, the disease or disorder to be treated is rheumatoid arthritis. In some embodiments, the disease or disorder to be treated is spondyloarthritis. In some embodiments, the disease or disorder to be treated is juvenile idiopathic arthritis. In some embodiments, the disease or disorder to be treated is osteoarthritis.

In some embodiments, provided herein are methods for the treatment or prevention of a disease or disorder with a therapeutically effective amount of a compound of formula I, or a pharmaceutically acceptable salt thereof, wherein the disease or disorder is associated with inflammation and/or necroptosis. In some embodiments said disease or disorder is selected from the specific diseases and disorders recited herein.

In some embodiments, provided herein are methods of inhibiting RIP1 kinase activity by contacting a cell with a compound of formula I or a pharmaceutically acceptable salt thereof.

Pharmaceutical Compositions and Administration

Provided herein are pharmaceutical compositions or medicaments containing the compounds of the invention (or stereoisomers, geometric isomers, tautomers, solvates, metabolites, isotopes, pharmaceutically acceptable salts, or prodrugs thereof), and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. In some embodiments, the "effective amount" of the compound to be administered will be governed by such considerations, and is the minimum amount necessary to inhibit RIP1 kinase activity in order to provide a therapeutic effect in the mammal being treated. In addition, such an effective amount may be below the amount that is toxic to normal cells, or the mammal as a whole.

In one example, the pharmaceutically effective amount of the compound of the invention administered intravenously or parenterally will be in the per dose range of about 0.1 to 100 mg/kg, alternatively about 0.1 to 20 mg/kg of patient body weight per day, or alternatively about 0.3 to 15 mg/kg/day.

In another embodiment, oral unit dosage forms, such as tablets and capsules, preferably contain from about 1 to about 1000 mg (e.g., 1 mg, 5 mg, 10 mg, 15 mg, 20 mg, 25 mg, 30 mg, 40 mg, 50 mg, 100 mg, 200 mg, 250 mg, 400 mg, 500 mg, 600 mg, 700 mg, 800 mg, 900 mg, or 1000 mg) of the compound of the invention. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

In some embodiments, a low dose of the compound of the invention is administered in order to provide therapeutic benefit while minimizing or preventing adverse effects.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration. In specific embodiments, the compound of formula I is administered orally. In other specific embodiments, the compound of formula I is administered intravenously.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied.

Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of formula I or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) 21$^{st}$ Edition, Lippincott Williams & Wilkins, Philadelphia, Pa.

Sustained-release preparations of a compound of the invention (e.g., compound of formula I or an embodiment thereof) can be prepared. Suitable examples of sustained-release preparations include semipermeable matrices of solid hydrophobic polymers containing a compound of formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I (or an embodiment thereof) is formulated in an acetate buffer, at pH 5. In another embodiment, the compounds of formula I or an embodiment thereof are sterile. The compound may be stored, for example, as a solid or amorphous composition, as a lyophilized formulation or as an aqueous solution.

An example of a suitable oral dosage form provided herein is a tablet containing about 1 to about 500 mg (e.g., about 1 mg, 5 mg, 10 mg, 25 mg, 30 mg, 50 mg, 80 mg, 100 mg, 150 mg, 250 mg, 300 mg and 500 mg) of the compound of the invention compounded with suitable amounts of anhydrous lactose, sodium croscarmellose, polyvinylpyrrolidone (PVP) K30, and magnesium stearate. The powdered ingredients are first mixed together and then mixed with a solution of the PVP. The resulting composition can be dried, granulated, mixed with the magnesium stearate and compressed to tablet form using conventional equipment.

Formulations of a compound of the invention (e.g., compound of formula I or an embodiment thereof) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described.

An embodiment, therefore, includes a pharmaceutical composition comprising a compound of formula I, or pharmaceutically acceptable salt thereof. In a further embodiment includes a pharmaceutical composition comprising a compound of formula I, or a pharmaceutically acceptable salt thereof, together with a pharmaceutically acceptable carrier or excipient.

When the binding target is located in the brain, certain embodiments of the invention provide for a compound of formula I (or an embodiment thereof) to traverse the blood-brain barrier. In these embodiments, the compounds provided herein exhibit sufficient brain penetration as potential therapeutics in neurological diseases. In some embodiments, brain penetration is assessed by evaluating free brain/plasma ratio ($B_u/P_u$) as measured in vivo pharmacokinetic studies in rodents or by other methods known to persons skilled in the art (see, e.g., Liu, X. et al., J. Pharmacol. Exp. Therap., 325:349-56, 2008).

Certain neurological diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods. Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford.

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I (or an embodiment thereof) across the blood-brain barrier include, but are not limited to, encapsulating the a compound of formula I or I-I (or an embodiment thereof) in liposomes that are coupled to antibody binding fragments that bind to receptors on the vascular endothelium of the blood-brain barrier (see, e.g., U.S. Patent Publication No. 2002/0025313), and coating a compound of formula I (or an embodiment thereof) in low-density lipoprotein particles (see, e.g., U.S. Patent Publication No. 2004/0204354) or apolipoprotein E (see, e.g., U.S. Patent Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Publication Nos. 2002/0065259, 2003/0162695, and 2005/0124533); activating potassium channels (see, e.g., U.S. Patent Publication No. 2005/0089473), inhibiting ABC drug transporters (see, e.g., U.S. Patent Publication No. 2003/0073713); coating a compound of formula I or I-I (or an embodiment thereof) with a transferrin and modulating activity of the one or more transferrin receptors (see, e.g., U.S. Patent Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

The compounds of the invention inhibit RIP1 kinase activity. Accordingly, the compounds of the invention are useful for the treatment of diseases and disorders mediated by this pathway and associated with inflammation and/or necroptotic cell death.

In some embodiments, the disease or disorder to be treated is a neurodegenerative disease or disorder. In some embodiments, the diseases and disorders to be treated are synucleopathies such as Parkinson's Disease, Lewy body dementia, multiple system atrophy, Parkinson-plus syndromes. In some embodiments, the diseases and disorders to be treated are taupathies such as Alzheimer's Disease and frontotemporal dementia. In some embodiments, the diseases and disorders to be treated are demyelination diseases such as multiple sclerosis.

In some embodiments, the diseases and disorders to be treated are other neurodegenerative diseases such as amyotrophic lateral sclerosis, spinal muscular atrophy, primary lateral sclerosis, Huntington's disease, ischemia, and stroke. Additional exemplary neurodegenerative diseases to be treated as provided herein include, but are not limited to, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathies, progressive supranuclear palsy, corticobasal degeneration, and demyelinating diseases.

In some embodiments, the disease or disorder to be treated is Alzheimer's disease. In some embodiments, the disease or disorder to be treated is Parkinson's disease. In some embodiments, the disease or disorder to be treated is Huntington's disease. In some embodiments, the disease or disorder to be treated is multiple sclerosis. In some embodiments, the disease or disorder to be treated is amyotrophic lateral sclerosis (ALS). In some embodiments, the disease or disorder to be treated is spinal muscular atrophy (SMA).

In some embodiments, the disease or disorder to be treated is an inflammatory disease or disorder. In some embodiments, the disease or disorder to be treated is selected from the group consisting of inflammatory bowel diseases (including Crohn's disease and ulcerative colitis), psoriasis, retinal detachment, retinitis pigmentosa, macular degeneration, pancreatitis, atopic dermatitis, arthritis (including rheumatoid arthritis, osteoarthritis, spondylarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, liver damage/diseases (non-alcohol steatohepatitis, alcohol steatohepatitis, autoimmune hepatitis autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury (AKI), Celiac disease, autoimmune idiopathic thrombocytopenic purpura, transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), spinal muscular atrophy (SMA), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), periodontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2, Gangliosidosis, Alpha-mannosidosis, Aspartylglucosaminuria, Cholesteryl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

In some embodiments, the disease or disorder to be treated is an inflammatory bowel disease. In some embodiments, the disease or disorder to be treated is Crohn's disease. In some embodiments, the disease or disorder to be treated is ulcerative colitis. In some embodiments, the disease or disorder to be treated is glaucoma. In some embodiments, the disease or disorder to be treated is psoriasis. In some embodiments, the disease or disorder to be treated is rheumatoid arthritis. In some embodiments, the disease or disorder to be treated is spondyloarthritis. In some embodiments, the disease or disorder to be treated is juvenile idiopathic arthritis. In some embodiments, the disease or disorder to be treated is osteoarthritis.

In some embodiments, the method of treatment provided herein is the treatment of one or more symptoms of a disease or disorder listed above.

Also provided herein is the use of a compound of the invention in therapy. In some embodiments, provided herein is the use of a compound of the invention for the treatment or prevention of the above diseases and disorders. Also provided herein is the use of a compound of the invention in the manufacture of a medicament for the treatment or prevention of the above diseases and disorders. Also provided herein are compounds of the invention for use in the treatment or prevention of the above diseases and disorders.

Also provided herein is a method of treating a disease or disorder as provided above in a mammal in need of such treatment, wherein the method comprises administering to said mammal a therapeutically effective amount of a compound of formula I, or a pharmaceutically acceptable salt thereof. In some embodiments, the mammal is a human.

Also provided herein is a method of treating a symptom of a disease or disorder in a mammal in need of such treatment, said disease or disorder being selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cysplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), and chronic obstructive pulmonary disease (COPD), wherein the method comprises administering to said mammal a therapeutically effective amount of a compound of formula I, or a pharmaceutically acceptable salt thereof.

Also provided herein is a method of treating a disease or disorder in a human patient in need of such treatment, said disease or disorder being selected from those provided above, wherein the method comprises orally administering a therapeutically effective amount of a compound of formula I, or a pharmaceutically acceptable salt thereof, as an orally acceptable pharmaceutical composition.

Combination Therapy

Compounds of the invention may be combined with one or more other compounds of the invention or one or more other therapeutic agent as any combination thereof, in the treatment of the diseases and disorders provided herein. For example, a compound of the invention may be administered simultaneously, sequentially or separately in combination with other therapeutic agents known to be useful for the treatment of a disease or disorder selected from those recited above.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

In some embodiments, a compound provided herein may be combined with another therapeutically active agent as recited in WO 2016/027253, the contents of which are hereby incorporated by reference in their entirety. In such embodiments, the compound that inhibits RIP1 kinase in the combinations recited in WO 2016/027253 is replaced by a compound of formula I of the present disclosure.

In some embodiments, a compound provided herein may be combined with a DLK inhibitor for the treatment of neurodegenerative diseases and disorders, such as those listed elsewhere herein, and including but not limited to the following: Parkinson's Disease, Lewy body dementia, multiple system atrophy, Parkinson-plus syndromes, Alzheimer's Disease, frontotemporal dementia, demyelination diseases such as multiple sclerosis, amyotrophic lateral sclerosis, spinal muscular atrophy, primary lateral sclerosis, Huntington's disease, ischemia, stroke, intracranial hemorrhage, cerebral hemorrhage, muscular dystrophy, progressive muscular atrophy, pseudobulbar palsy, progressive bulbar palsy, spinal muscular atrophy, inherited muscular atrophy, peripheral neuropathies, progressive supranuclear palsy, and corticobasal degeneration. DLK inhibitors are described, for example, in WO 2013/174780, WO 2014/177524, WO 2014/177060, WO 2014/111496, WO 2015/091889 and WO 2016/142310.

Synthetic Schemes

Compounds of the present invention can be prepared as described in the Experimental Section. While the reaction schemes are varied to adapt to individual compounds being prepared, the basic approaches are illustrated in Schemes A-D. Additional compounds are readily prepared by the following general schemes. Details of the preparations can be found in the experimental section which follows.

SCHEME A-Method 21

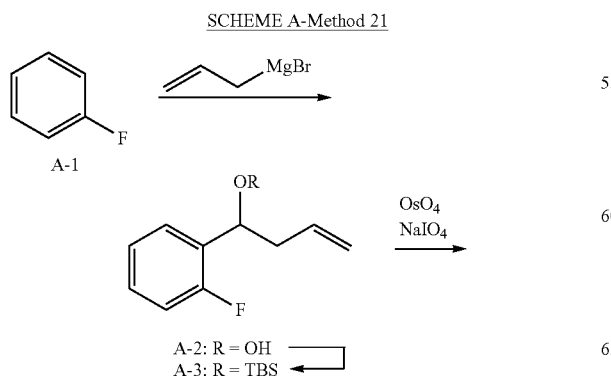

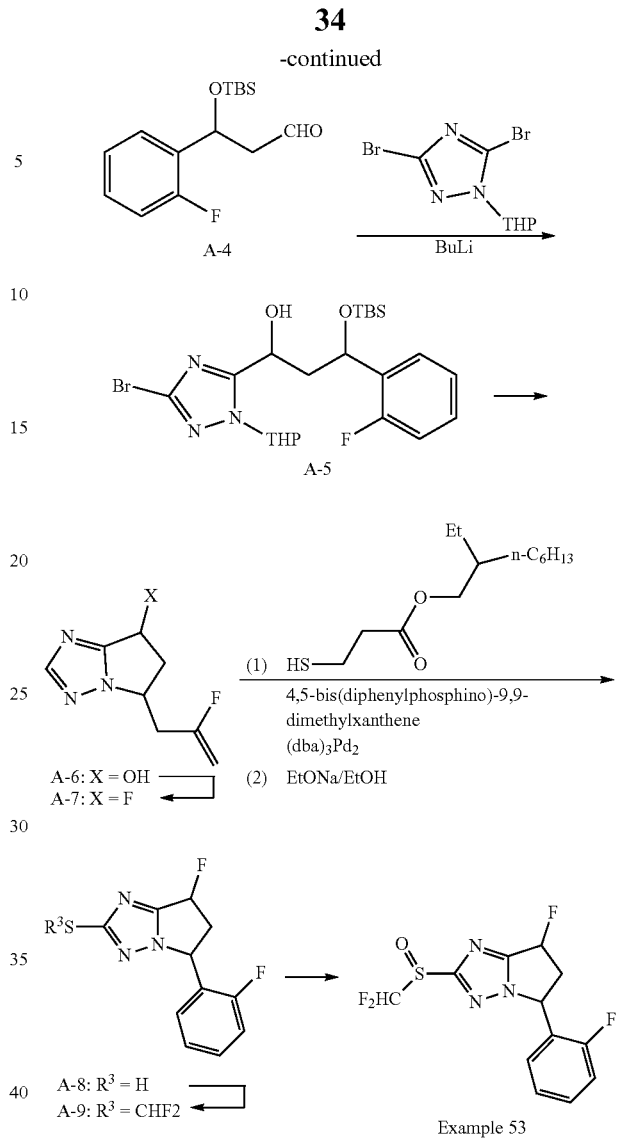

A variant of this procedure is described in Scheme B. This approach allows introduction of a variety of moieties into for the phenyl or heteroaryl moieties into the molecule.

In some instances the cyclopropyl or bicyclopropyl ring is elaborated after the an acyclic fragment is introduced onto the sulfur atom the 6,7-dihydro-5H-pyrrolo[1,2-b][1,2,4]triazole fragment Scheme B

SCHEME B

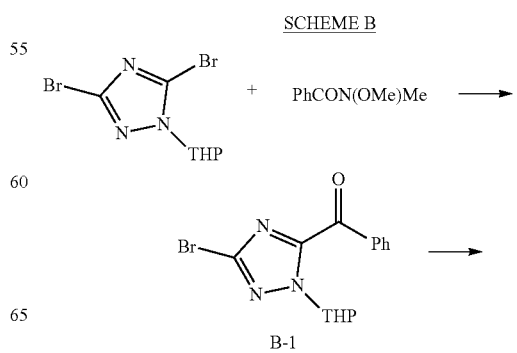

-continued
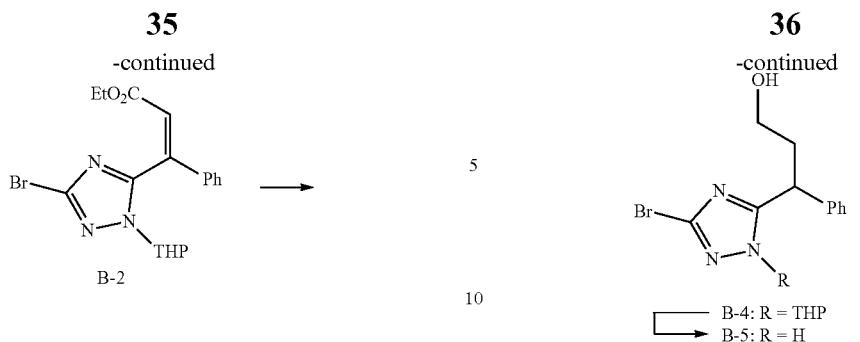
B-2
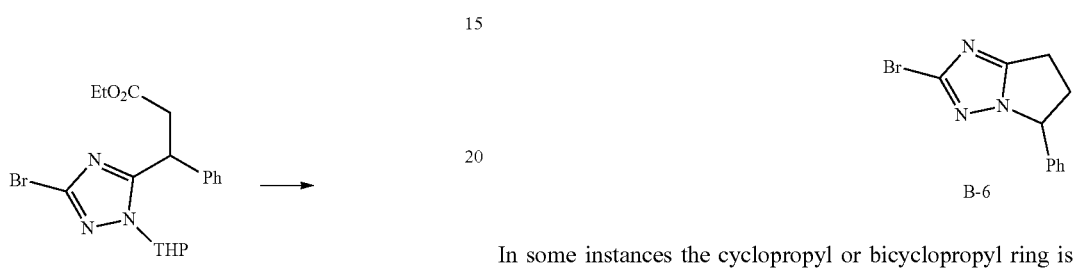
B-3
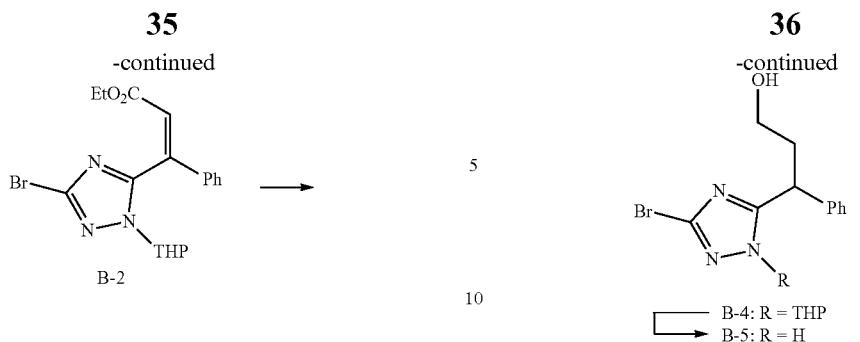
B-4: R = THP
B-5: R = H
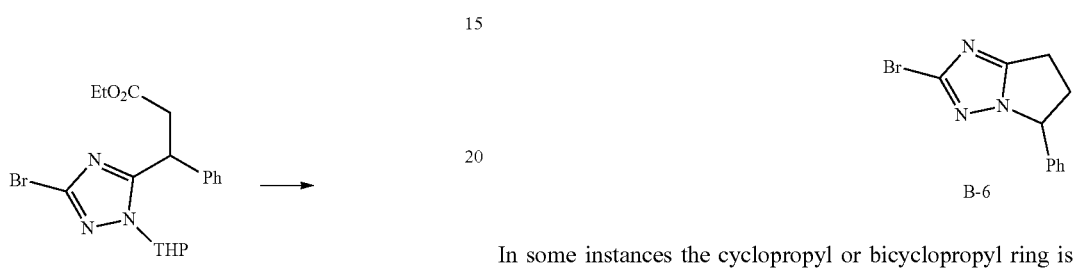
B-6
In some instances the cyclopropyl or bicyclopropyl ring is elaborated after introduction into the 6,7-dihydro-5H-pyrrolo[1,2-b][1,2,4]triazole fragment Scheme C
Scheme C
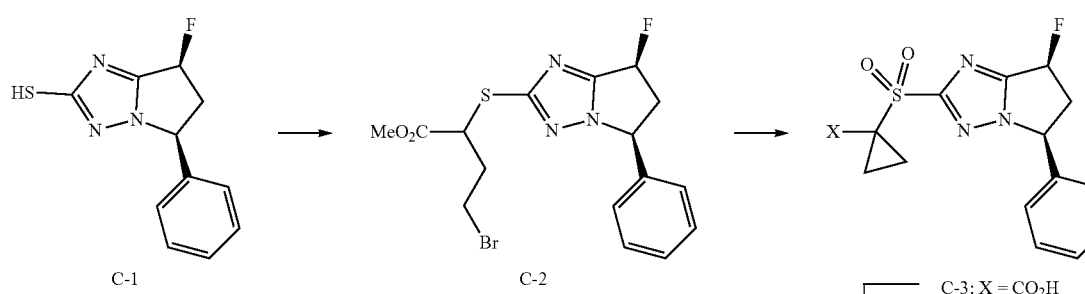
C-1    C-2
C-3: X = CO₂H
C-4: X = CH₂OH
C-5: X = CHO
155: X = CHF₂
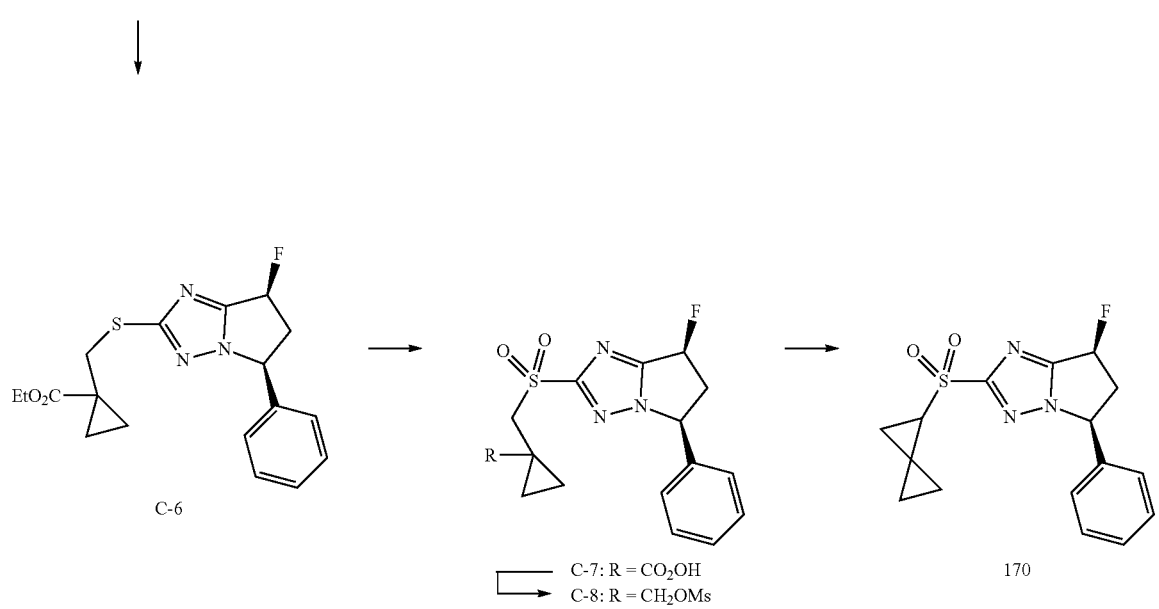
C-6
C-7: R = CO₂OH
C-8: R = CH₂OMs
170

Alternatively a elaborated R¹ fragment can be introduced by condensation a sodium sulfinate salt with (5S,7S)-2-bromo-7-fluoro-5-(3-fluorophenyl)-6,7-dihydro-5H-pyrrolo[1,2-b][1,2,4]triazole as depicted in scheme D

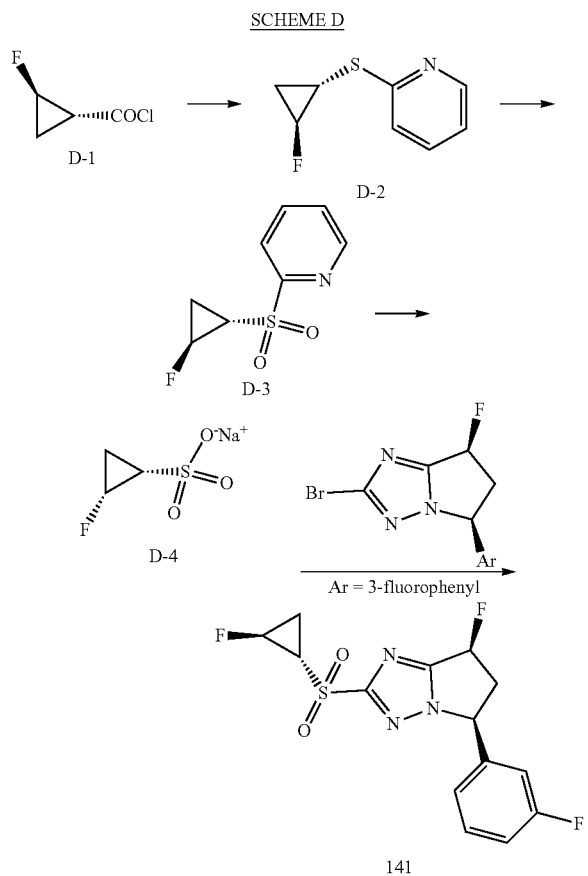

EXAMPLES

The invention will be more fully understood by reference to the following examples. They should not, however, be construed as limiting the scope of the invention.

These examples serve to provide guidance to a skilled artisan to prepare and use the compounds, compositions and methods of the invention. While particular embodiment of the present invention are described, the skilled artisan will appreciate that various changes and modifications can be made without departing from the spirit and scope of the inventions.

The chemical reactions in the examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, for example, by appropriately protecting interfering group, by utilizing other suitable reagents known in the art, for example, by appropriately protecting interfering groups by utilizing other suitable reagents known in the art other than those described, and/or by making routine modifications of reaction conditions.

In the examples below, unless otherwise indicated all temperatures are set forth in degrees Celsius. Commercially available reagents were purchased from suppliers such as Aldrich Chemical Company, Lancaster, TCI or Maybridge and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. ¹H NMR spectra were obtained in deuterated CDCl₃, d₆-DMSO, CH₃OD or d₆-acetone solvent solutions (reported in ppm) using or trimethylsilane (TMS) or residual non-deuterated solvent peaks as the reference standard. When peak multiplicities are reported, the following abbreviates are used: s (singlet), d (doublet), t (triplet), q (quartet), m (multiplet, br (broadened), dd (doublet of doublets), dt (doublet of triplets). Coupling constants, when given, ar reported in Hz (Hertz).

All abbreviations used to describe reagents, reaction conditions or equipment are intended to be consistent with the definitions set forth in the following list of Abbreviations. The chemical names of discrete compounds of the invention were typically obtained using the structure naming feature of ChemDraw naming program.

Abbreviations
ACN Acetonitrile
Boc tert-Butoxycarbonyl
DAST Diethylaminosulfur trifluoride
DCE 1,2-dichloroethane
DCM Dichloromethane
DMF N,N-Dimethylformamide
DMSO Dimethyl sulfoxide
DPPH 2,2-Diphenyl-1-picrylhydrazyl
HPLC High Pressure Liquid Chromatography
LCMS Liquid Chromatography Mass Spectrometry
PCC Pyridinium chlorochromate
RP Reverse phase
RT or R$_T$ Retention time
SEM 2-(Trimethylsilyl)ethoxymethyl
SFC Supercritical Fluid Chromatography
TFA Trifluoroacetic acid
THF Tetrahydrofuran Example 1: Synthetic Method 1

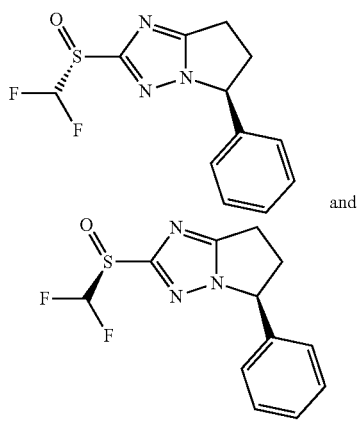

Step 1: tert-butyl N-(2-oxo-5-phenyl-pyrrolidin-1-yl)carbamate

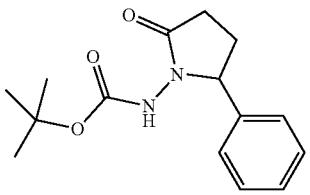 [SMILES: CC(C)(C)OC(=O)NN1C(=O)CCC1c1ccccc1]

To a solution of methyl 4-oxo-4-phenyl-butanoate (25000 mg, 130 mmol, 1.0 equiv) in tetrahydrofuran (200 mL) and acetic acid (100 mL) was added tert-butyl hydrazinecarboxylate (34379 mg, 260 mmol, 2.0 equiv). The resulting mixture was heated to 60° C. for 16 h. After this time, the mixture was cooled to 0° C. and to it was added sodium cyanoborohydride (24520 mg, 390 mmol, 3.0 equiv). The resulting mixture was stirred at 0° C. for 1 h, then at 70° C. for 6 h. After this time, the mixture was concentrated to a viscous oil, then neutralized with 3M NaOH (200 mL) and extracted with isopropyl acetate (3×100 mL). The combined organics were washed with saturated sodium bicarbonate (150 mL), water (150 mL), and brine (150 mL), dried over sodium sulfate and concentrated. The residue was purified by column chromatography (silica gel, 100-200 mesh, 0 to 100% isopropyl acetate in heptane) to afford tert-butyl N-(2-oxo-5-phenyl-pyrrolidin-1-yl)carbamate (26500 mg, 74% yield) as a white solid.

LCMS (5 to 95% acetonitrile in water+0.1% formic acid over 2.5 mins) retention time 1.51 min, ESI+ found [M+H]=277.

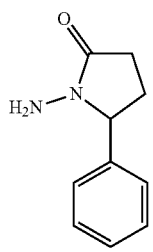 [SMILES: NN1C(=O)CCC1c1ccccc1]

Step 2: 1-amino-5-phenyl-pyrrolidin-2-one

Acetyl chloride (28.5 mL, 31400 mg, 400 mmol, 4.17 equiv) was added slowly to methanol (100 mL) at 0° C. The mixture was stirred 15 mins at 0° C., then to it was added a solution of tert-butyl N-(2-oxo-5-phenyl-pyrrolidin-1-yl) carbamate (26500 mg, 95.9 mmol, 1.00 equiv) in methanol (100 mL) at 0° C. The mixture was allowed to warm to RT slowly and stir 16 h. After this time, the mixture was concentrated to dryness, then partitioned between saturated sodium carbonate (300 mL) and isopropyl acetate (75 mL). The layers were separated, and the aqueous was extracted four more times with isopropyl acetate. The combined organics were dried over sodium sulfate and concentrated to afford 1-amino-5-phenyl-pyrrolidin-2-one (16500 mg, 98% yield) as a yellow oil which was used without further purification.

LCMS (5 to 95% acetonitrile in water+0.1% formic acid over 2.5 mins) retention time 1.26 min, ESI+ found [M+H]=177.

Step 3: 1-tert-butyl-3-(2-oxo-5-phenyl-pyrrolidin-1-yl)thiourea

To a solution of 1-amino-5-phenyl-pyrrolidin-2-one (8000 mg, 45.4 mmol, 1.0 equiv) in 1,4-dioxane (80 mL) was added tert-butyl isothiocyanate (17.1 mL, 15689 mg, 136.2 mmol, 3.0 equiv). The resulting mixture was heated to 95° C. for 72 h and then concentrated. The residue was purified by column chromatography (silica gel, 100-200 mesh, 0 to 100% isopropyl acetate in heptane) to afford 1-tert-butyl-3-(2-oxo-5-phenyl-pyrrolidin-1-yl)thiourea (2600 mg, 20% yield) as a white solid.

LCMS (5 to 95% acetonitrile in water+0.1% formic acid over 2.5 mins) retention time 1.48 min, ESI+ found [M+H]=292.

Step 4: 5-phenyl-6,7-dihydro-5H-pyrrolo[1,2-b][1,2,4]triazole-2-thiol

A solution of 1-tert-butyl-3-(2-oxo-5-phenyl-pyrrolidin-1-yl)thiourea (2600 mg, 8.9 mmol, 1.0 equiv) in concentrated (~37%) hydrochloric acid (20 mL) was heated to 90° C. for 16 hr. After this time the mixture was concentrated, and the residue was purified by column chromatography (silica gel, 100-200 mesh, 0 to 20% methanol in dichloromethane) to afford 5-phenyl-6,7-dihydro-5H-pyrrolo[1,2-b][1,2,4]triazole-2-thiol (1600 mg, 83% yield) as a white solid.

LCMS (5 to 95% acetonitrile in water+0.1% formic acid over 2.5 mins) retention time 1.02 min, ESI+ found [M+H]=218.

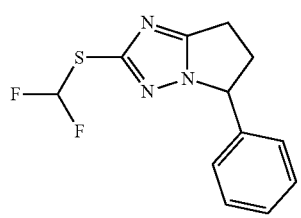

and

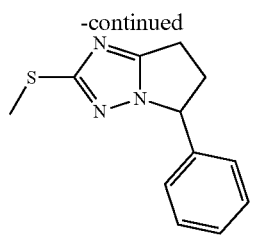

Step 5: 2-(difluoromethylsulfanyl)-5-phenyl-6,7-dihydro-5H-pyrrolo[1,2-b][1,2,4]triazole and 2-methylsulfanyl-5-phenyl-6,7-dihydro-5H-pyrrolo[1,2-b][1,2,4]triazole To a solution of 5-phenyl-6,7-dihydro-5H-pyrrolo[1,2-b][1,2,4]triazole-2-thiol (1400 mg, 6.4 mmol, 1.0 equiv) in N,N-dimethylformamide (10 mL) was added cesium carbonate (5200 mg, 16 mmol, 2.5 equiv) and sodium chlorodifluoroacetate (1200 mg, 8.1 mmol, 1.3 equiv). The resulting mixture was heated to 100° C. for 16 h, then was filtered through Celite and concentrated. The residue was purified by column chromatography (silica gel, 100-200 mesh, 0 to 10% methanol in dichloromethane) to afford a mixture of 2-(difluoromethylsulfanyl)-5-phenyl-6,7-dihydro-5H-pyrrolo[1,2-b][1,2,4]triazole and 2-methylsulfanyl-5-phenyl-6,7-dihydro-5H-pyrrolo[1,2-b][1,2,4]triazole (540 mg, 31% yield) as a brown oil.

LCMS (5 to 95% acetonitrile in water+0.1% formic acid over 2.5 mins) retention time 1.48 min, ESI+ found [M+H]=268 (difluoromethylated product) and retention time 1.30 min, ESI+ found [M+H]=232 (methylated product)

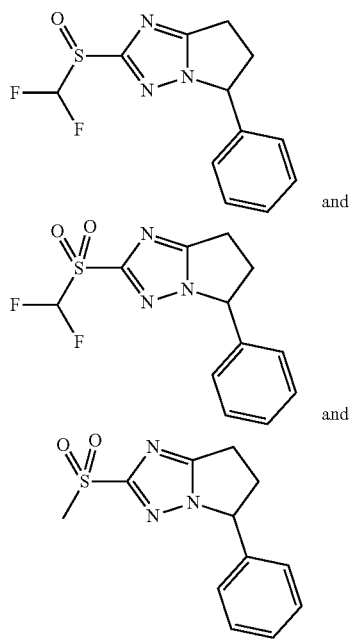

Step 6: 2-(difluoromethylsulfinyl)-5-phenyl-6,7-dihydro-5H-pyrrolo[1,2-b][1,2,4]triazole and 2-(difluoromethylsulfonyl)-5-phenyl-6,7-dihydro-5H-pyrrolo[1,2-b][1,2,4]triazole and 2-methylsulfonyl-5-phenyl-6,7-dihydro-5H-pyrrolo[1,2-b][1,2,4]triazole To a solution of 2-(difluoromethylsulfanyl)-5-phenyl-6,7-dihydro-5H-pyrrolo[1,2-b][1,2,4]triazole and 2-methylsulfanyl-5-phenyl-6,7-dihydro-5H-pyrrolo[1,2-b][1,2,4]triazole (mixture from the previous step) in dichloromethane (10 ml) was added 3-chloroperoxybenzoic acid (904 mg, 4.04 mmol, 2.0 equiv). The resulting mixture was stirred 16 h at RT. After this time, the mixture was diluted with DCM (100 mL) and quenched with a 1:1 mixture of saturated aqueous sodium thiosulfate (50 mL) and saturated aqueous sodium bicarbonate (50 mL). The dichloromethane layer was washed with water and brine, dried over sodium sulfate and concentrated. The residue was partially purified by column chromatography (silica gel, 100-200 mesh, 0 to 15% methanol in dichloromethane) to afford two fractions: one containing 2-(difluoromethylsulfinyl)-5-phenyl-6,7-dihydro-5H-pyrrolo[1,2-b][1,2,4]triazole and 2-methylsulfonyl-5-phenyl-6,7-dihydro-5H-pyrrolo[1,2-b][1,2,4]triazole (500 mg) and another fraction containing pure 2-(difluoromethylsulfonyl)-5-phenyl-6,7-dihydro-5H-pyrrolo[1,2-b][1,2,4]triazole (12.9 mg, 2% yield) as a white solid. The fraction containing a mixture of two compounds was further purified by reverse phase HPLC (Gemini-NX C18, 50×30 mm column; solvent A: 0.1% ammonium hydroxide in water; solvent B: acetonitrile; gradient of 10-60% B) to afford pure 2-(difluoromethylsulfinyl)-5-phenyl-6,7-dihydro-5H-pyrrolo[1,2-b][1,2,4]triazole (292 mg, 51% yield) and 2-methylsulfonyl-5-phenyl-6,7-dihydro-5H-pyrrolo[1,2-b][1,2,4]triazole (33 mg, 6% yield) as white solids.

2-(difluoromethylsulfinyl)-5-phenyl-6,7-dihydro-5H-pyrrolo[1,2-b][1,2,4]triazole: $^1$H NMR (400 MHz, DMSO-d6) δ 7.50-7.19 (m, 6H), 5.68 (dd, J=8.1, 6.2 Hz, 1H), 3.30-3.02 (m, 3H), 2.69-2.52 (m, 1H). LC-MS RT=3.96 min, m/z=284.0 (M+H)$^+$.

LCMS (5 to 95% acetonitrile in water+0.1% formic acid over 10 mins) retention time 3.96 min, ESI+ found [M+H]=284.0.

2-(difluoromethylsulfonyl)-5-phenyl-6,7-dihydro-5H-pyrrolo[1,2-b][1,2,4]triazole: $^1$H NMR (400 MHz, DMSO-d6) δ 7.62-7.22 (m, 6H), 5.77-5.70 (m, 1H), 3.30-3.03 (m, 3H), 2.78-2.54 (m, 1H). LC-MS RT=4.46 min, m/z=300.1 (M+H)$^+$.

LCMS (5 to 95% acetonitrile in water+0.1% formic acid over 10 mins) retention time 4.46 min, ESI+ found [M+H]=300.1.

2-methylsulfonyl-5-phenyl-6,7-dihydro-5H-pyrrolo[1,2-b][1,2,4]triazole: $^1$H NMR (400 MHz, DMSO-d6) δ 7.50-7.22 (m, 5H), 5.70-5.55 (m, 1H), 3.30 (s, 3H), 3.27-2.98 (m, 3H), 2.70-2.55 (m, 1H). LC-MS RT=3.53 min, m/z=264.1 (M+H)$^+$.

LCMS (5 to 95% acetonitrile in water+0.1% formic acid over 10 mins) retention time 3.53 min, ESI+ found [M+H]=264.1.

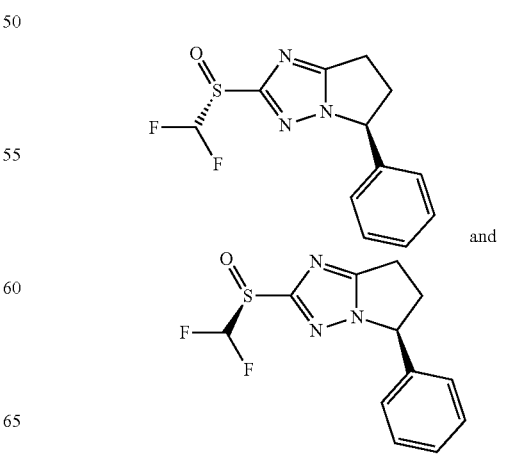

Step 7: (5S)-2-[(R)-difluoromethylsulfinyl]-5-phenyl-6,7-dihydro-5H-pyrrolo[1,2-b][1,2,4]triazole and (5S)-2-[(S)-difluoromethylsulfinyl]-5-phenyl-6,7-dihydro-5H-pyrrolo[1,2-b][1,2,4]triazole 2-(difluoromethylsulfinyl)-5-phenyl-6,7-dihydro-5H-pyrrolo[1,2-b][1,2,4]triazole (292 mg) was further purified by chiral SFC to afford arbitrarily assigned: (5S)-2-[(R)-difluoromethylsulfinyl]-5-phenyl-6,7-dihydro-5H-pyrrolo[1,2-b][1,2,4]triazole (Peak 3, SFC analytical retention time=1.12 min, Chiralpak AD, isocratic 10% MeOH+0.1% NH4OH, 2.5 min method) (58.4 mg, 20%) as a white solid. 1H NMR (400 MHz, DMSO-d6) δ 7.52-7.16 (m, 6H), 5.71-5.64 (m, 1H), 3.27-3.02 (m, 3H), 2.69-2.56 (m, 1H). LC-MS RT=3.94 min, m/z=284.1 (M+H)+.

LCMS (5 to 95% acetonitrile in water+0.1% formic acid over 10 mins) retention time 3.94 min, ESI+ found [M+H]=284.1.

(5S)-2-[(S)-difluoromethylsulfinyl]-5-phenyl-6,7-dihydro-5H-pyrrolo[1,2-b][1,2,4]triazole (Peak 4, SFC analytical retention time=1.38 min, Chiralpak AD, isocratic 10% MeOH+0.1% NH4OH, 2.5 min method) (52.1 mg, 18%) as a white solid. 1H NMR (400 MHz, DMSO-d6) δ 7.51-7.16 (m, 6H), 5.72-5.64 (m, 1H), 3.28-3.01 (m, 3H), 2.70-2.55 (m, 1H). LC-MS RT=3.98 min, m/z=284.1 (M+H)+.

LCMS (5 to 95% acetonitrile in water+0.1% formic acid over 10 mins) retention time 3.98 min, ESI+ found [M+H]=284.1.

SFC condition (prep): Performed in two stages: First column: Chiralpak AD 250×21.2 mm, 5 am, Mobile phase: A: CO2 B: 0.1% ammonium hydroxide in methanol, Isocratic 15% B, Flow rate: 70 mL/min, column temp 40° C. Second column: Whelk 0-1 (S,S) 150×21.2 mm, 5 m, Mobile phase: A: CO2 B: 0.1% ammonium hydroxide in methanol, Isocratic 30% B, Flow rate: 70 mL/min, column temp 40° C.

Example 2: Method 2

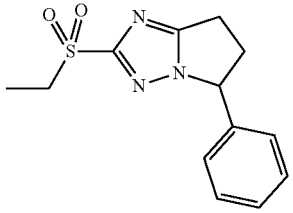 [SMILES: CCS(=O)(=O)c1nc2n(n1)C(c1ccccc1)CC2]

2-ethylsulfonyl-5-phenyl-6,7-dihydro-5H-pyrrolo[1,2-b][1,2,4]triazole

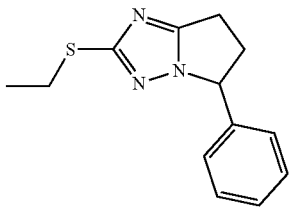 [SMILES: CCSc1nc2n(n1)C(c1ccccc1)CC2]

Step 1: 2-ethylsulfanyl-5-phenyl-6,7-dihydro-5H-pyrrolo[1,2-b][1,2,4]triazole To a solution of 5-phenyl-6,7-dihydro-5H-pyrrolo[1,2-b][1,2,4]triazole-2-thiol (300 mg, 1.38 mmol, 1.0 equiv, as prepared in Method 1) in N,N-dimethylformamide (4 mL) was added cesium carbonate (900 mg, 2.76 mmol, 2.0 equiv) and iodoethane (0.332 mL, 646.0 mg, 4.14 mmol, 3.0 equiv). The mixture was stirred at RT for 16 h. After this time, the mixture was filtered through Celite and concentrated. The residue was purified by column chromatography (silica gel, 100-200 mesh, 0 to 10% methanol in dichloromethane) to afford 2-ethylsulfanyl-5-phenyl-6,7-dihydro-5H-pyrrolo[1,2-b][1,2,4]triazole (100 mg, 29% yield) as a yellow oil.

LCMS (5 to 95% acetonitrile in water+0.1% formic acid over 2.5 mins) retention time 1.40 min, ESI+ found [M+H]=246.

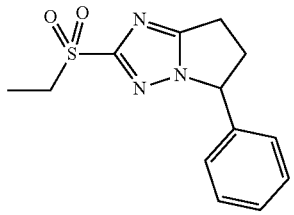 [SMILES: CCS(=O)(=O)c1nc2n(n1)C(c1ccccc1)CC2]

Step 2: 2-ethylsulfonyl-5-phenyl-6,7-dihydro-5H-pyrrolo[1,2-b][1,2,4]triazole To a solution of 2-ethylsulfanyl-5-phenyl-6,7-dihydro-5H-pyrrolo[1,2-b][1,2,4]triazole (100 mg, 0.41 mmol, 1.0 equiv) in acetonitrile (5 mL) was added 3-chloroperoxybenzoic acid (352 mg, 2.04 mmol, 5.0 equiv). The resulting mixture was stirred 16 h at RT. LCMS looks good. Quenched with saturated aqueous sodium thiosulfate (20 mL) and saturated aqueous sodium bicarbonate (20 mL), then extracted with isopropyl acetate (3×50 mL). The combined organics were washed with water and brine, dried over sodium sulfate and concentrated. The residue was partially purified by column chromatography (silica gel, 100-200 mesh, 0 to 15% methanol in dichloromethane) and further purified by achiral SFC (Torus 1-AA column, 5 to 60% 0.1% ammonium hydroxide in methanol gradient in CO2) to afford 2-ethylsulfonyl-5-phenyl-6,7-dihydro-5H-pyrrolo[1,2-b][1,2,4]triazole (38.3 mg, 34% yield) as a white solid. 1H NMR (400 MHz, DMSO-d6) δ 7.47-7.33 (m, 3H), 7.32-7.24 (m, 2H), 5.65 (dd, J=8.1, 6.2 Hz, 1H), 3.45-2.99 (m, 5H), 2.67-2.52 (m, 1H), 1.17 (t, J=7.4 Hz, 3H). LC-MS RT=3.80 min, m/z=278.1 (M+H)+.

LCMS (5 to 95% acetonitrile in water+0.1% formic acid over 10 mins) retention time 3.80 min, ESI+ found [M+H]=278.1.

Example 3: Method 3

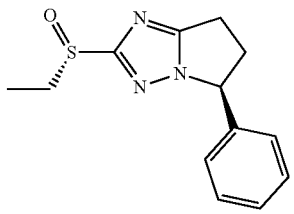 [SMILES: CC[S@](=O)c1nc2n(n1)[C@H](c1ccccc1)CC2]

(5S)-2-[(S)-ethylsulfinyl]-5-phenyl-6,7-dihydro-5H-pyrrolo[1,2-b][1,2,4]triazole To a solution of 2-ethylsulfanyl-5-phenyl-6,7-dihydro-5H-pyrrolo[1,2-b][1,2,4]triazole (90 mg, 0.37 mmol, 1.0 equiv) in acetonitrile (2 mL) cooled to 0° C. was added a solution of Oxone (113 mg, 0.18 mmol, 0.5 equiv) in water (1 mL). The reaction mixture was slowly warmed to RT and stirred 2 h. After this time, the mixture was diluted with water (50 mL) and extracted with isopropyl acetate (3×50 mL). The combined organics were washed with water and brine, dried over sodium sulfate and concentrated. The residue was partially purified by column chromatography (silica gel, 100-200 mesh, 0 to 15% methanol in dichloromethane) to afford 2-ethylsulfinyl-5-phenyl-6,7-dihydro-5H-pyrrolo[1,2-b][1,2,4]triazole (40 mg, 42% yield) as a white solid. The mixture of diastereomers was further purified by chiral SFC to afford arbitrarily assigned (5S)-2-[(S)-ethylsulfinyl]-5-phenyl-6,7-dihydro-5H-pyrrolo[1,2-b][1,2,4]triazole (3.6 mg, 4% yield) as a white solid. (Peak 3, SFC analytical retention time=0.94 min, Whelk 0-1 (S,S), isocratic 35% MeOH+0.1% NH₄OH, 2.5 min method) (50.8 mg, 9%) as a white solid. LC-MS RT=3.37 min, m/z=262.0 (M+H)+.

LCMS (5 to 95% acetonitrile in water+0.1% formic acid over 10 mins) retention time 3.37 min, ESI+ found [M+H]=262.0.

SFC condition (prep): Performed in two stages: First column: Whelk 0-1 (S,S) 150×21.2 mm, 5 m, Mobile phase: A: CO2 B: 0.1% ammonium hydroxide in methanol, Isocratic 35% B, Flow rate: 70 mL/min, column temp 40° C. Second column: Chiralpak IC 250×21.2 mm, 5 μm, Mobile phase: A: CO2 B: 0.1% ammonium hydroxide in methanol, Isocratic 40% B, Flow rate: 70 mL/min, column temp 25° C.

Examples 4 and 5: Method 4

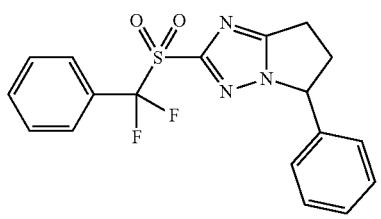

and

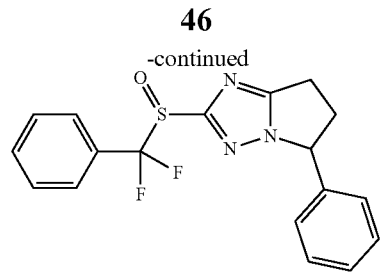

2-[difluoro(phenyl)methyl]sulfonyl-5-phenyl-6,7-dihydro-5H-pyrrolo[1,2-b][1,2,4]triazole and 2-difluoro(phenyl)methyl]sulfinyl-5-phenyl-6,7-dihydro-5H-pyrrolo[1,2-b][1,2,4]triazole

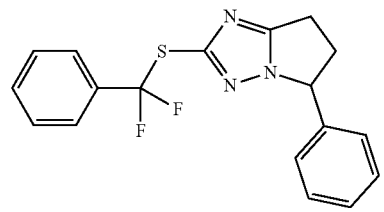 [SMILES: FC(F)(Sc1nc2n(n1)C(c1ccccc1)CC2)c1ccccc1]

Step 1: 2-[difluoro(phenyl)methyl]sulfanyl-5-phenyl-6,7-dihydro-5H-pyrrolo[1,2-b][1,2,4]triazole To a solution of 5-phenyl-6,7-dihydro-5H-pyrrolo[1,2-b][1,2,4]triazole-2-thiol (450 mg, 2.07 mmol, 1.0 equiv) in N,N-dimethylformamide (4 mL) was added cesium carbonate (1349 mg, 4.14 mmol, 2.0 equiv) and (bromodifluoromethyl)benzene (903 mg, 4.14 mmol, 2.0 equiv). The resulting mixture was stirred at RT for 16 h. After this time, the mixture was filtered through Celite and concentrated. The residue was purified by column chromatography (silica gel, 100-200 mesh, 0 to 10% methanol in dichloromethane) to afford 2-[difluoro(phenyl)methyl]sulfanyl-5-phenyl-6,7-dihydro-5H-pyrrolo[1,2-b][1,2,4]triazole (440 mg, 62% yield) as an orange oil.

LCMS (5 to 95% acetonitrile in water+0.1% formic acid over 2.5 mins) retention time 1.69 min, ESI+ found [M+H]=344.

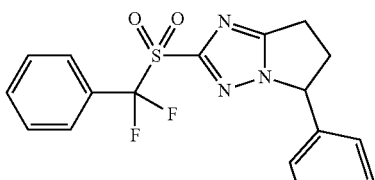

and

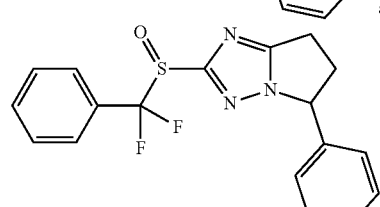

Step 2: 2-[difluoro(phenyl)methyl]sulfonyl-5-phenyl-6,7-dihydro-5H-pyrrolo[1,2-b][1,2,4]triazole and 2-[difluoro(phenyl)methyl]sulfinyl-5-phenyl-6,7-dihydro-5H-pyrrolo[1,2-b][1,2,4]triazole To a solution of 2-[difluoro(phenyl)methyl]sulfanyl-5-phenyl-6,7-dihydro-5H-pyrrolo[1,2-b][1,2,4]triazole (220 mg, 0.64 mmol, 1.0 equiv) in 1,2-dichloroethane (5 mL) was added 3-chloroperoxybenzoic acid (415 mg, 1.85 mmol, 2.89 equiv) and stirred 16 h. The reaction was quenched with saturated aqueous sodium thiosulfate (25 mL) and saturated aqueous sodium bicarbonate (25 mL), extracted with dichloromethane (3×50 mL). The combined organics were washed with saturated sodium bicarbonate, water and brine, dried over sodium sulfate and concentrated. The residue was purified by reverse phase HPLC (Gemini-NX C18, 50×30 mm column; solvent A: 0.1% formic acid in water; solvent B: acetonitrile; gradient of 20-70% B) to afford 2-[difluoro(phenyl)methyl]sulfonyl-5-phenyl-6,7-dihydro-5H-pyrrolo[1,2-b][1,2,4]triazole (47.1 mg, 16%) and 2-[difluoro(phenyl)methyl]sulfinyl-5-phenyl-6,7-dihydro-5H-pyrrolo[1,2-b][1,2,4]triazole (104.9 mg, 46%) as white solids. Analytical data for 2-[difluoro(phenyl)methyl]sulfonyl-5-phenyl-6,7-dihydro-5H-pyrrolo[1,2-b][1,2,4]triazole: 1H NMR (400 MHz, DMSO-d6) δ 7.78-7.68 (m, 1H), 7.65-7.56 (m, 4H), 7.48-7.35 (m, 3H), 7.30-7.23 (m, 2H), 5.72 (dd, J=8.6, 6.5 Hz, 1H), 3.33-3.05 (m, 3H), 2.73-2.57 (m, 1H). LC-MS RT=5.46 min, m/z=376.1 (M+H)+.

LCMS (5 to 95% acetonitrile in water+0.1% formic acid over 10 mins) retention time 5.46 min, ESI+ found [M+H]=376.1.

Analytical data for 2-[difluoro(phenyl)methyl]sulfinyl-5-phenyl-6,7-dihydro-5H-pyrrolo[1,2-b][1,2,4]triazole: 1H NMR (400 MHz, DMSO-d6) δ 7.60 (dt, J=7.7, 4.0 Hz, 1H), 7.54-7.19 (m, 8H), 7.19-7.05 (m, 1H), 6.99 (dd, J=7.4, 2.1 Hz, 1H), 5.54 (dd, J=8.5, 6.1 Hz, 1H), 3.23-2.89 (m, 3H). LC-MS RT=4.90 min, m/z=360.1 (M+H)+.

LCMS (5 to 95% acetonitrile in water+0.1% formic acid over 10 mins) retention time 4.90 min, ESI+ found [M+H]=360.1.

Example 6

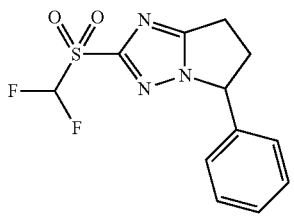 [SMILES: O=S(=O)(c1nc2n(n1)C(c1ccccc1)CC2)C(F)F]

The compound of Example 6 was prepared in Example 1 using Method 1 above.

Example 7: Method 5

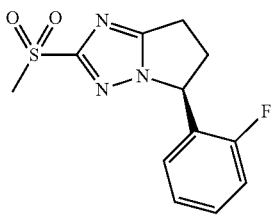 [SMILES: CS(=O)(=O)c1nc2n(n1)[C@H](c1ccccc1F)CC2]

(S)-5-(2-fluorophenyl)-2-methylsulfonyl-6,7-dihydro-5H-pyrrolo[1,2-b][1,2,4]triazole

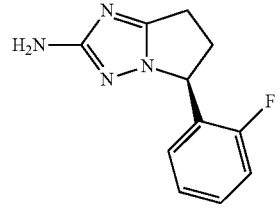 [SMILES: Nc1nc2n(n1)[C@H](c1ccccc1F)CC2]

Step 1: (S)-5-(2-fluorophenyl)-6,7-dihydro-5H-pyrrolo[1,2-b][1,2,4]triazol-2-amine To a mixture of (S)-5-(2-fluorophenyl)-6,7-dihydro-5H-pyrrolo[1,2-b][1,2,4]triazole-2-carboxylic acid (1.79 g, 7.24 mmol), 4 Å molecular sieve (1.0 g), triethylamine (3.03 mL, 21.72 mmol) in 1,4-dioxane (100 mL) was added azido diphenyl phosphate (4.13 mL, 18.10 mmol) via syringe under nitrogen atmosphere. The mixture was stirred at 20° C. for 2 h, and then added to a mixture of 1,4-dioxane (100 mL) and water (33 mL) at 95° C. under nitrogen atmosphere. The resulting mixture was heated at 95° C. for 18 h and quenched by addition of saturated aqueous sodium bicarbonate (4 mL). The mixture was concentrated under reduced pressure and the residue was purified by column chromatography (silica gel, 100-200 mesh, 0 to 5% methanol in dichloromethane) to afford (5S)-5-(2-fluorophenyl)-6,7-dihydro-5H-pyrrolo[1,2-b][1,2,4]triazol-2-amine (1.10 g, 70%) as a white solid. ¹H NMR (400 MHz, DMSO-d6) δ 7.41-7.33 (m, 1H), 7.27-7.15 (m, 2H), 7.12-7.04 (m, 1H), 5.46-5.42 (m, 1H), 5.29 (s, 2H), 3.11-3.00 (m, 1H), 2.91-2.73 (m, 2H), 2.41-2.31 (m, 1H).

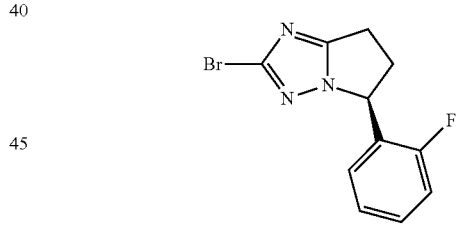

Step 2: (S)-2-bromo-5-(2-fluorophenyl)-6,7-dihydro-5H-pyrrolo[1,2-b][1,2,4]triazole A mixture of (5S)-5-(2-fluorophenyl)-6,7-dihydro-5H-pyrrolo[1,2-b][1,2,4]triazol-2-amine (600 mg, 2.75 mmol), copper(II) bromide (368 mg, 1.65 mmol) and tert-butyl nitrite (567 mg, 5.50 mmol) in acetonitrile (30 mL) was heated at 75° C. for 2 h and then quenched by addition of saturated aqueous ammonium chloride (20 mL). The mixture was extracted with dichloromethane (2×20 mL). The combined organic layers were dried over sodium sulfate and concentrated under reduced pressure. The residue was purified by column chromatography (silica gel, 100-200 mesh, 0 to 20% ethyl acetate in petroleum ether) to afford (5S)-2-bromo-5-(2-fluorophenyl)-6,7-dihydro-5H-pyrrolo[1,2-b][1,2,4]triazole (620 mg, 80%) as a yellow solid. LCMS $R_T$=0.716 min, m/z=282.0 [M+H]+.

LCMS (5 to 95% acetonitrile in water+0.03% trifluoacetic acid over 1.5 mins) retention time 0.716 min, ESI+ found [M+H]=282.0.

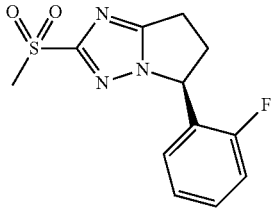 [SMILES: CS(=O)(=O)c1nc2n(n1)[C@H](c1ccccc1F)CC2]

Step 3: (S)-5-(2-fluorophenyl)-2-methylsulfonyl-6,7-dihydro-5H-pyrrolo[1,2-b][1,2,4]triazole A mixture of (5S)-2-bromo-5-(2-fluorophenyl)-6,7-dihydro-5H-pyrrolo[1,2-b][1,2,4]triazole (30 mg, 0.11 mmol), sodium methanesulfinate (18 mg, 0.17 mmol), (1R,2R)—$N^1,N^2$-dimethylcyclohexane-1,2-diamine (6 mg, 0.04 mmol) and bis((trifluoromethylsulfonyl)oxy) copper(II) (7 mg, 0.02 mmol) in dimethyl sulfoxide (2 mL) was heated to 110° C. for 12 h. After cooled the mixture was diluted with water (5 mL) and extracted with ethyl acetate (3×10 mL). The combined organic layers were dried over sodium sulfate and concentrated under reduced pressure. The residue was purified by RP-HPLC (acetonitrile 25-55%/0.05% hydrochloride in water) to afford arbitrarily assigned (S)-5-(2-fluorophenyl)-2-methylsulfonyl-6,7-dihydro-5H-pyrrolo[1,2-b][1,2,4]triazole (8.8 mg, 29%, 85% ee) as a white solid. $^1$H NMR (400 MHz, CD$_3$OD) δ 7.43-7.40 (m, 1H), 7.22-7.19 (m, 3H), 5.84-5.79 (m, 1H), 3.34-3.33 (m, 1H), 3.24 (s, 3H), 3.24-3.14 (m, 2H), 2.78-2.71 (m, 1H). LCMS $R_T$=0.638 min, m/z=282.0 [M+H]$^+$.

LCMS (5 to 95% acetonitrile in water+0.03% trifluoacetic acid over 1.5 mins) retention time 0.638 min, ESI+ found [M+H]=282.0.

Example 8: Method 6

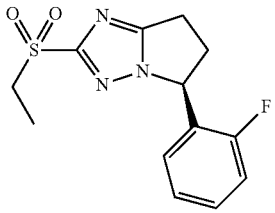 [SMILES: CCS(=O)(=O)c1nc2n(n1)[C@H](c1ccccc1F)CC2]

(S)-2-ethylsulfonyl-5-(2-fluorophenyl)-6,7-dihydro-5H-pyrrolo[1,2-b][1,2,4]triazole

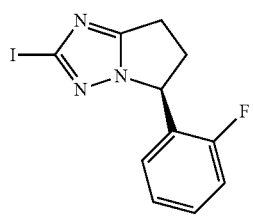 [SMILES: Fc1ccccc1[C@@H]1CCc2nc(I)nn21]

Step 1: (S)-5-(2-fluorophenyl)-2-iodo-6,7-dihydro-5H-pyrrolo[1,2-b][1,2,4]triazole A mixture of (S)-5-(2-fluorophenyl)-6,7-dihydro-5H-pyrrolo[1,2-b][1,2,4]triazol-2-amine (60 mg, 0.27 mmol), diiodomethane (368 mg, 1.37 mmol) and tert-butyl nitrite (56.7 mg, 0.55 mmol) in acetonitrile (5 mL) was heated at 75° C. for 2 h and then quenched by addition of saturated aqueous ammonium chloride (20 mL). The mixture was extracted with dichloromethane (2×20 mL). The combined organics were dried over sodium sulfate and concentrated under reduced pressure. The residue was purified by column chromatography (silica gel, 100-200 mesh, 0 to 20% ethyl acetate in petroleum ether) to afford (5S)-5-(2-fluorophenyl)-2-iodo-6,7-dihydro-5H-pyrrolo[1,2-b][1,2,4]triazole (65 mg, 72%) as a light yellow solid. LCMS $R_T$=0.703 min, m/z=329.8 [M+H]$^+$.

LCMS (5 to 95% acetonitrile in water+0.03% trifluoacetic acid over 1.5 mins) retention time 0.703 min, ESI+ found [M+H]=329.8.

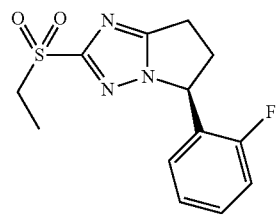 [SMILES: CCS(=O)(=O)c1nc2n(n1)[C@H](c1ccccc1F)CC2]

Step 2: (S)-2-ethylsulfonyl-5-(2-fluorophenyl)-6,7-dihydro-5H-pyrrolo[1,2-b][1,2,4]triazole A mixture of (S)-2-iodo-5-(2-fluorophenyl)-6,7-dihydro-5H-pyrrolo[1,2-b][1,2,4]triazole (30 mg, 0.09 mmol), sodium methanesulfinate (53 mg, 0.46 mmol), (1R,2R)—$N^1,N^2$-dimethylcyclohexane-1,2-diamine (1 mg, 0.01 mmol) and bis((trifluoromethylsulfonyl)oxy) copper(II) (4 mg, 0.01 mmol) in dimethyl sulfoxide (2.5 mL) was heated to 120° C. for 2 h under microwave conditions. After cooled the mixture was diluted with water (10 mL) and extracted with ethyl acetate (3×10 mL). The combined organic layers were dried over sodium sulfate and concentrated under reduced pressure. The residue was purified by RP-HPLC (acetonitrile 20-50%/0.225% formic acid in water) to afford arbitrarily assigned (S)-2-ethylsulfonyl-5-(2-fluorophenyl)-6,7-dihydro-5H-pyrrolo[1,2-b][1,2,4]triazole (8.3 mg, 31%) as a white solid. $^1$H NMR (400 MHz, CD$_3$OD) δ 7.41-7.38 (m, 1H), 7.21-7.17 (m, 3H), 5.83-5.79 (m, 1H), 3.37-3.25 (m, 3H), 3.25-3.08 (m, 2H), 2.75-2.70 (m, 1H), 1.25 (t, J=7.6 Hz, 3H). LCMS $R_T$=0.784 min, m/z=295.9 [M+H]$^+$.

LCMS (5 to 95% acetonitrile in water+0.03% trifluoacetic acid over 1.5 mins) retention time 0.784 min, ESI+ found [M+H]=295.9.

Example 9

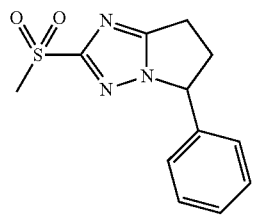 [SMILES: CS(=O)(=O)c1nc2n(n1)C(c1ccccc1)CC2]

The compound of Example 6 was prepared in Example 1 using Method 1 above.

Example 10: Method 7

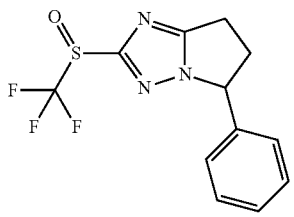 [SMILES: O=S(c1nc2n(n1)C(c1ccccc1)CC2)C(F)(F)F]

5-phenyl-2-(trifluoromethylsulfinyl)-6,7-dihydro-H-pyrrolo[1,2-b][1,2,4]triazole

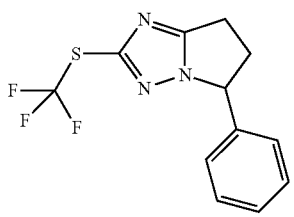 [SMILES: FC(F)(F)Sc1nc2n(n1)C(c1ccccc1)CC2]

Step 1: 5-phenyl-2-(trifluoromethylsulfanyl)-6,7-dihydro-5H-pyrrolo[1,2-b][1,2,4]triazole To a solution of 5-phenyl-6,7-dihydro-5H-pyrrolo[1,2-b][1,2,4]triazole-2-thiol (500 mg, 2.3 mmol, 1.0 equiv) in N,N-dimethylformamide (5 mL) was added cesium carbonate (750 mg, 2.3 mmol, 1.0 equiv) and 3,3-dimethyl-1-(trifluoromethyl)-1,2-benziodoxole (880 mg, 2.53 mmol, 1.1 equiv). The resulting mixture was stirred at RT for 72 h. After this time, the mixture was filtered through Celite and concentrated. The residue was purified by column chromatography (silica gel, 100-200 mesh, 0 to 10% methanol in dichloromethane) to afford 5-phenyl-2-(trifluoromethylsulfanyl)-6,7-dihydro-5H-pyrrolo[1,2-b][1,2,4]triazole (130 mg, 20% yield) as a yellow oil.

LCMS (5 to 95% acetonitrile in water+0.1% formic acid over 2.5 mins) retention time 1.59 min, ESI+ found [M+H]=286.

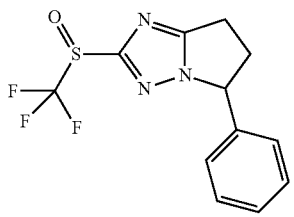 [SMILES: O=S(c1nc2n(n1)C(c1ccccc1)CC2)C(F)(F)F]

Step 2: 5-phenyl-2-(trifluoromethylsulfinyl)-6,7-dihydro-5H-pyrrolo[1,2-b][1,2,4]triazole To a solution of 5-phenyl-2-(trifluoromethylsulfanyl)-6,7-dihydro-H-pyrrolo[1,2-b][1,2,4]triazole (130 mg, 0.456 mmol, 1.0 equiv) in 1,2-dichloroethane (10 mL) was added 3-chloroperoxybenzoic acid (818 mg, 3.64 mmol, 8.0 equiv). The resulting mixture was heated to 50° C. and stirred 16 h. After this time, the mixture was diluted with dichloromethane (100 mL), washed with saturated sodium bicarbonate (3×50 mL), water, and brine, dried over sodium sulfate and concentrated. The residue was purified by reverse phase HPLC (Gemini-NX C18, 50×30 mm column; solvent A: 0.1% ammonium hydroxide in water; solvent B: acetonitrile; gradient of 20-60% B) to afford 5-phenyl-2-(trifluoromethylsulfinyl)-6,7-dihydro-5H-pyrrolo[1,2-b][1,2,4]triazole (27.7 mg, 20% yield) as a white solid. 1H NMR (400 MHz, DMSO-d6) δ 7.47-7.33 (m, 3H), 7.33-7.21 (m, 2H), 5.71 (dd, J=8.1, 6.1 Hz, 1H), 3.39-3.04 (m, 3H), 2.69-2.56 (m, 1H). LC-MS RT=4.49 min, m/z=302.1 (M+H)+.

LCMS (5 to 95% acetonitrile in water+0.1% formic acid over 10 mins) retention time 4.49 min, ESI+ found [M+H]=302.1.

Examples 11 and 12

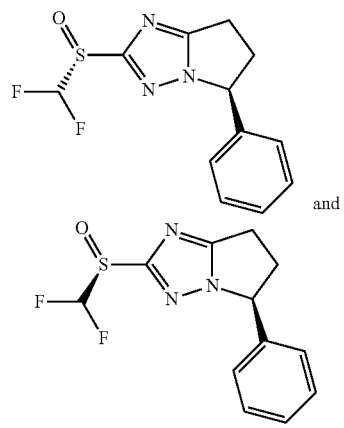

Compounds of Examples 11 and 12 were isolated from the mixture of Example 1 as provided in Method 1 above.

Example 13: Method 8

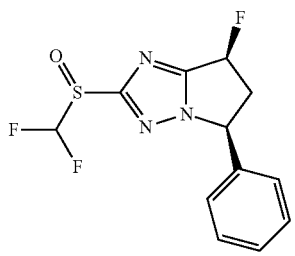 [SMILES: O=S(c1nc2n(n1)[C@H](c1ccccc1)C[C@@H]2F)C(F)F]

Rac-(5S,7S)-2-(((difluoromethyl)sulfinyl)-7-fluoro-5-phenyl-6,7-dihydro-5H-pyrrolo[1,2-b][1,2,4]triazole

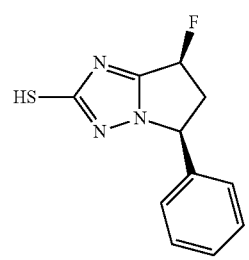 [SMILES: F[C@H]1C[C@@H](c2ccccc2)n2nc(S)nc21]

Step 1

Rac-(5S,7S)-7-fluoro-5-phenyl-6,7-dihydro-5H-pyrrolo[1,2-b][1,2,4]triazole-2-thiol A mixture of 4-methoxybenzyl mercaptan (437 mg, 2.84 mmol), rac-(5S,7S)-2-bromo-7-fluoro-5-phenyl-6,7-dihydro-5H-pyrrolo[1,2-b][1,2,4]triazole (400 mg, 1.42 mmol), tris(dibenzylideneacetone)dipalladium(0) (1299 mg, 1.42 mmol), 4,5-bis(diphenylphosphino)-9,9-dimethylxanthene (820 mg, 1.42 mmol) and triethylamine (430 mg, 4.25 mmol) in 1,4-dioxane (12 mL) was heated at 100° C. for 15 h under nitrogen atmosphere and concentrated under reduced pressure. The residue was purified by column chromatography (silica gel, 100-200 mesh, 0 to 30% ethyl acetate in petroleum ether) to afford rac-(5S,7S)-7-fluoro-2-[(4-methoxyphenyl)methylsulfanyl]-5-phenyl-6,7-dihydro-5H-pyrrolo[1,2-b][1,2,4]triazole (500 mg, 99%) as a light yellow solid. $^1$H NMR (400 MHz, CDCl$_3$) δ 7.38-7.35 (m, 3H), 7.28-7.25 (m, 2H), 7.19-7.17 (m, 2H), 6.80-6.78 (m, 2H), 6.0-5.98 (m, 0.5H), 5.86-5.84 (m, 0.5H), 5.39-5.34 (m, 1H), 4.35-4.29 (m, 2H), 3.59-3.49 (m, 1H), 2.87-2.76 (m, 1H).

A solution of rac-(5S,7S)-7-fluoro-2-[(4-methoxyphenyl)methylsulfanyl]-5-phenyl-6,7-dihydro-5H-pyrrolo[1,2-b][1,2,4]triazole (400 mg, 1.13 mmol) in 2,2,2-trifluoroacetic acid (7 mL) was heated at 90° C. for 16 h and then concentrated under reduced pressure to give crude rac-(5S,7S)-7-fluoro-5-phenyl-6,7-dihydro-5H-pyrrolo[1,2-b][1,2,4]triazole-2-thiol (290 mg, 100%) as a light yellow solid. LCMS R$_T$=0.785 min, m/z=236.1 [M+H]$^+$.

LCMS (10 to 80% acetonitrile in water+0.03% trifluoroacetic acid over 2 mins) retention time 0.785 min, ESI+ found [M+H]=236.1

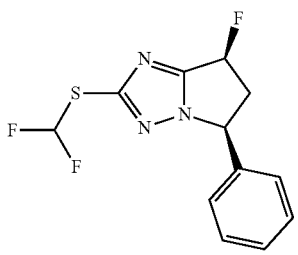

Step 2 rac-(5S,7S)-2-((difluoromethyl)thio)-7-fluoro-5-phenyl-6,7-dihydro-5H-pyrrolo[1,2-b][1,2,4]triazole A mixture of rac-(5S,7S)-7-fluoro-5-phenyl-6,7-dihydro-5H-pyrrolo[1,2-b][1,2,4]triazole-2-thiol (270 mg, 1.15 mmol), (2-chloro-2,2-difluoro-acetyl)oxy sodium (219 mg, 1.43 mmol) and cesium carbonate (1122 mg, 3.44 mmol) in 1-methyl-2-pyrrolidinone (15 mL) was heated at 100° C. for 3 h and diluted with water (15 mL). The resulting mixture was extracted with ethyl acetate (3×15 mL). The combined organic layers were washed with brine (10 mL), dried over anhydrous sodium sulfate and concentrated under reduced pressure. The residue was purified by RP-HPLC (acetonitrile 20-45%/0.05% HCl in water) to give rac-(5S,7S)-2-(difluoromethylsulfanyl)-7-fluoro-5-phenyl-6,7-dihydro-5H-pyrrolo[1,2-b][1,2,4]triazole (42 mg, 13%) as a white solid. LCMS R$_T$=1.108 min, m/z=286.1 [M+H]$^+$.

LCMS (10 to 80% acetonitrile in water+0.03% trifluoroacetic acid over 2 mins) retention time 1.108 min, ESI+ found [M+H]=286.1.

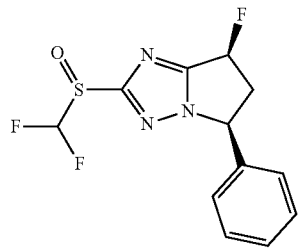 [SMILES: O=S(c1nc2n(n1)[C@H](c1ccccc1)C[C@@H]2F)C(F)F]

Step 3 rac-(5S,7S)-2-((difluoromethyl)sulfinyl)-7-fluoro-5-phenyl-6,7-dihydro-5H-pyrrolo[1,2-b][1,2,4]triazole A mixture of rac-(5S,7S)-2-(difluoromethylsulfanyl)-7-fluoro-5-phenyl-6,7-dihydro-5H-pyrrolo[1,2-b][1,2,4]triazole (35 mg, 0.12 mmol) and 3-chloroperoxybenzoic acid (27 mg, 0.13 mmol) in dichloromethane (4 mL) was stirred at 0° C. for 3 h and quenched by addition of saturated aqueous sodium bicarbonate (15 mL). The resulting mixture was extracted with ethyl acetate (3×15 mL). The combined organic layers were washed with brine (15 mL), dried over sodium sulfate and concentrated under reduced pressure. The residue was purified by RP-HPLC (acetonitrile 25-55%/0.05% ammonia hydroxide in water) to afford arbitrarily assigned rac-(5S,7S)-2-((difluoromethyl)sulfinyl)-7-fluoro-5-phenyl-6,7-dihydro-5H-pyrrolo[1,2-b][1,2,4]triazole (18 mg, 48%) as a white solid. $^1$H NMR (400 MHz, CDCl$_3$) δ 7.41-7.38 (m, 3H), 7.24-7.22 (m, 2H), 6.95-6.68 (m, 1H), 6.12-6.09 (m, 0.5H), 5.95-5.90 (m, 0.5H), 5.76-5.70 (m, 0.5H), 5.53-5.51 (m, 0.5H), 3.70-3.61 (m, 0.5H), 3.45-3.35 (m, 0.5H), 3.03-2.96 (m, 1H). LCMS R$_T$=0.989 min, m/z=302.1 [M+H]$^+$.

LCMS (10 to 80% acetonitrile in water+0.03% trifluoroacetic acid over 2 mins) retention time 0.989 min, ESI+ found [M+H]=302.1.

Example 14: Method 9

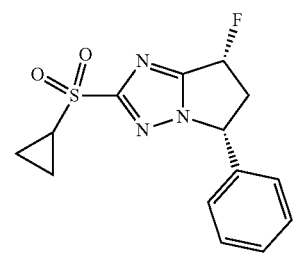 [SMILES: O=S(=O)(c1nc2n(n1)[C@@H](c1ccccc1)C[C@H]2F)C1CC1]

(5R,7R)-2-cyclopropylsulfonyl-7-fluoro-5-phenyl-6,7-dihydro-5H-pyrrolo[1,2-b][1,2,4]triazole A mixture of arbitrarily assigned (5R,7R)-2-bromo-7-fluoro-5-phenyl-6,7-dihydro-5H-pyrrolo[1,2-b][1,2,4]triazole (80 mg, 0.28 mmol), sodium cyclopropanesulfinate (182 mg, 1.42 mmol), (1R,2R)—N$^1$,N$^2$-dimethylcyclohexane-1, 2-diamine (20 mg, 0.14 mmol) and potassium carbonate (47 mg, 0.34 mmol) in dimethyl sulfoxide (5 mL) was heated at 110° C. for 2 h under microwave conditions and diluted with water (10 mL). The mixture was extracted with ethyl acetate (3×10 mL). The combined organic layers were dried over sodium sulfate and concentrated under reduced pressure. The residue was purified by RP-HPLC (acetonitrile 36-66%/0.05% ammonia hydroxide in water) to afford arbitrarily assigned (5R,7R)-2-cyclopropylsulfonyl-7-fluoro-5-phenyl-6,7-dihydro-5H-pyrrolo[1,2-b][1,2,4]triazole (40.3 mg, 46%) as a white solid. $^1$H NMR (400 MHz, CD$_3$OD) δ 7.45-7.37 (m, 3H), 7.29-7.26 (m, 2H), 6.21-6.18 (m, 0.5H), 6.07-6.04 (m, 0.5H), 5.70-5.62 (m, 1H), 3.84-3.69 (m, 1H), 2.91-2.78 (m, 2H), 1.33-1.28 (m, 2H), 1.19-1.11 (m, 2H). LCMS $R_T$=0.695 min, m/z=308.1 [M+H]$^+$.

LCMS (5 to 95% acetonitrile in water+0.03% trifluoacetic acid over 1.5 mins) retention time 0.695 min, ESI+ found [M+H]=308.1.

Examples 15 and 16

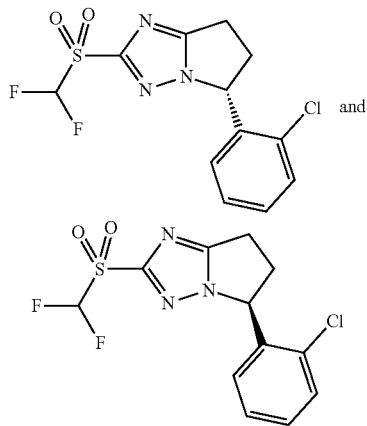

(5R)-5-(2-chlorophenyl)-2-(difluoromethylsulfonyl)-6,7-dihydro-5H-pyrrolo[1,2-b][1,2,4]triazole b][1,2,4]triazole and (5S)-5-(2-chlorophenyl)-2-(difluoromethylsulfonyl)-6,7-dihydro-5H-pyrrolo[1,2-b][1,2,4]triazole (5R)-5-(2-chlorophenyl)-2-(difluoromethylsulfonyl)-6,7-dihydro-5H-pyrrolo[1,2-b][1,2,4]triazole and (5S)-5-(2-chlorophenyl)-2-(difluoromethylsulfonyl)-6,7-dihydro-5H-pyrrolo[1,2-b][1,2,4]triazole were prepared according to Method 1 starting from methyl 4-(2-chlorophenyl)-4-oxobutanoate (Rieke Metals). Analytical data for arbitrarily assigned (5R)-5-(2-chlorophenyl)-2-(difluoromethylsulfonyl)-6,7-dihydro-5H-pyrrolo[1,2-b][1,2,4]triazole: (Peak 1, SFC analytical retention time=0.74 min, Chiralpak IC, isocratic 15% MeOH+0.1% NH$_4$OH, 2.5 min method) (52.0 mg, 9%) as a white solid. 1H NMR (400 MHz, DMSO-d6) δ 7.60-7.53 (m, 1H), 7.48-7.29 (m, 3H), 7.16 (dd, J=7.5, 1.9 Hz, 1H), 6.05 (dd, J=8.6, 6.4 Hz, 1H), 3.43-3.10 (m, 3H), 2.70-2.56 (m, 1H). LC-MS RT=4.86 min, m/z=334.0 (M+H)+.

LCMS (5 to 95% acetonitrile in water+0.1% formic acid over 10 mins) retention time 4.86 min, ESI+ found [M+H]=334.0.

Analytical data for arbitrarily assigned (5S)-5-(2-chlorophenyl)-2-(difluoromethylsulfonyl)-6,7-dihydro-5H-pyrrolo[1,2-b][1,2,4]triazole: (Peak 2, SFC analytical retention time=1.09 min, Chiralpak IC, isocratic 15% MeOH+0.1% NH$_4$OH, 2.5 min method) (52.2 mg, 9%) as a white solid. 1H NMR (400 MHz, DMSO-d6) δ 7.61-7.52 (m, 1H), 7.51-7.28 (m, 3H), 7.16 (dd, J=7.5, 1.9 Hz, 1H), 6.05 (dd, J=8.6, 6.4 Hz, 1H), 3.31-3.08 (m, 3H), 2.70-2.57 (m, 1H). LC-MS RT=4.86 min, m/z=334.0 (M+H)+.

LCMS (5 to 95% acetonitrile in water+0.1% formic acid over 10 mins) retention time 4.86 min, ESI+ found [M+H]=334.0.

SFC condition (prep): Chiralpak IC 250×21.2 mm, 5 μm, Mobile phase: A: CO2 B: 0.1% ammonium hydroxide in methanol, Isocratic 15% B, Flow rate: 70 mL/min, column temp 40° C.

Examples 17 and 18

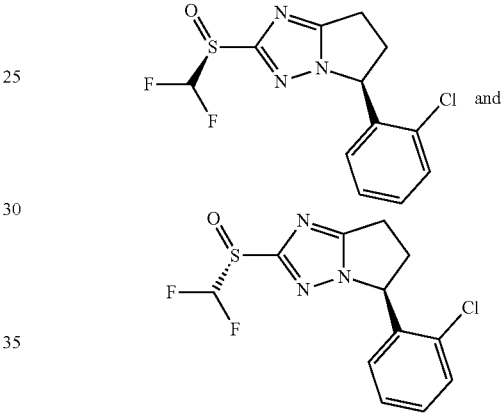

(5S)-5-(2-chlorophenyl)-2-[(S)-difluoromethylsulfinyl]-6,7-dihydro-5H-pyrrolo[1,2-b][1,2,4]triazole and (5S)-5-(2-chlorophenyl)-2-[(R)-difluoromethylsulfinyl]-6,7-dihydro-5H-pyrrolo[1,2-b][1,2,4]triazole were prepared according to Method 1 starting from methyl 4-(2-chlorophenyl)-4-oxobutanoate (Rieke Metals). Analytical data for (5S)-5-(2-chlorophenyl)-2-[(S)-difluoromethylsulfinyl]-6,7-dihydro-5H-pyrrolo[1,2-b][1,2,4]triazole: (Peak 2, SFC analytical retention time=0.96 min, Chiralpak IC, isocratic 15% MeOH+0.1% NH$_4$OH, 2.5 min method) (45.3 mg, 8%) as a white solid. 1H NMR (400 MHz, DMSO-d6) δ 7.56 (dd, J=7.8, 1.5 Hz, 1H), 7.53-7.18 (m, 3H), 7.06 (dd, J=7.5, 1.9 Hz, 1H), 5.99 (dd, J=8.6, 6.0 Hz, 1H), 3.35-3.22 (m, 1H), 3.20-3.08 (m, 2H), 2.59 (ddt, J=12.8, 8.8, 6.3 Hz, 1H). LC-MS RT=4.44 min, m/z=318.0 (M+H)+.

LCMS (5 to 95% acetonitrile in water+0.1% formic acid over 10 mins) retention time 4.44 min, ESI+ found [M+H]=318.0.

Analytical data for (5S)-5-(2-chlorophenyl)-2-[(R)-difluoromethylsulfinyl]-6,7-dihydro-5H-pyrrolo[1,2-b][1,2,4]triazole: (Peak 3, SFC analytical retention time=1.02 min, Chiralpak IC, isocratic 15% MeOH+0.1% NH$_4$OH, 2.5 min method) (50.8 mg, 9%) as a white solid. 1H NMR (400 MHz, DMSO-d6) δ 7.61-7.52 (m, 1H), 7.52-7.20 (m, 3H), 7.08 (dd, J=7.5, 1.9 Hz, 1H), 5.99 (dd, J=8.6, 5.9 Hz, 1H), 3.34-3.25 (m, 1H), 3.19-3.07 (m, 2H), 2.66-2.53 (m, 1H). LC-MS RT=4.43 min, m/z=318.0 (M+H)+.

LCMS (5 to 95% acetonitrile in water+0.1% formic acid over 10 mins) retention time 4.43 min, ESI+ found [M+H]=318.0.

SFC condition (prep): Chiralpak IC 250×21.2 mm, 5 m, Mobile phase: A: CO2 B: 0.1% ammonium hydroxide in methanol, Isocratic 15% B, Flow rate: 70 mL/min, column temp 25° C.

Example 19: Method 10

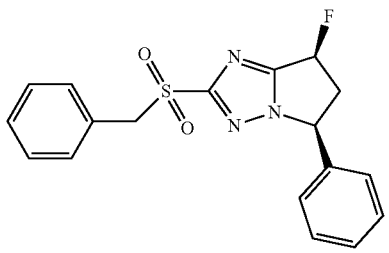 [SMILES: O=S(=O)(Cc1ccccc1)c1nc2n(n1)[C@H](c1ccccc1)C[C@@H]2F]

(5S,7S)-2-benzylsulfonyl-7-fluoro-5-phenyl-6,7-dihydro-5H-pyrrolo[1,2-b][1,2,4]triazole To a solution of (5S,7S)-2-benzylsulfanyl-7-fluoro-5-phenyl-6,7-dihydro-5H-pyrrolo[1,2-b][1,2,4]triazole (40 mg, 0.12 mmol) in dichloromethane (3 mL) was added 3-chloroperoxybenzoic acid (63 mg, 0.37 mmol). The result mixture was stirred at 25° C. for 12 h and diluted with dichloromethane (20 mL). The mixture was washed with aqueous sodium bicarbonate (2×10 mL), brine (10 mL), dried over sodium sulfate and concentrated under reduced pressure. The residue was purified by RP-HPLC (acetonitrile 40-70%/0.05% ammonia hydroxide in water) to afford arbitrarily assigned (5S,7S)-2-benzylsulfonyl-7-fluoro-5-phenyl-6,7-dihydro-5H-pyrrolo[1,2-b][1,2,4]triazole (13.8 mg, 30%). $^1$H NMR (400 MHz, CDCl$_3$) δ 7.45-7.38 (m, 5H), 7.32-7.25 (m, 3H), 7.13-7.11 (m, 2H), 6.10-5.94 (m, 1H), 5.49-5.45 (m, 1H), 4.65-4.57 (m, 2H), 3.69-3.58 (m, 1H), 3.01-2.90 (m, 1H). LCMS $R_T$=1.910 min, m/z=358.1 [M+H]$^+$.

LCMS (10 to 80% acetonitrile in water+0.03% trifluoacetic acid over 3 mins) retention time 1.910 min, ESI+ found [M+H]=358.1.

Example 20: Method 11

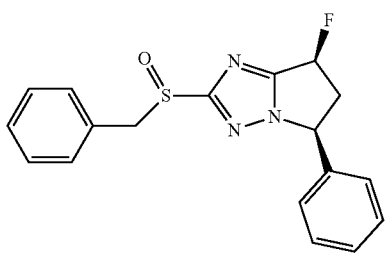 [SMILES: O=S(Cc1ccccc1)c1nc2n(n1)[C@H](c1ccccc1)C[C@@H]2F]

(5S,7S)-2-benzylsulfinyl-7-fluoro-5-phenyl-6,7-dihydro-5H-pyrrolo[1,2-b][1,2,4]triazole

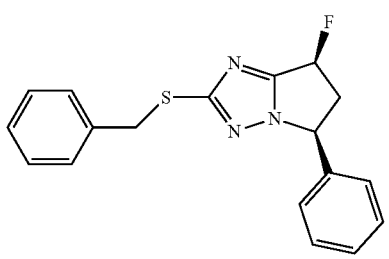 [SMILES: F[C@H]1C[C@@H](c2ccccc2)n2nc(SCc3ccccc3)nc21]

Step 1: (5S,7S)-2-benzylsulfanyl-7-fluoro-5-phenyl-6,7-dihydro-5H-pyrrolo[1,2-b][1,2,4]triazole A mixture of (5S,7S)-2-bromo-7-fluoro-5-phenyl-6,7-dihydro-5H-pyrrolo[1,2-b][1,2,4]triazole (10 mg, 0.35 mmol), benzyl mercaptan (100 mg, 0.81 mmol), 2-(dicyclohexylphosphino)-2',4',6'-triisopropylbiphenyl (169 mg, 0.35 mmol), triethylamine (108 mg, 1.06 mmol) and tris(dibenzylideneacetone)dipalladium(0) (325 mg, 0.35 mmol) in 1,4-dioxane (12 mL) was heated at 100° C. for 15 h under nitrogen atmosphere and concentrated under reduced pressure. The residue was purified by preparative TLC (35% ethyl acetate in petroleum ether, R$_f$=0.2) to afford arbitrarily assigned (5S,7S)-2-benzylsulfanyl-7-fluoro-5-phenyl-6,7-dihydro-5H-pyrrolo[1,2-b][1,2,4]triazole (80 mg, 69%) as a yellow solid. LCMS $R_T$=0.831 min, m/z=326.1 [M+H]$^+$.

LCMS (5 to 95% acetonitrile in water+0.03% trifluoacetic acid over 1.5 mins) retention time 0.831 min, ESI+ found [M+H]=326.1.

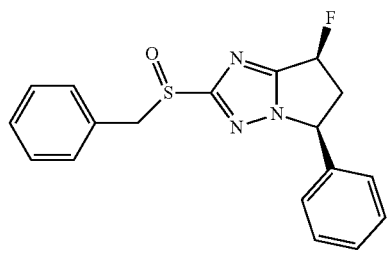 [SMILES: O=S(Cc1ccccc1)c1nc2n(n1)[C@H](c1ccccc1)C[C@@H]2F]

Step 2

(5S,7S)-2-benzylsulfinyl-7-fluoro-5-phenyl-6,7-dihydro-5H-pyrrolo[1,2-b][1,2,4]triazole To a solution of (5S,7S)-2-benzylsulfanyl-7-fluoro-5-phenyl-6,7-dihydro-5H-pyrrolo[1,2-b][1,2,4]triazole (25 mg, 0.08 mmol) in dichloromethane (2 mL) was added 3-chloroperoxybenzoic acid (13 mg, 0.08 mmol). The result mixture was stirred at 0° C. for 2 h and diluted with dichloromethane (20 mL). The mixture was washed with aqueous sodium bicarbonate (2×10 mL), brine (10 mL), dried over anhydrous sodium sulfate and concentrated under reduced pressure. The residue was purified by RP-HPLC (acetonitrile 40-70%/0.05% ammonia hydroxide in water) to give (5S,7S)-2-benzylsulfinyl-7-fluoro-5-phenyl-6,7-dihydro-5H-pyrrolo[1,2-b][1,2,4]triazole (8.49 mg, 32%) as a yellow solid. $^1$H NMR (400 MHz, CDCl$_3$) δ 7.40-7.36 (m, 3H), 7.28-7.26 (m, 3H), 7.21-7.15 (m, 3H), 7.12-7.09 (m, 1H), 6.12-5.96 (m, 1H), 5.47-5.43 (m, 1H), 4.56-4.39 (m, 2H), 3.67-3.59 (m, 1H), 3.00-2.89 (m, 1H). LCMS $R_T$=1.734 min, m/z=342.1 [M+H]$^+$.

LCMS (10 to 80% acetonitrile in water+0.03% trifluoacetic acid over 3 mins) retention time 1.734 min, ESI+ found [M+H]=342.1.

Examples 21 and 22: Method 12

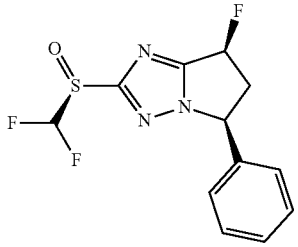

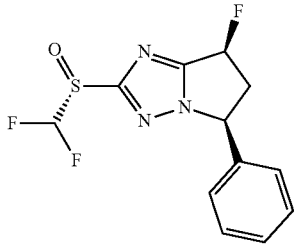

(5S,7S)-2-[(S)-difluoromethylsulfinyl]-7-fluoro-5-phenyl-6,7-dihydro-5H-pyrrolo[1,2-b][1,2,4]triazole and (5S,7S)-2-[(R)-difluoromethylsulfinyl]-7-fluoro-5-phenyl-6,7-dihydro-5H-pyrrolo[1,2-b][1,2,4]triazole

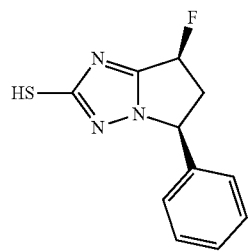 [SMILES: F[C@H]1C[C@@H](c2ccccc2)n2nc(S)nc21]

Step 1

(5S,7S)-7-fluoro-5-phenyl-6,7-dihydro-5H-pyrrolo[1,2-b][1,2,4]triazole-2-thiol

A mixture of triisopropylsilanethiol (1.02 g, 5.32 mmol), (5S,7S)-2-bromo-7-fluoro-5-phenyl-6,7-dihydro-5H-pyrrolo[1,2-b][1,2,4]triazole (1.00 g, 3.54 mmol), sodium tert-butoxide (1.02 g, 10.63 mmol) and Rockphos-Pd-G3 (297 mg, 0.35 mmol) in 1,4-dioxane (10 mL) was heated at 90° C. for 16 h and concentrated under reduced pressure. The residue was diluted with ethyl acetate (40 mL) and filtered. The filtrate was concentrated under reduced pressure to give crude (5S,7S)-7-fluoro-5-phenyl-6,7-dihydro-5H-pyrrolo[1,2-b][1,2,4]triazole-2-thiol (1.6 g, 100%) as a light yellow solid.

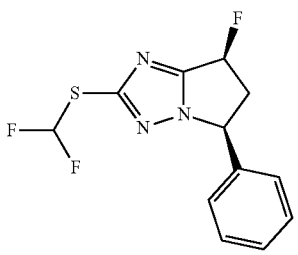 [SMILES: FC(F)Sc1nc2n(n1)[C@H](c1ccccc1)C[C@@H]2F]

Step 2

(5S,7S)-2-((difluoromethyl)thio)-7-fluoro-5-phenyl-6,7-dihydro-5H-pyrrolo[1,2-b][1,2,4]triazole A mixture of (5S,7S)-7-fluoro-5-phenyl-6,7-dihydro-5H-pyrrolo[1,2-b][1,2,4]triazole-2-thiol (800 mg, 3.40 mmol), (2-chloro-2,2-difluoro-acetyl)oxy sodium (648 mg, 4.25 mmol) and cesium carbonate (2769 mg, 8.50 mmol) in 1-methyl-2-pyrrolidinone (20 mL) was heated at 100° C. for 3 h and then diluted with water (15 mL). The resulting mixture was extracted with ethyl acetate (3×15 mL). The combined organic layers were washed with brine (10 mL), dried over anhydrous sodium sulfate and concentrated under reduced pressure. The residue was purified by column chromatography (silica gel, 100-200 mesh, 0 to 20% ethyl acetate in petroleum ether) to give (5S,7S)-2-(difluoromethylsulfanyl)-7-fluoro-5-phenyl-6,7-dihydro-5H-pyrrolo[1,2-b][1,2,4]triazole (200 mg, 21%) as a white solid. LCMS $R_T$=1.230 min, m/z=286.1 [M+H]$^+$.

LCMS (10 to 80% acetonitrile in water+0.03% trifluoroacetic acid over 2 mins) retention time 1.230 min, ESI+ found [M+H]=286.1.

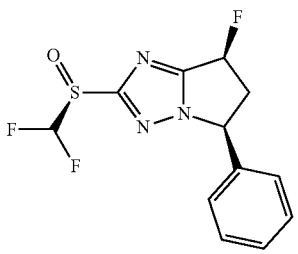

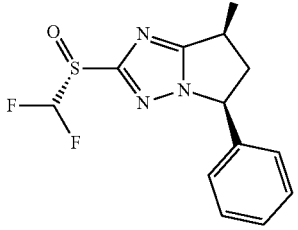

Step 3

(5S,7S)-2-[(S)-difluoromethylsulfinyl]-7-fluoro-5-phenyl-6,7-dihydro-5H-pyrrolo[1,2-b][1,2,4]triazole and (5S,7S)-2-[(R)-difluoromethylsulfinyl]-7-fluoro-5-phenyl-6,7-dihydro-5H-pyrrolo[1,2-b][1,2,4]triazole To a solution of (5S,7S)-2-(difluoromethylsulfanyl)-7-fluoro-5-phenyl-6,7-dihydro-5H-pyrrolo[1,2-b][1,2,4]triazole (200 mg, 0.70 mmol) in dichloromethane (15 mL) was added 3-chloroperoxybenzoic acid (213 mg, 1.05 mmol). The reaction was stirred at 0° C. for 16 h, and then diluted with dichloromethane (20 mL). The mixture washed with saturated aqueous sodium bicarbonate (2×10 mL), brine (10 mL), dried over anhydrous sodium sulfate and concentrated under reduced pressure. The residue was purified by RP-HPLC (acetonitrile 20-45%/0.225% HCl in water) to afford arbitrarily assigned (5S,7S)-2-(difluoromethylsulfinyl)-7-fluoro-5-phenyl-6,7-dihydro-5H-pyrrolo[1,2-b][1,2,4]triazole (90 mg, 43%) as a colorless oil. LCMS $R_T$=1.116 min, m/z=302.1 [M+H]$^+$.

LCMS (10 to 80% acetonitrile in water+0.03% trifluoacetic acid over 2 mins) retention time 1.116 min, ESI+ found [M+H]=302.1.

This racemic material (90 mg, 0.30 mmol) was further separated by chiral SFC to afford arbitrarily assigned:

(5S,7S)-2-[(S)-difluoromethylsulfinyl]-7-fluoro-5-phenyl-6,7-dihydro-5H-pyrrolo[1,2-b][1,2,4]triazole (Peak 1, retention time=2.977 min) (39.0 mg, 43%) as a white solid. $^1$H NMR (400 MHz, CD$_3$OD) δ 7.42-7.40 (m, 3H), 7.40-7.26 (m, 2H), 7.09-6.95 (m, 1H), 6.23-6.20 (m, 0.5H), 6.08-6.06 (m, 0.5H), 5.71-5.69 (m, 1H), 3.83-3.73 (m, 1H), 2.91-2.80 (m, 1H). LCMS $R_T$=1.630 min, m/z=302.0 [M+H]$^+$.

LCMS (10 to 80% acetonitrile in water+0.1% ammonia water over 3.0 mins) retention time 1.630 min, ESI+ found [M+H]=302.0.

(5S,7S)-2-[(R)-difluoromethylsulfinyl]-7-fluoro-5-phenyl-6,7-dihydro-5H-pyrrolo[1,2-b][1,2,4]triazole (Peak 2, retention time=3.832 min) (40.0 mg, 43%) as a white solid. $^1$H NMR (400 MHz, CD$_3$OD) δ 7.43-7.41 (m, 3H), 7.30-7.22 (m, 2H), 7.09-6.95 (m, 1H), 6.23-6.21 (m, 0.5H), 6.09-6.07 (m, 0.5H), 5.70-5.69 (m, 1H), 3.84-3.73 (m, 1H), 2.85-2.81 (m, 1H). LCMS $R_T$=1.602 min, m/z=302.0 [M+H]$^+$.

LCMS (10 to 80% acetonitrile in water+0.1% ammonia water over 3.0 mins) retention time 1.602 min, ESI+ found [M+H]=302.0.

SFC condition: Column: Chiralcel AD-3 150×4.6 mm I.D., 3 um Mobile phase: A: CO$_2$ B: iso-propanol (0.05% DEA) Gradient: from 5% to 40% of B in 5 min and hold 40% for 2.5 min, then 5% of B for 2.5 min Flow rate: 2.5 mL/min Column temp. 35 OC.

Examples 23: Method 13

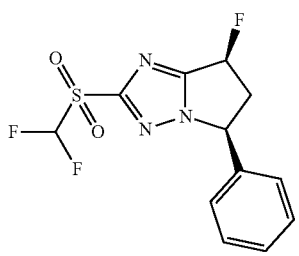 [SMILES: O=S(=O)(c1nc2n(n1)[C@H](c1ccccc1)C[C@@H]2F)C(F)F]

(5S,7S)-2-(difluoromethylsulfonyl)-7-fluoro-5-phenyl-6,7-dihydro-5H-pyrrolo[1,2-b][1,2,4]triazole A mixture of (5S,7S)-2-(difluoromethylsulfinyl)-7-fluoro-5-phenyl-6,7-dihydro-5H-pyrrolo[1,2-b][1,2,4]triazole (200 mg, 0.70 mmol) in dichloromethane (15 mL) was added 3-chloroperoxybenzoic acid (214 mg, 1.05 mmol). The reaction was stirred at 25° C. for 16 h and quenched by addition of saturated aqueous sodium bicarbonate (15 mL). The resulting mixture was extracted with ethyl acetate (3×15 mL). The combined organic layers were washed with brine (15 mL), dried over sodium sulfate and concentrated under reduced pressure. The residue was purified by RP-HPLC (acetonitrile 20-45%/0.225% HCl in water) to afford arbitrarily assigned (5S,7S)-2-(difluoromethylsulfonyl)-7-fluoro-5-phenyl-6,7-dihydro-5H-pyrrolo[1,2-b][1,2,4]triazole (21.1 mg, 9%) as a white solid. $^1$H NMR (400 MHz, CD$_3$OD) δ 7.44-7.42 (m, 3H), 7.30-7.27 (m, 2H), 7.08-6.95 (m, 1H), 6.24-6.22 (m, 0.5H), 6.10-6.08 (m, 0.5H), 5.74-5.72 (m, 1H), 3.84-3.74 (m, 1H), 2.93-2.82 (m, 1H). LCMS $R_T$=1.823 min, m/z=318.0 [M+H]+.

LCMS (10 to 80% acetonitrile in water+0.1% ammonia water over 3.0 mins) retention time 1.823 min, ESI+ found [M+H]=318.0.

Example 24: Method 14

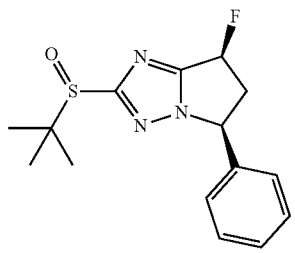 [SMILES: CC(C)(C)S(=O)c1nc2n(n1)[C@H](c1ccccc1)C[C@@H]2F]

(5S,7S)-2-(tert-butylsulfinyl)-7-fluoro-5-phenyl-6,7-dihydro-5H-pyrrolo[1,2-b][1,2,4]triazole

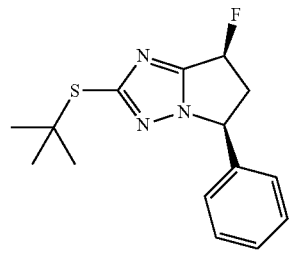 [SMILES: CC(C)(C)Sc1nc2n(n1)[C@H](c1ccccc1)C[C@@H]2F]

Step 1

(5S,7S)-2-(tert-butylthio)-7-fluoro-5-phenyl-6,7-dihydro-5H-pyrrolo[1,2-b][1,2,4]triazole A mixture of (5S,7S)-2-bromo-7-fluoro-5-phenyl-6,7-dihydro-5H-pyrrolo[1,2-b][1,2,4]triazole (200 mg, 0.71 mmol), 2-methyl-2-propanethiol (0.51 mL, 4.55 mmol), tris(dibenzylideneacetone) dipalladium(0) (629 mg, 0.69 mmol), triethylamine (215 mg, 2.13 mmol) and 4,5-bis(diphenylphosphino)-9,9-dimethylxanthene (416 mg, 0.72 mmol) in 1,4-dioxane (8 mL) was heated at 100° C. for 16 h under nitrogen atmosphere. Then the mixture was added sodium hypochlorite (2 mL) and stirred for 0.5 h. Then the mixture was diluted with water (15 mL) and extracted with ethyl acetate (3×15 mL). The combined organic layers were washed with brine (2×15 mL), dried over sodium sulfate and concentrated under reduced pressure. The residue was purified by column chromatography (silica gel, 100-200 mesh, 0 to 20% ethyl acetate in petroleum ether) to give (5S,7S)-2-tert-butylsulfanyl-7-fluoro-5-phenyl-6,7-dihydro-5H-pyrrolo[1,2-b][1,2,4]triazole (160 mg, 47%, 60% purity) as a brown solid. LCMS R$_T$=0.839 min, m/z=292.1 [M+H]$^+$.

LCMS (5 to 95% acetonitrile in water+0.03% trifluoacetic acid over 1.5 mins) retention time: 0.839 min, ESI+ found [M+H]=292.1

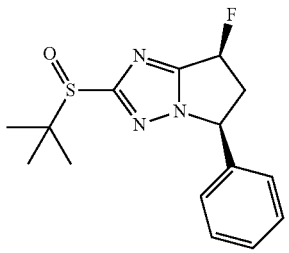 [SMILES: CC(C)(C)S(=O)c1nc2n(n1)[C@H](c1ccccc1)C[C@@H]2F]

Step 2

(5S,7S)-2-(tert-butylsulfinyl)-7-fluoro-5-phenyl-6,7-dihydro-5H-pyrrolo[1,2-b][1,2,4]triazole A mixture of (5S,7S)-2-tert-butylsulfanyl-7-fluoro-5-phenyl-6,7-dihydro-5H-pyrrolo[1,2-b][1,2,4]triazole (80 mg, 0.16 mmol) and 3-chloroperoxybenzoic acid (31 mg, 0.18 mmol) in dichloromethane (2 mL) was stirred at 0° C. for 1 h and quenched by addition of saturated aqueous sodium sulfite (2 mL). The resulting mixture was extracted with ethyl acetate (3×15 mL). The combined organic layers were washed with brine, dried over anhydrous sodium sulfate and concentrated under reduced pressure. The residue was purified by RP-HPLC (acetonitrile 26-56%/0.05% ammonia hydroxide in water) to give (5S,7S)-2-tert-butylsulfinyl-7-fluoro-5-phenyl-6,7-dihydro-5H-pyrrolo[1,2-b][1,2,4]triazole (25.8 mg, 50%) as a colorless oil. $^1$H NMR (400 MHz, CD$_3$OD) δ 7.40-7.38 (m, 3H), 7.25-7.22 (m, 2H), 6.19-6.16 (m, 0.5H), 6.05-6.02 (m, 0.5H), 5.64-5.62 (m, 1H), 3.80-3.70 (m, 1H), 2.86-2.78 (m, 1H), 1.70 (s, 9H). LCMS R$_T$=0.726 min, m/z=308.1 [M+H]$^+$.

LCMS (5 to 95% acetonitrile in water+0.03% trifluoacetic acid over 1.5 mins) retention time: 0.726 min, ESI+ found [M+H]=308.1.

Example 25: Method 15

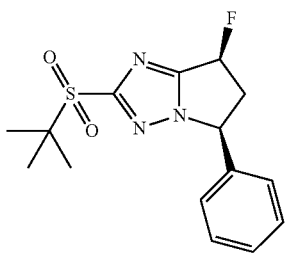 [SMILES: CC(C)(C)S(=O)(=O)c1nc2n(n1)[C@H](c1ccccc1)C[C@@H]2F]

(5S,7S)-2-(tert-butylsulfonyl)-7-fluoro-5-phenyl-6,7-dihydro-5H-pyrrolo[1,2-b][1,2,4]triazole A mixture of (5S,7S)-2-tert-butylsulfanyl-7-fluoro-5-phenyl-6,7-dihydro-5H-pyrrolo[1,2-b][1,2,4]triazole (80 mg, 0.16 mmol) and 3-chloroperoxybenzoicacid (84 mg, 0.41 mmol) in dichloromethane (2 mL) was stirred at 0° C. for 1 h and quenched by addition of saturated aqueous sodium sulfite (2 mL). The resulting mixture was extracted with ethyl acetate (3×15 mL). The combined organic layers were washed with brine, dried over anhydrous sodium sulfate and concentrated under reduced pressure. The residue was purified by RP-HPLC (acetonitrile 32-62%/0.05% ammonia hydroxide in water) to afford arbitrarily assigned (5S,7S)-2-tert-butylsulfonyl-7-fluoro-5-phenyl-6,7-dihydro-5H-pyrrolo[1,2-b][1,2,4]triazole (32.9 mg, 61%) as a white solid. $^1$H NMR (400 MHz, CD$_3$OD) δ 7.43-7.38 (m, 3H), 7.27-7.25 (m, 2H), 6.22-6.20 (m, 0.5H), 6.08-6.06 (m, 0.5H), 5.69-5.68 (m, 1H), 3.83-3.75 (m, 1H), 2.86-2.79 (m, 1H), 1.36 (s, 9H). LCMS R$_T$=0.612 min, m/z=324.1 [M+H]$^+$.

LCMS (5 to 95% acetonitrile in water+0.03% trifluoacetic acid over 1.5 mins) retention time: 0.612 min, ESI+ found [M+H]=324.1.

Example 26: Method 16

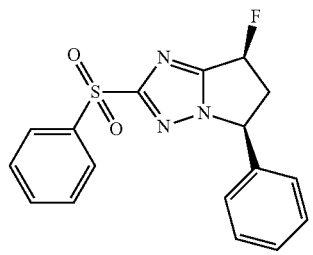 [SMILES: O=S(=O)(c1ccccc1)c1nc2n(n1)[C@H](c1ccccc1)C[C@@H]2F]

(5S,7S)-2-(benzenesulfonyl)-7-fluoro-5-phenyl-6,7-dihydro-5H-pyrrolo[1,2-b][1,2,4]triazole

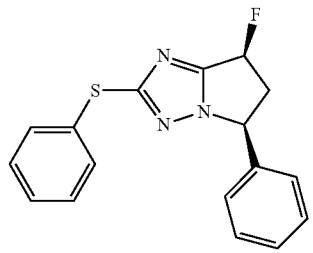 [SMILES: F[C@H]1C[C@@H](c2ccccc2)n2nc(Sc3ccccc3)nc21]

Step 1

(5S,7S)-7-fluoro-5-phenyl-2-(phenylthio)-6,7-dihydro-5H-pyrrolo[1,2-b][1,2,4]triazole A mixture of (5S,7S)-7-fluoro-5-phenyl-6,7-dihydro-5H-pyrrolo[1,2-b][1,2,4]triazole-2-thiol (0.1 mL, 0.64 mmol), phenylboronic acid (0.22 mL, 1.91 mmol), 2,2'-bipyridine (33 mg, 0.21 mmol), copper(I) thiophene-2-carboxylate (41 mg, 0.21 mmol), sodium carbonate (203 mg, 1.91 mmol) in 1,2-dichloroethane (3 mL) was stirred at 70° C. for 5 h. The mixture was quenched by addition of saturated aqueous ammonium chloride (20 mL). The resulting mixture was extracted with ethyl acetate (3×15 mL). The combined organic layers were concentrated under reduce pressure and the residue was purified by preparative TLC (50% ethyl acetate in petroleum ether) to afford (5S,7S)-7-fluoro-5- phenyl-2-phenylsulfanyl-6,7-dihydro-5H-pyrrolo[1,2-b][1,2,4]triazole (60 mg, 30%) as a colorless oil. LCMS $R_T$=1.309 min, m/z=312.1 [M+H]$^+$.

LCMS (10 to 80% acetonitrile in water+0.03% trifluoacetic acid over 2 mins) retention time 1.309 min, ESI+ found [M+H]=312.1.

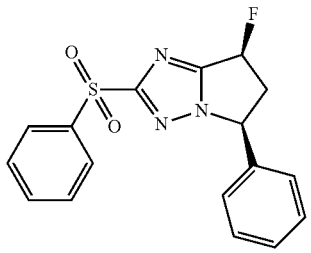 [SMILES: O=S(=O)(c1ccccc1)c1nc2n(n1)[C@H](c1ccccc1)C[C@@H]2F]

Step 2

(5S,7S)-2-(benzenesulfonyl)-7-fluoro-5-phenyl-6,7-dihydro-5H-pyrrolo[1,2-b][1,2,4]triazole A mixture of (5S,7S)-7-fluoro-5-phenyl-2-phenylsulfanyl-6,7-dihydro-5H-pyrrolo[1,2-b][1,2,4]triazole (30 mg, 0.10 mmol) and 3-chloroperoxybenzoic acid (83 mg, 0.48 mmol) in dichloromethane (3 mL) was stirred at 0° C. for 2 h and then diluted with dichloromethane (20 mL). The mixture was washed with saturated aqueous sodium bicarbonate (2×10 mL), brine (10 mL), dried over anhydrous sodium sulfate and concentrated under reduced pressure. The residue was purified by RP-HPLC (acetonitrile 40-70%/0.05% ammonia hydroxide in water) to afford arbitrarily assigned (5S,7S)-2-(benzenesulfonyl)-7-fluoro-5-phenyl-6,7-dihydro-5H-pyrrolo[1,2-b][1,2,4]triazole (10.8 mg, 32%) as a white solid. $^1$H NMR (400 MHz, CDCl$_3$) δ 8.13 (d, J=7.2 Hz, 2H), 7.73-7.62 (m, 1H), 7.61-7.53 (m, 2H), 7.40-7.38 (m, 3H), 7.22-7.20 (m, 2H), 6.04-5.88 (m, 1H), 5.49-5.46 (m, 1H), 3.67-3.54 (m, 1H), 2.99-2.89 (m, 1H). LCMS $R_T$=0.879 min, m/z=343.9 [M+H]$^+$.

Example 27, 28 and 29: Method 43

(5S,7S)-2-cyclopropylsulfinyl-7-fluoro-5-phenyl-6,7-dihydro-5H-pyrrolo[1,2-b][1,2,4]triazole and (5S,7S)-2-[(R)-cyclopropylsulfinyl]-7-fluoro-5-phenyl-6,7-dihydro-5H-pyrrolo[1,2-b][1,2,4]triazole and (5S,7S)-2-[(S)-cyclopropylsulfinyl]-7-fluoro-5-phenyl-6,7-dihydro-5H-pyrrolo[1,2-b][1,2,4]triazole Example 27

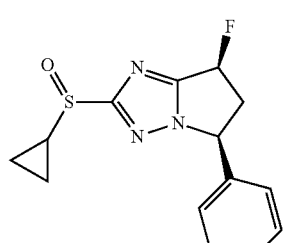

Example 27

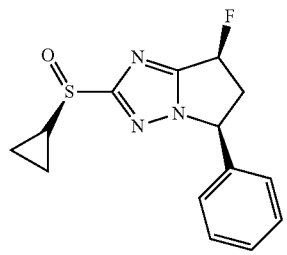

Example 27

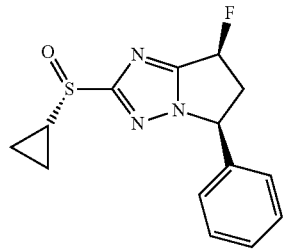

Step 1: 2-ethylhexyl 3-(((5S,7S)-7-fluoro-5-phenyl-6,7-dihydro-5H-pyrrolo[1,2-b][1,2,4]triazol-2-yl)thio)propanoate

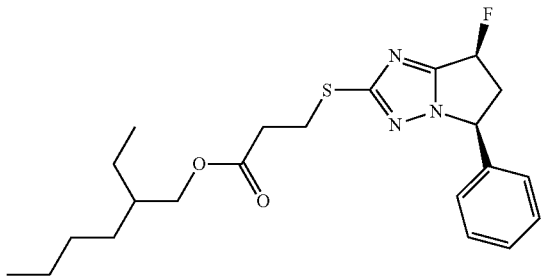 [SMILES: CCCCC(CC)COC(=O)CCSc1nc2n(n1)[C@H](c1ccccc1)C[C@@H]2F]

A mixture of tris(dibenzylideneacetone)dipalladium(0) (1.95 g, 2.13 mmol), (5S,7S)-2-bromo-7-fluoro-5-phenyl-6,7-dihydro-5H-pyrrolo[1,2-b][1,2,4]triazole (3.0 g, 10.6 mmol), 3-mercaptopropionic acid 2-ethylhexylester (3.0 g, 1.89 mmol), 4,5-bis(diphenylphosphino)-9,9-dimethylxanthene (6.1 g, 10.6 mmol) and triethylamine (3.2 g, 31.9 mmol) in 1,4-dioxane (60 mL) was stirred at 110° C. for 15 h under nitrogen atmosphere. The mixture was diluted with water (100 mL) and extracted with ethyl acetate (3×50 mL). The combined organic layers were dried over sodium sulfate and concentrated under reduced pressure. The residue was purified by column chromatography (silica gel, 100-200 mesh, 0 to 30% ethyl acetate in petroleum ether) to afford 2-ethylhexyl 3-[[(5S,7S)-7-fluoro-5-phenyl-6,7-dihydro-5H-pyrrolo[1,2-b][1,2,4]triazol-2-yl]sulfanyl]propanoate (2.7 g, 61%) as a light yellow oil. LCMS $R_T$=1.355 min, m/z=420.3 [M+H]$^+$.

LCMS (10 to 80% acetonitrile in water+0.03% trifluoroacetic acid over 2.0 mins) retention time 1.355 min, ESI+ found [M+H]=420.3.

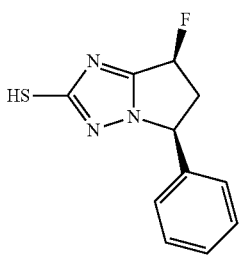 [SMILES: F[C@H]1C[C@@H](c2ccccc2)n2nc(S)nc21]

Step 2: (5S,7S)-7-fluoro-5-phenyl-6,7-dihydro-5H-pyrrolo[1,2-b][1,2,4]triazole-2-thiol To a solution of 1-ethylhexyl 3-[[(5S,7S)-7-fluoro-5-phenyl-6,7-dihydro-5H-pyrrolo[1,2-b][1,2,4]triazol-2-yl]sulfanyl]propanoate (2.7 g, 6.44 mmol) in ethanol (50 mL) was added sodium ethoxide (1.31 g, 19.31 mmol). The mixture was stirred at 25° C. for 1 h and concentrated under reduced pressure. The residue was diluted with water (30 mL), washed with ethyl acetate (20 mL) and adjusted to pH=6 by addition of citric acid. The resulting mixture was extracted with ethyl acetate (3×20 mL). The combined organic layers were dried over sodium sulfate and concentrated under reduced pressure to afford crude (5S,7S)-7-fluoro-5-phenyl-6,7-dihydro-5H-pyrrolo[1,2-b][1,2,4]triazole-2-thiol (2.1 g, 100%) as a yellow solid. LCMS $R_T$=0.454 min, m/z=236.1 [M+H]$^+$.

LCMS (5 to 95% acetonitrile in water+0.03% trifluoroacetic acid over 1.5 mins) retention time 0.454 min, ESI+ found [M+H]=236.1.

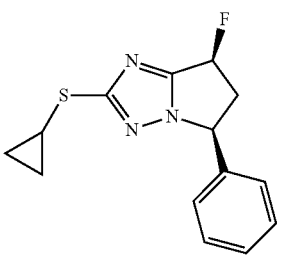 [SMILES: F[C@H]1C[C@@H](c2ccccc2)n2nc(SC3CC3)nc21]

Step 3: (5S,7S)-2-(cyclopropylthio)-7-fluoro-5-phenyl-6,7-dihydro-5H-pyrrolo[1,2-b][1,2,4]triazole To a mixture of 2,2'-bipyridine (22 mg, 0.14 mmol), (5S,7S)-7-fluoro-5-phenyl-6,7-dihydro-5H-pyrrolo[1,2-b][1,2,4]triazole-2-thiol (100 mg, 0.43 mmol), cyclopropylboronic acid (109 mg, 1.7 mmol), copper(I) thiophene-2-carboxylate (27 mg, 0.14 mmol) and sodium carbonate (135 mg, 1.27 mmol) in 1,2-dichloroethane (5 mL) was stirred at 70° C. for 5 h and concentrated under reduced pressure. The residue was purified by preparative TLC (50% ethyl acetate in petroleum ether, $R_f$=0.5) to afford (5S,7S)-2-(cyclopropylthio)-7-fluoro-5-phenyl-6,7-dihydro-5H-pyrrolo[1,2-b][1,2,4]triazole (30 mg, 17%) as a yellow oil. LCMS $R_T$=0.638 min, m/z=276.1 [M+H]$^+$.

Step 4

To a solution of (5S,7S)-2-cyclopropylsulfanyl-7-fluoro-5-phenyl-6,7-dihydro-5H-pyrrolo[1,2-b][1,2,4]triazole (20 mg, 0.07 mmol) in dichloromethane (1 mL) was added 3-chloroperoxybenzoic acid (85%, 15 mg, 0.07 mmol). The resulting mixture was stirred at 0° C. for 2 h and quenched by addition of saturated aqueous sodium bicarbonate (10 mL). The mixture was extracted with dichloromethane (2×20 mL). The combined organic layers were dried over sodium sulfate and concentrated under reduced pressure. The residue was purified by RP-HPLC (acetonitrile 40-70%/0.05% ammonia hydroxide in water) to give (5S,7S)-2-cyclopropylsulfinyl-7-fluoro-5-phenyl-6,7-dihydro-5H-pyrrolo[1,2-b][1,2,4]triazole (13.1 mg, 61%) as a yellow solid. $^1$H NMR (400 MHz, CDCl$_3$) δ 7.41-7.17 (m, 3H), 7.13-7.06 (m, 2H), 6.05-5.76 (m, 1H), 5.37-5.21 (m, 1H), 3.59-3.48 (m, 1H), 2.96-2.74 (m, 1H), 2.73-2.52 (m, 1H), 1.28-1.15 (m, 1H), 1.01-0.85 (m, 3H). LC-MS $R_T$=0.795 min, m/z=291.9 [M+H]$^+$.

(5S,7S)-2-[(R)-cyclopropylsulfinyl]-7-fluoro-5-phenyl-6,7-dihydro-5H-pyrrolo[1,2-b][1,2,4]triazole (Peak 2 on SFC, retention time=4.926 min) (20.8 mg, 13%) as a pink solid. $^1$H NMR (400 MHz, CDCl$_3$) δ 7.44-7.38 (m, 3H), 7.27-7.24 (m, 2H), 6.15-5.95 (m, 1H), 5.53-5.48 (m, 1H), 3.71-3.62 (m, 1H), 3.03-2.97 (m, 1H), 2.82-2.77 (m, 1H), 1.37-1.35 (m, 1H), 1.11-1.02 (m, 3H). LC-MS $R_T$=0.779 min, m/z=292.0 [M+H]+.

LCMS (5 to 95% acetonitrile in water+0.03% trifluoroacetic acid over 1.5 mins) retention time 0.779 min, ESI$^+$ found [M+H]=292.0.

(5S,7S)-2-[(S)-cyclopropylsulfinyl]-7-fluoro-5-phenyl-6,7-dihydro-5H-pyrrolo[1,2-b][1,2,4]triazole (Peak 1 on SFC, retention time=4.304 min) (25 mg, 15%) as a pink solid. $^1$H NMR (400 MHz, CDCl$_3$) δ 7.43-7.37 (m, 3H), 7.27-7.22 (m, 2H), 6.12-5.95 (m, 1H), 5.52-5.48 (m, 1H), 3.71-3.62 (m, 1H), 3.02-2.95 (m, 1H), 2.79-2.75 (m, 1H), 1.35-1.33 (m, 1H), 1.10-1.01 (m, 3H). LC-MS $R_T$=0.769 min, m/z=291.9 [M+H]+.

LCMS (5 to 95% acetonitrile in water+0.03% trifluoroacetic acid over 1.5 mins) retention time 0.769 min, ESI$^+$ found [M+H]=291.9.

Analytical SFC conditions: Column: ChiralPak AD-3 150×4.6 mm I.D., 3 μm; Mobile phase: A: CO2 B: Ethanol (0.05% DEA); Gradient: from 5% to 40% of B in 5.5 min and hold 40%; for 3 min, then 5% of B for 1.5 min; Flow rate: 2.5 mL/min Column temperature: 40° C.

Example 30: Method 17

(5S,7S)-2-cyclopropylsulfonyl-7-fluoro-5-phenyl-6,7-dihydro-5H-pyrrolo[1,2-b][1,2,4]triazole

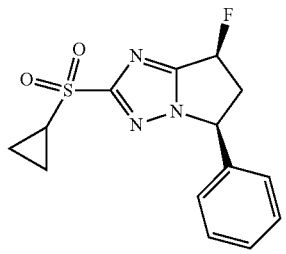 [SMILES: O=S(=O)(c1nc2n(n1)[C@H](c1ccccc1)C[C@@H]2F)C1CC1]

A mixture of (5S,7S)-2-bromo-7-fluoro-5-phenyl-6,7-dihydro-5H-pyrrolo[1,2-b][1,2,4]triazole (50 mg, 0.18 mmol), sodium cyclopropanesulfinate (113 mg, 0.89 mmol), copper (I) iodide (8 mg, 0.04 mmol), (1R,2R)—N1,N2-dimethyl-1,2-cyclohexanediamine (13 mg, 0.09 mmol) and potassium carbonate (29 mg, 0.21 mmol) in dimethyl sulfoxide (5 mL) was heated at 110° C. under microwave conditions for 1 h.

The mixture was diluted with water (5 mL) and extracted with ethyl acetate (2×10 mL). The combined organic layers were dried over sodium sulfate and concentrated under reduced pressure. The residue was purified by RP-HPLC (acetonitrile 33-63%/0.05% ammonia hydroxide in water) to afford (5S,7S)-2-cyclopropylsulfonyl-7-fluoro-5-phenyl-6,7-dihydro-5H-pyrrolo[1,2-b][1,2,4]triazole (26 mg, 47%) as a white solid. $^1$H NMR (400 MHz, CDCl$_3$) δ 7.42-7.39 (m, 3H), 7.26-7.24 (m, 2H), 6.11 (dd, J=1.6, 7.6 Hz, 0.5H), 5.99 (d, J=5.6 Hz, 0.5H), 5.56-5.49 (m, 1H), 3.70-3.61 (m, 1H), 3.06-2.92 (m, 1H), 2.78-2.71 (m, 1H), 1.52-1.43 (m, 2H), 1.16-1.11 (m, 2H). LC-MS R$_T$=0.736 min, m/z=308.1 [M+H]$^+$.

Example 31: Method 1

(4S,6S)-2-cyclopropylsulfonyl-4-fluoro-6-phenyl-5,6-dihydro-4H-pyrrolo[1,2-b]pyrazole

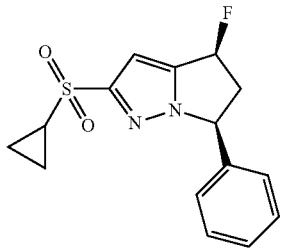 [SMILES: O=S(=O)(c1cc2n(n1)[C@H](c1ccccc1)C[C@@H]2F)C1CC1]

(4S,6S)-2-cyclopropylsulfonyl-4-fluoro-6-phenyl-5,6-dihydro-4H-pyrrolo[1,2-b]pyrazole was prepared according to Method 3 starting from cis-4-fluoro-6-phenyl-5,6-dihydro-4H-pyrrolo[1,2-b]pyrazole-2-thiol. The final compound was purified by chiral SFC to give (4S,6S)-2-cyclopropylsulfonyl-4-fluoro-6-phenyl-5,6-dihydro-4H-pyrrolo[1,2-b]pyrazole (Peak 2, Retention time=3.894 min) (24 mg, 43%) as a white solid. $^1$H NMR (400 MHz, CDCl$_3$) δ 7.40-7.35 (m, 3H), 7.22-7.20 (m, 2H), 6.89 (s, 1H), 6.10 (d, J=6.4 Hz, 0.5H), 5.95 (d, J=6.4 Hz, 0.5H), 5.55-5.52 (m, 1H), 3.56-3.48 (m, 1H), 2.92-2.82 (m, 1H), 2.65-2.61 (m, 1H), 1.38-1.36 (m, 2H), 1.05-1.03 (m, 2H). LC-MS R$_T$=0.835 min, m/z=306.9 [M+H]$^+$.

SFC condition: Column: OJ-H (250 mm×30 mm, 5 μm); Mobile phase: A: CO$_2$ B: 0.1% NH$_3$H$_2$O EtOH; Gradient: from 30% to 30% of B; Flow rate: 50 mL/min Column temperature: 40° C.

Example 32: Method 18

(5S,7S)-5-(2-chlorophenyl)-2-(cyclopropylsulfonyl)-7-fluoro-6,7-dihydro-5H-pyrrolo[1,2-b][1,2,4]triazole

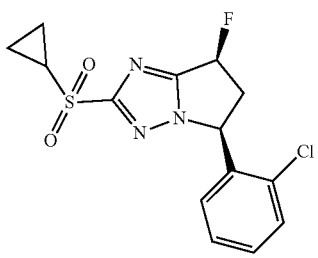 [SMILES: O=S(=O)(c1nc2n(n1)[C@H](c1ccccc1Cl)C[C@@H]2F)C1CC1]

(5S,7S)-5-(2-chlorophenyl)-2-(cyclopropylsulfonyl)-7-fluoro-6,7-dihydro-5H-pyrrolo[1,2-b][1,2,4]triazole was prepared according to Method 18 starting from (5S,7S)-7-fluoro-5-(2-chlorophenyl)-6,7-dihydro-5H-pyrrolo[1,2-b][1,2,4]triazole-2-thiol (prepared according to Method 21 starting from 2-chlorobenzaldehyde). The final compound was purified by RP-HPLC (acetonitrile 40-70%/0.05% ammonia hydroxide in water) to give (5S,7S)-5-(2-chlorophenyl)-2-(cyclopropylsulfonyl)-7-fluoro-6,7-dihydro-5H-pyrrolo[1,2-b][1,2,4]triazole (42.8 mg, 64%) as a white solid. $^1$H NMR (400 MHz, CDCl$_3$) δ 7.47-7.44 (m, 1H), 7.36-7.22 (m, 3H), 6.75 (dd, J=1.2, 7.6 Hz, 1H), 6.12-5.93 (m, 2H), 3.80-3.65 (m, 1H), 2.94-2.81 (m, 1H), 2.80-2.76 (m, 1H), 1.55-1.48 (m, 2H), 1.20-1.13 (m, 2H). LC-MS R$_T$=0.798 min, m/z=342.1 [M+H]$^+$.

Example 33: Method 18

(5S,7S)-2-cyclopropylsulfonyl-7-fluoro-5-(2-fluorophenyl)-6,7-dihydro-5H-pyrrolo[1,2-b][1,2,4]triazole

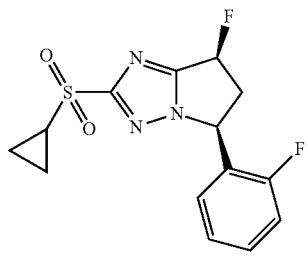 [SMILES: O=S(=O)(c1nc2n(n1)[C@H](c1ccccc1F)C[C@@H]2F)C1CC1]

(5S,7S)-2-cyclopropylsulfonyl-7-fluoro-5-(2-fluorophenyl)-6,7-dihydro-5H-pyrrolo[1,2-b][1,2,4]triazole was prepared according to method 18 starting from (5S,7S)-7-fluoro-5-(2-fluorophenyl)-6,7-dihydro-5H-pyrrolo[1,2-b][1,2,4]triazole-2-thiol (prepared according to Method 21 starting from 2-fluorobenzaldehyde). The final compound was purified by RP-HPLC (acetonitrile 44-74%/0.05% ammonia hydroxide in water) to give (5S,7S)-2-cyclopropylsulfonyl-7-fluoro-5-(2-fluorophenyl)-6,7-dihydro-5H-pyrrolo[1,2-b][1,2,4]triazole (30 mg, 53%) as a white solid. $^1$H NMR (400 MHz, CDCl$_3$) δ 7.40-7.37 (m, 1H), 7.19-7.15 (m, 2H), 7.12-6.99 (m, 1H), 6.14-5.98 (m, 1H), 5.88-5.84 (m, 1H), 3.77-3.71 (m, 1H), 3.00-2.90 (m, 1H), 2.79-2.75 (m, 1H), 1.52-1.48 (m, 2H), 1.19-1.15 (m, 2H). LCMS R$_T$=0.831 min, m/z=325.9 [M+H]$^+$.

Example 34

(5S,7S)-2-cyclopropylsulfonyl-7-fluoro-5-(4-fluorophenyl)-6,7-dihydro-5H-pyrrolo[1,2-b][1,2,4]triazole

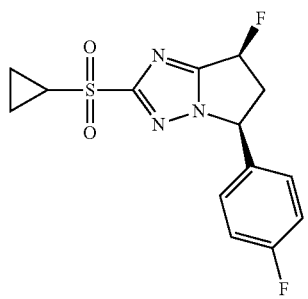 [SMILES: O=S(=O)(c1nc2n(n1)[C@H](c1ccc(F)cc1)C[C@@H]2F)C1CC1]

(5S,7S)-2-cyclopropylsulfonyl-7-fluoro-5-(4-fluorophenyl)-6,7-dihydro-5H-pyrrolo[1,2-b][1,2,4]triazole was prepared according to methos 18 starting from (5S,7S)-7-fluoro-5-(4-fluorophenyl)-6,7-dihydro-5H-pyrrolo[1,2-b][1,2,4]triazole-2-thiol (prepared according to Method 21 starting from 4-fluorobenzaldehyde). The final compound was purified by RP-HPLC (acetonitrile 28-58%/0.05% ammonia hydroxide in water) to give (5S,7S)-2-cyclopropylsulfonyl-7-fluoro-5-(4-fluorophenyl)-6,7-dihydro-5H-pyrrolo[1,2-b][1,2,4]triazole (33 mg, 43%) as a white solid. $^1$H NMR (400 MHz, CD$_3$OD) δ 7.41-7.29 (m, 2H), 7.19-7.15 (m, 2H), 6.24-6.02 (m, 1H), 5.68 (s, 1H), 3.83-3.69 (m, 1H), 2.94-2.76 (m, 2H), 1.38-1.30 (m, 2H), 1.22-1.08 (m, 2H). LCMS RT=0.961 min, m/z=326.2 [M+H]$^+$.

Example 35

(5S,7S)-2-cyclopropylsulfonyl-5-(2,6-difluorophenyl)-7-fluoro-6,7-dihydro-5H-pyrrolo[1,2-b][1,2,4]triazole

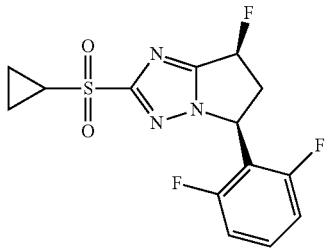 [SMILES: O=S(=O)(c1nc2n(n1)[C@H](c1c(F)cccc1F)C[C@@H]2F)C1CC1]

(5S,7S)-2-cyclopropylsulfonyl-5-(2,6-difluorophenyl)-7-fluoro-6,7-dihydro-5H-pyrrolo[1,2-b][1,2,4]triazole was prepared according to method 18 starting from (5S,7S)-5-(2,6-difluorophenyl)-7-fluoro-6,7-dihydro-5H-pyrrolo[1,2-b][1,2,4]triazole-2-thiol (prepared according to Method 21 starting from 2,6-difluorobenzaldehyde). The final compound was purified by RP-HPLC (acetonitrile 30-60/0.05% ammonia hydroxide in water) to give (5S,7S)-2-cyclopropylsulfanyl-5-(2,6-difluorophenyl)-7-fluoro-6,7-dihydro-5H-pyrrolo[1,2-b][1,2,4]triazole (24 mg, 28%) as a white solid. $^1$H NMR (400 MHz, CD$_3$OD) δ 7.57-7.44 (m, 1H), 7.11-7.07 (m, 2H), 6.26-6.07 (m, 1H), 6.03-5.95 (m, 1H), 3.93-3.79 (m, 1H), 3.03-2.88 (m, 1H), 2.88-2.79 (m, 1H), 1.36-1.25 (m, 2H), 1.20-1.11 (m, 2H). LCMS R$_T$=0.973 min, m/z=344.1 [M+H]$^+$.

Example 36

(5R,7R)-2-cyclopropylsulfonyl-5-(2,3-difluorophenyl)-7-fluoro-6,7-dihydro-5H-pyrrolo[1,2-b][1,2,4]triazole

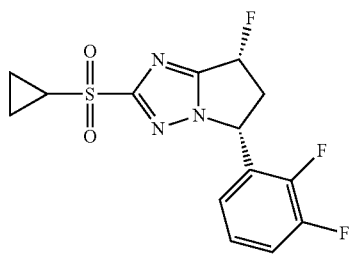 [SMILES: O=S(=O)(c1nc2n(n1)[C@@H](c1cccc(F)c1F)C[C@H]2F)C1CC1]

(5R,7R)-2-cyclopropylsulfonyl-5-(2,3-difluorophenyl)-7-fluoro-6,7-dihydro-5H-pyrrolo[1,2-b][1,2,4]triazole was prepared according to method 18 starting from (5R,7R)-5-(2,3-difluorophenyl)-7-fluoro-6,7-dihydro-5H-pyrrolo[1,2-b][1,2,4]triazole-2-thiol (prepared according to Method 21 starting from 2,3-difluorobenzaldehyde). The final compound was purified by RP-HPLC (acetonitrile 35-65%/0.225% formic acid in water) to give (5R,7R)-2-cyclopropylsulfonyl-5-(2,3-difluorophenyl)-7-fluoro-6,7-dihydro-5H-pyrrolo[1,2-b][1,2,4]triazole (51 mg, 56%) as a white solid. $^1$H NMR (400 MHz, CDCl$_3$) δ 7.25-7.17 (m, 1H), 7.16-7.08 (m, 1H), 6.81-6.68 (m, 1H), 6.13 (dd, J=2.0, 7.6 Hz, 0.5H), 5.99 (J=5.2 Hz, 0.5H), 5.91-5.81 (m, 1H), 3.78-3.70 (m, 1H), 3.03-2.89 (m, 1H), 2.79-2.69 (m, 1H), 1.51-1.48 (m, 2H), 1.18-1.14 (m, 2H). LCMS R$_T$=0.641 min, m/z=344.1 [M+H]$^+$.

Example 37

(5S,7S)-2-(cyclopropylsulfonyl)-5-(2,5-difluorophenyl)-7-fluoro-6,7-dihydro-5H-pyrrolo[1,2-b][1,2,4]triazole

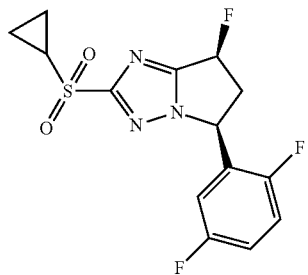 [SMILES: O=S(=O)(c1nc2n(n1)[C@H](c1cc(F)ccc1F)C[C@@H]2F)C1CC1]

(5S,7S)-2-cyclopropylsulfonyl-5-(2,5-difluorophenyl)-7-fluoro-6,7-dihydro-5H-pyrrolo[1,2-b][1,2,4]triazole was prepared according to method 18 starting from (5S,7S)-5-(2,5-difluorophenyl)-7-fluoro-6,7-dihydro-5H-pyrrolo[1,2-b][1,2,4]triazole-2-thiol (prepared according to Method 21 starting from 2,5-difluorobenzaldehyde). The final compound was purified by RP-HPLC (acetonitrile 30-60/0.05% ammonia hydroxide in water) to give (5S,7S)-2-cyclopropylsulfonyl-5-(2,5-difluorophenyl)-7-fluoro-6,7-dihydro-5H-pyrrolo[1,2-b][1,2,4]triazole (22 mg, 36%) as a white solid. $^1$H NMR (400 MHz, CDCl$_3$) δ 7.17-7.04 (m, 2H), 6.70-6.64 (m, 1H), 6.14-5.95 (m, 1H), 5.85-5.77 (m, 1H), 3.84-3.59 (m, 1H), 3.07-2.87 (m, 1H), 2.84-2.70 (m, 1H), 1.53-1.50 (m, 2H), 1.19-1.15 (m, 2H). LCMS R$_T$=1.001 min, m/z=344.1 [M+H]$^+$.

Example 38

(5S,7S)-2-(cyclopropylsulfonyl)-7-fluoro-5-(2,3,6-trifluorophenyl)-6,7-dihydro-5H-pyrrolo[1,2-b][1,2,4]triazole

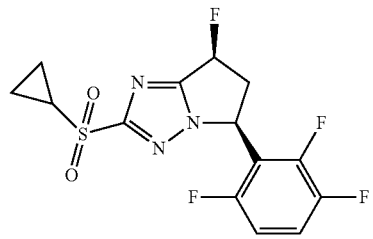 [SMILES: O=S(=O)(c1nc2n(n1)[C@H](c1c(F)ccc(F)c1F)C[C@@H]2F)C1CC1]

(5S,7S)-2-cyclopropylsulfonyl-7-fluoro-5-(2,36-trifluorophenyl)-6,7-dihydro-5H-pyrrolo[1,2-b][1,2,4]triazole was prepared according to method 18 starting from (5S,7S)-5-(2,3,6-trifluorophenyl)-7-fluoro-6,7-dihydro-5H-pyrrolo[1,2-b][1,2,4]triazole-2-thiol (prepared according to Method 21 starting from 2,3,6-trifluorobenzaldehyde). The final compound was purified by RP-HPLC (acetonitrile 40-50%/0.05% ammonia hydroxide in water) to give (5S,7S)-2-cyclopropylsulfonyl-7-fluoro-5-(2,3,6-trifluorophenyl)-6,7-dihydro-5H-pyrrolo[1,2-b][1,2,4]triazole (19.1 mg, 19%) as a white solid. $^1$H NMR (400 MHz, CD$_3$OD) δ 7.46-7.43 (m, 1H), 7.12-7.09 (m, 1H), 6.26 (dd, J=4.0, 8.0 Hz, 0.5H), 6.11 (d, J=7.6 Hz, 0.5H), 6.09-6.00 (m, 1H), 3.92-3.85 (m, 1H), 2.98-2.86 (m, 1H), 2.85-2.82 (m, 1H), 1.32-1.28 (m, 2H), 1.17-1.15 (m, 2H). LCMS R$_T$=0.988 min, m/z=362.1 [M+H]$^+$.

Example 39

(5S,7S)-2-cyclopropylsulfonyl-7-fluoro-5-(2,3,5-trifluorophenyl)-6,7-dihydro-5H-pyrrolo[1,2-b][1,2,4]triazole

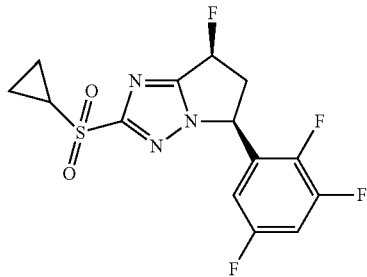 [SMILES: O=S(=O)(c1nc2n(n1)[C@H](c1cc(F)cc(F)c1F)C[C@@H]2F)C1CC1]

(5S,7S)-2-cyclopropylsulfonyl-7-fluoro-5-(2,3,5-trifluorophenyl)-6,7-dihydro-5H-pyrrolo[1,2-b][1,2,4]triazole was prepared according to method 18 starting from (5S,7S)-5-(2,3,5-trifluorophenyl)-7-fluoro-6,7-dihydro-5H-pyrrolo[1,2-b][1,2,4]triazole-2-thiol (prepared according to Method 21 starting from 2,3,5-trifluorobenzaldehyde). The final compound was purified by RP-HPLC (acetonitrile 39-69%/0.05% ammonia hydroxide in water) to give (5S,7S)-2-cyclopropylsulfonyl-7-fluoro-5-(2,3,5-trifluorophenyl)-6,7-dihydro-5H-pyrrolo[1,2-b][1,2,4]triazole (9.5 mg, 9%) as a brown solid. $^1$H NMR (400 MHz, CD$_3$OD) δ 7.32-7.25 (m, 1H), 6.81-6.78 (m, 1H), 6.24-6.08 (m, 1H), 5.97-5.92 (m, 1H), 3.90-3.77 (m, 1H), 2.98-2.85 (m, 2H), 1.36-1.29 (m, 2H), 1.20-1.14 (m, 2H). LCMS R$_T$=1.025 min, m/z=362.1 [M+H]$^+$.

Example 40

(5S,7S)-2-cyclopropylsulfonyl-5-(2,3-difluorophenyl)-7-fluoro-6,7-dihydro-5H-pyrrolo[1,2-b][1,2,4]triazole

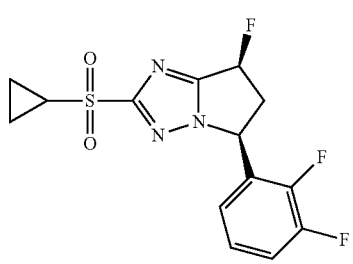 [SMILES: O=S(=O)(c1nc2n(n1)[C@H](c1cccc(F)c1F)C[C@@H]2F)C1CC1]

(5S,7S)-2-cyclopropylsulfonyl-5-(2,3-difluorophenyl)-7-fluoro-6,7-dihydro-5H-pyrrolo[1,2-b][1,2,4]triazole was prepared according to method 18 starting from (5S,7S)-5-(2,3-difluorophenyl)-7-fluoro-6,7-dihydro-5H-pyrrolo[1,2-b][1,2,4]triazole-2-thiol (prepared according to Method 21 starting from 2,3-difluorobenzaldehyde). The final compound was purified by RP-HPLC (acetonitrile 35-65%/0.225% formic acid in water) to give (5S,7S)-2-cyclopropylsulfonyl-5-(2,3-difluorophenyl)-7-fluoro-6,7-dihydro-5H-pyrrolo[1,2-b][1,2,4]triazole (45 mg, 53%) as a white solid. $^1$H NMR (400 MHz, CD$_3$OD) δ 7.37-7.28 (m, 1H), 7.25-7.17 (m, 1H), 6.97-6.91 (m, 1H), 6.21-6.19 (m, 0.5H), 6.07-6.05 (m, 0.5H), 5.97-5.89 (m, 1H), 3.89-3.74 (m, 1H), 2.95-2.80 (m, 2H), 1.34-1.25 (m, 2H), 1.16-1.13 (m, 2H). LCMS R$_T$=0.641 min, m/z=344.1 [M+H]+.

Example 41: Method 19

(5S,7S)-2-cyclopropylsulfonyl-7-deuterio-5-phenyl-6,7-dihydro-5H-pyrrolo[1,2-b][1,2,4]triazole

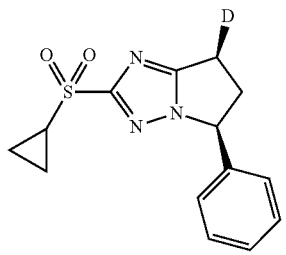 [SMILES: [2H][C@H]1C[C@@H](c2ccccc2)n2nc(S(=O)(=O)C3CC3)nc21]

Step 1: tert-butyl-[(2-cyclopropylsulfanyl-5-phenyl-6,7-dihydro-5H-pyrrolo[1,2-b][1,2,4]triazol-7-yl)oxy]-dimethyl-silane

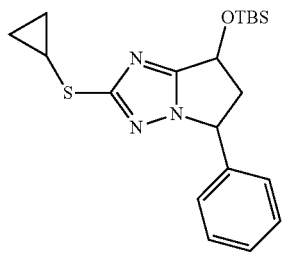 [SMILES: CC(C)(C)[Si](C)(C)OC1CC(c2ccccc2)n2nc(SC3CC3)nc21]

A mixture of 2,2'-bipyridine (315 mg, 2.0 mmol), 7-[tert-butyl(dimethyl)silyl]oxy-5-phenyl-6,7-dihydro-5H-pyrrolo[1,2-b][1,2,4]triazole-2-thiol (3.5 g, 10.0 mmol) sodium carbonate (3.2 g, 30.2 mmol) and copper(I) thiophene-2-carboxylate (1.9 g, 10.1 mmol) in 1,2-dichloroethane (100 mL) was stirred at 50° C. for 3 h and concentrated under reduced pressure. The residue was purified by column chromatography (silica gel, 100-200 mesh, 0 to 40% ethyl acetate in petroleum ether) to afford tert-butyl-[(2-cyclopropylsulfanyl-5-phenyl-6,7-dihydro-5H-pyrrolo[1,2-b][1,2,4]triazol-7-yl)oxy]-dimethyl-silane (2.5 g, 64%) as a brown solid.

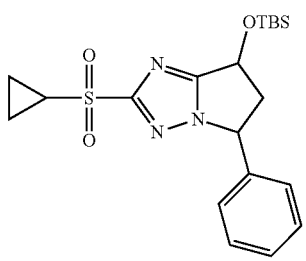 [SMILES: CC(C)(C)[Si](C)(C)OC1CC(c2ccccc2)n2nc(S(=O)(=O)C3CC3)nc21]

Step 2: tert-butyl-[(2-cyclopropylsulfonyl-5-phenyl-6,7-dihydro-5H-pyrrolo[1,2-b][1,2,4]triazol-7-yl)oxy]-dimethyl-silane A mixture of tert-butyl-[(2-cyclopropylsulfanyl-5-phenyl-6,7-dihydro-5H-pyrrolo[1,2-b][1,2,4]triazol-7-yl)oxy]-dimethyl-silane (2.5 g, 6.45 mmol) and 3-chloroperoxybenzoic acid (3.3 g, 19.4 mmol) in dichloromethane (20 mL) was stirred at 20° C. for 16 h and diluted with water (20 mL). The mixture was extracted with ethyl acetate (3×20 mL). The combined organic layers were washed with brine (20 mL), dried over sodium sulfate and concentrated under reduced pressure. The residue was purified by column chromatography (silica gel, 100-200 mesh, 0 to 50% ethyl acetate in petroleum ether) to afford tert-butyl-(2-cyclopropylsulfonyl-5-phenyl-6,7-dihydro-5H-pyrrolo[1,2-b][1,2,4]triazol-7-yl)oxy]-dimethyl-silane (2.0 g, 74%) as a white solid. LCMS $R_T$=0.858 min, m/z=420.0 [M+H]$^+$.

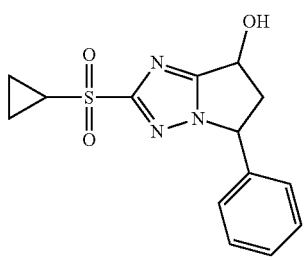 [SMILES: O=S(=O)(c1nc2n(n1)C(c1ccccc1)CC2O)C1CC1]

Step 3: 2-cyclopropylsulfonyl-5-phenyl-6,7-dihydro-5H-pyrrolo[1,2-b][1,2,4]triazol-7-ol To a solution of tert-butyl-[(2-cyclopropylsulfonyl-5-phenyl-6,7-dihydro-5H-pyrrolo[1,2-b][1,2,4]triazol-7-yl)oxy]-dimethyl-silane (2.0 g, 4.77 mmol) was added hydrochloric acid (4.0 M in 1,4-dioxane, 20 mL, 80.0 mmol). The mixture was stirred at 25° C. for 6 h and concentrated under reduced pressure. The residue was diluted with ethyl acetate (50 mL) and washed with brine (2×20 mL), dried over sodium sulfate and concentrated under reduced pressure. The residue was purified by column chromatography (silica gel, 100-200 mesh, 0 to 60% ethyl acetate in petroleum ether) to afford 2-cyclopropylsulfonyl-5-phenyl-6,7-dihydro-5H-pyrrolo[1,2-b][1,2,4]triazol-7-ol (1.4 g, 96%) as a white solid.

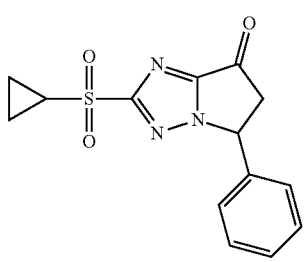 [SMILES: O=C1CC(c2ccccc2)n2nc(S(=O)(=O)C3CC3)nc21]

Step 4: 2-cyclopropylsulfonyl-5-phenyl-5,6-dihydropyrrolo[1,2-b][1,2,4]triazol-7-one To a solution of 2-cyclopropylsulfonyl-5-phenyl-6,7-dihydro-5H-pyrrolo[1,2-b][1,2,4]triazol-7-ol (1.38 g, 4.5 mmol) in 1,2-dichloroethane (20 mL) was added manganese dioxide (1.9 g, 22.6 mmol). The mixture was stirred at 60° C. for 4 h and diluted with water (20 mL). The resulting mixture was extracted with ethyl acetate (3×20 mL). The combined organic layers were washed with brine (2×20 mL), dried over sodium sulfate and concentrated under reduced pressure. The residue was purified by column chromatography (silica gel, 100-200 mesh, 0 to 30% ethyl acetate in petroleum ether) to afford 2-cyclopropylsulfonyl-5-phenyl-5,6-dihydropyrrolo[1,2-b][1,2,4]triazol-7-one (1.0 g, 73%) as a white solid. LCMS $R_T$=0.583 min, m/z=304.1 [M+H]$^+$.

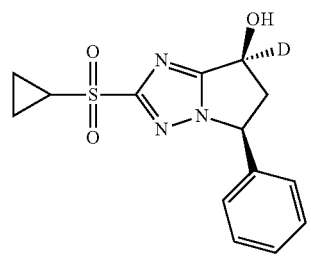 [SMILES: [2H][C@]1(O)C[C@@H](c2ccccc2)n2nc(S(=O)(=O)C3CC3)nc21]

Step 5: cis-2-cyclopropylsulfonyl-7-deuterio-5-phenyl-5,6-dihydropyrrolo[1,2-b][1,2,4]triazol-7-ol To a mixture of 2-cyclopropylsulfonyl-5-phenyl-5,6-dihydropyrrolo[1,2-b][1,2,4]triazol-7-one (0.95 g, 3.1 mmol) in methanol (10 mL) was added sodium borodeuteride (393 mg, 9.4 mmol). The mixture was stirred at 20° C. for 1 h and concentrated under reduced pressure. The residue was diluted with water (50 mL) and extracted with ethyl acetate (3×30 mL). The combined organic layers were washed with brine (40 mL), dried over sodium sulfate and concentrated to afford crude cis-2-cyclopropylsulfonyl-7-deuterio-5-phenyl-5,6-dihydropyrrolo[1,2-b][1,2,4]triazol-7-ol (0.5 g, 52%) as a yellow solid. LCMS $R_T$=0.566 min, m/z=307.1 [M+H]$^+$.

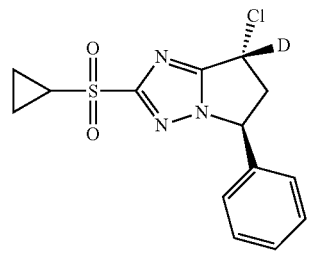 [SMILES: [2H][C@@]1(Cl)C[C@@H](c2ccccc2)n2nc(S(=O)(=O)C3CC3)nc21]

Step 6: trans-7-chloro-2-cyclopropylsulfonyl-7-deuterio-5-phenyl-5,6-dihydropyrrolo[1,2-b][1,2,4]triazole To a mixture of cis-2-cyclopropylsulfonyl-7-deuterio-5-phenyl-5,6-dihydropyrrolo[1,2-b][1,2,4]triazol-7-ol (50 mg, 0.16 mmol) in dichloromethane (10 mL) was added sulfuryl chloride (66 mg, 0.49 mmol). The mixture was stirred at 20° C. for 1 h and concentrated under reduced pressure. The residue was diluted with water (20 mL) and extracted with ethyl acetate (3×20 mL). The combined organic layers were washed with brine (30 mL), dried over sodium sulfate and concentrated to afford crude trans-7-chloro-2-cyclopropylsulfonyl-7-deuterio-5-phenyl-5,6-dihydropyrrolo[1,2-b][1,2,4]triazole (30 mg, 57%) as a yellow solid. LCMS $R_T$=0.889 min, m/z=325.0 [M+H]$^+$.

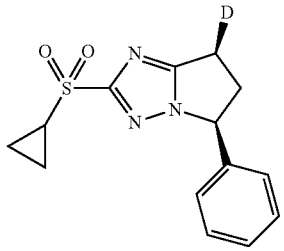 [SMILES: [2H][C@H]1C[C@@H](c2ccccc2)n2nc(S(=O)(=O)C3CC3)nc21]

Step 7: (5S,7S)-2-cyclopropylsulfonyl-7-deuterio-5-phenyl-6,7-dihydro-5H-pyrrolo[1,2-b][1,2,4]triazole A mixture of trans-7-chloro-2-cyclopropylsulfonyl-7-deuterio-5-phenyl-5,6-dihydropyrrolo[1,2-b][1,2,4]triazole (120 mg, 0.37 mmol) and Raney Nickle (108 mg, 1.85 mmol) in methanol (15 mL) was hydrogenated (15 psi) at 25° C. for 2 h and filtered. The filtrate was concentrated under reduced pressure. The residue was purified by column chromatography (silica gel, 100-200 mesh, 0 to 50% ethyl acetate in petroleum ether) to afford cis-2-cyclopropylsulfonyl-7-deuterio-5-phenyl-6,7-dihydro-5H-pyrrolo[1,2-b][1,2,4]triazole (50 mg, 47%) as a white solid. LCMS $R_T$=0.609 min, m/z=291.1 [M+H]$^+$.

The cis mixture was further separated by chiral SFC to give arbitrarily assigned:

(5R,7R)-2-cyclopropylsulfonyl-7-deuterio-5-phenyl-6,7-dihydro-5H-pyrrolo[1,2-b][1,2,4]triazole (Peak 1, retention time=3.083 min) (2.5 mg, 5%) as a white solid. $^1$H NMR (400 MHz, CD$_3$OD) δ 7.41-7.34 (m, 3H), 7.26-7.21 (m, 2H), 5.61-5.56 (m, 1H), 3.27-3.19 (m, 1H), 3.12-3.06 (m, 1H), 2.86-2.74 (m, 1H), 2.74-2.62 (m, 1H), 1.29-1.23 (m, 2H), 1.15-1.10 (m, 2H). LCMS $R_T$=1.455 min, m/z=291.1 [M+H]$^+$.

(5S,7S)-2-cyclopropylsulfonyl-7-deuterio-5-phenyl-6,7-dihydro-5H-pyrrolo[1,2-b][1,2,4]triazole (Peak 2, retention time=4.591 min) (11.4 mg, 22%) as a white solid. $^1$H NMR (400 MHz, CD$_3$OD) δ 7.42-7.30 (m, 3H), 7.27-7.22 (m, 2H), 5.60-5.55 (m, 1H), 3.27-3.19 (m, 1H), 3.13-3.06 (m, 1H), 2.85-2.72 (m, 1H), 2.76-2.60 (m, 1H), 1.30-1.24 (m, 2H), 1.16-1.11 (m, 2H). LCMS $R_T$=1.453 min, m/z=291.1 [M+H]$^+$.

SFC condition: Column: Chiralpak IC 100*4.6 mm I.D., 3 μm Mobile phase: 40% of ethanol (0.05% DEA) in CO$_2$ Flow rate: 3 mL/min Column temp: 40° C.

Example 42

(5S,7S)-2-(cyclopropylsulfonyl)-5-(3,5-difluorophenyl)-7-fluoro-6,7-dihydro-5H-pyrrolo[1,2-b][1,2,4]triazole

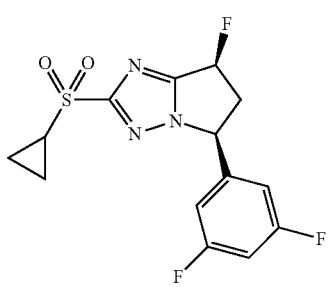 [SMILES: O=S(=O)(c1nc2n(n1)[C@H](c1cc(F)cc(F)c1)C[C@@H]2F)C1CC1]

(5S,7S)-2-(cyclopropylsulfonyl)-5-(3,5-difluorophenyl)-7-fluoro-6,7-dihydro-5H-pyrrolo[1,2-b][1,2,4]triazole was prepared according to method 18 starting from (5S,7S)-5-(3,5-difluorophenyl)-7-fluoro-6,7-dihydro-5H-pyrrolo[1,2-b][1,2,4]triazole-2-thiol (prepared according to Method 23 starting from 3,5-difluorobenzoic acid). The final compound was purified by RP-HPLC (acetonitrile 44-74%/0.05% ammonia hydroxide in water) to give (5S,7S)-2-cyclopropylsulfonyl-5-(3,5-difluorophenyl)-7-fluoro-6,7-dihydro-5H-pyrrolo[1,2-b][1,2,4]triazole (21.5 mg, 60%) as a white solid. $^1$H NMR (400 MHz, CDCl$_3$) δ 6.89-6.77 (m, 3H), 6.14-5.95 (m, 1H), 5.53-5.48 (m, 1H), 3.76-3.59 (m, 1H), 3.04-2.91 (m, 1H), 2.78-2.74 (m, 1H), 1.53-1.47 (m, 2H), 1.17-1.15 (m, 2H). LC-MS $R_T$=0.972 min, m/z=344.1 [M+H]

Example 43

(5S,7S)-5-(3-chlorophenyl)-2-(cyclopropylsulfonyl)-7-fluoro-6,7-dihydro-5H-pyrrolo[1,2-b][1,2,4]triazole

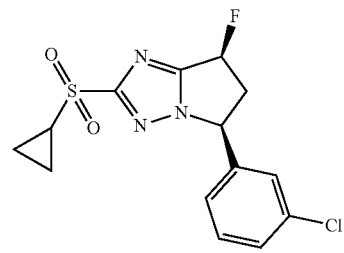 [SMILES: O=S(=O)(c1nc2n(n1)[C@H](c1cccc(Cl)c1)C[C@@H]2F)C1CC1]

(5S,7S)-5-(3-chlorophenyl)-2-cyclopropylsulfonyl-7-fluoro-6,7-dihydro-5H-pyrrolo[1,2-b][1,2,4]triazole was prepared according to method 18 starting from (5S,7S)-7-fluoro-5-(3-chlorophenyl)-6,7-dihydro-5H-pyrrolo[1,2-b][1,2,4]triazole-2-thiol (prepared according to Method 23 starting from ethyl 3-chlorobenzoate). The final compound was purified by RP-HPLC (acetonitrile 35-65%/0.225% formic acid in water) to give (5S,7S)-5-(3-chlorophenyl)-2-cyclopropylsulfonyl-7-fluoro-6,7-dihydro-5H-pyrrolo[1,2-b][1,2,4]triazole (85 mg, 59%) as a white solid. $^1$H NMR (400 MHz, CDCl$_3$) δ 7.41-7.31 (m, 2H), 7.26-7.24 (m, 1H), 7.16-7.10 (m, 1H), 6.14-5.95 (m, 1H), 5.56-5.45 (m, 1H), 3.78-3.57 (m, 1H), 3.06-2.87 (m, 1H), 2.80-2.70 (m, 1H), 1.52-1.39 (m, 2H), 1.22-1.07 (m, 2H). LCMS $R_T$=0.918 min, m/z=341.9 [M+H]$^+$.

Example 44

(5S,7S)-2-cyclopropylsulfonyl-5-(3,4-difluorophenyl)-7-fluoro-6,7-dihydro-5H-pyrrolo[1,2-b][1,2,4]triazole

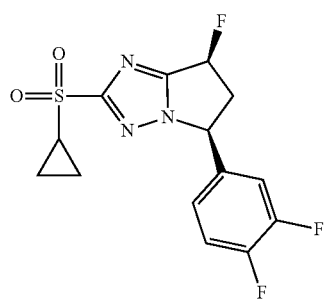 [SMILES: O=S(=O)(c1nc2n(n1)[C@H](c1ccc(F)c(F)c1)C[C@@H]2F)C1CC1]

Step 1: (5S,7S)-2-cyclopropylsulfanyl-5-(3,4-difluorophenyl)-7-fluoro-6,7-dihydro-5H-pyrrolo[1,2-b][1,2,4]triazole

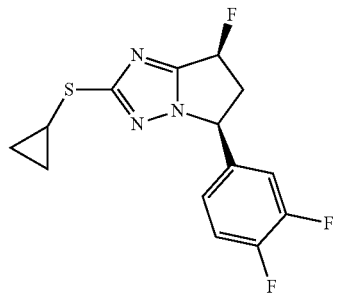 [SMILES: Fc1ccc([C@@H]2C[C@H](F)c3nc(SC4CC4)nn32)cc1F]

A mixture of 2,2'-bipyridine (17 mg, 0.11 mmol), (5S,7S)-5-(3,4-difluorophenyl)-7-fluoro-6,7-dihydro-5H-pyrrolo[1,2-b][1,2,4]triazole-2-thiol (150 mg, 0.55 mmol), cyclopropylboronic acid (143 mg, 0.55 mmol), copper(I) thiophene-2-carboxylate (105 mg, 0.55 mmol) and sodium carbonate (176 mg, 1.66 mmol) in 1,2-dichloroethane (7.5 mL) was stirred at 50° C. for 3 h and concentrated under reduced pressure. The residue was purified by preparative TLC (50% ethyl acetate in petroleum ether, $R_f$=0.5) to afford (5S,7S)-2-cyclopropyl sulfanyl-5-(3,4-difluorophenyl)-7-fluoro-6,7-dihydro-5H-pyrrolo[1,2-b][1,2,4]triazole (80 mg, 47%) as a yellow solid. LCMS $R_T$=0.868 min, m/z=312.0 [M+H]$^+$.

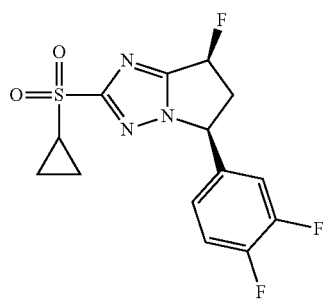 [SMILES: O=S(=O)(c1nc2n(n1)[C@H](c1ccc(F)c(F)c1)C[C@@H]2F)C1CC1]

Step 2: (5S,7S)-2-cyclopropylsulfonyl-5-(3,4-difluorophenyl)-7-fluoro-6,7-dihydro-5H-pyrrolo[1,2-b][1,2,4]triazole A mixture of ruthenium(III) chloride (5 mg, 0.03 mmol), sodium periodate (220 mg, 1.03 mmol) and (5S,7S)-2-cyclopropylsulfanyl-5-(3,4-difluorophenyl)-7-fluoro-6,7-dihydro-5H-pyrrolo[1,2-b][1,2,4]triazole (80 mg, 0.26 mmol) in acetonitrile (2.5 mL)/water (2.5 mL)/ethyl acetate (2.5 mL) was stirred at 30° C. for 1 h and filtered. The filtrate was diluted with water (10 mL) and extracted with ethyl acetate (3×10 mL). The combined organic layers were dried over sodium sulfate and concentrated under reduce pressure. The residue was purified by RP-HPLC (acetonitrile 35-65%/0.05% ammonia hydroxide in water) to afford (5S,7S)-2-cyclopropylsulfonyl-5-(3,4-difluorophenyl)-7-fluoro-6,7-dihydro-5H-pyrrolo[1,2-b][1,2,4]triazole (67.7 mg, 87%) as a white solid. $^1$H NMR (400 MHz, CDCl$_3$) δ 7.25-7.18 (m, 1H), 7.14-7.12 (m, 1H), 7.11-7.05 (m, 1H), 6.15-5.97 (m, 1H), 5.55-5.45 (m, 1H), 3.73-3.59 (m, 1H), 3.03-2.86 (m, 1H), 2.81-2.70 (m, 1H), 1.52-1.46 (m, 2H), 1.20-1.13 (m, 2H). LCMS $R_T$=0.902 min, m/z=343.9 [M+H]$^+$.

Example 45

(5S,7S)-5-(2-chloro-3-fluoro-phenyl)-2-cyclopropylsulfonyl-7-fluoro-6,7-dihydro-5H-pyrrolo[1,2-b][1,2,4]triazole

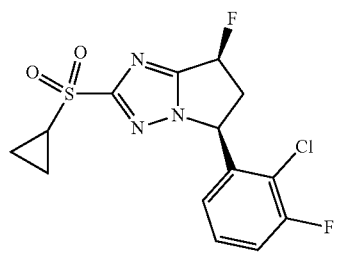 [SMILES: O=S(=O)(c1nc2n(n1)[C@H](c1cccc(F)c1Cl)C[C@@H]2F)C1CC1]

(5S,7S)-5-(2-chloro-3-fluoro-phenyl)-2-cyclopropylsulfonyl-7-fluoro-6,7-dihydro-5H-pyrrolo[1,2-b][1,2,4]triazole was prepared according to method 18 starting from (5S,7S)-5-(2-chloro-3-fluorophenyl)-7-fluoro-6,7-dihydro-5H-pyrrolo[1,2-b][1,2,4]triazole-2-thiol (prepared according to Method 23 starting from 2-chloro-3-fluorobenzoic acid). The final compound was purified by chiral SFC to give (5S,7S)-5-(2-chloro-3-fluoro-phenyl)-2-cyclopropylsulfonyl-7-fluoro-6,7-dihydro-5H-pyrrolo[1,2-b][1,2,4]triazole (10.1 mg, 22% yield) as a white solid. $^1$H NMR (400 MHz, CD$_3$OD) δ 7.40-7.32 (m, 2H), 6.78-6.75 (m, 1H), 6.23-6.06 (m, 2H), 3.92-3.81 (m, 1H), 2.92-2.78 (m, 2H), 1.36-1.32 (m, 2H), 1.21-1.17 (m, 2H). LC-MS $R_T$=0.914 min, m/z=360.0 [M+H]$^+$.

SFC condition (prep): Column: DAICEL CHIRALCEL OJ-H (250 mm×30 mm, 5 μm); Mobile phase: A: CO$_2$ B: 0.1% NH$_3$H$_2$O EtOH; Gradient: from 25% to 25% of B; Flow rate: 50 mL/min Column temperature: 40° C.

Example 46

(5S,7S)-5-(3-chloro-2-fluoro-phenyl)-2-cyclopropylsulfonyl-7-fluoro-6,7-dihydro-5H-pyrrolo[1,2-b][1,2,4]triazole

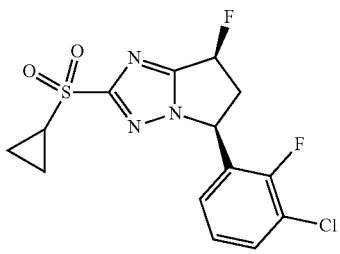 [SMILES: O=S(=O)(c1nc2n(n1)[C@H](c1cccc(Cl)c1F)C[C@@H]2F)C1CC1]

(5S,7S)-5-(3-chloro-2-fluoro-phenyl)-2-cyclopropylsulfonyl-7-fluoro-6,7-dihydro-5H-pyrrolo[1,2-b][1,2,4]triazole was prepared according to method 18 starting from (5S,7S)-5-(3-chloro-2-fluorophenyl)-7-fluoro-6,7-dihydro-5H-pyrrolo[1,2-b][1,2,4]triazole-2-thiol (prepared according to Method 23 starting from 3-chloro-2-fluorobenzoic acid). The final compound was purified by RP-HPLC (acetonitrile 40-70%/0.05% hydrochloric acid in water) to give (5S,7S)-5-(3-chloro-2-fluoro-phenyl)-2-cyclopropylsulfonyl-7-fluoro-6,7-dihydro-5H-pyrrolo[1,2-b][1,2,4]triazole (41.2 mg, 26%) as white solid. $^1$H NMR (400 MHz, CD$_3$OD) δ 7.58-7.53 (m, 1H), 7.23 (t, J=8.0 Hz, 1H), 7.13-7.08 (m, 1H), 6.24-6.07 (m, 1H), 5.96-5.91 (m, 1H), 3.90-3.76 (m, 1H), 2.95-2.83 (m, 2H), 1.36-1.30 (m, 2H), 1.20-1.14 (m, 2H). LCMS R$_T$=0.923 min, m/z=359.9 [M+H]$^+$.

Example 47

(5S,7S)-5-(5-chloro-2-fluoro-phenyl)-2-(cyclopropylsulfonyl)-7-fluoro-6,7-dihydro-5H-pyrrolo[1,2-b][1,2,4]triazole

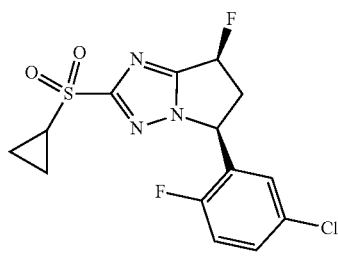 [SMILES: O=S(=O)(c1nc2n(n1)[C@H](c1cc(Cl)ccc1F)C[C@@H]2F)C1CC1]

(5S,7S)-5-(5-chloro-2-fluoro-phenyl)-2-cyclopropylsulfonyl-7-fluoro-6,7-dihydro-5H-pyrrolo[1,2-b][1,2,4]triazole was prepared according to method 18 starting from (5S,7S)-5-(5-chloro-2-fluorophenyl)-7-fluoro-6,7-dihydro-5H-pyrrolo[1,2-b][1,2,4]triazole-2-thiol (prepared according to Method 23 starting from 5-chloro-2-fluorobenzoic acid). The final compound was purified by RP-HPLC (acetonitrile 45-75/0.225% formic acid in water) to give (5S,7S)-5-(5-chloro-2-fluoro-phenyl)-2-cyclopropylsulfonyl-7-fluoro-6,7-dihydro-5H-pyrrolo[1,2-b][1,2,4]triazole (40 mg, 46%) as a white solid. $^1$H NMR (400 MHz, CDCl$_3$) 7.38-7.31 (m, 1H), 7.17-7.04 (m, 1H), 6.98-6.94 (m, 1H), 6.17-5.96 (m, 1H), 5.81-5.76 (m, 1H), 3.77-3.69 (m, 1H), 3.00-2.89 (m, 1H), 2.83-2.73 (m, 1H), 1.55-1.45 (m, 2H), 1.23-1.12 (m, 2H). LCMS R$_T$=0.995 min, m/z=360.1 [M+H]$^+$.

Example 48

(5S,7S)-2-cyclopropylsulfonyl-7-fluoro-5-(3-fluoro-phenyl)-6,7-dihydro-5H-pyrrolo 5-[1,2-b][1,2,4]triazole

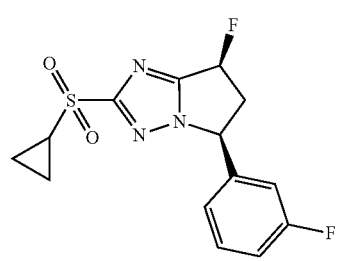 [SMILES: O=S(=O)(c1nc2n(n1)[C@H](c1cccc(F)c1)C[C@@H]2F)C1CC1]

(5S,7S)-2-cyclopropylsulfonyl-7-fluoro-5-(3-fluorophenyl)-6,7-dihydro-5H-pyrrolo[1,2-b][1,2,4]triazole was prepared according to method 18 starting from (5S,7S)-7-fluoro-5-(3-fluorophenyl)-6,7-dihydro-5H-pyrrolo[1,2-b][1, 2,4]triazole-2-thiol (prepared according to Method 23 starting from 3-fluorobenzaldehyde). The final compound was purified by RP-HPLC (acetonitrile 30-60%/0.05% ammonia hydroxide in water) to give (5S,7S)-2-cyclopropylsulfonyl-7-fluoro-5-(3-fluorophenyl)-6,7-dihydro-5H-pyrrolo[1,2-b][1,2,4]triazole (37 mg, 47%) as a white solid. $^1$H NMR (400 MHz, CD$_3$OD) δ 7.48-7.43 (m, 1H), 7.15-7.04 (m, 3H), 6.25-6.02 (m, 1H), 5.77-5.65 (m, 1H), 3.82-3.75 (m, 1H), 2.91-2.80 (m, 2H), 1.38-1.25 (m, 2H), 1.21-1.07 (m, 2H). LCMS R$_T$=1.005 min, m/z=326.1 [M+H]$^+$.

Example 49

(5S,7S)-2-(3,3-difluorocyclobutyl)sulfinyl-7-fluoro-5-phenyl-6,7-dihydro-5H-pyrrolo[1,2-b][1,2,4]triazole

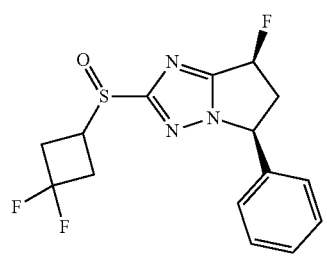 [SMILES: O=S(c1nc2n(n1)[C@H](c1ccccc1)C[C@@H]2F)C1CC(F)(F)C1]

To a solution of (5S,7S)-2-(3,3-difluorocyclobutyl)sulfanyl-7-fluoro-5-phenyl-6,7-dihydro-5H-pyrrolo[1,2-b][1,2,4]triazole (30 mg, 0.09 mmol) in dichloromethane (2 mL) was added 3-chloroperoxybenzoic acid (85%, 19 mg, 0.09 mmol). The mixture was stirred at 0° C. for 2 h and quenched by addition of saturated aqueous sodium bicarbonate (10 mL). The resulting mixture was extracted with ethyl acetate (3×15 mL). The combined organic layers were washed with brine (30 mL), dried over sodium sulfate and concentrated under reduced pressure. The residue was purified by RP-HPLC (acetonitrile 25-55%/0.05% ammonia hydroxide in water) to afford (5S,7S)-2-(3,3-difluorocyclobutyl)sulfinyl-7-fluoro-5-phenyl-6,7-dihydro-5H-pyrrolo[1,2-b][1,2,4]triazole (16.4 mg, 51%) as a yellow oil. $^1$H NMR (400 MHz, CDCl$_3$) δ 7.43-7.40 (m, 3H), 7.25-7.22 (m, 2H), 6.10-5.94 (m, 1H), 5.52-5.47 (m, 1H), 3.78-3.72 (m, 1H), 3.71-3.58 (m, 1H), 3.46-3.26 (m, 1H), 3.02-2.92 (m, 2H), 2.91-2.80 (m, 1H), 2.78-2.65 (m, 1H). LCMS R$_T$=0.997 min, m/z=342.1 [M+H]$^+$.

Example 50: Method 20

(5S,7S)-2-(3,3-difluorocyclobutyl)sulfonyl-7-fluoro-5-phenyl-6,7-dihydro-5H-pyrrolo[1,2-b][1,2,4]triazole

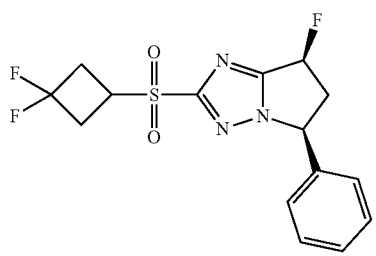 [SMILES: O=S(=O)(c1nc2n(n1)[C@H](c1ccccc1)C[C@@H]2F)C1CC(F)(F)C1]

Step 1: 3-(((5S,7S)-7-fluoro-5-phenyl-6,7-dihydro-5H-pyrrolo[1,2-b][1,2,4]triazol-2-yl)thio)cyclobutanone

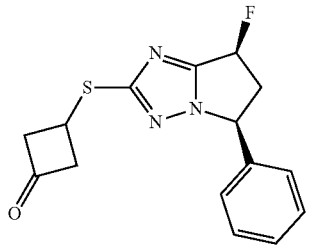 [SMILES: O=C1CC(Sc2nc3n(n2)[C@H](c2ccccc2)C[C@@H]3F)C1]

A mixture of (5S,7S)-7-fluoro-5-phenyl-6,7-dihydro-5H-pyrrolo[1,2-b][1,2,4]triazole-2-thiol (400 mg, 1.70 mmol) and 3-bromocyclobutanone (329 mg, 2.21 mmol) in N,N-dimethylformamide (10 mL) was added sodium hydride (60%, 102 mg, 2.55 mmol) at 0° C. under nitrogen atmosphere. The mixture was stirred at 20° C. for 16 h and quenched by addition of water (20 mL). The resulting mixture was extracted with ethyl acetate (3×20 mL). The combined organic layers were dried over sodium sulfate and concentrated under reduced pressure. The residue was purified by column chromatography (silica gel, 100-200 mesh, 0 to 30% ethyl acetate in petroleum ether) to afford 3-[[(5S,7S)-7-fluoro-5-phenyl-6,7-dihydro-5H-pyrrolo[1,2-b][1,2,4]triazol-2-yl]sulfanyl]cyclobutanone (300 mg, 58%) as a yellow oil. LCMS $R_T$=1.660 min, m/z=304.1 [M+H]$^+$.

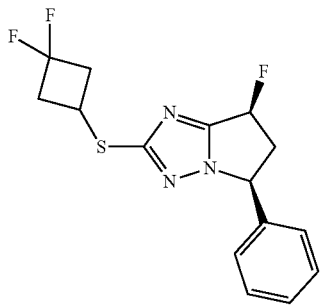 [SMILES: F[C@H]1C[C@@H](c2ccccc2)n2nc(SC3CC(F)(F)C3)nc21]

Step 2: (5S,7S)-2-(3,3-difluorocyclobutyl)sulfanyl-7-fluoro-5-phenyl-6,7-dihydro-5H-pyrrolo[1,2-b][1,2,4]triazole To a solution of 3-[[(5S,7S)-7-fluoro-5-phenyl-6,7-dihydro-5H-pyrrolo[1,2-b][1,2,4]triazol-2-yl]sulfanyl]cyclobutanone (120 mg, 0.40 mmol) in dichloromethane (2 mL) was added diethylaminosulfur trifluoride (0.5 mL, 1.98 mmol). The mixture was stirred at 25° C. for 2 h and diluted with dichloromethane (20 mL). The separated organic layer was washed with saturated aqueous sodium bicarbonate (2×15 mL), brine (20 mL), dried over sodium sulfate and concentrated under reduced pressure. The residue was purified by preparative TLC (30% ethyl acetate in petroleum ether) to afford (5S,7S)-2-(3,3-difluorocyclobutyl)sulfanyl-7-fluoro-5-phenyl-6,7-dihydro-5H-pyrrolo[1,2-b][1,2,4]triazole (60 mg, 47%) as a brown oil. LCMS $R_T$=0.721 min, m/z=326.1 [M+H]$^+$.

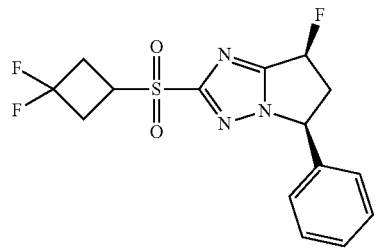 [SMILES: O=S(=O)(c1nc2n(n1)[C@H](c1ccccc1)C[C@@H]2F)C1CC(F)(F)C1]

Step 3: (5S,7S)-2-(3,3-difluorocyclobutyl)sulfonyl-7-fluoro-5-phenyl-6,7-dihydro-5H-pyrrolo[1,2-b][1,2,4]triazole To a solution of (5S,7S)-2-(3,3-difluorocyclobutyl)sulfanyl-7-fluoro-5-phenyl-6,7-dihydro-5H-pyrrolo[1,2-b][1,2,4]triazole (60 mg, 0.18 mmol) in dichloromethane (1.0 mL) was added 3-chloroperoxybenzoic acid (85%, 112 mg, 0.55 mmol). The mixture was stirred at 25° C. for 2 h and quenched by addition of saturated aqueous sodium bicarbonate (10 mL). The resulting mixture was extracted with ethyl acetate (3×15 mL). The combined organic layers were washed with brine (30 mL), dried over sodium sulfate and concentrated under reduced pressure. The residue was purified by RP-HPLC (acetonitrile 35-65%/0.05% ammonia hydroxide in water) to afford (5S,7S)-2-(3,3-difluorocyclobutyl)sulfonyl-7-fluoro-5-phenyl-6,7-dihydro-5H-pyrrolo[1,2-b][1,2,4]triazole (28 mg, 42%) as a white solid. $^1$H NMR (400 MHz, CDCl$_3$) δ 7.44-7.41 (m, 3H), 7.27-7.23 (m, 2H), 6.13-6.11 (m, 0.5H), 6.00-5.97 (m, 0.5H), 5.55-5.52 (m, 1H), 4.00-3.96 (m, 1H), 3.72-3.65 (m, 1H), 3.26-3.22 (m, 2H), 3.07-2.90 (m, 3H). LCMS $R_T$=1.064 min, m/z=358.1 [M+H]$^+$.

Example 51, 52 and 53: Method 21

(5S,7S)-2-((S)-(difluoromethyl)sulfinyl)-7-fluoro-5-(2-fluorophenyl)-6,7-dihydro-5H-pyrrolo[1,2-b][1,2,4]triazole (51), (5S,7S)-2-((R)-(difluoromethyl)sulfinyl)-7-fluoro-5-(2-fluorophenyl)-6,7-dihydro-5H-pyrrolo[1,2-b][1,2,4]triazole (52) and (5S,7S)-2-((difluoromethyl)sulfonyl)-7-fluoro-5-(2-fluorophenyl)-6,7-dihydro-5H-pyrrolo[1,2-b][1,2,4]triazole (53)

(51)

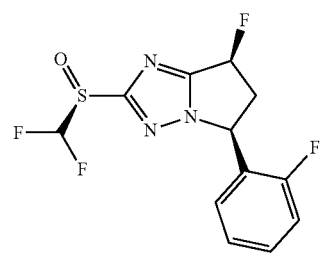

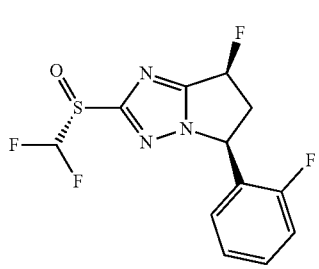

(52)

(53)

Step 1: 1-(2-fluorophenyl)but-3-en-1-ol

To a solution of 2-fluorobenzaldehyde (15.0 g, 120.86 mmol) in tetrahydrofuran (250 mL) was added allylmagnesium bromide (1.0 M in tetrahydrofuran, 150.0 mL, 150.0 mmol) at 0° C. under nitrogen atmosphere. After addition, the mixture was allowed to warm to 25° C. and stirred for 2 h before quenched by addition of saturated aqueous ammonium chloride (100 mL). The resulting mixture was extracted with ethyl acetate (2×100 mL). The combined organic layers were dried over sodium sulfate and concentrated under reduce pressure. The residue was purified by column chromatography (silica gel, 100-200 mesh, 0 to 5% ethyl acetate in petroleum ether) to afford 1-(2-fluorophenyl)but-3-en-1-ol (6.0 g, 24%) as a yellow oil. $^1$H NMR (400 MHz, CDCl$_3$) δ 7.49-7.27 (m, 1H), 7.29-7.12 (m, 2H), 7.05-7.00 (m, 1H), 5.89-5.80 (m, 1H), 5.20-5.13 (m, 2H), 5.15-5.07 (m, 1H), 2.66-2.55 (m, 1H), 2.57-5.48 (m, 1H).

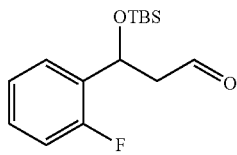 [SMILES: CC(C)(C)[Si](C)(C)OC(CC=O)c1ccccc1F]

Step 2: tert-butyl((1-(2-fluorophenyl)but-3-en-1-yl)oxy)dimethylsilane

To a solution of 1-(2-fluorophenyl)but-3-en-1-ol (6.0 g, 36.1 mmol) in dichloromethane (50 mL) was added imidazole (4.9 g, 72.2 mmol) and tert-butyldimethylchlorosilane (7.1 g, 146.9 mmol). The reaction mixture was stirred at 25° C. for 16 h and quenched by addition of water (100 mL). The mixture was extracted with dichloromethane (2×100 mL). The combined organic layers were washed with brine (100 mL), dried over sodium sulfate and concentrated under reduced pressure. The residue was purified by column chromatography (silica gel, 100-200 mesh, 100% petroleum ether) to afford tert-butyl-[1-(2-fluorophenyl)but-3-enoxy]-dimethyl-silane (8.5 g, 84%) as a light oil. $^1$H NMR (400 MHz, CDCl$_3$) δ 7.60-7.36 (m, 1H), 7.34-7.18 (m, 2H), 7.13-7.02 (m, 1H), 5.97-5.85 (m, 1H), 5.21-5.07 (m, 3H), 2.60-2.48 (m, 2H), 0.99 (s, 9H), 0.15 (s, 3H), 0.00 (s, 3H).

Step 3: 3-((tert-butyldimethylsilyl)oxy)-3-(2-fluorophenyl)propanal

To a solution of tert-butyl-[1-(2-fluorophenyl)but-3-enoxy]-dimethyl-silane (8.50 g, 30.3 mmol) in water (100 mL) and tetrahydrofuran (100 mL) was added osmium tetroxide (0.15 g, 0.6 mmol). After stirred for 30 min at 25° C., sodium periodate (25.90 g, 121.2 mmol) was added in small portions over 2 h. The resulting mixture was stirred for 2 h at 25° C. and quenched by addition of cold saturated aqueous sodium thiosulfate (100 mL). The mixture was stirred for 30 min and then extracted with ethyl acetate (3×200 mL). The combined organic layers were washed with water (50 mL), brine (50 mL), dried over sodium sulfate and concentrated under reduced pressure. The residue was purified by column chromatography (silica gel, 100-200 mesh, 0 to 5% ethyl acetate in petroleum ether) to afford 3-[tert-butyl(dimethyl)silyl]oxy-3-(2-fluorophenyl)propanal (5.5 g, 64%) as a black oil. $^1$H NMR (400 MHz, CDCl$_3$) δ 9.84-9.77 (m, 1H), 7.53-7.51 (m, 1H), 7.31-7.24 (m, 1H), 7.21-7.13 (m, 1H), 7.09-6.98 (m, 1H), 5.58-5.55 (m, 1H), 2.85-2.80 (m, 1H), 2.74-2.64 (m, 1H), 0.92-0.85 (m, 9H), 0.09 (s, 3H), −0.09 (s, 3H).

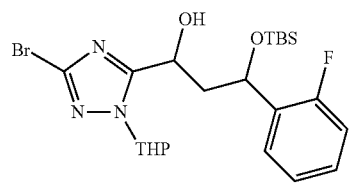

Step 4: 1-(3-bromo-1-(tetrahydro-2H-pyran-2-yl)-1H-1,2,4-triazol-5-yl)-3-((tert-butyldimethylsilyl)oxy)-3-(2-fluorophenyl)propan-1-ol To a cooled (−78° C.) solution of 3,5-dibromo-1-tetrahydropyran-2-yl-1,2,4-triazole (6.3 g, 20.1 mmol) in tetrahydrofuran (50 mL) was added n-butyllithium (2.5 M in hexanes, 8.6 mL, 21.4 mmol) under nitrogen atmosphere. The mixture was stirred at −78° C. for 30 min, then a solution of 3-[tert-butyl(dimethyl)silyl]oxy-3-(2-fluorophenyl)propanal (5.5 g, 19.5 mmol) in tetrahydrofuran (25 mL) was added dropwise. After addition, the mixture was stirred at −78° C. for 1.5 h and then quenched by addition of saturated aqueous ammonium chloride (50 mL). The resulting mixture was extracted with ethyl acetate (2×100 mL). The combined organic layers were dried over sodium sulfate and concentrated under reduce pressure. The residue was purified by column chromatography (silica gel, 100-200 mesh, 0 to 10% ethyl acetate in petroleum ether) to afford 1-(5-bromo-2-tetrahydropyran-2-yl-1,2,4-triazol-3-yl)-3- tert-butyl(dimethyl) silyl]oxy-3-(2-fluorophenyl)propan-1-ol (8.0 g, 80%) as a yellow oil.

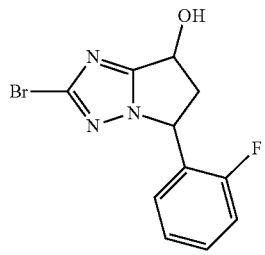 [SMILES: OC1CC(c2ccccc2F)n2nc(Br)nc21]

Step 5: 2-bromo-5-(2-fluorophenyl)-6,7-dihydro-5H-pyrrolo[1,2-b][1,2,4]triazol-7-ol A mixture of 1-(5-bromo-2-tetrahydropyran-2-yl-1,2,4-triazol-3-yl)-3-[tert-butyl (dimethyl)silyl]oxy-3-(2-fluorophenyl)propan-1-ol (8.0 g, 15.55 mmol) and trifluoroacetic acid (30.0 mL) in dichloromethane (3.0 mL) was stirred at 50° C. for 5 h and concentrated under reduced pressure. The residue was adjusted to pH=9 by addition of saturated aqueous sodium bicarbonate and extracted with dichloromethane (2×50 mL). The combined organic layers were washed with water (50 mL), brine (50 mL), dried over sodium sulfate and concentrated under reduced pressure. The residue was purified by column chromatography (silica gel, 100-200 mesh, 0 to 30% ethyl acetate in petroleum ether) to afford 2-bromo-5-(2-fluorophenyl)-6,7-dihydro-5H-pyrrolo[1,2-b][1,2,4]triazol-7-ol (2.0 g, 43%) as a light yellow solid. LCMS $R_T$=0.505 min, m/z=298.1 [M+H]$^+$.

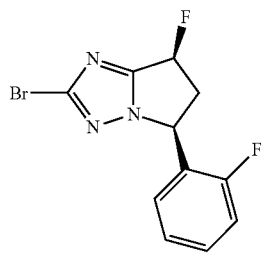

Step 6: (5S,7S)-2-bromo-7-fluoro-5-(2-fluorophenyl)-6,7-dihydro-5H-pyrrolo[1,2-b][1,2,4]triazole To a solution of 2-bromo-5-(2-fluorophenyl)-6,7-dihydro-5H-pyrrolo[1,2-b][1,2,4]triazol-7-ol (750 mg, 2.52 mmol) in toluene (20 mL) was added diethylaminosulfur trifluoride (1.62 g, 10.0 6 mmol) at 0° C. The reaction mixture was stirred at 0° C. for 1 h and then slowly added into ice water (20 mL) at 0° C. The mixture was extracted with dichloromethane (2×50 mL). The combined organic layers were washed with water (50 mL), brine (50 mL), dried over sodium sulfate and concentrated under reduced pressure. The residue was purified by column chromatography (silica gel, 100-200 mesh, 0 to 15% ethyl acetate in petroleum ether) to afford rac-(5S,7S)-2-bromo-7-fluoro-5-(2-fluorophenyl)-6,7-dihydro-5H-pyrrolo[1,2-b][1,2,4]triazole (250 mg, 33%) as a light yellow solid. $^1$H NMR (400 MHz, CDCl$_3$) δ 7.40-7.27 (q, J=6.6 Hz, 1H), 7.20-7.10 (m, 2H), 7.01-6.97 (m, 1H), 6.10-5.89 (m, 1H), 5.84-5.75 (m, 1H), 3.70-3.53 (m, 1H), 2.96-2.75 (m, 1H). LCMS $R_T$=1.112 min, m/z=300.0 [M+H]$^+$.

This cis mixture was further separated by chiral SFC to give:

(5S,7S)-2-bromo-7-fluoro-5-(2-fluorophenyl)-6,7-dihydro-5H-pyrrolo[1,2-b][1,2,4]triazole (Peak 2, retention time=3.408 min) (100 mg, 40%) as a white solid. (The 5R,7R-isomer was also collected (Peak 1, retention time=3.139 min) (100 mg, 40%)).

SFC condition: Column: ChiralPak AD-3 150×4.6 mm I.D., 3 um mobile phase: A: CO2 B: ethanol (0.05% DEA) Gradient: from 5% to 40% of B in 5 min and hold 40% for 2.5 min, then 5% of B for 2.5 min Flow rate: 2.5 mL/min Column temp.: 35° C.

Step 7: (5S,7S)-7-fluoro-5-(2-fluorophenyl)-6,7-dihydro-5H-pyrrolo[1,2-b][1,2,4]triazole-2-thiol

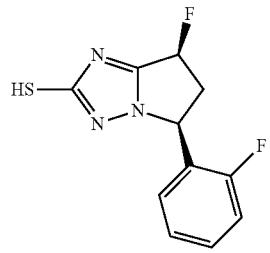 [SMILES: Fc1ccccc1[C@@H]1C[C@H](F)c2nc(Br)nn21]

A mixture of (5S,7S)-2-bromo-7-fluoro-5-(2-fluorophenyl)-6,7-dihydro-5H-pyrrolo[1,2-b][1,2,4]triazole (500 mg, 1.67 mmol), N,N-diisopropylethylamine (0.89 mL, 5.00 mmol), tris(dibenzylideneacetone)dipalladium (305 mg, 0.33 mmol), 4,5-bis(diphenylphosphino)-9,9-dimethylxanthene (964 mg, 1.67 mmol) and 3-mercaptopropionic acid-2-ethylhexylester (582 mg, 2.67 mmol) in 1,4-dioxane (30 mL) was stirred at 110° C. for 16 h and diluted with water (10 mL). The mixture was extracted with ethyl acetate (2×20 mL). The combined organic layers were concentrated under reduced pressure and the residue was purified by column chromatography (silica gel, 100-200 mesh, 0-20% ethyl acetate in petroleum ether) to give crude 2-ethylhexyl 3-[[(5S,7S)-7-fluoro-5-(2-fluorophenyl)-6,7-dihydro-5H-pyrrolo[1,2-b][1,2,4]triazol-2-yl]sulfanyl]propanoate (530 mg, 73%) as a light yellow solid.

A mixture of the above crude (480 mg, 1.1 mmol) and sodium ethoxide (224 mg, 3.29 mmol) in ethanol (10 mL) was stirred at 20° C. for 30 min and concentrated under reduced pressure. The residue was diluted with water (20 mL) and washed with ethyl acetate (20 mL). The aqueous phase was adjusted to pH=6 by addition of citric acid and extracted with ethyl acetate (3×20 mL). The combined organic layers were dried over sodium sulfate and concentrated under reduced pressure to give crude (5S,7S)-7-fluoro-5-(2-fluorophenyl)-6,7-dihydro-5H-pyrrolo[1,2-b][1,2,4]triazole-2-thiol (300 mg, 100%, two batches combined) as a yellow solid.

Step 8: (5S,7S)-2-((difluoromethyl)thio)-7-fluoro-5-(2-fluorophenyl)-6,7-dihydro-5H-pyrrolo[1,2-b][1,2,4]triazole

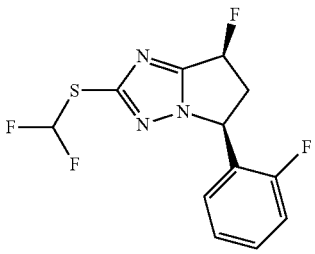 [SMILES: Fc1ccccc1[C@@H]1C[C@H](F)c2nc(SC(F)F)nn21]

A mixture of sodium (2-chloro-2,2-difluoro-acetyl)oxide (113 mg, 0.74 mmol), (5S,7S)-7-fluoro-5-(2-fluorophenyl)-6,7-dihydro-5H-pyrrolo[1,2-b][1,2,4]triazole-2-thiol (150 mg, 0.59 mmol) and cesium carbonate (482 mg, 1.48 mmol) in 1-methyl-2-pyrrolidinone (5 mL) was stirred at 100° C. for 3 h. The reaction was diluted with water (20 mL) and extracted with ethyl acetate (3×25 mL). The combined organic layers were concentrated under reduced pressure. The residue was purified by column chromatography (silica gel, 100-200 mesh, 0-20% ethyl acetate in petroleum ether) to give (5S,7S)-2-(difluoromethylsulfanyl)-7-fluoro-5-(2-fluorophenyl)-6,7-dihydro-5H-pyrrolo[1,2-b][1,2,4]triazole (43 mg, 24%) as a white solid.

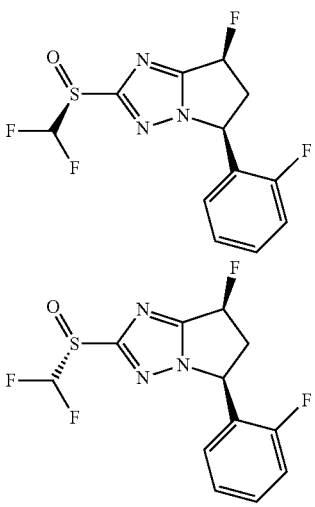

Step 9: (5S,7S)-2-((S)-(difluoromethyl)sulfinyl)-7-fluoro-5-(2-fluorophenyl)-6,7-dihydro-5H-pyrrolo[1,2-b][1,2,4]triazole and (5S,7S)-2-((R)-(difluoromethyl)sulfinyl)-7-fluoro-5-(2-fluorophenyl)-6,7-dihydro-5H-pyrrolo[1,2-b][1,2,4]triazole A mixture of (5S,7S)-2-(difluoromethylsulfanyl)-7-fluoro-5-(2-fluorophenyl)-6,7-dihydro-5H-pyrrolo[1,2-b][1,2,4]triazole (70 mg, 0.23 mmol) and 3-chloroperoxybenzoic acid (70 mg, 0.35 mmol) in dichloromethane (15 mL) was stirred at 25° C. for 16 h and quenched by addition of saturated aqueous sodium bicarbonate (15 mL). The resulting mixture was extracted with ethyl acetate (3×20 mL). The combined organic layers were dried over sodium sulfate and concentrated under reduced pressure. The residue was purified by RP-HPLC (acetonitrile 20-45%/0.225% HCl in water) to give (5S,7S)-2-(difluoromethylsulfinyl)-7-fluoro-5-(2-fluorophenyl)-6,7-dihydro-5H-pyrrolo[1,2-b][1,2,4]triazole (65 mg, 88%) as a white solid. This racemic material was further separated by chiral SFC to give: 5S,7S)-2-(S)-difluoromethylsulfinyl]-7-fluoro-5-(2-fluorophenyl)-6,7-dihydro-5H-pyrrolo[1,2-b][1,2,4]triazole (Peak 1, retention time=2.437 min) (22.6 mg, 48%) as a white solid. $^1$H NMR (400 MHz, CD$_3$OD) δ 7.44-7.24 (m, 1H), 7.22-6.96 (m, 4H), 6.24 (dd, J=2.4, 7.2 Hz, 0.5H), 6.10 (d, J=4.8 Hz, 0.5H), 5.98-5.90 (m, 1H), 3.88-3.78 (m, 1H), 2.94-2.86 (m, 1H). LC-MS $R_T$=1.671 min, m/z=320.1 [M+H]$^+$.

(5S,7S)-2-[(R)-difluoromethylsulfinyl]-7-fluoro-5-(2-fluorophenyl)-6,7-dihydro-5H-pyrrolo[1,2-b][1,2,4]triazole (Peak 2, retention time=3.071 min) (17.9 mg, 39%) as a white solid. $^1$H NMR (400 MHz, CD$_3$OD) δ 7.48-7.45 (m, 1H), 7.24-6.96 (m, 4H), 6.23 (dd, J=3.2, 7.2 Hz, 0.5H), 6.10 (d, J=7.6 Hz, 0.5H), 5.98-5.90 (m, 1H), 3.87-3.78 (m, 1H), 2.95-2.84 (m, 1H). LC-MS $R_T$=1.651 min, m/z=320.1 [M+H].

SFC condition: Column: ChiralPak AD-3 150×4.6 mm I.D., 3 um Mobile phase: A: C02 B: Ethanol (0.05% DEA); Gradient: from 5% to 40% of B in 5.5 min and hold 40% for 3 min, Flow rate: 2.5 mL/min Column temperature: 30° C.

Step 10: (5S,7S)-2-((difluoromethyl)sulfonyl)-7-fluoro-5-(2-fluorophenyl)-6,7-dihydro-5H-pyrrolo[1,2-b][1,2,4]triazole

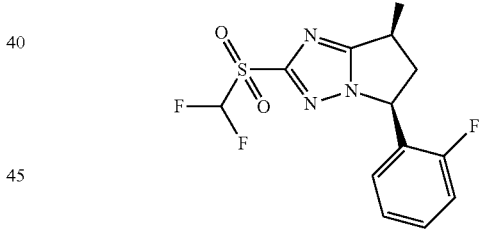

A mixture of (5S,7S)-2-(difluoromethylsulfinyl)-7-fluoro-5-(2-fluorophenyl)-6,7-dihydro-5H-pyrrolo[1,2-b][1,2,4]triazole (20 mg, 0.06 mmol) and 3-chloroperoxybenzoic acid (85%, 25 mg, 0.13 mmol) in dichloromethane (6 mL) was stirred at 40° C. for 16 h and diluted with water (20 mL). The mixture was extracted with ethyl acetate (3×30 mL). The combined organic layers were washed with brine (3×20 mL), dried over sodium sulfate and concentrated under reduced pressure. The residue was purified by RP-HPLC (acetonitrile 20-45%/0.225% HCl in water) to give (5S,7S)-2-(difluoromethylsulfonyl)-7-fluoro-5-(2-fluorophenyl)-6,7-dihydro-5H-pyrrolo[1,2-b][1,2,4]triazole (14.9 mg, 70%) as a white solid. $^1$H NMR (400 MHz, CD$_3$OD) δ 7.49-7.46 (m, 1H), 7.26-7.17 (m, 3H), 7.97 (t, J=52.4 Hz, 1H), 6.24 (dd, J=2.8, 8.0 Hz, 0.5H), 6.10 (d, J=2.4 Hz, 0.5H), 6.00-5.94 (m, 1H), 3.88-3.79 (m, 1H), 2.96-2.88 (m, 1H). LC-MS $R_T$=1.847 min, m/z=336.0 [M+H]$^+$

Example 54 and 55

(5S,7S)-2-((difluoromethyl)sulfinyl)-7-fluoro-5-(3-fluorophenyl)-6,7-dihydro-5H-pyrrolo[1,2-b][1,2,4]triazole (54) and (5S,7S)-2-((difluoromethyl)sulfonyl)-7-fluoro-5-(3-fluorophenyl)-6,7-dihydro-5H-pyrrolo[1,2-b][1,2,4]triazole (55)

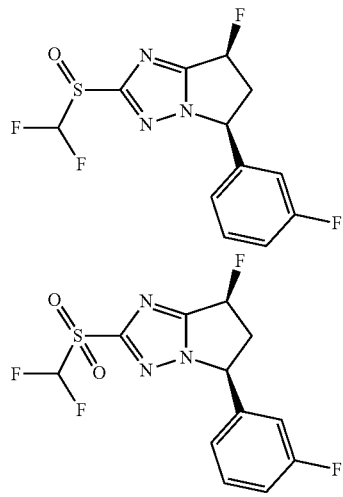

(5S,7S)-2-((difluoromethyl)sulfinyl)-7-fluoro-5-(3-fluorophenyl)-6,7-dihydro-5H-pyrrolo[1,2-b][1,2,4]triazole and (5S,7S)-2-((difluoromethyl)sulfonyl)-7-fluoro-5-(3-fluorophenyl)-6,7-dihydro-5H-pyrrolo[1,2-b][1,2,4]triazole were prepared according to method 21 starting from 3-fluorobenzaldehyde. (5S,7S)-2-((difluoromethyl)sulfinyl)-7-fluoro-5-(3-fluorophenyl)-6,7-dihydro-5H-pyrrolo[1,2-b][1,2,4]triazole (38.0 mg, 18%, white solid) was purified by RP-HPLC (acetonitrile 15-45%/0.05% ammonia hydroxide in water). $^1$H NMR (400 MHz, CD$_3$OD) δ 7.44-7.42 (m, 1H), 7.22-6.95 (m, 4H), 6.21-6.05 (m, 1H), 5.72-5.70 (m, 1H), 3.82-3.70 (m, 1H), 2.91-2.80 (m, 1H). LC-MS R$_T$=0.955 min, m/z=320.1 [M+H]$^+$.

(5S,7S)-2-(difluoromethylsulfonyl)-7-fluoro-5-(3-fluorophenyl)-6,7-dihydro-5H-pyrrolo[1,2-b][1,2,4]triazole (40.0 mg, 18%, white solid) was purified by RP-HPLC (acetonitrile 40-50%/0.05% ammonia hydroxide in water). $^1$H NMR (400 MHz, CD$_3$OD) δ 7.46-7.44 (m, 1H), 7.15-6.83 (m, 4H), 6.23-6.07 (m, 1H), 5.75-5.74 (m, 1H), 3.83-3.73 (m, 1H), 2.93-2.82 (m, 1H). LC-MS R$_T$=1.027 min, m/z=336.1 [M+H]$^+$.

Example 55 and 56

(5S,7S)-2-(difluoromethylsulfinyl)-7-fluoro-5-(4-fluorophenyl)-6,7-dihydro-5H-pyrrolo[1,2-b][1,2,4]triazole and (5S,7S)-2-(difluoromethylsulfonyl)-7-fluoro-5-(4-fluorophenyl)-6,7-dihydro-5H-pyrrolo[1,2-b][1,2,4]triazole

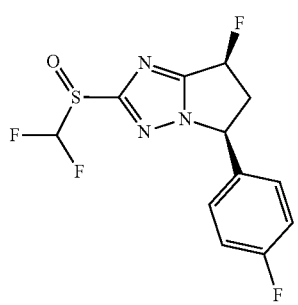

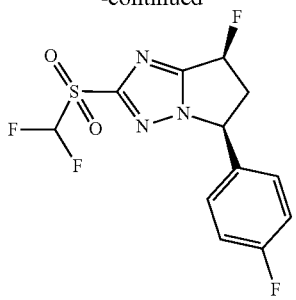

(5S,7S)-2-(difluoromethylsulfinyl)-7-fluoro-5-(4-fluorophenyl)-6,7-dihydro-5H-pyrrolo[1,2-b][1,2,4]triazole and (5S,7S)-2-(difluoromethylsulfonyl)-7-fluoro-5-(4-fluorophenyl)-6,7-dihydro-5H-pyrrolo[1,2-b][1,2,4]triazole were prepared according to method 21 starting from 4-fluorobenzaldehyde. (5S,7S)-2-(difluoromethylsulfinyl)-7-fluoro-5-(4-fluorophenyl)-6,7-dihydro-5H-pyrrolo[1,2-b][1,2,4]triazole (17.3 mg, 10%, colorless oil) was purified by RP-HPLC (acetonitrile 36-66%/0.05% ammonia hydroxide in water). $^1$H NMR (400 MHz, CD$_3$OD) δ 7.34-7.31 (m, 2H), 7.19-6.94 (m, 3H), 6.22 (dd, J=2.4, 7.2 Hz, 0.5H), 6.07 (d, J=7.2H, 0.5H), 5.71-5.70 (m, 1H), 3.82-3.72 (m, 1H), 2.91-2.81 (m, 1H). LCMS R$_T$=0.979 min, m/z=320.1 [M+H]$^+$.

Example 57

(4R,6R)-2-(difluoromethylsulfonyl)-4-fluoro-6-phenyl-5,6-dihydro-4H-pyrrolo[1,2-b]pyrazole and (4S,6S)-2-(difluoromethylsulfonyl)-4-fluoro-6-phenyl-5,6-dihydro-4H-pyrrolo[1,2-b]pyrazole

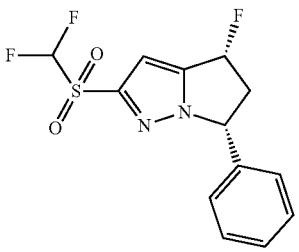

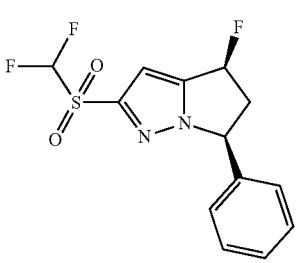

Step 1: 2-ethylhexyl 3-[cis-4-fluoro-6-phenyl-5,6-dihydro-4H-pyrrolo[1,2-b]pyrazol-2-yl]sulfanyl] propanoate

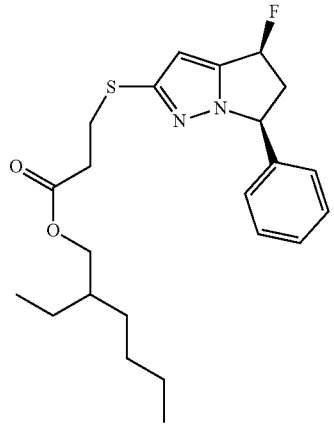 [SMILES: CCCCC(CC)COC(=O)CCSc1cc2n(n1)[C@H](c1ccccc1)C[C@@H]2F]

A mixture of N,N-diisopropylethylamine (0.6 mL, 3.2 mmol), cis-2-bromo-4-fluoro-6-phenyl-5,6-dihydro-4H-pyrrolo[1,2-b]pyrazole (300 mg, 1.1 mmol), tris(dibenzylideneacetone)dipalladium(0) (200 mg, 0.2 mmol), 4,5-bis(diphenylphosphino)-9,9-dimethylxanthene (600 mg, 1.1 mmol) and 3-mercaptopropionic acid 2-ethylhexylester (300 mg, 1.4 mmol) in 1,4-dioxane (150 mL) was stirred at 115° C. for 15 h and concentrated under reduced pressure. The residue was purified by column chromatography (silica gel, 100-200 mesh, 0 to 30% ethyl acetate in petroleum ether) to afford 2-ethylhexyl 3-[[cis-4-fluoro-6-phenyl-5,6-dihydro-4H-pyrrolo[1,2-b]pyrazol-2-yl]sulfanyl]propanoate (300 mg, 67%) as a light yellow oil. LCMS $R_T$=0.919 min, m/z=419.2 [M+H]$^+$.

Step 2: cis-2-(difluoromethylsulfanyl)-4-fluoro-6-phenyl-5,6-dihydro-4H-pyrrolo[1,2-b]pyrazole

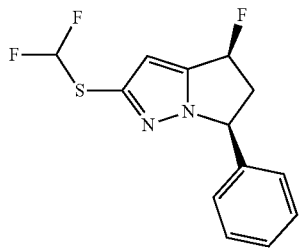 [SMILES: FC(F)Sc1cc2n(n1)[C@H](c1ccccc1)C[C@@H]2F]

A solution of 2-ethylhexyl 3-[[cis-4-fluoro-6-phenyl-5,6-dihydro-4H-pyrrolo[1,2-b]pyrazol-2-yl]sulfanyl]propanoate (200 mg, 0.48 mmol) in N,N-dimethylformamide (1 mL) was added sodium ethoxide (2.0 M in ethanol, 0.38 mL, 0.76 mmol). The mixture was stirred at 0° C. for 0.5 h and sodium (2-chloro-2,2-difluoro-acetyl)oxide (109 mg, 0.72 mmol) and potassium carbonate (99 mg, 0.72 mmol) were added. The resulting mixture was stirred at 80° C. for 1 h and diluted. The mixture was extracted with ethyl acetate (3×20 mL). The combined organic layers were washed with brine (3×15 mL), dried over sodium sulfate and concentrated under reduced pressure. The residue was purified by preparative TLC (eluting with 30% ethyl acetate in petroleum ether) to give cis-2-(difluoromethylsulfanyl)-4-fluoro-6-phenyl-5,6-dihydro-4H-pyrrolo[1,2-b]pyrazole (25 mg, 18%) as a colorless oil. LCMS $R_T$=0.747 min, m/z=285.1 [M+H]$^+$.

Step 3: (4R,6R)-2-(difluoromethylsulfonyl)-4-fluoro-6-phenyl-5,6-dihydro-4H-pyrrolo[1,2-b]pyrazole and (4S,6S)-2-(difluoromethylsulfonyl)-4-fluoro-6-phenyl-5,6-dihydro-4H-pyrrolo[1,2-b]pyrazole

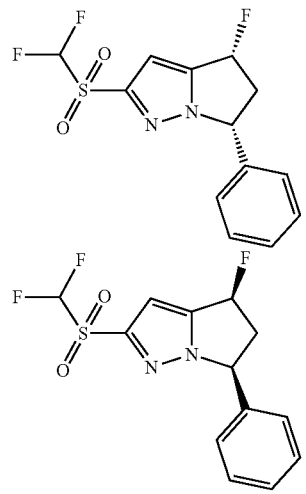

To a mixture of ruthenium(III) chloride (2 mg, 0.01 mmol) and cis-2-(difluoromethylsulfanyl)-4-fluoro-6-phenyl-5,6-dihydro-4H-pyrrolo[1,2-b]pyrazole (24 mg, 0.08 mmol) in ethyl acetate (2 mL), acetonitrile (2 mL) and water (2 mL) was added sodium periodate (90 mg, 0.42 mmol). The mixture was stirred at 25° C. for 2 h and diluted with water (30 mL). The mixture was extracted with ethyl acetate (3×30 mL). The combined organic layers were washed with brine (20 mL), dried over sodium sulfate and concentrated under reduced pressure. The residue was purified by preparative TLC to give a crude, which was further separated by chiral SFC to afford (stereochemistry arbitrarily assigned):

(4R,6R)-2-(difluoromethylsulfonyl)-4-fluoro-6-phenyl-5,6-dihydro-4H-pyrrolo[1,2-b]pyrazole (Peak 1, Retention time=3.877 min) (6.9 mg, 26%) as a white solid. $^1$H NMR (400 MHz, CDCl$_3$) δ 7.42-7.36 (m, 3H), 7.20-7.18 (m, 2H), 7.09 (d, J=2.4 Hz, 1H), 6.26 (t, J=53.2 Hz, 1H), 6.13 (d, J=4.4 Hz, 0.5H), 5.99 (d, J=6.8 Hz, 0.5H), 5.61-5.55 (m, 1H), 3.60-3.50 (m, 1H), 2.97-2.87 (m, 1H). LC-MS $R_T$=0.863 min, m/z=316.8 [M+H]$^+$.

(4S,6S)-2-(difluoromethylsulfonyl)-4-fluoro-6-phenyl-5,6-dihydro-4H-pyrrolo[1,2-b]pyrazole (Peak 2, Retention time=6.030 min) (8.5 mg, 31%) as a white solid. $^1$H NMR (400 MHz, CDCl3) δ 7.39-7.36 (m, 3H), 7.20-7.18 (m, 2H), 7.09 (d, J=2.4 Hz, 1H), 6.40-6.14 (m, 1H), 6.13 (s, 0.5H), 5.99 (d, J=6.8 Hz, 0.5H), 5.60-5.58 (m, 1H), 3.60-3.52 (m, 1H), 2.97-2.87 (m, 1H). LC-MS $R_T$=0.711 min, m/z=317.1 [M+H]+.

SFC condition (prep): Phenomenex-Cellulose-2 (250 mm*30 mm, 5 μm); Mobile phase: A: CO$_2$ B: 0.1% NH$_3$H$_2$O EtOH; Gradient: from 45% to 45% of B; Flow rate: 60 mL/min Column temperature: 40° C.

Example 58

(5S,7S)-2-(difluoromethylsulfonyl)-5-(2,6-difluorophenyl)-7-fluoro-6,7-dihydro-5H-pyrrolo[1,2-b][1,2,4]triazole

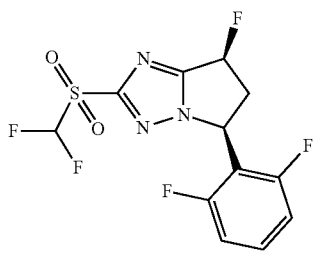 [SMILES: O=S(=O)(c1nc2n(n1)[C@H](c1c(F)cccc1F)C[C@@H]2F)C(F)F]

(5S,7S)-2-(difluoromethylsulfonyl)-5-(2,6-difluorophenyl)-7-fluoro-6,7-dihydro-5H-pyrrolo[1,2-b][1,2,4]triazole was prepared according to method 21 starting from 2,6-difluorobenzaldehyde. The final compound was purified by RP-HPLC (acetonitrile 35-65%/0.05% ammonia hydroxide in water) to give (5S,7S)-2-(difluoromethylsulfonyl)-5-(2,6-difluorophenyl)-7-fluoro-6,7-dihydro-5H-pyrrolo[1,2-b][1,2,4]triazole (33 mg, 34%) as a white solid. $^1$H NMR (400 MHz, CDCl$_3$) δ 7.48-7.38 (m, 1H), 6.99 (t, J=8.4 Hz, 2H), 6.43 (t, J=52.8 Hz, 1H), 6.25-6.04 (m, 1H), 6.00-5.90 (m, 1H), 3.91-3.74 (m, 1H), 3.18-3.01 (m, 1H). LCMS R$_T$=1.033 min, m/z=354.1 [M+H]$^+$.

Example 59

(5S,7S)-2-((difluoromethyl)sulfonyl)-7-fluoro-5-(2,3,6-trifluorophenyl)-6,7-dihydro-5H-pyrrolo[1,2-b][1,2,4]triazole

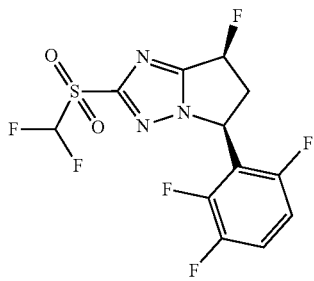 [SMILES: O=S(=O)(c1nc2n(n1)[C@H](c1c(F)ccc(F)c1F)C[C@@H]2F)C(F)F]

(5S,7S)-2-(difluoromethylsulfonyl)-7-fluoro-5-(2,3,6-trifluorophenyl)-6,7-dihydro-5H-pyrrolo[1,2-b][1,2,4]triazole was prepared according to method 21 starting from 2,3,6-trifluorobenzaldehyde. The final compound was purified by RP-HPLC (acetonitrile 40-50%/0.05% ammonia hydroxide in water) to give (5S,7S)-2-(difluoromethylsulfonyl)-7-fluoro-5-(2,3,6-trifluorophenyl)-6,7-dihydro-5H-pyrrolo[1,2-b][1,2,4]triazole (11.7 mg, 15%) as a white solid. $^1$H NMR (400 MHz, CD$_3$OD) δ 7.47-7.44 (m, 1H), 7.11-6.83 (m, 2H), 6.28-6.13 (m, 1H), 6.07-6.03 (m, 1H), 3.94-3.87 (m, 1H), 3.06-2.95 (m, 1H). LCMS R$_T$=1.841 min, m/z=372.0 [M+H]$^+$.

Example 60

(5S,7S)-2-(difluoromethylsulfonyl)-7-fluoro-5-(2,3,5-trifluorophenyl)-6,7-dihydro-5H-pyrrolo[1,2-b][1,2,4]triazole

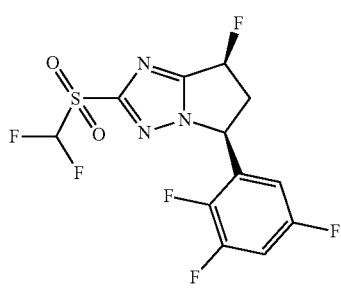 [SMILES: O=S(=O)(c1nc2n(n1)[C@H](c1cc(F)cc(F)c1F)C[C@@H]2F)C(F)F]

(5S,7S)-2-(difluoromethylsulfonyl)-7-fluoro-5-(2,3,5-trifluorophenyl)-6,7-dihydro-5H-pyrrolo[1,2-b][1,2,4]triazole was prepared according to method 21 starting from 2,3,5-trifluorobenzaldehyde. The final compound was purified by RP-HPLC (acetonitrile 40-70%/0.05% ammonia hydroxide in water) to give (5S,7S)-2-(difluoromethylsulfonyl)-7-fluoro-5-(2,3,5-trifluorophenyl)-6,7-dihydro-5H-pyrrolo[1,2-b][1,2,4]triazole (18.8 mg, 26%) as a white solid. $^1$H NMR (400 MHz, CD$_3$OD) δ 7.33-7.26 (m, 1H), 6.99 (t, J=52.4 Hz, 1H), 6.86-6.78 (m, 1H), 6.27-6.11 (m, 1H), 6.02-5.97 (m, 1H), 3.92-3.79 (m, 1H), 3.01-2.89 (m, 1H). LCMS R$_T$=1.081 min, m/z=372.1 [M+H]$^+$.

Example 61

(5S,7S)-5-(3-chlorophenyl)-2-(difluoromethylsulfonyl)-7-fluoro-6,7-dihydro-5H-pyrrolo[1,2-b][1,2,4]triazole

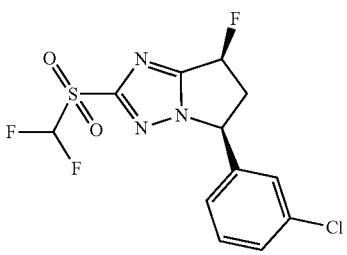 [SMILES: O=S(=O)(c1nc2n(n1)[C@H](c1cccc(Cl)c1)C[C@@H]2F)C(F)F]

(5S,7S)-5-(3-chlorophenyl)-2-(difluoromethylsulfonyl)-7-fluoro-6,7-dihydro-5H-pyrrolo[1,2-b][1,2,4]triazole was prepared according to method 16 starting from ethyl 3-chlorobenzoate. The final compound was purified by RP-HPLC (acetonitrile 50-80%/0.05% ammonia hydroxide in water) to give (5S,7S)-5-(3-chlorophenyl)-2-(difluoromethylsulfonyl)-7-fluoro-6,7-dihydro-5H-pyrrolo[1,2-b][1,2,4]triazole (350 mg, 79%) as a white solid. $^1$H NMR (400 MHz, CDCl$_3$) δ 7.49-7.33 (m, 2H), 7.33-7.27 (m, 1H), 7.13-7.11 (m, 1H), 6.68-6.27 (m, 1H), 6.26-5.98 (m, 1H), 5.62-5.50 (m, 1H), 3.85-3.56 (m, 1H), 3.12-2.86 (m, 1H). LC-MS R$_T$=1.962 min, m/z=352.0 [M+H]$^+$.

Example 62: Method 24

2-[(5S,7S)-2-(difluoromethylsulfonyl)-7-fluoro-6,7-dihydro-5H-pyrrolo[1,2-b][1,2,4]triazol-5-yl]benzonitrile

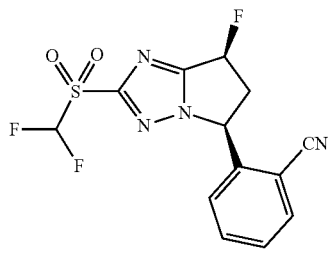 [SMILES: N#Cc1ccccc1[C@@H]1C[C@H](F)c2nc(S(=O)(=O)C(F)F)nn21]

Step 1: 2-ethylhexyl 3-(((5S,7S)-5-(2-chlorophenyl)-7-fluoro-6,7-dihydro-5H-pyrrolo[1,2-b][1,2,4]triazol-2-yl)thio)propanoate

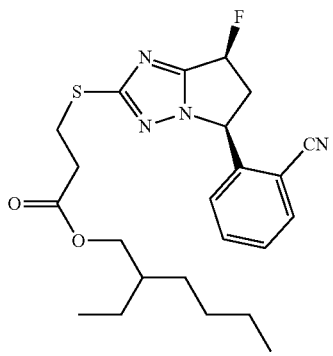 [SMILES: CCCCC(CC)COC(=O)CCSc1nc2n(n1)[C@H](c1ccccc1C#N)C[C@@H]2F]

A mixture of (5S,7S)-2-bromo-5-(2-chlorophenyl)-7-fluoro-6,7-dihydro-5H-pyrrolo[1,2-b][1,2,4]triazole (1.0 g, 3.2 mmol), N,N-diisopropylethylamine (1.69 mL, 9.5 mmol), tris(dibenzylideneacetone)dipalladium(0) (579 mg, 0.63 mmol), 4,5-bis(diphenylphosphino)-9,9-dimethylxanthene (1.8 g, 3.2 mmol) and 3-mercaptopropionicacid 2-ethylhexylester (1.0 g, 4.7 mmol) in 1,4-dioxane (50 mL) was stirred at 110° C. for 15 h and concentrated under reduced pressure. The residue was purified by column chromatography (silica gel, 100-200 mesh, 15 to 20% ethyl acetate in petroleum ether) to afford 2-ethylhexyl 3-[[(5S,7S)-5-(2-chlorophenyl)-7-fluoro-6,7-dihydro-5H-pyrrolo[1,2-b][1,2,4]triazol-2-yl]sulfanyl]propanoate (1.0 g, 70%) as a light yellow oil. LC-MS R$_T$=0.955 min, m/z=454.2 [M+H]$^+$.

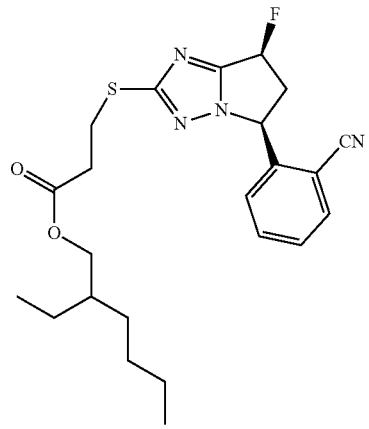 [SMILES: CCCCC(CC)COC(=O)CCSc1nc2n(n1)[C@H](c1ccccc1C#N)C[C@@H]2F]

Step 2: 2-ethylhexyl 3-(((5S,7S)-5-(2-cyanophenyl)-7-fluoro-6,7-dihydro-5H-pyrrolo[1,2-b][1,2,4]triazol-2-yl)thio)propanoate A mixture of 2-ethylhexyl 3-[[(5S,7S)-5-(2-chlorophenyl)-7-fluoro-6,7-dihydro-5H-pyrrolo[1,2-b][1,2,4]triazol-2-yl]sulfanyl]propanoate (500 mg, 1.1 mmol), potassium hexacyanoferrate(II) trihydrate (465 mg, 1.1 mmol), potassium acetate (14 mg, 0.14 mmol), t-BuXPhos Phos palladium(II) biphenyl-2-amine mesylate (88 mg, 0.11 mmol) and 2-di-tert-butylphosphino-2',4',6'-triisopropylbiphenyl (47 mg, 0.11 mmol) in 1,4-dioxane (5 mL) and water (15 mL) was stirred at 100° C. for 18 h and filtered. The filtrate was diluted with water (10 mL) and extracted with ethyl acetate (3×10 mL). The combined organic layers were dried over sodium sulfate and concentrated under reduced pressure. The residue was purified by column chromatography (silica gel, 100-200 mesh, 0 to 50% ethyl acetate in petroleum ether) to afford 2-ethylhexyl 3-[[(5S,7S)-5-(2-cyanophenyl)-7-fluoro-6,7-dihydro 5H-pyrrolo[1,2-b][1,2,4]triazol-2-yl]sulfanyl]propanoate (74 mg, 15%) as light brown oil. LC-MS R$_T$=0.899 min, m/z=445.3 [M+H]$^+$.

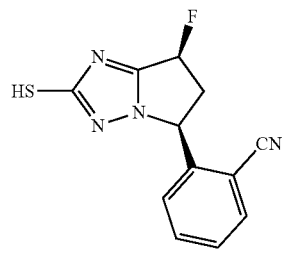 [SMILES: N#Cc1ccccc1[C@@H]1C[C@H](F)c2nc(S)nn21]

Step 3: 2-((5S,7S)-7-fluoro-2-mercapto-6,7-dihydro-5H-pyrrolo[1,2-b][1,2,4]triazol-5-yl) benzonitrile A mixture of sodium ethoxide (2.0 M in ethanol, 0.17 mL, 0.34 mmol), 2-ethylhexyl 3-[[(5S,7S)-5-(2-cyanophenyl)-7-fluoro-6,7-dihydro-5H-pyrrolo[1,2-b][1,2,4]triazol-2-yl]

sulfanyl]propanoate (74 mg, 0.17 mmol) in ethanol (0.4 mL) was stirred at 10° C. for 2 h and concentrated under reduced pressure. The residue was diluted with water (20 mL) and washed with ethyl acetate (20 mL). The aqueous phase was adjusted to pH=6 by addition of hydrochloric acid (1.0 M) and extracted with ethyl acetate (3×20 mL). The combined organic layers were dried over sodium sulfate and concentrated under reduced pressure to afford crude 2-[(5S,7S)-7-fluoro-2-sulfanyl-6,7-dihydro-5H-pyrrolo[1,2-b][1,2,4]triazol-5-yl]benzonitrile (43 mg, 99%) as a red solid. LC-MS $R_T$=0.590 min, m/z=261.1 [M+H].

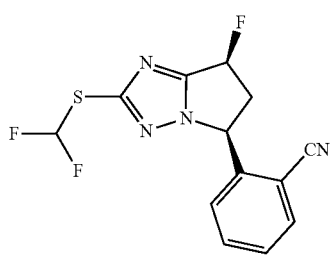 [SMILES: N#Cc1ccccc1[C@@H]1C[C@H](F)c2nc(SC(F)F)nn21]

Step 4: 2-((5S,7S)-2-((difluoromethyl)thio)-7-fluoro-6,7-dihydro-5H-pyrrolo[1,2-b][1,2,4]triazol-5-yl)benzonitrile A mixture of sodium (2-chloro-2,2-difluoro-acetyl)oxide (32 mg, 0.21 mmol), 2-[(5S,7S)-7-fluoro-2-sulfanyl-6,7-dihydro-5H-pyrrolo[1,2-b][1,2,4]triazol-5-yl]benzonitrile (43 mg, 0.17 mmol) and potassium carbonate (57 mg, 0.41 mmol) in N,N-dimethylacetamide (3.6 mL) was stirred at 90° C. for 10 min and quenched by addition of water (10 mL). The resulting mixture was extracted with ethyl acetate (3×10 mL). The combined organic layers were washed with brine (3×5 mL), dried over sodium sulfate and concentrated under reduced pressure. The residue was purified by column chromatography (silica gel, 100-200 mesh, 0 to 20% ethyl acetate in petroleum ether) to give 2-[(5S,7S)-2-(difluoromethylsulfanyl)-7-fluoro-6,7-dihydro-5H-pyrrolo[1,2-b][1,2,4]triazol-5-yl]benzonitrile (27 mg, 53%) as a light yellow oil. LC-MS $R_T$=0.682 min, m/z=311.1 [M+H]$^+$

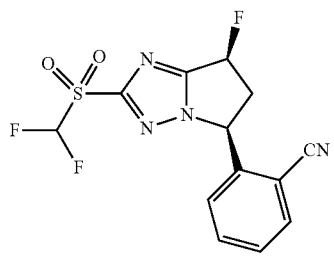 [SMILES: N#Cc1ccccc1[C@@H]1C[C@H](F)c2nc(S(=O)(=O)C(F)F)nn21]

Step 5: 2-[(5S,7S)-2-(difluoromethylsulfonyl)-7-fluoro-6,7-dihydro-5H-pyrrolo[1,2-b][1,2,4]triazol-5-yl]benzonitrile A mixture of ruthenium(III) chloride (2 mg, 0.01 mmol), 2-[(5S,7S)-2-(difluoromethylsulfanyl)-7-fluoro-6,7-dihydro-5H-pyrrolo[1,2-b][1,2,4]triazol-5-yl]benzonitrile (27 mg, 0.09 mmol) and sodium periodate (19 mg, 0.09 mmol) in ethyl acetate (0.3 mL)/acetonitrile (0.3 mL)/water (0.3 mL) was stirred at 25° C. for 10 min. The resulting mixture was diluted with water (10 mL) and extracted with ethyl acetate (3×10 mL). The combined organic layers were washed with brine (3×5 mL), dried over sodium sulfate and concentrated under reduced pressure. The residue was purified by RP-HPLC (acetonitrile 45-75%/0.05% ammonia hydroxide in water) to afford 2-[(5S,7S)-2-(difluoromethylsulfonyl)-7-fluoro-6,7-dihydro-5H-pyrrolo[1,2-b][1,2,4]triazol-5-yl]benzonitrile (5.3 mg, 18%) as a white solid. $^1$H NMR (400 MHz, CDCl$_3$) δ 7.85-7.77 (m, 1H), 7.68-7.63 (m, 1H), 7.57-7.52 (m, 1H), 6.95 (d, J=8.0 Hz, 1H), 6.45 (t, J=52.8 Hz, 1H), 6.20-6.03 (m, 2H), 3.96-3.81 (m, 1H), 3.02-2.92 (m, 1H). LC-MS $R_T$=0.919 min, m/z=343.1 [M+H]+.

Example 63: Method 23

(5S,7S)-2-(difluoromethylsulfonyl)-5-(3,4-difluorophenyl)-7-fluoro-6,7-dihydro-H-pyrrolo[1,2-b][1,2,4]triazole

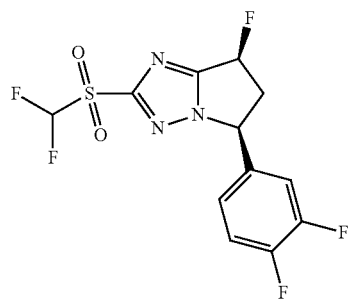 [SMILES: O=S(=O)(c1nc2n(n1)[C@H](c1ccc(F)c(F)c1)C[C@@H]2F)C(F)F]

Step 1: methyl 3,4-difluorobenzoate

To a solution of 3,4-difluorobenzoic acid (50.0 g, 316.3 mmol) in methanol (150 mL) was added concentrated sulfuric acid (26.0 mL, 478.4 mmol). After addition, the mixture was stirred at 80° C. for 15 h and cooled to room temperature. The mixture was extracted with dichloromethane (3×200 mL). The combined organic layers were dried over sodium sulfate and concentrated under reduced pressure to afford crude methyl 3,4-difluorobenzoate (54.0 g, 99%) as a yellow oil.

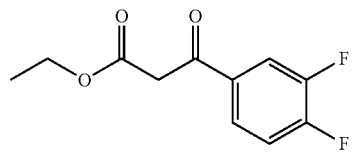 [SMILES: CCOC(=O)CC(=O)c1ccc(F)c(F)c1]

Step 2: ethyl 3-(3,4-difluorophenyl)-3-oxo-propanoate

To a solution of ethyl acetate (31.0 mL, 278.9 mmol) in tetrahydrofuran (300 mL) was added lithium bis(trimethylsilyl)amide (1.0 M in tetrahydrofuran, 349.0 mL, 349.0 mmol) at −78° C. under nitrogen atmosphere, followed by methyl 3,4-difluorobenzoate (40.0 g, 232.4 mmol). After addition, the mixture was stirred at −78° C. for 2 h and quenched by addition of saturated aqueous ammonium chloride (100 mL). The resulting mixture was extracted with ethyl acetate (3×200 mL). The combined organic layers were dried over sodium sulfate and concentrated under reduced pressure. The residue was purified by column chromatography (silica gel, 100-200 mesh, 0 to 20% ethyl acetate in petroleum ether) to give ethyl 3-(3,4-difluorophenyl)-3-oxo-propanoate (27.0 g, 51%) as a brown oil. $^1$H NMR (400 MHz, CDCl$_3$) δ 7.86-7.66 (m, 1H), 7.23 (s, 2H), 4.19-4.01 (m, 2H), 3.05-2.81 (m, 2H), 1.34-1.20 (m, 3H).

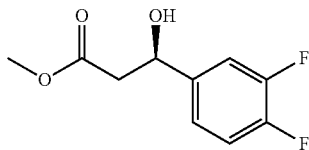

Step 3: methyl (3R)-3-(3,4-difluorophenyl)-3-hydroxy-propanoate

To a mixture of potassium formate (99.50 g, 1.2 mol) and [[(1R,2R)-2-amino-1,2-diphenyl-ethyl]-(p-tolylsulfonyl) amino]-chloro-ruthenium; 1-isopropyl-4-methyl-benzene (0.75 g, 1.18 mmol) in methanol (250 mL) was added ethyl 3-(3,4-difluorophenyl)-3-oxo-propanoate (27.00 g, 118.3 mmol) under nitrogen atmosphere and stirred at 40° C. for 18 h. The resulting mixture was diluted with water (200 mL) and extracted with ethyl acetate (3×300 mL). The combined organic layers were dried over sodium sulfate and concentrated under reduced pressure. The residue was purified by column chromatography (silica gel, 100-200 mesh, 0 to 15% ethyl acetate in petroleum ether) to afford methyl (3R)-3-(3,4-difluorophenyl)-3-hydroxy-propanoate (25.0 g, 98%) as a red oil. $^1$H NMR (400 MHz, CDCl$_3$) δ 7.33-7.25 (m, 1H), 7.24-7.16 (m, 1H), 7.07-7.02 (m, 1H), 5.10-4.98 (m, 1H), 3.78 (s, 3H), 2.77-2.72 (m, 2H).

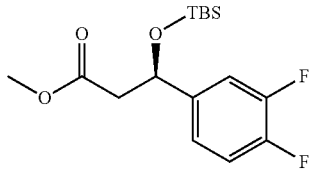

Step 4: methyl (3R)-3-[tert-butyl(dimethyl)silyl]oxy-3-(3,4-difluorophenyl)propanoate To a solution of methyl (3R)-3-(3,4-difluorophenyl)-3-hydroxy-propanoate (25.0 g, 115.6 mmol) in dichloromethane (200 mL) was added imidazole (15.8 g, 231.3 mmol) and tert-butyldimethylchlorosilane (22.7 g, 150.3 mmol). After addition, the mixture was stirred at 25° C. for 16 h and quenched by addition of water (100 mL). The resulting mixture was extracted with dichloromethane (3×300 mL). The combined organic layers were dried over sodium sulfate and concentrated under reduced pressure. The residue was purified by column chromatography (silica gel, 100-200 mesh, 0 to 5% ethyl acetate in petroleum ether) to afford methyl (3R)-3-[tert-butyl(dimethyl)silyl]oxy-3-(3,4-difluorophenyl)propanoate (24.0 g, 63%) as a colorless oil. $^1$H NMR (400 MHz, CDCl$_3$) δ 7.19-7.18 (m, 1H), 7.13-7.02 (m, 2H), 5.11-5.09 (m, 1H), 3.68 (s, 3H), 2.69-2.66 (m, 1H), 2.53-2.50 (m, 1H), 0.86-0.84 (m, 9H), 0.10 (s, 3H), 0.03 (s, 3H).

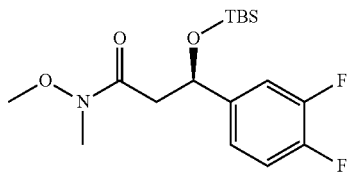

Step 5: (3R)-3-[tert-butyl(dimethyl)silyl]oxy-3-(3,4-difluorophenyl)-N-methoxy-N-methyl-propanamide To a solution of methyl (3R)-3-[tert-butyl(dimethyl)silyl]oxy-3-(3,4-difluorophenyl) propanoate (24.0 g, 72.6 mmol) and N,O-dimethylhydroxylamine hydrochloride (14.2 g, 145.3 mmol) in tetrahydrofuran (250 mL) was added isopropylmagnesium chloride (2.0 M in tetrahydrofuran, 109.0 mL, 218.0 mmol) at −78° C. under nitrogen atmosphere. After addition, the mixture was allowed to warm to 15° C. and stirred for 16 h. The mixture was then quenched by addition of saturated aqueous ammonium chloride (200 mL) and extracted with ethyl acetate (2×500 mL). The combined organic layers were dried over sodium sulfate and concentrated under reduced pressure. The residue was purified by column chromatography (silica gel, 100-200 mesh, 0 to 20% ethyl acetate in petroleum ether) to afford (3R)-3-[tert-butyl(dimethyl)silyl]oxy-3-(3,4-difluorophenyl)-N-methoxy-N-methyl-propanamide (18.0 g, 69%) as a colorless oil. LC-MS R$_T$=1.156 min, m/z=360.0 [M+H]$^+$.

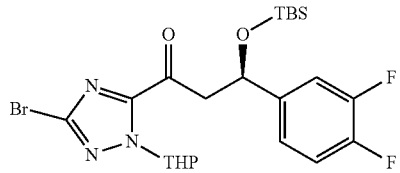

Step 6: (3R)-1-(5-bromo-2-tetrahydropyran-2-yl-1,2,4-triazol-3-yl)-3-[tert-butyl(dimethyl)silyl]oxy-3-(3,4-difluorophenyl)propan-1-one To a cooled (−78 OC) solution of (3R)-3-[tert-butyl(dimethyl)silyl]oxy-3-(3,4-difluorophenyl)-N-methoxy-N-methyl-propanamide (17.0 g, 47.3 mmol) and 3,5-dibromo-1-tetrahydropyran-2-yl-1,2,4-triazole (14.7 g, 47.3 mmol) in tetrahydrofuran (200 mL) was added isopropylmagnesium chloride (2.0 M in tetrahydrofuran, 28.0 mL, 56.0 mmol) under nitrogen atmosphere. After addition, the mixture was stirred at 15° C. for 16 h and then quenched by addition of saturated aqueous ammonium chloride (200 mL). The resulting mixture was extracted with ethyl acetate (2×500 mL). The combined organic layers were dried over sodium sulfate and concentrated under reduced pressure. The residue was purified by column chromatography (silica gel, 100-200 mesh, 0 to 10% ethyl acetate in petroleum ether) to afford (3R)-1-(5-bromo-2-tetrahydropyran-2-yl-1,2,4-triazol-3-yl)-3-[tert-butyl(dimethyl)silyl]oxy-3-(3,4-difluorophenyl)propan-1-one (19.0 g, 76%) as a white solid. $^1$H NMR (400 MHz, CDCl$_3$) δ 7.25-7.19 (m, 1H), 7.15-7.07 (m, 2H), 6.24-6.22 (m, 1H), 5.31-5.27 (m, 1H), 4.10-4.02 (m, 1H), 3.75-3.65 (m, 1H), 3.56-3.53 (m, 1H), 3.27-3.23 (m, 1H), 2.35-2.23 (m, 1H), 1.99-1.90 (m, 1H), 1.79-1.67 (m, 2H), 1.30-1.22 (m, 2H), 0.79 (d, J=2.0 Hz, 9H), −0.04 (d, J=7.6 Hz, 3H), −0.18 (d, J=8.0 Hz, 3H). LCMS R$_T$=1.282 min, m/z=552.1 [M+Na]$^+$.

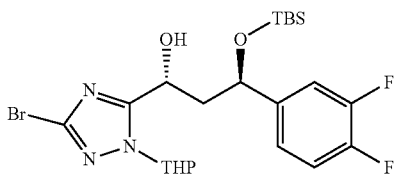

Step 7: (1R,3R)-1-(5-bromo-2-tetrahydropyran-2-yl-1,2,4-triazol-3-yl)-3-[tert-butyl(dimethyl)silyl]oxy-3-(3,4-difluorophenyl)propan-1-ol To a mixture of triethylamine (50.0 mL, 358.2 mmol), formic acid (7.0 mL, 179.1 mmol) and [[(1R,2R)-2-amino-1,2-diphenyl-ethyl]-(p-tolylsulfonyl)amino]-chloro-ruthenium; 1-isopropyl-4-methyl-benzene (230 mg, 0.4 mmol) in methanol (150 mL) was added (3R)-1-(5-bromo-2-tetrahydropyran-2-yl-1,2,4-triazol-3-yl)-3-[tert-butyl (dimethyl)silyl]oxy-3-(3,4-difluorophenyl)propan-1-one (19.0 g, 35.8 mmol) under nitrogen atmosphere. After addition, the mixture was stirred at 30° C. for 16 h and diluted with water (200 mL). The resulting mixture was extracted with ethyl acetate (3×200 mL). The combined organic layers were dried over sodium sulfate and concentrated under reduced pressure. The resulting residue was purified by s column chromatography (silica gel, 100-200 mesh, 0 to 15% ethyl acetate in petroleum ether) to afford (1R,3R)-1-(5-bromo-2-tetrahydropyran-2-yl-1,2,4-triazol-3-yl)-3-[tert-butyl(dimethyl)silyl]oxy-3-(3,4-difluorophenyl)propan-1-ol (17.0 g, 89%) as a colorless oil. $^1$H NMR (400 MHz, CDCl$_3$) δ 7.22-7.08 (m, 2H), 7.06 (s, 1H), 5.64-5.49 (m, 1H), 5.15-5.12 (m, 1H), 5.12-5.08 (m, 1H), 5.07-5.03 (m, 1H), 4.07-3.99 (m, 1H), 3.69-3.63 (m, 1H), 2.34-2.23 (m, 2H), 2.14-2.07 (m, 1H), 1.70-1.62 (m, 4H), 1.26 (t, J=7.2 Hz, 2H), 0.93 (d, J=4.4 Hz, 9H), 0.10 (d, J=1.2 Hz, 3H), −0.09 (d, J=5.6 Hz, 3H).

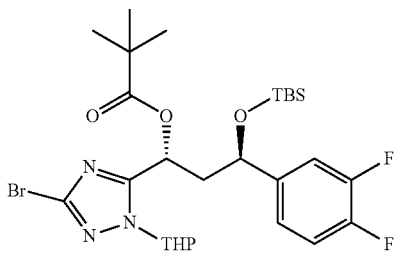

Step 8: [(1R,3R)-1-(5-bromo-2-tetrahydropyran-2-yl-1,2,4-triazol-3-yl)-3-[tert-butyl(dimethyl)silyl]oxy-3-(3,4-difluorophenyl)propyl]2,2-dimethylpropanoate To a solution of triethylamine (12.0 mL, 84.5 mmol), 4-dimethylaminopyridine (3.4 g, 28.2 mmol) and (1R,3R)-1-(5-bromo-2-tetrahydropyran-2-yl-1,2,4-triazol-3-yl)-3-[tert-butyl(dimethyl)silyl]oxy-3-(3,4-difluorophenyl)propan-1-ol (15.0 g, 28.2 mmol) in dichloromethane (200 mL) was added pivaloyl chloride (5.0 g, 41.5 mmol) under nitrogen atmosphere. After addition, the mixture was stirred at 15° C. for 1.5 h and diluted with water (300 mL). The mixture was extracted with dichloromethane (3×200 mL). The combined organic layers were dried over sodium sulfate and concentrated under reduced pressure. The residue was purified by column chromatography (silica gel, 100-200 mesh, 0 to 15% ethyl acetate in petroleum ether) to give [(1R,3R)-1-(5-bromo-2-tetrahydropyran-2-yl-1,2,4-triazol-3-yl)-3-tert-butyl (dimethyl)silyl]oxy-3-(3,4-difluorophenyl)propyl]2,2-dimethylpropanoate (16.0 g, 92%) as a colorless oil. $^1$H NMR (400 MHz, CDCl$_3$) δ 7.16-7.05 (m, 2H), 6.99-6.97 (m, 1H), 6.18-6.17 (m, 0.5H), 5.95-5.70 (m, 1H), 5.57-5.48 (m, 0.5H), 4.85-4.70 (m, 1H), 4.12-3.95 (m, 1H), 3.77-3.60 (m, 1H), 2.49-2.24 (m, 2H), 2.15-2.00 (m, 2H), 1.99-1.88 (m, 1H), 1.77-1.60 (m, 3H), 1.24 (d, J=3.2 Hz, 9H), 0.91 (d, J=3.6 Hz, 9H), 0.03 (d, J=11.2 Hz, 3H), −0.21 (s, 3H).

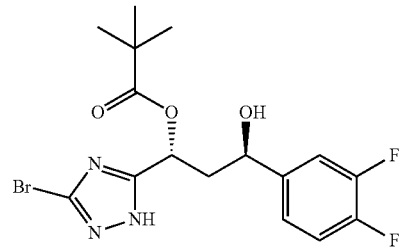 [SMILES: CC(C)(C)C(=O)O[C@H](C[C@@H](O)c1ccc(F)c(F)c1)c1nc(Br)n[nH]1]

Step 9: [(1R,3R)-1-(3-bromo-1H-1,2,4-triazol-5-yl)-3-(3,4-difluorophenyl)-3-hydroxy-propyl]2,2-dimethylpropanoate A mixture of [(1R,3R)-1-(5-bromo-2-tetrahydropyran-2-yl-1,2,4-triazol-3-yl)-3-[tert-butyl(dimethyl)silyl]oxy-3-(3,4-difluorophenyl)propyl]2,2-dimethylpropanoate (16.0 g, 25.9 mmol) in hydrochloric acid (4.0 M in methanol, 60 mL, 240.0 mmol) was stirred at 15° C. for 1.5 h and concentrated under reduced pressure. The residue was adjusted to pH=7 by addition of saturated aqueous sodium carbonate and then extracted with ethyl acetate (3×100 mL). The combined organic layers were washed with brine (50 mL), dried over sodium sulfate and concentrated under reduced pressure. The residue was purified by column chromatography (silica gel, 100-200 mesh, 0 to 15% ethyl acetate in petroleum ether) to give [(1R,3R)-1-(3-bromo-1H-1,2,4-triazol-5-yl)-3-(3,4-difluorophenyl)-3-hydroxy-propyl]2,2-dimethylpropanoate (9.0 g, 83%) as a white solid. $^1$H NMR (400 MHz, CDCl$_3$) δ 7.25-7.10 (m, 2H), 7.08 (s, 1H), 6.13-6.11 (m, 1H), 4.84-4.82 (m, 1H), 2.63-2.26 (m, 2H), 1.29-1.21 (m, 9H).

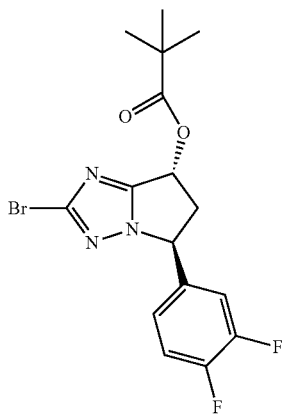 [SMILES: CC(C)(C)C(=O)O[C@@H]1C[C@@H](c2ccc(F)c(F)c2)n2nc(Br)nc21]

Step 10: [(5S,7R)-2-bromo-5-(3,4-difluorophenyl)-6,7-dihydro-5H-pyrrolo[1,2,2-b][1,2,4]triazol-7-yl]2,2-dimethylpropanoate To a solution of [(1R,3R)-1-(3-bromo-1H-1,2,4-triazol-5-yl)-3-(3,4-difluorophenyl)-3-hydroxy-propyl]2,2-dimethylpropanoate (9.0 g, 21.5 mmol), triphenylphosphine (6.8 g, 25.8 mmol) in tetrahydrofuran (135 mL) was added diisopropyl azodicarboxylate (5.2 g, 25.8 mmol) under nitrogen atmosphere. After addition, the mixture was stirred at 25° C. for 1.5 h and diluted with water (100 mL). The resulting mixture was extracted with ethyl acetate (3×100 mL). The combined organic layers were dried over sodium sulfate and concentrated under reduced pressure. The residue was purified by column chromatography (silica gel, 100-200 mesh, 0 to 20% ethyl acetate in petroleum ether) to afford [(5S,7R)-2-bromo-5-(3,4-difluorophenyl)-6,7-dihydro-5H-pyrrolo[1,2-b][1,2,4]triazol-7-yl]2,2-dimethylpropanoate (4.0 g, 46%) as a white solid. $^1$H NMR (400 MHz, CDCl$_3$) δ 7.25-7.16 (m, 1H), 7.03-6.96 (m, 1H), 6.93-6.91 (m, 1H), 6.16 (t, J=5.2 Hz, 1H), 5.58 (t, J=6.4 Hz, 1H), 3.03 (t, J=6.0 Hz, 2H), 1.24 (s, 9H).

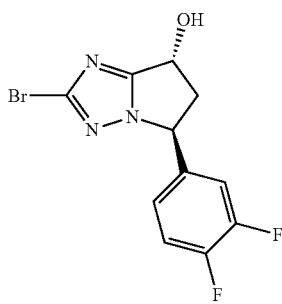 [SMILES: O[C@@H]1C[C@@H](c2ccc(F)c(F)c2)n2nc(Br)nc21]

Step 11: (5S,7R)-2-bromo-5-(3,4-difluorophenyl)-6,7-dihydro-5H-pyrrolo[1,2-b][1,2,4]triazol-7-ol To a solution of [(5S,7R)-2-bromo-5-(3,4-difluorophenyl)-6,7-dihydro-5H-pyrrolo[1,2-b][1,2,4]triazol-7-yl]2,2-dimethylpropanoate (2.0 g, 5 mmol) in methanol (15 mL) was added sodium hydroxide (600 mg, 14.99 mmol) in water (15 mL). After addition, the mixture was stirred at 15° C. for 16 h and diluted with water (20 mL). The mixture was extracted with ethyl acetate (3×30 mL). The combined organic layers were washed with brine (30 mL), dried over sodium sulfate and concentrated under reduced pressure. The residue was purified by column chromatography (silica gel, 100-200 mesh, 0 to 50% ethyl acetate in petroleum ether) to afford (5S,7R)-2-bromo-5-(3,4-difluorophenyl)-6,7-dihydro-5H-pyrrolo[1,2-b][1,2,4]triazol-7-ol (1.3 g, 82%) as a white solid. $^1$H NMR (400 MHz, CD$_3$OD) δ 7.30-7.31 (m, 1H), 7.25-7.22 (m, 1H), 7.20-7.07 (m, 1H), 5.69 (t, J=6.8 Hz, 1H), 5.31-5.29 (m, 1H), 3.04-2.86 (m, 2H).

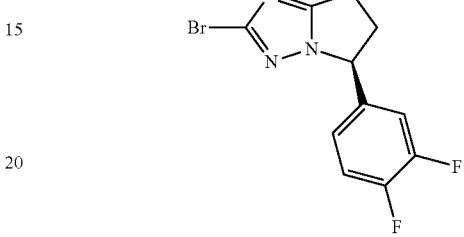

Step 12: (5S,7S)-2-bromo-5-(3,4-difluorophenyl)-7-fluoro-6,7-dihydro-5H-pyrrolo[1,2-b][1,2,4]triazole To a cooled (−30° C.) solution of (5S,7R)-2-bromo-5-(3,4-difluorophenyl)-6,7-dihydro-5H-pyrrolo[1,2-b][1,2,4]triazol-7-ol (2.2 g, 7.0 mmol) in toluene (20 mL) was added a solution of diethylaminosulfur trifluoride (4 mL, 27.8 mmol) in toluene (10 mL) under nitrogen atmosphere. After addition, the mixture was stirred at 0° C. for 1 h and diluted with ethyl acetate (50 mL). The resulting mixture was poured into saturated aqueous sodium bicarbonate (50 mL) and extracted with ethyl acetate (3×40 mL). The combined organic layers were dried over sodium sulfate and concentrated under reduced pressure. The residue was purified by column chromatography (silica gel, 100-200 mesh, 0-20% ethyl acetate in petroleum ether) to afford (5S,7S)-2-bromo-5-(3,4-difluorophenyl)-7-fluoro-6,7-dihydro-5H-pyrrolo[1,2-b][1,2,4]triazole (1.0 g, 45%) as a brown solid. $^1$H NMR (400 MHz, CDCl$_3$) δ 7.26-7.17 (m, 1H), 7.14-7.06 (m, 1H), 7.06-6.99 (m, 1H), 6.11-5.88 (m, 1H), 5.49-5.36 (m, 1H), 3.67-3.49 (m, 1H), 2.96-2.77 (m, 1H).

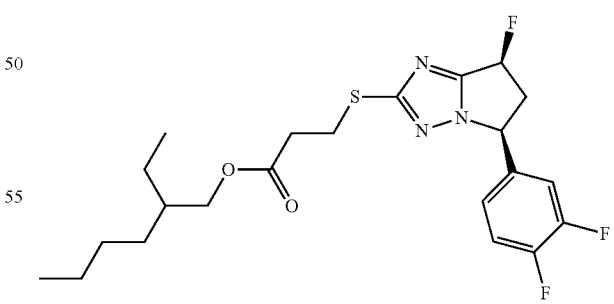

Step 13: 2-ethylhexyl 3-[[(5S,7S)-5-(3,4-difluorophenyl)-7-fluoro-6,7-dihydro-5H-pyrrolo[1,2-b][1,2,4]triazol-2-yl]sulfanyl]propanoate A mixture of tris(dibenzylideneacetone)dipalladium(0) (432 mg, 0.47 mmol), (5S,7S)-2-bromo-5-(3,4-difluorophenyl)-7-fluoro-6,7-dihydro-5H-pyrrolo[1,2-b][1,2,4]triazole (500 mg, 1.57 mmol), N,N-diisopropylethylamine (0.8 mL, 4.72 mmol), 3-mercaptopropionic acid 2-ethylhexylester (412 mg, 1.89 mmol) and 4,5-bis(diphenylphosphino)-9,9-dimethylxanthene (910 mg, 1.57 mmol) in 1,4-dioxane (10 mL) was stirred at 110° C. for 15 h under nitrogen atmosphere. The mixture was diluted with water (30 mL) and extracted with ethyl acetate (3×30 mL). The combined organic layers were dried over sodium sulfate and concentrated under reduced pressure. The residue was purified by column chromatography (silica gel, 100-200 mesh, 0 to 20% ethyl acetate in petroleum ether) to afford 2-ethylhexyl 3-[[(5S,7S)-5-(3,4-difluorophenyl)-7-fluoro-6,7-dihydro-5H-pyrrolo[1,2-b][1,2,4]triazol-2-yl]sulfanyl]propanoate (500 mg, 31%) as a light yellow oil. LCMS $R_T$=1.05 min, m/z=456.1 [M+H]$^+$.

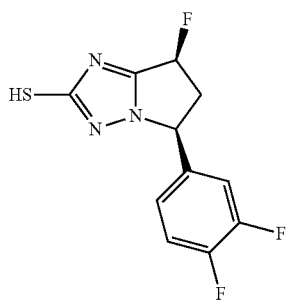 [SMILES: Fc1ccc([C@@H]2C[C@H](F)c3nc(S)nn32)cc1F]

Step 14: (5S,7S)-5-(3,4-difluorophenyl)-7-fluoro-6,7-dihydro-5H-pyrrolo[1,2-b][1,2,4]triazole-2-thiol To a solution of 2-ethylhexyl 3-[[(5S,7S)-5-(3,4-difluorophenyl)-7-fluoro-6,7-dihydro-5H-pyrrolo[1,2-b][1,2,4]triazol-2-yl]sulfanyl]propanoate (500 mg, 1.10 mmol) in ethanol (7 mL) was added sodium ethoxide (224 mg, 3.29 mmol). The mixture was stirred at 25° C. for 1 h and concentrated under reduced pressure. The residue was diluted with water (20 mL), washed with ethyl acetate (20 mL) and adjusted to pH=6 by addition of citric acid. The resulting mixture was extracted with ethyl acetate (3×20 mL). The combined organic layers were dried over sodium sulfate and concentrated under reduced pressure to afford crude (5S,7S)-5-(3,4-difluorophenyl)-7-fluoro-6,7-dihydro-5H-pyrrolo[1,2-b][1,2,4]triazole-2-thiol (100 mg, 34%) as a yellow solid. LCMS $R_T$=0.692 min, m/z=272.0 [M+H]$^+$.

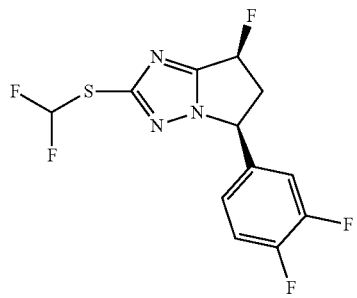 [SMILES: Fc1ccc([C@@H]2C[C@H](F)c3nc(SC(F)F)nn32)cc1F]

Step 15: (5S,7S)-2-(difluoromethylsulfanyl)-5-(3,4-difluorophenyl)-7-fluoro-6,7-dihydro-5H-pyrrolo[1,2-b][1,2,4]triazole A mixture of sodium (2-chloro-2,2-difluoro-acetyl)oxide (70 mg, 0.46 mmol), (5S,7S)-5-(3,4-difluorophenyl)-7-fluoro-6,7-dihydro-5H-pyrrolo[1,2-b][1,2,4]triazole-2-thiol (100 mg, 0.37 mmol) and potassium carbonate (127 mg, 0.92 mmol) in N,N-dimethylformamide (5 mL) was stirred at 90° C. for 10 min under nitrogen atmosphere. The mixture was diluted with water (10 mL) and extracted with ethyl acetate (3×15 mL). The combined organic layers were dried over sodium sulfate and concentrated under reduced pressure. The residue was purified by preparative TLC (50% ethyl acetate in petroleum ether, $R_f$=0.5) to afford (5S,7S)-2-(difluoromethylsulfanyl)-5-(3,4-difluorophenyl)-7-fluoro-6,7-dihydro-5H-pyrrolo[1,2-b][1,2,4]triazole (50 mg, 47%) as a light yellow oil. LCMS $R_T$=0.874 min, m/z=322.0 [M+H]$^+$.

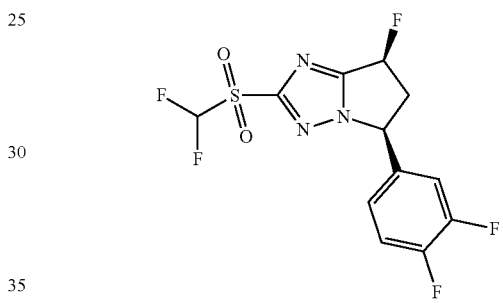

Step 16: (5S,7S)-2-(difluoromethylsulfonyl)-5-(3,4-difluorophenyl)-7-fluoro-6,7-dihydro-5H-pyrrolo[1,2-b][1,2,4]triazole A mixture of ruthenium(III) chloride (3 mg, 0.16 mmol), sodium periodate (133 mg, 0.62 mmol) and (5S,7S)-2-(difluoromethylsulfanyl)-5-(3,4-difluorophenyl)-7-fluoro-6,7-dihydro-5H-pyrrolo[1,2-b][1,2,4]triazole (50 mg, 0.16 mmol) in acetonitrile (1 mL), water (1 mL) and ethyl acetate (1 mL) was stirred at 30° C. for 1 h under nitrogen atmosphere and filtered. The filtrate was diluted with water (10 mL) and extracted with ethyl acetate (3×10 mL). The combined organic layers were dried over sodium sulfate and concentrated under reduced pressure. The residue was purified by RP-HPLC (acetonitrile 45-75%/0.05% ammonia hydroxide in water) to afford (5S,7S)-2-(difluoromethylsulfonyl)-5-(3,4-difluorophenyl)-7-fluoro-6,7-dihydro-5H-pyrrolo[1,2-b][1,2,4]triazole (14.2 mg, 32%) as a white solid. $^1$H NMR (400 MHz, CDCl$_3$) δ 7.26-7.19 (m, 1H), 7.12-7.11 (m, 1H), 7.05-7.04 (m, 1H), 6.44 (t, J=53.2 Hz, 1H), 6.20-5.99 (m, 1H), 5.58-5.57 (m, 1H), 3.81-3.62 (m, 1H), 3.09-2.93 (m, 1H). LCMS $R_T$=1.025 min, m/z=354.1 [M+H]$^+$.

Example 64

(5S,7S)-5-(2-chloro-3-fluoro-phenyl)-2-(difluoromethylsulfonyl)-7-fluoro-6,7-dihydro-5H-pyrrolo[1,2-b][1,2,4]triazole

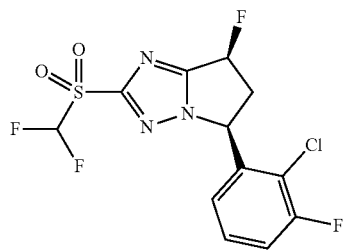 [SMILES: O=S(=O)(c1nc2n(n1)[C@H](c1cccc(F)c1Cl)C[C@@H]2F)C(F)F]

(5S,7S)-5-(2-chloro-3-fluoro-phenyl)-2-(difluoromethylsulfonyl)-7-fluoro-6,7-dihydro-5H-pyrrolo[1,2-b][1,2,4]triazole was prepared according to method 23 starting from 2-chloro-3-fluorobenzoic acid. The final compound was purified chiral SFC to give (5S,7S)-5-(2-chloro-3-fluoro-phenyl)-2-(difluoromethylsulfonyl)-7-fluoro-5H-pyrrolo[1,2-b][1,2,4]triazole (12.8 mg, 23%) as a white solid. $^1$H NMR (400 MHz, CD$_3$OD) δ 7.40-7.35 (m, 2H), 7.00 (t, J=52.4 Hz, 1H), 6.77-6.75 (m, 1H), 6.26-6.10 (m, 2H), 3.95-3.81 (m, 1H), 2.92-2.81 (m, 1H). LC-MS R$_T$=0.957 min, m/z=371.4 [M+H]$^+$.

SFC condition (prep): Column: DAICEL CHIRALCEL OJ-H (250 mm*30 mm, 5 μm); Mobile phase: A: CO$_2$ B: 0.1% NH$_3$H$_2$O EtOH; Gradient: from 25% to 25% of B; Flow rate: 50 mL/min Column temperature: 40° C.

Example 63

(5S,7S)-5-(3-chloro-2-fluoro-phenyl)-2-(difluoromethylsulfonyl)-7-fluoro-6,7-dihydro-5H-pyrrolo[1,2-b][1,2,4]triazole

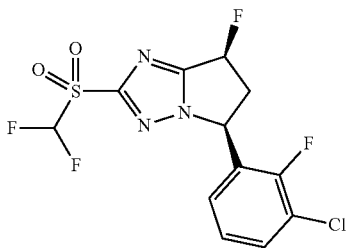 [SMILES: O=S(=O)(c1nc2n(n1)[C@H](c1cccc(Cl)c1F)C[C@@H]2F)C(F)F]

(5S,7S)-5-(3-chloro-2-fluoro-phenyl)-2-(difluoromethylsulfonyl)-7-fluoro-6,7-dihydro-5H-pyrrolo[1,2-b][1,2,4]triazole was prepared according to method 23 starting from 3-chloro-2-fluorobenzoic acid. The final compound was purified by column chromatography (silica gel, 100-200 mesh, 0 to 30% ethyl acetate in petroleum ether) to give (5S,7S)-5-(3-chloro-2-fluoro-phenyl)-2-(difluoromethylsulfonyl)-7-fluoro-6,7-dihydro-5H-pyrrolo[1,2-b][1,2,4]triazole (21.0 mg, 23%) as a white solid. $^1$H NMR (400 MHz, CD$_3$OD) δ 7.59-7.54 (m, 1H), 7.24 (t, J=8.0 Hz, 1H), 7.13-7.08 (m, 1H), 6.99 (t, J=52.4 Hz, 1H), 6.27-6.10 (m, 1H), 6.01-5.95 (m, 1H), 3.90-3.80 (m, 1H), 2.99-2.85 (m, 1H). LCMS R$_T$=0.953 min, m/z=369.9 [M+H]$^+$.

Example 66

(5S,7S)-5-(5-chloro-2-fluorophenyl)-2-((difluoromethyl)sulfonyl)-7-fluoro-6,7-dihydro-5H-pyrrolo[1,2-b][1,2,4]triazole

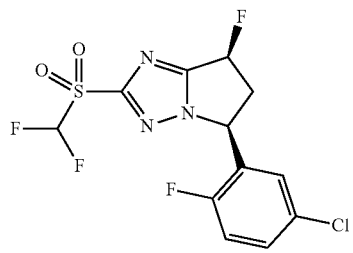 [SMILES: O=S(=O)(c1nc2n(n1)[C@H](c1cc(Cl)ccc1F)C[C@@H]2F)C(F)F]

(5S,7S)-5-(5-chloro-2-fluoro-phenyl)-2-(difluoromethylsulfonyl)-7-fluoro-6,7-dihydro-5H-pyrrolo[1,2-b][1,2,4]triazole was prepared according to method 23 starting from 5-chloro-2-fluorobenzoic acid. The final compound was purified by RP-HPLC (acetonitrile 48-78%/0.225 formic acid in water) to give (5S,7S)-5-(5-chloro-2-fluoro-phenyl)-2-(difluoromethylsulfonyl)-7-fluoro-6,7-dihydro-5H-pyrrolo[1,2-b][1,2,4]triazole (34 mg, 44%) as a white solid. $^1$H NMR (400 MHz, CDCl$_3$) δ 7.41-7.35 (m, 1H), 7.12 (t, J=9.2 Hz, 1H), 6.97-6.93 (m, 1H), 6.45 (t, J=52.8 Hz, 1H), 6.15-6.02 (m, 1H), 5.87-5.80 (m, 1H), 3.85-3.65 (m, 1H), 3.07-2.94 (m, 1H). LCMS R$_T$=1.051 min, m/z=370.1 [M+H]$^+$.

Example 67

(5S,7S)-2-((difluoromethyl)sulfonyl)-5-(2,5-difluorophenyl)-7-fluoro-6,7-dihydro-5H-pyrrolo[1,2-b][1,2,4]triazole

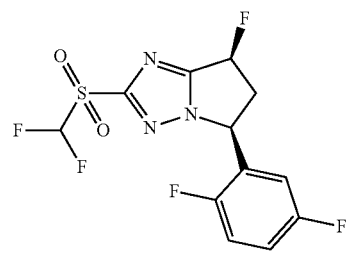 [SMILES: O=S(=O)(c1nc2n(n1)[C@H](c1cc(F)ccc1F)C[C@@H]2F)C(F)F]

(5S,7S)-2-(difluoromethylsulfonyl)-5-(2,5-difluorophenyl)-7-fluoro-6,7-dihydro-5H-pyrrolo[1,2-b][1,2,4]triazole was prepared according to method 21 starting from 2,5-difluorobenzaldehyde. The final compound was purified by RP-HPLC (acetonitrile 35-65%/0.05% ammonia hydroxide in water) to give (5S,7S)-2-(difluoromethylsulfonyl)-5-(2,5-difluorophenyl)-7-fluoro-6,7-dihydro-5H-pyrrolo[1,2-b][1,2,4]triazole (90 mg, 51%) as a white solid. $^1$H NMR (400 MHz, CDCl$_3$) δ 7.20-7.06 (m, 2H), 6.71-6.64 (m, 1H), 6.44 (t, J=52.4 Hz, 1H), 6.19-6.00 (m, 1H), 5.95-5.88 (m, 1H), 3.82-3.65 (m, 1H), 3.05-2.95 (m, 1H). LCMS R$_T$=1.059 min, m/z=354.1 [M+H]$^+$.

Example 68

(5S,7S)-2-(difluoromethylsulfonyl)-5-(2,3-difluorophenyl)-7-fluoro-6,7-dihydro-5H-pyrrolo[1,2-b][1,2,4]triazole

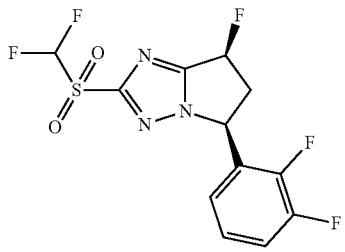 [SMILES: O=S(=O)(c1nc2n(n1)[C@H](c1cccc(F)c1F)C[C@@H]2F)C(F)F]

(5S,7S)-2-(difluoromethylsulfonyl)-5-(2,3-difluorophenyl)-7-fluoro-6,7-dihydro-5H-pyrrolo[1,2-b][1,2,4]triazole was prepared according to method 21 starting from 2,3-difluorobenzaldehyde. The final compound was purified by RP-HPLC (acetonitrile 35-65%/0.225% formic acid in water) to give (5S,7S)-2-(difluoromethylsulfonyl)-5-(2,3-difluorophenyl)-7-fluoro-6,7-dihydro-5H-pyrrolo[1,2-b][1,2,4]triazole (26.1 mg, 37%) as a white solid. $^1$H NMR (400 MHz, CDCl$_3$) δ 7.26-7.21 (m, 1H), 7.13-7.11 (m, 1H), 6.71-6.69 (m, 1H), 6.43 (t, J=53.2 Hz, 1H), 6.14 (d, J=5.6 Hz, 0.5H), 6.00 (d, J=5.2 Hz, 0.5H), 5.98-5.92 (m, 1H), 3.80-3.70 (m, 1H), 3.05-2.94 (m, 1H). LCMS R$_T$=0.839 min, m/z=354.0 [M+H]$^+$.

Example 69

(5S,7S)-2-(difluoromethylsulfonyl)-5-(3,5-difluorophenyl)-7-fluoro-6,7-dihydro-5H-pyrrolo[1,2-b][1,2,4]triazole

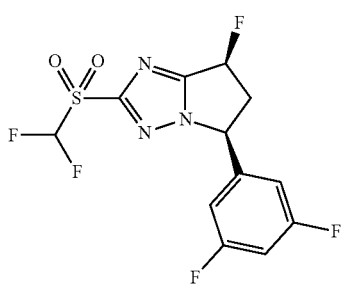 [SMILES: O=S(=O)(c1nc2n(n1)[C@H](c1cc(F)cc(F)c1)C[C@@H]2F)C(F)F]

(5S,7S)-2-(difluoromethylsulfonyl)-5-(3,5-difluorophenyl)-7-fluoro-6,7-dihydro-5H-pyrrolo[1,2-b][1,2,4]triazole was prepared according to method 23 starting from 3,5-difluorobenzoic acid. The final compound was purified first by RP-HPLC (acetonitrile 43-73%/0.04% ammonia hydroxide+10 mM NH$_4$HCO$_3$ in water), and then by SFC to give (5S,7S)-2-(difluoromethylsulfonyl)-5-(3,5-difluorophenyl)-7-fluoro-6,7-dihydro-5H-pyrrolo[1,2-b][1,2,4]triazole (50 mg, 50%, white solid): $^1$H NMR (400 MHz, CDCl$_3$) δ 6.92-6.85 (m, 1H), 6.84-6.77 (m, 2H), 6.44 (t, J=53.2 Hz, 1H), 6.17-6.01 (m, 1H), 5.59-5.57 (m, 1H), 3.77-3.69 (m, 1H), 3.07-2.97 (m, 1H). LC-MS R$_T$=1.030 min, m/z=354.1 [M+H]$^+$.

SFC condition (prep): column: chiralcel OD-3 150×4.6 mm I.D., 3 μm; mobile phase: A: CO$_2$ B: ethanol (0.05% DEA); gradient: from 5% to 40% of B in 5 min and from 40% to 5% of B in 0.5 min, hold 5% of B for 1.5 min; flow rate: 2.5 mL/min; column temp.: 35° C.

Example 70

(5S,7S)-2-((difluoromethyl)sulfinyl)-7-fluoro-5-(3-fluorophenyl)-6,7-dihydro-5H-pyrrolo[1,2-b][1,2,4]triazole and (5S,7S)-2-((difluoromethyl)sulfonyl)-7-fluoro-5-(3-fluorophenyl)-6,7-dihydro-5H-pyrrolo[1,2-b][1,2,4]triazole

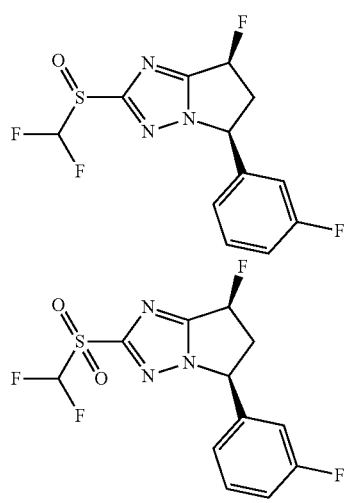

(5S,7S)-2-((difluoromethyl)sulfinyl)-7-fluoro-5-(3-fluorophenyl)-6,7-dihydro-5H-pyrrolo[1,2-b][1,2,4]triazole and (5S,7S)-2-((difluoromethyl)sulfonyl)-7-fluoro-5-(3-fluorophenyl)-6,7-dihydro-5H-pyrrolo[1,2-b][1,2,4]triazole were prepared according to method 17 starting from 3-fluorobenzaldehyde.

(5S,7S)-2-((difluoromethyl)sulfinyl)-7-fluoro-5-(3-fluorophenyl)-6,7-dihydro-5H-pyrrolo[1,2-b][1,2,4]triazole (38.0 mg, 18%, white solid) was purified by RP-HPLC (acetonitrile 15-45%/0.05% ammonia hydroxide in water). $^1$H NMR (400 MHz, CD$_3$OD) δ 7.44-7.42 (m, 1H), 7.22-6.95 (m, 4H), 6.21-6.05 (m, 1H), 5.72-5.70 (m, 1H), 3.82-3.70 (m, 1H), 2.91-2.80 (m, 1H). LC-MS R$_T$=0.955 min, m/z=320.1 [M+H]$^+$.

(5S,7S)-2-(difluoromethylsulfonyl)-7-fluoro-5-(3-fluorophenyl)-6,7-dihydro-5H-pyrrolo[1,2-b][1,2,4]triazole (40.0 mg, 18%, white solid) was purified by RP-HPLC (acetonitrile 40-50%/0.05% ammonia hydroxide in water). $^1$H NMR (400 MHz, CD$_3$OD) δ 7.46-7.44 (m, 1H), 7.15-6.83 (m, 4H), 6.23-6.07 (m, 1H), 5.75-5.74 (m, 1H), 3.83-3.73 (m, 1H), 2.93-2.82 (m, 1H). LC-MS R$_T$=1.027 min, m/z=336.1 [M+H]$^+$.

Example 71: Method 25

(5S,7S)-7-fluoro-2-[(S)-fluoromethylsulfinyl]-5-phenyl-6,7-dihydro-5H-pyrrolo[1,2-b][1,2,4]triazole and (5S,7S)-7-fluoro-2-[(R)-fluoromethylsulfinyl]-5-phenyl-6,7-dihydro-5H-pyrrolo[1,2-b][1,2,4]triazole

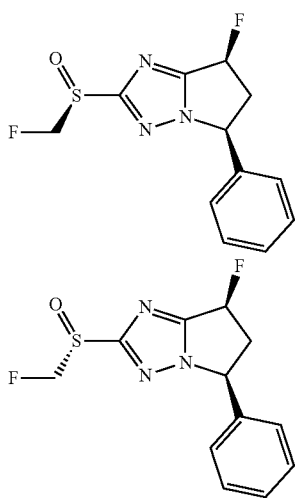

Step 1: (5S,7S)-7-fluoro-2-(fluoromethylsulfanyl)-5-phenyl-6,7-dihydro-5H-pyrrolo[1,2-b][1,2,4]triazole

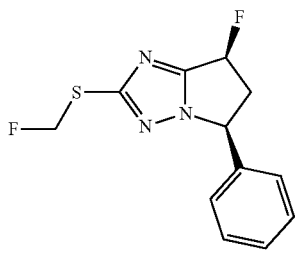 [SMILES: FCSc1nc2n(n1)[C@H](c1ccccc1)C[C@@H]2F]

To a cooled (0° C.) solution of (5S,7S)-7-fluoro-2-methylsulfanyl-5-phenyl-6,7-dihydro-5H-pyrrolo[1,2-b][1,2,4]triazole (149 mg, 0.60 mmol) in acetonitrile (4 mL) was added 1-chloromethyl-4-fluoro-1,4-diazoniabicyclo[2.2.2]octanebis (tetrafluoroborate) (222 mg, 0.63 mmol). The mixture was stirred at 0° C. for 2 h and concentrated under reduced pressure. The residue was purified by preparative TLC (50% ethyl acetate in petroleum ether, $R_f$=0.4) to give (5S,7S)-7-fluoro-2-(fluoromethylsulfanyl)-5-phenyl-6,7-dihydro-5H-pyrrolo[1,2-b][1,2,4]triazole (65 mg, 41%) as a colorless oil. $^1$H NMR (400 MHz, CDCl$_3$) δ 7.44-7.34 (m, 3H), 7.25-7.22 (m, 2H), 6.14-6.06 (m, 1H), 6.06-6.03 (m, 0.5H), 6.01-5.93 (m, 1H), 5.92-5.88 (m, 0.5H), 5.47-5.36 (m, 1H), 3.67-3.48 (m, 1H), 2.97-2.79 (m, 1H).

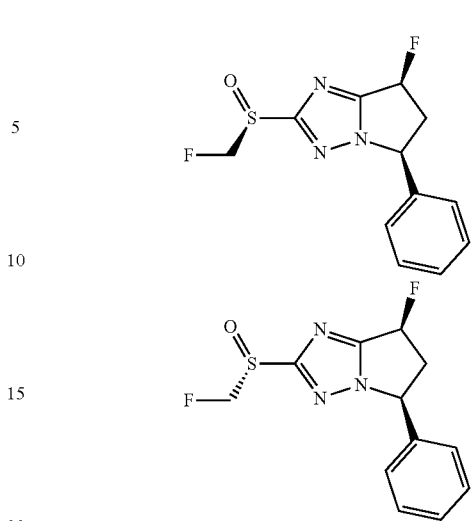

Step 2: (5S,7S)-7-fluoro-2-[(S)-fluoromethylsulfinyl]-5-phenyl-6,7-dihydro-5H-pyrrolo[1,2-b][1,2,4]triazole and (5S,7S)-7-fluoro-2-[(R)-fluoromethylsulfinyl]-5-phenyl-6,7-dihydro-5H-pyrrolo[1,2-b][1,2,4]triazole To a cooled (0° C.) solution of (5S,7S)-7-fluoro-2-(fluoromethylsulfanyl)-5-phenyl-6,7-dihydro-5H-pyrrolo[1,2-b][1,2,4]triazole (65 mg, 0.24 mmol) in dichloromethane (2 mL) was added 3-chloroperoxybenzoic acid (85%, 42 mg, 0.24 mmol). The mixture was stirred at 0° C. for 2 h and diluted with dichloromethane (20 mL). The mixture was washed with saturated aqueous sodium bicarbonate (2×10 mL), brine (2×10 mL), dried over sodium sulfate and concentrated under reduced pressure. The residue was purified by preparative TLC (47% ethyl acetate and 6% ethanol in petroleum ether, $R_f$=0.4, 0.3) to afford two isomers:

(5S,7S)-7-fluoro-2-[(S)-fluoromethylsulfinyl]-5-phenyl-6,7-dihydro-5H-pyrrolo[1,2-b][1,2,4]triazole (Peak 1 on SFC, retention time=3.597 min) (14.1 mg, 20%) as a white solid. $^1$H NMR (400 MHz, CDCl$_3$) δ 7.42-7.38 (m, 3H), 7.26-7.21 (m, 2H), 6.14-5.96 (m, 1H), 5.72-5.66 (m, 1H), 5.61-5.55 (m, 1H), 5.54-5.48 (m, 1H), 3.72-3.61 (m, 1H), 3.05-2.94 (m, 1H). LC-MS $R_T$=0.701 min, m/z=284.1 [M+H]$^+$.

(5S,7S)-7-fluoro-2-[(R)-fluoromethylsulfinyl]-5-phenyl-6,7-dihydro-5H-pyrrolo[1,2-b][1,2,4]triazole (Peak 2 on SFC, retention time=3.947 min) (15.7 mg, 21%) as a white solid. $^1$H NMR (400 MHz, CDCl$_3$) δ 7.44-7.38 (m, 3H), 7.26-7.22 (m, 2H), 6.13-5.96 (m, 1H), 5.73-5.62 (m, 1H), 5.61-5.48 (m, 2H), 3.74-3.59 (m, 1H), 3.06-2.93 (m, 1H). LC-MS $R_T$=0.692 min, m/z=284.1 [M+H]$^+$.

Analytical SFC conditions: SFC condition: Column: ChiralPak AD-3 Mobile phase: A: C02 B: Ethanol (0.05% DEA) Gradient: from 5% to 40% of B in 5.5 min and hold 40% for 3 min, then 5% of B for 1.5 min Flow rate: 2.5 mL/min Column temperature: 40° C.

Example 72

(5S,7S)-7-fluoro-2-((fluoromethyl)sulfonyl)-5-phenyl-6,7-dihydro-5H-pyrrolo[1,2-b][1,2,4]triazole

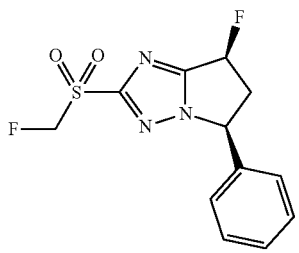 [SMILES: O=S(=O)(CF)c1nc2n(n1)[C@H](c1ccccc1)C[C@@H]2F]

To a solution of (5S,7S)-7-fluoro-2-(fluoromethylsulfanyl)-5-phenyl-6,7-dihydro-5H-pyrrolo[1,2-b][1,2,4]triazole (60 mg, 0.22 mmol) in dichloromethane (10 mL) was added 3-chloroperoxybenzoic acid (85%, 91 mg, 0.45 mmol). The reaction mixture was stirred at 20° C. for 16 h and diluted with dichloromethane (20 mL). The mixture was washed with saturated aqueous sodium bicarbonate (2×10 mL), dried over sodium sulfate and concentrated under reduced pressure. The residue was purified by RP-HPLC (acetonitrile 22-52%/0.05% hydrochloric acid in water) to give (5S,7S)-7-fluoro-2-(fluoromethylsulfonyl)-5-phenyl-6,7-dihydro-5H-pyrrolo[1,2-b][1,2,4]triazole (23 mg, 34%) as a white solid. $^1$H NMR (400 MHz, CDCl$_3$) δ 7.42-7.40 (m, 3H), 7.26-7.23 (m, 2H), 6.14-5.98 (m, 1H), 5.59-5.53 (m, 1H), 5.49 (s, 1H), 5.37 (s, 1H), 3.74-3.63 (m, 1H), 3.07-2.96 (m, 1H). LCMS R$_T$=0.932 min, m/z=300.1 [M+H]$^+$.

Examples 74 and 75

(5S,7S)-7-fluoro-2-[(S)-fluoromethylsulfinyl]-5-(2-fluorophenyl)-6,7-dihydro-5H-pyrrolo[1,2-b][1,2,4]triazole and (5S,7S)-7-fluoro-2-[(R)-fluoromethylsulfinyl]-5-(2-fluorophenyl)-6,7-dihydro-5H-pyrrolo[1,2-b][1,2,4]triazole

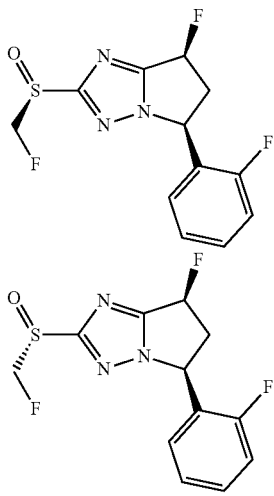

(5S,7S)-7-fluoro-2-[(S)-fluoromethylsulfinyl]-5-(2-fluorophenyl)-6,7-dihydro-5H-pyrrolo[1,2-b][1,2,4]triazole and (5S,7S)-7-fluoro-2-[(R)-fluoromethylsulfinyl]-5-(2-fluorophenyl)-6,7-dihydro-5H-pyrrolo[1,2-b][1,2,4]triazole were prepared according to method 25 starting from (5S,7S)-7-fluoro-5-(2-fluorophenyl)-2-(methylthio)-6,7-dihydro-5H-pyrrolo[1,2-b][1,2,4]triazole. The final compounds were purified by preparative TLC (50% ethyl acetate in petroleum ether, R$_f$=0.4, 0.3) to give: (5S,7S)-7-fluoro-2-[(S)-fluoromethylsulfinyl]-5-(2-fluorophenyl)-6,7-dihydro-5H-pyrrolo[1,2-b][1,2,4]triazole (Peak 1 on SFC, Retention time=3.300 min) (10.4 mg, 15%) as a white solid. $^1$H NMR (400 MHz, CD$_3$OD) δ 7.45-7.43 (m, 1H), 7.34-6.98 (m, 3H), 6.22-6.06 (m, 1H), 6.06-5.91 (m, 1H), 5.87-5.77 (m, 1H), 5.75-5.64 (m, 1H), 3.88-3.73 (m, 1H), 2.93-2.80 (m, 1H). LC-MS R$_T$=0.828 min, m/z=301.9 [M+H]$^+$.

(5S,7S)-7-fluoro-2-[(R)-fluoromethylsulfinyl]-5-(2-fluorophenyl)-6,7-dihydro-5H-pyrrolo[1,2-b][1,2,4]triazole (Peak 2 on SFC, Retention time=3.476 min) (21.6 mg, 23%) as a white solid. $^1$H NMR (400 MHz, CD$_3$OD) δ 7.45-7.23 (m, 1H), 7.22-7.13 (m, 3H), 6.21 (d, J=1.6 Hz, 0.5H), 6.07 (d, J=1.6 Hz, 0.5H), 5.80-5.78 (m, 1H), 5.77-5.75 (m, 1H), 5.74-5.64 (m, 1H), 3.87-3.74 (m, 1H), 2.93-2.81 (m, 1H). LC-MS R$_T$=0.828 min, m/z=302.1 [M+H]$^+$.

Analytical SFC conditions: SFC condition: Column: ChiralPak AD-3 Mobile phase: A: C02 B: Ethanol (0.05% DEA) Gradient: from 5% to 40% of B in 5 min and hold 40% for 2.5 min, then 5% of B for 2.5 min Flow rate: 2.5 mL/min Column temperature: 35° C.

Examples 76 and 77

(5S,7S)-5-(2,3-difluorophenyl)-7-fluoro-2-[(S)-fluoromethylsulfinyl]-6,7-dihydro-5H-pyrrolo[1,2-b][1,2,4]triazole and (5S,7S)-5-(2,3-difluorophenyl)-7-fluoro-2-[(R)-fluoromethylsulfinyl]-6,7-dihydro-5H-pyrrolo[1,2-b][1,2,4]triazole

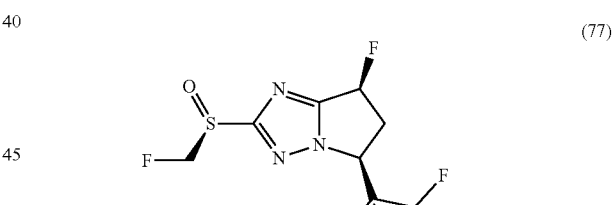
(77)

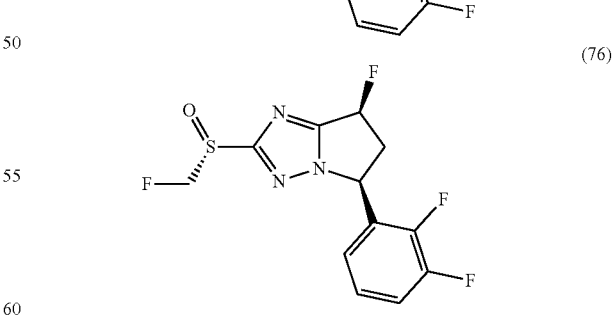
(76)

(5S,7S)-5-(2,3-difluorophenyl)-7-fluoro-2-[(S)-fluoromethylsulfinyl]-6,7-dihydro-5H-pyrrolo[1,2-b][1,2,4]triazole and (5S,7S)-5-(2,3-difluorophenyl)-7-fluoro-2-[(R)-fluoromethylsulfinyl]-6,7-dihydro-5H-pyrrolo[1,2-b][1,2,4]triazole were prepared according to method 25 starting from (5S,7S)-5-(2,3-difluorophenyl)-7-fluoro-2-(methylthio)-6, 7-dihydro-5H-pyrrolo[1,2-b][1,2,4]triazole. The final compounds were purified by chiral SFC to give:

(5S,7S)-5-(2,3-difluorophenyl)-7-fluoro-2-[(S)-fluoromethylsulfinyl]-6,7-dihydro-5H-pyrrolo[1,2-b][1,2,4]triazole (Peak 1, retention time=3.277 min) (31.9 mg, 26%) as a white solid. $^1$H NMR (400 MHz, CD$_3$OD) δ 7.35-7.33 (m, 1H), 7.21-7.20 (m, 1H), 6.96-6.94 (m, 1H), 6.23-6.07 (m, 1H), 5.96-5.94 (m, 1H), 5.84-5.78 (m, 1H), 5.74-5.66 (m, 1H), 3.88-3.78 (m, 1H), 2.95-2.84 (m, 1H). LC-MS R$_T$=0.720 min, m/z=320.1 [M+H]$^+$.

(5S,7S)-5-(2,3-difluorophenyl)-7-fluoro-2-[(R)-fluoromethylsulfinyl]-6,7-dihydro-5H-pyrrolo[1,2-b][1,2,4]triazole (Peak 2, retention time=3.552 min) (36.4 mg, 30%) as a white solid. $^1$H NMR (400 MHz, CD$_3$OD) δ 7.37-7.33 (m, 1H), 7.22-7.20 (m, 1H), 6.96-6.94 (m, 1H), 6.23-6.07 (m, 1H), 5.96-5.94 (m, 1H), 5.84-5.78 (m, 1H), 5.74-5.66 (m, 1H), 3.87-3.78 (m, 1H), 2.95-2.85 (m, 1H). LC-MS R$_T$=0.712 min, m/z=320.1 [M+H]$^+$.

SFC condition: Chiralcel OD-3 150×4.6 mm I.D., 3 μm Mobile phase: A: C02 B: ethanol (0.05% DEA) Gradient: from 5% to 40% of B in 5 min and hold 40% for 2.5 min, then 5% of B for 1.5 min Flow rate: 2.5 mL/min Column temperature.: 40° C.

Examples 78 and 79

(5S,7S)-5-(2,5-difluorophenyl)-7-fluoro-2-((S)-(fluoromethyl)sulfinyl)-6,7-dihydro-5H-pyrrolo[1,2-b][1,2,4]triazole and (5S,7S)-5-(2,5-difluorophenyl)-7-fluoro-2-((R)-(fluoromethyl)sulfinyl)-6,7-dihydro-5H-pyrrolo[1,2-b][1,2,4]triazole

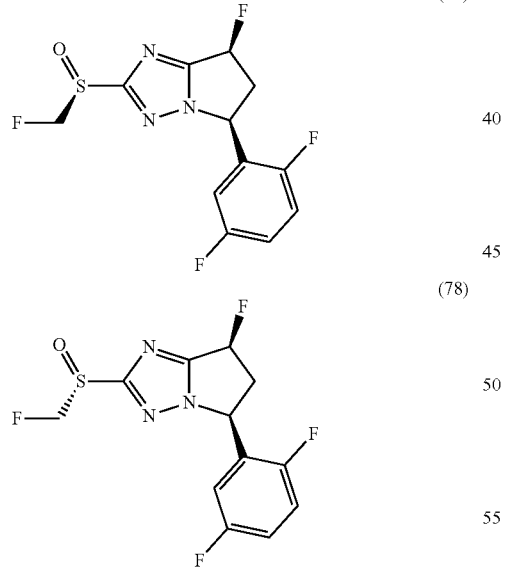

(79)

(78)

(5S,7S)-5-(2,5-difluorophenyl)-7-fluoro-2-((S)-(fluoromethyl)sulfinyl)-6,7-dihydro-5H-pyrrolo[1,2-b][1,2,4]triazole and (5S,7S)-5-(2,5-difluorophenyl)-7-fluoro-2-((R)-(fluoromethyl)sulfinyl)-6,7-dihydro-5H-pyrrolo[1,2-b][1,2,4]triazole were prepared according to method 25 starting from (5S,7S)-5-(2,5-difluorophenyl)-7-fluoro-2-(methylthio)-6,7-dihydro-5H-pyrrolo[1,2-b][1,2,4]triazole. The final compounds were purified by preparative TLC ((50% ethyl acetate in petroleum ether, Rf=0.2) to give: (5S,7S)-5-(2,5-difluorophenyl)-7-fluoro-2-[(S)-fluoromethylsulfinyl]-6,7-dihydro-5H-pyrrolo[1,2-b][1,2,4]triazole (Peak 1 on SFC, retention time=2.985 min) (14.5 mg, 18%) as a white solid. $^1$H NMR (400 MHz, CD$_3$OD) δ 7.26-7.19 (m, 2H), 6.97-6.91 (m, 1H), 6.22-6.06 (m, 1H), 5.89-5.67 (m, 3H), 3.88-3.74 (m, 1H), 2.93-2.82 (m, 1H). LC-MS R$_T$=0.869 min, m/z=320.1 [M+H]$^+$.

(5S,7S)-5-(2,5-difluorophenyl)-7-fluoro-2-[(R)-fluoromethylsulfinyl]-6,7-dihydro-5H-pyrrolo[1,2-b][1,2,4]triazole (Peak 2 on SFC, retention time=3.221 min) (20 mg, 25%) as a white solid. $^1$H NMR (400 MHz, CD$_3$OD) δ 7.26-7.19 (m, 2H), 7.18-6.91 (m, 1H), 6.20-6.06 (m, 1H), 5.89-5.65 (m, 3H), 3.87-3.74 (m, 1H), 2.93-2.82 (m, 1H). LC-MS R$_T$=0.853 min, m/z=320.1 [M+H]$^+$.

Analytical SFC conditions: SFC condition: Column: ChiralPak AD-3 Mobile phase: A: C02 B: Ethanol (0.05% DEA) Gradient: from 5% to 40% of B in 5 min and hold 40% for 2.5 min, then 5% of B for 2.5 min Flow rate: 2.5 mL/min Column temperature: 35 OC.

Examples 80 and 81

(5S,7S)-5-(2,6-difluorophenyl)-7-fluoro-2-((S)-(fluoromethyl)sulfinyl)-6,7-dihydro-5H-pyrrolo[1,2-b][1,2,4]triazole and (5S,7S)-5-(2,6-difluorophenyl)-7-fluoro-2-((R)-(fluoromethyl)sulfinyl)-6,7-dihydro-5H-pyrrolo[1,2-b][1,2,4]triazole

(81)

(80)

(5S,7S)-5-(2,6-difluorophenyl)-7-fluoro-2-((S)-(fluoromethyl)sulfinyl)-6,7-dihydro-5H-pyrrolo[1,2-b][1,2,4]triazole and (5S,7S)-5-(2,6-difluorophenyl)-7-fluoro-2-((R)-(fluoromethyl)sulfinyl)-6,7-dihydro-5H-pyrrolo[1,2-b][1,2,4]triazole were prepared according to method 25 starting from (5S,7S)-5-(2,6-difluorophenyl)-7-fluoro-2-(methylthio)-6,7-dihydro-5H-pyrrolo[1,2-b][1,2,4]triazole. The final compound was purified by RP-HPLC (acetonitrile 30-60%/0.05% HCl in water) to give: (5S,7S)-5-(2,6-difluorophenyl)-7-fluoro-2-[(S)-fluoromethylsulfinyl]-6,7-dihydro-5H-pyrrolo[1,2-b][1,2,4]triazole (Peak 1 on SFC, retention time=3.157 min) (9.7 mg, 13%) as a white solid. $^1$H NMR (400 MHz, CD$_3$OD) δ 7.52-7.46 (m, 1H), 7.10-7.05 (m, 2H), 6.23-6.08 (m, 1H), 6.00-5.98 (m, 1H), 5.80-

5.75 (m, 1H), 5.74-5.65 (m, 1H), 3.89-3.82 (m, 1H), 3.01-2.99 (m, 1H). LC-MS $R_T$=0.836 min, m/z=320.1 [M+H]⁺.

(5S,7S)-5-(2,6-difluorophenyl)-7-fluoro-2-[(R)-fluoromethylsulfinyl]-6,7-dihydro-5H-pyrrolo[1,2-b][1,2,4]triazole (Peak 2 on SFC, retention time=3.53 min) (2.7 mg, 4%) as a white solid. ¹H NMR (400 MHz, CDCl₃) δ 7.43-7.39 (m, 1H), 7.00-6.95 (m, 2H), 6.03-5.87 (m, 1H), 5.63-5.61 (m, 1H), 5.60-5.49 (m, 2H), 3.85-3.75 (m, 1H), 3.14-3.02 (m, 1H). LC-MS $R_T$=0.585 min, m/z=320.1 [M+H]⁺.

Analytical SFC conditions: SFC condition: Column: ChiralPak AD-3 Mobile phase: A: C02 B: Ethanol (0.05% DEA) Gradient: from 5% to 40% of B in 5 min and hold 40% for 2.5 min, then 5% of B for 2.5 min Flow rate: 2.5 mL/min Column temperature: 35° C.

Examples 82 and 83

(5S,7S)-7-fluoro-2-[(S)-fluoromethylsulfinyl]-5-(3-fluorophenyl)-6,7-dihydro-5H-pyrrolo[1,2-b][1,2,4]triazole and (5S,7S)-7-fluoro-2-[(R)-fluoromethylsulfinyl]-5-(3-fluorophenyl)-6,7-dihydro-5H-pyrrolo[1,2-b][1,2,4]triazole

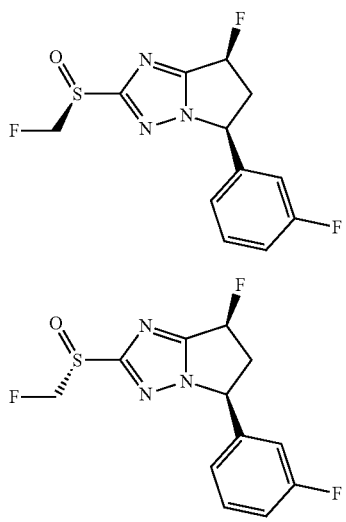

(5S,7S)-7-fluoro-5-(3-fluorophenyl)-2-(methylthio)-6,7-dihydro-5H-pyrrolo[1,2-b][1,2,4]triazole. The final compounds were purified by chiral SFC to give:

(5S,7S)-7-fluoro-2-[(S)-fluoromethysulfinyl]-5-(3-fluorophenyl)-6,7-dihydro-5H-pyrrolo[1,2-b][1,2,4]triazole (Peak 1, retention time=3.305 min) (22.6 mg, 22%) as a white solid. ¹H NMR (400 MHz, CDCl₃) δ 7.39-7.37 (m, 1H), 7.17-7.00 (m, 2H), 6.95 (d, J=9.2 Hz, 1H), 6.12-5.95 (m, 1H), 5.70-5.68 (m, 1H), 5.63-5.52 (m, 2H), 3.73-3.60 (m, 1H), 3.02-2.92 (m, 1H). LC-MS $R_T$=0.857 min, m/z=302.1 [M+H]⁺.

(5S,7S)-7-fluoro-2-[(R)-fluoromethylsulfinyl]-5-(3-fluorophenyl)-6,7-dihydro-5H-pyrrolo[1,2-b][1,2,4]triazole (Peak 2, retention time=3.695 min) (24.7 mg, 25%) as a white solid. ¹H NMR (400 MHz, CDCl₃) δ 7.40-7.38 (m, 1H), 7.10-7.09 (m, 2H), 6.97-6.95 (m, 1H), 6.12-5.96 (m, 1H), 5.72-5.60 (m, 2H), 5.58-5.51 (m, 1H), 3.73-3.63 (m, 1H), 3.03-2.92 (m, 1H). LC-MS $R_T$=0.837 min, m/z=302.1 [M+H].

SFC condition: Column: AD (250 mm*30 mm, 5 μm); Mobile phase: A: CO₂ B: 0.1% NH₃H₂O MeOH; Gradient: from 25% to 25% of B; Flow rate: 50 mL/min Column temperature: 35° C.

Examples 84 and 85

(5S,7S)-5-(3,5-difluorophenyl)-7-fluoro-2-((S)-(fluoromethyl)sulfinyl)-6,7-)-6,7-dihydro-5H-pyrrolo[1,2-b][1,2,4]triazole and (5S,7S)-5-(3,5-difluorophenyl)-7-fluoro-2-((R)-(fluoromethyl)sulfinyl)-6,7-dihydro-5H-pyrrolo[1,2-b][1,2,4]triazole

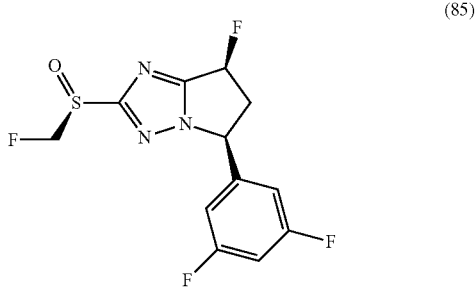

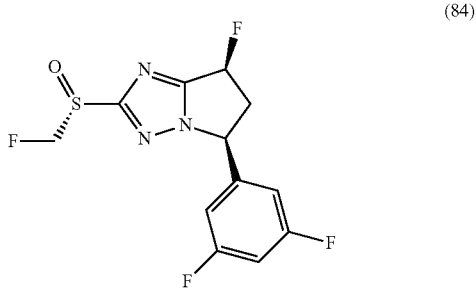

The title compounds were prepared according to method 25 starting from (5S,7S)-5-(3,5-difluorophenyl)-7-fluoro-2-(methylthio)-6,7-dihydro-5H-pyrrolo[1,2-b][1,2,4]triazole. The final compounds were purified by chiral SFC to give:

(5S,7S)-5-(3,5-difluorophenyl)-7-fluoro-2-[(S)-fluoromethylsulfinyl]-6,7-dihydro-5H-pyrrolo[1,2-b][1,2,4]triazole (Peak 1, retention time=2.932 min) (7.4 mg, 21%). ¹H NMR (400 MHz, CD₃OD) δ 7.00-6.98 (m, 1H), 6.95-6.91 (m, 2H), 6.20-6.18 (m, 1H), 5.87-5.67 (m, 3H), 3.80-3.72 (m, 1H), 2.91-2.80 (m, 1H). LC-MS $R_T$=0.625 min, m/z=320.1 [M+H]⁺.

(5S,7S)-5-(3,5-difluorophenyl)-7-fluoro-2-[(R)-fluoromethylsulfinyl]-6,7-dihydro-5H-pyrrolo[1,2-b][1,2,4]triazole (peak 2, retention time=3.144 min) (5.4 mg, 15%) as a white solid. ¹H NMR (400 MHz, CD₃OD) δ 7.01-6.98 (m, 1H), 6.95-6.91 (m, 2H), 6.20-6.06 (m, 1H), 5.86-5.65 (m, 3H), 3.82-3.74 (m, 1H), 2.91-2.81 (m, 1H). LC-MS $R_T$=0.617 min, m/z=320.1 [M+H]⁺.

SFC condition: Column: Phenomenex-Amylose-1 (250 mm*30 mm, 5 μm)., 3 um Mobile phase: A: C02 B: 0.1% NH₃.H₂O-MeOH Gradient: from 20% to 20% of B, Flow rate: 50 mL/min Column temperature.: 40° C.

Examples 86 and 87

(5S,7S)-5-(2-chlorophenyl)-7-fluoro-2-((S)-(fluoromethyl)sulfinyl)-6,7-dihydro-5H-pyrrolo[1,2-b][1,2,4]triazole and (5S,7S)-5-(2-chlorophenyl)-7-fluoro-2-((R)-(fluoromethyl)sulfinyl)-6,7-dihydro-5H-pyrrolo[1,2-b][1,2,4]triazole

Examples 88, 89 and 102

2-[(5S,7S)-7-fluoro-5-phenyl-6,7-dihydro-5H-pyrrolo[1,2-b][1,2,4]triazol-2-yl]sulfanyl]acetonitrile (89), 2-[[(5S,7S)-7-fluoro-5-phenyl-6,7-dihydro-5H-pyrrolo[1,2-b][1,2,4]triazol-2-yl]sulfinyl]acetonitrile (102) and 2-[[(5S,7S)-7-fluoro-5-phenyl-6,7-dihydro-5H-pyrrolo[1,2-b][1,2,4]triazol-2-yl]sulfonyl]acetonitrile (88)

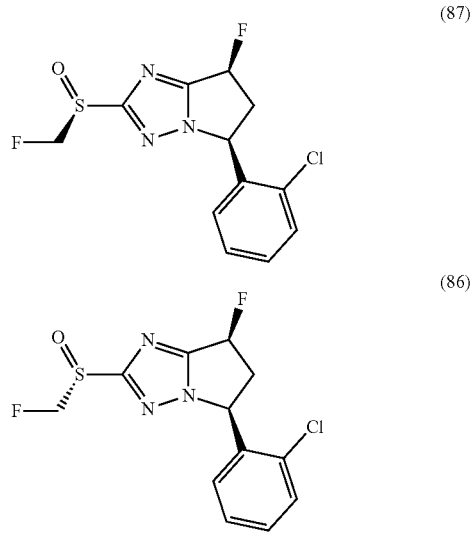

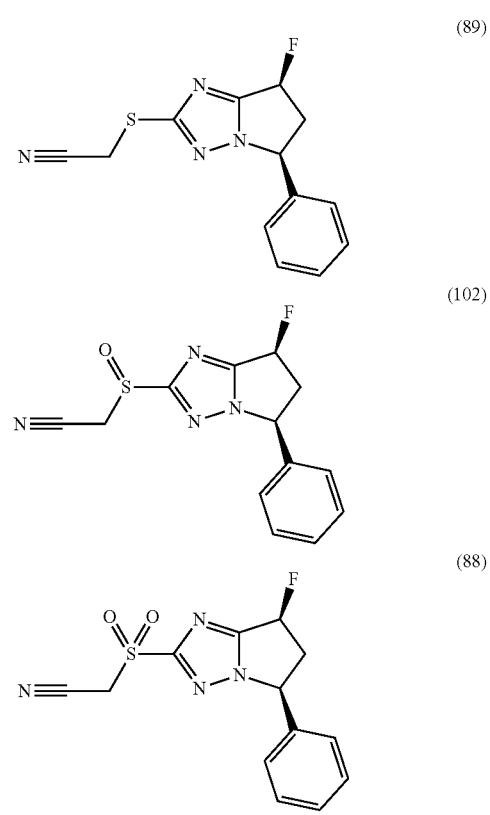

(5S,7S)-5-(2-chlorophenyl)-7-fluoro-2-((S)-(fluoromethyl)sulfinyl)-6,7-dihydro-5H-pyrrolo[1,2-b][1,2,4]triazole and (5S,7S)-5-(2-chlorophenyl)-7-fluoro-2-((R)-(fluoromethyl)sulfinyl)-6,7-dihydro-5H-pyrrolo[1,2-b][1,2,4]triazole were prepared according to Method 10 starting from (5S,7S)-5-(2-chlorophenyl)-7-fluoro-2-(methylthio)-6,7-dihydro-5H-pyrrolo[1,2-b][1,2,4]triazole. The final compounds were purified by preparative TLC (50% ethyl acetate in petroleum ether, $R_f$=0.2) to give: (5S,7S)-5-(2-chlorophenyl)-7-fluoro-2-[(S)-fluoromethylsulfinyl]-6,7-dihydro-5H-pyrrolo[1,2-b][1,2,4]triazole (Peak 1 on SFC, retention time=3.763 min) (35 mg, 25%) as a white solid $^1$H NMR (400 MHz, CD$_3$OD) δ 7.54-7.52 (m, 1H), 7.41-7.30 (m, 2H), 6.91-6.89 (m, 1H), 6.21-6.18 (m, 0.5H), 6.08-6.05 (m, 1.5H), 5.86-5.68 (m, 2H), 3.91-3.79 (m, 1H), 2.84-2.74 (m, 1H). LC-MS $R_T$=0.929 min, m/z=318.1 [M+H]$^+$.

(5S,7S)-5-(2-chlorophenyl)-7-fluoro-2-[(R)-fluoromethylsulfinyl]-6,7-dihydro-5H-pyrrolo[1,2-b][1,2,4]triazole (Peak 2 on SFC, retention time=3.971 min) (20 mg, 14%) as a white solid. $^1$H NMR (400 MHz, CD$_3$OD) δ 7.54-7.52 (m, 1H), 7.41-7.33 (m, 2H), 6.91-6.89 (m, 1H), 6.21-6.18 (m, 0.5H), 6.08-6.05 (m, 1.5H), 5.87-5.69 (m, 2H), 3.90-3.77 (m, 1H), 2.85-2.74 (m, 1H). LC-MS $R_T$=1.536 min, m/z=318.0 [M+H]$^+$.

Analytical SFC conditions: SFC condition: Column: ChiralPak AD-3 Mobile phase: A: C02 B: Ethanol (0.05% DEA) Gradient: from 5% to 40% of B in 5 min and hold 40% for 2.5 min, then 5% of B for 2.5 min Flow rate: 2.5 mL/min Column temperature: 35° C.

2-[(5S,7S)-7-fluoro-5-phenyl-6,7-dihydro-5H-pyrrolo[1,2-b][1,2,4]triazol-2-yl]sulfanyl]acetonitrile, 2-[(5S,7S)-7-fluoro-5-phenyl-6,7-dihydro-5H-pyrrolo[1,2-b][1,2,4]triazol-2-yl]sulfinyl]acetonitrile and 2-[(5S,7S)-7-fluoro-5-phenyl-6,7-dihydro-5H-pyrrolo[1,2-b][1,2,4]triazol-2-yl]sulfonyl]acetonitrile was prepared according to method 26 starting from (5S,7S)-7-fluoro-5-phenyl-6,7-dihydro-5H-pyrrolo[1,2-b][1,2,4]triazole-2-thiol and chloroacetonitrile.

2-[(5S,7S)-7-fluoro-5-phenyl-6,7-dihydro-5H-pyrrolo[1,2-b][1,2,4]triazol-2-yl]sulfanyl]acetonitrile was purified by RP-HPLC (acetonitrile 30-60%/0.05% ammonia hydroxide in water) (250 mg, 85%) as light yellow solid. $^1$H NMR (400 MHz, DMSO-d$_6$) δ 7.43-7.36 (m, 3H), 7.25-7.21 (m, 2H), 6.26-6.09 (m, 1H), 5.65-5.62 (m, 1H), 4.29-4.19 (m, 2H), 3.73-3.64 (m, 1H), 2.69-2.56 (m, 1H). LCMS $R_T$=0.825 min, m/z=274.9 [M+H]$^+$.

2-[[(5S,7S)-7-fluoro-5-phenyl-6,7-dihydro-5H-pyrrolo[1,2-b][1,2,4]triazol-2-yl]sulfinyl]acetonitrile was purified by RP-HPLC (acetonitrile 45-75%/0.05% ammonia hydroxide in water) (20.8 mg, 39%) as a yellow oil. H NMR (400 MHz, CDCl$_3$) δ 7.43-7.40 (m, 3H), 7.30-7.25 (m, 2H), 6.16-5.99 (m, 1H), 5.63-5.54 (m, 1H), 4.41-4.31 (m, 1H), 4.15-4.06

(m, 1H), 3.72-3.66 (m, 1H), 3.08-2.95 (m, 1H). LC-MS R$_T$=0.847 min, m/z=291.1 [M+H]$^+$.

2-[[(5S,7S)-7-fluoro-5-phenyl-6,7-dihydro-5H-pyrrolo[1,2-b][1,2,4]triazol-2-yl]sulfonyl]acetonitrile was purified by RP-HPLC (acetonitrile 40-70%/0.05% ammonia hydroxide in water) (16.7 mg, 37%) as a yellow oil. $^1$H NMR (400 MHz, CDCl$_3$) δ 7.51-7.35 (m, 4H), 7.33-7.15 (m, 1H), 6.17-6.00 (m, 1H), 5.65-5.57 (m, 1H), 4.52-4.39 (m, 2H), 3.79-3.64 (m, 1H), 3.10-2.99 (m, 1H). LCMS R$_T$=0.956 min, m/z=307.1 [M+H]$^+$.

Example 90

2-(((4S,6S)-4-fluoro-6-phenyl-5,6-dihydro-4H-pyrrolo[1,2-b]pyrazol-2-yl)sulfonyl)acetonitrile

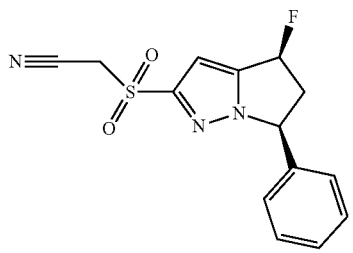 [SMILES: N#CCS(=O)(=O)c1cc2n(n1)[C@H](c1ccccc1)C[C@@H]2F]

2-(((4S,6S)-4-fluoro-6-phenyl-5,6-dihydro-4H-pyrrolo[1,2-b]pyrazol-2-yl)sulfonyl) acetonitrile was prepared according to method 26 starting from (4S,6S)-4-fluoro-6-phenyl-5,6-dihydro-4H-pyrrolo[1,2-b]pyrazole-2-thiol and chloroacetonitrile. The final compound was purified by RP-HPLC (acetonitrile 32-62%/0.1% bicarbonate in water) to give 2-(((4S,6S)-4-fluoro-6-phenyl-5,6-dihydro-4H-pyrrolo[1,2-b]pyrazol-2-yl)sulfonyl)acetonitrile (14 mg, 40%) as a white solid. $^1$H NMR (400 MHz, CDCl$_3$) δ 7.42-7.38 (m, 3H), 7.23-7.21 (m, 2H), 7.11 (d, J=2.8 Hz, 1H), 6.14 (d, J=6.8 Hz, 0.5H), 5.99 (d, J=6.4 Hz, 0.5H), 5.70-5.55 (m, 1H), 4.27-4.17 (m, 2H), 3.65-3.50 (m, 1H), 2.97-2.87 (m, 1H). LC-MS R$_T$=0.787 min, m/z=306.1 [M+H]$^+$.

Examples 91 and 92

2-((S)-((4S,6S)-4-fluoro-6-phenyl-5,6-dihydro-4H-pyrrolo[1,2-b]pyrazol-2-yl)sulfinyl)acetonitrile (92) and 2-((R)-((4S,6S)-4-fluoro-6-phenyl-5,6-dihydro-4H-pyrrolo[1,2-b]pyrazol-2-yl)sulfinyl)acetonitrile (91)

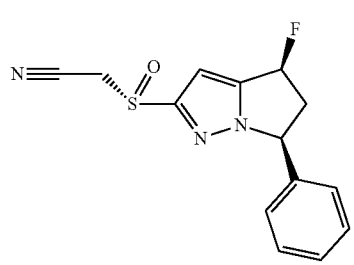

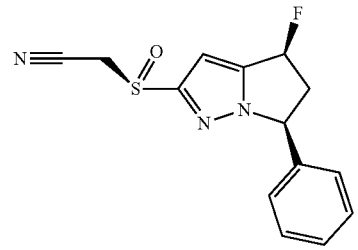

2-((S)-((4S,6S)-4-fluoro-6-phenyl-5,6-dihydro-4H-pyrrolo[1,2-b]pyrazol-2-yl)sulfinyl)acetonitrile and 2-((R)-((4S,6S)-4-fluoro-6-phenyl-5,6-dihydro-4H-pyrrolo[1,2-b]pyrazol-2-yl)sulfinyl)acetonitrile were prepared according to Method 11 starting from (4S,6S)-4-fluoro-6-phenyl-5,6-dihydro-4H-pyrrolo[1,2-b]pyrazole-2-thiol and chloroacetonitrile. The final compounds were purified by chiral SFC to give: 2-((S)-((4S,6S)-4-fluoro-6-phenyl-5,6-dihydro-4H-pyrrolo[1,2-b]pyrazol-2-yl)sulfinyl) acetonitrile (Peak 1, Retention time=3.727 min) (7 mg, 12%) as a white solid. $^1$H NMR (400 MHz, CDCl$_3$) δ 7.41-7.35 (m, 3H), 7.27-7.21 (m, 2H), 7.08 (s, 1H), 6.13 (d, J=6.8 Hz, 0.5H), 5.99 (d, J=6.4 Hz, 0.5H), 5.55-5.50 (m, 1H), 4.09 (d, J=15.6 Hz, 1H), 3.84 (d, J=16.0 Hz, 1H), 3.62-3.49 (m, 1H), 2.93-2.83 (m, 1H). LC-MS R$_T$=0.718 min, m/z=290.1 [M+H]+.

2-((R)-((4S,6S)-4-fluoro-6-phenyl-5,6-dihydro-4H-pyrrolo[1,2-b]pyrazol-2-yl) sulfinyl) acetonitrile (Peak 2, Retention time=3.964 min) (6 mg, 11%) as a white solid. $^1$H NMR (400 MHz, CDCl$_3$) δ 7.40-7.36 (m, 3H), 7.21-7.19 (m, 2H), 7.07 (s, 1H), 6.13 (d, J=6.8 Hz, 0.5H), 5.98 (d, J=6.8 Hz, 0.5H), 5.55-5.50 (m, 1H), 4.10 (d, J=15.6 Hz, 1H), 3.81 (d, J=15.6 Hz, 1H), 3.61-3.50 (m, 1H), 2.93-2.83 (m, 1H). LC-MS R$_T$=0.711 min, m/z=290.1 [M+H]$^+$.

SFC condition: Phenomenex-Amylose-1 (250 mm*30 mm, 5 μm); Mobile phase: A: CO$_2$ B: 0.1% NH$_3$H$_2$O EtOH; Gradient: from 20% to 20% of B; Flow rate: 50 mL/min Column temperature: 40° C.

Examples 93 and 94

2-[(S)-[(5S,7S)-5-(2-chlorophenyl)-7-fluoro-6,7-dihydro-5H-pyrrolo[1,2-b][1,2,4]triazol-2-yl]sulfinyl]acetonitrile and 2-[(R)-[(5S,7S)-5-(2-chlorophenyl)-7-fluoro-6,7-dihydro-5H-pyrrolo[1,2-b][1,2,4]triazol-2-yl]sulfinyl]acetonitrile

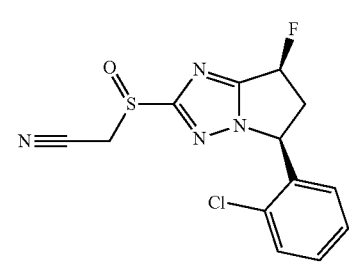

(94)

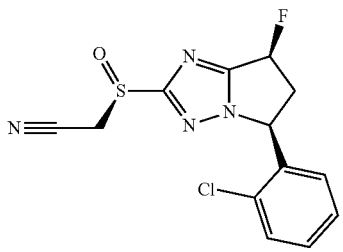

2-[(S)-[(5S,7S)-5-(2-chlorophenyl)-7-fluoro-6,7-dihydro-5H-pyrrolo[1,2-b][1,2,4]triazol-2-yl]sulfinyl]acetonitrile and 2-[(R)-[(5S,7S)-5-(2-chlorophenyl)-7-fluoro-6,7-dihydro-5H-pyrrolo[1,2-b][1,2,4]triazol-2-yl]sulfinyl]acetonitrile were prepared according to method 26 starting from (5S,7S)-5-(2-chlorophenyl)-7-fluoro-6,7-dihydro-5H-pyrrolo[1,2-b][1,2,4]triazole-2-thiol and chloroacetonitrile. The final compounds were purified by chiral SFC to give:

2-[(S)-[(5S,7S)-5-(2-chlorophenyl)-7-fluoro-6,7-dihydro-5H-pyrrolo[1,2-b][1,2,4]triazol-2-yl]sulfinyl]acetonitrile (Peak 1, retention time=4.505 min) (22 mg, 29%) as a white solid. $^1$H NMR (400 MHz, CDCl$_3$) δ 7.46 (dd, J=1.2, 8.4 Hz, 1H), 7.36-7.30 (m, 1H), 7.29-7.27 (m, 0.5H), 7.25-7.23 (m, 0.5H), 6.75 (dd, J=1.2, 7.6 Hz, 1H), 6.12 (d, J=5.6 Hz, 0.5H), 6.05-5.96 (m, 1.5H), 4.37 (d, J=15.6 Hz, 1H), 4.14 (d, J=15.6 Hz, 1H), 3.83-3.67 (m, 1H), 2.98-2.84 (m, 1H). LC-MS $R_T$=0.956 min, m/z=325.1 [M+H]$^+$.

2-[(R)-[(5S,7S)-5-(2-chlorophenyl)-7-fluoro-6,7-dihydro-5H-pyrrolo[1,2-b][1,2,4]triazol-2-yl]sulfinyl]acetonitrile (Peak 2, retention time=5.032 min) (17 mg, 20%) as a white solid. $^1$H NMR (400 MHz, CDCl$_3$) δ 7.46 (dd, J=1.2, 8.8 Hz, 1H), 7.37-7.27 (m, 2H), 6.77 (d, J=9.2 Hz, 1H), 6.11 (d, J=5.2 Hz, 0.5H), 6.06-5.95 (m, 1.5H), 4.40 (d, J=15.6 Hz, 1H), 4.10 (d, J=15.6 Hz, 1H), 3.83-3.68 (m, 1H), 2.99-2.84 (m, 1H). LC-MS $R_T$=0.949 min, m/z=325.1 [M+H]$^+$.

SFC condition: column: chiralpak AD-3 150×4.6 mm I.D., 3 μm mobile phase: A: CO$_2$ B: ethanol (0.05% DEA) gradient: from 5% to 40% of B in 5 min and hold 40% for 2.5 min, then 5% of B for 2.5 min; flow rate: 2.5 mL/min; column temp.: 35° C.

Examples 95 and 96

2-[(S)-[(5S,7S)-7-fluoro-5-(2-fluorophenyl)-6,7-dihydro-5H-pyrrolo[1,2-b][1,2,4]triazol-2-yl]sulfinyl]acetonitrile (95) and 2-[(R)-[(5S,7S)-7-fluoro-5-(2-fluorophenyl)-6,7-dihydro-5H-pyrrolo[1,2-b][1,2,4]triazol-2-yl]sulfinyl]acetonitrile (96)

(95)

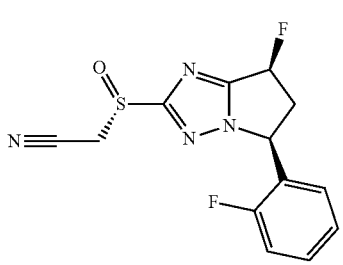

(96)

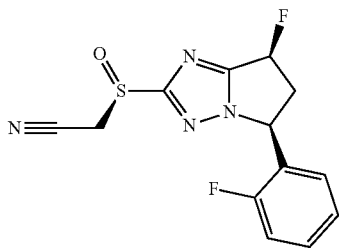

2-[(S)-[(5S,7S)-7-fluoro-5-(2-fluorophenyl)-6,7-dihydro-5H-pyrrolo[1,2-b][1,2,4]triazol-2-yl]sulfinyl]acetonitrile and 2-[(R)-[(5S,7S)-7-fluoro-5-(2-fluorophenyl)-6,7-dihydro-5H-pyrrolo[1,2-b][1,2,4]triazol-2-yl]sulfinyl]acetonitrile were prepared according to Method 11 starting from (5S,7S)-5-(2-fluorophenyl)-7-fluoro-6,7-dihydro-5H-pyrrolo[1,2-b][1,2,4]triazole-2-thiol and chloroacetonitrile. The final compounds were purified by chiral SFC to give:

2-[(S)-[(5S,7S)-7-fluoro-5-(2-fluorophenyl)-6,7-dihydro-5H-pyrrolo[1,2-b][1,2,4]triazol-2-yl]sulfinyl]acetonitrile (Peak 1, Retention time=3.929 min) (33 mg, 33%) as a white solid. $^1$H NMR (400 MHz, CDCl$_3$) δ 7.40-7.38 (m, 1H), 7.18-7.13 (m, 2H), 7.10-6.99 (m, 1H), 6.15-6.00 (m, 1H), 5.90-5.88 (m, 1H), 4.34 (d, J=15.6 Hz, 1H), 4.14 (d, J=15.6 Hz, 1H), 3.79-3.67 (m, 1H), 3.02-2.91 (m, 1H). LCMS $R_T$=0.775 min, m/z=308.9 [M+H]$^+$.

2-[(R)-[(5S,7S)-7-fluoro-5-(2-fluorophenyl)-6,7-dihydro-5H-pyrrolo[1,2-b][1,2,4]triazol-2-yl]sulfinyl]acetonitrile (Peak 2, Retention time=4.366 min) (33 mg, 33%) as a white solid. $^1$H NMR (400 MHz, CDCl$_3$) δ 7.41-7.39 (m, 1H), 7.20-7.14 (m, 2H), 7.01-6.98 (m, 1H), 6.15-6.00 (m, 1H), 5.99-5.89 (m, 1H), 4.40 (d, J=15.6 Hz, 1H), 4.10 (d, J=15.6 Hz, 1H), 3.79-3.67 (m, 1H), 3.03-2.93 (m, 1H). LCMS $R_T$=0.762 min, m/z=308.9 [M+H]$^+$.

SFC condition: Column: Chiral Amylose-C (250 mm*30 mm, 5 m); Condition: 0.10% NH$_3$H$_2$O EtOH; Begin B 30% End B 30%; Flow Rate (60 mL/min), Column temperature 40° C.

Examples 97 and 98

2-[(S)-[(5S,7S)-7-fluoro-5-(3-fluorophenyl)-6,7-dihydro-5H-pyrrolo[1,2-b][1,2,4]triazol-2-yl]sulfinyl]acetonitrile (97) and 2-[(R)-[(5S,7S)-7-fluoro-5-(3-fluorophenyl)-6,7-dihydro-5H-pyrrolo[1,2-b][1,2,4]triazol-2-yl]sulfinyl]acetonitrile (98)

(97)

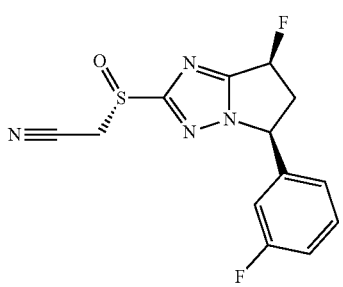

(98)

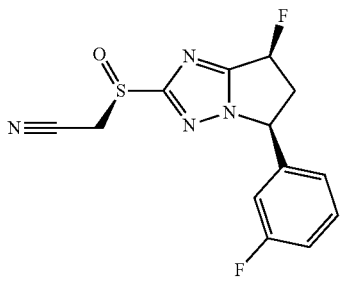

(100)

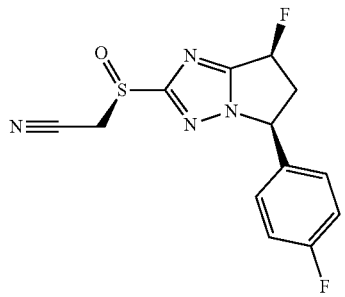

2-[(S)-[(5S,7S)-7-fluoro-5-(3-fluorophenyl)-6,7-dihydro-5H-pyrrolo[1,2-b][1,2,4]triazol-2-yl]sulfinyl]acetonitrile and 2-[(R)-[(5S,7S)-7-fluoro-5-(3-fluorophenyl)-6,7-dihydro-5H-pyrrolo[1,2-b][1,2,4]triazol-2-yl]sulfinyl]acetonitrile were prepared according to method 26 starting from (5S,7S)-5-(3-fluorophenyl)-7-fluoro-6,7-dihydro-5H-pyrrolo[1,2-b][1,2,4]triazole-2-thiol and chloroacetonitrile. The final compounds were purified by chiral SFC to give:

2-[(S)-[(5S,7S)-7-fluoro-5-(3-fluorophenyl)-6,7-dihydro-5H-pyrrolo[1,2-b][1,2,4]triazol-2-yl]sulfinyl]acetonitrile (Peak 1, retention time=3.324 min) (20 mg, 23%) as a white solid. $^1$H NMR (400 MHz, CDCl$_3$) δ 7.40-7.35 (m, 1H), 7.16-6.89 (m, 3H), 6.18-5.95 (m, 1H), 5.68-5.58 (m, 1H), 4.31-4.10 (m, 2H), 3.78-3.68 (m, 1H), 3.00-2.88 (m, 1H). LCMS R$_T$=0.914 min, m/z=309.1 [M+H]$^+$.

2-[(R)-[(5S,7S)-7-fluoro-5-(3-fluorophenyl)-6,7-dihydro-5H-pyrrolo[1,2-b][1,2,4]triazol-2-yl]sulfinyl]acetonitrile (Peak 2, retention time=3.948 min) (17 mg, 20%) as a white solid. $^1$H NMR (400 MHz, CDCl$_3$) δ 7.43-7.37 (m, 1H), 7.17-6.92 (m, 3H), 6.18-5.96 (m, 1H), 5.58-5.54 (m, 1H), 4.44-4.03 (m, 2H), 3.81-3.62 (m, 1H), 3.04-2.89 (m, 1H). LCMS R$_T$=0.894 min, m/z=309.1 [M+H]$^+$.

SFC condition: Column: Chiralpak IC-3 100×4.6 mm I.D., 3 μm Mobile phase: A: CO2 B: ethanol (0.05% DEA) Gradient: from 5% to 40% of B in 3.5 min and hold 40% for 2.5 min, then 5% of B for 1.5 min, Flow rate: 3 mL/min Column temp: 40° C.

Examples 99 and 100

2-[(S)-[(5S,7S)-7-fluoro-5-(4-fluorophenyl)-6,7-dihydro-5H-pyrrolo[1,2-b][1,2,4]triazol-2-yl]sulfinyl]acetonitrile (99) and 2-[(R)-[(5S,7S)-7-fluoro-5-(4-fluorophenyl)-6,7-dihydro-5H-pyrrolo[1,2-b][1,2,4]triazol-2-yl]sulfinyl]acetonitrile (100)

(99)

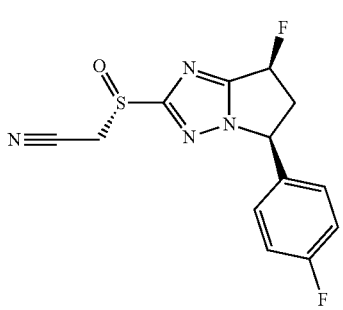

2-[(S)-[(5S,7S)-7-fluoro-5-(4-fluorophenyl)-6,7-dihydro-5H-pyrrolo[1,2-b][1,2,4]triazol-2-yl]sulfinyl]acetonitrile and 2-[(R)-[(5S,7S)-7-fluoro-5-(4-fluorophenyl)-6,7-dihydro-5H-pyrrolo[1,2-b][1,2,4]triazol-2-yl]sulfinyl]acetonitrile were prepared according to method 26 starting from (5S,7S)-7-fluoro-5-(4-fluorophenyl)-6,7-dihydro-5H-pyrrolo[1,2-b][1,2,4]triazole-2-thiol and chloroacetonitrile. The final compounds were purified by chiral SFC to give:

2-[(S)-[(5S,7S)-7-fluoro-5-(4-fluorophenyl)-6,7-dihydro-5H-pyrrolo[1,2-b][1,2,4]triazol-2-yl]sulfinyl]acetonitrile (Peak 1, retention time=3.293 min) (189 mg, 22%) as a white solid. $^1$H NMR (400 MHz, CDCl$_3$) δ 7.37-7.25 (m, 2H), 7.12-7.08 (m, 2H), 6.14-5.98 (m, 1H), 5.62-5.58 (m, 1H), 4.37-4.07 (m, 2H), 3.74-3.68 (m, 1H), 3.00-2.89 (m, 1H). LCMS R$_T$=0.907 min, m/z=309.1 [M+H]$^+$.

2-[(R)-[(5S,7S)-7-fluoro-5-(4-fluorophenyl)-6,7-dihydro-5H-pyrrolo[1,2-b][1,2,4]triazol-2-yl]sulfinyl]acetonitrile (Peak 2, retention time=3.964 min) (22 mg, 26%) as a white solid. $^1$H NMR (400 MHz, CDCl$_3$) δ 7.27-7.22 (m, 2H), 7.14-7.10 (m, 2H), 6.19-5.96 (m, 1H), 5.70-5.55 (m, 1H), 4.39-4.06 (m, 2H), 3.79-3.61 (m, 1H), 3.02-2.92 (m, 1H). LCMS R$_T$=0.899 min, m/z=309.1 [M+H]$^+$ SFC condition: Chiralpak IC-3 100×4.6 mm I.D., 3 μm; Mobile phase: A: CO2 B: ethanol (0.05% DEA); Gradient: from 5% to 40% of B in 3.5 min and hold 40% for 2.5 min, then 5% of B for 1.5 min; Flow rate: 3 mL/min; Column temp: 40° C.

Example 101

2-[(S)-[(5R,7R)-5-(2-chlorophenyl)-7-fluoro-6,7-dihydro-5H-pyrrolo[1,2-b][1,2,4]triazol-2-yl]sulfinyl]acetonitrile

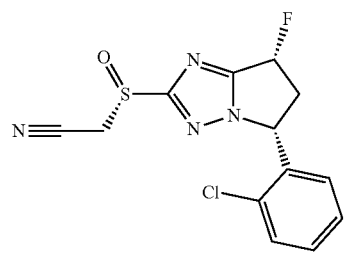 [SMILES: N#CC[S@](=O)c1nc2n(n1)[C@@H](c1ccccc1Cl)C[C@H]2F]

Arbitrary assigned 2-[(S)-[(5R,7R)-5-(2-chlorophenyl)-7-fluoro-6,7-dihydro-5H-pyrrolo[1,2-b][1,2,4]triazol-2-yl]

sulfinyl]acetonitrile was prepared according to method 26 starting from (5R,7R)-5-(2-chlorophenyl)-7-fluoro-6,7-dihydro-5H-pyrrolo[1,2-b][1,2,4]triazole-2-thiol and chloroacetonitrile. The final compound was purified by chiral SFC to give:

2-[(S)-[(5R,7R)-5-(2-chlorophenyl)-7-fluoro-6,7-dihydro-5H-pyrrolo[1,2-b][1,2,4]triazol-2-yl]sulfinyl]acetonitrile (Peak 1, retention time=5.070 min) (11 mg, 17%) as a arbitrarily assigned white solid. $^1$H NMR (400 MHz, CD$_3$OD) δ 7.53 (d, J=8.4 Hz, 1H), 7.41-7.35 (m, 1H), 7.34-7.28 (m, 1H), 6.89 (d, J=7.6 Hz, 1H), 6.21 (d, J=5.2 Hz, 0.5H), 6.12-6.05 (m, 1.5H), 3.90-3.76 (m, 1H), 3.38-3.31 (m, 2H), 2.87-2.72 (m, 1H). LC-MS R$_T$=0.741 min, m/z=325.0 [M+H]$^+$.

SFC condition: column: chiralpak AD-3 150×4.6 mm I.D. 3 μm; mobile phase: A: CO$_2$ B: ethanol (0.05% DEA); gradient: from 5% to 40% of B in 5 min and hold 40% for 2.5 min, then 5% of B for 2.5 min flow rate: 2.5 mL/min column temp.: 35° C.

Example 103: Method 27

2-[[(5S,7S)-7-fluoro-5-phenyl-6,7-dihydro-5H-pyrrolo[1,2-b][1,2,4]triazol-2-yl]sulfinyl]-2-methyl-propanenitrile

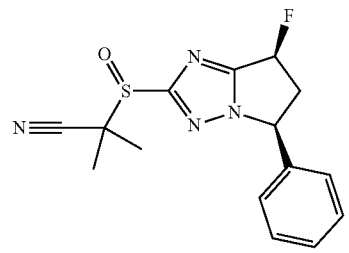 [SMILES: CC(C)(C#N)S(=O)c1nc2n(n1)[C@H](c1ccccc1)C[C@@H]2F]

To a solution of 2-[[(5S,7S)-7-fluoro-5-phenyl-6,7-dihydro-5H-pyrrolo[1,2-b][1,2,4]triazol-2-yl]sulfinyl]acetonitrile (40 mg, 0.14 mmol) (prepared sing the general procedure of method 16) in tetrahydrofuran (2 mL) was added sodium hydride (60%, 22 mg, 0.55 mmol). After stirred at 20° C. for 5 min, the reaction mixture was added iodomethane (2.0 g, 14.1 mmol). The resulting mixture was stirred at 20° C. for another 2 h and quenched by addition of saturated aqueous ammonium chloride (10 mL). The resulting mixture was extracted with ethyl acetate (2×10 mL). The combined organic layers were dried over sodium sulfate and concentrated under reduced pressure. The residue was purified by RP-HPLC (acetonitrile 25-55%/0.05% ammonia hydroxide in water) to afford 2-[[(5S,7S)-7-fluoro-5-phenyl-6,7-dihydro-5H-pyrrolo[1,2-b][1,2,4]triazol-2-yl]sulfinyl]-2-methyl-propanenitrile (14.3 mg, 29%) as a yellow solid. $^1$H NMR (400 MHz, CDCl$_3$) δ 7.42-7.38 (m, 3H), 7.27-7.21 (m, 2H), 6.14-6.11 (m, 0.5H), 5.99-5.97 (m, 0.5H), 5.59-5.54 (m, 1H), 3.74-3.62 (m, 1H), 3.03-2.92 (m, 1H), 1.79-1.77 (m, 6H). LC-MS R$_T$=0.796 min, m/z=340.9 [M+Na]$^+$.

Example 104

2-(((5S,7S)-7-fluoro-5-phenyl-6,7-dihydro-5H-pyrrolo[1,2-b][1,2,4]triazol-2-yl)sulfonyl)-2-methylpropanenitrile

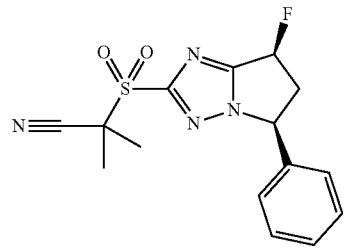 [SMILES: CC(C)(C#N)S(=O)(=O)c1nc2n(n1)[C@H](c1ccccc1)C[C@@H]2F]

2-(((5S,7S)-7-fluoro-5-phenyl-6,7-dihydro-5H-pyrrolo[1,2-b][1,2,4]triazol-2-yl)sulfonyl)-2-methylpropanenitrile was prepared according to Method 24 starting from 2-[[(5S,7S)-7-fluoro-5-phenyl-6,7-dihydro-5H-pyrrolo[1,2-b][1,2,4]triazol-2-yl]sulfonyl]acetonitrile. The final compound was purified by RP-HPLC (40-70/0.04% NH$_3$H$_2$O+10 mM NH$_4$HCO$_3$ in water) to give 2-(((5S,7S)-7-fluoro-5-phenyl-6,7-dihydro-5H-pyrrolo[1,2-b][1,2,4]triazol-2-yl)sulfonyl)-2-methylpropanenitrile (13.6 mg, 40%) as a white solid. $^1$H NMR (400 MHz, CDCl$_3$) δ 7.43-7.40 (m, 3H), 7.27-7.22 (m, 2H), 6.17-6.00 (m, 1H), 5.64-5.61 (m, 1H), 3.76-3.66 (m, 1H), 3.08-2.97 (m, 1H), 1.89-1.87 (m, 6H). LCMS R$_T$=1.794 min, m/z=335.1 [M+H]$^+$.

Example 105: Method 26

(5S,7S)-7-fluoro-2-methylsulfinyl-5-phenyl-6,7-dihydro-5H-pyrrolo[1,2-b][1,2,4]triazole

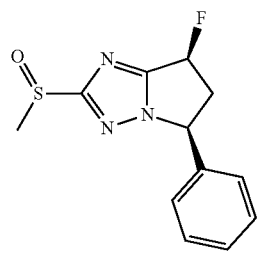 [SMILES: CS(=O)c1nc2n(n1)[C@H](c1ccccc1)C[C@@H]2F]

Step 1: (5S,7S)-7-fluoro-2-methylsulfanyl-5-phenyl-6,7-dihydro-5H-pyrrolo[1,2-b][1,2,4]triazole

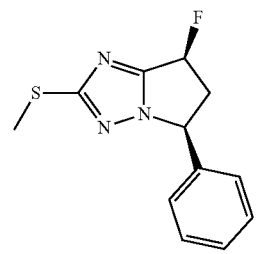 [SMILES: CSc1nc2n(n1)[C@H](c1ccccc1)C[C@@H]2F]

To a mixture of (5S,7S)-7-fluoro-5-phenyl-6,7-dihydro-5H-pyrrolo[1,2-b][1,2,4]triazole-2-thiol (200 mg, 0.85 mmol) and potassium carbonate (352 mg, 2.55 mmol) in acetonitrile (3 mL) was added iodomethane (1.2 g, 8.45 mmol). The mixture was stirred at 25° C. for 1 h and filtered. The filtrate was concentrated under reduced pressure and the residue was purified by column chromatography (silica gel, 100-200 mesh, 0 to 20% ethyl acetate in petroleum ether) to afford (5S,7S)-7-fluoro-2-methylsulfanyl-5-phenyl-6,7-dihydro-5H-pyrrolo[1,2-b][1,2,4]triazole (190 mg, 90%) as a light brown solid.

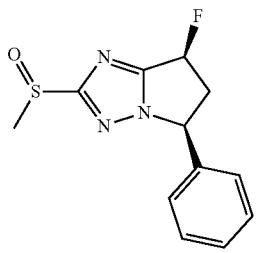 [SMILES: CS(=O)c1nc2n(n1)[C@H](c1ccccc1)C[C@@H]2F]

Step 2: (5S,7S)-7-fluoro-2-methylsulfinyl-5-phenyl-6,7-dihydro-5H-pyrrolo[1,2-b][1,2,4]triazole To a solution of (5S,7S)-7-fluoro-2-methylsulfanyl-5-phenyl-6,7-dihydro-5H-pyrrolo[1,2-b][1,2,4]triazole (40 mg, 0.16 mmol) in dichloromethane (5 mL) was added 3-chloroperoxybenzoic acid (85%, 33 mg, 0.16 mmol). The resulting mixture was stirred at 0° C. for 2 h and diluted with dichloromethane (20 mL). The mixture was washed with saturated aqueous sodium bicarbonate (2×10 mL), brine (2×10 mL), dried over sodium sulfate and concentrated under reduced pressure. The residue was purified by RP-HPLC (acetonitrile 40-70%/0.05% ammonia hydroxide in water) to give (5S,7S)-7-fluoro-2-methylsulfinyl-5-phenyl-6,7-dihydro-5H-pyrrolo[1,2-b][1,2,4]triazole (23.4 mg, 54%) as a yellow oil. $^1$H NMR (400 MHz, CDCl$_3$) δ 7.51-7.34 (m, 3H), 7.27-7.26 (m, 2H), 6.18-5.91 (m, 1H), 5.51-5.50 (m, 1H), 3.79-3.52 (m, 1H), 3.08-3.05 (m, 3H), 3.02-2.90 (m, 1H). LCMS $R_T$=1.218 & 1.256 min, m/z=266.1 [M+H]$^+$.

Example 106

(5S,7S)-7-fluoro-2-methylsulfonyl-5-phenyl-6,7-dihydro-5H-pyrrolo[1,2-b][1,2,4]triazole

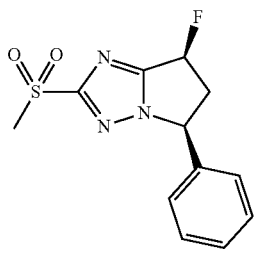 [SMILES: CS(=O)(=O)c1nc2n(n1)[C@H](c1ccccc1)C[C@@H]2F]

To a solution of (5S,7S)-7-fluoro-2-methylsulfanyl-5-phenyl-6,7-dihydro-5H-pyrrolo[1,2-b][1,2,4]triazole (70 mg, 0.28 mmol) in dichloromethane (5 mL) was added 3-chloroperoxybenzoic acid (85%, 285 mg, 1.40 mmol). The mixture was stirred at 25° C. for 2 h and diluted with dichloromethane (20 mL). The mixture was washed with saturated aqueous sodium bicarbonate (2×10 mL), brine (2×10 mL), dried over sodium sulfate and concentrated under reduced pressure. The residue was purified by RP-HPLC (acetonitrile 40-70%/0.05% ammonia hydroxide in water) to give (5S,7S)-7-fluoro-2-methylsulfonyl-5-phenyl-6,7-dihydro-5H-pyrrolo[1,2-b][1,2,4]triazole (75.0 mg, 91%) as a white solid. $^1$H NMR (400 MHz, CDCl$_3$) δ 7.41-7.35 (m, 3H), 7.30-7.27 (m, 2H), 6.16-5.95 (m, 1H), 5.53-5.46 (m, 1H), 3.75-3.63 (m, 1H), 3.28-3.20 (m, 3H), 3.05-2.95 (m, 1H). LC-MS $R_T$=1.471 min, m/z=282.1 [M+H]$^+$.

Examples 107 and Example 108

(5S,7S)-2-ethylsulfinyl-7-fluoro-5-phenyl-6,7-dihydro-5H-pyrrolo[1,2-b][1,2,4]triazole and (5S,7S)-2-ethylsulfonyl-7-fluoro-5-phenyl-6,7-dihydro-5H-pyrrolo[1,2-b][1,2,4]triazole

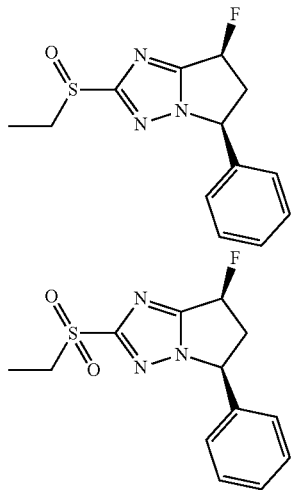

(5S,7S)-2-ethylsulfinyl-7-fluoro-5-phenyl-6,7-dihydro-5H-pyrrolo[1,2-b][1,2,4]triazole and (5S,7S)-2-ethylsulfonyl-7-fluoro-5-phenyl-6,7-dihydro-5H-pyrrolo[1,2-b][1,2,4]triazole were prepared according to method 26 starting from (5S,7S)-7-fluoro-5-phenyl-6,7-dihydro-5H-pyrrolo[1,2-b][1,2,4]triazole-2-thiol and iodoethane. (5S,7S)-2-ethylsulfinyl-7-fluoro-5-phenyl-6,7-dihydro-5H-pyrrolo[1,2-b][1,2,4]triazole was purified by RP-HPLC (acetonitrile 25-55%/0.05% ammonia hydroxide in water) (16.7 mg, 52%) as a white solid. $^1$H NMR (400 MHz, CDCl$_3$) δ 7.44-7.35 (m, 3H), 7.26-7.24 (m, 2H), 6.12-5.95 (m, 1H), 5.53-5.48 (m, 1H), 3.73-3.58 (m, 1H), 3.30-3.22 (m, 2H), 3.02-2.92 (m, 1H), 1.33 (t, J=7.6 Hz, 3H). LCMS $R_T$=0.756 min, m/z=280.1 [M+H]$^+$.

(5S,7S)-2-ethylsulfonyl-7-fluoro-5-phenyl-6,7-dihydro-5H-pyrrolo[1,2-b][1,2,4]triazole was purified by RP-HPLC (acetonitrile 30-60%/0.05% ammonia hydroxide in water) (13.3 mg, 39%) as a white solid. $^1$H NMR (400 MHz, CDCl$_3$) δ 7.44-7.40 (m, 3H), 7.26-7.24 (m, 2H), 6.14-5.97 (m, 1H), 5.56-5.51 (m, 1H), 3.75-3.60 (m, 1H), 3.43-3.36 (m, 2H), 3.06-2.95 (m, 1H), 1.39 (t, J=7.6 Hz, 3H). LCMS $R_T$=0.799 min, m/z=295.9 [M+H]$^+$.

Example 109 and Example 110

(5S,7S)-7-fluoro-2-isopropylsulfinyl-5-phenyl-6,7-dihydro-5H-pyrrolo[1,2-b][1,2,4]triazole and (5S,7S)-7-fluoro-2-isopropylsulfonyl-5-phenyl-6,7-dihydro-5H-pyrrolo[1,2-b][1,2,4]triazole

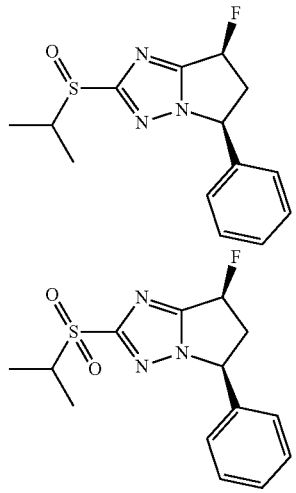

(5S,7S)-7-fluoro-2-isopropylsulfinyl-5-phenyl-6,7-dihydro-5H-pyrrolo[1,2-b][1,2,4]triazole and (5S,7S)-7-fluoro-2-isopropylsulfonyl-5-phenyl-6,7-dihydro-5H-pyrrolo[1,2-b][1,2,4]triazole were prepared according to method 26 starting from (5S,7S)-7-fluoro-5-phenyl-6,7-dihydro-5H-pyrrolo[1,2-b][1,2,4]triazole-2-thiol and 2-bromopropane.

(5S,7S)-7-fluoro-2-isopropylsulfinyl-5-phenyl-6,7-dihydro-5H-pyrrolo[1,2-b][1,2,4]triazole was purified by RP-HPLC (acetonitrile 50-80%/0.05% ammonia hydroxide in water) (21.2 mg, 44%) as a yellow oil. 1H NMR (400 MHz, CDCl$_3$) δ 7.28-7.25 (m, 3H), 7.16-7.09 (m, 2H), 6.00-5.84 (m, 1H), 5.41-5.37 (m, 1H), 3.58-3.46 (m, 1H), 3.41-3.21 (m, 1H), 2.96-2.71 (m, 1H), 1.23-1.09 (m, 6H). LCMS R$_T$=0.785 min, m/z=293.9 [M+H]$^+$.

(5S,7S)-7-fluoro-2-isopropylsulfonyl-5-phenyl-6,7-dihydro-5H-pyrrolo[1,2-b][1,2,4]triazole was purified by RP-HPLC (acetonitrile 40-70%/0.05% ammonia hydroxide in water) (23.4 mg, 49%) as a yellow oil. $^1$H NMR (400 MHz, CDCl$_3$) δ 7.47-7.30 (m, 3H), 7.28-7.14 (m, 2H), 6.22-5.89 (m, 1H), 5.59-5.53 (m, 1H), 3.75-3.58 (m, 1H), 3.57-3.45 (m, 1H), 3.08-2.90 (m, 1H), 1.40-1.25 (m, 6H). LCMS R$_T$=0.826 min, m/z=309.9 [M+H]$^+$.

Example 111 and Example 112

(5S,7S)-2-(cyclopropylmethylsulfinyl)-7-fluoro-5-phenyl-6,7-dihydro-5H-pyrrolo[1,2-b][1,2,4]triazole and (5S,7S)-2-(cyclopropylmethylsulfonyl)-7-fluoro-5-phenyl-6,7-dihydro-5H-pyrrolo[1,2-b][1,2,4]triazole

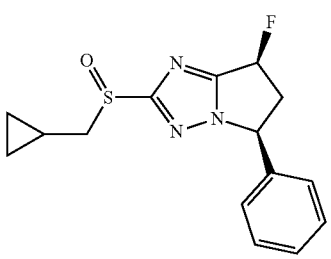

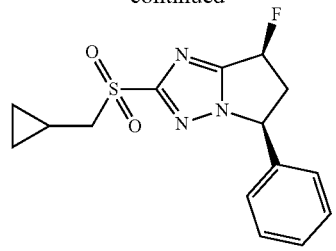

(5S,7S)-2-(cyclopropylmethylsulfinyl)-7-fluoro-5-phenyl-6,7-dihydro-5H-pyrrolo[1,2-b][1,2,4]triazole and (5S,7S)-2-(cyclopropylmethylsulfonyl)-7-fluoro-5-phenyl-6,7-dihydro-5H-pyrrolo[1,2-b][1,2,4]triazole were prepared according to method 26 starting from (5S,7S)-7-fluoro-5-phenyl-6,7-dihydro-5H-pyrrolo[1,2-b][1,2,4]triazole-2-thiol and cyclopropylmethyl bromide.

(5S,7S)-2-(cyclopropylmethylsulfinyl)-7-fluoro-5-phenyl-6,7-dihydro-5H-pyrrolo[1,2-b][1,2,4]triazole was purified by RP-HPLC (acetonitrile 40-70%/0.05% ammonia hydroxide in water) (13.7 mg, 28%) as a yellow oil. H NMR (400 MHz, CDCl$_3$) δ 7.38-7.24 (m, 3H), 7.19-7.02 (m, 2H), 5.99-5.85 (m, 1H), 5.41-5.35 (m, 1H), 3.61-3.48 (m, 1H), 3.18-2.83 (m, 3H), 1.05-0.98 (m, 1H), 0.60-0.45 (m, 2H), 0.25-0.16 (m, 2H). LCMS R$_T$=0.811 min, m/z=305.9 [M+H]$^+$.

(5S,7S)-2-(cyclopropylmethylsulfonyl)-7-fluoro-5-phenyl-6,7-dihydro-5H-pyrrolo[1,2-b][1,2,4]triazole was purified by RP-HPLC (acetonitrile 30-70%/0.05% ammonia hydroxide in water) (14.7 mg, 29%) as a yellow oil. $^1$H NMR (400 MHz, CDCl$_3$) δ 7.41-7.32 (m, 3H), 7.27-7.16 (m, 2H), 6.14-5.98 (m, 1H), 5.57-5.53 (m, 1H), 3.82-3.58 (m, 1H), 3.35-3.23 (m, 2H), 3.12-2.95 (m, 1H), 1.27-1.13 (m, 1H), 0.69-0.48 (m, 2H), 0.31-0.11 (m, 2H). LC-MS R$_T$=0.831 min, m/z=321.9 [M+H]$^+$.

Example 113 and Example 114

(5S,7S)-7-fluoro-5-phenyl-2-(2,2,2-trifluoroethylsulfinyl)-6,7-dihydro-5H-pyrrolo[1,2-b][1,2,4]triazole and (5S,7S)-7-fluoro-5-phenyl-2-(2,2,2-trifluoroethyl sulfonyl)-6,7-dihydro-5H-pyrrolo[1,2-b][1,2,4]triazole

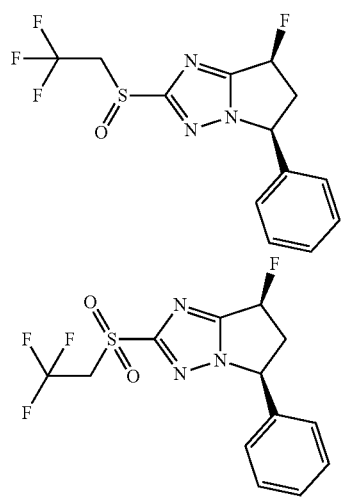

(5S,7S)-7-fluoro-5-phenyl-2-(2,2,2-trifluoroethylsulfinyl)-6,7-dihydro-5H-pyrrolo[1,2-b][1,2,4]triazole and (5S,7S)-7-fluoro-5-phenyl-2-(2,2,2-trifluoroethylsulfonyl)-6,7-dihydro-5H-pyrrolo[1,2-b][1,2,4]triazole were prepared according to method 26 starting from (5S,7S)-7-fluoro-5-phenyl-6,7-dihydro-5H-pyrrolo[1,2-b][1,2,4]triazole-2-thiol and 2-iodo-1,1,1-trifluoroethane. (5S,7S)-7-fluoro-5-phenyl-2-(2,2,2-trifluoroethylsulfinyl)-6,7-dihydro-5H-pyrrolo[1,2-b][1,2,4]triazole was purified by preparative TLC (50% ethyl acetate in petroleum ether) (10 mg, 35.3%) as a colorless oil. $^1$H NMR (400 MHz, CDCl$_3$) δ 7.46-7.39 (m, 3H), 7.27-7.22 (m, 2H), 6.15-5.97 (m, 1H), 5.55-5.50 (m, 1H), 4.20-4.09 (m, 1H), 4.04-3.95 (m, 1H), 3.76-3.61 (m, 1H), 3.06-2.93 (m, 1H). LCMS R$_T$=0.837 min, m/z=333.9 [M+H]$^+$.

(5S,7S)-7-fluoro-5-phenyl-2-(2,2,2-trifluoroethylsulfonyl)-6,7-dihydro-5H-pyrrolo[1,2-b][1,2,4]triazole was purified by preparative TLC (50% ethyl acetate in petroleum ether) (19 mg, 30%) as a white solid. $^1$H NMR (400 MHz, CDCl$_3$) δ 7.49-7.38 (m, 3H), 7.25-7.18 (m, 2H), 6.19-5.97 (m, 1H), 5.63-5.53 (m, 1H), 4.26-4.19 (m, 2H), 3.75-3.63 (m, 1H), 3.07-3.06 (m, 1H). LCMS R$_T$=0.674 min, m/z=350.1 [M+H]$^+$.

Example 115 and Example 116

(5S,7S)-7-fluoro-2-(methoxymethylsulfinyl)-5-phenyl-6,7-dihydro-5H-pyrrolo[1,2-b][1,2,4]triazole and (5S,7S)-7-fluoro-2-(methoxymethylsulfonyl)-5-phenyl-6,7-dihydro-5H-pyrrolo[1,2-b][1,2,4]triazole

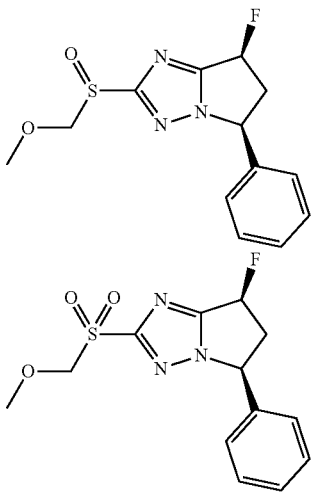

(5S,7S)-7-fluoro-2-(methoxymethylsulfinyl)-5-phenyl-6,7-dihydro-5H-pyrrolo[1,2-b][1,2,4]triazole and (5S,7S)-7-fluoro-2-(methoxymethylsulfonyl)-5-phenyl-6,7-dihydro-5H-pyrrolo[1,2-b][1,2,4]triazole were prepared according to method 26 starting from (5S,7S)-7-fluoro-5-phenyl-6,7-dihydro-5H-pyrrolo[1,2-b][1,2,4]triazole-2-thiol and chloro(methoxy)methane.

(5S,7S)-7-fluoro-2-(methoxymethylsulfinyl)-5-phenyl-6,7-dihydro-5H-pyrrolo[1,2-b][1,2,4]triazole was purified by RP-HPLC (acetonitrile 40-50%/0.05% ammonia hydroxide in water) (49.4 mg, 44%) as a yellow oil. $^1$H NMR (400 MHz, CDCl$_3$) δ 7.48-7.40 (m, 3H), 7.27-7.22 (m, 2H), 6.16-5.96 (m, 1H), 5.57-5.51 (m, 1H), 5.01-4.85 (m, 2H), 3.70-3.68 (m, 3H), 3.69-3.55 (m, 1H), 3.03-2.82 (m, 1H). LC-MS RT=0.761 min, m/z=295.9 [M+H]$^+$.

(5S,7S)-7-fluoro-2-(methoxymethylsulfonyl)-5-phenyl-6,7-dihydro-5H-pyrrolo[1,2-b][1,2,4]triazole was purified by RP-HPLC (acetonitrile 30-65%/0.05% ammonia hydroxide in water) (22.6 mg, 20%) as a yellow oil. $^1$H NMR (400 MHz, CDCl$_3$) δ 7.52-7.40 (m, 3H), 7.27-7.19 (m, 2H), 6.15-5.99 (m, 1H), 5.58-5.55 (m, 1H), 4.86-4.77 (m, 2H), 3.79-3.61 (m, 4H), 3.06-2.94 (m, 1H). LC-MS R$_T$=1.580 min, m/z=312.1 [M+H]$^+$.

Example 117: Method 43

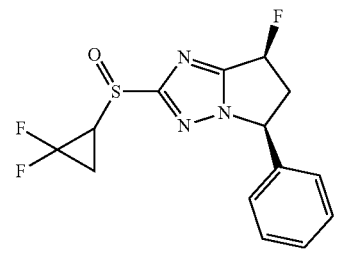 [SMILES: O=S(c1nc2n(n1)[C@H](c1ccccc1)C[C@@H]2F)C1CC1(F)F]

(5S,7S)-2-((2,2-difluorocyclopropyl)sulfinyl)-7-fluoro-5-phenyl-6,7-dihydro-5H-pyrrolo[1,2-b][1,2,4]triazole A mixture of (5S,7S)-2-(2,2-difluorocyclopropyl)sulfanyl-7-fluoro-5-phenyl-6,7-dihydro-5H-pyrrolo[1,2-b][1,2,4]triazole (50 mg, 0.16 mmol) (made analogously to example 16) and 3-chloroperoxybenzoic acid (85%, 49 mg, 0.24 mmol) in dichloromethane (6 mL) was stirred at 25° C. for 16 h and quenched by addition of saturated aqueous sodium bicarbonate (20 mL). The mixture was extracted with dichloromethane (3×20 mL). The combined organic layers were washed with brine (20 mL), dried over sodium sulfate and concentrated under reduced pressure. The residue was purified by RP-HPLC (acetonitrile 40-50%/0.05% ammonia hydroxide in water) to give (5S,7S)-2-(2,2-difluorocyclopropyl)sulfinyl-7-fluoro-5-phenyl-6,7-dihydro-5H-pyrrolo[1,2-b][1,2,4]triazole (2 mg, 3%) as a white solid. $^1$H NMR (400 MHz, CD$_3$OD) δ 7.50-7.38 (m, 3H), 7.29-7.25 (m, 2H), 6.21-6.19 (m, 0.5H), 6.07-6.04 (m, 0.5H), 5.69-5.65 (m, 1H), 3.87-3.72 (m, 2H), 2.90-2.82 (m, 1H), 2.45-2.37 (m, 1H), 2.25-2.10 (m, 1H). LC-MS RT=1.571 & 1.619 min, m/z=328.1 [M+H]$^+$.

Example 118, Example 119 and Example 120

(5S,7S)-2-((2,2-difluorocyclopropyl)sulfonyl)-7-fluoro-5-phenyl-6,7-dihydro-5H-pyrrolo[1,2-b][1,2,4]triazole and (5S,7S)-2-(((S)-2,2-difluorocyclopropyl)sulfonyl)-7-fluoro-5-phenyl-6,7-dihydro-5H-pyrrolo[1,2-b][1,2,4]triazole and (5S,7S)-2-(((R)-2,2-difluorocyclopropyl)sulfonyl)-7-fluoro-5-phenyl-6,7-dihydro-5H-pyrrolo[1,2-b][1,2,4]triazole

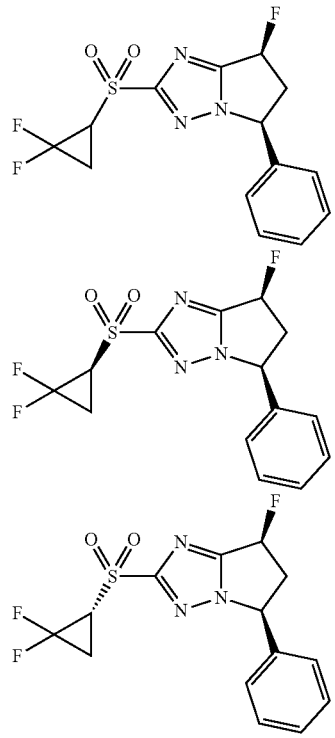

(5S,7S)-2-((2,2-difluorocyclopropyl)sulfonyl)-7-fluoro-5-phenyl-6,7-dihydro-5H-pyrrolo[1,2-b][1,2,4]triazole was prepared according to method 28 starting from (5S,7S)-7-fluoro-5-phenyl-6,7-dihydro-5H-pyrrolo[1,2-b][1,2,4]triazole-2-thiol). The final compound was purified by RP-HPLC (acetonitrile 40-50% o/0.05% ammonia hydroxide in water) to give (5S,7S)-2-(2,2-difluorocyclopropyl)sulfonyl-7-fluoro-5-phenyl-6,7-dihydro-5H-pyrrolo[1,2-b][1,2,4]triazole (2 mg, 3%) as a white solid. $^1$H NMR (400 MHz, CD$_3$OD) δ 7.50-7.39 (m, 3H), 7.29-7.25 (m, 2H), 6.22-6.06 (m, 1H), 5.75-5.66 (m, 1H), 3.90-3.22 (m, 2H), 2.91-2.84 (m, 1H), 2.50-2.40 (m, 1H), 2.38-2.25 (m, 1H). LC-MS R$_T$=1.727 & 1.782 min, m/z=344.1 [M+H]$^+$.

A batch of the racemic material was further separated by chiral SFC to give:

(5S,7S)-2-(((S)-2,2-difluorocyclopropyl)sulfonyl)-7-fluoro-5-phenyl-6,7-dihydro-5H-pyrrolo[1,2-b][1,2,4]triazole (Peak 1, Retention time=3.214 min) (117 mg, 28%) as a white solid. $^1$H NMR (400 MHz, CD$_3$OD) δ 7.44-7.37 (m, 3H), 7.29-7.27 (m, 2H), 6.22-6.06 (m, 1H), 5.71-5.66 (m, 1H), 3.89-3.76 (m, 2H), 2.91-2.83 (m, 1H), 2.42-2.38 (m, 1H), 2.29-2.25 (m, 1H). LC-MS R$_T$=1.771 min, m/z=344.0 [M+H]$^+$.

(5S,7S)-2-(((R)-2,2-difluorocyclopropyl)sulfonyl)-7-fluoro-5-phenyl-6,7-dihydro-5H-pyrrolo[1,2-b][1,2,4]triazole (Peak 2, Retention time=4.159 min) (139 mg, 35%) as a white solid. $^1$H NMR (400 MHz, CD$_3$OD) δ 7.45-7.38 (m, 3H), 7.30-7.27 (m, 2H), 6.22-6.06 (m, 1H), 5.71-5.67 (m, 1H), 3.88-3.74 (m, 2H), 2.90-2.82 (m, 1H), 2.42-2.38 (m, 1H), 2.30-2.26 (m, 1H). LC-MS R$_T$=1.770 min, m/z=344.1 [M+H]$^+$.

SFC condition: Column: ChiralPak AD-3 Mobile phase: A: CO2 B: Ethanol (0.05% DEA) Gradient: from 5% to 40% of B in 5.5 min and hold 40% for 3 min, then 5% of B for 1.5 min Flow rate: 2.5 mL/min Column temperature: 40° C.

Example 119 and Example 124: Method 28

(5S,7S)-7-fluoro-5-(2-fluorophenyl)-2-[(1S)-2,2-difluorocyclopropyl]sulfonyl-6,7-dihydro-5H-pyrrolo[1,2-b][1,2,4]triazole and (5S,7S)-7-fluoro-5-(2-fluorophenyl)-2-[(1R)-2,2-difluorocyclopropyl]sulfonyl-6,7-dihydro-5H-pyrrolo[1,2-b][1,2,4]triazole

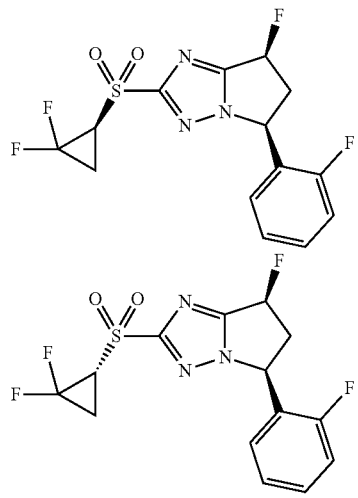

Step 1: vinyl 4-methylbenzenesulfonate

A solution of n-butyllithium (2.5 M in hexanes, 40.0 mL, 100.0 mmol) in tetrahydrofuran (110 mL) was stirred at 35° C. for 4 h under nitrogen atmosphere and then cooled to −78° C. A solution of p-toluenesulfonyl chloride (15.3 g, 80.3 mmol) in tetrahydrofuran (40 mL) was added dropwise over 30 min. The resulting mixture was stirred at −78° C. for 1 h and at 25° C. for 1 h, and then poured into water (250 mL). The solution was extracted with ethyl acetate (2×100 mL). The combined organic layers were washed with brine (100 mL), dried over sodium sulfate and then concentrated under reduced pressure. The residue was purified by column chromatography (silica gel, 100-200 mesh, 0 to 10% ethyl acetate in petroleum ether) to give vinyl 4-methylbenzenesulfonate (12.0 g, 75%) as colorless oil. $^1$H NMR (400 MHz, CDCl$_3$) δ 7.87-7.73 (m, 2H), 7.50-7.29 (m, 2H), 6.65-6.51 (m, 1H), 4.92-4.80 (m, 1H), 4.74-4.51 (m, 1H), 2.51-2.36 (m, 3H).

Step 2: 2,2-difluorocyclopropyl 4-methylbenzenesulfonate

To a solution of vinyl 4-methylbenzenesulfonate (10.0 g, 50 mmol) and sodium fluoride (0.21 g, 5.05 mmol) in o-xylene (10 mL) was added trimethylsilyl 2,2-difluoro-2-(fluorosulfonyl)acetate (59.64 mL, 303 mmol) dropwise at 120° C. The resulting mixture was stirred at 120° C. for 2 h and concentrated under reduced pressure. The residue was purified by column chromatography (silica gel, 100-200 mesh, 0 to 10% ethyl acetate in petroleum ether) to afford (2,2-difluorocyclopropyl) 4-methylbenzenesulfonate (8.0 g, 64%) as a light yellow solid. $^1$H NMR (400 MHz, CDCl$_3$) δ 7.82-7.80 (m, 2H), 7.37-7.24 (m, 2H), 4.25-4.19 (m, 1H), 2.46 (s, 3H), 1.70-1.53 (m, 2H).

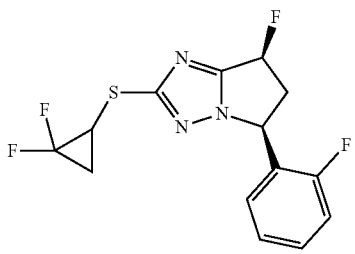 [SMILES: Fc1ccccc1[C@@H]1C[C@H](F)c2nc(SC3CC3(F)F)nn21]

Step 3: (5S,7S)-2-(2,2-difluorocyclopropyl)sulfanyl-7-fluoro-5-(2-fluorophenyl)-6,7-dihydro-5H-pyrrolo[1,2-b][1,2,4]triazole To a mixture of (5S,7S)-7-fluoro-5-(2-fluorophenyl)-6,7-dihydro-5H-pyrrolo[1,2-b][1,2,4]triazole-2-thiol (170 mg, 0.67 mmol) and cesium carbonate (656 mg, 2.01 mmol) in N,N-dimethylformamide (50 mL) was added (2,2-difluorocyclopropyl) 4-methylbenzenesulfonate (833 mg, 3.36 mmol). The mixture was stirred at 50° C. for 16 h and quenched by addition of water (50 mL). The resulting mixture was extracted with ethyl acetate (2×100 mL). The combined organic layers were dried over sodium sulfate and concentrated under reduced pressure. The residue was purified by column chromatography (silica gel, 100-200 mesh, 0 to 5% ethyl acetate in petroleum ether) to afford (5S,7S)-2-(2,2-difluorocyclopropyl)sulfanyl-7-fluoro-5-(2-fluorophenyl)-6,7-dihydro-5H-pyrrolo[1,2-b][1,2,4]triazole (170 mg, 77%) as a yellow oil. LC-MS R$_T$=0.734 min, m/z=330.1 [M+H]$^+$.

Step 4: (5S,7S)-7-fluoro-5-(2-fluorophenyl)-2-[(1S)-2,2-difluorocyclopropyl]sulfonyl-6,7-dihydro-5H-pyrrolo[1,2-b][1,2,4]triazole and (5S,7S)-7-fluoro-5-(2-fluorophenyl)-2-[(1R)-2,2-difluorocyclopropyl]sulfonyl-6,7-dihydro-5H-pyrrolo[1,2-b][1,2,4]triazole A mixture of ruthenium(III) chloride (10 mg, 0.05 mmol), sodium periodate (441 mg, 2.06 mmol) and (5S,7S)-2-(2,2-difluorocyclopropyl)sulfanyl-7-fluoro-5-(2-fluorophenyl)-6,7-dihydro-5H-pyrrolo[1,2-b][1,2,4]triazole (170 mg, 0.52 mmol) in acetonitrile (10 mL)/water (10 mL)/ethyl acetate (10 mL) was stirred at 30° C. for 16 h and extracted with ethyl acetate (2×50 mL). The combined organic layers were washed with brine (50 mL), dried over sodium sulfate and concentrated under reduced pressure. The residue was purified by RP-HPLC (acetonitrile 40-70%/0.05% ammonia hydroxide in water) to afford (5S,7S)-2-(2,2-difluorocyclopropyl)sulfonyl-7-fluoro-5-(2-fluorophenyl)-6,7-dihydro-5H-pyrrolo[1,2-b][1,2,4]triazole (80 mg, 43%) as a white solid. The racemic mixture was further separated by chiral SFC to arbitrarily afford:

(5S,7S)-7-fluoro-5-(2-fluorophenyl)-2-[(1S)-2,2-difluorocyclopropyl]sulfonyl-6,7-dihydro-5H-pyrrolo[1,2-b][1,2,4]triazole (Peak 1, retention time=2.766 min) (5 mg, 6%) as a white solid. $^1$H NMR (400 MHz, CD$_3$OD) δ 7.50-7.41 (m, 1H), 7.27-7.11 (m, 3H), 6.26-6.06 (m, 1H), 5.96-5.87 (m, 1H), 3.92-3.74 (m, 2H), 2.96-2.80 (m, 1H), 2.46-2.41 (m, 1H), 2.30-2.27 (m, 1H). LC-MS R$_T$=1.010 min, m/z=362.1 [M+H]$^+$.

(5S,7S)-7-fluoro-5-(2-fluorophenyl)-2-[(1R)-2,2-difluorocyclopropyl]sulfonyl-6,7-dihydro-5H-pyrrolo[1,2-b][1,2,4]triazole (Peak 2, retention time=3.151 min) (11 mg, 13%) as a white solid. $^1$H NMR (400 MHz, CD$_3$OD) δ 7.50-7.41 (m, 1H), 7.26-7.10 (m, 3H), 6.26-6.06 (m, 1H), 5.95-5.88 (m, 1H), 3.95-3.72 (m, 2H), 2.99-2.77 (m, 1H), 2.49-2.36 (m, 1H), 2.34-2.22 (m, 1H). LC-MS R$_T$=1.009 min, m/z=362.1 [M+H]$^+$.

SFC condition: column: chiralpak AD-3 150×4.6 mm I.D., 3 μm; mobile phase: A: CO$_2$ B: methanol (0.05% DEA); gradient: from 5% to 40% of B in 5.5 min, then 5% of B for 1.5 min flow rate: 2.5 mL/min column temperature: 40° C.

Example 120 and Example 125

(5S,7S)-5-(2-chlorophenyl)-7-fluoro-2-[(1S)-2,2-difluorocyclopropyl]sulfonyl-6,7-dihydro-5H-pyrrolo[1,2-b][1,2,4]triazole and (5S,7S)-5-(2-chlorophenyl)-7-fluoro-2-[(1R)-2,2-difluorocyclopropyl]sulfonyl-6,7-dihydro-5H-pyrrolo[1,2-b][1,2,4]triazole

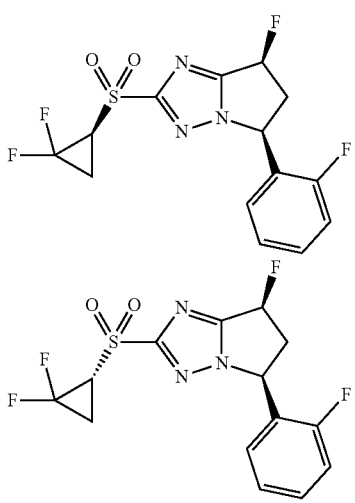

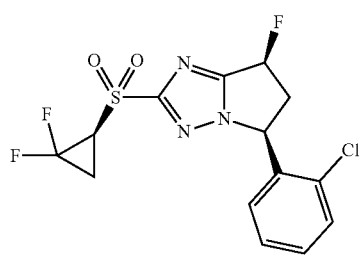

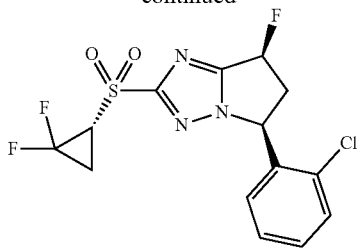

(5S,7S)-5-(2-chlorophenyl)-7-fluoro-2-[(1S)-2,2-difluorocyclopropyl]sulfonyl-6,7-dihydro-5H-pyrrolo[1,2-b][1,2,4]triazole and (5S,7S)-5-(2-chlorophenyl)-7-fluoro-2-[(1R)-2,2-difluorocyclopropyl]sulfonyl-6,7-dihydro-5H-pyrrolo[1,2-b][1,2,4]triazole were prepared according to method 28 starting from (5S,7S)-5-(2-chlorophenyl)-7-fluoro-6,7-dihydro-5H-pyrrolo[1,2-b][1,2,4]triazole-2-thiol. The final compounds were purified first by RP-HPLC (acetonitrile 15-45%/0.05% ammonia hydroxide in water) then chiral SFC to give:

(5S,7S)-5-(2-chlorophenyl)-7-fluoro-2-[(1S)-2,2-difluorocyclopropyl]sulfonyl-6,7-dihydro-5H-pyrrolo[1,2-b][1,2,4]triazole (Peak 1, retention time=3.228 min) (27 mg, 32%) as a white solid. $^1$H NMR (400 MHz, CDCl$_3$) δ 7.48 (d, J=8.0 Hz, 1H), 7.38-7.28 (m, 2H), 6.79-6.71 (m, 1H), 6.16-6.10 (m, 0.5H), 6.08-6.01 (m, 1H), 6.00-5.96 (m, 0.5H), 3.80-3.68 (m, 1H), 3.58-3.47 (m, 1H), 2.98-2.87 (m, 1H), 2.65-2.57 (m, 1H), 2.22-2.14 (m, 1H). LC-MS R$_T$=1.061 min, m/z=378.1 [M+H]$^+$.

(5S,7S)-5-(2-chlorophenyl)-7-fluoro-2-[(1R)-2,2-difluorocyclopropyl]sulfonyl-6,7-dihydro-5H-pyrrolo[1,2-b][1,2,4]triazole (Peak 2, retention time=3.615 min) (26 mg, 31%) as a white solid. $^1$H NMR (400 MHz, CDCl$_3$) δ 7.47 (d, J=7.6 Hz, 1H), 7.38-7.28 (m, 2H), 6.75 (d, J=7.6 Hz, 1H), 6.13 (d, J=6.8 Hz, 0.5H), 6.07-6.01 (m, 1H), 5.99 (d, J=7.2 Hz, 0.5H), 3.84-3.67 (m, 1H), 3.56-3.45 (m, 1H), 3.00-2.85 (m, 1H), 2.69-2.49 (m, 1H), 2.23-2.09 (m, 1H). LC-MS R$_T$=1.062 min, m/z=378.1 [M+H]$^+$.

SFC condition: column: chiralpak AD-3 150×4.6 mm I.D., 3 μm; mobile phase: A: CO$_2$ B: methanol (0.05% DEA); gradient: from 5% to 40% of B in 5.5 min, then 5% of B for 1.5 min flow rate: 2.5 mL/min column temperature: 40° C.

Example 121, Example 128 and Example 129

(5S,7S)-2-(2,2-difluorocyclopropyl)sulfonyl-5-(2,3-difluorophenyl)-7-fluoro-6,7-dihydro-5H-pyrrolo[1,2-b][1,2,4]triazole and (5S,7S)-5-(2,3-difluorophenyl)-7-fluoro-2-[(1S)-2,2-difluorocyclopropyl]sulfonyl-6,7-dihydro-5H-pyrrolo[1,2-b][1,2,4]triazole and (5S,7S)-5-(2,3-difluorophenyl)-7-fluoro-2-[(1R)-2,2-difluorocyclopropyl]sulfonyl-6,7-dihydro-5H-pyrrolo[1,2-b][1,2,4]triazole

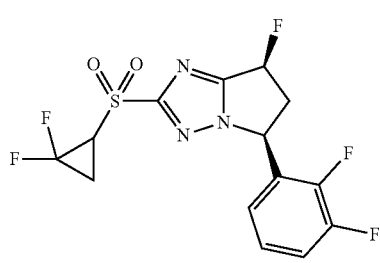

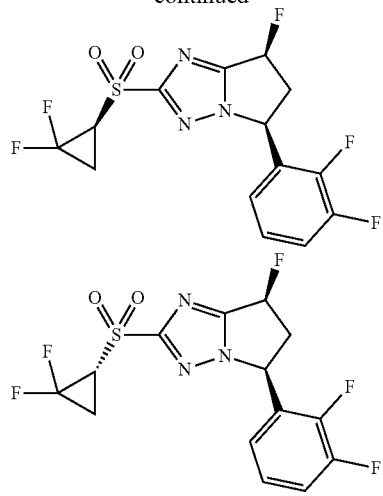

(5S,7S)-2-(2,2-difluorocyclopropyl)sulfonyl-5-(2,3-difluorophenyl)-7-fluoro-6,7-dihydro-5H-pyrrolo[1,2-b][1,2,4]triazole was prepared according to method 26 starting from (5S,7S)-5-(2,3-difluorophenyl)-7-fluoro-6,7-dihydro-5H-pyrrolo[1,2-b][1,2,4]triazole-2-thiol. The final compound was purified by RP-HPLC (acetonitrile 40-70%/0.05% ammonia hydroxide in water) to give (5S,7S)-2-(2,2-difluorocyclopropyl) sulfonyl-5-(2,3-difluorophenyl)-7-fluoro-6,7-dihydro-5H-pyrrolo[1,2-b][1,2,4]triazole (72.4 mg, 44%) as a white solid. $^1$H NMR (400 MHz, CDCl$_3$) δ 7.27-7.22 (m, 1H), 7.15-7.10 (m, 1H), 6.77-6.70 (m, 1H), 6.16-6.00 (m, 1H), 5.95-5.85 (m, 1H), 3.80-3.68 (m, 1H), 3.52-3.47 (m, 1H), 3.05-2.92 (m, 1H), 2.70-2.52 (m, 1H), 2.20-2.10 (m, 1H). LC-MS R$_T$=1.823 min, m/z=380.0 [M+H]$^+$.

The racemic material was further separated by chiral SFC to give:

(5S,7S)-5-(2,3-difluorophenyl)-7-fluoro-2-[(1S)-2,2-difluorocyclopropyl]sulfonyl-6,7-dihydro-5H-pyrrolo[1,2-b][1,2,4]triazole (Peak 1, retention time=2.263 min) (26.6 mg, 38%) as a white solid. $^1$H NMR (400 MHz, CDCl$_3$) δ 7.27-7.22 (m, 1H), 7.20-7.10 (m, 1H), 6.77-6.72 (m, 1H), 6.16-6.00 (m, 1H), 5.95-5.85 (m, 1H), 3.83-3.73 (m, 1H), 3.55-3.46 (m, 1H), 3.03-2.95 (m, 1H), 2.59-2.54 (m, 1H), 2.16-2.12 (m, 1H). LC-MS R$_T$=1.830 min, m/z=380.0 [M+H]$^+$.

(5S,7S)-5-(2,3-difluorophenyl)-7-fluoro-2-[(1R)-2,2-difluorocyclopropyl]sulfonyl-6,7-dihydro-5H-pyrrolo[1,2-b][1,2,4]triazole (Peak 2, retention time=2.606 min)) (26 mg, 37% yield) as a white solid. $^1$H NMR (400 MHz, CDCl$_3$) δ 7.27-7.22 (m, 1H), 7.20-7.08 (m, 1H), 6.77-6.72 (m, 1H), 6.16-6.00 (m, 1H), 5.98-5.85 (m, 1H), 3.80-3.72 (m, 1H), 3.52-3.44 (m, 1H), 3.05-2.88 (m, 1H), 2.75-2.55 (m, 1H), 2.17-2.13 (m, 1H). LC-MS R$_T$=1.826 min, m/z=380.0 [M+H]$^+$.

SFC condition Column: Chiralpak AS (150 mm*4.6 mm, 3 μm), Mobile phase: A: CO$_2$ B: ethanol (0.05% DEA), Gradient: from 5% to 40% of B in 5 min and hold 40% for 2.5 min, then 5% of B for 2.5 min, Flow rate: 2.5 mL/min, Column temperature: 35° C.

Example 122, Example 126 and Example 127

(5S,7S)-2-(2,2-difluorocyclopropyl)sulfonyl-5-(2,5-difluorophenyl)-7-fluoro-6,7-dihydro-5H-pyrrolo[1,2-b][1,2,4]triazole and (5S,7S)-5-(2,5-difluorophenyl)-7-fluoro-2-[(1S)-2,2-difluorocyclopropyl]sulfonyl-6,7-dihydro-5H-pyrrolo[1,2-b][1,2,4]triazole and (5S,7S)-5-(2,5-difluorophenyl)-7-fluoro-2-[(1R)-2,2-difluorocyclopropyl]sulfonyl-6,7-dihydro-5H-pyrrolo[1,2-b][1,2,4]triazole

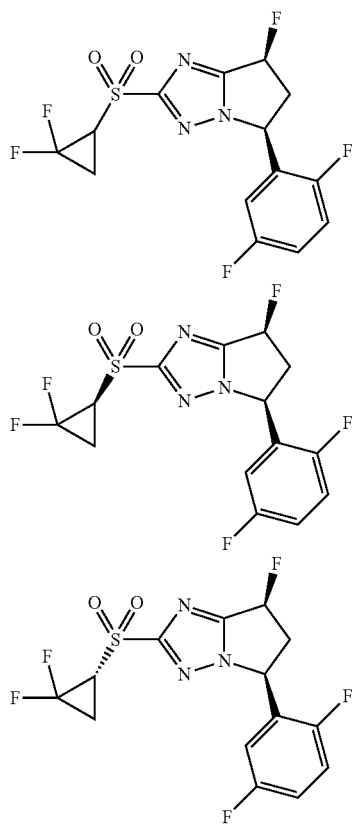

(5S,7S)-2-(2,2-difluorocyclopropyl)sulfonyl-5-(2,5-difluorophenyl)-7-fluoro-6,7-dihydro-5H-pyrrolo[1,2-b][1,2,4]triazole was prepared according to method 28 starting from (5S,7S)-5-(2,5-difluorophenyl)-7-fluoro-6,7-dihydro-5H-pyrrolo[1,2-b][1,2,4]triazole-2-thiol. The final compound was purified by RP-HPLC (acetonitrile 40-70%/0.05% ammonia hydroxide in water) to give (5S,7S)-2-(2,2-difluorocyclopropyl) sulfonyl-5-(2,5-difluorophenyl)-7-fluoro-6,7-dihydro-5H-pyrrolo[1,2-b][1,2,4]triazole (12 mg, 22%) as a white solid. $^1$H NMR (400 MHz, CDCl$_3$) δ 7.18-7.09 (m, 2H), 6.75-6.68 (m, 1H), 6.15-5.99 (m, 1H), 5.90-5.85 (m, 1H), 3.79-3.68 (m, 1H), 3.53-3.47 (m, 1H), 3.03-2.92 (m, 1H), 2.65-2.55 (m, 1H), 2.25-2.15 (m, 1H). LC-MS $R_T$=1.024 min, m/z=380.1 [M+H]$^+$.

Another batch of the racemic material was further separated by chiral SFC to give:

(5S,7S)-5-(2,5-difluorophenyl)-7-fluoro-2-[(1S)-2,2-difluorocyclopropyl]sulfonyl-6,7-dihydro-5H-pyrrolo[1,2-b][1,2,4]triazole (Peak 1, retention time=2.668 min) (5 mg, 10%) as a white solid. $^1$H NMR (400 MHz, CDCl$_3$) δ 7.20-7.05 (m, 2H), 6.75-6.68 (m, 1H), 6.16-6.00 (m, 1H), 5.95-5.85 (m, 1H), 3.80-3.68 (m, 1H), 3.60-3.47 (m, 1H), 3.03-2.98 (m, 1H), 2.70-2.52 (m, 1H), 2.20-2.15 (m, 1H). LCMS $R_T$=1.808 min, m/z=380.0 [M+H]$^+$.

(5S,7S)-2-[(1R)-2,2-difluorocyclopropyl]sulfonyl-5-(2,5-difluorophenyl)-7-fluoro-6,7-dihydro-5H-pyrrolo[1,2-b][1,2,4]triazole (Peak 2, retention time=2.945 min) (4.9 mg, 10%) as a white solid. $^1$H NMR (400 MHz, CDCl$_3$) δ 7.20-7.05 (m, 2H), 6.75-6.68 (m, 1H), 6.16-5.95 (m, 1H), 5.90-5.80 (m, 1H), 3.82-3.65 (m, 1H), 3.62-3.40 (m, 1H), 3.07-2.92 (m, 1H), 2.62-2.55 (m, 1H), 2.20-2.12 (m, 1H). LCMS $R_T$=1.808 min, m/z=380.1 [M+H]$^+$.

SFC condition: Column: Chiralpak AD-3 150×4.6 mm I.D., 3 µm Mobile phase: A: CO$_2$ B: ethanol (0.05% DEA) Gradient: from 5% to 40% of B in 5 min and hold 40% for 2.5 min, then 5% of B for 2.5 min Flow rate: 2.5 mL/min Column temp.: 35° C.

Example 123

(5S,7S)-2-(2,2-difluorocyclopropyl)sulfonyl-5-(2,6-difluorophenyl)-7-fluoro-6,7-dihydro-5H-pyrrolo[1,2-b][1,2,4]triazole

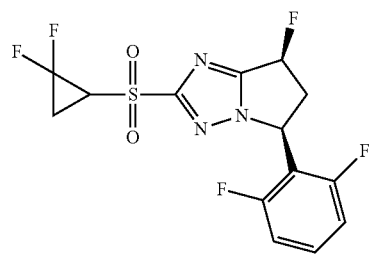 [SMILES: O=S(=O)(c1nc2n(n1)[C@H](c1c(F)cccc1F)C[C@@H]2F)C1CC1(F)F]

(5S,7S)-2-(2,2-difluorocyclopropyl)sulfonyl-5-(2,6-difluorophenyl)-7-fluoro-6,7-dihydro-5H-pyrrolo[1,2-b][1,2,4]triazole was prepared according to method 28 starting from (5S,7S)-5-(2,6-difluorophenyl)-7-fluoro-6,7-dihydro-5H-pyrrolo[1,2-b][1,2,4]triazole-2-thiol. The final compound was purified by RP-HPLC (acetonitrile 36-66%/0.05% ammonia hydroxide in water) to give (5S,7S)-2-(2,2-difluorocyclopropyl)sulfonyl-5-(2,6-difluorophenyl)-7-fluoro-6,7-dihydro-5H-pyrrolo[1,2-b][1,2,4]triazole (19 mg, 25%) as a white solid. $^1$H NMR (400 MHz, CDCl$_3$) δ 7.44-7.38 (m, 1H), 6.99-6.94 (m, 2H), 6.20-6.03 (m, 1H), 5.91-5.87 (m, 1H), 3.84-3.76 (m, 1H), 3.49-3.43 (m, 1H), 3.15-3.00 (m, 1H), 2.70-2.53 (m, 1H), 2.14-2.08 (m, 1H). LCMS $R_T$=1.004 min, m/z=380.1 [M+H]$^+$.

Example 132: Method 29

(5S,7S)-7-fluoro-5-phenyl-2-(trifluoromethylsulfinyl)-6,7-dihydro-5H-pyrrolo[1,2-b][1,2,4]triazole

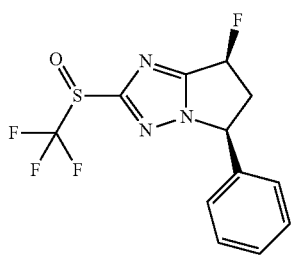 [SMILES: O=S(c1nc2n(n1)[C@H](c1ccccc1)C[C@@H]2F)C(F)(F)F]

(5S,7S)-7-fluoro-5-phenyl-2-(trifluoromethylsulfonyl)-6,7-dihydro-5H-pyrrolo[1,2-b][1,2,4]triazole was prepared according to method 29 starting from (5S,7S)-7-fluoro-5-phenyl-6,7-dihydro-5H-pyrrolo[1,2-b][1,2,4]triazole-2-thiol. To a solution of (5S,7S)-7-fluoro-5-phenyl-2-(trifluoromethylsulfanyl)-6,7-dihydro-5H-pyrrolo[1,2-b][1,2,4]triazole (65 mg, 0.21 mmol) in chloroform (6 mL) was added 3-chloroperoxybenzoic acid (85%, 131 mg, 0.64 mmol). The reaction mixture was stirred at 60° C. for 16 h and quenched by addition of saturated aqueous sodium thiosulfate (15 mL). The resulting mixture was extracted with ethyl acetate (3×15 mL). The combined organic layers were dried over sodium sulfate and concentrated under reduced pressure. The residue was purified by RP-HPLC (acetonitrile 40-70%/0.05% ammonia hydroxide in water) to afford (5S,7S)-7-fluoro-5-phenyl-2-(trifluoromethylsulfinyl)-6,7-dihydro-5H-pyrrolo[1,2-b][1,2,4]triazole (24.8 mg, 36%) as a yellow oil. $^1$H NMR (400 MHz, CDCl$_3$) δ 7.44-7.40 (m, 3H), 7.27-7.24 (m, 2H), 6.17-6.13 (m, 0.5H), 6.03-6.00 (m, 0.5H), 5.58-5.55 (m, 1H), 3.75-3.65 (m, 1H), 3.07-2.96 (m, 1H). LCMS R$_T$=0.862 min, m/z=319.9 [M+H]$^+$.

Example 135

(5S,7S)-7-fluoro-5-(3-fluorophenyl)-2-(trifluoromethylsulfonyl)-6,7-dihydro-5H-pyrrolo[1,2-b][1,2,4]triazole

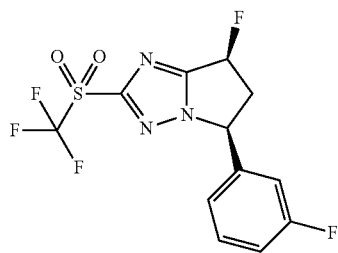 [SMILES: O=S(=O)(c1nc2n(n1)[C@H](c1cccc(F)c1)C[C@@H]2F)C(F)(F)F]

Step 1: (5S,7S)-7-fluoro-5-(3-fluorophenyl)-2-(trifluoromethylsulfanyl)-6,7-dihydro-5H-pyrrolo[1,2-b][1,2,4]triazole

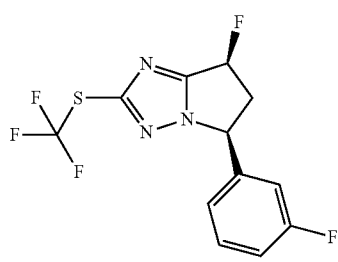 [SMILES: Fc1cccc([C@@H]2C[C@H](F)c3nc(SC(F)(F)F)nn32)c1]

To a solution of 3,3-dimethyl-1-(trifluoromethyl)-1,2-benziodoxole (72 mg, 0.22 mmol) in dichloromethane (2 mL) was added (5S,7S)-7-fluoro-5-(3-fluorophenyl)-6,7-dihydro-5H-pyrrolo[1,2-b][1,2,4]triazole-2-thiol (50 mg, 0.20 mmol) at −78° C. The mixture was stirred at −78° C. for 3.5 h and concentrated under reduced pressure. The residue was purified by preparative TLC (30% ethyl acetate in petroleum ether) to afford (5S,7S)-7-fluoro-5-(3-fluorophenyl)-2-(trifluoromethylsulfanyl)-6,7-dihydro-5H-pyrrolo[1,2-b][1,2,4]triazole (40 mg, 63%) as a colorless oil. LCMS R$_T$=0.761 min, m/z=322.1 [M+H]$^+$.

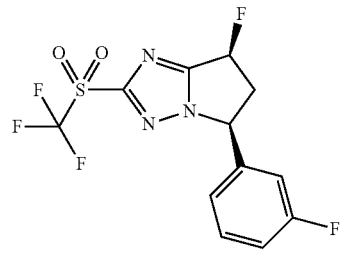

Step 2: (5S,7S)-7-fluoro-5-(3-fluorophenyl)-2-(trifluoromethylsulfonyl)-6,7-dihydro-5H-pyrrolo[1,2-b][1,2,4]triazole A mixture of ruthenium(III) chloride (2 mg, 0.01 mmol), sodium periodate (80 mg, 0.37 mmol) and (5S,7S)-7-fluoro-5-(3-fluorophenyl)-2-(trifluoromethylsulfanyl)-6,7-dihydro-5H-pyrrolo[1,2-b][1,2,4]triazole (30 mg, 0.09 mmol) in acetonitrile (1 mL), water (1 mL) and ethyl acetate (1 mL) was stirred at 30° C. for 20 min and filtered. The filtrate was diluted with water (10 mL) and extracted with ethyl acetate (3×10 mL). The combined organic layers were dried over sodium sulfate and concentrated under reduced pressure. The residue was purified by preparative TLC (30% ethyl acetate in petroleum ether, R$_f$=0.4) to give (5S,7S)-7-fluoro-5-(3-fluorophenyl)-2-(trifluoromethylsulfonyl)-6,7-dihydro-5H-pyrrolo[1,2-b][1,2,4]triazole (18 mg, 50%) as a faint yellow solid. $^1$H NMR (400 MHz, CD$_3$OD) δ 7.48-7.44 (m, 1H), 7.17-7.06 (m, 3H), 6.26-6.10 (m, 1H), 5.79-5.76 (m, 1H), 3.86-3.75 (m, 1H), 2.96-2.85 (m, 1H). LCMS R$_T$=1.135 min, m/z=354.1 [M+H]$^+$.

Example 133

(5S,7S)-7-fluoro-5-(2-fluorophenyl)-2-(trifluoromethylsulfonyl)-6,7-dihydro-5H-pyrrolo[1,2-b][1,2,4]triazole

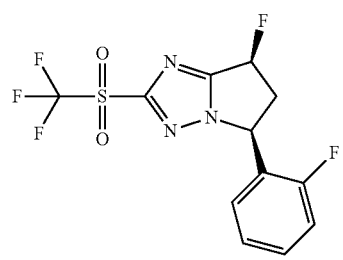 [SMILES: O=S(=O)(c1nc2n(n1)[C@H](c1ccccc1F)C[C@@H]2F)C(F)(F)F]

(5S,7S)-7-fluoro-5-(2-fluorophenyl)-2-(trifluoromethylsulfonyl)-6,7-dihydro-5H-pyrrolo[1,2-b][1,2,4]triazole was prepared according to method 29 starting from (5S,7S)-7-fluoro-5-(2-fluorophenyl)-6,7-dihydro-5H-pyrrolo[1,2-b][1,2,4]triazole-2-thiol. The final compound was purified by RP-HPLC (acetonitrile 47-77%/0.05% ammonia hydroxide in water) to give (5S,7S)-7-fluoro-5-(2-fluorophenyl)-2-(trifluoromethylsulfonyl)-6,7-dihydro-5H-pyrrolo[1,2-b][1,2, 4]triazole (37 mg, 41%) as a white solid. ¹H NMR (400 MHz, CDCl₃) δ 7.45-7.41 (m, 1H), 7.21-7.14 (m, 2H), 6.99-6.95 (m, 1H), 6.18 (d, J=7.2 Hz, 0.5H), 6.05 (d, J=7.2 Hz, 0.5H), 5.96-5.93 (m, 1H), 3.84-3.70 (m, 1H), 3.08-2.92 (m, 1H). LC-MS R$_T$=0.929 min, m/z=353.8 [M+H]⁺.

Example 134

(5S,7S)-5-(2-chlorophenyl)-7-fluoro-2-(trifluoromethylsulfonyl)-6,7-dihydro-5H-pyrrolo[1,2-b][1,2,4]triazole

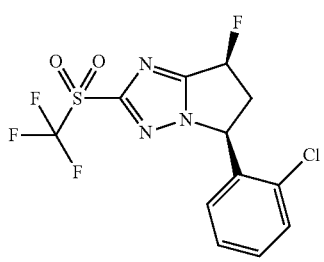 [SMILES: O=S(=O)(c1nc2n(n1)[C@H](c1ccccc1Cl)C[C@@H]2F)C(F)(F)F]

(5S,7S)-5-(2-chlorophenyl)-7-fluoro-2-(trifluoromethylsulfonyl)-6,7-dihydro-5H-pyrrolo[1,2-b][1,2,4]triazole was prepared according to method 29 starting from (5S,7S)-5-(2-chlorophenyl)-7-fluoro-6,7-dihydro-5H-pyrrolo[1,2-b][1,2,4]triazole-2-thiol. The final compound was purified by RP-HPLC (acetonitrile 50-80/o/0.05% ammonia hydroxide in water) to give (5S,7S)-5-(2-chlorophenyl)-7-fluoro-2-(trifluoromethylsulfonyl)-6,7-dihydro-5H-pyrrolo[1,2-b][1,2,4]triazole (98 mg, 74%) as yellow oil. ¹H NMR (400 MHz, CDCl₃) δ 7.49 (d, J=7.6 Hz, 1H), 7.40-7.27 (m, 2H), 6.70 (d, J=7.6 Hz, 1H), 6.17 (d, J=7.2 Hz, 0.5H), 6.13-6.07 (m, 1H), 6.02 (d, J=5.2 Hz, 0.5H), 3.87-3.71 (m, 1H), 3.03-2.92 (m, 1H). LC-MS R$_T$=0.900 min, m/z=370.0 [M+H]⁺.

Example 136

(5S,7S)-5-(2,3-difluorophenyl)-7-fluoro-2-(trifluoromethylsulfonyl)-6,7-dihydro-5H-pyrrolo[1,2-b][1,2,4]triazole

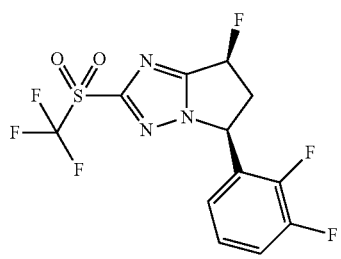 [SMILES: O=S(=O)(c1nc2n(n1)[C@H](c1cccc(F)c1F)C[C@@H]2F)C(F)(F)F]

(5S,7S)-5-(2,3-difluorophenyl)-7-fluoro-2-(trifluoromethylsulfonyl)-6,7-dihydro-5H-pyrrolo[1,2-b][1,2,4]triazole was prepared according to method 29 starting from (5S,7S)-5-(2,3-difluorophenyl)-7-fluoro-6,7-dihydro-5H-pyrrolo[1,2-b][1,2,4]triazole-2-thiol. The final compound was purified by RP-HPLC (acetonitrile 40-70%/0.05% ammonia hydroxide in water) to give (5S,7S)-5-(2,3-difluorophenyl)-7-fluoro-2-(trifluoromethylsulfonyl)-6,7-dihydro-5H-pyrrolo[1,2-b][1,2,4]triazole (48 mg, 43%) as a white solid. ¹H NMR (400 MHz, CDCl₃) δ 7.27-7.22 (m, 1H), 7.20-7.14 (m, 1H), 6.74-6.70 (m, 1H), 6.20-6.04 (m, 1H), 5.96-5.94 (m, 1H), 3.86-3.72 (m, 1H), 3.09-2.98 (m, 1H). LC-MS R$_T$=2.022 min, m/z=372.0 [M+H]⁺.

Example 137

(5S,7S)-7-fluoro-5-phenyl-2-(trifluoromethylsulfonyl)-6,7-dihydro-5H-pyrrolo[1,2-b][1,2,4]triazole

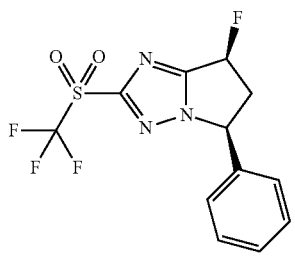 [SMILES: O=S(=O)(c1nc2n(n1)[C@H](c1ccccc1)C[C@@H]2F)C(F)(F)F]

(5S,7S)-7-fluoro-5-phenyl-2-(trifluoromethylsulfonyl)-6,7-dihydro-5H-pyrrolo[1,2-b][1,2,4]triazole was prepared according to method 29 starting from (5S,7S)-7-fluoro-5-phenyl-6,7-dihydro-5H-pyrrolo[1,2-b][1,2,4]triazole-2-thiol. The final compound was purified by RP-HPLC (acetonitrile 43-63%/0.05% ammonium bicarbonate in water) to give (5S,7S)-7-fluoro-5-phenyl-2-(trifluoromethylsulfonyl)-6,7-dihydro-5H-pyrrolo[1,2-b][1,2,4]triazole (20 mg, 28%) as a yellow oil. ¹H NMR (400 MHz, CDCl₃) δ 7.44-7.42 (m, 3H), 7.27-7.24 (m, 2H), 6.19-6.05 (m, 1H), 5.64-5.60 (m, 1H), 3.79-3.65 (m, 1H), 3.12-3.01 (m, 1H). LCMS R$_T$=1.123 min, m/z=336.1 [M+H]⁺.

Example 138

(5S,7S)-5-(2,5-difluorophenyl)-7-fluoro-2-(trifluoromethylsulfonyl)-6,7-dihydro-5H-pyrrolo[1,2-b][1,2,4]triazole

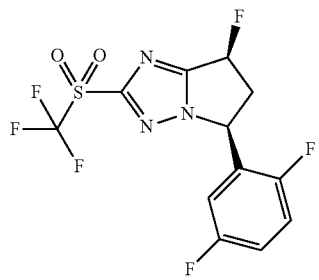 [SMILES: O=S(=O)(c1nc2n(n1)[C@H](c1cc(F)ccc1F)C[C@@H]2F)C(F)(F)F]

(5S,7S)-5-(2,5-difluorophenyl)-7-fluoro-2-(trifluoromethylsulfonyl)-6,7-dihydro-5H-pyrrolo[1,2-b][1,2,4]triazole was prepared according to method 29 starting from (5S,7S)-5-(2,5-difluorophenyl)-7-fluoro-6,7-dihydro-5H-pyrrolo[1,2-b][1,2,4]triazole-2-thiol. The final compound was purified by RP-HPLC (acetonitrile 50-80%/0.05% ammonia hydroxide in water) to give (5S,7S)-5-(2,5-difluorophenyl)-7-fluoro-2-(trifluoromethylsulfonyl)-6,7-dihydro-5H-pyrrolo[1,2-b][1,2,4]triazole (17 mg, 31%) as a white solid. ¹H NMR (400 MHz, CDCl₃) δ 7.17-7.12 (m, 2H), 6.70-6.67 (m, 1H), 6.19-6.03 (m, 1H), 5.90-5.89 (m, 1H), 3.84-3.70 (m, 1H), 3.08-2.97 (m, 1H). LC-MS R$_T$=1.134 min, m/z=372.1 [M+H]$^+$.

Example 139

(5S,7S)-5-(2,6-difluorophenyl)-7-fluoro-2-(trifluoromethylsulfonyl)-6,7-dihydro-5H-pyrrolo[1,2-b][1,2,4]triazole

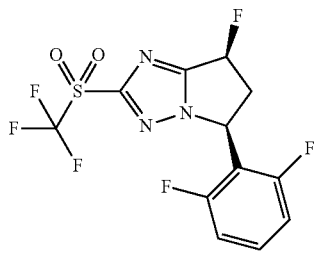 [SMILES: O=S(=O)(c1nc2n(n1)[C@H](c1c(F)cccc1F)C[C@@H]2F)C(F)(F)F]

(5S,7S)-5-(2,6-difluorophenyl)-7-fluoro-2-(trifuoromethylsulfonyl)-6,7-dihydro-5H-pyrrolo-[1,2-b][1,2,4]triazole was prepared according to method 29 starting from (5S,7S)-5-(2,6-difluorophenyl)-7-fluoro-6,7-dihydro-5H-pyrrolo[1,2-b][1,2,4]triazole-2-thiol. The final compound was purified by column chromatography (silica gel, 100-200 mesh, 0 to 20% ethyl acetate in petroleum ether) to give (5S,7S)-5-(2,6-difluorophenyl)-7-fluoro-2-(trifluoromethylsulfonyl)-6,7-dihydro-5H-pyrrolo[1,2-b][1,2,4]triazole (15 mg, 28%) as a white solid. $^1$H NMR (400 MHz, CD$_3$OD) δ 7.55-7.51 (m, 1H), 7.13-7.08 (m, 2H), 6.29-6.13 (m, 1H), 6.08-6.06 (m, 1H), 3.95-3.83 (m, 1H), 3.04-2.92 (m, 1H). LCMS R$_T$=1.124 min, m/z=372.1 [M+H]$^+$ Example 140

(5R,7R)-5-(2,3-difluorophenyl)-7-fluoro-2-(trifluoromethylsulfonyl)-6,7-dihydro-5H-pyrrolo[1,2-b][1,2,4]triazole

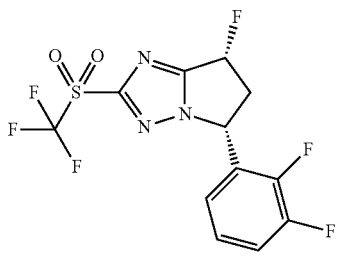 [SMILES: O=S(=O)(c1nc2n(n1)[C@@H](c1cccc(F)c1F)C[C@H]2F)C(F)(F)F]

Arbitrarily assigned (5R,7R)-5-(2,3-difluorophenyl)-7-fluoro-2-(trifluoromethylsulfonyl)-6,7-dihydro-5H-pyrrolo[1,2-b][1,2,4]triazole was prepared according to method 29 starting from (5R,7R)-5-(2,3-difluorophenyl)-7-fluoro-6,7-dihydro-5H-pyrrolo[1,2-b][1,2,4]triazole-2-thiol. The final compound was purified by RP-HPLC (acetonitrile 50-80%/0.05% ammonia hydroxide in water) to give arbitrarily assigned (5R,7R)-5-(2,3-difluorophenyl)-7-fluoro-2-(trifluoromethylsulfonyl)-6,7-dihydro-5H-pyrrolo[1,2-b][1,2,4]triazole (60 mg, 32%) as a white solid. $^1$H NMR (400 MHz, CDCl$_3$) δ 7.27-7.24 (m, 1H), 7.23-7.14 (m, 1H), 6.75-6.71 (m, 1H), 6.21-6.05 (m, 1H), 6.02-5.95 (m, 1H), 3.88-3.75 (m, 1H), 3.08-2.97 (m, 1H). LC-MS R$_T$=2.031 min, m/z=372.0 [M+H]$^+$.

Example 141 and Example 142: Method 30

(5S,7S)-7-fluoro-5-(3-fluorophenyl)-2-[(1S,2S)-2-fluorocyclopropyl]sulfonyl-6,7-dihydro-5H-pyrrolo[1,2-b][1,2,4]triazole and (5S,7S)-7-fluoro-5-(3-fluorophenyl)-2-[(1R,2R)-2-fluorocyclopropyl]sulfonyl-6,7-dihydro-5H-pyrrolo[1,2-b][1,2,4]triazole

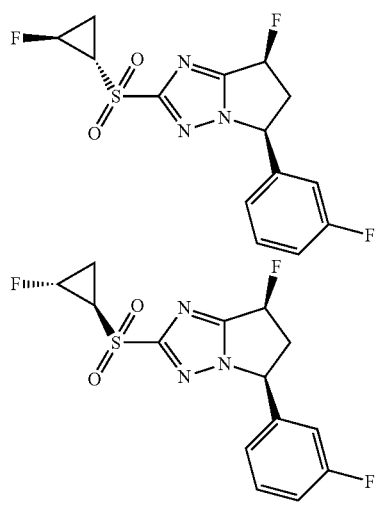

Step 1: Trans-2-fluorocyclopropanecarbonyl Chloride

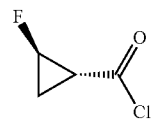

A mixture of trans-2-fluorocyclopropanecarboxylic acid (25.0 g, 240 mmol) and N,N-dimethylformamide (1.8 g, 24 mmol) in dichloromethane (227 mL) was added oxalyl chloride (30.5 mL, 360 mmol) at 0° C. The mixture was stirred at 20° C. for 16 h and concentrated under reduced pressure to give crude trans-2-fluorocyclopropanecarbonyl chloride (29.4 g, 99%).

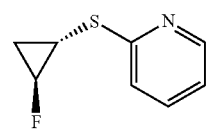 [SMILES: F[C@H]1C[C@@H]1Sc1ccccn1]

Step 2: 2-[trans-2-fluorocyclopropyl]sulfanylpyridine

A cooled (0° C.) solution of trans-2-fluorocyclopropanecarbonyl chloride (29.4 g, 240.2 mol) in dichloromethane (454 mL) was added 4-dimethylaminopyridine (2.9 g, 24 mmol) and sodium 1-oxidopyridine-2-thione (53.7 g, 360 mmol) portionwise under dark. After addition, the mixture was stirred for 2 h and quenched by addition of water (200 mL). The separated organic layer was filtered through a short pad of Celite and washed with dichloromethane (2×100 mL). The combined organic layers were concentrated under reduced pressure (without heating). The residue was dissolved in ethyl acetate (300 mL) and irradiated with a 600 W halogen lamp until complete consumption of the Barton ester. The crude was then used directly into the next step without further purification.

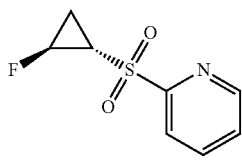 [SMILES: O=S(=O)(c1ccccn1)[C@H]1C[C@@H]1F]

Step 3: 2-[trans-2-fluorocyclopropyl]sulfonylpyridine

To a cooled (0° C.) mixture of crude 2-[trans-2-fluorocyclopropyl]sulfanylpyridine in ethyl acetate (300 mL) and water (300 mL) was added ruthenium(III) chloride (249 mg, 1.2 mmol) and sodium periodate (205.3 g, 959.7 mmol). The reaction was stirred for 16 h at 20° C. and extracted with ethyl acetate (3×100 mL). The combined organic layers were washed with brine (200 mL), dried over magnesium sulfate and concentrated under reduced pressure. The residue was purified by column chromatography (silica gel, 100-200 mesh, 0 to 30% ethyl acetate in petroleum ether) to afford 2-[trans-2-fluorocyclopropyl]sulfonylpyridine (13.5 g, 28%) as a colorless oil. $^1$H NMR (400 MHz, DMSO-$d_6$) δ 8.85-8.84 (m, 1H), 8.21-8.17 (m, 1H), 8.08-8.06 (m, 1H), 7.81-7.80 (m, 1H), 5.30-5.27 (m, 0.5H), 5.13-5.12 (m, 0.5H), 3.68-3.63 (m, 1H), 1.94-1.87 (m, 1H), 1.64-1.59 (m, 1H).

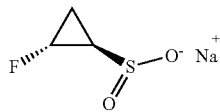

Step 4: Sodium trans-2-fluorocyclopropanesulfinate

To a mixture of 2-[trans-2-fluorocyclopropyl]sulfonylpyridine (7.5 g, 37.3 mmol) in tetrahydrofuran (150 mL) was added sodium ethanethiolate (3.8 g, 44.7 mmol) at 0° C. After addition, the mixture was stirred at 18° C. for 16 h and concentrated under reduced pressure. The residue was purified by column chromatography (silica gel, 100-200 mesh, 0 to 30% methanol in dichloromethane) to give the sodium trans-2-fluorocyclopropanesulfinate (4.5 g, 83%) as a white solid. $^1$H NMR (400 MHz, DMSO-$d_6$) δ 4.55-4.52 (m, 0.5H), 4.38-4.36 (m, 0.5H), 2.15-2.08 (m, 1H), 1.02-0.89 (m, 2H).

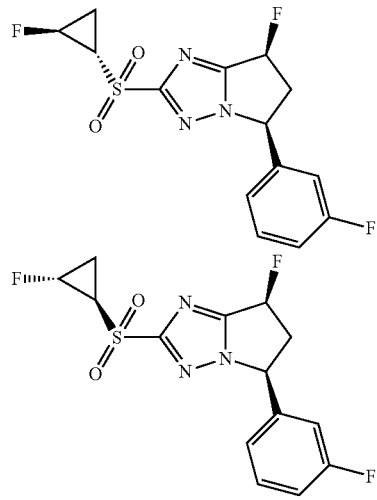

Step 5

(5S,7S)-7-fluoro-5-(3-fluorophenyl)-2-[(1S,2S)-2-fluorocyclopropyl]sulfonyl-6,7-dihydro-5H-pyrrolo[1,2-b][1,2,4]triazole and (5S,7S)-7-fluoro-5-(3-fluorophenyl)-2-[(1R,2R)-2-fluorocyclopropyl]sulfonyl-6,7-dihydro-5H-pyrrolo[1,2-b][1,2,4]triazole To a solution of (5S,7S)-2-bromo-7-fluoro-5-(3-fluorophenyl)-6,7-dihydro-5H-pyrrolo[1,2-b][1,2,4]triazole (300 mg, 1.00 mmol), sodium trans-2-fluorocyclopropanesulfinate (292 mg, 2.00 mmol), copper(I) trifluoromethanesulfonate benzene complex (100 mg, 0.20 mmol), potassium iodide (83 mg, 0.50 mmol) and (1R,2R)—N~1~,N~2~--dimethyl-1,2-cyclohexanediamine (71 mg, 0.50 mmol) in dimethyl sulfoxide (10 mL) was heated at 100° C. for 2 h under microwave conditions. After cooled, the reaction mixture was extracted with ethyl acetate (2×50 mL). The combined organic layers were washed with brine (50 mL), dried over sodium sulfate and concentrated under reduced pressure. The residue was purified by RP-HPLC (acetonitrile 31-61%/0.05% ammonia hydroxide in water) to afford (5S,7S)-7-fluoro-2-[trans-2-fluorocyclopropyl]sulfonyl-5-(3-fluorophenyl)-6,7-dihydro-5H-pyrrolo[1,2-b][1,2,4]triazole (75 mg, 22%) as a white solid. This trans mixture was further separated by chiral SFC to give:

(5S,7S)-7-fluoro-2-[(1S,2S)-2-fluorocyclopropyl]sulfonyl-5-(3-fluorophenyl)-6,7-dihydro-5H-pyrrolo[1,2-b][1,2,4]triazole (Peak 1, retention time=4.035 min) (6 mg, 7%) as a white solid. $^1$H NMR (400 MHz, CDCl$_3$) δ 7.45-7.37 (m, 1H), 7.15-7.09 (m, 1H), 7.08-7.04 (m, 1H), 7.02-6.95 (m, 1H), 6.16-5.98 (m, 1H), 5.58-5.51 (m, 1H), 5.24-5.04 (m, 1H), 3.77-3.62 (m, 1H), 3.23-3.12 (m, 1H), 3.08-2.95 (m, 1H), 1.90-1.75 (m, 2H). LC-MS R$_T$=0.974 min, m/z=344.1 [M+H]$^+$.

(5S,7S)-7-fluoro-2-[(1R,2R)-2-fluorocyclopropyl]sulfonyl-5-(3-fluorophenyl)-6,7-dihydro-5H-pyrrolo[1,2-b][1,2,4]triazole (Peak 2, retention time=4.600 min) (15 mg, 20%) as a white solid. $^1$H NMR (400 MHz, CDCl$_3$) δ 7.45-7.37 (m, 1H), 7.15-7.09 (m, 1H), 7.08-7.04 (m, 1H), 7.02-6.96 (m, 1H), 6.14-5.98 (m, 1H), 5.59-5.49 (m, 1H), 5.22-5.06 (m, 1H), 3.80-3.64 (m, 1H), 3.24-3.10 (m, 1H), 3.08-2.94 (m, 1H), 1.93-1.75 (m, 2H). LC-MS R$_T$=0.974 min, m/z=344.1 [M+H]$^+$.

SFC condition: column: chiralpak AY 150×4.6 mm I.D., 3 μm, mobile phase: A: $CO_2$ B: ethanol (0.05% DEA), gradient: from 5% to 40% of B in 5 min and hold 40% for 2.5 min, then 5% of B for 2.5 min, flow rate: 2.5 mL/min, column temp.: 35° C.

Example 126 and Example 127

(5S,7S)-5-(3,4-difluorophenyl)-7-fluoro-2-[(1S,2S)-2-fluorocyclopropyl]sulfonyl-6,7-dihydro-5H-pyrrolo[1,2-b][1,2,4]triazole and (5S,7S)-5-(3,4-difluorophenyl)-7-fluoro-2-[(1R,2R)-2-fluorocyclopropyl]sulfonyl-6,7-dihydro-5H-pyrrolo[1,2-b][1,2,4]triazole

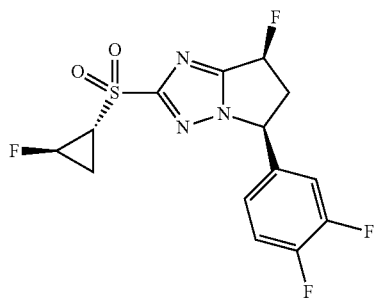 [SMILES: O=S(=O)(c1nc2n(n1)[C@H](c1ccc(F)c(F)c1)C[C@@H]2F)[C@@H]1C[C@H]1F]

(5S,7S)-5-(3,4-difluorophenyl)-7-fluoro-2-[(1S,2S)-2-fluorocyclopropyl]sulfonyl-6,7-dihydro-5H-pyrrolo[1,2-b][1,2,4]triazole and (5S,7S)-5-(3,4-difluorophenyl)-7-fluoro-2-[(1R,2R)-2-fluorocyclopropyl]sulfonyl-6,7-dihydro-5H-pyrrolo[1,2-b][1,2,4]triazole were prepared according to method 29 starting from (5S,7S)-2-bromo-5-(3,4-difluorophenyl)-7-fluoro-6,7-dihydro-5H-pyrrolo[1,2-b][1,2,4]triazole. The final compounds were purified by chiral SFC to give arbitrarily assigned:

(5S,7S)-5-(3,4-difluorophenyl)-7-fluoro-2-[(1S,2S)-2-fluorocyclopropyl]sulfonyl-6,7-dihydro-5H-pyrrolo[1,2-b][1,2,4]triazole (Peak 1, Retention time=3.495 min) (15 mg, 5%) as a white solid. $^1$H NMR (400 MHz, $CDCl_3$) δ 7.27-7.21 (m, 1H), 7.20-7.10 (m, 1H), 7.06-7.03 (m, 1H), 6.14 (d, J=8.4 Hz, 0.5H), 6.00 (d, J=8.0 Hz, 0.5H), 5.53-5.21 (m, 1H), 5.15-5.10 (m, 0.5H), 5.06-3.02 (m, 0.5H), 3.73-3.64 (m, 1H), 3.16-3.12 (m, 1H), 3.03-2.92 (m, 1H), 1.89-1.80 (m, 2H). LC-MS $R_T$=0.972 min, m/z=362.1 [M+H]$^+$.

(5S,7S)-5-(3,4-difluorophenyl)-7-fluoro-2-[(1R,2R)-2-fluorocyclopropyl]sulfonyl-6,7-dihydro-5H-pyrrolo[1,2-b][1,2,4]triazole (Peak 2, Retention time=3.709 min) (17 mg, 6%) as a white solid. $^1$H NMR (400 MHz, $CDCl_3$) δ 7.27-7.22 (m, 1H), 7.16-7.10 (m, 1H), 7.07-7.03 (m, 1H), 6.13 (d, J=6.8 Hz, 0.5H), 6.00 (d, J=8.4 Hz, 0.5H), 5.54-5.21 (m, 1H), 5.15-5.10 (m, 0.5H), 5.06-5.02 (m, 0.5H), 3.73-3.64 (m, 1H), 3.19-3.12 (m, 1H), 3.04-2.93 (m, 1H), 1.88-1.78 (m, 2H). LC-MS $R_T$=0.792 min, m/z=362.1 [M+H]$^+$.

SFC condition: AY-H (250 mm×30 mm, 5 μm); Mobile phase: A: $CO_2$ B: 0.1% $NH_3H_2O$ EtOH; Gradient: from 25% to 25% of B; Flow rate: 50 mL/min Column temperature: 40° C.

Example 145 and Example 146

(5S,7S)-7-fluoro-5-phenyl-2-[(1S,2S)-2-fluorocyclopropyl]sulfonyl-6,7-dihydro-5H-pyrrolo[1,2-b][1,2,4]triazole and (5S,7S)-7-fluoro-5-phenyl-2-[(1R,2R)-2-fluorocyclopropyl]sulfonyl-6,7-dihydro-5H-pyrrolo[1,2-b][1,2,4]triazole

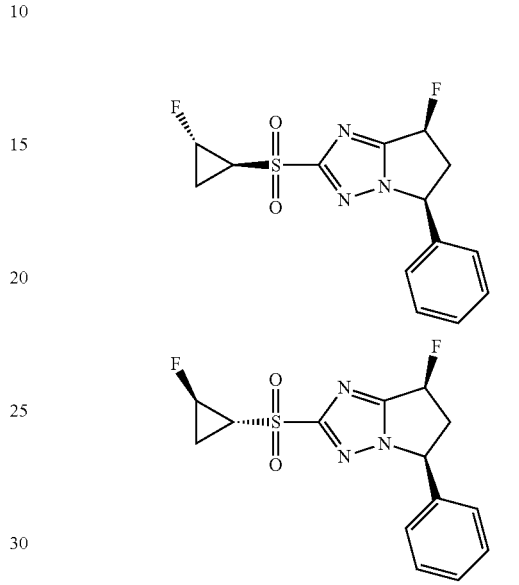

(5S,7S)-7-fluoro-5-phenyl-2-[(1S,2S)-2-fluorocyclopropyl]sulfonyl-6,7-dihydro-5H-pyrrolo[1,2-b][1,2,4]triazole and (5S,7S)-7-fluoro-5-phenyl-2-[(1R,2R)-2-fluoro cyclopropyl]sulfonyl-6,7-dihydro-5H-pyrrolo[1,2-b][1,2,4]triazole were prepared according to method 20 starting from (5S,7S)-2-bromo-7-fluoro-5-phenyl-6,7-dihydro-5H-pyrrolo[1,2-b][1,2,4]triazole. The final compounds were purified by chiral SFC to give arbitrarily assigned:

(5S,7S)-7-fluoro-5-phenyl-2-[(1S,2S)-2-fluorocyclopropyl]sulfonyl-6,7-dihydro-5H-pyrrolo[1,2-b][1,2,4]triazole (Peak 1, retention time=4.973 min) (2.5 mg, 2%) as a white solid. $^1$H NMR (400 MHz, $CD_3OD$) δ 7.47-7.41 (m, 3H), 7.32-7.30 (m, 2H), 6.24-6.08 (m, 1H), 5.71-5.69 (m, 1H), 5.22-5.06 (m, 1H), 3.83-3.76 (m, 1H), 3.41-3.32 (m, 1H), 2.95-2.86 (m, 1H), 1.89-1.84 (m, 1H), 1.75-1.70 (m, 1H). LCMS $R_T$=0.669 min, m/z=326.1 [M+H]$^+$.

(5S,7S)-7-fluoro-5-phenyl-2-[(1R,2R)-2-fluorocyclopropyl]sulfonyl-6,7-dihydro-5H-pyrrolo[1,2-b][1,2,4]triazole (Peak 2, retention time=5.569 min) (2.7 mg, 2%) as a white solid. $^1$H NMR (400 MHz, $CD_3OD$) δ 7.47-7.41 (m, 3H), 7.31-7.29 (m, 2H), 6.24-6.08 (m, 1H), 5.71-5.69 (m, 1H), 5.22-5.05 (m, 1H), 3.83-3.76 (m, 1H), 3.41-3.33 (m, 1H), 2.95-2.86 (m, 1H), 1.90-1.74 (m, 2H). LCMS $R_T$=0.670 min, m/z=326.1 [M+H]$^+$.

SFC condition: Column: ChiralPak AY-3 150×4.6 mm I.D., 3 um Mobile phase: A: $CO_2$ B: Ethanol (0.05% DEA) Gradient: from 5% to 40% of B in 5.5 min and hold 40% for 3 min, then 5% of B for 1.5 min Flow rate: 2.5 mL/min Column temperature: 40° C.

Example 147

(5S,7S)-7-fluoro-5-phenyl-2-((pyridin-2-ylmethyl)sulfinyl)-6,7-dihydro-5H-pyrrolo[1,2-b][1,2,4]triazole

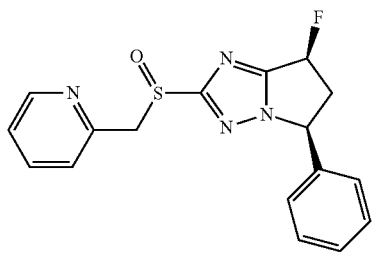 [SMILES: O=S(Cc1ccccn1)c1nc2n(n1)[C@H](c1ccccc1)C[C@@H]2F]

(5S,7S)-7-fluoro-5-phenyl-2-(2-pyridylmethylsulfinyl)-6,7-dihydro-5H-pyrrolo[1,2-b][1,2,4]triazole was prepared according to method 26 starting from (5S,7S)-7-fluoro-5-phenyl-6,7-dihydro-5H-pyrrolo[1,2-b][1,2,4]triazole-2-thiol and 2-(chloromethyl)pyridine hydrochloride. The final compound was purified by column chromatography (silica gel, 0-65% ethyl acetate in petroleum ether) to give (5S,7S)-7-fluoro-5-phenyl-2-(2-pyridylmethylsulfinyl)-6,7-dihydro-5H-pyrrolo[1,2-b][1,2,4]triazole (20 mg, 62%) as a white solid. $^1$H NMR (400 MHz, CD$_3$OD) δ 8.49-8.46 (m, 1H), 7.77-7.74 (m, 1H), 7.42-7.32 (m, 5H), 7.26-7.25 (m, 1H), 7.18-7.15 (m, 1H), 6.19-6.03 (m, 1H), 5.64-5.60 (m, 1H), 4.76-4.71 (m, 2H), 3.80-3.70 (m, 1H), 2.88-2.74 (m, 1H). LC-MS R$_T$=1.428 min, m/z=343.1 [M+H]$^+$.

Example 148

(5S,7S)-2-(2,2-difluoroethylsulfinyl)-7-fluoro-5-phenyl-6,7-dihydro-5H-pyrrolo[1,2-b][1,2,4]triazole

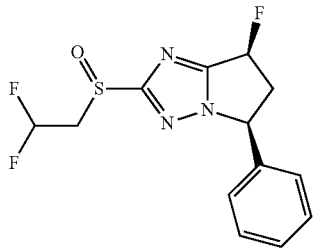 [SMILES: O=S(CC(F)F)c1nc2n(n1)[C@H](c1ccccc1)C[C@@H]2F]

(5S,7S)-2-(2,2-difluoroethylsulfinyl)-7-fluoro-5-phenyl-6,7-dihydro-5H-pyrrolo[1,2-b][1,2,4]triazole was prepared according to method 26 starting from (5S,7S)-7-fluoro-5-phenyl-6,7-dihydro-5H-pyrrolo[1,2-b][1,2,4]triazole-2-thiol and 2-iodo-1,1-difluoroethane. The final compound was purified by preparative TLC (40% ethyl acetate in petroleum ether, R$_f$=0.2) to give (5S,7S)-2-(2,2-difluoroethylsulfinyl)-7-fluoro-5-phenyl-6,7-dihydro-5H-pyrrolo[1,2-b][1,2,4]triazole (23.1 mg, 43%) as a white solid. $^1$H NMR (400 MHz, CDCl$_3$) δ 7.45-7.40 (m, 3H), 7.27-7.24 (m, 2H), 6.31-6.15 (m, 1H), 6.13-5.97 (m, 1H), 5.54-5.50 (m, 1H), 3.93-3.75 (m, 1H), 3.73-3.62 (m, 2H), 3.05-2.98 (m, 1H). LC-MS R$_T$=0.806 min, m/z=315.9 [M+H]$^+$.

Example 149: Method 31

(5S,7S)-2-(1,1-difluoroethylsulfonyl)-7-fluoro-5-phenyl-6,7-dihydro-5H-pyrrolo[1,2-b][1,2,4]triazole

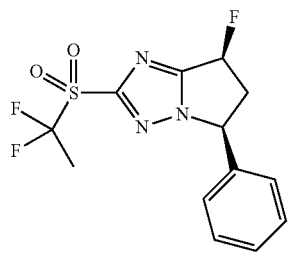 [SMILES: CC(F)(F)S(=O)(=O)c1nc2n(n1)[C@H](c1ccccc1)C[C@@H]2F]

(5S,7S)-2-(1,1-difluoroethylsulfonyl)-7-fluoro-5-phenyl-6,7-dihydro-5H-pyrrolo[1,2-b][1,2,4]triazole was prepared according to method 31 starting from 2,2-difluoropropanoic acid. The final compound was purified by RP-HPLC (acetonitrile 35-65%/0.05% ammonia hydroxide in water) to give (5S,7S)-2-(1,1-difluoroethylsulfonyl)-7-fluoro-5-phenyl-6,7-dihydro-5H-pyrrolo[1,2-b][1,2,4]triazole (2 mg, 18%) as yellow solid. $^1$H NMR (400 MHz, CD$_3$OD) δ 7.44-7.41 (m, 3H), 7.28-7.25 (m, 2H), 6.24-6.08 (m, 1H), 5.75-5.70 (m, 1H), 3.86-3.72 (m, 1H), 2.93-2.82 (m, 1H), 2.06 (t, J=6.8 Hz, 3H). LCMS R$_T$=1.081 min, m/z=332.1 [M+H]$^+$.

Example 150

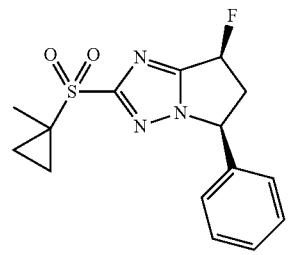 [SMILES: CC1(S(=O)(=O)c2nc3n(n2)[C@H](c2ccccc2)C[C@@H]3F)CC1]

(5S,7S)-7-fluoro-2-(1-methylcyclopropyl)sulfonyl-5-phenyl-6,7-dihydro-5H-pyrrolo[1,2-b][1,2,4]triazole (5S,7S)-7-fluoro-2-(1-methylcyclopropyl)sulfonyl-5-phenyl-6,7-dihydro-5H-pyrrolo[1,2-b][1,2,4]triazole was prepared according to method 31 starting from 1-methylcyclopropanecarboxylic acid. The final compound was purified by RP-HPLC (acetonitrile 38-68/0.05% ammonia hydroxide in water) to give (5S,7S)-7-fluoro-2-(1-methylcyclopropyl)sulfonyl-5-phenyl-6,7-dihydro-5H-pyrrolo[1,2-b][1,2,4]triazole (2 mg, 28%) as a white solid. $^1$H NMR (400 MHz, CDCl$_3$) δ 7.42-7.38 (m, 3H), 7.27-7.23 (m, 2H), 6.13-6.11 (m, 0.5H), 6.00-5.97 (m, 0.5H), 5.56-5.53 (m, 1H), 3.71-3.62 (m, 1H), 3.05-2.94 (m, 1H), 1.75-1.68 (m, 2H), 1.52 (s, 3H), 0.94-0.87 (m, 2H). LCMS R$_T$=0.831 min, m/z=321.9 [M+H]$^+$.

Example 151 and Example 152

(5S,7S)-7-fluoro-5-phenyl-2-(pyrazol-1-ylmethylsulfinyl)-6,7-dihydro-5H-pyrrolo[1,2-b][1,2,4]triazole and (5S,7S)-7-fluoro-5-phenyl-2-(pyrazol-1-ylmethylsulfonyl)-6,7-dihydro-5H-pyrrolo[1,2-b][1,2,4]triazole

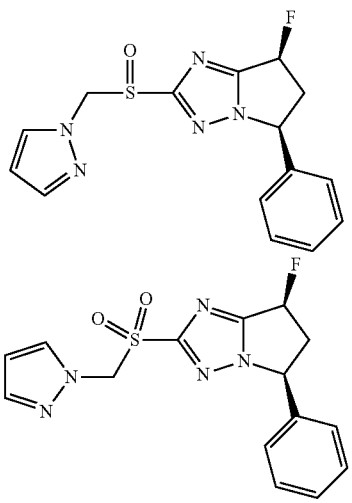

(5S,7S)-7-fluoro-5-phenyl-2-(pyrazol-1-ylmethylsulfinyl)-6,7-dihydro-5H-pyrrolo[1,2-b][1,2,4]triazole and (5S,7S)-7-fluoro-5-phenyl-2-(pyrazol-1-ylmethyl)-6,7-dihydro-5H-pyrrolo[1,2-b][1,2,4]triazole were prepared according to method 26 starting from (5S,7S)-7-fluoro-5-phenyl-6,7-dihydro-5H-pyrrolo[1,2-b][1,2,4]triazole-2-thiol and 1-(bromomethyl)pyrazole.

(5S,7S)-7-fluoro-5-phenyl-2-(pyrazol-1-ylmethylsulfinyl)-6,7-dihydro-5H-pyrrolo[1,2-b][1,2,4]triazole was purified by preparative TLC (66% ethyl acetate in petroleum ether) (16 mg, 41%) as a white solid. $^1$H NMR (400 MHz, CDCl$_3$) δ 7.56-7.53 (m, 2H), 7.41-7.39 (m, 3H), 7.26-7.22 (m, 2H), 6.27 (s, 1H), 6.15-5.98 (m, 1H), 5.69-5.55 (m, 2H), 5.53-5.47 (m, 1H), 3.69-3.60 (m, 1H), 3.02-2.92 (m, 1H). LC-MS R$_T$=0.876 min, m/z=332.2 [M+H]$^+$.

(5S,7S)-7-fluoro-5-phenyl-2-(pyrazol-1-ylmethylsulfonyl)-6,7-dihydro-5H-pyrrolo[1,2-b][1,2,4]triazole was purified by RP-HPLC (acetonitrile 35-65%/0.05% ammonia hydroxide in water) (15 mg, 38%) as a white solid. $^1$H NMR (400 MHz, CDCl$_3$) δ 7.61 (s, 1H), 7.45-7.35 (m, 3H), 7.34-7.30 (m, 1H), 7.21-7.19 (m, 2H), 6.28-6.27 (m, 1H), 6.10-5.96 (m, 1H), 5.75-5.65 (m, 2H), 5.55-5.48 (m, 1H), 3.75-3.60 (m, 1H), 3.05-2.92 (m, 1H). LC-MS R$_T$=0.905 min, m/z=348.1 [M+H]$^+$.

Example 153 and Example 154

(5S,7S)-7-fluoro-2-(1,1,2,2,2-pentafluoroethylsulfinyl)-5-phenyl-6,7-dihydro-5H-pyrrolo[1,2-b][1,2,4]triazole and (5S,7S)-7-fluoro-2-(1,1,2,2,2-pentafluoroethyl sulfonyl)-5-phenyl-6,7-dihydro-5H-pyrrolo[1,2-b][1,2,4]triazole

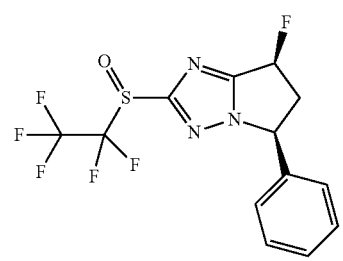

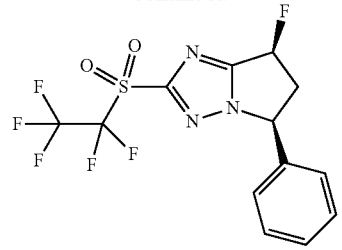

(5S,7S)-7-fluoro-2-(1,1,2,2,2-pentafluoroethylsulfinyl)-5-phenyl-6,7-dihydro-5H-pyrrolo[1,2-b][1,2,4]triazole and (5S,7S)-7-fluoro-2-(1,1,2,2,2-pentafluoroethylsulfonyl)-5-phenyl-6,7-dihydro-5H-pyrrolo[1,2-b][1,2,4]triazole were prepared according to method 26 starting from (5S,7S)-7-fluoro-5-phenyl-6,7-dihydro-5H-pyrrolo[1,2-b][1,2,4]triazole-2-thiol and pentafluoroethyl iodide. (5S,7S)-7-fluoro-2-(1,1,2,2,2-pentafluoroethylsulfonyl)-5-phenyl-6,7-dihydro-5H-pyrrolo[1,2-b][1,2,4]triazole was purified by RP-HPLC (acetonitrile 40-50%/0.05% ammonia hydroxide in water) (6.7 mg, 4%) as a white solid. $^1$H NMR (400 MHz, CD$_3$OD) δ 7.43-7.40 (m, 3H), 7.29-7.25 (m, 2H), 6.25-6.22 (m, 0.5H), 6.11-6.08 (m, 0.5H), 5.73-5.70 (m, 1H), 3.85-3.75 (m, 1H), 2.91-2.80 (m, 1H). LCMS R$_T$=1.959 min, m/z=370.0 [M+H]$^+$.

(5S,7S)-7-fluoro-2-(1,1,2,2,2-pentafluoroethylsulfinyl)-5-phenyl-6,7-dihydro-5H-pyrrolo[1,2-b][1,2,4]triazole was purified by RP-HPLC (acetonitrile 40-50%/0.05% ammonia hydroxide in water) (30.4 mg, 23%) as a white solid. $^1$H NMR (400 MHz, CD$_3$OD) δ 7.46-7.41 (m, 3H), 7.29-7.26 (m, 2H), 6.27-6.24 (m, 0.5H), 6.13-6.10 (m, 0.5H), 5.77-5.75 (m, 1H), 3.85-3.75 (m, 1H), 2.95-2.84 (m, 1H). LCMS R$_T$=2.113 min, m/z=386.0 [M+H]$^+$.

Example 155: Method 17

(5S,7S)-2-[1-(difluoromethyl)cyclopropyl]sulfonyl-7-fluoro-5-phenyl-6,7-dihydro-5H-pyrrolo[1,2-b][1,2,4]triazole

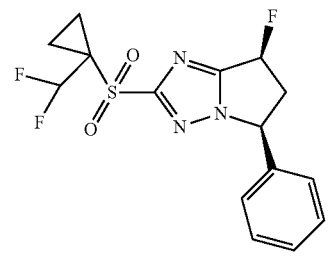 [SMILES: O=S(=O)(c1nc2n(n1)[C@H](c1ccccc1)C[C@@H]2F)C1(C(F)F)CC1]

Step 1: methyl 4-bromo-2-[[(5S,7S)-7-fluoro-5-phenyl-6,7-dihydro-5H-pyrrolo[1,2-b][1,2,4]triazol-2-yl]sulfanyl]butanoate

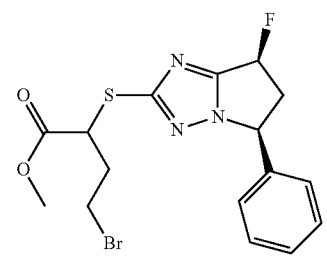 [SMILES: COC(=O)C(CCBr)Sc1nc2n(n1)[C@H](c1ccccc1)C[C@@H]2F]

To a solution of (5S,7S)-7-fluoro-5-phenyl-6,7-dihydro-5H-pyrrolo[1,2-b][1,2,4]triazole-2-thiol (500 mg, 2.13 mmol) in acetonitrile (10 mL) was added potassium carbonate (441 mg, 3.19 mmol) and methyl 2,4-dibromobutanoate (829 mg, 3.19 mmol). The mixture was stirred at 20° C. for 3 h and filtered. The filtrate was concentrated under reduced pressure. The residue was purified by preparative TLC (50% ethyl acetate in petroleum ether, $R_f$=0.5) to give methyl 4-bromo-2-[[(5S,7S)-7-fluoro-5-phenyl-6,7-dihydro-5H-pyrrolo[1,2-b][1,2,4]triazol-2-yl]sulfanyl]butanoate (520 mg, 59%) as a colorless oil.

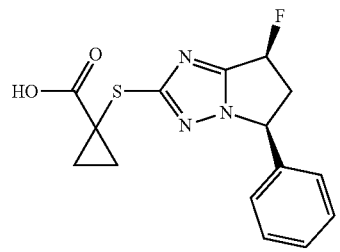 [SMILES: O=C(O)C1(Sc2nc3n(n2)[C@H](c2ccccc2)C[C@@H]3F)CC1]

Step 2: 1-[[(5S,7S)-7-fluoro-5-phenyl-6,7-dihydro-5H-pyrrolo[1,2-b][1,2,4]triazol-2-yl]sulfanyl]cyclopropanecarboxylic acid To a solution of methyl 4-bromo-2-[[(5S,7S)-7-fluoro-5-phenyl-6,7-dihydro-5H-pyrrolo[1,2-b][1,2,4]triazol-2-yl]sulfanyl]butanoate (520 mg, 1.26 mmol) in acetonitrile (2 mL) was added sodium tert-butoxide (1.0 M in tetrahydrofuran, 2.51 mL, 2.51 mmol). The mixture was stirred at 25° C. for 3 h and quenched by addition of water (20 mL). The resulting was adjusted to pH=4 by addition of aqueous hydrochloric acid (1.0 M) and extracted with ethyl acetate (2×15 mL). The combined organic layers were dried over sodium sulfate and concentrated under reduced pressure to afford crude 1-[[(5S,7S)-7-fluoro-5-phenyl-6,7-dihydro-5H-pyrrolo[1,2-b][1,2,4]triazol-2-yl]sulfanyl]cyclopropanecarboxylic acid (380 mg, 95%) as a brown solid.

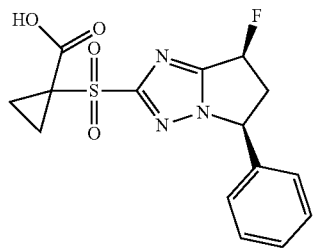 [SMILES: O=C(O)C1(S(=O)(=O)c2nc3n(n2)[C@H](c2ccccc2)C[C@@H]3F)CC1]

Step 3: 1-[[(5S,7S)-7-fluoro-5-phenyl-6,7-dihydro-5H-pyrrolo[1,2-b][1,2,4]triazol-2-yl]sulfonyl]cyclopropanecarboxylic acid A mixture of 1-[[(5S,7S)-7-fluoro-5-phenyl-6,7-dihydro-5H-pyrrolo[1,2-b][1,2,4]triazol-2-yl]sulfanyl]cyclopropanecarboxylic acid (200 mg, 0.63 mmol), sodium periodate (536 mg, 2.51 mmol) and ruthenium(III) chloride (1.3 mg, 0.01 mmol) in water (1 mL)/ethyl acetate (1 mL)/acetonitrile (1 mL) was stirred at 20° C. for 2 h and diluted with ethyl acetate (50 mL). The mixture was washed with brine (30 mL). The separated organic layer was dried over sodium sulfate and concentrated under reduced pressure to afford crude 1-[[(5S,7S)-7-fluoro-5-phenyl-6,7-dihydro-5H-pyrrolo[1,2-b][1,2,4]triazol-2-yl]sulfonyl]cyclopropanecarboxylic acid (120 mg, 55%) as a dark brown solid.

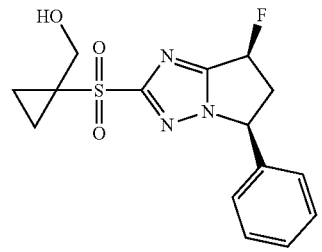 [SMILES: O=S(=O)(c1nc2n(n1)[C@H](c1ccccc1)C[C@@H]2F)C1(CO)CC1]

Step 4: [1-[[(5S,7S)-7-fluoro-5-phenyl-6,7-dihydro-5H-pyrrolo[1,2-b][1,2,4]triazol-2-yl]sulfonyl]cyclopropyl]methanol To a cooled (0° C.) solution of 1-[[(5S,7S)-7-fluoro-5-phenyl-6,7-dihydro-5H-pyrrolo[1,2-b][1,2,4]triazol-2-yl]sulfonyl]cyclopropanecarboxylic acid (120 mg, 0.34 mmol) and triethylamine (0.06 mL, 0.44 mmol) in tetrahydrofuran (3 mL) was added isobutyl chloroformate (0.06 mL, 0.44 mmol) under nitrogen atmosphere. The mixture was stirred at 20° C. for 30 min and filtered. The filtrate was added sodium borohydride (26 mg, 0.68 mmol) in water (0.40 mL) at 0° C. and stirred at 20° C. for 2 h. The mixture was quenched by the addition of saturated aqueous ammonium chloride (10 mL) and extracted with ethyl acetate (2×10 mL). The combined organic layers were washed with saturated aqueous sodium bicarbonate (10 mL), brine (10 mL), dried over sodium sulfate and concentrated under reduced pressure to give crude [1-[[(5S,7S)-7-fluoro-5-phenyl-6,7-dihydro-5H-pyrrolo[1,2-b][1,2,4]triazol-2-yl]sulfonyl]cyclopropyl]methanol (110 mg, 96%) as a light brown oil.

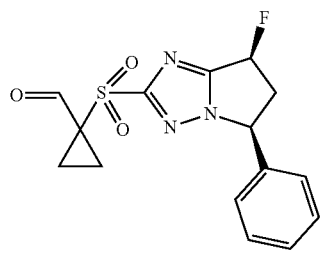 [SMILES: O=CC1(S(=O)(=O)c2nc3n(n2)[C@H](c2ccccc2)C[C@@H]3F)CC1]

Step 5: 1-[[(5S,7S)-7-fluoro-5-phenyl-6,7-dihydro-5H-pyrrolo[1,2-b][1,2,4]triazol-2-yl]sulfonyl]cyclopropanecarbaldehyde To a solution of [1-[[(5S,7S)-7-fluoro-5-phenyl-6,7-dihydro-5H-pyrrolo[1,2-b][1,2,4]triazol-2-yl]sulfonyl]cyclopropyl]methanol (100 mg, 0.30 mmol) in dichloromethane (2 mL) was added pyridinium chlorochromate (96 mg, 0.44 mmol). The mixture was stirred at 20° C. for 18 h and another batch of pyridinium chlorochromate (192 mg, 0.88 mmol) was added. The resulting mixture was stirred for 48 h and concentrated under reduced pressure. The residue was purified by preparative TLC (50% ethyl acetate in petroleum ether, Rf=0.4) to afford 1-[[(5S,7S)-7-fluoro-5-phenyl-6,7-dihydro-5H-pyrrolo[1,2-b][1,2,4]triazol-2-yl]sulfonyl]cyclopropanecarbaldehyde (70 mg, 70%) as a light yellow oil. ¹H NMR (400 MHz, CDCl₃) δ 10.21 (s, 1H), 7.46-7.37 (m, 3H), 7.25-7.21 (m, 2H), 6.14-5.92 (m, 1H), 5.60-5.46 (m, 1H) 3.76-3.54 (m, 1H), 3.12-2.89 (m, 1H), 2.06-2.01 (m, 2H), 1.84-1.71 (m, 2H).

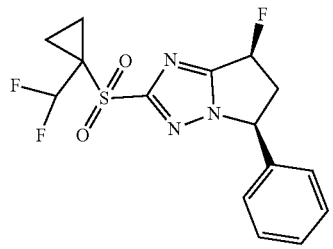 [SMILES: O=S(=O)(c1nc2n(n1)[C@H](c1ccccc1)C[C@@H]2F)C1(C(F)F)CC1]

Step 6: (5S,7S)-2-[1-(difluoromethyl)cyclopropyl]
sulfonyl-7-fluoro-5-phenyl-6,7-dihydro-5H-pyrrolo
[1,2-b][1,2,4]triazole A mixture of 1-[[(5S,7S)-7-fluoro-5-phenyl-6,7-dihydro-5H-pyrrolo[1,2-b][1,2,4]triazol-2-yl]sulfonyl]cyclopropanecarbaldehyde (60 mg, 0.18 mmol) and diethylaminosulfur trifluoride (2.0 mL, 0.18 mmol) was heated at 40° C. for 1 h. The mixture was diluted with dichloromethane (20 mL) and poured into ice cooled saturated aqueous sodium bicarbonate. The aqueous layer was extracted with dichloromethane (2×10 mL). The combined organic layers were washed with water (10 mL), brine (20 mL), dried over sodium sulfate and concentrated under reduced pressure. The residue was purified by RP-HPLC (acetonitrile 43-73%/0.05% ammonia hydroxide in water) to give (5S,7S)-2-[1-(difluoromethyl)cyclopropyl]sulfonyl-7-fluoro-5-phenyl-6,7-dihydro-5H-pyrrolo[1,2-b][1,2,4]triazole (28.8 mg, 44%) as a white solid. ¹H NMR (400 MHz, CDCl₃) δ 7.42-7.37 (m, 3H), 7.26-7.18 (m, 2H), 6.57 (t, J=56.8 Hz, 1H), 6.12-5.96 (m, 1H), 5.56-5.53 (m, 1H), 3.74-3.60 (m, 1H), 3.02-2.92 (m, 1H), 1.90-1.84 (m, 2H), 1.50-1.44 (m, 2H). LCMS R_T=1.043 min, m/z=358.1 [M+H]⁺.

Example 156: Method 18

2,2-difluoro-2-[[(5S,7S)-7-fluoro-5-phenyl-6,7-dihydro-5H-pyrrolo[1,2-b][1,2,4]triazol-2-yl]sulfonyl]
ethanol

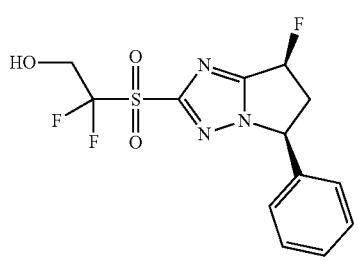 [SMILES: O=S(=O)(c1nc2n(n1)[C@H](c1ccccc1)C[C@@H]2F)C(F)(F)CO]

Step 1: ethyl 2,2-difluoro-2-[[(5S,7S)-7-fluoro-5-phenyl-6,7-dihydro-5H-pyrrolo[1,2-b][1,2,4]triazol-2-yl]sulfanyl]acetate

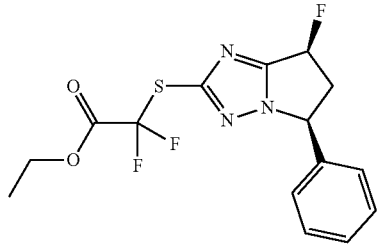 [SMILES: CCOC(=O)C(F)(F)Sc1nc2n(n1)[C@H](c1ccccc1)C[C@@H]2F]

A mixture of (5S,7S)-7-fluoro-5-phenyl-6,7-dihydro-5H-pyrrolo[1,2-b][1,2,4]triazole-2-thiol (300 mg, 1.28 mmol), ethyl bromodifluoroacetate (388 mg, 1.91 mmol) and cesium carbonate (831 mg, 2.55 mmol) in N,N-dimethylformamide (5 mL) was stirred at 10° C. for 3 h under nitrogen atmosphere and diluted with ethyl acetate (50 mL). The mixture was washed with water (50 mL), brine (50 mL), dried over sodium sulfate and concentrated under reduced pressure. The residue was purified by column chromatography (silica gel, 100-200 mesh, 0 to 20% ethyl acetate in petroleum ether) to afford ethyl 2,2-difluoro-2-[[(5S,7S)-7-fluoro-5-phenyl-6,7-dihydro-5H-pyrrolo[1,2-b][1,2,4]triazol-2-yl]sulfanyl]acetate (280 mg, 61%) as a yellow oil. LCMS R_T=0.892 min, m/z=358.0 [M+H]⁺.

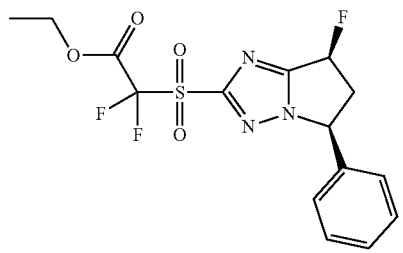 [SMILES: CCOC(=O)C(F)(F)S(=O)(=O)c1nc2n(n1)[C@H](c1ccccc1)C[C@@H]2F]

Step 2: ethyl 2,2-difluoro-2-[[(5S,7S)-7-fluoro-5-phenyl-6,7-dihydro-5H-pyrrolo[1,2-b][1,2,4]triazol-2-yl]sulfonyl]acetate A mixture of ruthenium(III) chloride (15 mg, 0.07 mmol), sodium periodate (748 mg, 3.5 mmol) and ethyl 2,2-difluoro-2-[[(5S,7S)-7-fluoro-5-phenyl-6,7-dihydro-5H-pyrrolo[1,2-b][1,2,4]triazol-2-yl]sulfanyl]acetate (250 mg, 0.70 mmol) in ethyl acetate (4 mL), water (4 mL) and acetonitrile (4 mL) was stirred at 35° C. for 5 h and quenched by addition of saturated aqueous sodium sulfite (10 mL). The mixture was extracted with ethyl acetate (3×30 mL). The combined organic layers were washed with water (20 mL), brine (20 mL) and concentrated under reduced pressure. The residue was purified by column chromatography (silica gel, 100-200 mesh, 0 to 40% ethyl acetate in petroleum ether) to afford ethyl 2,2-difluoro-2-[[(5S,7S)-7-fluoro-5-phenyl-6,7-dihydro-5H-pyrrolo[1,2-b][1,2,4]triazol-2-yl]sulfonyl]acetate (120 mg, 44%) as a yellow solid.

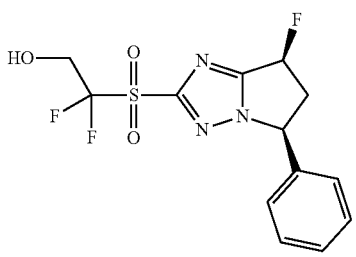 [SMILES: O=S(=O)(c1nc2n(n1)[C@H](c1ccccc1)C[C@@H]2F)C(F)(F)CO]

Step 3: 2,2-difluoro-2-[[(5S,7S)-7-fluoro-5-phenyl-6,7-dihydro-H-pyrrolo[1,2-b][1,2,4]triazol-2-yl]sulfonyl]ethanol To a mixture of ethyl 2,2-difluoro-2-[[(5S,7S)-7-fluoro-5-phenyl-6,7-dihydro-5H-pyrrolo[1,2-b][1,2,4]triazol-2-yl]sulfonyl]acetate (90 mg, 0.23 mmol) in methanol (4 mL) was added sodium borohydride (26 mg, 0.69 mmol). After addition, the mixture was stirred at 10° C. for 2 h and quenched by addition of saturated aqueous ammonium chloride (10 mL). The mixture was diluted with water (20 mL) and extracted with ethyl acetate (3×30 mL). The combined organic layers were washed with brine (20 mL) and concentrated under reduced pressure. The residue was purified by RP-HPLC (acetonitrile 36-66%/0.05% ammonia hydroxide in water) to afford 2,2-difluoro-2-[[(5S,7S)-7-fluoro-5-phenyl-6,7-dihydro-5H-pyrrolo[1,2-b][1,2,4]triazol-2-yl]sulfonyl]ethanol (30 mg, 36%) as a white solid. $^1$H NMR (400 MHz, CD$_3$OD) δ 7.43-7.40 (m, 3H), 7.28-7.25 (m, 2H), 6.24-6.08 (m, 1H), 5.73-5.71 (m, 1H), 4.19 (t, J=14.4 Hz, 2H), 3.84-3.73 (m, 1H), 2.91-2.80 (m, 1H). LCMS R$_T$=0.972 min, m/z=348.1 [M+H]$^+$.

Example 157: Method 19

1-[[(5S,7S)-7-fluoro-5-phenyl-6,7-dihydro-5H-pyrrolo[1,2-b][1,2,4]triazol-2-yl]sulfonyl]cyclopropanecarbonitrile

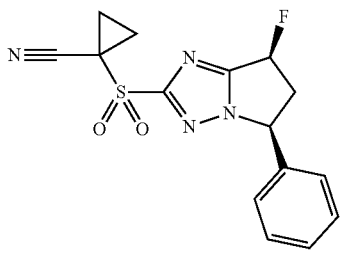 [SMILES: N#CC1(S(=O)(=O)c2nc3n(n2)[C@H](c2ccccc2)C[C@@H]3F)CC1]

Step 1: 1-(((5S,7S)-7-fluoro-5-phenyl-6,7-dihydro-5H-pyrrolo[1,2-b][1,2,4]triazol-2-yl)thio)cyclopropanecarboxamide

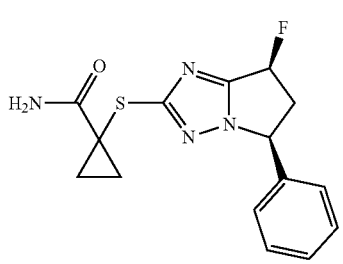 [SMILES: NC(=O)C1(Sc2nc3n(n2)[C@H](c2ccccc2)C[C@@H]3F)CC1]

A mixture of 1-[[(5S,7S)-7-fluoro-5-phenyl-6,7-dihydro-5H-pyrrolo[1,2-b][1,2,4]triazol-2-yl]sulfanyl]cyclopropanecarboxylic acid (150 mg, 0.47 mmol), ammonium chloride (75 mg, 1.41 mmol), 1-[Bis(dimethylamino)methylene]-1H-1,2,3-triazolo[4,5-b]pyridinium 3-oxid hexafluorophosphate (196 mg, 0.52 mmol) and N,N-diisopropylethylamine (182 mg, 1.41 mmol) in N,N-dimethylformamide (2 mL) was stirred at 20° C. for 2 h and diluted with water (10 mL). The resulting mixture was extracted ethyl acetate (3×10 mL). The combined organic layers were washed with water (10 mL), brine (10 mL), dried over sodium sulfate and concentrated under reduced pressure to afford crude 1-[[(5S,7S)-7-fluoro-5-phenyl-6,7-dihydro-5H-pyrrolo[1,2-b][1,2,4]triazol-2-yl]sulfanyl]cyclopropanecarboxamide (160 mg, 100%) as a brown solid. LC-MS R$_T$=0.617 min, m/z=319.1 [M+H]$^+$.

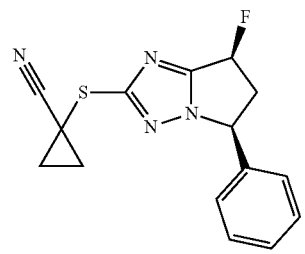 [SMILES: N#CC1(Sc2nc3n(n2)[C@H](c2ccccc2)C[C@@H]3F)CC1]

Step 2: 1-(((5S,7S)-7-fluoro-5-phenyl-6,7-dihydro-5H-pyrrolo[1,2-b][1,2,4]triazol-2-yl)thio)cyclopropanecarbonitrile To a solution of 1-[[(5S,7S)-7-fluoro-5-phenyl-6,7-dihydro-5H-pyrrolo[1,2-b][1,2,4]triazol-2-yl]sulfanyl]cyclopropanecarboxamide (160 mg, 0.50 mmol) in 1,4-dioxane (3 mL) was added triethylamine (153 mg, 1.51 mmol) and trifluoroacetic anhydride (211 mg, 1.01 mmol) dropwise. The reaction mixture was stirred at 25° C. for 2 h and quenched by addition of water (10 mL). The mixture was extracted with ethyl acetate (3×20 mL). The combined organic layers were washed with saturated aqueous sodium bicarbonate (20 mL), dried over sodium sulfate and concentrated under reduced pressure. The residue was purified by preparative TLC (50% ethyl acetate in petroleum ether, R$_f$=0.4) to give 1-[(5S,7S)-7-fluoro-5-phenyl-6,7-dihydro-5H-pyrrolo[1,2-b][1,2,4]triazol-2-yl]sulfanyl]cyclopropanecarbonitrile (150 mg, 99%) as a white solid. LC-MS R$_T$=0.687 min, m/z=301.2 [M+H]$^+$.

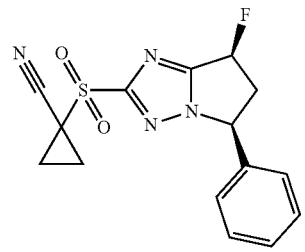 [SMILES: N#CC1(S(=O)(=O)c2nc3n(n2)[C@H](c2ccccc2)C[C@@H]3F)CC1]

Step 3: 1-(((5S,7S)-7-fluoro-5-phenyl-6,7-dihydro-5H-pyrrolo[1,2-b][1,2,4]triazol-2-yl)sulfonyl)cyclopropanecarbonitrile A mixture of 1-[[(5S,7S)-7-fluoro-5-phenyl-6,7-dihydro-5H-pyrrolo[1,2-b][1,2,4]triazol-2-yl]sulfanyl]cyclopropanecarbonitrile (150 mg, 0.50 mmol) and 3-chloroperoxybenzoic acid (85%, 406 mg, 2 mmol) in 1,2-dichloroethane (10 mL) was stirred at 30° C. for 5 h and quenched by addition of saturated aqueous sodium bicarbonate (10 mL). The resulting mixture was extracted with ethyl acetate (3×10 mL). The combined organic layers were washed with brine (3×10 mL), dried over sodium sulfate and concentrated under reduced pressure. The residue was purified by RP-HPLC (acetonitrile 40-70%/0.05% ammonia hydroxide in water) to give 1-[[(5S,7S)-7-fluoro-5-phenyl-6,7-dihydro-5H-pyrrolo[1,2-b][1,2,4]triazol-2-yl]sulfonyl]cyclopropanecarbonitrile (32.4 mg, 32%) as a white solid. $^1$H NMR (400 MHz, CDCl$_3$) δ 7.52-7.40 (m, 2H), 7.38-7.25 (m, 3H), 6.16-6.00 (m, 1H), 5.67-5.59 (m, 1H), 3.78-3.64 (m, 1H), 3.08-2.96 (m, 1H), 2.20-2.09 (m, 2H), 1.95-1.80 (m, 2H). LC-MS R$_T$=0.842 min, m/z=354.9 [M+Na]$^+$.

Example 158, Example 159 and Example 160: Method 20

(5S,7S)-7-fluoro-2-(1-fluoroethylsulfonyl)-5-phenyl-6,7-dihydro-5H-pyrrolo[1,2-b][1,2,4]triazole and (5S,7S)-7-fluoro-5-phenyl-2-[(1S)-1-fluoroethyl]sulfonyl-6,7-dihydro-5H-pyrrolo[1,2-b][1,2,4]triazole and (5S,7S)-7-fluoro-5-phenyl-2-[(1R)-1-fluoroethyl]sulfonyl-6,7-dihydro-5H-pyrrolo[1,2-b][1,2,4]triazole

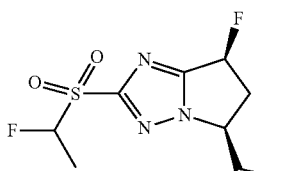

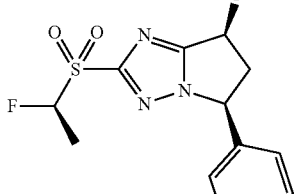

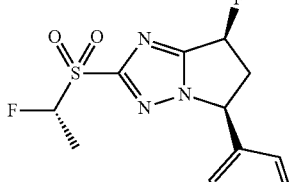

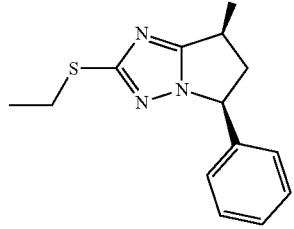

Step 1: (5S,7S)-2-ethylsulfanyl-7-fluoro-5-phenyl-6,7-dihydro-5H-pyrrolo[1,2-b][1,2,4]triazole

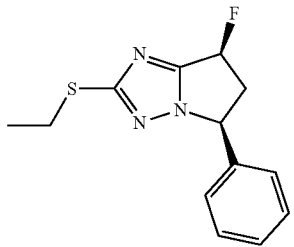 [SMILES: CCSc1nc2n(n1)[C@H](c1ccccc1)C[C@@H]2F]

To a solution of (5S,7S)-7-fluoro-5-phenyl-6,7-dihydro-5H-pyrrolo[1,2-b][1,2,4]triazole-2-thiol (100 mg, 0.43 mmol) in acetonitrile (10 mL) was added potassium carbonate (1.3 mL, 1.28 mmol) and iodoethane (133 mg, 0.85 mmol). The reaction was stirred at 20° C. for 1 h and diluted with water (10 mL). The mixture was extracted with ethyl acetate (3×20 mL). The combined organic layers were dried over sodium sulfate and concentrated under reduced pressure. The residue was purified by column chromatography (silica gel, 100-200 mesh, 0 to 30% ethyl acetate in petroleum ether) to afford (5S,7S)-2-ethylsulfanyl-7-fluoro-5-phenyl-6,7-dihydro-5H-pyrrolo[1,2-b][1,2,4]triazole (110 mg, 98%) as a yellow solid. LC-MS R$_T$=0.700 min, m/z=264.1 [M+H]$^+$.

Step 2: (5S,7S)-7-fluoro-2-(1-fluoroethylsulfanyl)-5-phenyl-6,7-dihydro-H-pyrrolo[1,2-b][1,2,4]triazole

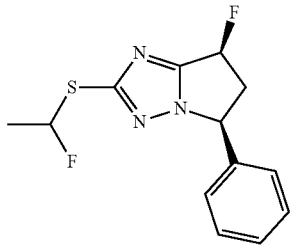 [SMILES: CC(F)Sc1nc2n(n1)[C@H](c1ccccc1)C[C@@H]2F]

To a solution of (5S,7S)-2-ethylsulfanyl-7-fluoro-5-phenyl-6,7-dihydro-5H-pyrrolo[1,2-b][1,2,4]triazole (110 mg, 0.42 mmol) in acetonitrile (8 mL) was added triethylamine (63 mg, 0.63 mmol) and 1-chloromethyl-4-fluoro-1,4-diazoniabicyclo[2.2.2]octanebis(tetrafluoroborate) (222 mg, 0.63 mmol). The reaction was stirred at 0° C. for 1 h and diluted with water (20 mL). The resulting mixture was extracted with ethyl acetate (3×20 mL). The combined organic layers were dried over sodium sulfate and concentrated under reduced pressure. The residue was purified by column chromatography (silica gel, 100-200 mesh, 0 to 30% ethyl acetate in petroleum ether) to afford (5S,7S)-7-fluoro-2-(1-fluoroethylsulfanyl)-5-phenyl-6,7-dihydro-5H-pyrrolo[1,2- b][1,2,4]triazole (80 mg, 68%) as a yellow solid. LC-MS R$_T$=0.696 min, m/z=282.1 [M+H]+.

Step 3: (5S,7S)-7-fluoro-2-(1-fluoroethylsulfonyl)-5-phenyl-6,7-dihydro-5H-pyrrolo[1,2-b][1,2,4]triazole and (5S,7S)-7-fluoro-5-phenyl-2-[(1S)-1-fluoroethyl]sulfonyl-6,7-dihydro-5H-pyrrolo[1,2-b][1,2,4]triazole and (5S,7S)-7-fluoro-5-phenyl-2-[(1R)-1-fluoroethyl]sulfonyl-6,7-dihydro-5H-pyrrolo[1,2-b][1,2,4]triazole A mixture of (5S,7S)-7-fluoro-2-(1-fluoroethylsulfanyl)-5-phenyl-6,7-dihydro-5H-pyrrolo[1,2-b][1,2,4]triazole (30 mg, 0.11 mmol) and 3-chloroperoxybenzoic acid (85%, 300 mg, 1.48 mmol) in dichloromethane (10 mL) was stirred at 40° C. for 16 h. The mixture was diluted with water (20 mL) and extracted with ethyl acetate (3×20 mL). The combined organic layers were washed with saturated aqueous ammonium chloride (20 mL), dried over sodium sulfate and concentrated under reduced pressure. The residue was purified by RP-HPLC (acetonitrile 30-60%/0.05% ammonia hydroxide in water) to afford (5S,7S)-7-fluoro-2-(1-fluoroethylsulfonyl)-5-phenyl-6,7-dihydro-5H-pyrrolo[1,2-b][1,2,4]triazole (17 mg, 46%) as a white solid. $^1$H NMR (400 MHz, CDCl$_3$) δ 7.43-7.40 (m, 3H), 7.27-7.23 (m, 2H), 6.15-5.98 (m, 1H), 5.74-5.56 (m, 2H), 3.76-3.66 (m, 1H), 3.07-2.96 (m, 1H), 1.88-1.80 (m, 3H). LC-MS R$_T$=1.692 min, m/z=314.1 [M+H]$^+$.

A batch of the racemic material was further separated by chiral SFC to give: (5S,7S)-7-fluoro-2-[(1S)-1-fluoroethyl]sulfonyl-5-phenyl-6,7-dihydro-5H-pyrrolo[1,2-b][1,2,4]triazole (Peak 1, retention time=3.814 min) (11.2 mg, 32%) as a white solid. $^1$H NMR (400 MHz, CDCl$_3$) δ 7.45-7.40 (m, 3H), 7.27-7.23 (m, 2H), 6.14-5.98 (m, 1H), 5.74-5.72 (m, 0.5H), 5.62-5.57 (m, 1.5H), 3.74-3.64 (m, 1H), 3.06-2.96 (m, 1H), 1.88-1.80 (m, 3H). LCMS R$_T$=1.705 min, m/z=314.1 [M+H]$^+$.

(5S,7S)-7-fluoro-2-[(1R)-1-fluoroethyl]sulfonyl-5-phenyl-6,7-dihydro-5H-pyrrolo[1,2-b][1,2,4]triazole (Peak 2, retention time=3.979 min) (9.4 mg, 27%) as a white solid $^1$H NMR (400 MHz, CDCl$_3$) δ 7.43-7.40 (m, 3H), 7.27-7.23 (m, 2H), 6.15-5.98 (m, 1H), 5.74-5.71 (m, 0.5H), 5.62-5.56 (m, 1.5H), 3.74-3.63 (m, 1H), 3.07-2.96 (m, 1H), 1.88-1.79 (m, 3H). LCMS R$_T$=1.704 min, m/z=314.1 [M+H]$^+$.

SFC condition: Column: ChiralPak OD_3_EtOH_DEA_5_40_25 mL_7 min; Mobile phase: A: CO$_2$ B: Ethanol (0.05% DEA); Gradient: from 5% to 40% of B in 5.5 min and hold 40% for 3 min, then 5% of B for 1.5 min; Flow rate: 2.5 mL/min; Column temperature: 40° C.

Example 165: Method 35

(5S,7S)-7-fluoro-2-(1-fluoro-1-methyl-ethyl)sulfonyl-5-phenyl-6,7-dihydro-5H-pyrrolo[1,2-b][1,2,4]triazole

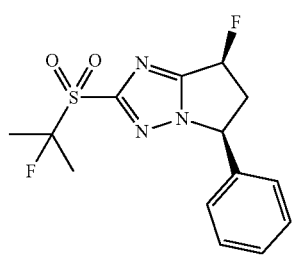 [SMILES: CC(C)(F)S(=O)(=O)c1nc2n(n1)[C@H](c1ccccc1)C[C@@H]2F]

To a solution of (5S,7S)-7-fluoro-2-(1-fluoroethylsulfonyl)-5-phenyl-6,7-dihydro-5H-pyrrolo[1,2-b][1,2,4]triazole (50 mg, 0.16 mmol) in tetrahydrofuran (9 mL) was added lithium bis(trimethylsilyl)amide (1.0 M in tetrahydrofuran, 0.4 mL, 0.4 mmol) and iodomethane (1.2 g, 8.44 mmol). The reaction was stirred at −78° C. for 1 h and quenched by addition of water (10 mL). The reaction mixture was extracted with ethyl acetate (3×10 mL). The combined organic layers were dried over sodium sulfate and concentrated under reduced pressure. The residue was purified by preparative TLC (40% ethyl acetate in petroleum ether, R$_f$=0.3) to afford (5S,7S)-7-fluoro-2-(1-fluoro-1-methylethyl)sulfonyl-5-phenyl-6,7-dihydro-5H-pyrrolo[1,2-b][1,2,4]triazole (3.1 mg, 6%) as a white solid. $^1$H NMR (400 MHz, CD$_3$OD) δ 7.45-7.40 (m, 3H), 7.28-7.26 (m, 2H), 6.24-6.21 (m, 0.5H), 6.09-6.07 (m, 0.5H), 5.72-5.69 (m, 1H), 3.82-3.73 (m, 1H), 2.91-2.81 (m, 1H), 1.87-1.69 (m, 6H). LCMS R$_T$=1.745 min, m/z=328.1 [M+H]$^+$.

Example 161

(5S,7S)-7-fluoro-5-phenyl-2-(propylsulfonyl)-6,7-dihydro-5H-pyrrolo[1,2-b][1,2,4]triazole

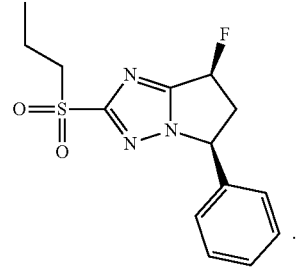 [SMILES: CCCS(=O)(=O)c1nc2n(n1)[C@H](c1ccccc1)C[C@@H]2F]

(5S,7S)-7-fluoro-5-phenyl-2-(propylsulfonyl)-6,7-dihydro-5H-pyrrolo[1,2-b][1,2,4]triazole was prepared according to method 26 starting from (5S,7S)-7-fluoro-5-phenyl-6,7-dihydro-5H-pyrrolo[1,2-b][1,2,4]triazole-2-thiol and 1-bromopropane. The final compound was purified by RP-HPLC (acetonitrile 39-69%/0.05% ammonia hydroxide) to give (5S,7S)-7-fluoro-5-phenyl-2-(propylsulfonyl)-6,7-dihydro-5H-pyrrolo[1,2-b][1,2,4]triazole (63.8 mg, 63%) as a white solid. $^1$H NMR (400 MHz, CDCl$_3$) δ 7.44-7.40 (m, 3H), 7.27-7.24 (m, 2H), 6.13-6.11 (m, 0.5H), 5.99-5.97 (m, 0.5H), 5.54-5.52 (m, 1H), 3.71-3.65 (m, 1H), 3.36-3.32 (m, 2H), 3.04-2.94 (m, 1H), 1.92-1.82 (m, 2H), 1.05 (t, J=7.2 Hz, 3H). LCMS R$_T$=0.847 min, m/z=309.9 [M+H]$^+$.

Example 162

(5S,7S)-7-fluoro-5-phenyl-2-[rac-(1S,2S)-2-methylcyclopropyl]sulfonyl-6,7-dihydro-5H-pyrrolo[1,2-b][1,2,4]triazole

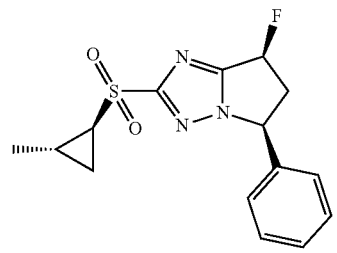 [SMILES: C[C@H]1C[C@@H]1S(=O)(=O)c1nc2n(n1)[C@H](c1ccccc1)C[C@@H]2F]

(5S,7S)-7-fluoro-5-phenyl-2-[rac-(1S,2S)-2-methylcyclopropyl]sulfonyl-6,7-dihydro-5H-pyrrolo[1,2-b][1,2,4]triazole was prepared according to method 18 starting from (5S,7S)-7-fluoro-5-phenyl-6,7-dihydro-5H-pyrrolo[1,2-b][1,2,4]triazole-2-thiol and trans-2-methylcyclopropyl]boronic acid. The final compound was purified by RP-HPLC (acetonitrile 36-66%/0.225% Formic acid in water) to give (5S,7S)-7-fluoro-5-phenyl-2-[rac-(1S,2S)-2-methylcyclopropyl]sulfonyl-6,7-dihydro-5H-pyrrolo[1,2-b][1,2,4]triazole (1.5 mg, 5%) as a white solid. $^1$H NMR (400 MHz, CDCl$_3$) δ 7.42-7.40 (m, 3H), 7.25-7.22 (m, 2H), 6.12-6.10 (m, 0.5H), 5.99-5.97 (m, 0.5H), 5.54-5.51 (m, 1H), 3.74-3.63 (m, 1H), 3.05-2.94 (m, 1H), 2.48-2.44 (m, 1H), 1.89-1.86 (m, 1H), 1.63-1.61 (m, 1H), 1.16 (t, J=5.6 Hz, 3H), 0.97-0.95 (m, 1H). LCMS R$_T$=0.689 min, m/z=322.1 [M+H]$^+$.

Example 163

(5S,7S)-7-fluoro-5-phenyl-2-[rac-(1S,2R)-2-(trifluoromethyl)cyclopropyl]sulfonyl-6,7-dihydro-5H-pyrrolo[1,2-b][1,2,4]triazole

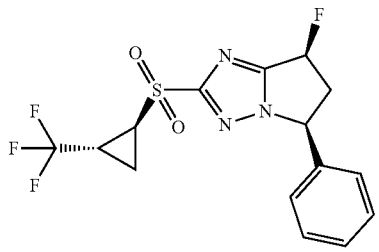 [SMILES: O=S(=O)(c1nc2n(n1)[C@H](c1ccccc1)C[C@@H]2F)[C@H]1C[C@@H]1C(F)(F)F]

(5S,7S)-7-fluoro-5-phenyl-2-[rac-(1S,2R)-2-(trifluoromethyl)cyclopropyl]sulfonyl-6,7-dihydro-5H-pyrrolo[1,2-b][1,2,4]triazole was prepared according to method 18 starting from (5S,7S)-7-fluoro-5-phenyl-6,7-dihydro-5H-pyrrolo[1,2-b][1,2,4]triazole-2-thiol and trans-2-(trifluoromethyl)cyclopropyl]boronic acid. The final compound was purified by preparative TLC (30% ethyl acetate in petroleum ether, R$_f$=0.4) to give (5S,7S)-7-fluoro-5-phenyl-2-[rac-(1S,2R)-2-(trifluoromethyl) cyclopropyl]sulfonyl-6,7-dihydro-5H-pyrrolo[1,2-b][1,2,4]triazole (11 mg, 25.1%) as a white solid. $^1$H NMR (400 MHz, CDCl$_3$) δ 7.42-7.40 (m, 3H), 7.27-7.23 (m, 2H), 6.14-6.12 (m, 0.5H), 6.00-5.98 (m, 0.5H), 5.57-5.53 (m, 1H), 3.72-3.66 (m, 1H), 3.13-2.96 (m, 2H), 2.57-2.51 (m, 1H), 1.92-1.88 (m, 1H), 1.60-1.55 (m, 1H). LCMS R$_T$=0.846 min, m/z=376.1 [M+H]$^+$.

Example 164: Method 7a (5S,7S)-7-fluoro-2-(((1R,3S)-3-fluorocyclobutyl)sulfonyl)-5-phenyl-6,7-dihydro-5H-pyrrolo[1,2-b][1,2,4]triazole

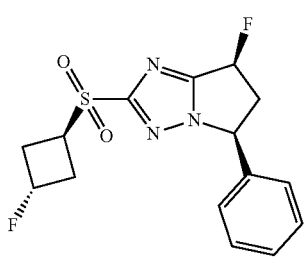 [SMILES: O=S(=O)(c1nc2n(n1)[C@H](c1ccccc1)C[C@@H]2F)[C@H]1C[C@H](F)C1]

Step 1: (1R,3S)-3-(((5S,7S)-7-fluoro-5-phenyl-6,7-dihydro-5H-pyrrolo[1,2-b][1,2,4]triazol-2-yl)thio)cyclobutanol

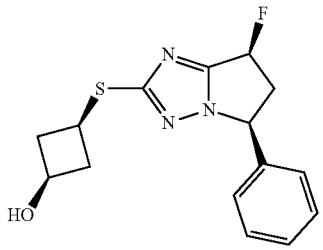 [SMILES: O[C@H]1C[C@@H](Sc2nc3n(n2)[C@H](c2ccccc2)C[C@@H]3F)C1]

To a mixture of 3-[[(5S,7S)-7-fluoro-5-phenyl-6,7-dihydro-5H-pyrrolo[1,2-b][1,2,4]triazol-2-yl]sulfanyl]cyclobutanone (300 mg, 0.99 mmol) in methanol (10 mL) was added sodium borohydride (112 mg, 2.97 mmol). The mixture was stirred at 20° C. for 1 h and concentrated under reduced pressure. The residue was diluted with water (50 mL) and extracted with ethyl acetate (3×50 mL). The combined organic layers were washed with brine (50 mL), dried over sodium sulfate and concentrated under reduced pressure to afford (1R,3S)-3-(((5S,7S)-7-fluoro-5-phenyl-6,7-dihydro-5H-pyrrolo[1,2-b][1,2,4]triazol-2-yl)thio)cyclobutanol (300 mg, 99%) as a yellow solid. LCMS R$_T$=0.616 min, m/z=306.1 [M+H]$^+$.

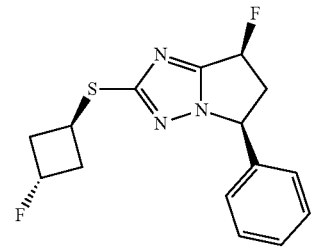 [SMILES: F[C@H]1C[C@@H](c2ccccc2)n2nc(S[C@H]3C[C@H](F)C3)nc21]

Step 2: (5S,7S)-7-fluoro-2-(((1R,3S)-3-fluorocyclobutyl)thio)-5-phenyl-6,7-dihydro-5H-pyrrolo[1,2-b][1,2,4]triazole To a cooled solution (−50° C.) of (1R,3S)-3-(((5S,7S)-7-fluoro-5-phenyl-6,7-dihydro-5H-pyrrolo[1,2-b][1,2,4]triazol-2-yl)thio)cyclobutanol (300 mg, 0.98 mmol) in toluene (10 mL) was added diethylaminosulfur trifluoride (633 mg, 3.93 mmol). The mixture was stirred at −50° C. for 1 h and quenched by addition of saturated aqueous sodium bicarbonate (50 mL). The resulting mixture was extracted with ethyl acetate (3×50 mL). The combined organic layers were dried over sodium sulfate and concentrated under reduced pressure to afford (5S,7S)-7-fluoro-2-(((1R,3S)-3-fluorocyclobutyl)thio)-5-phenyl-6,7-dihydro-5H-pyrrolo[1,2-b][1,2,4]triazole (150 mg, 50%) as a white solid. LCMS R$_T$=3.205 min, m/z=307.9 [M+H]$^+$.

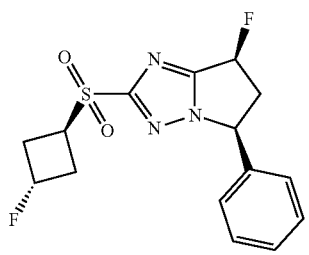 [SMILES: O=S(=O)(c1nc2n(n1)[C@H](c1ccccc1)C[C@@H]2F)[C@H]1C[C@H](F)C1]

Step 3: (5S,7S)-7-fluoro-2-(((1R,3S)-3-fluorocyclobutyl)sulfonyl)-5-phenyl-6,7-dihydro-5H-pyrrolo[1,2-b][1,2,4]triazole A mixture of ruthenium(III) chloride (10 mg, 0.05 mmol), sodium periodate (418 mg, 1.95 mmol) and (5S,7S)-7-fluoro-2-(((1R,3S)-3-fluorocyclobutyl)thio)-5-phenyl-6,7-dihydro-5H-pyrrolo[1,2-b][1,2,4]triazole (150 mg, 0.49 mmol) in acetonitrile (5 mL), water (5 mL) and ethyl acetate (5 mL) was stirred at 30° C. for 4 h. The mixture was diluted with water (10 mL) and extracted with ethyl acetate (3×10 mL). The combined organics were washed with brine, dried over sodium sulfate and concentrated under reduced pressure. The residue was purified by RP-HPLC (acetonitrile 40-70%/ammonia hydroxide in water) to afford (5S,7S)-7-fluoro-2-(((1R,3S)-3-fluorocyclobutyl)sulfonyl)-5-phenyl-6,7-dihydro-5H-pyrrolo[1,2-b][1,2,4]triazole (24 mg, 14%) as a white solid. $^1$H NMR (400 MHz, CDCl$_3$) δ 7.42-7.40 (m, 3H), 7.27-7.23 (m, 2H), 6.12-5.96 (m, 1H), 5.55-5.50 (m, 1H), 5.40-5.24 (m, 1H), 4.15-4.11 (m, 1H), 3.71-3.66 (m, 1H), 3.06-2.99 (m, 3H), 2.67-2.64 (m, 2H). LCMS R$_T$=0.679 min, m/z=340.1 [M+H]$^+$.

Example 166

(5S,7S)-7-fluoro-5-phenyl-2-tetrahydrofuran-3-ylsulfonyl-6,7-dihydro-5H-pyrrolo[1,2-b][1,2,4]triazole

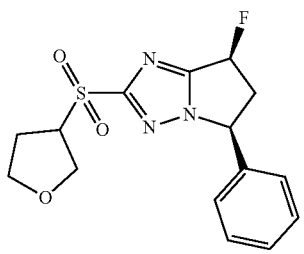 [SMILES: O=S(=O)(c1nc2n(n1)[C@H](c1ccccc1)C[C@@H]2F)C1CCOC1]

(5S,7S)-7-fluoro-5-phenyl-2-tetrahydrofuran-3-ylsulfonyl-6,7-dihydro-5H-pyrrolo[1,2-b][1,2,4]triazole was prepared according to method 26 starting from (5S,7S)-7-fluoro-5-phenyl-6,7-dihydro-5H-pyrrolo[1,2-b][1,2,4]triazole-2-thiol and 3-bromotetrahydrofuran. The final compound was purified by RP-HPLC (acetonitrile 26-56%/0.225% acetate acid in water) to give (5S,7S)-7-fluoro-5-phenyl-2-tetrahydrofuran-3-ylsulfonyl-6,7-dihydro-5H-pyrrolo[1,2-b][1,2,4]triazole (26.2 mg, 13%) as a white solid. $^1$H NMR (400 MHz, CDCl$_3$) δ 7.41-7.39 (m, 3H), 7.26-7.21 (m, 2H), 6.13-5.96 (m, 1H), 5.56-5.53 (m, 1H), 4.33-4.30 (m, 1H), 4.20-4.02 (m, 2H), 4.00-3.77 (m, 2H), 3.75-3.60 (m, 1H), 3.03-2.95 (m, 1H), 2.60-2.54 (m, 1H), 2.30-2.22 (m, 1H). LC-MS R$_T$=0.905 min, m/z=338.1 [M+H]$^+$.

Example 167: Method 16

(5S,7S)-2-((2,2-difluoro-1-methylcyclopropyl)sulfonyl)-7-fluoro-5-phenyl-6,7-dihydro-5H-pyrrolo[1,2-b][1,2,4]triazole

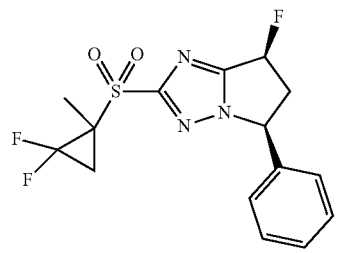 [SMILES: CC1(S(=O)(=O)c2nc3n(n2)[C@H](c2ccccc2)C[C@@H]3F)CC1(F)F]

Step 1: (5S,7S)-2-((2,2-difluoro-1-methylcyclopropyl)thio)-7-fluoro-5-phenyl-6,7-dihydro-5H-pyrrolo[1,2-b][1,2,4]triazole

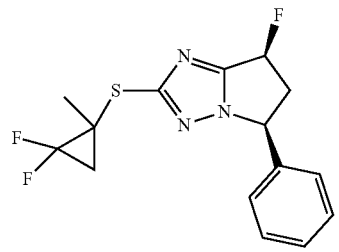 [SMILES: CC1(Sc2nc3n(n2)[C@H](c2ccccc2)C[C@@H]3F)CC1(F)F]

A mixture of (5S,7S)-7-fluoro-5-phenyl-6,7-dihydro-5H-pyrrolo[1,2-b][1,2,4]triazole-2-thiol (400 mg, 1.7 mmol), 2,2-difluoro-1-methyl-cyclopropanecarboxylic acid (694 mg, 5.1 mmol), silver nitrate (577 mg, 3.4 mmol) and ammonium persulfate (776 mg, 3.4 mmol) in acetonitrile (12 mL) and water (4 mL) was stirred at 80° C. for 3 h. The reaction was diluted with water (35 mL) and extracted with ethyl acetate (3×35 mL). The combined organic layers were washed with brine (2×35 mL), dried over sodium sulfate and concentrated under reduced pressure. The residue was first purified by column chromatography (silica gel, 100-200 mesh, 0 to 24% ethyl acetate in petroleum ether), then by preparative TLC (35% ethyl acetate in petroleum ether, R$_f$=0.4) to give (5S,7S)-2-(2,2-difluoro-1-methyl-cyclopropyl)sulfanyl-7-fluoro-5-phenyl-6,7-dihydro-5H-pyrrolo[1,2-b][1,2,4]triazole (18 mg, 3%) as a colorless oil. LC-MS RT=0.740 min, m/z=326.1 [M+H]$^+$.

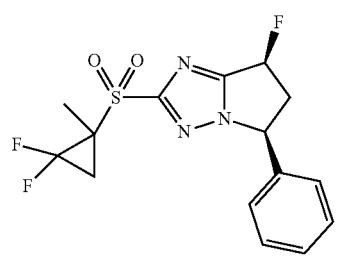 [SMILES: CC1(S(=O)(=O)c2nc3n(n2)[C@H](c2ccccc2)C[C@@H]3F)CC1(F)F]

Step 2: (5S,7S)-2-((2,2-difluoro-1-methylcyclopropyl)sulfonyl)-7-fluoro-5-phenyl-6,7-dihydro-5H-pyrrolo[1,2-b][1,2,4]triazole A mixture of ruthenium(III) chloride (0.8 mg), sodium periodate (33 mg, 0.15 mmol) and (5S,7S)-2-(2,2-difluoro-1-methyl-cyclopropyl)sulfanyl-7-fluoro-5-phenyl-6,7-dihydro-5H-pyrrolo[1,2-b][1,2,4]triazole (16 mg, 0.04 mmol) in acetonitrile (0.4 mL), water (0.4 mL) and ethyl acetate (0.4 mL) was stirred at 25° C. for 1 h and diluted with ethyl acetate (8 mL). The solution was washed with brine (2×8 mL), dried over sodium sulfate and concentrated under reduced pressure. The residue was purified by RP-HPLC (acetonitrile 45-75%/0.05% hydrochloric acid in water) to give (5S,7S)-2-(2,2-difluoro-1-methyl-cyclopropyl)sulfonyl-7-fluoro-5-phenyl-6,7-dihydro-5H-pyrrolo[1,2-b][1,2,4]triazole (4.8 mg, 34%) as a white solid. $^1$H NMR (400 MHz, CD$_3$OD) δ 7.45-7.40 (m, 3H), 7.28-7.25 (m, 2H), 6.22-6.06 (m, 1H), 5.77-5.65 (m, 1H), 3.83-3.75 (m, 1H), 2.90-2.83 (m, 1H), 2.62-2.57 (m, 1H), 1.96-1.93 (m, 1H), 1.61-1.57 (m, 3H). LC-MS R$_T$=0.708 min, m/z=358.1 [M+H]$^+$.

Example 168: Method 36

((1R,3S)-3-(((5S,7S)-7-fluoro-5-phenyl-6,7-dihydro-5H-pyrrolo[1,2-b][1,2,4]triazol-2-yl)sulfonyl)cyclobutyl)methanol

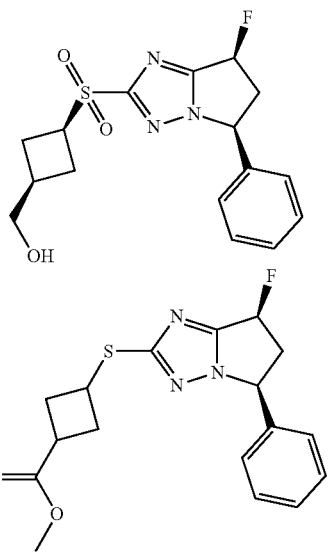

Step 1: methyl 3-[[(5S,7S)-7-fluoro-5-phenyl-6,7-dihydro-5H-pyrrolo[1,2-b][1,2,4]triazol-2-yl]thio]cyclobutanecarboxylate To a solution of (5S,7S)-7-fluoro-5-phenyl-6,7-dihydro-5H-pyrrolo[1,2-b][1,2,4]triazole-2-thiol (500 mg, 2.13 mmol) in N,N-dimethylformamide (10 mL) was added methyl 3-bromocyclobutanecarboxylate (820 mg, 4.25 mmol) and potassium carbonate (881 mg, 6.38 mmol). The reaction mixture was stirred at 25° C. for 2 h and poured into water (15 mL). The mixture was extracted with ethyl acetate (3×15 mL). The combined organic layers were dried over sodium sulfate and concentrated under reduced pressure. The residue was purified by column chromatography (silica gel, 100-200 mesh, 0 to 50% ethyl acetate in petroleum ether) to afford methyl 3-[[(5S,7S)-7-fluoro-5-phenyl-6,7-dihydro-5H-pyrrolo[1,2-b][1,2,4]triazol-2-yl]sulfanyl]cyclobutanecarboxylate (610 mg, 83%) as a colorless oil.

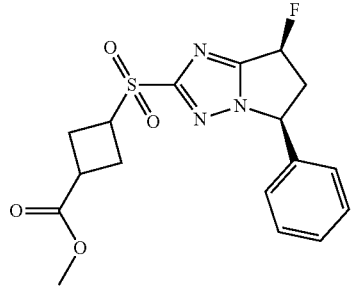 [SMILES: COC(=O)C1CC(S(=O)(=O)c2nc3n(n2)[C@H](c2ccccc2)C[C@@H]3F)C1]

Step 2: methyl 3-[[(5S,7S)-7-fluoro-5-phenyl-6,7-dihydro-5H-pyrrolo[1,2-b][1,2,4]triazol-2-yl]sulfonyl]cyclobutanecarboxylate To a solution of methyl 3-[[(5S,7S)-7-fluoro-5-phenyl-6,7-dihydro-5H-pyrrolo[1,2-b][1,2,4]triazol-2-yl]sulfanyl]cyclobutanecarboxylate (590 mg, 1.70 mmol) in dichloromethane (20 mL) was added 3-chloroperoxybenzoic acid (85%, 1700 mg, 8.49 mmol). The mixture was stirred at 25° C. for 2 h and quenched by addition of saturated aqueous sodium carbonate (20 mL). The resulting mixture was extracted with dichloromethane (3×20 mL). The combined organic layers were dried over sodium sulfate and concentrated under reduced pressure. The residue was purified by column chromatography (silica gel, 100-200 mesh, 0 to 40% ethyl acetate in petroleum ether) to give methyl 3-[[(5S,7S)-7-fluoro-5-phenyl-6,7-dihydro-5H-pyrrolo[1,2-b][1,2,4]triazol-2-yl]sulfonyl]cyclobutanecarboxylate (540 mg, 84%) as a white solid.

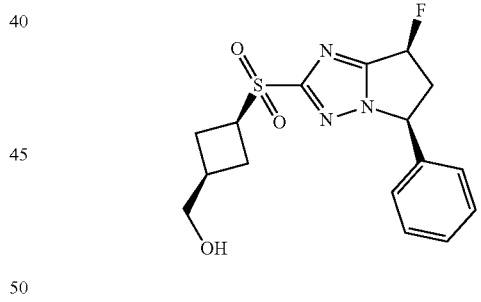

Step 3: ((1R,3S)-3-(((5S,7S)-7-fluoro-5-phenyl-6,7-dihydro-5H-pyrrolo[1,2-b][1,2,4]triazol-2-yl)sulfonyl)cyclobutyl)methanol To a solution of methyl 3-[[(5S,7S)-7-fluoro-5-phenyl-6,7-dihydro-5H-pyrrolo[1,2-b][1,2,4]triazol-2-yl]sulfonyl]cyclobutanecarboxylate (470 mg, 1.24 mmol) in tetrahydrofuran (10 mL) was added lithium borohydride (54 mg, 2.48 mmol) at 25° C. The mixture was stirred at 25° C. for 2 h and quenched by addition of water (20 mL). The resulting mixture was extracted with ethyl acetate (3×20 mL). The combined organic layers were dried over sodium sulfate and concentrated under reduced pressure. The residue was first purified by column chromatography (silica gel, 100-200 mesh, 0 to 80% ethyl acetate in petroleum ether), then by chiral SFC to give ((1R,3S)-3-(((5S,7S)-7-fluoro-5-phenyl-6,7-dihydro-5H-pyrrolo[1,2-b][1,2,4]triazol-2-yl)sulfonyl)

cyclobutyl)methanol (LHS stereochemistry arbitrarily assigned) (150 mg, 38%) as a colorless oil. $^1$H NMR (400 MHz, CDCl$_3$) δ 7.41-7.38 (m, 3H), 7.26-7.21 (m, 2H), 6.11-5.95 (m, 1H), 5.53-5.49 (m, 1H), 4.10-4.05 (m, 1H), 3.70-3.61 (m, 3H), 2.99-2.95 (m, 1H), 2.60-2.56 (m, 1H), 2.50-2.34 (m, 4H). LC-MS R$_T$=0.862 min, m/z=352.1 [M+H]$^+$.

SFC condition: Column: ChiralPak AD-3 150×4.6 mm I.D., 3 um Mobile phase: A: C02 B: Ethanol (0.05% DEA), Gradient: from 5% to 40% of B in 5.5 min, then 5% of B for 1.5 min, Flow rate: 2.5 mL/min, Column temp.: 40° C.

Example 169

((1R,3S)-3-(((5S,7S)-7-fluoro-5-phenyl-6,7-dihydro-5H-pyrrolo[1,2-b][1,2,4]triazol-2-yl)sulfonyl)cyclobutyl)methanol

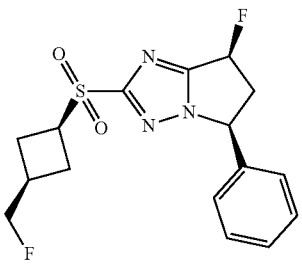 [SMILES: O=S(=O)(c1nc2n(n1)[C@H](c1ccccc1)C[C@@H]2F)[C@H]1C[C@@H](CF)C1]

To a solution of ((1R,3S)-3-(((5S,7S)-7-fluoro-5-phenyl-6,7-dihydro-5H-pyrrolo[1,2-b][1,2,4]triazol-2-yl)sulfonyl) cyclobutyl)methanol (129 mg, 0.28 mmol) in toluene (8 mL) was added diethylaminosulfur trifluoride (0.15 mL, 1.14 mmol) at 0° C. The mixture was stirred at 0° C. for 1 h and quenched by addition of saturated sodium bicarbonate (20 mL). The resulting mixture was extracted with ethyl acetate (3×20 mL). The combined organic layers were dried over sodium sulfate and concentrated under reduced pressure. The resulting residue was purified by RP-HPLC (acetonitrile 42-72%/0.225% formic acid in water) to afford ((1R,3S)-3-(((5S,7S)-7-fluoro-5-phenyl-6,7-dihydro-5H-pyrrolo[1,2-b][1,2,4]triazol-2-yl)sulfonyl)cyclobutyl)methanol (9.9 mg, 10%) as a white solid. $^1$H NMR (400 MHz, CDCl$_3$) δ 7.40-7.38 (m, 3H), 7.26-7.21 (m, 2H), 6.12-5.95 (m, 1H), 5.55-5.50 (m, 1H), 5.43-4.29 (m, 2H), 4.15-4.06 (m, 1H), 3.70-3.64 (m, 1H), 3.01-2.91 (m, 1H), 2.75-2.65 (m, 1H), 2.57-2.47 (m, 2H), 2.46-2.36 (m, 2H). LC-MS R$_T$=0.976 min, m/z=354.1 [M+H]$^+$.

Example 170: Method 23

(5S,7S)-7-fluoro-5-phenyl-2-spiro[2.2]pentan-2-ylsulfonyl-6,7-dihydro-5H-pyrrolo[1,2-b][1,2,4]triazole

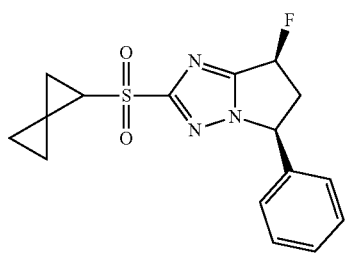 [SMILES: O=S(=O)(c1nc2n(n1)[C@H](c1ccccc1)C[C@@H]2F)C1CC12CC2]

Step 1: ethyl 1-(methylsulfonyloxymethyl)cyclopropanecarboxylate

To a solution of ethyl 1-(hydroxymethyl)cyclopropane-1-carboxylate (5.0 g, 34.7 mmol) in dichloromethane (40 mL) and triethylamine (10.5 g, 104 mmol) was added methanesulfonyl chloride (3.66 mL, 47 mmol). The mixture was stirred at 0° C. for 2 h and diluted with dichloromethane (50 mL). The solution was then washed with citric acid (2×40 mL), brine (15 mL), dried over sodium sulfate and concentrated under reduced pressure. The residue was purified by column chromatography (silica gel, 100-200 mesh, 0 to 20% ethyl acetate in petroleum ether) to give ethyl 1-(methylsulfonyloxymethyl)cyclopropanecarboxylate (3.0 g, 39%) as a white solid. $^1$H NMR (400 MHz, CDCl$_3$) δ 4.34-4.30 (m, 2H), 4.20-4.13 (m, 2H), 3.08 (s, 3H), 1.45-1.41 (m, 2H), 1.29-1.24 (m, 3H), 1.07-1.03 (m, 2H).

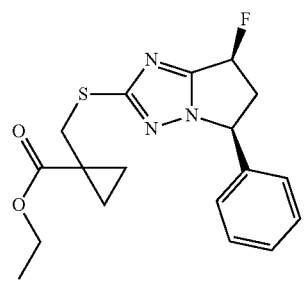 [SMILES: CCOC(=O)C1(CSc2nc3n(n2)[C@H](c2ccccc2)C[C@@H]3F)CC1]

Step 2: ethyl 1-[[(5S,7S)-7-fluoro-5-phenyl-6,7-dihydro-5H-pyrrolo[1,2-b][1,2,4]triazol-2-yl]sulfanylmethyl]cyclopropanecarboxylate To a solution of (5S,7S)-7-fluoro-5-phenyl-6,7-dihydro-5H-pyrrolo[1,2-b][1,2,4]triazole-2-thiol (1.0 g, 4.3 mmol) and 1-(methylsulfonyloxymethyl)cyclopropane carboxylate (945 mg, 4.25 mmol) in N,N-dimethylformamide (40 mL) was added sodium hydride (60%, 450 mg, 11.2 mmol). After addition, the mixture was stirred at 0° C. for 4 h and quenched by addition of saturated aqueous ammonium chloride (40 mL). The resulting solution was extracted with ethyl acetate (2×40 mL). The combined organic layers were washed with water (20 mL), dried over sodium sulfate and concentrated under reduced pressure. The residue was purified by column chromatography (silica gel, 100-200 mesh, 0 to 50% ethyl acetate in petroleum ether) to give ethyl 1-[[(5S,7S)-7-fluoro-5-phenyl-6,7-dihydro-5H-pyrrolo[1,2-b][1,2,4]triazol-2-yl]sulfanylmethyl]cyclopropanecarboxylate (1.2 g, 79%) as a yellow solid.

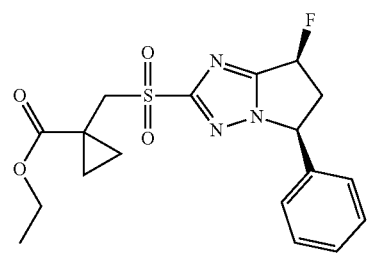 [SMILES: CCOC(=O)C1(CS(=O)(=O)c2nc3n(n2)[C@H](c2ccccc2)C[C@@H]3F)CC1]

Step 3: ethyl 1-[[(5S,7S)-7-fluoro-5-phenyl-6,7-dihydro-5H-pyrrolo[1,2-b][1,2,4]triazol-2-yl]sulfonylmethyl]cyclopropanecarboxylate To a solution of ethyl 1-[[(5S,7S)-7-fluoro-5-phenyl-6,7-dihydro-5H-pyrrolo[1,2-b][1,2,4]triazol-2-yl]sulfanylmethyl]cyclopropanecarboxylate (1.0 g, 2.77 mmol) in dichloromethane (20 mL) was added 3-chloroperoxybenzoic acid (85%, 1.7 g, 8.3 mmol). The mixture was stirred at 25° C. for 2 h and quenched by addition of saturated aqueous sodium bicarbonate (20 mL). The resulting mixture was extracted with ethyl acetate (3×30 mL). The combined the organics were washed with brine (30 mL), dried over sodium sulfate and concentrated under reduced pressure. The residue was purified by column chromatography (silica gel, 100-200 mesh, 0 to 100% ethyl acetate in petroleum ether) to give ethyl 1-[(5S,7S)-7-fluoro-5-phenyl-6,7-dihydro-5H-pyrrolo[1,2-b][1,2,4]triazol-2-yl]sulfonylmethyl]cyclopropanecarboxylate (1.0 g, 92%) as a yellow oil. LCMS $R_T$=1.063 min, m/z=394 [M+H]$^+$.

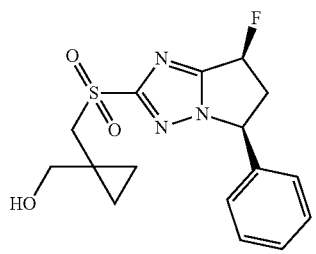 [SMILES: O=S(=O)(CC1(CO)CC1)c1nc2n(n1)[C@H](c1ccccc1)C[C@@H]2F]

Step 4: [1-[[(5S,7S)-7-fluoro-5-phenyl-6,7-dihydro-5H-pyrrolo[1,2-b][1,2,4]triazol-2-yl]sulfonylmethyl]cyclopropyl]methanol To a solution of ethyl 1-[[(5S,7S)-7-fluoro-5-phenyl-6,7-dihydro-5H-pyrrolo[1,2-b][1,2,4]triazol-2-yl]sulfonylmethyl]cyclopropanecarboxylate (1.0 g, 2.54 mmol) in dichloromethane (20 mL) was added diisobutylaluminum hydride (1.0 M in dichloromethane, 12.7 mL, 12.7 mmol) under nitrogen atmosphere. The mixture was stirred at 20° C. for 16 h and quenched by slow addition of sodium sulfate decahydrate (1.0 g). The precipitate was filtered and the filtrate was concentrated under reduced pressure to give crude [1-[[(5S,7S)-7-fluoro-5-phenyl-6,7-dihydro-5H-pyrrolo[1,2-b][1,2,4]triazol-2-yl]sulfonylmethyl]cyclopropyl]methanol (740 mg, 83%) as a yellow oil. LCMS $R_T$=0.886 min, m/z=352.2 [M+H]$^+$.

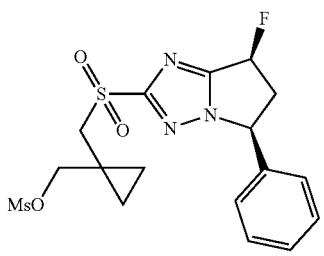 [SMILES: CS(=O)(=O)OCC1(CS(=O)(=O)c2nc3n(n2)[C@H](c2ccccc2)C[C@@H]3F)CC1]

Step 5: [1-[[(5S,7S)-7-fluoro-5-phenyl-6,7-dihydro-5H-pyrrolo[1,2-b][1,2,4]triazol-2-yl]sulfonylmethyl]cyclopropyl]methyl methanesulfonate To a solution of [1-[[(5S,7S)-7-fluoro-5-phenyl-6,7-dihydro-5H-pyrrolo[1,2-b][1,2,4]triazol-2-yl]sulfonylmethyl]cyclopropyl]methanol (740 mg, 2.11 mmol) and triethylamine (1.2 g, 11.86 mmol) in dichloromethane (20 mL) was added methanesulfonyl chloride (840 mg, 7.33 mmol). The mixture was stirred at 0° C. for 2 h and diluted with dichloromethane (50 mL). The solution was washed with water (2×30 mL), dried over sodium sulfate and concentrated under reduced pressure. The residue was purified by column chromatography (silica gel, 100-200 mesh, 0 to 100% ethyl acetate in petroleum ether) to give [1-[[(5S,7S)-7-fluoro-5-phenyl-6,7-dihydro-5H-pyrrolo[1,2-b][1,2,4]triazol-2-yl]sulfonylmethyl]cyclopropyl]methyl methanesulfonate (450 mg, 50%) as a white solid.

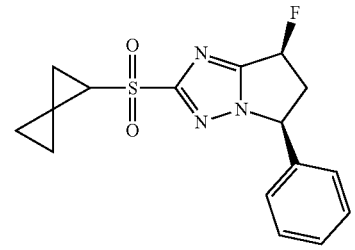 [SMILES: O=S(=O)(c1nc2n(n1)[C@H](c1ccccc1)C[C@@H]2F)C1CC12CC2]

Step 6: (5S,7S)-7-fluoro-5-phenyl-2-spiro[2.2]pentan-2-ylsulfonyl-6,7-dihydro-5H-pyrrolo[1,2-b][1,2,4]triazole To a solution of [1-[[(5S,7S)-7-fluoro-5-phenyl-6,7-dihydro-5H-pyrrolo[1,2-b][1,2,4]triazol-2-yl]sulfonylmethyl]cyclopropyl]methyl methanesulfonate (150 mg, 0.35 mmol) in tetrahydrofuran (8 mL) was added lithium bis(trimethylsilyl)amide (1.0 M in tetrahydrofuran, 1.05 mL, 1.05 mmol) at −70° C. under nitrogen protection. The mixture was stirred at −70° C. for 2 h and quenched by addition of saturated aqueous ammonium chloride (20 mL). The resulting mixture was extracted with ethyl acetate (2×20 mL). The combined organic layers were washed with water (2×10 mL), brine (10 mL), dried over sodium sulfate and concentrated under reduced pressure. The residue was purified by RP-HPLC (acetonitrile 25-60%/0.05% ammonia hydroxide in water) to afford (5S,7S)-7-fluoro-5-phenyl-2-spiro[2.2]pentan-2-ylsulfonyl-6,7-dihydro-5H-pyrrolo[1,2-b][1,2,4]triazole (7.3 mg, 6%) as a white solid. 1H NMR (400 MHz, CDCl$_3$) δ 7.43-7.40 (m, 3H), 7.27-7.22 (m, 2H), 6.12-5.95 (m, 1H), 5.53-5.50 (m, 1H), 3.75-3.67 (m, 1H), 3.09-2.98 (m, 2H), 1.97-1.94 (m, 1H), 1.61-1.57 (m, 1H), 1.28-1.24 (m, 1H), 1.18-1.12 (m, 1H), 0.98-0.85 (m, 2H). LCMS $R_T$=1.768 min, m/z=334.1[M+H]$^+$.

Example 171 and Example 172

(5S,7S)-7-fluoro-5-phenyl-2-[(1R)-2,2-difluorocyclobutyl]sulfonyl-6,7-dihydro-5H-pyrrolo[1,2-b][1,2,4]triazole and (5S,7S)-7-fluoro-5-phenyl-2-[(1S)-2,2-difluorocyclobutyl]sulfonyl-6,7-dihydro-5H-pyrrolo[1,2-b][1,2,4]triazole

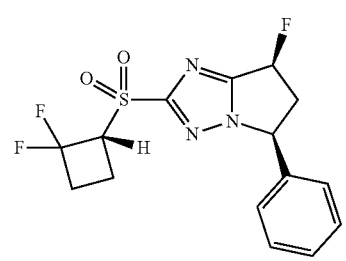

179

-continued

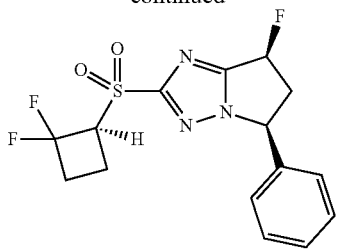

(5S,7S)-7-fluoro-5-phenyl-2-[(1R)-2,2-difluorocyclobutyl]sulfonyl-6,7-dihydro-5H-pyrrolo[1,2-b][1,2,4]triazole and (5S,7S)-7-fluoro-5-phenyl-2-[(1S)-2,2-difluorocyclobutyl]sulfonyl-6,7-dihydro-5H-pyrrolo[1,2-b][1,2,4]triazole were prepared according to method 20 starting from 2-bromocyclobutanone. The final compound was purified by chiral SFC to give: (5S,7S)-7-fluoro-5-phenyl-2-[(1R)-2,2-difluorocyclobutyl]sulfonyl-6,7-dihydro-5H-pyrrolo[1,2-b][1,2,4]triazole (Peak 2, retention time=4.129 min) (12.2 mg, 22%, 68% ee) as a yellow solid. ¹H NMR (400 MHz, CDCl₃) δ 7.42-7.38 (m, 3H), 7.26-7.20 (m, 2H), 6.12-5.96 (m, 1H), 5.55-5.50 (m, 1H), 4.62-4.56 (m, 1H), 3.71-3.62 (m, 1H), 2.99-2.90 (m, 1H), 2.88-2.77 (m, 1H), 2.57-2.50 (m, 2H), 2.30-2.22 (m, 1H). LC-MS RT=0.918 min, m/z=358.0 [M+H]⁺.

(5S,7S)-7-fluoro-5-phenyl-2-[(1S)-2,2-difluorocyclobutyl]sulfonyl-6,7-dihydro-5H-pyrrolo[1,2-b][1,2,4]triazole (Peak 1, retention time=3.512 min) (8.5 mg, 15%, 63% ee) as a white solid. ¹H NMR (400 MHz, CDCl₃) δ 7.41-7.38 (m, 3H), 7.26-7.20 (m, 2H), 6.13-5.96 (m, 1H), 5.56-5.50 (m, 1H), 4.64-4.56 (m, 1H), 3.73-3.64 (m, 1H), 3.03-2.93 (m, 1H), 2.88-2.78 (m, 1H), 2.70-2.55 (m, 2H), 2.30-2.27 (m, 1H). LC-MS RT=0.915 min, m/z=357.9 [M+H]⁺.

SFC condition (prep): Column: AD-H (250 mm×30 mm, 5 um); Mobile phase: A: CO₂ B: 0.1% NH₃H₂O MeOH; Gradient: hold 25% of B; Flow rate: 50 mL/min Column temperature: 40° C.

Example 173 and Example 174: Method 1

(5S)-2-[(S)-difluoromethylsulfinyl]-5-(3,5-difluorophenyl)-6,7-dihydro-5H-pyrrolo[1,2-b][1,2,4]triazole and (5S)-2-[(R)-difluoromethylsulfinyl]-5-(3,5-difluorophenyl)-6,7-dihydro-5H-pyrrolo[1,2-b][1,2,4]triazole

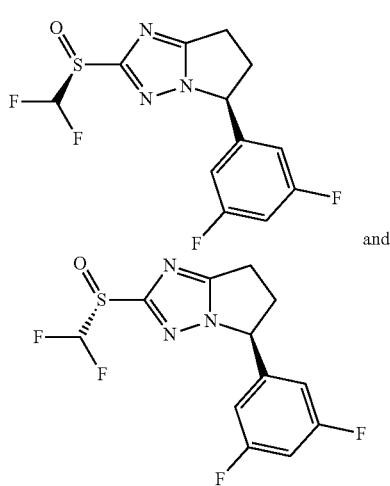

180

The diastereomeric mixture of 2-(difluoromethylsulfinyl)-5-(3,5-difluorophenyl)-6,7-dihydro-5H-pyrrolo[1,2-b][1,2,4]triazole was separated by chiral SFC. Analytical data for arbitrarily assigned:

(5S)-2-[(S)-difluoromethylsulfinyl]-5-(3,5-difluorophenyl)-6,7-dihydro-5H-pyrrolo[1,2-b][1,2,4]triazole: (Peak 2, SFC analytical retention time=0.73 min, Whelk 0-1 (S,S), isocratic 15% MeOH+0.1% NH₄OH, 2.5 min method) (5.5 mg, 1%) as a white solid. 1H NMR (400 MHz, DMSO-d6) δ 7.53-7.19 (m, 2H), 7.15-7.04 (m, 2H), 5.72 (dd, J=8.2, 6.3 Hz, 1H), 3.27-3.12 (m, 2H), 3.07 (ddd, J=16.1, 9.7, 6.1 Hz, 1H), 2.70-2.52 (m, 1H).

LC-MS RT=4.30 min, m/z=320.0 (M+H)+.

(5S)-2-[(R)-difluoromethylsulfinyl]-5-(3,5-difluorophenyl)-6,7-dihydro-5H-pyrrolo[1,2-b][1,2,4]triazole: (Peak 4, SFC analytical retention time=1.13 min, Whelk 0-1 (S,S), isocratic 15% MeOH+0.1% NH₄OH, 2.5 min method) (8.7 mg, 2%) as a white solid. 1H NMR (400 MHz, DMSO-d6) δ 7.52-7.20 (m, 2H), 7.17-7.04 (m, 2H), 5.72 (dd, J=8.2, 6.3 Hz, 1H), 3.29-3.14 (m, 2H), 3.13-3.02 (m, 1H), 2.70-2.57 (m, 1H). LC-MS RT=4.26 min, m/z=320.0 (M+H)+.

SFC condition (prep): Whelk 0-1 (S,S) 250×21.2 mm, 5 um, Mobile phase: A: CO2 B: 0.1% ammonium hydroxide in methanol, Isocratic 18% B, Flow rate: 80 mL/min, column temp 30° C.

Example 175: Method 38

2-(Difluoromethylsulfonyl)-5-(3,5-difluorophenyl)-6,7-dihydro-5H-pyrrolo[1,2-b][1,2,4]triazole

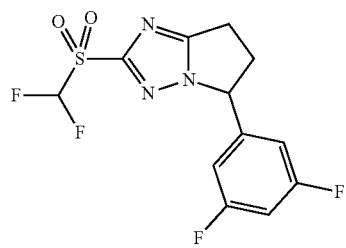 [SMILES: O=S(=O)(c1nc2n(n1)C(c1cc(F)cc(F)c1)CC2)C(F)F]

To a solution of 2-(difluoromethylsulfinyl)-5-(3,5-difluorophenyl)-6,7-dihydro-5H-pyrrolo[1,2-b][1,2,4]triazole (70 mg, 0.22 mmol, 1.0 equiv) in dichloromethane (5 mL) was added 3-chloroperoxybenzoic acid (393 mg, 1.75 mmol, 8.0 equiv). The mixture was stirred at RT for 16 h. After this time, the reaction was quenched with saturated aqueous sodium thiosulfate (25 mL) and saturated sodium bicarbonate (25 mL). The layers were separated, and the aqueous was extracted three more times with dichloromethane (3×50 mL). The combined organics were washed with water and brine, dried over sodium sulfate and concentrated. The residue was purified by reverse phase HPLC (Gemini-NX C18, 50×30 mm column; solvent A: 0.1% formic acid in water; solvent B: acetonitrile; gradient of 20-60% B) to afford 2-(difluoromethylsulfonyl)-5-(3,5-difluorophenyl)-6,7-dihydro-5H-pyrrolo[1,2-b][1,2,4]triazole (24 mg, 33%) as a white solid. 1H NMR (400 MHz, DMSO-d6) δ 7.59-7.24 (m, 2H), 7.22-7.10 (m, 2H), 5.82-5.70 (m, 1H), 3.26-3.01 (m, 3H), 2.71-2.60 (m, 1H). LC-MS RT=4.73 min, m/z=336.0 (M+H)+.

Example 176

2-(Difluoromethylsulfinyl)-5-(3,5-difluorophenyl)-6,7-dihydro-5H-pyrrolo[1,2-b][1,2,4]triazole

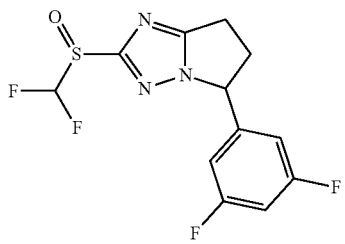 [SMILES: O=S(c1nc2n(n1)C(c1cc(F)cc(F)c1)CC2)C(F)F]

Prepared according to method 1 starting from ethyl 4-(3,5-difluorophenyl)-4-oxo-butanoate (Rieke Metals) (140 mg, 26% yield for the final step). 1H NMR (400 MHz, DMSO-d6) δ 7.52-7.19 (m, 2H), 7.18-7.00 (m, 2H), 5.77-5.67 (m, 1H), 3.28-3.14 (m, 2H), 3.07 (ddd, J=16.3, 9.8, 6.2 Hz, 1H), 2.71-2.57 (m, 1H). LC-MS RT=4.35 min, m/z=320.0 (M+H)+.

Example 177: Method 39

5-Phenyl-2-(2,2,2-trifluoroethylsulfinyl)-6,7-dihydro-5H-pyrrolo[1,2-b][1,2,4]triazole

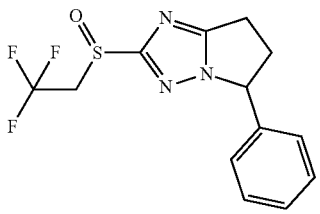 [SMILES: O=S(CC(F)(F)F)c1nc2n(n1)C(c1ccccc1)CC2]

Step 1: 5-phenyl-2-(2,2,2-trifluoroethylsulfanyl)-6,7-dihydro-5H-pyrrolo[1,22-b][1,2,4]triazole

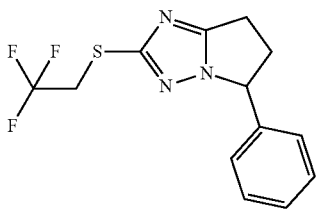 [SMILES: FC(F)(F)CSc1nc2n(n1)C(c1ccccc1)CC2]

To a solution of 5-phenyl-6,7-dihydro-5H-pyrrolo[1,2-b][1,2,4]triazole-2-thiol (800 mg, 3.68 mmol, 1.0 equiv) in N,N-dimethylformamide (10 mL) was added cesium carbonate (3600 mg, 11.0 mmol, 3.0 equiv) and 2,2,2-trifluoroethyl trifluoromethanesulfonate (2.19 mL, 3520 mg, 14.7 mmol, 4.0 equiv). The resulting heterogeneous mixture was stirred at RT for 16 h. After this time, the mixture was filtered through Celite and concentrated. The residue was purified by column chromatography (silica gel, 100-200 mesh, 0 to 10% methanol in dichloromethane) to afford 5-phenyl-2-(2,2,2-trifluoroethylsulfanyl)-6,7-dihydro-5H-pyrrolo[1,2-b][1,2,4]triazole (270 mg, 25%) as a yellow oil.

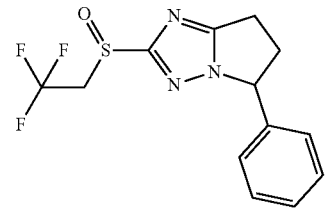 [SMILES: O=S(CC(F)(F)F)c1nc2n(n1)C(c1ccccc1)CC2]

Step 2: 5-phenyl-2-(2,2,2-trifluoroethylsulfinyl)-6,7-dihydro-5H-pyrrolo[1,2-b][1,2,4]triazole To a solution of 5-phenyl-2-(2,2,2-trifluoroethylsulfanyl)-6,7-dihydro-5H-pyrrolo[1,2-b][1,2,4]triazole (270 mg, 0.90 mmol, 1.0 equiv) in 1,2-dichloroethane (5 mL) was added 3-chloroperoxybenzoic acid (303 mg, 1.35 mmol, 1.5 equiv). The resulting mixture was stirred at RT for 16 h. After this time, the reaction was quenched with saturated aqueous sodium thiosulfate (50 mL) and saturated sodium bicarbonate (50 mL). The layers were separated, and the aqueous was extracted three more times with dichloromethane (3×50 mL). The combined organics were washed with water and brine, dried over sodium sulfate and concentrated. The residue was purified by reverse phase HPLC (Gemini-NX C18, 50×30 mm column; solvent A: 0.1% formic acid in water; solvent B: acetonitrile; gradient of 20-60% B) to afford 5-phenyl-2-(2,2,2-trifluoroethylsulfinyl)-6,7-dihydro-5H-pyrrolo[1,2-b][1,2,4]triazole (111 mg, 39%) as a white solid. 1H NMR (400 MHz, DMSO-d6) δ 7.46-7.33 (m, 3H), 7.31-7.20 (m, 2H), 5.66 (q, J=7.2 Hz, 1H), 4.52-4.38 (m, 2H), 3.29-2.98 (m, 3H), 2.69-2.56 (m, 1H). LC-MS RT=4.33 min, m/z=316.0 (M+H)+.

Example 178: Method 40

(5S,7S)-7-Fluoro-2-(1-fluorocyclopropyl)sulfonyl-5-phenyl-6,7-dihydro-5H-pyrrolo[1,2-b][1,2,4]triazole

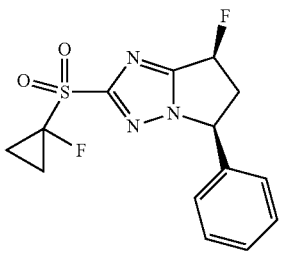 [SMILES: O=S(=O)(c1nc2n(n1)[C@H](c1ccccc1)C[C@@H]2F)C1(F)CC1]

To a solution of (5S,7S)-2-cyclopropylsulfonyl-7-fluoro-5-phenyl-6,7-dihydro-5H-pyrrolo[1,2-b][1,2,4]triazole (1000 mg, 3.25 mmol, 1.0 equiv) in tetrahydrofuran (15 mL) cooled to −78° C. was added a solution of 2,2,6,6-tetramethylpiperidinyl magnesium chloride-lithium chloride complex (Sigma-Aldrich, 1M in tetrahydrofuran/toluene, 3.9 mL, 1.2 equiv). The resulting mixture was stirred for 30 mins at −78° C., then to it was added N-fluorobenzenesulfonimide as a solid (1230 mg, 3.9 mmol, 1.2 equiv). The resulting mixture was stirred at −78° C. for 30 mins, then was quenched with 5% aqueous citric acid (100 mL). The mixture was extracted with isopropyl acetate (3×75 mL). The combined organics were washed with saturated aqueous sodium bicarbonate, water and brine, dried over sodium sulfate and concentrated. The residue was partially purified by column chromatography (silica gel, 100-200 mesh, 0 to 90% isopropyl acetate in heptane), then was further purified by reverse phase HPLC (Gemini-NX C18, 50×30 mm column; solvent A: 0.1% formic acid in water; solvent B: acetonitrile; gradient of 20-60% B) to afford (5S,7S)-7-fluoro-2-(1-fluorocyclopropyl)sulfonyl-5-phenyl-6,7-dihydro-5H-pyrrolo[1,2-b][1,2,4]triazole (27 mg, 3% yield) as a colorless residue. 1H NMR (400 MHz, DMSO-d6) δ 7.52-7.36 (m, 3H), 7.34-7.24 (m, 2H), 6.31 (ddd, J=56.1, 7.3, 2.2 Hz, 1H), 5.82 (ddd, J=8.4, 6.5, 3.4 Hz, 1H), 3.79 (dddd, J=25.0, 15.5, 8.5, 7.3 Hz, 1H), 2.77 (dddd, J=27.1, 15.1, 3.4, 2.1 Hz, 1H), 1.86-1.63 (m, 4H). LC-MS RT=4.89 min, m/z=326.0 (M+H)+.

mmol). The mixture was purged with nitrogen and stirred at 120° C. for 18 h. The resulting mixture was filtered. The filtrate was diluted water (20 mL) and extracted with ethyl acetate (3×10 mL). The combined organic layers were dried over sodium sulfate and concentrate under reduced pressure. The residue was first purified by RP-HPLC (acetonitrile 23-53%/0.05% ammonium bicarbonate in water), then by SFC to give 3-[(5S,7S)-2-(difluoromethylsulfonyl)-7-fluoro-6,7-dihydro-5H-pyrrolo[1,2-b][1,2,4]triazol-5-yl]benzonitrile (3.6 mg, 1.5%) as a white solid. $^1$H NMR (400 MHz, CDCl$_3$) δ 7.73 (d, J=8.0 Hz, 1H), 7.64-7.53 (m, 2H),

TABLE II

Chiral Separations Conditions (CPCT) - Instrument: PIC 200 Chiral - Solvent: A CO$_2$ - Detector Wavelength 215 nm - Column Dimension 150 × 21.2 mm 5 μm

| number | Amount/yield | Solvent B | % B Initial | % B Final | Sample Solvent | Column | Flow Rate | Run Time (min) |
|---|---|---|---|---|---|---|---|---|
| 179 | 7.1 mg/33% | 0.1% NH4OH in MeOH | 20 | 20 | MeOH | Chiralpak AD | 70 | 9 |
| 180 | 6.1 mg/26% | 0.1% NH4OH in MeOH | 20 | 20 | MeOH | Cellulose-4 | 70 | 9 |
| 181 | 6.8 mg/30% | 0.1% NH4OH in MeOH | 20 | 20 | MeOH | Cellulose-4 | 70 | 9 |
| 182 | 7 mg/32% | 0.1% NH4OH in MeOH | 20 | 20 | MeOH | Chiralpak AD | 70 | 9 |
| 183 | 1.7 mg/12% | 0.1% NH4OH in MeOH | 20 | 20 | MeOH/ACN | Whelko-01 | 70 | 30 |
| 184 | 2.9 mg/26% | 0.1% NH4OH in MeOH | 25 | 25 | MeOH | Chiralpak AD | 70 | 40 |
| 185 | 1.9 mg/13% | 0.1% NH4OH in MeOH | 20 | 20 | MeOH/ACN | Whelko-01 | 70 | 30 |
| 186 | 2.9 mg/26% | 0.1% NH4OH in MeOH | 25 | 25 | MeOH | Chiralpak AD | 70 | 40 |
| 187 | 4.7 mg/25% | 0.1% NH4OH in MeOH | 40 | 40 | MeOH/ACN | Chiralcel OX | 70 | 46 |
| 188 | 4 mg/26% | 0.1% NH4OH in MeOH | 40 | 40 | MeOH/ACN | Chiralcel OX | 70 | 31 |
| 189 | 5.4 mg/28% | 0.1% NH4OH in MeOH | 40 | 40 | MeOH/ACN | Chiralcel OX | 70 | 46 |
| 190 | 2 mg/13% | 0.1% NH4OH in MeOH | 40 | 40 | MeOH/ACN | Chiralcel OX | 70 | 31 |
| 191 | 8.8 mg/34% | 0.1% NH4OH in MeOH | 35 | 35 | MeOH | Chiralpak IG | 70 | 24 |

Example 192: Method 41

3-[(5S,7S)-2-(difluoromethylsulfonyl)-7-fluoro-6,7-dihydro-5H-pyrrolo[1,2-b][1,2,4]triazol-5-yl]benzonitrile

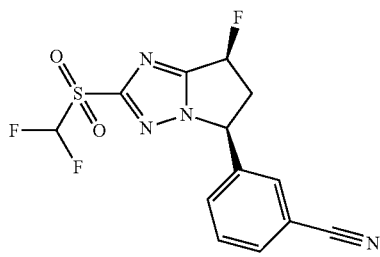 [SMILES: N#Cc1cccc([C@@H]2C[C@H](F)c3nc(S(=O)(=O)C(F)F)nn32)c1]

To a solution of (5S,7S)-5-(3-chlorophenyl)-2-(difluoromethylsulfonyl)-7-fluoro-6,7-dihydro-5H-pyrrolo[1,2-b][1,2,4]triazole (250 mg, 0.71 mmol, made as in method 16), tris(dibenzylideneacetone)dipalladium(0) (130 mg, 0.14 mmol) and 1,1-bis(diphenylphosphino)ferrocene (158 mg, 0.28 mmol) in N,N-dimethylacetamide (12 mL) was added with zinc (5 mg, 0.09 mmol) and zinc cyanide (150 mg, 1.28

7.47 (d, J=8.0 Hz, 1H), 6.43 (t, J=53.2 Hz, 1H), 6.21-6.02 (m, 1H), 5.66-5.62 (m, 1H), 3.84-3.67 (m, 1H), 3.10-2.96 (m, 1H). LCMS R$_T$=1.058 min, m/z=343.1 [M+H]$^+$.

SFC condition: Column: Chiralcel OJ-H (150*4.6 mm, 5 um) Mobile phase: A: CO$_2$ B: Ethanol (0.05% DEA) Gradient: from 5% to 40% of B in 5.5 min, then 5% B for 1.5 min, Flow rate: 2.5 mL/min Column temp. 40° C.

Example 226: Method 42

(5S,7S)-7-fluoro-2-trans-(3-fluorocyclobutyl)sulfonyl-5-(3-fluorophenyl)-6,7-dihydro-5H-pyrrolo[1,2-b][1,2,4]triazole

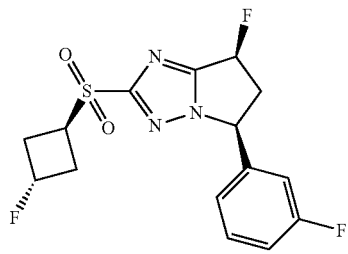

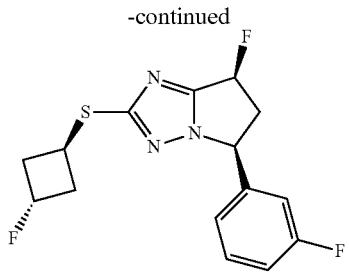

To a cooled (−30° C.) solution of cis-3-[[(5S,7S)-7-fluoro-5-(3-fluorophenyl)-6,7-dihydro-5H-pyrrolo[1,2-b][1,2,4]triazol-2-yl]sulfanyl]cyclobutanol (480 mg, 1.48 mmol) in toluene (12 mL) was added diethylaminosulfur trifluoride (0.78 mL, 5.94 mmol) over 20 min under nitrogen atmosphere. After addition, the mixture was stirred at 0° C. for 1 h, diluted with ethyl acetate (30 mL) and poured into saturated aqueous sodium bicarbonate (20 mL). The mixture was extracted with ethyl acetate (2×20 mL). The combined organic layers were dried over sodium sulfate and concentrated under reduced pressure. The residue was purified by column chromatography (silica gel, 100-200 mesh, 0-20% ethyl acetate in petroleum ether) to afford (5S,7S)-7-fluoro-2-trans-(3-fluorocyclobutyl)sulfanyl-5-(3-fluorophenyl)-6,7-dihydro-5H-pyrrolo[1,2-b][1,2,4]triazole (170 mg, 35%) as a brown solid. LCMS $R_T$=0.976 min, m/z=325.9 [M+H]$^+$.

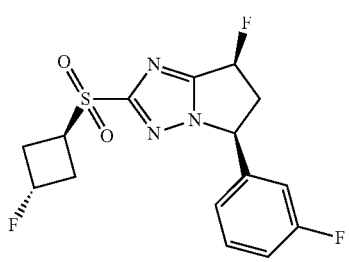 [SMILES: O=S(=O)(c1nc2n(n1)[C@H](c1cccc(F)c1)C[C@@H]2F)[C@H]1C[C@H](F)C1]

To a mixture of (5S,7S)-7-fluoro-2-trans-(3-fluorocyclobutyl)sulfanyl-5-(3-fluorophenyl)-6,7-dihydro-5H-pyrrolo[1,2-b][1,2,4]triazole (150 mg, 0.46 mmol), ruthenium (iii) chloride (10 mg, 0.05 mmol) and sodium periodate (395 mg, 1.84 mmol) in acetonitrile (3 mL), water (3 mL) and ethyl acetate (3 mL) was stirred at 30° C. for 1 h and filtered. The filtrate was diluted with water (10 mL) and extracted with ethyl acetate (3×10 mL). The combined organic layers were dried over sodium sulfate and concentrated under reduced pressure. The residue was purified by RP-HPLC (acetonitrile 42-72%/0.05% ammonia hydroxide in water) to afford (5S,7S)-7-fluoro-2-trans-(3-fluorocyclobutyl)sulfonyl-5-(3-fluorophenyl)-6,7-dihydro-5H-pyrrolo[1,2-b][1,2,4]triazole (92.0 mg, 91%) as a white solid. $^1$H NMR (400 MHz, CDCl$_3$) δ 7.45-7.39 (m, 1H), 7.15-7.10 (m, 1H), 7.09-7.03 (m, 1H), 7.02-6.94 (m, 1H), 6.15-5.92 (m, 1H), 5.56-5.49 (m, 1H), 5.44-5.19 (m, 1H), 4.18-4.07 (m, 1H), 3.78-3.57 (m, 1H), 3.11-2.96 (m, 3H), 2.76-2.61 (m, 2H). LCMS RT=0.918 min, m/z=357.9 [M+H]+.

Example 193: Method 42

(5S,7S)-5-(3,5-difluorophenyl)-7-fluoro-2-trans-(3-fluorocyclobutyl)sulfonyl-6,7-dihydro-5H-pyrrolo[1,2-b][1,2,4]triazole

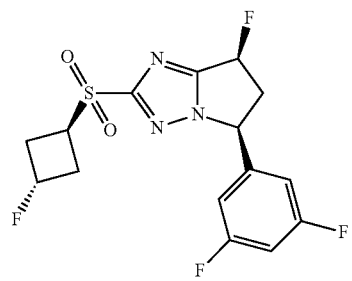 [SMILES: O=S(=O)(c1nc2n(n1)[C@H](c1cc(F)cc(F)c1)C[C@@H]2F)[C@H]1C[C@H](F)C1]

(5S,7S)-5-(3,5-difluorophenyl)-7-fluoro-2-trans-(3-fluorocyclobutyl)sulfonyl-6,7-dihydro-5H-pyrrolo[1,2-b][1,2,4]triazole was prepared using method 42 starting from (5S,7S)-7-fluoro-5-(3,5-difluorophenyl)-6,7-dihydro-5H-pyrrolo[1,2-b][1,2,4]triazole-2-thiol. The final compound was purified by column chromatography (silica gel, 100-200 mesh, 0 to 50% ethyl acetate in petroleum ether) to give (5S,7S)-5-(3,5-diluophenyurophenyl)-7-fluoro-2-trans-(3-fluorocyclobutyl)sulfonyl-6,7-dihydro-5H-pyrrolo[1,2-b][1,2,4]triazole (20.0 mg, 10.2%) as a yellow solid. $^1$H NMR (400 MHz, CDCl$_3$) δ 6.88-6.83 (m, 1H), 6.79-6.77 (m, 2H), 6.12-5.95 (m, 1H), 5.53-5.51 (m, 1H), 5.50-5.25 (m, 1H), 4.17-4.12 (m, 1H), 3.75-3.64 (m, 1H), 3.15-2.98 (m, 3H), 2.75-2.66 (m, 2H). LCMS RT=1.142 min, m/z=376.1 [M+H]$^+$.

Example 195: Method 44

Cis-[[(5S,7S)-7-fluoro-5-(3-fluorophenyl)-6,7-dihydro-5H-pyrrolo[1,2-b][1,2,4]triazol-2-yl]sulfonyl]cyclobutanol

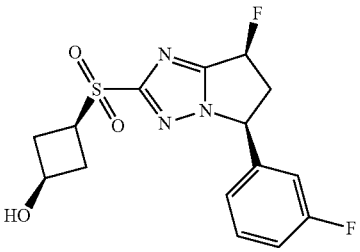 [SMILES: O=S(=O)(c1nc2n(n1)[C@H](c1cccc(F)c1)C[C@@H]2F)[C@H]1C[C@@H](O)C1]

Cis-3-[[(5S,7S)-7-fluoro-5-(3-fluorophenyl)-6,7-dihydro-5H-pyrrolo[1,2-b][1,2,4]triazol-2-yl]sulfonyl]cyclobutanol was prepared according to method 44 starting from (5S,7S)-7-fluoro-5-(3-fluorophenyl)-6,7-dihydro-5H-pyrrolo[1,2-b][1,2,4]triazole-2-thiol. The final compound was purified by RP-HPLC (acetonitrile 28-58%/0.05% ammonia hydroxide in water) to afford cis-3-[[(5S,7S)-7-fluoro-5-(3-fluorophenyl)-6,7-dihydro-5H-pyrrolo[1,2-b][1,2,4]triazol-2-yl]sulfonyl]cyclobutanol (20.6 mg, 21%) as colorless oil. $^1$H NMR (400 MHz, CDCl$_3$) δ 7.43-7.34 (m, 1H), 7.14-7.06 (m, 1H), 7.05-6.99 (m, 1H), 6.98-6.89 (m, 1H), 6.16-5.94 (m, 1H), 5.61-5.50 (m, 1H), 4.33-4.19 (m, 1H), 3.80-3.60 (m, 2H), 3.01-2.88 (m, 1H), 2.77-2.62 (m, 2H), 2.60-2.35 (m, 3H). LCMS R$_T$=0.825 min, m/z=356.1 [M+H]$^+$.

Example 225: Method 44

Cis-3-[[(5S,7S)-7-fluoro-5-phenyl-6,7-dihydro-5H-pyrrolo[1,2-b][1,2,4]triazol-2-yl]sulfonyl]cyclobutanol

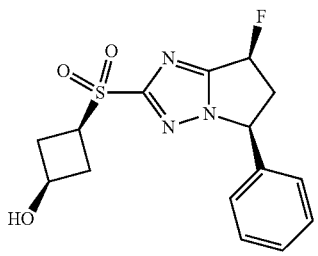 [SMILES: O=S(=O)(c1nc2n(n1)[C@H](c1ccccc1)C[C@@H]2F)[C@H]1C[C@@H](O)C1]

Step 1: 3-(((5S,7S)-7-fluoro-5-phenyl-6,7-dihydro-5H-pyrrolo[1,2-b][1,2,4]triazol-2-yl)sulfonyl)cyclobutanone To a solution of (5S,7S)-7-fluoro-5-phenyl-6,7-dihydro-5H-pyrrolo[1,2-b][1,2,4]triazole-2-thiol (650 mg, 2.8 mmol) and 3-bromocyclobutanone (535 mg, 3.6 mmol) in N,N-dimethylformamide (30 mL) was added sodium hydride (60%, 165 mg, 4.1 mmol) at 0° C. under nitrogen atmosphere. The solution was stirred at 20° C. for 2 h and quenched by addition of water (20 mL). The resulting mixture was extracted with ethyl acetate (3×30 mL). The combined organic layers were dried over sodium sulfate and concentrated under reduced pressure. The residue was purified by purified by column chromatography (silica gel, 100-200 mesh, 0 to 30% ethyl acetate in petroleum ether) to afford 3-[[(5S,7S)-7-fluoro-5-phenyl-6,7-dihydro-5H-pyrrolo[1,2-b][1,2,4]triazol-2-yl]sulfanyl]cyclobutanone (800 mg, 96%) as yellow oil.

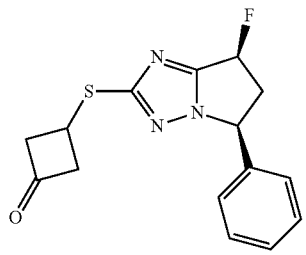 [SMILES: O=C1CC(Sc2nc3n(n2)[C@H](c2ccccc2)C[C@@H]3F)C1]

Step 2: cis-3-(((5S,7S)-7-fluoro-5-phenyl-6,7-dihydro-5H-pyrrolo[1,2-b][1,2,4]triazol-2-yl)thio)cyclobutanol To a mixture of 3-[[(5S,7S)-7-fluoro-5-phenyl-6,7-dihydro-5H-pyrrolo[1,2-b][1,2,4]triazol-2-yl]sulfanyl]cyclobutanone (200 mg, 0.66 mmol) in methanol (10 mL) was added sodium borohydride (74.8 mg, 2.0 mmol). The mixture was stirred at 20° C. for 1 h and quenched by addition of water (30 mL). The resulting mixture was extracted with ethyl acetate (3×30 mL). The combined organic layers were washed with brine (40 mL), dried over sodium sulfate and concentrated under reduced pressure. The residue was purified by column chromatography (silica gel, 100-200 mesh, 0 to 80% ethyl acetate in petroleum ether) to afford cis-3-(((5S,7S)-7-fluoro-5-phenyl-6,7-dihydro-5H-pyrrolo[1,2-b][1,2,4]triazol-2-yl)thio)cyclobutanol (140 mg, 70%) as a light yellow solid.

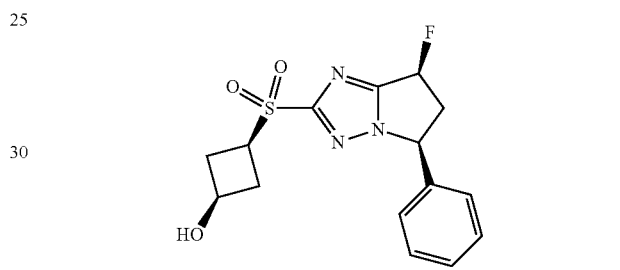

Step 3: Cis-3-[[(5S,7S)-7-fluoro-5-phenyl-6,7-dihydro-5H-pyrrolo[1,2-b][1,2,4]triazol-2-yl]sulfonyl]cyclobutanol A mixture of 3-[[(5S,7S)-7-fluoro-5-(3-fluorophenyl)-6,7-dihydro-5H-pyrrolo[1,2-b][1,2,4]triazol-2-yl]sulfanyl]cyclobutanol (90 mg, 0.28 mmol) and 3-chloroperoxybenzoic acid (85%, 226 mg, 1.11 mmol) in dichloromethane (9 mL) was stirred at 25° C. for 4 h. The reaction mixture was diluted with water (30 mL) and extracted with dichloromethane (3×20 mL). The combined organic layers were washed with saturated aqueous sodium bicarbonate (2×20 mL), brine (20 mL), dried over sodium sulfate and concentrated under reduced pressure. The residue was purified by RP-HPLC (acetonitrile 28-58%/0.05% ammonia hydroxide in water) to afford 3-[[(5S,7S)-7-fluoro-5-(3-fluorophenyl)-6,7-dihydro-5H-pyrrolo[1,2-b][1,2,4]triazol-2-yl]sulfonyl]cyclobutanol (20.6 mg, 21%) as colorless oil. $^1$H NMR (400 MHz, CD$_3$OD) δ 7.44-7.39 (m, 3H), 7.27-7.25 (m, 2H), 6.20-6.18 (m, 0.5H), 6.05-6.03 (m, 0.5H), 5.67-5.65 (m, 1H), 4.21-4.15 (m, 1H), 3.77-3.72 (m, 2H), 2.90-2.80 (m, 1H), 2.57-2.51 (m, 2H), 2.38-2.35 (m, 2H). LCMS R$_T$=0.585 min, m/z=338.1 [M+H]$^+$.

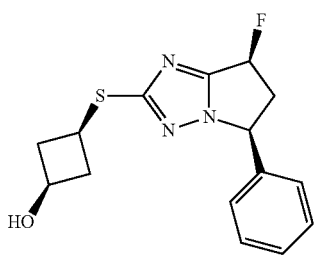 [SMILES: O[C@H]1C[C@@H](Sc2nc3n(n2)[C@H](c2ccccc2)C[C@@H]3F)C1]

Example 196 and Example 197

(5S,7S)-7-fluoro-5-(4-fluorophenyl)-2-[(1S,2S)-2-fluorocyclopropyl]sulfonyl-6,7-dihydro-5H-pyrrolo[1,2-b][1,2,4]triazole and (5S,7S)-7-fluoro-5-(4-fluorophenyl)-2-[(1R,2R)-2-fluorocyclopropyl]sulfonyl-6,7-dihydro-5H-pyrrolo[1,2-b][1,2,4]triazole

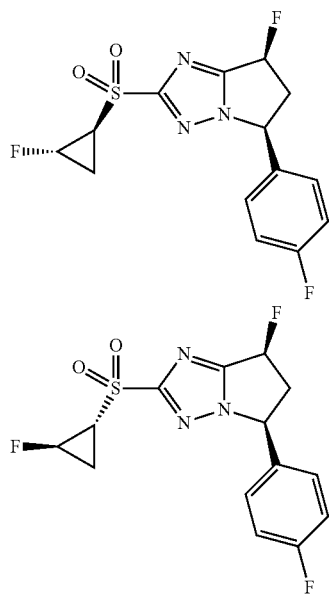

(5S,7S)-7-fluoro-5-(4-fluorophenyl)-2-[(1S,2S)-2-fluorocyclopropyl]sulfonyl-6,7-dihydro-5H-pyrrolo[1,2-b][1,2,4]triazole and (5S,7S)-7-fluoro-5-(4-fluorophenyl)-2-[(1R,2R)-2-fluorocyclopropyl]sulfonyl-6,7-dihydro-5H-pyrrolo[1,2-b][1,2,4]triazole were prepared according to method 30 (starting from (5S,7S)-2-bromo-7-fluoro-5-(4-fluorophenyl)-6,7-dihydro-5H-pyrrolo[1,2-b][1,2,4]triazole. The final compound was purified first by flash chromatography on silica (solvent gradient: 0 to 25% ethyl acetate in petroleum ether), and then by SFC to give:

(5S,7S)-7-fluoro-2-[(1S,2S)-2-fluorocyclopropyl]sulfonyl-5-(4-fluorophenyl)-6,7-dihydro-5H-pyrrolo[1,2-b][1,2,4]triazole (Peak 1, retention time=3.735 min) (14.5 mg, 13%) as a white solid. $^1$H NMR (400 MHz, CDCl$_3$) δ 7.30-7.26 (m, 2H), 7.14-7.07 (m, 2H), 6.17-5.94 (m, 1H), 5.57-5.50 (m, 1H), 5.27-4.98 (m, 1H), 3.79-3.56 (m, 1H), 3.20-3.15 (m, 1H), 3.05-2.91 (m, 1H), 1.90-1.76 (m, 2H). LCMS R$_T$=0.952 min, m/z=344.1 [M+H]$^+$.

(5S,7S)-7-fluoro-2-[(1R,2R)-2-fluorocyclopropyl]sulfonyl-5-(4-fluorophenyl)-6,7-dihydro-5H-pyrrolo[1,2-b][1,2,4]triazole (Peak 2, retention time=4.033 min) (22.0 mg, 19.8%) as a white solid. $^1$H NMR (400 MHz, CDCl$_3$) δ 7.30-7.27 (m, 1H), 7.26-7.23 (m, 1H), 7.14-7.06 (m, 2H), 6.20-5.92 (m, 1H), 5.57-5.49 (m, 1H), 5.27-4.98 (m, 1H), 3.79-3.56 (m, 1H), 3.19-3.08 (m, 1H), 3.05-2.90 (m, 1H), 1.91-1.76 (m, 2H). LCMS R$_T$=0.956 min, m/z=344.1 [M+H]$^+$.

SFC condition: Column: Chiralcel AD-3 (150*4.6 mm, 3 um) Mobile phase: A: CO$_2$ B: Ethanol (0.05% DEA) Gradient: from 5% to 40% of B in 5.5 min and 5% of B for 1.5 min, Flow rate: 2.5 mL/min Column temp. 40° C.

Example 198: Method 45

(5S,7S)-2-[2-(Difluoromethoxy)ethylsulfonyl]-7-fluoro-5-phenyl-6,7-dihydro-5H-pyrrolo[1,2-b][1,2,4]triazole

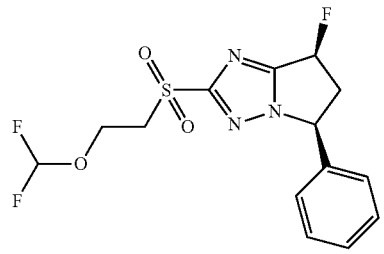 [SMILES: O=S(=O)(CCOC(F)F)c1nc2n(n1)[C@H](c1ccccc1)C[C@@H]2F]

Step 1: (5S,7S)-2-[2-(difluoromethoxy)ethylsulfanyl]-7-fluoro-5-phenyl-6,7-dihydro-5H-pyrrolo[1,2-b][1,2,4]triazole

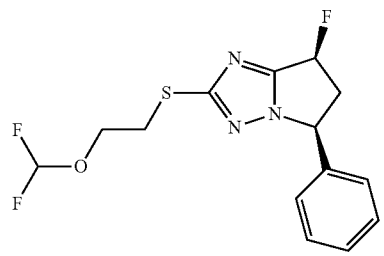 [SMILES: FC(F)OCCSc1nc2n(n1)[C@H](c1ccccc1)C[C@@H]2F]

To a mixture of 2-[[(5S,7S)-7-fluoro-5-phenyl-6,7-dihydro-5H-pyrrolo[1,2-b][1,2,4]triazol-2-yl]sulfanyl]ethanol (200 mg, 0.72 mmol) and copper(I) iodide (30 mg, 0.2 mmol) in acetonitrile (1.0 mL) was added a solution of difluoro(fluorosulfonyl)acetic acid (500 mg, 2.8 mmol) in acetonitrile (0.5 mL) at 50° C. The mixture was stirred at 50° C. for 40 min and concentrated under reduced pressure. The residue was purified by column chromatography (silica gel, 100-200 mesh, 0 to 50% ethyl acetate in petroleum ether) to give (5S,7S)-2-[2-(difluoromethoxy)ethylsulfanyl]-7-fluoro-5-phenyl-6,7-dihydro-5H-pyrrolo[1,2-b][1,2,4]triazole (45 mg, 19%) as yellow oil. LCMS R$_T$=0.726 min, m/z=330.1 [M+H]$^+$.

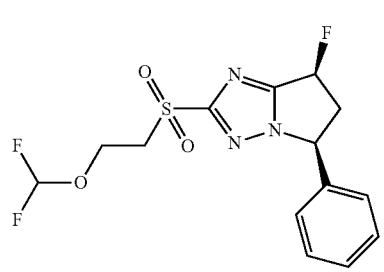 [SMILES: O=S(=O)(CCOC(F)F)c1nc2n(n1)[C@H](c1ccccc1)C[C@@H]2F]

Step 2: (5S,7S)-2-[2-(difluoromethoxy)ethylsulfonyl]-7-fluoro-5-phenyl-6,7-dihydro-5H-pyrrolo[1,2-b][1,2,4]triazole A mixture of (5S,7S)-2-[2-(difluoromethoxy)ethylsulfanyl]-7-fluoro-5-phenyl-6,7-dihydro-5H-pyrrolo[1,2-b][1,2, 4]triazole (45 mg, 0.14 mmol), ruthenium(iii) chloride (6 mg, 0.03 mmol) and sodium periodate (117 mg, 0.55 mmol). in acetonitrile (1.8 mL), water (1.8 mL) and ethyl acetate (1.8 mL) was stirred at 30° C. for 1 h and filtered. The filtrate was concentrated under reduced pressure and the residue was purified by RP-HPLC (acetonitrile 25-55%/0.225% formic acid in water) to afford (5S,7S)-2-[2-(difluoromethoxy)ethylsulfonyl]-7-fluoro-5-phenyl-6,7-dihydro-5H-pyrrolo[1,2-b][1,2,4]triazole (5.3 mg, 10.3%) as a white solid. $^1$H NMR (400 MHz, CD$_3$OD) δ 7.43-7.39 (m, 3H), 7.30-7.27 (m, 2H), 6.22 (t. J=74.8 Hz, 1H), 6.21-6.03 (m, 1H), 5.68-5.66 (m, 1H), 4.25 (t, J=5.6 Hz, 2H), 3.82-3.74 (m, 3H), 1.31-1.28 (m, 1H). LCMS $R_T$=0.943 min, m/z=362.1 [M+H]$^+$.

Example 199 and Example 200

(5S,7S)-5-(3-chloro-5-fluoro-phenyl)-7-fluoro-2-[(1S,2S)-2-fluorocyclopropyl]sulfonyl-6,7-dihydro-5H-pyrrolo[1,2-b][1,2,4]triazole and (5S,7S)-5-(3-chloro-5-fluoro-phenyl)-7-fluoro-2-[(1R,2R)-2-fluorocyclopropyl]sulfonyl-6,7-dihydro-5H-pyrrolo[1,2-b][1,2,4]triazole

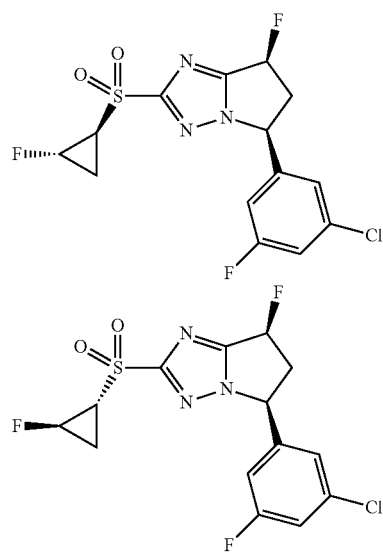

(5S,7S)-5-(3-chloro-5-fluoro-phenyl)-7-fluoro-2-[(1S,2S)-2-fluorocyclopropyl]sulfonyl-6,7-dihydro-5H-pyrrolo[1,2-b][1,2,4]triazole and (5S,7S)-5-(3-chloro-5-fluoro-phenyl)-7-fluoro-2-[(1R,2R)-2-fluorocyclopropyl]sulfonyl-6,7-dihydro-5H-pyrrolo[1,2-b][1,2,4]triazole were prepared according to method 30 starting from (5S,7S)-2-bromo-5-(3-chloro-5-fluorophenyl)-7-fluoro-6,7-dihydro-5H-pyrrolo[1,2-b][1,2,4]triazole (prepared according to method 23). The final compound was purified first by RP-HPLC (acetonitrile 42-72%/0.225% formic acid in water), and then by SFC to afford:

(5S,7S)-5-(3-chloro-5-fluoro-phenyl)-7-fluoro-2-[(1S,2S)-2-fluorocyclopropyl]sulfonyl-6,7-dihydro-5H-pyrrolo[1,2-b][1,2,4]triazole (Peak 1, retention time=4.266 min) (15.5 mg, 34%) as a white solid. $^1$H NMR (400 MHz, CDCl$_3$) δ 7.17-7.13 (m, 1H), 7.09 (s, 1H), 6.90-6.87 (m, 1H), 6.14-5.98 (m, 1H), 5.52-5.47 (m, 1H), 5.25-5.05 (m, 1H), 3.76-3.61 (m, 1H), 3.20-3.10 (m, 1H), 3.05-2.94 (m, 1H), 1.93-1.76 (m, 2H). LCMS $R_T$=1.030 min, m/z=378.1 [M+H]$^+$.

(5S,7S)-5-(3-chloro-5-fluoro-phenyl)-7-fluoro-2-[(1R,2R)-2-fluorocyclopropyl]sulfonyl-6,7-dihydro-5H-pyrrolo[1,2-b][1,2,4]triazole (Peak 2, retention time=4.480 min) (8.6 mg, 19%) as a white solid. $^1$H NMR (400 MHz, CDCl$_3$) δ 7.17-7.13 (m, 1H), 7.09 (s, 1H), 6.90-6.87 (m, 1H), 6.14-5.98 (m, 1H), 5.52-5.47 (m, 1H), 5.24-5.05 (m, 1H), 3.76-3.61 (m, 1H), 3.22-3.13 (m, 1H), 3.05-2.94 (m, 1H), 1.89-1.75 (m, 2H). LCMS RT=0.952 min, m/z=377.9 [M+H]+.

SFC condition: Column: Chiralcel OD-3 (150*4.6 mm, 3 um) Mobile phase: A: CO$_2$ B: Ethanol (0.05% DEA) Gradient: from 5% to 40% of B in 5 min and hold 40% of B for 2.5 min, Flow rate: 2.5 mL/min Column temp. 35° C.

Example 201 and Example 202

(5S,7S)-5-(2,5-difluorophenyl)-7-fluoro-2-[(1S,2S)-2-fluorocyclopropyl]sulfonyl-6,7-dihydro-5H-pyrrolo[1,2-b][1,2,4]triazole and (5S,7S)-5-(2,5-difluorophenyl)-7-fluoro-2-[(1R,2R)-2-fluorocyclopropyl]sulfonyl-6,7-dihydro-5H-pyrrolo[1,2-b][1,2,4]triazole

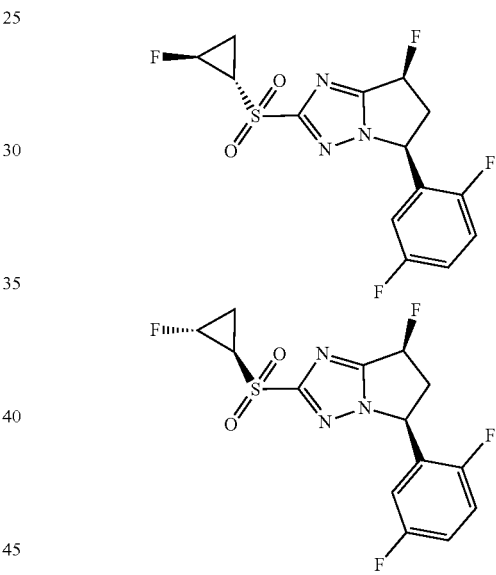

(5S,7S)-5-(2,5-difluorophenyl)-7-fluoro-2-[(1S,2S)-2-fluorocyclopropyl]sulfonyl-6,7-dihydro-5H-pyrrolo[1,2-b][1,2,4]triazole and (5S,7S)-5-(2,5-difluorophenyl)-7-fluoro-2-[(1R,2R)-2-fluorocyclopropyl]sulfonyl-6,7-dihydro-5H-pyrrolo[1,2-b][1,2,4]triazole were prepared according to method 30 starting from (5S,7S)-2-bromo-5-(2,5-difluorophenyl)-7-fluoro-6,7-dihydro-5H-pyrrolo[1,2-b][1,2,4]triazole. The final compound was purified first by RP-HPLC (acetonitrile 40-70%/0.05% ammonia hydroxide in water), and then by SFC to give:

(5S,7S)-5-(2,5-difluorophenyl)-7-fluoro-2-[(1S,2S)-2-fluorocyclopropyl]sulfonyl-6,7-dihydro-5H-pyrrolo[1,2-b][1,2,4]triazole (Peak 1, retention time=2.467 min) (25.4 mg, 23%) as a white solid. $^1$H NMR (400 MHz, CDCl$_3$) δ 7.19-7.04 (m, 2H), 6.75-6.65 (m, 1H), 6.18-5.95 (m, 1H), 5.89-5.80 (m, 1H), 5.29-5.01 (m, 1H), 3.83-3.64 (m, 1H), 3.26-3.14 (m, 1H), 3.05-2.89 (m, 1H), 1.92-1.76 (m, 2H). LCMS $R_T$=0.955 min, m/z=362.1 [M+H]$^+$.

(5S,7S)-5-(2,5-difluorophenyl)-7-fluoro-2-[(1R,2R)-2-fluorocyclopropyl]sulfonyl-6,7-dihydro-5H-pyrrolo[1,2-b]

[1,2,4]triazole (Peak 2, retention time=2.544 min) (61.4 mg, 55%) as a white solid. ¹H NMR (400 MHz, CDCl₃) δ 7.20-7.05 (m, 2H), 6.76-6.67 (m, 1H), 6.17-5.97 (m, 1H), 5.88-5.80 (m, 1H), 5.29-5.05 (m, 1H), 3.82-3.65 (m, 1H), 3.23-3.11 (m, 1H), 3.05-2.90 (m, 1H), 1.94-1.77 (m, 2H). LCMS RT=0.952 min, m/z=362.1 [M+H]⁺.

SFC condition: Column: Chiralcel AS-3 (150*4.6 mm, 3 um) Mobile phase: A: CO₂ B: Ethanol (0.05% DEA) Gradient: from 5% to 40% of B in 5 min and from 40% to 5% of B in 0.5 min, hold 5% of B for 1.5 min, Flow rate: 2.5 mL/min Column temp. 35 OC.

Example 203

(5S,7S)-5-(3-chlorophenyl)-2-cyclopropylsulfonyl-7-fluoro-6,7-dihydro-5H-pyrrolo[1,2-b][1,2,4]triazole

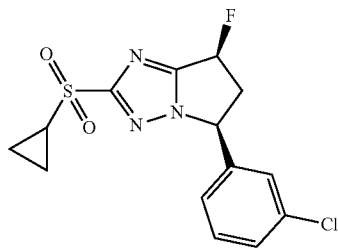 [SMILES: O=S(=O)(c1nc2n(n1)[C@H](c1cccc(Cl)c1)C[C@@H]2F)C1CC1]

(5S,7S)-5-(3-chlorophenyl)-2-cyclopropylsulfonyl-7-fluoro-6,7-dihydro-5H-pyrrolo[1,2-b][1,2,4]triazole was prepared according to method 18 starting from (5S,7S)-5-(3-chlorophenyl)-7-fluoro-6,7-dihydro-5H-pyrrolo 1,2-b][1,2,4]triazole-2-thiol. The final compound was purified by RP-HPLC (acetonitrile 35-65%/0.225% formic acid in water) to afford (5S,7S)-5-(3-chlorophenyl)-2-cyclopropylsulfonyl-7-fluoro-6,7-dihydro-5H-pyrrolo[1,2-b][1,2,4]triazole (145 mg, 81%) as a white solid. ¹H NMR (400 MHz, CDCl₃) δ 7.41-7.31 (m, 2H), 7.26-7.24 (m, 1H), 7.16-7.10 (m, 1H), 6.14-5.95 (m, 1H), 5.56-5.48 (m, 1H), 3.78-3.57 (m, 1H), 3.06-2.87 (m, 1H), 2.80-2.70 (m, 1H), 1.52-1.39 (m, 2H), 1.22-1.07 (m, 2H). LCMS R_T=0.917 min, m/z=341.9 [M+H]⁺.

Example 204: Method 42

(5S,7S)-5-(2,3-difluorophenyl)-7-fluoro-2-trans-(3-fluorocyclobutyl)sulfonyl-6,7-dihydro-5H-pyrrolo[1,2-b][1,2,4]triazole

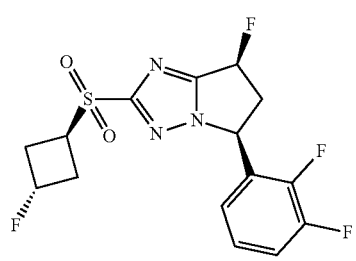 [SMILES: O=S(=O)(c1nc2n(n1)[C@H](c1cccc(F)c1F)C[C@@H]2F)[C@H]1C[C@H](F)C1]

(5S,7S)-5-(2,3-difluorophenyl)-7-fluoro-2-trans-(3-fluorocyclobutyl)sulfonyl-6,7-dihydro-5H-pyrrolo[1,2-b][1,2,4]triazole was prepared according to method 42 starting from (5S,7S)-7-fluoro-5-(2,3-difluorophenyl)-6,7-dihydro-5H-pyrrolo[1,2-b][1,2,4]triazole-2-thiol. The final compound was purified by RP-HPLC (acetonitrile 45-75%/0.05% ammonia hydroxide in water) to give (5S,7S)-5-(2,3-difluorophenyl)-7-fluoro-2-trans-(3-fluorocyclobutyl) sulfonyl-6,7-dihydro-5H-pyrrolo[1,2-b][1,2,4]triazole (11.9 mg, 31%) as a white solid. H NMR (400 MHz, CDCl₃) δ 7.27-7.19 (m, 1H), 7.17-7.10 (m, 1H), 6.75-6.72 (m, 1H), 6.17-5.95 (m, 1H), 5.92-5.81 (m, 1H), 5.46-5.19 (m, 1H), 4.24-4.08 (m, 1H), 3.85-3.64 (m, 1H), 3.14-2.91 (m, 3H), 2.79-2.61 (m, 2H). LCMS RT=1.845 min, m/z=376.1 [M+H]⁺.

Example 205 and Example 206

(5S,7S)-7-fluoro-5-(2-fluorophenyl)-2-[(1S,2S)-2-fluorocyclopropyl]sulfonyl-6,7-dihydro-5H-pyrrolo [1,2-b][1,2,4]triazole and (5S,7S)-7-fluoro-5-(2-fluorophenyl)-2-[(1R,2R)-2-fluorocyclopropyl] sulfonyl-6,7-dihydro-5H-pyrrolo[1,2-b][1,2,4] triazole

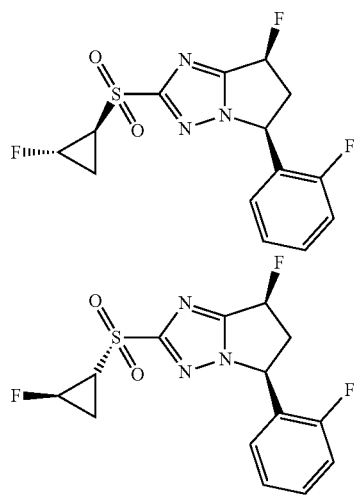

(5S,7S)-7-fluoro-5-(2-fluorophenyl)-2-[(1S,2S)-2-fluorocyclopropyl]sulfonyl-6,7-dihydro-5H-pyrrolo[1,2-b][1,2,4] triazole and (5S,7S)-7-fluoro-5-(2-fluorophenyl)-2-[(1R,2R)-2-fluorocyclopropyl]sulfonyl-6,7-dihydro-5H-pyrrolo [1,2-b][1,2,4]triazole were prepared according to method 30 starting from (5S,7S)-2-bromo-7-fluoro-5-(2-fluorophenyl)-6,7-dihydro-5H-pyrrolo[1,2-b][1,2,4]triazole. The final compound was purified first by RP-HPLC (acetonitrile 42-72%/0.05% ammonia hydroxide in water), and then by SFC to give:

(5S,7S)-7-fluoro-5-(2-fluorophenyl)-2-[(1S,2S)-2-fluorocyclopropyl]sulfonyl-6,7-dihydro-5H-pyrrolo[1,2-b][1,2,4] triazole (Peak 1, retention time=2.623 min) (37.5 mg, 31.3%) as a white solid. ¹H NMR (400 MHz, CDCl₃) δ 7.44-7.37 (m, 1H), 7.21-7.13 (m, 2H), 6.99 (t, J=6.8 Hz, 1H), 6.16-5.98 (m, 1H), 5.89-5.87 (m, 1H), 5.27-5.04 (m, 1H), 3.81-3.64 (m, 1H), 3.25-3.14 (m, 1H), 3.06-2.90 (m, 1H), 1.91-1.75 (m, 2H). LCMS R_T=0.897 min, m/z=343.9 [M+H]⁺.

(5S,7S)-7-fluoro-5-(2-fluorophenyl)-2-[(1R,2R)-2-fluorocyclopropyl]sulfonyl-6,7-dihydro-5H-pyrrolo[1,2-b][1,2, 4]triazole (Peak 2, retention time=2.747 min) (36.4 mg, 30%) as a white solid. ¹H NMR (400 MHz, CDCl₃) δ 7.44-7.36 (m, 1H), 7.21-7.12 (m, 2H), 6.99 (t, J=7.2 Hz, 1H), 6.19-5.96 (m, 1H), 5.88-5.85 (m, 1H), 5.28-5.07 (m, 1H), 3.83-3.63 (m, 1H), 3.18-3.16 (m, 1H), 3.06-2.90 (m, 1H), 1.94-1.74 (m, 2H). LCMS $R_T$=0.896 min, m/z=343.9 [M+H]$^+$.

SFC condition: Column: Chiralcel AS-3 (150*4.6 mm, 3 um) Mobile phase: A: CO$_2$ B: Ethanol (0.05% DEA) Gradient: from 5% to 40% of B in 5 min and from 40% to 5% of B in 0.5 min, hold 5% of B for 1.5 min, Flow rate: 2.5 mL/min Column temp. 35 OC.

Example 207 and Example 218

(5S,7S)-5-(5-chloro-2-fluoro-phenyl)-7-fluoro-2-[(1S,2S)-2-fluorocyclopropyl]sulfonyl-6,7-dihydro-5H-pyrrolo[1,2-b][1,2,4]triazole and (5S,7S)-5-(5-chloro-2-fluoro-phenyl)-7-fluoro-2-[(1R,2R)-2-fluorocyclopropyl]sulfonyl-6,7-dihydro-5H-pyrrolo[1,2-b][1,2,4]triazole

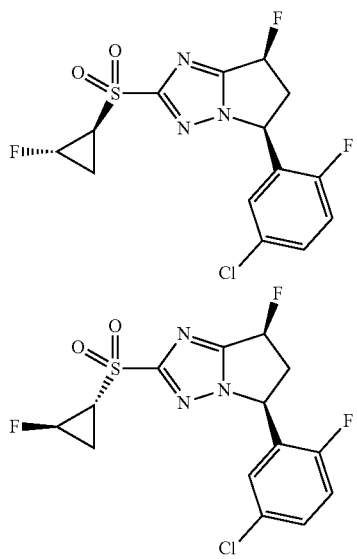

(5S,7S)-5-(5-chloro-2-fluoro-phenyl)-7-fluoro-2-[(1S,2S)-2-fluorocyclopropyl]sulfonyl-6,7-dihydro-5H-pyrrolo[1,2-b][1,2,4]triazole and (5S,7S)-5-(5-chloro-2-fluoro-phenyl)-7-fluoro-2-[(1R,2R)-2-fluorocyclopropyl]sulfonyl-6,7-dihydro-5H-pyrrolo[1,2-b][1,2,4]triazole were prepared according to method 30 starting from (5S,7S)-2-bromo-5-(5-chloro-2-fluorophenyl)-7-fluoro-6,7-dihydro-5H-pyrrolo[1,2-b][1,2,4]triazole. The final compound was purified first by RP-HPLC (42-72% acetonitrile/0.05% hydrochloric acid in water), and then by SFC to give:

(5S,7S)-5-(5-chloro-2-fluoro-phenyl)-7-fluoro-2-[(1S,2S)-2-fluorocyclopropyl]sulfonyl-6,7-dihydro-5H-pyrrolo[1,2-b][1,2,4]triazole (Peak 1, retention time=4.275 min) (10.2 mg, 10%) as a white solid. $^1$H NMR (400 MHz, CDCl$_3$) δ 7.40-7.32 (m, 1H), 7.12 (t, J=9.2 Hz, 1H), 7.00-6.95 (m, 1H), 6.17-5.95 (m, 1H), 5.84-5.76 (m, 1H), 5.27-5.06 (m, 1H), 3.80-3.63 (m, 1H), 3.22-3.12 (m, 1H), 3.03-2.91 (m, 1H), 1.93-1.81 (m, 2H). LCMS $R_T$=1.018 min, m/z=378.1 [M+H]$^+$.

(5S,7S)-5-(5-chloro-2-fluoro-phenyl)-7-fluoro-2-[(1R,2R)-2-fluorocyclopropyl]sulfonyl-6,7-dihydro-5H-pyrrolo[1,2-b][1,2,4]triazole (Peak 2, retention time=4.504 min) (14.1 mg, 14%) as a white solid. $^1$H NMR (400 MHz, CD$_3$OD) δ 7.51-7.44 (m, 1H), 7.30-7.19 (m, 2H), 6.29-6.05 (m, 1H), 5.95-5.80 (m, 1H), 5.30-5.02 (m, 1H), 3.94-3.71 (m, 1H), 3.50-3.38 (m, 1H), 3.01-2.81 (m, 1H), 1.94-1.81 (m, 1H), 1.78-1.67 (m, 1H). LCMS $R_T$=1.010 min, m/z=378.1 [M+H]$^+$.

SFC condition: Column: Chiralcel OD-3 (150×4.6 mm, 3 um) Mobile phase: A: CO$_2$ B: Ethanol (0.05% DEA) Gradient: from 5% to 40% of B in 5 min and from 40% to 5% of B in 0.5 min, hold 5% of B for 1.5 min, Flow rate: 2.5 mL/min Column temp. 35° C.

Example 219 and Example 208

(5S,7S)-5-(3-chloro-2-fluoro-phenyl)-7-fluoro-2-[(1S,2S)-2-fluorocyclopropyl]sulfonyl-6,7-dihydro-5H-pyrrolo[1,2-b][1,2,4]triazole and (5S,7S)-5-(3-chloro-2-fluoro-phenyl)-7-fluoro-2-[(1R,2R)-2-fluorocyclopropyl]sulfonyl-6,7-dihydro-5H-pyrrolo[1,2-b][1,2,4]triazole

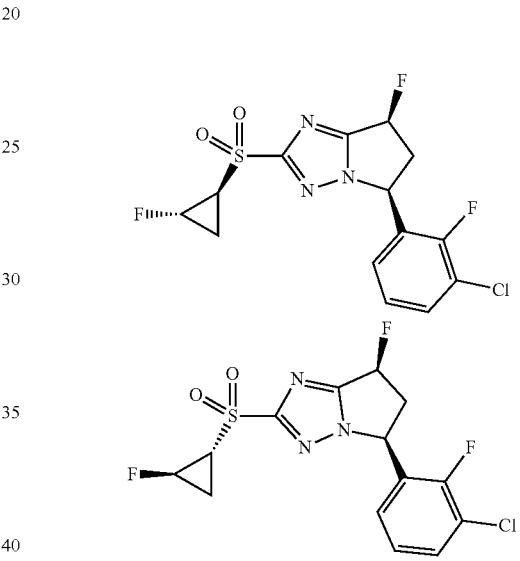

(5S,7S)-5-(3-chloro-2-fluoro-phenyl)-7-fluoro-2-[(1S,2S)-2-fluorocyclopropyl]sulfonyl-6,7-dihydro-5H-pyrrolo[1,2-b][1,2,4]triazole and (5S,7S)-5-(3-chloro-2-fluoro-phenyl)-7-fluoro-2-[(1R,2R)-2-fluorocyclopropyl]sulfonyl-6,7-dihydro-5H-pyrrolo[1,2-b][1,2,4]triazole were prepared according to method 30 starting from (5S,7S)-2-bromo-5-(3-chloro-2-fluorophenyl)-7-fluoro-6,7-dihydro-5H-pyrrolo[1,2-b][1,2,4]triazole. The final compound was purified first by RP-HPLC (45-72% acetonitrile/0.05% hydrochloric acid in water), and then by SFC to give:

(5S,7S)-5-(3-chloro-2-fluoro-phenyl)-7-fluoro-2-[(1S,2S)-2-fluorocyclopropyl]sulfonyl-6,7-dihydro-5H-pyrrolo[1,2-b][1,2,4]triazole (Peak 1, retention time=4.561 min) (9.9 mg, 14%) as a white solid. $^1$H NMR (400 MHz, CDCl$_3$) δ 7.48-7.44 (m, 1H), 7.15-7.10 (m, 1H), 6.88-6.84 (m, 1H), 6.15-5.98 (m, 1H), 5.90-5.85 (m, 1H), 5.24-5.08 (m, 1H), 3.81-3.66 (m, 1H), 3.23-3.11 (m, 1H), 3.03-2.92 (m, 1H), 1.89-1.84 (m, 2H). LCMS $R_T$=1.029 min, m/z=378.1 [M+H]$^+$.

(5S,7S)-5-(3-chloro-2-fluoro-phenyl)-7-fluoro-2-[(1R,2R)-2-fluorocyclopropyl]sulfonyl-6,7-dihydro-5H-pyrrolo[1,2-b][1,2,4]triazole (Peak 2, retention time=4.332 min) (20.0 mg, 29%) as a white solid. $^1$H NMR (400 MHz, CDCl$_3$) δ 7.48-7.43 (m, 1H), 7.16-7.10 (m, 1H), 6.89-6.85 (m, 1H), 6.15-5.98 (m, 1H), 5.90-5.85 (m, 1H), 5.24-5.03

(m, 1H), 3.81-3.66 (m, 1H), 3.23-3.14 (m, 1H), 3.03-2.92 (m, 1H), 1.90-1.80 (m, 2H). LCMS $R_T$=0.939 min, m/z=337.9 [M+H]$^+$.

SFC condition: Column: Chiralcel AD-3 (150×4.6 mm, 3 um) Mobile phase: A: CO$_2$ B: Ethanol (0.05% DEA) Gradient: from 5% to 40% of B in 5.5 min and 5% of B for 1.5 min, Flow rate: 2.5 mL/min Column temp. 40° C.

Example 209 and Example 212: Method 46

(1R,2S)-2-[[(5S,7S)-7-fluoro-5-phenyl-6,7-dihydro-5H-pyrrolo[1,2-b][1,2,4]triazol-2-yl]sulfonyl]cyclopropanecarbonitrile and (1S,2R)-2-[[(5S,7S)-7-fluoro-5-phenyl-6,7-dihydro-5H-pyrrolo[1,2-b][1,2,4]triazol-2-yl]sulfonyl]cyclopropanecarbonitrile

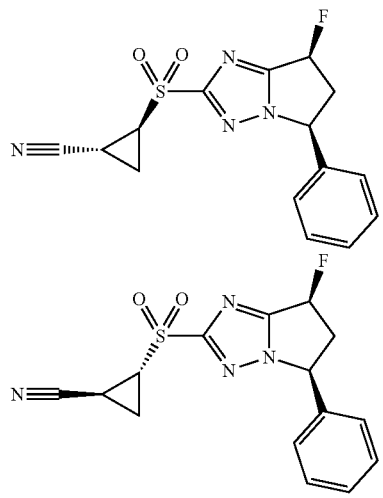

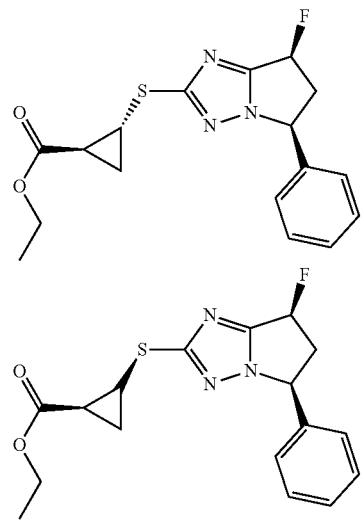

Step 1: ethyl trans-2-[[(5S,7S)-7-fluoro-5-phenyl-6,7-dihydro-5H-pyrrolo[1,2-b][1,2,4]triazol-2-yl]sulfanyl]cyclopropanecarboxylate and ethyl cis-2-(((5S,7S)-7-fluoro-5-phenyl-6,7-dihydro-5H-pyrrolo[1,2-b][1,2,4]triazol-2-yl)thio)cyclopropanecarboxylate

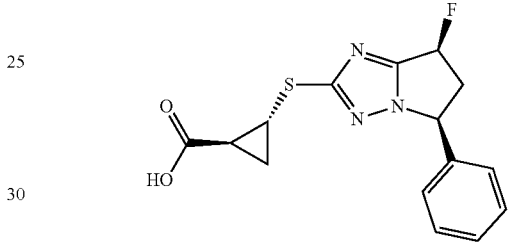

A mixture of 2,2'-bipyridine (71 mg, 0.45 mmol), (5S,7S)-7-fluoro-5-phenyl-6,7-dihydro-5H-pyrrolo[1,2-b][1,2,4]triazole-2-thiol (535 mg, 2.3 mmol), sodium carbonate (723 mg, 6.8 mmol), (2-ethoxycarbonylcyclopropyl)boronic acid (387 mg, 2.5 mmol) and copper(I) thiophene-2-carboxylate (445 mg, 2.3 mmol) in 1,2-dichloroethane (25 mL) was stirred at 50° C. for 3 h under nitrogen atmosphere. The mixture was poured into water (10 mL) and extracted with dichloromethane (3×10 mL). The combined organic layers were washed with brine (20 mL), dried over sodium sulfate and concentrated under reduced pressure. The residue was purified by column chromatography (silica gel, 100-200 mesh, 0 to 50% ethyl acetate in petroleum ether) to give ethyl trans-2-[[(5S,7S)-7-fluoro-5-phenyl-6,7-dihydro-5H-pyrrolo[1,2-b][1,2,4]triazol-2-yl]sulfanyl]cyclopropanecarboxylate (195 mg, 25%) and ethyl cis-2-[(5S,7S)-7-fluoro-5-phenyl-6,7-dihydro-5H-pyrrolo[1,2-b][1,2,4]triazol-2-yl]sulfanyl]cyclopropanecarboxylate (210 mg, 27%), both as light yellow solids.

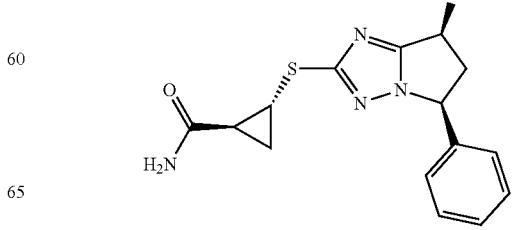

Step 2: trans-2-[[(5S,7S)-7-Fluoro-5-phenyl-6,7-dihydro-5H-pyrrolo[1,2-b][1,2,4]triazol-2-yl]sulfanyl]cyclopropanecarboxylic acid To a solution of ethyl trans-2-[[(5S,7S)-7-fluoro-5-phenyl-6,7-dihydro-5H-pyrrolo[1,2-b][1,2,4]triazol-2-yl]sulfanyl]cyclopropanecarboxylate (180 mg, 0.5 mmol) in tetrahydrofuran (10 mL) and water (2 mL) was added lithium hydroxide hydrate (37 mg, 1.6 mmol). The reaction mixture was stirred at 25° C. for 4 h and concentrated under reduced pressure. The residue was adjusted to pH=3 by addition of hydrochloric acid (4 M) and extracted with ethyl acetate (3×15 mL). The combined organic layers were washed with brine (20 mL), dried over sodium sulfate and concentrated under reduced pressure to afford crude trans-2-[[(5S,7S)-7-fluoro-5-phenyl-6,7-dihydro-5H-pyrrolo[1,2-b][1,2,4]triazol-2-yl]sulfanyl]cyclopropane carboxylic acid (150 mg, 91%) as a white solid. LCMS $R_T$=0.902 min, m/z=320.1 [M+H]$^+$.

Step 3: trans-[[(5S,7S)-7-Fluoro-5-phenyl-6,7-dihydro-5H-pyrrolo[1,2-b][1,2,4]triazol-2-yl]sulfanyl]cyclopropanecarboxamide To a mixture of 1-hydroxybenzotriazole (64 mg, 0.5 mmol), ammonium chloride (50 mg, 0.94 mmol), N,N-diisopropylethylamine (182 mg, 1.4 mmol) and trans-2-[[(5S,7S)-7-fluoro-5-phenyl-6,7-dihydro-5H-pyrrolo[1,2-b][1,2,4]triazol-2-yl]sulfanyl]cyclopropanecarboxylic acid (150 mg, 0.47 mmol) in N,N-dimethylformamide (5.0 mL) was added 1-(3-dimethylaminopropyl)-3-ethylcarbodiimide hydrochloride (90 mg, 0.47 mmol). The mixture was stirred at 25° C. for 18 h and poured into water (30 mL). The resulting solution was extracted with ethyl acetate (3×20 mL). The combined organic layers were concentrated under reduced pressure and the residue was purified by column chromatography (silica gel, 100-200 mesh, 0 to 8% methanol in ethyl acetate) to afford trans-2-[[(5S,7S)-7-fluoro-5-phenyl-6,7-dihydro-5H-pyrrolo[1,2-b][1,2,4]triazol-2-yl]sulfanyl]cyclopropanecarboxamide (100 mg, 67%) as a colorless oil. LCMS $R_T$=0.590 min, m/z=319.1 [M+H]$^+$.

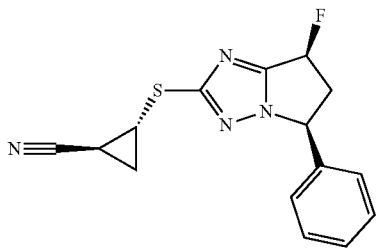 [SMILES: N#C[C@@H]1C[C@H]1Sc1nc2n(n1)[C@H](c1ccccc1)C[C@@H]2F]

Step 4: trans-2-[[(5S,7S)-7-Fluoro-5-phenyl-6,7-dihydro-5H-pyrrolo[1,2-b][1,2,4]triazol-2-yl]sulfanyl]cyclopropanecarbonitrile To a solution of trans-2-[[(5S,7S)-7-fluoro-5-phenyl-6,7-dihydro-5H-pyrrolo[1,2-b][1,2,4]triazol-2-yl]sulfanyl]cyclopropanecarboxamide (100 mg, 0.31 mmol) in 1,4-dioxane (10 mL) was added triethylamine (158 mg, 1.57 mmol) and trifluoroacetic anhydride (198 mg, 0.94 mmol). The reaction mixture was stirred at 25° C. for 4 h and quenched by addition of water (20 mL). The mixture was extracted with ethyl acetate (3×15 mL). The combined organic layers were washed with saturated aqueous sodium bicarbonate (20 mL), dried over sodium sulfate and concentrated under reduced pressure. The residue was purified by column chromatography (silica gel, 100-200 mesh, 0 to 70% ethyl acetate in petroleum ether) to afford trans-2-[[(5S,7S)-7-fluoro-5-phenyl-6,7-dihydro-5H-pyrrolo[1,2-b][1,2,4]triazol-2-yl]sulfanyl]cyclopropane carbonitrile (70 mg, 74%) as a white solid. LCMS $R_T$=0.811 min, m/z=301.1 [M+H]$^+$.

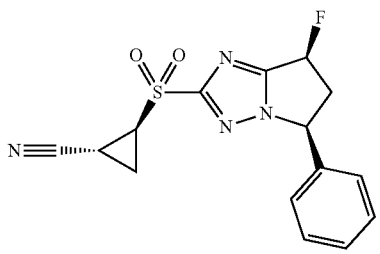

-continued

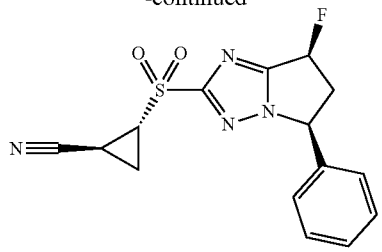

Step 5: (1R,2S)-2-[[(5S,7S)-7-fluoro-5-phenyl-6,7-dihydro-5H-pyrrolo[1,2-b][1,2,4]triazol-2-yl]sulfonyl]cyclopropanecarbonitrile and (1S,2R)-2-[[(5S,7S)-7-fluoro-5-phenyl-6,7-dihydro-5H-pyrrolo[1,2-b][1,2,4]triazol-2-yl]sulfonyl]cyclopropanecarbonitrile A mixture of trans-2-[[(5S,7S)-7-fluoro-5-phenyl-6,7-dihydro-5H-pyrrolo[1,2-b][1,2,4]triazol-2-yl]sulfanyl]cyclopropanecarbonitrile (70 mg, 0.23 mmol) and 3-chloroperoxybenzoicacid (85%, 187 mg, 0.93 mmol) in dichloromethane (10 mL) was stirred at 25° C. for 4 h. The mixture was diluted with water (30 mL) and extracted with dichloromethane (3×15 mL). The combined organic layers were washed with saturated aqueous sodium bicarbonate (20 mL), brine (15 mL), dried over sodium sulfate and concentrated under reduced pressure. The residue was purified by column chromatography (silica gel, 100-200 mesh, 0 to 80% ethyl acetate in petroleum ether) to afford trans-2-[[(5S,7S)-7-fluoro-5-phenyl-6,7-dihydro-5H-pyrrolo[1,2-b][1,2,4]triazol-2-yl]sulfonyl]cyclopropanecarbonitrile (60 mg, 77%) as a white solid. LCMS $R_T$=0.653 min, m/z=333.1 [M+H]$^+$.

The above racemic mixture (60 mg, 0.18 mmol) was further separated by chiral SFC to afford:

(1R,2S)-2-[[(5S,7S)-7-fluoro-5-phenyl-6,7-dihydro-5H-pyrrolo[1,2-b][1,2,4]triazol-2-yl]sulfonyl]cyclopropanecarbonitrile (Peak 1, retention time=2.795 min) (19.7 mg, 33%) as a white solid. 1H NMR (400 MHz, CD$_3$OD) δ 7.45-7.40 (m, 3H), 7.31-7.29 (m, 2H), 6.23-6.21 (m, 0.5H), 6.09-6.07 (m, 0.5H), 5.70-5.69 (m, 1H), 3.85-3.69 (m, 2H), 2.93-2.82 (m, 1H), 2.54-2.50 (m, 1H), 1.90-1.83 (m, 2H). LCMS $R_T$=0.655 min, m/z=333.1 [M+H]$^+$.

(1S,2R)-2-[[(5S,7S)-7-fluoro-5-phenyl-6,7-dihydro-5H-pyrrolo[1,2-b][1,2,4]triazol-2-yl]sulfonyl]cyclopropanecarbonitrile (Peak 2, retention time=3.005 min) (11.4 mg, 19%) as a white solid. $^1$H NMR (400 MHz, CD$_3$OD) δ 7.45-7.40 (m, 3H), 7.30-7.28 (m, 2H), 6.24-6.21 (m, 0.5H), 6.10-6.07 (m, 0.5H), 5.71-5.68 (m, 1H), 3.86-3.68 (m, 2H), 2.55-2.52 (m, 1H), 2.51-2.50 (m, 1H), 1.91-1.84 (m, 2H). LCMS $R_T$=0.655 min, m/z=333.1 [M+H]$^+$.

SFC conditions: Column: Daicel chiralpak AS-H (250 mm×30 mm, 5 um) Mobile phase: A: CO2 B: 0.1% ammonium hydroxide Ethanol Gradient: from 30% B to 30% B Flow rate: 65 mL/min Column temperature: 40° C.

Example 210: Method 47

Cis-3-[[(5S,7S)-7-fluoro-5-phenyl-6,7-dihydro-5H-pyrrolo[1,2-b][1,2,4]triazol-2-yl]sulfonyl]cyclobutanecarbonitrile

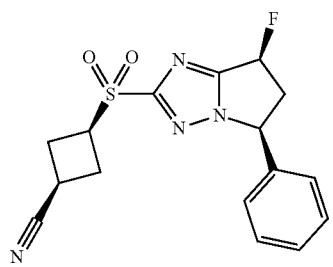 [SMILES: N#C[C@H]1C[C@@H](S(=O)(=O)c2nc3n(n2)[C@H](c2ccccc2)C[C@@H]3F)C1]

Step 1: trans-[3-[[(5S,7S)-7-fluoro-5-phenyl-6,7-dihydro-5H-pyrrolo[1,2-b][1,2,4]triazol-2-yl]sulfanyl]cyclobutyl] 4-nitrobenzoate

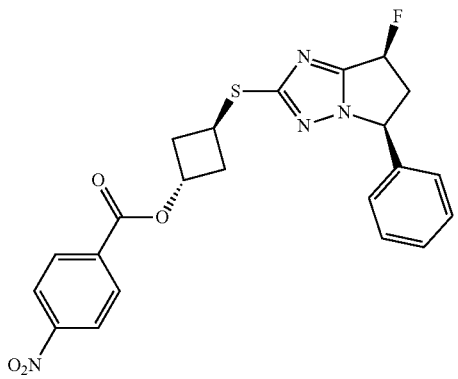 [SMILES: O=C(O[C@H]1C[C@H](Sc2nc3n(n2)[C@H](c2ccccc2)C[C@@H]3F)C1)c1ccc([N+](=O)[O-])cc1]

To a mixture of cis-3-[[(5S,7S)-7-fluoro-5-phenyl-6,7-dihydro-5H-pyrrolo[1,2-b][1,2,4]triazol-2-yl]sulfanyl]cyclobutanol (500 mg, 1.6 mmol), 4-nitrobenzoic acid (355 mg, 2.1 mmol) and triphenylphosphine (644 mg, 2.5 mmol) in tetrahydrofuran (15 mL) was added diisopropyl azodicarboxylate (497 mg, 2.5 mmol) at 0° C. under nitrogen atmosphere. The mixture was stirred at 50° C. for 16 h and diluted with water (30 mL). The resulting mixture was extracted with ethyl acetate (3×30 mL). The combined organic layers were washed with brine (10 mL), dried over sodium sulfate and concentrated under reduced pressure. The residue was purified by column chromatography (silica gel, 100-200 mesh, 0 to 50% ethyl acetate in petroleum ether) to give trans-[3-[[(5S,7S)-7-fluoro-5-phenyl-6,7-dihydro-5H-pyrrolo[1,2-b][1,2,4]triazol-2-yl]sulfanyl]cyclobutyl] 4-nitrobenzoate (950 mg, 43%) as a white solid. LCMS $R_T$=0.824 min, m/z=455.1 [M+H]$^+$.

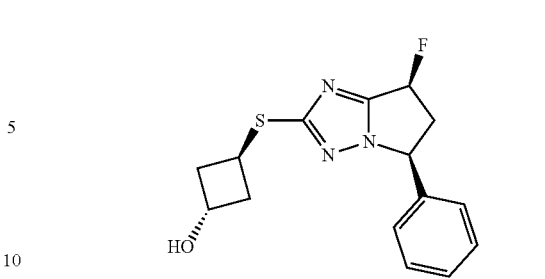

Step 2: trans-3-[[(5S,7S)-7-fluoro-5-phenyl-6,7-dihydro-5H-pyrrolo[1,2-b][1,2,4]triazol-2-yl]sulfanyl]cyclobutanol A mixture of potassium carbonate (175 mg, 1.3 mmol) and trans-[3-[[(5S,7S)-7-fluoro-5-phenyl-6,7-dihydro-5H-pyrrolo[1,2-b][1,2,4]triazol-2-yl]sulfanyl]cyclobutyl] 4-nitrobenzoate (850 mg, 0.64 mmol) in methanol (15 mL) and water (5 mL) was stirred at 25° C. for 1.5 h. The reaction was diluted with water (30 mL) and extracted with ethyl acetate (3×30 mL). The combined organic layers were washed with brine (10 mL), dried over sodium sulfate and concentrated under reduced pressure. The residue was purified by column chromatography (silica gel, 100-200 mesh, 0 to 50% ethyl acetate in petroleum ether) to afford trans-3-[[(5S,7S)-7-fluoro-5-phenyl-6,7-dihydro-5H-pyrrolo[1,2-b][1,2,4]triazol-2-yl]sulfanyl]cyclobutanol (430 mg, 43% purity, 41%) as a white solid.

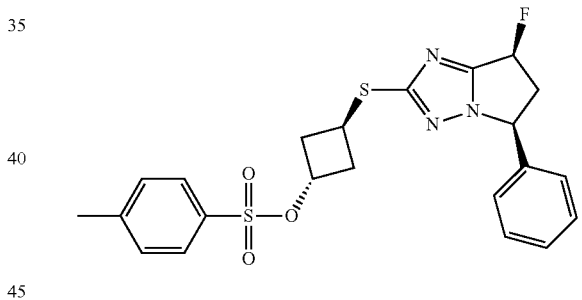

Step 3: trans-3-(((5S,7S)-7-fluoro-5-phenyl-6,7-dihydro-5H-pyrrolo[1,2-b][1,2,4]triazol-2-yl)thio)cyclobutyl 4-methylbenzenesulfonate To a mixture of trans-3-(((5S,7S)-7-fluoro-5-phenyl-6,7-dihydro-5H-pyrrolo[1,2-b][1,2,4]triazol-2-yl)thio)cyclobutanol (200 mg, 43% purity, 0.28 mmol), triethylamine (71 mg, 0.7 mmol) and 4-dimethylaminopyridine (7 mg, 0.06 mmol) in dichloromethane (10 mL) was added p-toluenesulfonyl chloride (80 mg, 0.42 mmol). The mixture was stirred at 20° C. for 2.5 h and quenched by addition of water (20 mL). The mixture was extracted with ethyl acetate (3×20 mL). The combined organic layers were washed with brine (30 mL), dried over sodium sulfate and concentrated under reduced pressure. The residue was purified by column chromatography (silica gel, 100-200 mesh, 0 to 50% ethyl acetate in petroleum ether) to afford trans-3-(((5S,7S)-7-fluoro-5-phenyl-6,7-dihydro-5H-pyrrolo[1,2-b][1,2,4]triazol-2-yl)thio)cyclobutyl 4-methylbenzenesulfonate (120 mg, 93%) as a white solid.

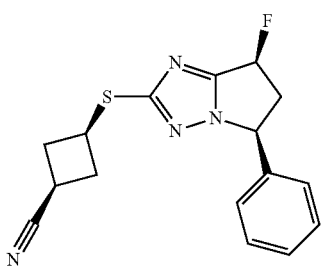 [SMILES: N#C[C@H]1C[C@@H](Sc2nc3n(n2)[C@H](c2ccccc2)C[C@@H]3F)C1]

Step 4: cis-3-(((5S,7S)-7-fluoro-5-phenyl-6,7-dihydro-5H-pyrrolo[1,2-b][1,2,4]triazol-2-yl)thio)cyclobutanecarbonitrile A mixture of trans-3-(((5S,7S)-7-fluoro-5-phenyl-6,7-dihydro-5H-pyrrolo[1,2-b][1,2,4]triazol-2-yl)thio)cyclobutyl 4-methylbenzenesulfonate (90 mg, 0.2 mmol) and sodium cyanide (19 mg, 0.39 mmol) in dimethyl sulfoxide (9 mL) was stirred at 100° C. for 16 h under nitrogen atmosphere. The reaction mixture was diluted with water (10 mL) and extracted with ethyl acetate (3×10 mL). The combined organic layers were dried over sodium sulfate and concentrated under reduced pressure. The residue purified by column chromatography (silica gel, 100-200 mesh, 0 to 40% ethyl acetate in petroleum ether) to give cis-3-(((5S,7S)-7-fluoro-5-phenyl-6,7-dihydro-5H-pyrrolo[1,2-b][1,2,4]triazol-2-yl)thio)cyclobutanecarbonitrile (80.0 mg, 81%) as colorless oil. LCMS $R_T$=0.685 min, m/z=315.1 [M+H]$^+$.

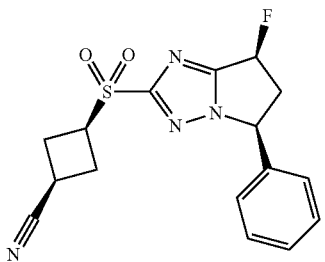 [SMILES: N#C[C@H]1C[C@@H](S(=O)(=O)c2nc3n(n2)[C@H](c2ccccc2)C[C@@H]3F)C1]

Step 5: cis3-[[(5S,7S)-7-fluoro-5-phenyl-6,7-dihydro-5H-pyrrolo[1,2-b][1,2,4]triazol-2-yl]sulfonyl]cyclobutanecarbonitrile A mixture of 3-chloroperoxybenzoic acid (85%, 155 mg, 0.76 mmol) and cis-3-(((5S,7S)-7-fluoro-5-phenyl-6,7-dihydro-5H-pyrrolo[1,2-b][1,2,4]triazol-2-yl)thio)cyclobutanecarbonitrile (60 mg, 0.19 mmol) in dichloromethane (4 mL) was stirred at 25° C. for 2 h and quenched by addition of saturated aqueous sodium bicarbonate (10 mL). The resulting mixture was extracted with dichloromethane (3×10 mL). The combined organic layers were washed with brine (10 mL), dried over sodium sulfate and concentrated under reduced pressure. The residue was purified by RP-HPLC (acetonitrile 28-58/0.05% hydrochloric acid in water) to afford cis-3-[[(5S,7S)-7-fluoro-5-phenyl-6,7-dihydro-5H-pyrrolo[1,2-b][1,2,4]triazol-2-yl]sulfonyl]cyclobutanecarbonitrile (14.6 mg, 21%) as a white solid. $^1$H NMR (400 MHz, DMSO-d$_6$) δ 7.46-7.38 (m, 3H), 7.28-7.26 (m, 2H), 6.35-6.18 (m, 1H), 5.77-5.73 (m, 1H), 4.43-4.35 (m, 1H), 3.83-3.69 (m, 1H), 3.49-3.43 (m, 1H), 2.79-2.74 (m, 1H), 2.72-2.57 (m, 4H). LCMS $R_T$=0.908 min, m/z=347.1 [M+H]$^+$.

Example 211: Method 34 trans-3-[[(5S,7S)-7-Fluoro-5-phenyl-6,7-dihydro-5H-pyrrolo[1,2-b][1,2,4]triazol-2-yl]sulfonyl]cyclobutanecarbonitrile

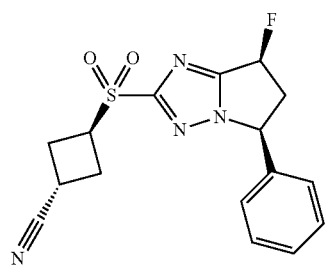 [SMILES: N#C[C@H]1C[C@H](S(=O)(=O)c2nc3n(n2)[C@H](c2ccccc2)C[C@@H]3F)C1]

Step 1: cis-3-(((5S,7S)-7-fluoro-5-phenyl-6,7-dihydro-5H-pyrrolo[1,2-b][1,2,4]triazol-2-yl)thio)cyclobutyl 4-methylbenzenesulfonate

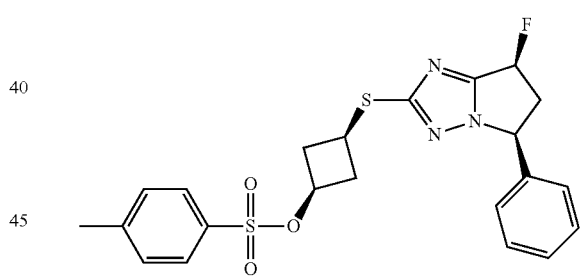

To a mixture of cis-3-(((5S,7S)-7-fluoro-5-phenyl-6,7-dihydro-5H-pyrrolo[1,2-b][1,2,4]triazol-2-yl)thio)cyclobutanol (110 mg, 0.36 mmol), triethylamine (91 mg, 0.9 mmol) and 4-dimethylaminopyridine (8.8 mg, 0.07 mmol) in dichloromethane (5 mL) was added p-toluenesulfonyl chloride (103 mg, 0.54 mmol). The mixture was stirred at 20° C. for 2.5 h and quenched by addition of water (20 mL). The resulting solution was extracted with ethyl acetate (3×20 mL). The combined organic layers were washed with brine (30 mL), dried over sodium sulfate and concentrated under reduced pressure. The residue was purified by column chromatography (silica gel, 100-200 mesh, 0 to 50% ethyl acetate in petroleum ether) to afford cis-3-(((5S,7S)-7-fluoro-5-phenyl-6,7-dihydro-5H-pyrrolo[1,2-b][1,2,4]triazol-2-yl)thio) cyclobutyl 4-methylbenzenesulfonate (165 mg, 99%) as a white solid.

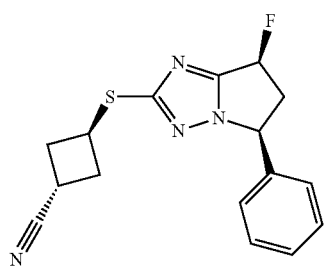 [SMILES: N#C[C@H]1C[C@H](Sc2nc3n(n2)[C@H](c2ccccc2)C[C@@H]3F)C1]

Step 2: trans-3-(((5S,7S)-7-fluoro-5-phenyl-6,7-dihydro-5H-pyrrolo[1,2-b][1,2,4]triazol-2-yl)thio)cyclobutanecarbonitrile A mixture of cis-3-(((5S,7S)-7-fluoro-5-phenyl-6,7-dihydro-5H-pyrrolo[1,2-b][1,2,4]triazol-2-yl)thio)cyclobutyl 4-methylbenzenesulfonate (145 mg, 0.32 mmol) and sodium cyanide (23 mg, 0.47 mmol) in dimethyl sulfoxide (10 mL) was stirred at 100° C. for 16 h under nitrogen atmosphere. The reaction mixture was diluted with water (10 mL) and extracted with ethyl acetate (3×10 mL). The combined organic layers were dried over sodium sulfate and concentrated under reduced pressure. The residue was purified by column chromatography (silica gel, 100-200 mesh, 0 to 40% ethyl acetate in petroleum ether) to give trans-3-(((5S,7S)-7-fluoro-5-phenyl-6,7-dihydro-5H-pyrrolo[1,2-b][1,2,4]triazol-2-yl)thio)cyclobutanecarbonitrile (80.0 mg, 81%) as colorless oil.

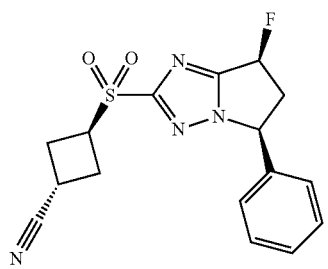 [SMILES: N#C[C@H]1C[C@H](S(=O)(=O)c2nc3n(n2)[C@H](c2ccccc2)C[C@@H]3F)C1]

Step 3: trans-3-[[(5S,7S)-7-fluoro-5-phenyl-6,7-dihydro-5H-pyrrolo[1,2-b][1,2,4]triazol-2-yl]sulfonyl]cyclobutanecarbonitrile A mixture of 3-chloroperoxybenzoic acid (85%, 180 mg, 0.89 mmol) and trans-3-(((5S,7S)-7-fluoro-5-phenyl-6,7-dihydro-5H-pyrrolo[1,2-b][1,2,4]triazol-2-yl)thio)cyclobutanecarbonitrile) (70 mg, 0.22 mmol) in dichloromethane (5 mL) was stirred at 25° C. for 2 h and quenched by addition of saturated aqueous sodium bicarbonate (10 mL). The resulting mixture was extracted with dichloromethane (3×10 mL). The combined organic layers were washed with brine (10 mL), dried over sodium sulfate and concentrated under reduced pressure. The residue was purified by RP-HPLC (acetonitrile 30-60/0.05% hydrochloric acid in water) to afford trans-3-[[(5S,7S)-7-fluoro-5-phenyl-6,7-dihydro-5H-pyrrolo[1,2-b][1,2,4]triazol-2-yl]sulfonyl]cyclobutanecarbonitrile (24.5 mg, 31%) as a white solid. $^1$H NMR (400 MHz, DMSO-$d_6$) 7.47-7.38 (m, 3H), 7.30-7.26 (m, 2H), 6.42-6.18 (m, 1H), 5.86-5.67 (m, 1H), 4.45-4.38 (m, 1H), 3.92-3.60 (m, 1H), 3.53-3.43 (m, 1H), 2.83-2.71 (m, 5H). LCMS $R_T$=0.923 min, m/z=347.1 [M+H]$^+$.

Example 213: Method 49

(5S,7S)-2-trans-[3-(difluoromethoxy)cyclobutyl]sulfonyl-7-fluoro-5-phenyl-6,7-dihydro-5H-pyrrolo[1,2-b][1,2,4]triazole

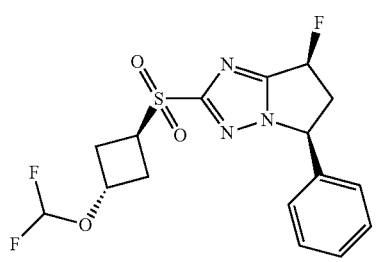 [SMILES: O=S(=O)(c1nc2n(n1)[C@H](c1ccccc1)C[C@@H]2F)[C@H]1C[C@H](OC(F)F)C1]

Step 1: (5S,7S)-2-trans-((3-(difluoromethoxy)cyclobutyl)thio)-7-fluoro-5-phenyl-6,7-dihydro-5H-pyrrolo[1,2-b][1,2,4]triazole

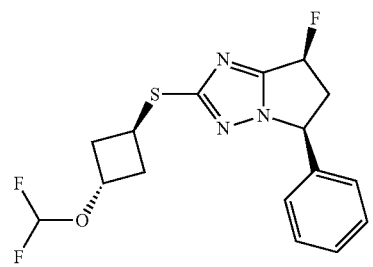 [SMILES: FC(F)O[C@H]1C[C@H](Sc2nc3n(n2)[C@H](c2ccccc2)C[C@@H]3F)C1]

To a solution of trans-3-(((5S,7S)-7-fluoro-5-phenyl-6,7-dihydro-5H-pyrrolo[1,2-b][1,2,4]triazol-2-yl)thio)cyclobutanol (200 mg, 0.28 mmol) and copper(I) iodide (16 mg, 0.08 mmol) in acetonitrile (2.0 mL) was added a solution of difluoro(fluorosulfonyl)acetic acid (75 mg, 0.42 mmol) in acetonitrile (1.0 mL) at 50° C. The mixture was stirred at 50° C. for 40 min and quenched by addition of water (30 mL). The resulting solution was extracted with ethyl acetate (3×30 mL). The combined organic layers were dried over sodium sulfate and concentrated under reduced pressure. The residue was purified by preparative TLC (40% ethyl acetate in petroleum ether, $R_f$=0.4) to give (5S,7S)-2-trans-[3-(difluoromethoxy)cyclobutyl]sulfanyl-7-fluoro-5-phenyl-6,7-dihydro-5H-pyrrolo[1,2-b][1,2,4]triazole (70 mg, 70%) as yellow oil. LCMS $R_T$=0.759 min, m/z=356.1 [M+H]$^+$.

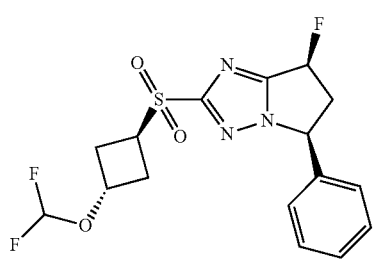 [SMILES: O=S(=O)(c1nc2n(n1)[C@H](c1ccccc1)C[C@@H]2F)[C@H]1C[C@H](OC(F)F)C1]

Step 2: (5S,7S)-2-trans-[3-(difluoromethoxy)cyclobutyl]sulfonyl-7-fluoro-5-phenyl-6,7-dihydro-5H-pyrrolo[1,2-b][1,2,4]triazole To a solution of (5S,7S)-2-trans-[3-(difluoromethoxy)cyclobutyl]sulfanyl-7-fluoro-5-phenyl-6,7-dihydro-5H-pyrrolo[1,2-b][1,2,4]triazole (60 mg, 0.17 mmol) in dichloromethane (3 mL) was added 3-chloroperoxybenzoic acid (85%, 137 mg, 0.68) at 25° C. The mixture was stirred at 25° C. for 1.5 h and quenched by addition of saturated aqueous sodium bicarbonate (10 mL). The resulting mixture was extracted with dichloromethane (3×10 mL). The combined organic layers were wished with brine (10 mL), dried over sodium sulfate and concentrated under reduced pressure. The residue was purified by RP-HPLC (acetonitrile 35-65/0.05% hydrochloric acid in water) to afford (5S,7S)-2-trans-[3-(difluoromethoxy)cyclobutyl]sulfonyl-7-fluoro-5-phenyl-6,7-dihydro-5H-pyrrolo[1,2-b][1,2,4]triazole (27.6 mg, 42%) as a white solid. $^1$H NMR (400 MHz, DMSO-d$_6$) δ 7.44-7.42 (m, 3H), 7.27-7.26 (m, 2H), 6.68 (t, J=75.6 Hz, 1H), 6.34-6.18 (m, 1H), 5.80-5.72 (m, 1H), 4.85-4.72 (m, 1H), 4.25-4.17 (m, 1H), 3.80-3.70 (m, 1H), 2.85-2.73 (m, 3H), 2.70-2.61 (m, 2H). LCMS R$_T$=1.026 min, m/z=388.1 [M+H]$^+$.

Example 214

(5S,7S)-5-(3-chloro-5-fluoro-phenyl)-2-cyclopropylsulfonyl-7-fluoro-6,7-dihydro-5H-pyrrolo[1,2-b][1,2,4]triazole

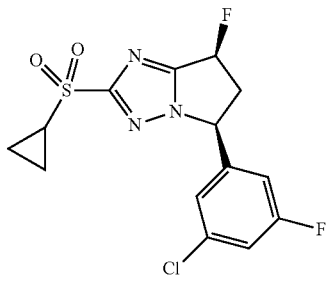 [SMILES: O=S(=O)(c1nc2n(n1)[C@H](c1cc(F)cc(Cl)c1)C[C@@H]2F)C1CC1]

(5S,7S)-5-(3-chloro-5-fluoro-phenyl)-2-cyclopropylsulfonyl-7-fluoro-6,7-dihydro-5H-pyrrolo[1,2-b][1,2,4]triazole was prepared according to method 18 starting from (5S,7S)-5-(3-chloro-5-fluorophenyl)-7-fluoro-6,7-dihydro-5H-pyrrolo[1,2-b][1,2,4]triazole-2-thiol (prepared according to method 23 starting from 3-chloro-5-fluorobenzoic acid). The final compound was purified by RP-HPLC (acetonitrile 40-70%/0.05% hydrochloric acid in water) to afford (5S,7S)-5-(3-chloro-5-fluoro-phenyl)-2-cyclopropylsulfonyl-7-fluoro-6,7-dihydro-5H-pyrrolo[1,2-b][1,2,4]triazole (18.3 mg, 33%) as a white solid. $^1$H NMR (400 MHz, CDCl$_3$) δ 7.16-7.12 (m, 1H), 7.08 (s, 1H), 6.90-6.86 (m, 1H), 6.13-5.96 (m, 1H), 5.51-5.46 (m, 1H), 3.75-3.60 (m, 1H), 3.02-2.91 (m, 1H), 2.80-2.72 (m, 1H), 1.52-1.46 (m, 2H), 1.20-1.13 (m, 2H). LCMS R$_T$=0.926 min, m/z=359.9 [M+H]$^+$.

Example 215

(5S,7S)-5-(3-chloro-5-fluoro-phenyl)-2-(difluoromethylsulfonyl)-7-fluoro-6,7-dihydro-5H-pyrrolo[1,2-b][1,2,4]triazole

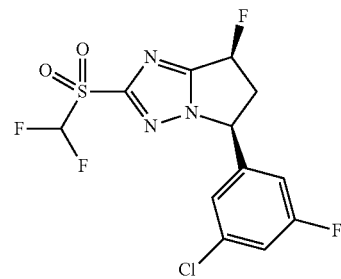 [SMILES: O=S(=O)(c1nc2n(n1)[C@H](c1cc(F)cc(Cl)c1)C[C@@H]2F)C(F)F]

(5S,7S)-5-(3-chloro-5-fluoro-phenyl)-2-(difluoromethylsulfonyl)-7-fluoro-6,7-dihydro-5H-pyrrolo[1,2-b][1,2,4]triazole was prepared according to method 6 starting from (5S,7S)-5-(3-chloro-5-fluorophenyl)-7-fluoro-6,7-dihydro-5H-pyrrolo[1,2-b][1,2,4]triazole-2-thiol (prepared according to method 6 starting from 3-chloro-5-fluorobenzoic acid. The final compound was purified by RP-HPLC (acetonitrile 45-75%/0.05% hydrochloric acid) to afford (5S,7S)-5-(3-chloro-5-fluoro-phenyl)-2-(difluoromethylsulfonyl)-7-fluoro-6,7-dihydro-5H-pyrrolo[1,2-b][1,2,4]triazole (40.9 mg, 62%) as a yellow solid. $^1$H NMR (400 MHz, CDCl$_3$) δ 7.18-7.14 (m, 1H), 7.07 (s, 1H), 6.88-6.84 (m, 1H), 6.44 (t, J=52.8 Hz, 1H), 6.17-6.00 (m, 1H), 5.58-5.53 (m, 1H), 3.79-3.64 (m, 1H), 3.07-2.96 (m, 1H). LCMS R$_T$=0.972 min, m/z=369.9 [M+H]$^+$.

Example 216 and Example 217

(5S,7S)-5-(2,3-difluorophenyl)-7-fluoro-2-[(1S,2S)-2-fluorocyclopropyl]sulfonyl-6,7-dihydro-5H-pyrrolo[1,2-b][1,2,4]triazole and (5S,7S)-5-(2,3-difluorophenyl)-7-fluoro-2-[(1R,2R)-2-fluorocyclopropyl]sulfonyl-6,7-dihydro-5H-pyrrolo[1,2-b][1,2,4]triazole

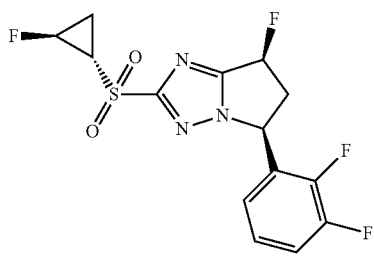

-continued

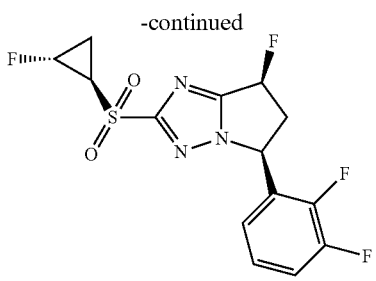

(5S,7S)-5-(2,3-difluorophenyl)-7-fluoro-2-[(1S,2S)-2-fluorocyclopropyl]sulfonyl-6,7-dihydro-5H-pyrrolo[1,2-b][1,2,4]triazole and (5S,7S)-5-(2,3-difluorophenyl)-7-fluoro-2-[(1R,2R)-2-fluorocyclopropyl]sulfonyl-6,7-dihydro-5H-pyrrolo[1,2-b][1,2,4]triazole were prepared according to method 30 starting from (5S,7S)-2-bromo-5-(2,3-difluorophenyl)-7-fluoro-6,7-dihydro-5H-pyrrolo[1,2-b][1,2,4]triazole. The final compound was purified first by preparative TLC (50% ethyl acetate in petroleum ether, $R_f$=0.6), and then by SFC to give:

(5S,7S)-5-(2,3-difluorophenyl)-7-fluoro-2-[(1S,2S)-2-fluorocyclopropyl]sulfonyl-6,7-dihydro-5H-pyrrolo[1,2-b][1,2,4]triazole (Peak 1, retention time=3.199 min) (22.5 mg, 20%) as a white solid. $^1$H NMR (400 MHz, CDCl$_3$) δ 7.27-7.19 (m, 1H), 7.18-7.07 (m, 1H), 6.84-6.67 (m, 1H), 6.21-5.97 (m, 1H), 5.90-5.88 (m, 1H), 5.30-5.01 (m, 1H), 3.79-3.73 (m, 1H), 3.25-3.16 (m, 1H), 3.08-2.86 (m, 1H), 2.01-1.75 (m, 2H). LCMS $R_T$=1.817 min, m/z=362.1 [M+H]$^+$.

Example 220: Method 50

2-(Difluoromethylsulfonyl)-7-phenyl-6,7-dihydro-5H-pyrrolo[1,2-b][1,2,4]triazole

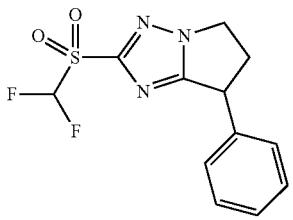 [SMILES: O=S(=O)(c1nc2n(n1)CCC2c1ccccc1)C(F)F]

Step 1: (5-bromo-2-tetrahydropyran-2-yl-1,2,4-triazol-3-yl)-phenyl-methanone

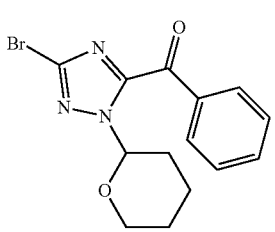 [SMILES: O=C(c1ccccc1)c1nc(Br)nn1C1CCCCO1]

To a cooled (−78° C.) solution of N-methoxy-N-methyl-benzamide (4.3 g, 26.0 mmol) and 3,5-dibromo-1-tetrahydropyran-2-yl-1,2,4-triazole (9.7 g, 31.2 mmol) in tetrahydrofuran (45 mL) was added isopropylmagnesium chloride (2.0 M in tetrahydrofuran, 15.6 mL, 31.2 mmol) dropwise under nitrogen atmosphere. The mixture was stirred at −78° C. for about 1 h and then at 15° C. for 16 h before quenched by addition of saturated aqueous ammonium chloride (100 mL). The resulting mixture was extracted with ethyl acetate (3×100 mL). The combined organic layers were dried over sodium sulfate and concentrated under reduced pressure. The residue was purified by column chromatography (silica gel, 100-200 mesh, 0 to 8% ethyl acetate in petroleum ether) to afford (5-bromo-2-tetrahydropyran-2-yl-1,2,4-triazol-3-yl)-phenyl-methanone (7.1 g, 81%) as colorless oil. LCMS $R_T$=0.795 min, m/z=254.0 [M+H]$^+$.

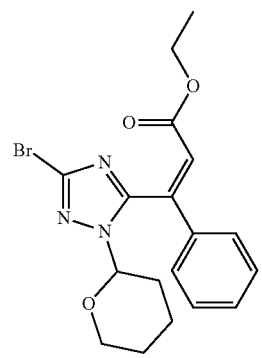 [SMILES: CCOC(=O)/C=C(/c1ccccc1)c1nc(Br)nn1C1CCCCO1]

Step 2: ethyl (E)-3-(5-bromo-2-tetrahydropyran-2-yl-1,2,4-triazol-3-yl)-3-phenyl-prop-2-enoate To an ice-cold suspension of sodium hydride (60%, 1014 mg, 25.3 mmol) in tetrahydrofuran (80 mL) was added triethyl phosphonoacetate (4.61 mL, 23.2 mmol). The reaction mixture was stirred at 20° C. for 15 min and a solution of (5-bromo-2-tetrahydropyran-2-yl-1,2,4-triazol-3-yl)-phenyl-methanone (7.1 g, 21.1 mmol) in tetrahydrofuran (20 mL) was added. The mixture was stirred at 20° C. for 1 h and quenched by addition of saturated aqueous ammonium chloride (100 mL). The solution was extracted with ethyl acetate (3×100 mL). The combined organic layers were dried over sodium sulfate and concentrated under reduced pressure. The residue was purified by column chromatography (silica gel, 100-200 mesh, 0 to 10% ethyl acetate in petroleum ether) to afford ethyl (E)-3-(5-bromo-2-tetrahydropyran-2-yl-1,2,4-triazol-3-yl)-3-phenyl-prop-2-enoate (8.0 g, 93%) as colorless oil. LCMS $R_T$=0.803 min, m/z=324.1 [M+H-85]$^+$.

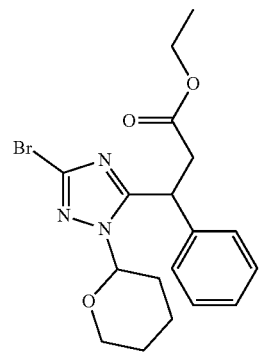 [SMILES: CCOC(=O)CC(c1ccccc1)c1nc(Br)nn1C1CCCCO1]

Step 3: ethyl 3-(5-bromo-2-tetrahydropyran-2-yl-1,2,4-triazol-3-yl)-3-phenyl-propanoate A mixture of ethyl (E)-3-(5-bromo-2-tetrahydropyran-2-yl-1,2,4-triazol-3-yl)-3-phenyl-prop-2-enoate (3.5 g, 8.6 mmol) and platinum oxide (0.6 g, 2.57 mmol) in ethyl acetate (20 mL) was hydrogenated (15 psi) at 20° C. for 16 h and filtered. The filtrate was concentrated under reduced pressure and the residue was purified by column chromatograph (silica gel, 100-200 mesh, 0-15% ethyl acetate in petroleum ether) to afford ethyl 3-(5-bromo-2-tetrahydropyran-2-yl-1,2,4-triazol-3-yl)-3-phenyl-propanoate (3.5 g, 99%) as a colorless oil. LCMS $R_T$=0.940 min, m/z=326.0 [M+H-85]$^+$.

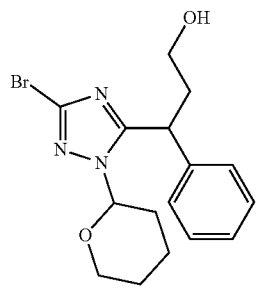 [SMILES: OCCC(c1ccccc1)c1nc(Br)nn1C1CCCCO1]

Step 4: 3-(5-bromo-2-tetrahydropyran-2-yl-1,2,4-triazol-3-yl)-3-phenyl-propan-1-ol To a solution of lithium borohydride (1.04 g, 47.8 mmol) in tetrahydrofuran (25 mL) was added ethyl 3-(5-bromo-2-tetrahydropyran-2-yl-1,2,4-triazol-3-yl)-3-phenyl-propanoate (6.50 g, 15.9 mmol). The mixture was stirred at 15° C. for 1 h and quenched by addition of saturated aqueous ammonium chloride (100 mL). The resulting mixture was extracted with ethyl acetate (3×100 mL). The combined organic layers were washed with water (100 mL), brine (100 mL), dried over sodium sulfate and concentrated under reduced pressure. The residue was purified by column chromatography (silica gel, 100-200 mesh, 0 to 50% ethyl acetate in petroleum ether) to afford 3-(5-bromo-2-tetrahydropyran-2-yl-1,2,4-triazol-3-yl)-3-phenyl-propan-1-ol (5.5 g, 94%) as a colorless oil. LCMS $R_T$=0.809 min, m/z=282.0 [M+H-85]$^+$.

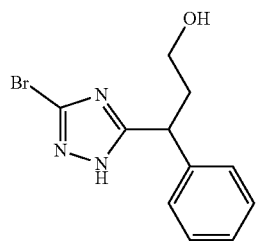 [SMILES: OCCC(c1ccccc1)c1nc(Br)n[nH]1]

Step 5: 3-(3-bromo-1H-1,2,4-triazol-5-yl)-3-phenyl-propan-1-ol

A mixture of 3-(5-bromo-2-tetrahydropyran-2-yl-1,2,4-triazol-3-yl)-3-phenyl-propan-1-ol (5.0 g, 13.7 mmol) and hydrochloric acid (4.0 M in methanol, 17.0 mL, 68.0 mmol) in methanol (50 mL) was stirred at 20° C. for 1 h and quenched by addition of saturated sodium carbonate (50 mL). The resulting solution was extracted with ethyl acetate (3×50 mL). The combined organic layers were dried over sodium sulfate and concentrated under reduced pressure. The residue was purified by column chromatography (100-200 mesh, silica gel, 50% ethyl acetate in petroleum ether) to afford 3-(3-bromo-1H-1,2,4-triazol-5-yl)-3-phenyl-propan-1-ol (2.4 g, 62%) as a white solid. LCMS $R_T$=0.538 min, m/z=282.0 [M+H]$^+$.

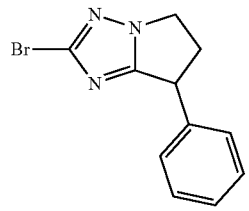 [SMILES: Brc1nc2n(n1)CCC2c1ccccc1]

Step 6: 2-bromo-7-phenyl-6,7-dihydro-5H-pyrrolo[1,2-b][1,2,4]triazole

To a solution of 3-(3-bromo-1H-1,2,4-triazol-5-yl)-3-phenyl-propan-1-ol (2.4 g, 8.5 mmol) and triphenylphosphine (2.7 g, 10.2 mmol) in tetrahydrofuran (50 mL) was added diisopropyl azodicarboxylate (2 mL, 10.2 mmol) at 25° C. under nitrogen atmosphere. The reaction was stirred at 25° C. for 12 h and concentrated under reduced pressure. The residue was purified by column chromatography (silica gel, 100-200 mesh, 0-20% ethyl acetate in petroleum ether) to afford 2-bromo-7-phenyl-6,7-dihydro-5H-pyrrolo[1,2-b][1,2,4]triazole (2.3 g, 60%) as a white solid. LCMS $R_T$=0.641 min, m/z=266.0 [M+H]$^+$.

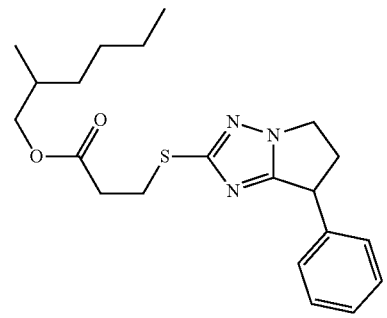 [SMILES: CCCCC(C)COC(=O)CCSc1nc2n(n1)CCC2c1ccccc1]

Step 7: 2-ethylhexyl 3-[(7-phenyl-6,7-dihydro-5H-pyrrolo[1,2-b][1,2,4]triazol-2-yl)sulfanyl]propanoate To a mixture of 2-bromo-7-phenyl-6,7-dihydro-5H-pyrrolo[1,2-b][1,2,4]triazole (190 mg, 0.72 mmol), N,N-diisopropylethylamine (0.38 mL, 2.2 mmol) and tris(dibenzylideneacetone) dipalladium(0) (198 mg, 0.22 mmol) was added 3-mercaptopropionic acid 2-ethylhexylester (189 mg, 0.86 mmol) and 4,5-bis(diphenylphosphino)-9,9-dimethylxanthene (416 mg, 0.72 mmol) in 1,4-dioxane (5 mL). The mixture was stirred at 110° C. for 15 h under nitrogen atmosphere and filtered. The filtrate was concentrated under reduced pressure and the residue was purified by column chromatography (silica gel, 100-200 mesh, 0 to 15% ethyl acetate in petroleum ether) to afford 2-ethylhexyl 3-[(7-phenyl-6,7-dihydro-5H-pyrrolo[1,2-b][1,2,4]triazol-2-yl)sulfanyl]propanoate (630 mg, 22% purity, 48%) as yellow oil. LCMS $R_T$=1.106 min, m/z=402.2 [M+H]$^+$.

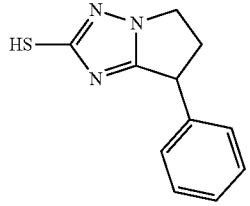

Step 8: 7-phenyl-6,7-dihydro-5H-pyrrolo[1,2-b][1,2,4]triazole-2-thiol

To a solution of 2-ethylhexyl 3-[(7-phenyl-6,7-dihydro-5H-pyrrolo[1,2-b][1,2,4]triazol-2-yl)sulfanyl]propanoate (630 mg, 1.57 mmol, crude) in ethanol (10 mL) was added sodium ethoxide (2 M in ethanol, 2.35 mL, 4.70 mmol). The reaction mixture was stirred at 25° C. for 1 h and concentrated under reduced pressure. The residue was diluted with water (30 mL) and washed with ethyl acetate (20 mL). The aqueous phase was adjusted to pH=6 by addition of citric acid and extracted with ethyl acetate (2×50 mL). The combined organic layers were dried over sodium sulfate and concentrated under reduce pressure to afford crude 7-phenyl-6,7-dihydro-5H-pyrrolo[1,2-b][1,2,4]triazole-2-thiol (200 mg, 42%) as a yellow solid. LCMS $R_T$=0.412 min, m/z=218.1 [M+H]$^+$.

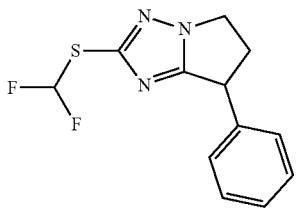 [SMILES: FC(F)Sc1nc2n(n1)CCC2c1ccccc1]

Step 9: 2-(difluoromethylsulfanyl)-7-phenyl-6,7-dihydro-5H-pyrrolo[1,2-b][1,2,4]triazole A mixture of sodium (2-chloro-2,2-difluoro-acetyl)oxide (88 mg, 0.58 mmol), 7-phenyl-6,7-dihydro-5H-pyrrolo[1,2-b][1,2,4]triazole-2-thiol (100 mg, 0.46 mmol) and potassium carbonate (159 mg, 1.15 mmol) in N,N-dimethylformamide (1.5 mL) was stirred at 90° C. for 10 min under nitrogen atmosphere. After cooled, the mixture was diluted with water (20 mL) and extracted with ethyl acetate (3×20 mL). The combined organic layers were washed with brine (20 mL), dried over sodium sulfate and concentrated under reduced pressure. The residue was purified by preparative TLC (30% ethyl acetate in petroleum ether, $R_f$=0.5) to give 2-(difluoromethylsulfanyl)-7-phenyl-6,7-dihydro-5H-pyrrolo[1,2-b][1,2,4]triazole (20 mg, 16%) as a light oil. LCMS $R_T$=0.682 min, m/z=268.1 [M+H]$^+$.

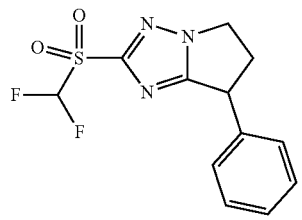 [SMILES: O=S(=O)(c1nc2n(n1)CCC2c1ccccc1)C(F)F]

Step 10: 2-(difluoromethylsulfonyl)-7-phenyl-6,7-dihydro-5H-pyrrolo[1,2-b][1,2,4]triazole A mixture of 2-(difluoromethylsulfanyl)-7-phenyl-6,7-dihydro-5H-pyrrolo[1,2-b][1,2,4]triazole (20 mg, 0.08 mmol), ruthenium(iii) chloride (2 mg, 0.008 mmol) and sodium periodate (64 mg, 0.30 mmol) in acetonitrile (0.5 mL), water (0.5 mL) and ethyl acetate (0.5 mL) was stirred at 30° C. for 1 h and filtered. The filtrate was diluted with water (10 mL) and extracted with ethyl acetate (3×5 mL). The combined organic layers were dried over sodium sulfate and concentrated under reduced pressure. The residue was purified by RP-HPLC (acetonitrile 37-67%/0.05% hydrochloride in water) to afford 2-(difluoromethylsulfonyl)-7-phenyl-6,7-dihydro-5H-pyrrolo[1,2-b][1,2,4]triazole (8.2 mg, 36%) as a white solid. $^1$H NMR (400 MHz, CDCl$_3$) δ 7.40-7.31 (m, 3H), 7.24-7.21 (m, 2H), 6.42 (t, J=53.2 Hz, 1H), 4.59-4.55 (m, 1H), 4.52-4.45 (m, 1H), 4.41-4.33 (m, 1H), 3.40-3.30 (m, 1H), 2.89-2.79 (m, 1H).

LCMS $R_T$=0.896 min, m/z=299.9 [M+H]$^+$.

Example 221 and Example 222

(1S,2S)-2-[[(5S,7S)-7-fluoro-5-phenyl-6,7-dihydro-5H-pyrrolo[1,2-b][1,2,4]triazol-2-yl]sulfonyl]cyclopropanecarbonitrile and (1R,2R)-2-[[(5S,7S)-7-fluoro-5-phenyl-6,7-dihydro-5H-pyrrolo[1,2-b][1,2,4]triazol-2-yl]sulfonyl]cyclopropanecarbonitrile

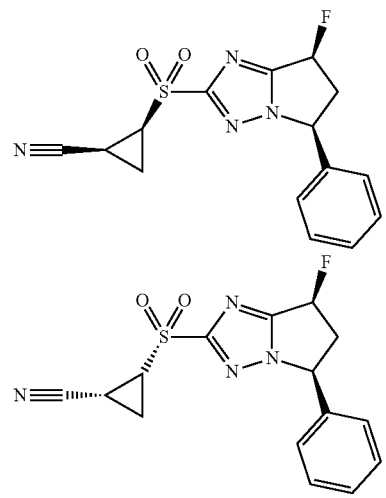

(1S,2S)-2-[[(5S,7S)-7-fluoro-5-phenyl-6,7-dihydro-5H-pyrrolo[1,2-b][1,2,4]triazol-2-yl]sulfonyl]cyclopropanecarbonitrile and (1R,2R)-2-[[(5S,7S)-7-fluoro-5-phenyl-6,7-dihydro-5H-pyrrolo[1,2-b][1,2,4]triazol-2-yl]sulfonyl]

cyclopropanecarbonitrile were prepared according to method 46 starting from cis-ethyl 2-(((5S,7S)-7-fluoro-5-phenyl-6,7-dihydro-5H-pyrrolo[1,2-b][1,2,4]triazol-2-yl)thio)cyclopropane carboxylate. The final compounds were purified first by RP-HPLC (acetonitrile 50-80%/0.05% ammonia hydroxide in water) and then by chiral SFC to give:

(1S,2S)-2-[[(5S,7S)-7-fluoro-5-phenyl-6,7-dihydro-5H-pyrrolo[1,2-b][1,2,4]triazol-2-yl]sulfonyl]cyclopropanecarbonitrile (Peak 1, retention time=4.876 min) (20.3 mg, 31%) as a white solid. $^1$H NMR (400 MHz, CD$_3$OD) δ 7.44-7.40 (m, 3H), 7.30-7.28 (m, 2H), 6.22-6.20 (m, 0.5H), 6.09-6.06 (m, 0.5H), 5.71-5.68 (m, 1H), 3.81-3.75 (m, 1H), 3.42-3.38 (m, 1H), 2.58-2.57 (m, 1H), 2.46-2.42 (m, 1H), 1.97-1.94 (m, 1H), 1.82-1.78 (m, 1H). LCMS R$_T$=0.628 min, m/z=333.1 [M+H]$^+$.

(1R,2R)-2-[[(5S,7S)-7-fluoro-5-phenyl-6,7-dihydro-5H-pyrrolo[1,2-b][1,2,4]triazol-2-yl]sulfonyl]cyclopropanecarbonitrile (Peak 2, retention time=5.573 min) (25.6 mg, 39%) as a white solid. 1H NMR (400 MHz, DMSO-d$_6$) δ 7.45-7.40 (m, 3H), 7.30-7.28 (m, 2H), 6.37-6.34 (m, 0.5H), 6.23-6.21 (m, 0.5H), 5.81-5.78 (m, 1H), 3.83-3.75 (m, 1H), 3.63-3.34 (m, 1H), 2.72-2.68 (m, 2H), 1.89-1.81 (m, 2H). LCMS R$_T$=0.627 min, m/z=333.1 [M+H]$^+$.

SFC conditions: Column: Phenomenex-Amylose-1 (250 mm×30 mm, 5 um) Mobile phase: A: C02 B: Ethanol (0.1% ammonium hydroxide) Gradient: from 40% to 40% of B Flow rate: 50 mL/min Column temperature: 35° C.

Example 223: Method 37

2-[[(5S,7S)-7-Fluoro-5-phenyl-6,7-dihydro-5H-pyrrolo[1,2-b][1,2,4]triazol-2-yl]sulfonyl]ethanol

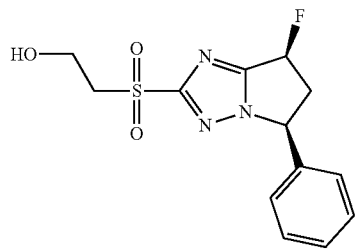 [SMILES: O=S(=O)(CCO)c1nc2n(n1)[C@H](c1ccccc1)C[C@@H]2F]

Step 1: 2-[[(5S,7S)-7-fluoro-5-phenyl-6,7-dihydro-5H-pyrrolo[1,2-b][1,2,4]triazol-2-yl]sulfanyl]ethanol

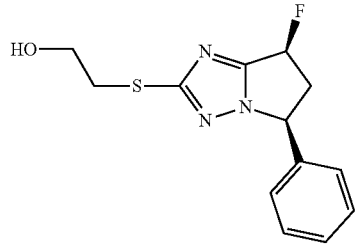 [SMILES: OCCSc1nc2n(n1)[C@H](c1ccccc1)C[C@@H]2F]

To a solution of (5S,7S)-7-fluoro-5-phenyl-6,7-dihydro-5H-pyrrolo[1,2-b][1,2,4]triazole-2-thiol (100 mg, 0.43 mmol) and 2-bromoethanol (200 mg, 1.6 mmol) in acetonitrile (3 mL) was added potassium carbonate (100 mg, 0.72 mmol) at 20° C. The resulting solution was stirred for 2 h and filtered. The filtrate was concentrated under reduced pressure and the residue was purified by column chromatography (silica gel, 100-200 mesh, 0 to 100% ethyl acetate in petroleum ether) to give 2-[[(5S,7S)-7-fluoro-5-phenyl-6,7-dihydro-5H-pyrrolo[1,2-b][1,2,4]triazol-2-yl]sulfanyl]ethanol (70 mg, 59%) as a yellow oil. LCMS R$_T$=0.593 min, m/z=280.1 [M+H]$^+$.

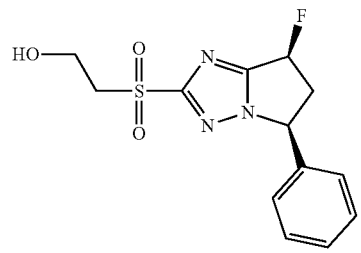 [SMILES: O=S(=O)(CCO)c1nc2n(n1)[C@H](c1ccccc1)C[C@@H]2F]

Step 2: 2-[[(5S,7S)-7-fluoro-5-phenyl-6,7-dihydro-5H-pyrrolo[1,2-b][1,2,4]triazol-2-yl]sulfonyl]ethanol A mixture of 2-[[(5S,7S)-7-fluoro-5-phenyl-6,7-dihydro-5H-pyrrolo[1,2-b][1,2,4]triazol-2-yl]sulfanyl]ethanol (50 mg, 0.18 mmol), ruthenium(iii) chloride (7 mg, 0.04 mmol) and sodium periodate (153 mg, 0.72 mmol) in acetonitrile (2 mL), water (2 mL) and ethyl acetate (2 mL) was stirred at 30° C. for 16 h and diluted with ethyl acetate (30 mL). The solution was washed with water (10 mL) and concentrated under reduced pressure. The residue was purified by RP-HPLC (acetonitrile 25-55%/0.225% formic acid in water) to give 2-[[(5S,7S)-7-fluoro-5-phenyl-6,7-dihydro-5H-pyrrolo[1,2-b][1,2,4]triazol-2-yl]sulfonyl]ethanol (18.7 mg, 31%) as a white solid. $^1$H NMR (400 MHz, DMSO-d$_6$) δ 7.45-7.40 (m, 3H), 7.40-7.24 (m, 2H), 6.34-6.17 (m, 1H), 5.77-5.73 (m, 1H), 4.99-4.95 (m, 1H), 3.79-3.72 (m, 3H), 3.63-3.59 (m, 2H), 2.67-2.66 (m, 1H). LCMS R$_T$=0.777 min, m/z=312.1 [M+H]$^+$.

Example 224

(5S,7S)-7-fluoro-2-(2-methoxyethylsulfonyl)-5-phenyl-6,7-dihydro-5H-pyrrolo[1,2-b][1,2,4]triazole

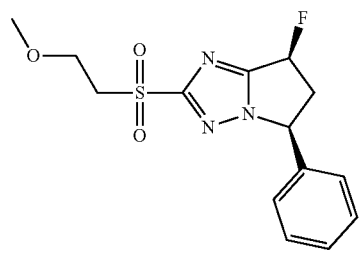 [SMILES: COCCS(=O)(=O)c1nc2n(n1)[C@H](c1ccccc1)C[C@@H]2F]

(5S,7S)-7-fluoro-2-(2-methoxyethylsulfonyl)-5-phenyl-6,7-dihydro-5H-pyrrolo[1,2-b][1,2,4]triazole was prepared according to method 26 starting from (5S,7S)-5-phenyl-7-fluoro-6,7-dihydro-5H-pyrrolo[1,2-b][1,2,4]triazole-2-thiol and 1-bromo-2-methoxyethane. The final compound was purified by RP-HPLC (acetonitrile 32-62%/0.225% formic acid in water) to give (5S,7S)-7-fluoro-2-(2-methoxyethylsulfonyl)-5-phenyl-6,7-dihydro-5H-pyrrolo[1,2-b][1,2,4]triazole (36.2 mg, 40%) as a white solid. $^1$H NMR (400 MHz, CD$_3$OD) δ 7.44-7.39 (m, 3H), 7.29-7.26 (m, 2H), 6.21-6.04 (m, 1H), 5.70-5.67 (m, 1H), 3.79-3.64 (m, 5H), 3.13 (s, 3H), 2.90-2.82 (m, 1H). LCMS R$_T$=0.865 min, m/z=326.1 [M+H]$^+$.

Example 227

(5S,7S)-7-fluoro-5-(3-fluorophenyl)-2-(oxetan-3-ylsulfonyl)-6,7-dihydro-5H-pyrrolo[1,2-b][1,2,4]triazole

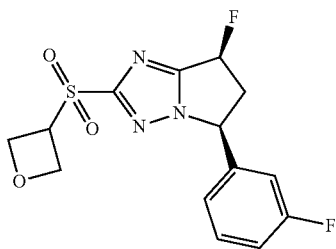 [SMILES: O=S(=O)(c1nc2n(n1)[C@H](c1cccc(F)c1)C[C@@H]2F)C1COC1]

(5S,7S)-7-fluoro-5-(3-fluorophenyl)-2-(oxetan-3-ylsulfonyl)-6,7-dihydro-5H-pyrrolo[1,2-b][1,2,4]triazole was prepared according to method 26 starting from (5S,7S)-7-fluoro-5-(3-fluorophenyl)-6,7-dihydro-5H-pyrrolo[1,2-b][1,2,4]triazole-2-thiol and oxetan-3-yl 4-methylbenzenesulfonate. The final compound was purified by RP-HPLC (acetonitrile 35-65%/0.05% ammonia hydroxide in water) to give (5S,7S)-7-fluoro-5-(3-fluorophenyl)-2-(oxetan-3-ylsulfonyl)-6,7-dihydro-5H-pyrrolo[1,2-b][1,2,4]triazole (8.3 mg, 25%) as colorless oil. H NMR (400 MHz, CDCl$_3$) δ 7.46-7.35 (m, 1H), 7.15-7.08 (m, 1H), 7.06-7.01 (m, 1H), 6.99-6.92 (m, 1H), 6.16-5.94 (m, 1H), 5.59-5.50 (m, 1H), 5.12-5.04 (m, 2H), 4.97-4.89 (m, 2H), 4.80-4.70 (m, 1H), 3.79-3.59 (m, 1H), 3.08-2.91 (m, 1H). LCMS R$_T$=0.883 min, m/z=342.1 [M+H]$^+$.

Example 228

(5S,7S)-7-fluoro-2-(oxetan-3-ylsulfonyl)-5-phenyl-6,7-dihydro-5H-pyrrolo[1,2-b][1,2,4]triazole

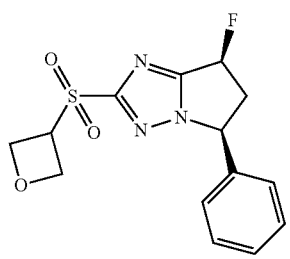 [SMILES: O=S(=O)(c1nc2n(n1)[C@H](c1ccccc1)C[C@@H]2F)C1COC1]

(5S,7S)-7-fluoro-2-(oxetan-3-ylsulfonyl)-5-phenyl-6,7-dihydro-5H-pyrrolo[1,2-b][1,2,4]triazole was prepared according to method 26 starting from (5S,7S)-5-phenyl-7-fluoro-6,7-dihydro-5H-pyrrolo[1,2-b][1,2,4]triazole-2-thiol and oxetan-3-yl 4-methylbenzenesulfonate. The final compound was purified by RP-TLC (50% ethyl acetate in petroleum ether, R$_f$=0.3) to afford (5S,7S)-7-fluoro-2-(oxetan-3-ylsulfonyl)-5-phenyl-6,7-dihydro-5H-pyrrolo[1,2-b][1,2,4]triazole (33.5 mg, 32%) as a white solid. $^1$H NMR (400 MHz, CDCl$_3$) δ 7.42-7.38 (m, 3H), 7.25-7.12 (m, 2H), 6.14-6.12 (m, 0.5H), 6.00-5.98 (m, 0.5H), 5.54-5.52 (m, 1H), 5.12-5.06 (m, 2H), 4.93-4.89 (m, 2H), 4.77-4.74 (m, 1H), 3.71-3.65 (m, 1H), 3.06-2.95 (m, 1H). LCMS R$_T$=0.706 min, m/z=324.1 [M+H]$^+$.

RIP1 Kinase Inhibition Assays (Biochemical Assay)

The compounds of the present invention were tested for their capacity to inhibit RIP1K activity as described below.

Enzyme Assay:

The ability of the receptor interacting protein kinase (RIPK1) to catalyze the hydrolysis of adenosine-5'-triphosphate (ATP) is monitored using the Transcreener ADP (adenosine-5'-diphosphate) assay (BellBrook Labs). Purified human RIP1 kinase domain (2-375) (50 nM) derived from a baculovirus-infected insect cell expression system is incubated with test compounds for 2 hours in 50 mM Hepes buffer (pH 7.5) containing 30 mM MgCl$_2$, 1 mM dithiothreitol, 50 uM ATP, 0.002% Brij-35, and 0.5% dimethyl sulfoxide (DMSO). Reactions are quenched by the addition of 1× Bell Brooks Stop buffer B (20 mM Hepes (ph7.5), 40 mM ethylenediaminetetraacetic acid and 0.02% Brij-35) containing an additional 12 mM EDTA and 55 ug/mL ADP2 antibody and 4 nM ADP-AlexaFluor® 633 tracer. The tracer bound to the antibody is displaced by the ADP generated during the RIP1K reaction, which causes a decrease in fluorescence polarization that is measured by laser excitation at 633 nm with a FP microplate reader M1000. Fractional activity was plotted against test article concentration. Using Genedata Screener software (Genedata; Basel, Switzerland), the data were fit to the tight-binding apparent inhibition constant (K$_i^{app}$) Morrison equation [Williams, J. W. and Morrison, J. F. (1979) The kinetics of reversible tight-binding inhibition. Methods Enzymol 63: 437-67]. The following equation was used to calculate fractional activity and K$_i^{app}$:

$$\text{Fractional activity} = \frac{V_i}{V_o} = 1 - \frac{([E]_T + [I]_T + K_i^{app}) - \sqrt{([E]_T + [I]_T + K_i^{app})^2 - 4[E]_T[I]_T}}{2[E]_T}$$

where [E]$_T$ and [I]$_T$ are the total concentrations of active enzyme and test article, respectively.

Exemplary compounds of the present invention are provided in Table 1 along with their physiochemical characterization and in vitro RIP1 kinase inhibitory activity data. "Method" in the first column of each table refers to the synthetic method(s) used to prepare each compound as shown in the Examples above. In certain examples, chiral column retention times (min) are provided for certain stereoisomers. Unless otherwise specified, the stereochemistry shown in each structure represents relative configuration of a single stereoisomer, and absolute configuration (i.e., "R" and/or "S") is arbitrarily assigned. In some embodiments, where the Method is described to include the separation of stereoisomers, a single stereoisomer of a compound of Table 1 is provided.

TABLE 1

| Example Synthetic Method | Structure | Ki (μM) | Stereo | ¹H NMR | MS (m/z) R.T. (min) |
|---|---|---|---|---|---|
| 1 Method 1 | 2-(difluoromethylsulfinyl)-5-phenyl-6,7-dihydro-5H-pyrrolo[1,2-b][1,2,4]triazole | 0.058 | Mixture of Diastereomers | ¹H NMR (400 MHz, DMSO-d6) δ 7.50-7.19 (m, 6H), 5.68 (dd, J = 8.1, 6.2 Hz, 1H), 3.30-3.02 (m, 3H), 2.69-2.52 (m, 1H). LC-MS RT = 3.78 min, m/z = 257.1 (M + H)⁺. | 284.0 3.96 |
| 2 Method 2 | 2-ethylsulfonyl-5-phenyl-6,7-dihydro-5H-pyrrolo[1,2-b][1,2,4]triazole | 0.864 | Mixture of Enantiomers | 1H NMR (400 MHz, DMSO-d6) δ 7.47-7.33 (m, 3H), 7.32-7.24 (m, 2H), 5.65 (dd, J = 8.1, 6.2 Hz, 1H), 3.45-2.99 (m, 5H), 2.67-2.52 (m, 1H), 1.17 (t, J = 7.4 Hz, 3H). | 278.1 3.80 |
| 3 Method 3 | (5S)-2-[(S)-ethylsulfinyl]-5-phenyl-6,7-dihydro-5H-pyrrolo[1,2-b][1,2,4]triazole | 0.162 | Single Unknown Stereoisomer | — | 262.0 3.37 |
| 4 Method 4 | 2-[difluoro(phenyl)methyl]sulfonyl-5-phenyl-6,7-dihydro-5H-pyrrolo[1,2-b][1,2,4]triazole | 0.152 | Mixture of Enantiomers | 1H NMR (400 MHz, DMSO-d6) δ 7.78-7.68 (m, 1H), 7.65-7.56 (m, 4H), 7.48-7.35 (m, 3H), 7.30-7.23 (m, 2H), 5.72 (dd, J = 8.6, 6.5 Hz, 1H), 3.33-3.05 (m, 3H), 2.73-2.57 (m, 1H). | 376.1 5.46 |
| 5 Method 4 | 2-[difluoro(phenyl)methyl]sulfinyl-5-phenyl-6,7-dihydro-5H-pyrrolo[1,2-b][1,2,4]triazole | 0.548 | Mixture of Diastereomers | 1H NMR (400 MHz, DMSO-d6) δ 7.60 (dt, J = 7.7, 4.0 Hz, 1H), 7.54-7.19 (m, 8H), 7.19-7.05 (m, 1H), 6.99 (dd, J = 7.4, 2.1 Hz, 1H), 5.54 (dd, J = 8.5, 6.1 Hz, 1H), 3.23-2.89 (m, 3H). | 360.1 4.90 |

TABLE 1-continued

| Example Synthetic Method | Structure | Ki (µM) | Stereo | ¹H NMR | MS (m/z) R.T. (min) |
|---|---|---|---|---|---|
| 6 Method 1 | 2-(difluoromethylsulfonyl)-5-phenyl-6,7-dihydro-5H-pyrrolo[1,2-b][1,2,4]triazole | 0.101 | Mixture of Enantiomers | ¹H NMR (400 MHz, DMSO-d6) δ 7.62-7.22 (m, 6H), 5.77-5.70 (m, 1H), 3.30-3.03 (m, 3H), 2.78-2.54 (m, 1H). | 300.1 4.46 |
| 7 Method 5 | (S)-5-(2-fluorophenyl)-2-methylsulfonyl-6,7-dihydro-5H-pyrrolo[1,2-b][1,2,4]triazole | 0.250 | Single Unknown Stereoisomer | ¹H NMR (400 MHz, CD₃OD) δ 7.43-7.40 (m, 1H), 7.22-7.19 (m, 3H), 5.84-5.79 (m, 1H), 3.34-3.33 (m, 1H), 3.24 (s, 3H), 3.24-3.14 (m, 2H), 2.78-2.71 (m, 1H) | 282.0 0.638 |
| 8 Method 6 | (S)-2-ethylsulfonyl-5-(2-fluorophenyl)-6,7-dihydro-5H-pyrrolo[1,2-b][1,2,4]triazole | 0.290 | Single Unknown Stereoisomer | ¹H NMR (400 MHz, CD₃OD) δ 7.41-7.38 (m, 1H), 7.21-7.17 (m, 3H), 5.83-5.79 (m, 1H), 3.37-3.25 (m, 3H), 3.25-3.08 (m, 2H), 2.75-2.70 (m, 1H), 1.25 (t, J = 7.6 Hz, 3H) | 295.9 0.784 |
| 9 Method 1 | 2-methylsulfonyl-5-phenyl-6,7-dihydro-5H-pyrrolo[1,2-b][1,2,4]triazole | 1.037 | Mixture of Enantiomers | ¹H NMR (400 MHz, DMSO-d6) δ 7.50-7.22 (m, 5H), 5.70-5.55 (m, 1H), 3.30 (s, 3H), 3.27-2.98 (m, 3H), 2.70-2.55 (m, 1H) | 264.1 3.53 |
| 10 Method 7 | 5-phenyl-2-(trifluoromethylsulfinyl)-6,7-dihydro-5H-pyrrolo[1,2-b][1,2,4]triazole | 0.089 | Mixture of Diastereomers | 1H NMR (400 MHz, DMSO-d6) δ 7.47-7.33 (m, 3H), 7.33-7.21 (m, 2H), 5.71 (dd, J = 8.1, 6.1 Hz, 1H), 3.39-3.04 (m, 3H), 2.69-2.56 (m, 1H). | 302.1 4.49 |

TABLE 1-continued

| Example Synthetic Method | Structure | Ki (μM) | Stereo | ¹H NMR | MS (m/z) R.T. (min) |
|---|---|---|---|---|---|
| 11 Method 1 | (5S)-2-[(R)-difluoromethylsulfinyl]-5-phenyl-6,7-dihydro-5H-pyrrolo[1,2-b][1,2,4]triazole | 0.010 | Single Unknown Stereoisomer | 1H NMR (400 MHz, DMSO-d6) δ 7.52-7.16 (m, 6H), 5.71-5.64 (m, 1H), 3.27-3.02 (m, 3H), 2.69-2.56 (m, 1H). | 284.1 3.94 |
| 12 Method 1 | (5S)-2-[(S)-difluoromethylsulfinyl]-5-phenyl-6,7-dihydro-5H-pyrrolo[1,2-b][1,2,4]triazole | 0.048 | Single Unknown Stereoisomer | 1H NMR (400 MHz, DMSO-d6) δ 7.51-7.16 (m, 6H), 5.72-5.64 (m, 1H), 3.28-3.01 (m, 3H), 2.70-2.55 (m, 1H). | 284.1 3.98 |
| 13 Method 8 | rac-(5S,7S)-2-(difluoromethylsulfinyl)-7-fluoro-5-phenyl-6,7-dihydro-5H-pyrrolo[1,2-b][1,2,4]triazole | 0.042 | Mixture of Diastereomers | ¹H NMR (400 MHz, CDCl₃) δ 7.41-7.38 (m, 3H), 7.24-7.22 (m, 2H), 6.95-6.68 (m, 1H), 6.12-6.09 (m, 0.5H), 5.95-5.90 (m, 0.5H), 5.76-5.70 (m, 0.5H), 5.53-5.51 (m, 0.5H), 3.70-3.61 (m, 0.5H), 3.45-3.35 (m, 0.5H), 3.03-2.96 (m, 1H) | 302.1 0.989 |
| 14 Method 9 | (5R,7R)-2-cyclopropylsulfonyl-7-fluoro-5-phenyl-6,7-dihydro-5H-pyrrolo[1,2-b][1,2,4]triazole | 0.980 | Single Unknown Stereoisomer | ¹H NMR (400 MHz, CD₃OD) δ 7.45-7.37 (m, 3H), 7.29-7.26 (m, 2H), 6.21-6.18 (m, 0.5H), 6.07-6.04 (m, 0.5H), 5.70-5.62 (m, 1H), 3.84-3.69 (m, 1H), 2.91-2.78 (m, 2H), 1.33-1.28 (m, 2H), 1.19-1.11 (m, 2H) | 308.1 0.695 |
| 15 Method 1 | (5R)-5-(2-chlorophenyl)-2-(difluoromethylsulfonyl)-6,7-dihydro-5H-pyrrolo[1,2-b][1,2,4]triazole b][1,2,4]triazole | 1.601 | Single Unknown Stereoisomer | 1H NMR (400 MHz, DMSO-d6) δ 7.60-7.53 (m, 1H), 7.48-7.29 (m, 3H), 7.16 (dd, J = 7.5, 1.9 Hz, 1H), 6.05 (dd, J = 8.6, 6.4 Hz, 1H), 3.43-3.10 (m, 3H), 2.70-2.56 (m, 1H). | 334.0 4.86 |

TABLE 1-continued

| Example Synthetic Method | Structure | Ki (μM) | Stereo | ¹H NMR | MS (m/z) R.T. (min) |
|---|---|---|---|---|---|
| 16 Method 1 | (5S)-5-(2-chlorophenyl)-2-(difluoromethylsulfonyl)-6,7-dihydro-5H-pyrrolo[1,2-b][1,2,4]triazole | 0.056 | Single Unknown Stereoisomer | 1H NMR (400 MHz, DMSO-d6) δ 7.61-7.52 (m, 1H), 7.51-7.28 (m, 3H), 7.16 (dd, J = 7.5, 1.9 Hz, 1H), 6.05 (dd, J = 8.6, 6.4 Hz, 1H), 3.31-3.08 (m, 3H), 2.70-2.57 (m, 1H). | 334.0 4.86 |
| 17 Method 1 | (5S)-5-(2-chlorophenyl)-2-[(S)-difluoromethylsulfinyl]-6,7-dihydro-5H-pyrrolo[1,2-b][1,2,4]triazole | 0.050 | Single Unknown Stereoisomer | 1H NMR (400 MHz, DMSO-d6) δ 7.56 (dd, J = 7.8, 1.5 Hz, 1H), 7.53-7.18 (m, 3H), 7.06 (dd, J = 7.5, 1.9 Hz, 1H), 5.99 (dd, J = 8.6, 6.0 Hz, 1H), 3.35-3.22 (m, 1H), 3.20-3.08 (m, 2H), 2.59 (ddt, J = 12.8, 8.8, 6.3 Hz, 1H). | 318.0 4.44 |
| 18 Method 1 | (5S)-5-(2-chlorophenyl)-2-[(R)-difluoromethylsulfinyl]-6,7-dihydro-5H-pyrrolo[1,2-b][1,2,4]triazole | 0.008 | Single Unknown Stereoisomer | 1H NMR (400 MHz, DMSO-d6) δ 7.61-7.52 (m, 1H), 7.52-7.20 (m, 3H), 7.08 (dd, J = 7.5, 1.9 Hz, 1H), 5.99 (dd, J = 8.6, 5.9 Hz, 1H), 3.34-3.25 (m, 1H), 3.19-3.07 (m, 2H), 2.66-2.53 (m, 1H). | 318.0 4.43 |
| 19 Method 10 | (5S,7S)-2-benzylsulfonyl-7-fluoro-5-phenyl-6,7-dihydro-5H-pyrrolo[1,2-b][1,2,4]triazole | 0.015 | Single Unknown Stereoisomer | ¹H NMR (400 MHz, CDCl₃) δ 7.45-7.38 (m, 5H), 7.32-7.25 (m, 3H), 7.13-7.11 (m, 2H), 6.10-5.94 (m, 1H), 5.49-5.45 (m, 1H), 4.65-4.57 (m, 2H), 3.69-3.58 (m, 1H), 3.01-2.90 (m, 1H) | 358.1 1.910 |
| 20 Method 11 | (5S,7S)-2-benzylsulfinyl-7-fluoro-5-phenyl-6,7-dihydro-5H-pyrrolo[1,2-b][1,2,4]triazole | 0.024 | Mixture of Diastereomers | ¹H NMR (400 MHz, CDCl₃) δ 7.40-7.36 (m, 3H), 7.28-7.26 (m, 3H), 7.21-7.15 (m, 3H), 7.12-7.09 (m, 1H), 6.12-5.96 (m, 1H), 5.47-5.43 (m, 1H), 4.56-4.39 (m, 2H), 3.67-3.59 (m, 1H), 3.00-2.89 (m, 1H) | 342.1 1.734 |

TABLE 1-continued

| Example Synthetic Method | Structure | Ki (μM) | Stereo | ¹H NMR | MS (m/z) R.T. (min) |
|---|---|---|---|---|---|
| 21 Method 12 | (5S,7S)-2-[(S)-difluoromethylsulfinyl]-7-fluoro-5-phenyl-6,7-dihydro-5H-pyrrolo[1,2-b][1,2,4]triazole | 0.100 | Single Unknown Stereoisomer | ¹H NMR (400 MHz, CD₃OD) δ 7.42-7.40 (m, 3H), 7.40-7.26 (m, 2H), 7.09-6.95 (m, 1H), 6.23-6.20 (m, 0.5H), 6.08-6.06 (m, 0.5H), 5.71-5.69 (m, 1H), 3.83-3.73 (m, 1H), 2.91-2.80 (m, 1H) | 302.0 1.630 |
| 22 Method 12 | (5S,7S)-2-[(R)-difluoromethylsulfinyl]-7-fluoro-5-phenyl-6,7-dihydro-5H-pyrrolo[1,2-b][1,2,4]triazole | 0.003 | Single Unknown Stereoisomer | ¹H NMR (400 MHz, CD₃OD) δ 7.43-7.41 (m, 3H), 7.30-7.22 (m, 2H), 7.09-6.95 (m, 1H), 6.23-6.21 (m, 0.5H), 6.09-6.07 (m, 0.5H), 5.70-5.69 (m, 1H), 3.84-3.73 (m, 1H), 2.85-2.81 (m, 1H) | 302.0 1.602 |
| 23 Method 13 | (5S,7S)-2-(difluoromethylsulfonyl)-7-fluoro-5-phenyl-6,7-dihydro-5H-pyrrolo[1,2-b][1,2,4]triazole | 0.005 | Single Unknown Stereoisomer | ¹H NMR (400 MHz, CD₃OD) δ 7.44-7.42 (m, 3H), 7.30-7.27 (m, 2H), 7.08-6.95 (m, 1H), 6.24-6.22 (m, 0.5H), 6.10-6.08 (m, 0.5H), 5.74-5.72 (m, 1H), 3.84-3.74 (m, 1H), 2.93-2.82 (m, 1H) | 318.0 1.823 |
| 24 Method 14 | (5S,7S)-2-tert-butylsulfinyl-7-fluoro-5-phenyl-6,7-dihydro-5H-pyrrolo[1,2-b][1,2,4]triazole | 0.020 | Mixture of Diastereomers | ¹H NMR (400 MHz, CD₃OD) δ 7.40-7.38 (m, 3H), 7.25-7.22 (m, 2H), 6.19-6.16 (m, 0.5H), 6.05-6.02 (m, 0.5H), 5.64-5.62 (m, 1H), 3.80-3.70 (m, 1H), 2.86-2.78 (m, 1H), 1.70 (s, 9H) | 308.1 0.726 |

TABLE 1-continued

| Example Synthetic Method | Structure | Ki (μM) | Stereo | ¹H NMR | MS (m/z) R.T. (min) |
|---|---|---|---|---|---|
| 25 Method 15 | (5S,7S)-2-tert-butylsulfonyl-7-fluoro-5-phenyl-6,7-dihydro-5H-pyrrolo[1,2-b][1,2,4]triazole | 0.032 | Single Unknown Stereoisomer | ¹H NMR (400 MHz, CD₃OD) δ 7.43-7.38 (m, 3H), 7.27-7.25 (m, 2H), 6.22-6.20 (m, 0.5H), 6.08-6.06 (m, 0.5H), 5.69-5.68 (m, 1H), 3.83-3.75 (m, 1H), 2.86-2.79 (m, 1H), 1.36 (s, 9H) | 324.1 0.612 |
| 26 Method 16 | (5S,7S)-2-(benzenesulfonyl)-7-fluoro-5-phenyl-6,7-dihydro-5H-pyrrolo[1,2-b][1,2,4]triazole | 3.2 | Single Unknown Stereoisomer | ¹H NMR (400 MHz, CDCl₃) δ 8.13 (d, J = 7.2 Hz, 2H), 7.73-7.62 (m, 1H), 7.61-7.53 (m, 2H), 7.40-7.38 (m, 3H), 7.22-7.20 (m, 2H), 6.04-5.88 (m, 1H), 5.49-5.46 (m, 1H), 3.67-3.54 (m, 1H), 2.99-2.89 (m, 1H) | 343.9 0.879 |
| 27 Method 43 | (5S,7S)-2-cyclopropylsulfinyl-7-fluoro-5-phenyl-6,7-dihydro-5H-pyrrolo[1,2-b][1,2,4]triazole | 0.033 | Mixture of Diastereomers | ¹H NMR (400 MHz, CDCl₃) δ 7.41-7.17 (m, 3H), 7.13-7.06 (m, 2H, 6.05-5.76 (m, 1H), 5.37-5.21 (m, 1H, 3.59-3.48 (m, 1H), 2.96-2.74 (m, 1H), 2.73-2.52 (m, 1H, 1.28-1.15 (m, 1H, 1.01-0.85 (m, 3H). | 291.9 0.795 |
| 28 Method 43 | (5S,7S)-2-[(R)-cyclopropylsulfinyl]-7-fluoro-5-phenyl-6,7-dihydro-5H-pyrrolo[1,2-b][1,2,4]triazole | 0.089 | Single Unknown Stereoisomer | ¹H NMR (400 MHz, CDCl₃) δ 7.44-7.38 (m, 3H), 7.27-7.24 (m, 2H), 6.15-5.95 (m, 1H), 5.53-5.48 (m, 1H), 3.71-3.62 (m, 1H), 3.03-2.97 (m, 1H), 2.82-2.77 (m, 1H), 1.37-1.35 (m, 1H), 1.11-1.02 (m, 3H). | 292.0 0.779 |

TABLE 1-continued

| Example Synthetic Method | Structure | Ki (μM) | Stereo | ¹H NMR | MS (m/z) R.T. (min) |
|---|---|---|---|---|---|
| 29 Method 43 | (5S,7S)-2-[(S)-cyclopropylsulfinyl]-7-fluoro-5-phenyl-6,7-dihydro-5H-pyrrolo[1,2-b][1,2,4]triazole | 0.004 | Single Unknown Stereoisomer | ¹H NMR (400 MHz, CDCl₃) δ 7.43-7.37 (m, 3H), 7.27-7.22 (m, 2H), 6.12-5.95 (m, 1H), 5.52-5.48 (m, 1H), 3.71-3.62 (m, 1H), 3.02-2.95 (m, 1H), 2.79-2.75 (m, 1H), 1.35-1.33 (m, 1H), 1.10-1.01 (m, 3H). | 291.9 0.769 |
| 30 Method 17 | (5S,7S)-2-cyclopropylsulfonyl-7-fluoro-5-phenyl-6,7-dihydro-5H-pyrrolo[1,2-b][1,2,4]triazole | 0.004 | Single Known Stereoisomer | ¹H NMR (40 MHz, CDCl₃) δ 7.42-7.39 (m, 3H), 7.26-7.24 (m, 2H), 6.11 (dd, J = 1.6, 7.6 Hz, 0.5H), 5.99 (d, J = 5.6 Hz, 0.5H), 5.56-5.49 (m, 1H), 3.70-3.61 (m, 1H), 3.06-2.92 (m, 1H), 2.78-2.71 (m, 1H), 1.52-1.43 (m, 2H), 1.16-1.11 (m, 2H). | 308.1 0.736 |
| 31 Method 18 | (4S,6S)-2-cyclopropylsulfonyl-4-fluoro-6-phenyl-5,6-dihydro-4H-pyrrolo[1,2-b]pyrazole | 0.010 | Single Unknown Stereoisomer | ¹H NMR (400 MHz, CDCl₃) δ 7.40-7.35 (m, 3H), 7.22-7.20 (m, 2H), 6.89 (s, 1H), 6.10 (d, J = 6.4 Hz, 0.5H), 5.95 (d, J = 6.4 Hz, 0.5H), 5.55-5.52 (m, 1H), 3.56-3.48 (m, 1H), 2.92-2.82 (m, 1H), 2.65-2.61 (m, 1H), 1.38-1.36 (m, 2H), 1.05-1.03 (m, 2H). | 306.9 0.835 |
| 32 Method 18 | (5S,7S)-5-(2-chlorophenyl)-2-cyclopropylsulfonyl-7-fluoro-6,7-dihydro-5H-pyrrolo[1,2-b][1,2,4]triazole | 0.003 | Single Unknown Stereoisomer | ¹H NMR (400 MHz, CDCl₃) δ 7.47-7.44 (m, 1H), 7.36-7.22 (m, 3H), 6.75 (dd, J = 1.2, 7.6 Hz, 1H), 6.12-5.93 (m, 2H), 3.80-3.65 (m, 1H), 2.94-2.81 (m, 1H), 2.80-2.76 (m, 1H), 1.55-1.48 (m, 2H), 1.20-1.13 (m, 2H). | 342.1 0.798 |

TABLE 1-continued

| Example Synthetic Method | Structure | Ki (µM) | Stereo | ¹H NMR | MS (m/z) R.T. (min) |
|---|---|---|---|---|---|
| 33 Method 18 | (5S,7S)-2-cyclopropylsulfonyl-7-fluoro-5-(2-fluorophenyl)-6,7-dihydro-5H-pyrrolo[1,2-b][1,2,4]triazole | 0.005 | Single Unknown Stereoisomer | ¹H NMR (400 MHz, CDCl₃) δ 7.40-7.37 (m, 1H), 7.19-7.15 (m, 2H), 7.12-6.99 (m, 1H), 6.14-5.98 (m, 1H), 5.88-5.84 (m, 1H), 3.77-3.71 (m, 1H), 3.00-2.90 (m, 1H), 2.79-2.75 (m, 1H), 1.52-1.48 (m, 2H), 1.19-1.15 (m, 2H). | 325.9 0.831 |
| 34 Method 18 | (5S,7S)-2-cyclopropylsulfonyl-7-fluoro-5-(4-fluorophenyl)-6,7-dihydro-5H-pyrrolo[1,2-b][1,2,4]triazole | 0.010 | Single Unknown Stereoisomer | ¹H NMR (400 MHz, CD₃OD) δ 7.41-7.29 (m, 2H, 7.19-7.15 (m, 2H, 6.24-6.02 (m, 1H), 5.68 (s, 1H), 3.83-3.69 (m, 1H), 2.94-2.76 (m, 2H), 1.38-1.30 (m, 2H), 1.22-1.08 (m, 2H). | 326.2 0.961 |
| 35 Method 18 | (5S,7S)-2-cyclopropylsulfonyl-5-(2,6-difluorophenyl)-7-fluoro-6,7-dihydro-5H-pyrrolo[1,2-b][1,2,4]triazole | 0.005 | Single Unknown Stereoisomer | ¹H NMR (400 MHz, CD₃OD) δ 7.57-7.44 (m, 1H), 7.11-7.07 (m, 2H, 6.26-6.07 (m, 1H), 6.03-5.95 (m, 1H), 3.93-3.79 (m, 1H), 3.03-2.88 (m, 1H), 2.88-2.79 (m, 1H), 1.36-1.25 (m, 2H, 1.20-1.11 (m, 2H). | 344.1 0.973 |
| 36 Method 18 | (5R,7R)-2-cyclopropylsulfonyl-5-(2,3-difluorophenyl)-7-fluoro-6,7-dihydro-5H-pyrrolo[1,2-b][1,2,4]triazole | 0.880 | Single Unknown Stereoisomer | ¹H NMR (400 MHz, CDCl₃) δ 7.25-7.17 (m, 1H), 7.16-7.08 (m, 1H), 6.81-6.68 (m, 1H), 6.13 (dd, J = 2.0, 7.6 Hz, 0.5H), 5.99 (J = 5.2 Hz, 0.5H), 5.91-5.81 (m, 1H), 3.78-3.70 (m, 1H), 3.03-2.89 (m, 1H), 2.79-2.69 (m, 1H), 1.51-1.48 (m, 2H), 1.18-1.14 (m, 2H). | 344.1 0.641 |

TABLE 1-continued

| Example Synthetic Method | Structure | Ki (μM) | Stereo | ¹H NMR | MS (m/z) R.T. (min) |
|---|---|---|---|---|---|
| 37 Method 18 | (5S,7S)-2-cyclopropylsulfonyl-5-(2,5-difluorophenyl)-7-fluoro-6,7-dihydro-5H-pyrrolo[1,2-b][1,2,4]triazole | 0.006 | Single Unknown Stereoisomer | ¹H NMR (400 MHz, CDCl₃) δ 7.17-7.04 (m, 2H, 6.70-6.64 (m, 1H, 6.14-5.95 (m, 1H, 5.85-5.77 (m, 1H, 3.84-3.59 (m, 1H, 3.07-2.87 (m, 1H, 2.84-2.70 (m, 1H, 1.53-1.50 (m, 2H, 1.19-1.15 (m, 2H). | 344.1 1.001 |
| 38 Method 18 | (5S,7S)-2-cyclopropylsulfonyl-7-fluoro-5-(2,3,6-trifluorophenyl)-6,7-dihydro-5H-pyrrolo[1,2-b][1,2,4]triazole | 0.010 | Single Unknown Stereoisomer | ¹H NMR (400 MHz, CD₃OD) δ 7.46-7.43 (m, 1H), 7.12-7.09 (m, 1H), 6.26 (dd, J = 4.0, 8.0 Hz, 0.5H), 6.11 (d, J = 7.6 Hz, 0.5H), 6.09-6.00 (m, 1H), 3.92-3.85 (m, 1H), 2.98-2.86 (m, 1H), 2.85-2.82 (m, 1H), 1.32-1.28 (m, 2H), 1.17-1.15 (m, 2H). | 362.1 0.988 |
| 39 Method 19 | rac-(5S,7S)-2-cyclopropylsulfonyl-7-fluoro-5-(2,3,5-trifluorophenyl)-6,7-dihydro-5H-pyrrolo[1,2-b][1,2,4]triazole | 0.006 | Single Unknown Stereoisomer | ¹H NMR (400 MHz, CD₃OD) δ 7.32-7.25 (m, 1H, 6.81-6.78 (m, 1H, 6.24-6.08 (m, 1H, 5.97-5.92 (m, 1H, 3.90-3.77 (m, 1H, 2.98-2.85 (m, 2H, 1.36-1.29 (m, 2H, 1.20-1.14 (m, 2H). | 362.1 1.025 |
| 40 Method 18 | (5S,7S)-2-cyclopropylsulfonyl-5-(2,3-difluorophenyl)-7-fluoro-6,7-dihydro-5H-pyrrolo[1,2-b][1,2,4]triazole | 0.005 | Single Unknown Stereoisomer | ¹H NMR (400 MHz, CD₃OD) δ 7.37-7.28 (m, 1H), 7.25-7.17 (m, 1H), 6.97-6.91 (m, 1H), 6.21-6.19 (m, 0.5H), 6.07-6.05 (m, 0.5H), 5.97-5.89 (m, 1H), 3.89-3.74 (m, 1H), 2.95-2.80 (m, 2H), 1.34-1.25 (m, 2H), 1.16-1.13 (m, 2H). | 344.1 0.641 |

TABLE 1-continued

| Example Synthetic Method | Structure | Ki (μM) | Stereo | ¹H NMR | MS (m/z) R.T. (min) |
|---|---|---|---|---|---|
| 41 Method 19 | (5S,7S)-2-cyclopropylsulfonyl-7-deuterio-5-phenyl-6,7-dihydro-5H-pyrrolo[1,2-b][1,2,4]triazole | 0.140 | Single Unknown Stereoisomer | ¹H NMR (400 MHz, CD₃OD) δ 7.42-7.30 (m, 3H), 7.27-7.22 (m, 2H), 5.60-5.55 (m, 1H), 3.27-3.19 (m, 1H), 3.13-3.06 (m, 1H), 2.85-2.72 (m, 1H), 2.76-2.60 (m, 1H), 1.30-1.24 (m, 2H), 1.16-1.11 (m, 2H). | 291.1 1.453 |
| 42 Method 18 | (5S,7S)-2-cyclopropylsulfonyl-5-(3,5-difluorophenyl)-7-fluoro-6,7-dihydro-5H-pyrrolo[1,2-b][1,2,4]triazole | <0.005 | Single Unknown Stereoisomer | ¹H NMR (400 MHz, CDCl₃) δ 6.89-6.77 (m, 3H), 6.14-5.95 (m, 1H), 5.53-5.48 (m, 1H), 3.76-3.59 (m, 1H), 3.04-2.91 (m, 1H), 2.78-2.74 (m, 1H), 1.53-1.47 (m, 2H), 1.17-1.15 (m, 2H). | 344.1 0.972 |
| 43 Method 18 | (5S,7S)-5-(3-chlorophenyl)-2-cyclopropylsulfonyl-7-fluoro-6,7-dihydro-5H-pyrrolo[1,2-b][1,2,4]triazole | 0.039 | Single Unknown Stereoisomer | ¹H NMR (40 MHz, CDCl₃) δ 7.41-7.31 (m, 2H), 7.26-7.24 (m, 1H), 7.16-7.10 (m, 1H), 6.14-5.95 (m, 1H), 5.56-5.45 (m, 1H), 3.78-3.57 (m, 1H), 3.06-2.87 (m, 1H), 2.80-2.70 (m, 1H), 1.52-1.39 (m, 2H), 1.22-1.07 (m, 2H). | 341.9 0.918 |
| 44 Method 18 | (5S,7S)-2-cyclopropylsulfonyl-5-(3,4-difluorophenyl)-7-fluoro-6,7-dihydro-5H-pyrrolo[1,2-b][1,2,4]triazole | 0.021 | Single Unknown Stereoisomer | ¹H NMR (400 MHz, CDCl₃) δ 7.25-7.18 (m, 1H), 7.14-7.12 (m, 1H), 7.11-7.05 (m, 1H), 6.15-5.97 (m, 1H), 5.55-5.45 (m, 1H), 3.73-3.59 (m, 1H), 3.03-2.86 (m, 1H), 2.81-2.70 (m, 1H), 1.52-1.46 (m, 2H), 1.20-1.13 (m, 2H). | 343.9 0.902 |

TABLE 1-continued

| Example Synthetic Method | Structure | Ki (μM) | Stereo | ¹H NMR | MS (m/z) R.T. (min) |
|---|---|---|---|---|---|
| 45 Method 18 | (5S,7S)-5-(2-chloro-3-fluoro-phenyl)-2-cyclopropylsulfonyl-7-fluoro-6,7-dihydro-5H-pyrrolo[1,2-b][1,2,4]triazole | <0.005 | Single Unknown Stereoisomer | ¹H NMR (400 MHz, CD₃OD) δ 7.40-7.32 (m, 2H), 6.78-6.75 (m, 1H), 6.23-6.06 (m, 2H), 3.92-3.81 (m, 1H), 2.92-2.78 (m, 2H), 1.36-1.32 (m, 2H), 1.21-1.17 (m, 2H). | 360.0 0.914 |
| 46 Method 19 | (5S,7S)-5-(3-chloro-2-fluoro-phenyl)-2-cyclopropylsulfonyl-7-fluoro-6,7-dihydro-5H-pyrrolo[1,2-b][1,2,4]triazole | 0.020 | Single Unknown Stereoisomer | ¹H NMR (400 MHz, CD₃OD) δ 7.58-7.53 (m, 1H), 7.23 (t, J = 8.0 Hz, 1H), 7.13-7.08 (m, 1H), 6.24-6.07 (m, 1H), 5.96-5.91 (m, 1H), 3.90-3.76 (m, 1H), 2.95-2.83 (m, 2H), 1.36-1.30 (m, 2H), 1.20-1.14 (m, 2H). | 359.9 0.923 |
| 47 Method 18 | (5S,7S)-5-(5-chloro-2-fluoro-phenyl)-2-cyclopropylsulfonyl-7-fluoro-6,7-dihydro-5H-pyrrolo[1,2-b][1,2,4]triazole | 0.067 | Single Unknown Stereoisomer | ¹H NMR (400 MHz, CDCl₃) 7.38-7.31 (m, 1H), 7.17-7.04 (m, 1H), 6.98-6.94 (m, 1H), 6.17-5.96 (m, 1H), 5.81-5.76 (m, 1H), 3.77-3.69 (m, 1H), 3.00-2.89 (m, 1H), 2.83-2.73 (m, 1H), 1.55-1.45 (m, 2H), 1.23-1.12 (m, 2H). | 360.1 0.995 |
| 48 Method 18 | (5S,7S)-2-cyclopropylsulfonyl-7-fluoro-5-(3-fluorophenyl)-6,7-dihydro-5H-pyrrolo[1,2-b][1,2,4]triazole | <0.005 | Single Unknown Stereoisomer | ¹H NMR (400 MHz, CD₃OD) δ 7.48-7.43 (m, 1H, 7.15-7.04 (m, 3H, 6.25-6.02 (m, 1H, 5.77-5.65 (m, 1H, 3.82-3.75 (m, 1H, 2.91-2.80 (m, 2H, 1.38-1.25 (m, 2H, 1.21-1.07 (m, 2H). | 326.1 1.005 |

TABLE 1-continued

| Example Synthetic Method | Structure | Ki (µM) | Stereo | ¹H NMR | MS (m/z) R.T. (min) |
|---|---|---|---|---|---|
| 49 Method 20 | (5S,7S)-2-(3,3-difluorocyclobutyl)sulfinyl-7-fluoro-5-phenyl-6,7-dihydro-5H-pyrrolo[1,2-b][1,2,4]triazole | 0.012 | Mixture of Diastereomers | ¹H NMR (400 MHz, CDCl₃) δ 7.43-7.40 (m, 3H), 7.25-7.22 (m, 2H), 6.10-5.94 (m, 1H), 5.52-5.47 (m, 1H), 3.78-3.72 (m, 1H), 3.71-3.58 (m, 1H), 3.46-3.26 (m, 1H), 3.02-2.92 (m, 2H), 2.91-2.80 (m, 1H), 2.78-2.65 (m, 1H). | 342.1 0.997 |
| 50 Method 20 | (5S,7S)-2-(3,3-difluorocyclobutyl)sulfonyl-7-fluoro-5-phenyl-6,7-dihydro-5H-pyrrolo[1,2-b][1,2,4]triazole | 0.017 | Single Unknown Stereoisomer | ¹H NMR (400 MHz, CDCl₃) δ 7.44-7.41 (m, 3H), 7.27-7.23 (m, 2H), 6.13-6.11 (m, 0.5H), 6.00-5.97 (m, 0.5H), 5.55-5.52 (m, 1H), 4.00-3.96 (m, 1H), 3.72-3.65 (m, 1H), 3.26-3.22 (m, 2H), 3.07-2.90 (m, 3H). | 358.1 1.064 |
| 51 Method 21 | (5S,7S)-2-[(S)-difluoromethylsulfinyl]-7-fluoro-5-(2-fluorophenyl)-6,7-dihydro-5H-pyrrolo[1,2-b][1,2,4]triazole | 0.140 | Single Unknown Stereoisomer | ¹H NMR (400 MHz, CD₃OD) δ 7.44-7.24 (m, 1H), 7.22-6.96 (m, 4H), 6.24 (dd, J = 2.4, 7.2 Hz, 0.5H), 6.10 (d, J = 4.8 Hz, 0.5H), 5.98-5.90 (m, 1H), 3.88-3.78 (m, 1H, 2.94-2.86 (m, 1H). | 320.1 1.671 |
| 52 Method 21 | (5S,7S)-2-[(R)-difluoromethylsulfinyl]-7-fluoro-5-(2-fluorophenyl)-6,7-dihydro-5H-pyrrolo[1,2-b][1,2,4]triazole | 0.003 | Single Unknown Stereoisomer | ¹H NMR (400 MHz, CD₃OD) δ 7.48-7.45 (m, 1H), 7.24-6.96 (m, 4H), 6.23 (dd, J = 3.2, 7.2 Hz, 0.5H), 6.10 (d, J = 7.6 Hz, 0.5H), 5.98-5.90 (m, 1H, 3.87-3.78 (m, 1H, 2.95-2.84 (m, 1H). | 320.1 1.651 |

TABLE 1-continued

| Example Synthetic Method | Structure | Ki (μM) | Stereo | ¹H NMR | MS (m/z) R.T. (min) |
|---|---|---|---|---|---|
| 53 Method 21 | (5S,7S)-2-(difluoromethylsulfonyl)-7-fluoro-5-(2-fluorophenyl)-6,7-dihydro-5H-pyrrolo[1,2-b][1,2,4]triazole | 0.013 | Single Unknown Stereoisomer | ¹H NMR (400 MHz, CD$_3$OD) δ 7.49-7.46 (m, 1H), 7.26-7.17 (m, 3H), 7.97 (t, J = 52.4 Hz, 1H), 6.24 (dd, J = 2.8, 8.0 Hz, 0.5H), 6.10 (d, J = 2.4 Hz, 0.5H), 6.00-5.94 (m, 1H), 3.88-3.79 (m, 1H), 2.96-2.88 (m, 1H). | 336.0 1.847 |
| 54 Method 21 | (5S,7S)-2-(difluoromethylsulfinyl)-7-fluoro-5-(3-fluorophenyl)-6,7-dihydro-5H-pyrrolo[1,2-b][1,2,4]triazole | 0.017 | Mixture of Diastereomers | ¹H NMR (400 MHz, CD$_3$OD) δ 7.44-7.42 (m, 1H), 7.22-6.95 (m, 4H), 6.21-6.05 (m, 1H), 5.72-5.70 (m, 1H), 3.82-3.70 (m, 1H), 2.91-2.80 (m, 1H). | 320.1 0.955 |
| 55 Method 21 | (5S,7S)-2-(difluoromethylsulfinyl)-7-fluoro-5-(4-fluorophenyl)-6,7-dihydro-5H-pyrrolo[1,2-b][1,2,4]triazole | 0.016 | Mixture of Diastereomers | ¹H NMR (400 MHz, CD$_3$OD) δ 7.34-7.31 (m, 2H), 7.19-6.94 (m, 3H), 6.22 (dd, J = 2.4, 7.2 Hz, 0.5H), 6.07 (d, J = 7.2H, 0.5H), 5.71-5.70 (m, 1H), 3.82-3.72 (m, 1H), 2.91-2.81 (m, 1H). | 320.1 0.979 |
| 56 Method 21 | (5S,7S)-2-(difluoromethylsulfonyl)-7-fluoro-5-(4-fluorophenyl)-6,7-dihydro-5H-pyrrolo[1,2-b][1,2,4]triazole | 0.055 | Single Unknown Stereoisomer | ¹H NMR (400 MHz, CD$_3$OD) δ 7.37-7.34 (m, 2H), 7.20-7.16 (m, 2H), 6.96 (t, J = 52.4 Hz, 1H), 6.24 (dd, J = 2.0, 7.2 Hz, 0.5H), 6.09 (d, J = 2.4 Hz, 0.5H), 5.80-5.75 (m, 1H), 3.84-3.76 (m, 1H), 2.94-2.87 (m, 1H). | 336.1 1.051 |

TABLE 1-continued

| Example Synthetic Method | Structure | Ki (μM) | Stereo | ¹H NMR | MS (m/z) R.T. (min) |
|---|---|---|---|---|---|
| 57 Method 21 | (4R,6R)-2-(difluoromethylsulfonyl)-4-fluoro-6-phenyl-5,6-dihydro-4H-pyrrolo[1,2-b]pyrazole | 0.009 | Single Unknown Stereoisomer | ¹H NMR (400 MHz, CDCl$_3$) δ 7.42-7.36 (m, 3H), 7.20-7.18 (m, 2H), 7.09 (d, J = 2.4 Hz, 1H), 6.26 (t, J = 53.2 Hz, 1H), 6.13 (d, J = 4.4 Hz, 0.5H), 5.99 (d, J = 6.8 Hz, 0.5H), 5.61-5.55 (m, 1H), 3.60-3.50 (m, 1H), 2.97-2.87 (m, 1H). | 316.8 0.863 |
| 58 Method 21 | (5S,7S)-2-(difluoromethylsulfonyl)-5-(2,6-difluorophenyl)-7-fluoro-6,7-dihydro-5H-pyrrolo[1,2-b][1,2,4]triazole | 0.034 | Single Unknown Stereoisomer | ¹H NMR (400 MHz, CDCl$_3$) δ 7.48-7.38 (m, 1H), 6.99 (t, J = 8.4 Hz, 2H), 6.43 (t, J = 52.8 Hz, 1H), 6.25-6.04 (m, 1H), 6.00-5.90 (m, 1H), 3.91-3.74 (m, 1H), 3.18-3.01 (m, 1H). | 354.1 1.033 |
| 59 Method 21 | (5S,7S)-2-(difluoromethylsulfonyl)-7-fluoro-5-(2,3,6-trifluorophenyl)-6,7-dihydro-5H-pyrrolo[1,2-b][1,2,4]triazole | 0.007 | Single Unknown Stereoisomer | ¹H NMR (400 MHz, CD$_3$OD) δ 7.47-7.44 (m, 1H), 7.11-6.83 (m, 2H), 6.28-6.13 (m, 1H), 6.07-6.03 (m, 1H), 3.94-3.87 (m, 1H), 3.06-2.95 (m, 1H). | 372.0 1.841 |
| 60 Method 21 | (5S,7S)-2-(difluoromethylsulfonyl)-7-fluoro-5-(2,3,5-trifluorophenyl)-6,7-dihydro-5H-pyrrolo[1,2-b][1,2,4]triazole | 0.007 | Single Unknown Stereoisomer | ¹H NMR (400 MHz, CD$_3$OD) δ 7.33-7.26 (m, 1H), 6.99 (t, J = 52.4 Hz, 1H), 6.86-6.78 (m, 1H), 6.27-6.11 (m, 1H), 6.02-5.97 (m, 1H), 3.92-3.79 (m, 1H), 3.01-2.89 (m, 1H). | 372.1 1.081 |

TABLE 1-continued

| Example Synthetic Method | Structure | Ki (μM) | Stereo | ¹H NMR | MS (m/z) R.T. (min) |
|---|---|---|---|---|---|
| 61 Method 43 | (5S,7S)-5-(3-chlorophenyl)-2-(difluoromethylsulfonyl)-7-fluoro-6,7-dihydro-5H-pyrrolo[1,2-b][1,2,4]triazole | 0.039 | Single Unknown Stereoisomer | ¹H NMR (400 MHz, CDCl₃) δ 7.49-7.33 (m, 2H), 7.33-7.27 (m, 1H), 7.13-7.11 (m, 1H), 6.68-6.27 (m, 1H), 6.26-5.98 (m, 1H), 5.62-5.50 (m, 1H), 3.85-3.56 (m, 1H), 3.12-2.86 (m, 1H). | 352.0 1.962 |
| 62 Method 24 | 2-[(5S,7S)-2-(difluoromethylsulfonyl)-7-fluoro-6,7-dihydro-5H-pyrrolo[1,2-b][1,2,4]triazol-5-yl]benzonitrile | 0.266 | Single Unknown Stereoisomer | ¹H NMR (400 MHz, CDCl₃) δ 7.85-7.77 (m, 1H), 7.68-7.63 (m, 1H), 7.57-7.52 (m, 1H), 6.95 (d, J = 8.0 Hz, 1H), 6.45 (t, J = 52.8 Hz, 1H), 6.20-6.03 (m, 2H), 3.96-3.81 (m, 1H), 3.02-2.92 (m, 1H). | 343.1 0.919 |
| 63 Method 23 | (5S,7S)-2-(difluoromethylsulfonyl)-5-(3,4-difluorophenyl)-7-fluoro-6,7-dihydro-5H-pyrrolo[1,2-b][1,2,4]triazole | 0.034 | Single Unknown Stereoisomer | ¹H NMR (400 MHz, CDCl₃) δ 7.26-7.19 (m, 1H), 7.12-7.11 (m, 1H), 7.05-7.04 (m, 1H), 6.44 (t, J = 53.2 Hz, 1H), 6.20-5.99 (m, 1H), 5.58-5.57 (m, 1H), 3.81-3.62 (m, 1H), 3.09-2.93 (m, 1H). | 354.1 1.025 |
| 64 Method 23 | (5S,7S)-5-(2-chloro-3-fluoro-phenyl)-2-(difluoromethylsulfonyl)-7-fluoro-6,7-dihydro-5H-pyrrolo[1,2-b][1,2,4]triazole | <0.005 | Single Unknown Stereoisomer | ¹H NMR (400 MHz, CD₃OD) δ 7.40-7.35 (m, 2H), 7.00 (t, J = 52.4 Hz, 1H), 6.77-6.75 (m, 1H), 6.26-6.10 (m, 2H), 3.95-3.81 (m, 1H), 2.92-2.81 (m, 1H). | 371.4 0.957 |

TABLE 1-continued

| Example Synthetic Method | Structure | Ki (μM) | Stereo | ¹H NMR | MS (m/z) R.T. (min) |
|---|---|---|---|---|---|
| 65 Method 23 | (5S,7S)-5-(3-chloro-2-fluoro-phenyl)-2-(difluoromethylsulfonyl)-7-fluoro-6,7-dihydro-5H-pyrrolo[1,2-b][1,2,4]triazole | 0.018 | Single Unknown Stereoisomer | ¹H NMR (400 MHz, CD₃OD) δ 7.59-7.54 (m, 1H), 7.24 (t, J = 8.0 Hz, 1H), 7.13-7.08 (m, 1H), 6.99 (t, J = 52.4 Hz, 1H), 6.27-6.10 (m, 1H), 6.01-5.95 (m, 1H), 3.90-3.80 (m, 1H), 2.99-2.85 (m, 1H). | 369.9 0.953 |
| 66 Method 23 | (5S,7S)-5-(5-chloro-2-fluoro-phenyl)-2-(difluoromethylsulfonyl)-7-fluoro-6,7-dihydro-5H-pyrrolo[1,2-b][1,2,4]triazole | 0.069 | | ¹H NMR (400 MHz, CDCl₃) δ 7.41-7.35 (m, 1H), 7.12 (t, J = 9.2 Hz, 1H), 6.97-6.93 (m, 1H), 6.45 (t, J = 52.8 Hz, 1H), 6.15-6.02 (m, 1H), 5.87-5.80 (m, 1H), 3.85-3.65 (m, 1H), 3.07-2.94 (m, 1H). | 370.1 1.051 |
| 67 Method 21 | (5S,7S)-2-(difluoromethylsulfonyl)-5-(2,5-difluorophenyl)-7-fluoro-6,7-dihydro-5H-pyrrolo[1,2-b][1,2,4]triazole | 0.005 | Single Unknown Stereoisomer | ¹H NMR (400 MHz, CDCl₃) δ 7.20-7.06 (m, 2H), 6.71-6.64 (m, 1H), 6.44 (t, J = 52.4 Hz, 1H), 6.19-6.00 (m, 1H), 5.95-5.88 (m, 1H), 3.82-3.65 (m, 1H), 3.05-2.95 (m, 1H). | 354.1 1.059 |
| 68 Method 21 | (5S,7S)-2-(difluoromethylsulfonyl)-5-(2,3-difluorophenyl)-7-fluoro-6,7-dihydro-5H-pyrrolo[1,2-b][1,2,4]triazole | 0.006 | Single Unknown Stereoisomer | ¹H NMR (400 MHz, CDCl₃) δ 7.26-7.21 (m, 1H), 7.13-7.11 (m, 1H), 6.71-6.69 (m, 1H), 6.43 (t, J = 53.2 Hz, 1H), 6.14 (d, J = 5.6 Hz, 0.5H), 6.00 (d, J = 5.2 Hz, 0.5H), 5.98-5.92 (m, 1H), 3.80-3.70 (m, 1H), 3.05-2.94 (m, 1H). | 354.0 0.839 |

TABLE 1-continued

| Example Synthetic Method | Structure | Ki (μM) | Stereo | $^1$H NMR | MS (m/z) R.T. (min) |
|---|---|---|---|---|---|
| 69 Method 23 | (5S,7S)-2-(difluoromethylsulfonyl)-5-(3,5-difluorophenyl)-7-fluoro-6,7-dihydro-5H-pyrrolo[1,2-b][1,2,4]triazole | <0.005 | Single Unknown Stereoisomer | $^1$H NMR (400 MHz, CDCl$_3$) δ 6.92-6.85 (m, 1H), 6.84-6.77 (m, 2H), 6.44 (t, J = 53.2 Hz, 1H), 6.17-6.01 (m, 1H), 5.59-5.57 (m, 1H), 3.77-3.69 (m, 1H), 3.07-2.97 (m, 1H). | 354.1 1.030 |
| 70 Method 21 | (5S,7S)-2-(difluoromethylsulfonyl)-7-fluoro-5-(3-fluorophenyl)-6,7-dihydro-5H-pyrrolo[1,2-b][1,2,4]triazole | 0.005 | Single Unknown Stereoisomer | $^1$H NMR (400 MHz, CD$_3$OD) δ 7.46-7.44 (m, 1H), 7.15-6.83 (m, 4H), 6.23-6.07 (m, 1H), 5.75-5.74 (m, 1H), 3.83-3.73 (m, 1H), 2.93-2.82 (m, 1H). | 336.1 1.027 |
| 71 Method 25 | (5S,7S)-7-fluoro-2-[(S)-fluoromethylsulfinyl]-5-phenyl-6,7-dihydro-5H-pyrrolo[1,2-b][1,2,4]triazole | 0.090 | | $^1$H NMR (400 MHz, CDCl$_3$) δ 7.42-7.38 (m, 3H), 7.26-7.21 (m, 2H), 6.14-5.96 (m, 1H), 5.61-5.55 (m, 1H), 5.54-5.48 (m, 1H), 3.72-3.61 (m, 1H), 3.05-2.94 (m, 1H). | 284.1 0.701 |
| 72 Method 25 | (5S,7S)-7-fluoro-2-(fluoromethylsulfonyl)-5-phenyl-6,7-dihydro-5H-pyrrolo[1,2-b][1,2,4]triazole | 0.023 | Single Unknown Stereoisomer | $^1$H NMR (400 MHz, CDCl$_3$) δ 7.42-7.40 (m, 3H), 7.26-7.23 (m, 2H), 6.14-5.98 (m, 1H), 5.59-5.53 (m, 1H), 5.49 (s, 1H), 5.37 (s, 1H), 3.74-3.63 (m, 1H), 3.07-2.96 (m, 1H). | 300.1 0.932 |

TABLE 1-continued

| Example Synthetic Method | Structure | Ki (μM) | Stereo | ¹H NMR | MS (m/z) R.T. (min) |
|---|---|---|---|---|---|
| 73 Method 25 | (5S,7S)-7-fluoro-2-[(R)-fluoromethylsulfinyl]-5-phenyl-6,7-dihydro-5H-pyrrolo[1,2-b][1,2,4]triazole | 0.003 | Single Unknown Stereoisomer | ¹H NMR (400 MHz, CDCl₃) δ 7.44-7.38 (m, 3H), 7.26-7.22 (m, 2H), 6.13-5.96 (m, 1H), 5.73-5.62 (m, 1H), 5.61-5.48 (m, 2H), 3.74-3.59 (m, 1H), 3.06-2.93 (m, 1H). | 284.1 0.692 |
| 74 Method 25 | (5S,7S)-7-fluoro-2-[(R)-fluoromethylsulfinyl]-5-(2-fluorophenyl)-6,7-dihydro-5H-pyrrolo[1,2-b][1,2,4]triazole | <0.005 | Single Unknown Stereoisomer | ¹H NMR (400 MHz, CD₃OD) δ 7.45-7.23 (m, 1H), 7.22-7.13 (m, 3H), 6.21 (d, J = 1.6 Hz, 0.5H), 6.07 (d, J = 1.6 Hz, 0.5H), 5.80-5.78 (m, 1H), 5.77-5.75 (m, 1H), 5.74-5.64 (m, 1H), 3.87-3.74 (m, 1H), 2.93-2.81 (m, 1H). | 302.1 0.828 |
| 75 Method 25 | (5S,7S)-7-fluoro-2-[(S)-fluoromethylsulfinyl]-5-(2-fluorophenyl)-6,7-dihydro-5H-pyrrolo[1,2-b][1,2,4]triazole | 0.140 | Single Unknown Stereoisomer | ¹H NMR (400 MHz, CD₃OD) δ 7.45-7.43 (m, 1H), 7.34-6.98 (m, 3H), 6.22-6.06 (m, 1H), 6.06-5.91 (m, 1H), 5.87-5.77 (m, 1H), 5.75-5.64 (m, 1H), 3.88-3.73 (m, 1H), 2.93-2.80 (m, 1H). | 301.9 0.828 |
| 76 Method 25 | (5S,7S)-5-(2,3-difluorophenyl)-7-fluoro-2-[(R)-fluoromethylsulfinyl]-6,7-dihydro-5H-pyrrolo[1,2-b][1,2,4]triazole | <0.005 | Single Unknown Stereoisomer | ¹H NMR (400 MHz, CD₃OD) δ 7.37-7.33 (m, 1H), 7.22-7.20 (m, 1H), 6.96-6.94 (m, 1H), 6.23-6.07 (m, 1H), 5.96-5.94 (m, 1H), 5.84-5.78 (m, 1H), 5.74-5.66 (m, 1H), 3.87-3.78 (m, 1H), 2.95-2.85 (m, 1H). | 0.712 320.1 |

TABLE 1-continued

| Example Synthetic Method | Structure | Ki (μM) | Stereo | ¹H NMR | MS (m/z) R.T. (min) |
|---|---|---|---|---|---|
| 77 Method 25 | (5S,7S)-5-(2,3-difluorophenyl)-7-fluoro-2-[(S)-fluoromethylsulfinyl]-6,7-dihydro-5H-pyrrolo[1,2-b][1,2,4]triazole | 0.280 | Single Unknown Stereoisomer | ¹H NMR (400 MHz, CD$_3$OD) δ 7.35-7.33 (m, 1H), 7.21-7.20 (m, 1H), 6.96-6.94 (m, 1H), 6.23-6.07 (m, 1H), 5.96-5.94 (m, 1H), 5.84-5.78 (m, 1H), 5.74-5.66 (m, 1H), 3.88-3.78 (m, 1H), 2.95-2.84 (m, 1H). | 320.1 0.720 |
| 78 Method 25 | (5S,7S)-5-(2,5-difluorophenyl)-7-fluoro-2-[(R)-fluoromethylsulfinyl]-6,7-dihydro-5H-pyrrolo[1,2-b][1,2,4]triazole | <0.005 | Single Unknown Stereoisomer | ¹H NMR (400 MHz, CD$_3$OD) δ 7.26-7.19 (m, 2H), 7.18-6.91 (m, 1H), 6.20-6.06 (m, 1H), 5.89-5.65 (m, 3H), 3.87-3.74 (m, 1H), 2.93-2.82 (m, 1H). | 320.1 0.853 |
| 79 Method 25 | (5S,7S)-5-(2,5-difluorophenyl)-7-fluoro-2-[(S)-fluoromethylsulfinyl]-6,7-dihydro-5H-pyrrolo[1,2-b][1,2,4]triazole | 0.190 | Single Unknown Stereoisomer | ¹H NMR (400 MHz, CD$_3$OD) δ 7.26-7.19 (m, 2H, 6.97-6.91 (m, 1H, 6.22-6.06 (m, 1H, 5.89-5.67 (m, 3H, 3.88-3.74 (m, 1H, 2.93-2.82 (m, 1H). | 320.1 0.869 |
| 80 Method 25 | (5S,7S)-5-(2,6-difluorophenyl)-7-fluoro-2-[(R)-fluoromethylsulfinyl]-6,7-dihydro-5H-pyrrolo[1,2-b][1,2,4]triazole | <0.005 | Single Unknown Stereoisomer | ¹H NMR (400 MHz, CDCl$_3$) δ 7.43-7.39 (m, 1H, 7.00-6.95 (m, 2H, 6.03-5.87 (m, 1H, 5.63-5.61 (m, 1H, 5.60-5.49 (m, 2H, 3.85-3.75 (m, 1H, 3.14-3.02 (m, 1H). | 320.1 0.585 |

TABLE 1-continued

| Example Synthetic Method | Structure | Ki (μM) | Stereo | ¹H NMR | MS (m/z) R.T. (min) |
|---|---|---|---|---|---|
| 81 Method 25 | (5S,7S)-5-(2,6-difluorophenyl)-7-fluoro-2-[(S)-fluoromethylsulfinyl]-6,7-dihydro-5H-pyrrolo[1,2-b][1,2,4]triazole | 0.290 | Single Unknown Stereoisomer | ¹H NMR (400 MHz, CD₃OD) δ 7.52-7.46 (m, 1H, 7.10-7.05 (m, 2H, 6.23-6.08 (m, 1H, 6.00-5.98 (m, 1H, 5.80-5.75 (m, 1H, 5.74-5.65 (m, 1H, 3.89-3.82 (m, 1H, 3.01-2.99 (m, 1H). | 320.1 0.836 |
| 82 Method 25 | (5S,7S)-7-fluoro-2-[(R)-fluoromethylsulfinyl]-5-(3-fluorophenyl)-6,7-dihydro-5H-pyrrolo[1,2-b][1,2,4]triazole | <0.005 | Single Unknown Stereoisomer | ¹H NMR (400 MHz, CDCl₃) δ 7.40-7.38 (m, 1H), 7.10-7.09 (m, 2H), 6.97-6.95 (m, 1H), 6.12-5.96 (m, 1H), 5.72-5.60 (m, 2H), 5.58-5.51 (m, 1H), 3.73-3.63 (m, 1H), 3.03-2.92 (m, 1H). | 302.1 0.837 |
| 83 Method 25 | (5S,7S)-7-fluoro-2-[(S)-fluoromethylsulfinyl]-5-(3-fluorophenyl)-6,7-dihydro-5H-pyrrolo[1,2-b][1,2,4]triazole | 0.130 | Single Unknown Stereoisomer | ¹H NMR (400 MHz, CDCl₃) δ 7.39-7.37 (m, 1H), 7.17-7.00 (m, 2H), 6.95 (d, J = 9.2 Hz, 1H), 6.12-5.95 (m, 1H), 5.70-5.68 (m, 1H), 5.63-5.52 (m, 2H), 3.73-3.60 (m, 1H), 3.02-2.92 (m, 1H). | 302.1 0.857 |
| 84 Method 25 | (5S,7S)-5-(3,5-difluorophenyl)-7-fluoro-2-[(R)-fluoromethylsulfinyl]-6,7-dihydro-5H-pyrrolo[1,2-b][1,2,4]triazole | <0.005 | Single Unknown Stereoisomer | ¹H NMR (400 MHz, CD₃OD) δ 7.01-6.98 (m, 1H), 6.95-6.91 (m, 2H), 6.20-6.06 (m, 1H), 5.86-5.65 (m, 3H), 3.82-3.74 (m, 1H), 2.91-2.81 (m, 1H). | 320.1 0.617 |

TABLE 1-continued

| Example Synthetic Method | Structure | Ki (μM) | Stereo | ¹H NMR | MS (m/z) R.T. (min) |
|---|---|---|---|---|---|
| 85 Method 25 | (5S,7S)-5-(3,5-difluorophenyl)-7-fluoro-2-[(S)-fluoromethylsulfinyl]-6,7-dihydro-5H-pyrrolo[1,2-b][1,2,4]triazole | 0.180 | Single Unknown Stereoisomer | ¹H NMR (400 MHz, CD₃OD) δ 7.00-6.98 (m, 1H), 6.95-6.91 (m, 2H), 6.20-6.18 (m, 1H), 5.87-5.67 (m, 3H), 3.80-3.72 (m, 1H), 2.91-2.80 (m, 1H). | 320.1 0.625 |
| 86 Method 25 | (5S,7S)-5-(2-chlorophenyl)-7-fluoro-2-[(R)-fluoromethylsulfinyl]-6,7-dihydro-5H-pyrrolo[1,2-b][1,2,4]triazole | <0.005 | Single Unknown Stereoisomer | ¹H NMR (400 MHz, CD₃OD) δ 7.54-7.52 (m, 1H), 7.41-7.33 (m, 2H), 6.91-6.89 (m, 1H), 6.21-6.18 (m, 0.5H), 6.08-6.05 (m, 1.5H), 5.87-5.69 (m, 2H), 3.90-3.77 (m, 1H), 2.85-2.74 (m, 1H). | 318.0 1.536 |
| 87 Method 25 | (5S,7S)-5-(2-chlorophenyl)-7-fluoro-2-[(S)-fluoromethylsulfinyl]-6,7-dihydro-5H-pyrrolo[1,2-b][1,2,4]triazole | 0.100 | Single Unknown Stereoisomer | ¹H NMR (400 MHz, CD₃OD) δ 7.54-7.52 (m, 1H), 7.41-7.30 (m, 2H), 6.91-6.89 (m, 1H), 6.21-6.18 (m, 0.5H), 6.08-6.05 (m, 1.5H), 5.86-5.68 (m, 2H), 3.91-3.79 (m, 1H), 2.84-2.74 (m, 1H). | 318.1 0.929 |
| 88 Method 26 | 2-[[(5S,7S)-7-fluoro-5-phenyl-6,7-dihydro-5H-pyrrolo[1,2-b][1,2,4]triazol-2-yl]sulfonyl]acetonitrile | 0.032 | Single Unknown Stereoisomer | ¹H NMR (400 MHz, CDCl₃) δ 7.51-7.35 (m, 4H), 7.33-7.15 (m, 1H), 6.17-6.00 (m, 1H), 5.65-5.57 (m, 1H), 4.52-4.39 (m, 2H), 3.79-3.64 (m, 1H), 3.10-2.99 (m, 1H). | 307.1 0.956 |

TABLE 1-continued

| Example Synthetic Method | Structure | Ki (µM) | Stereo | ¹H NMR | MS (m/z) R.T. (min) |
|---|---|---|---|---|---|
| 89 Method 26 | 2-[[(5S,7S)-7-fluoro-5-phenyl-6,7-dihydro-5H-pyrrolo[1,2-b][1,2,4]triazol-2-yl]sulfanyl]acetonitrile | 0.010 | Single Unknown Stereoisomer | ¹H NMR (400 MHz, DMSO-d6) δ 7.43-7.36 (m, 3H), 7.25-7.21 (m, 2H), 6.26-6.09 (m, 1H), 5.65-5.62 (m, 1H), 4.29-4.19 (m, 2H), 3.73-3.64 (m, 1H), 2.69-2.56 (m, 1H). | 274.9 0.825 |
| 90 Method 26 | 2-2-(((4S,6S)-4-fluoro-6-phenyl-5,6-dihydro-4H-pyrrolo[1,2-b]pyrazol-2-yl)sulfonyl)acetonitrile | 0.008 | Single Unknown Stereoisomer | ¹H NMR (400 MHz, CDCl₃) δ 7.42-7.38 (m, 3H, 7.23-7.21 (m, 2H), 7.11 (d, J = 2.8 Hz, 1H), 6.14 (d, J = 6.8 Hz, 0.5H), 5.99 (d, J = 6.4 Hz, 0.5H), 5.70-5.55 (m, 1H), 4.27-4.17 (m, 2H), 3.65-3.50 (m, 1H), 2.97-2.87 (m, 1H). | 306.1 0.787 |
| 91 Method 26 | 2-2-((R)-((4S,6S)-4-fluoro-6-phenyl-5,6-dihydro-4H-pyrrolo[1,2-b]pyrazol-2-yl)sulfinyl)acetonitrile | 0.150 | Single Unknown Stereoisomer | ¹H NMR (400 MHz, CDCl₃) δ 7.40-7.36 (m, 3H), 7.21-7.19 (m, 2H), 7.07 (s, 1H), 6.13 (d, J = 6.8 Hz, 0.5H), 5.98 (d, J = 6.8 Hz, 0.5H), 5.55-5.50 (m, 1H), 4.10 (d, J = 15.6 Hz, 1H), 3.81 (d, J = 15.6 Hz, 1H), 3.61-3.50 (m, 1H), 2.93-2.83 (m, 1H). | 290.1 0.711 |
| 92 Method 26 | 2-2-((S)-((4S,6S)-4-fluoro-6-phenyl-5,6-dihydro-4H-pyrrolo[1,2-b]pyrazol-2-yl)sulfinyl)acetonitrile | 0.019 | Single Unknown Stereoisomer | ¹H NMR (400 MHz, CDCl₃) δ 7.41-7.35 (m, 3H), 7.27-7.21 (m, 2H), 7.08 (s, 1H), 6.13 (d, J = 6.8 Hz, 0.5H), 5.99 (d, J = 6.4 Hz, 0.5H), 5.55-5.50 (m, 1H), 4.09 (d, J = 15.6 Hz, 1H), 3.84 (d, J = 16.0 Hz, 1H), 3.62-3.49 (m, 1H), 2.93-2.83 (m, 1H). | 290.1 0.718 |

TABLE 1-continued

| Example Synthetic Method | Structure | Ki (μM) | Stereo | ¹H NMR | MS (m/z) R.T. (min) |
|---|---|---|---|---|---|
| 93 Method 24 | 2-[(S)-[(5S,7S)-5-(2-chlorophenyl)-7-fluoro-6,7-dihydro-5H-pyrrolo[1,2-b][1,2,4]triazol-2-yl]sulfinyl]acetonitrile | 0.092 | Single Unknown Stereoisomer | ¹H NMR (400 MHz, CDCl₃) δ 7.46 (dd, J = 1.2, 8.4 Hz, 1H), 7.36-7.30 (m, 1H), 7.29-7.27 (m, 0.5H), 7.25-7.23 (m, 0.5H), 6.75 (dd, J = 1.2, 7.6 Hz, 1H), 6.12 (d, J = 5.6 Hz, 0.5H), 6.05-5.96 (m, 1.5H), 4.37 (d, J = 15.6 Hz, 1H), 4.14 (d, J = 15.6 Hz, 1H), 3.83-3.67 (m, 1H), 2.98-2.84 (m, 1H). | 325.1 0.956 |
| 94 Method 26 | 2-[(R)-[rac-(5S,7S)-5-(2-chlorophenyl)-7-fluoro-6,7-dihydro-5H-pyrrolo[1,2-b][1,2,4]triazol-2-yl]sulfinyl]acetonitrile | 0.004 | Single Unknown Stereoisomer | ¹H NMR (400 MHz, CDCl₃) δ 7.46 (dd, J = 1.2, 8.8 Hz, 1H), 7.37-7.27 (m, 2H), 6.77 (d, J = 9.2 Hz, 1H), 6.11 (d, J = 5.2 Hz, 0.5H), 6.06-5.95 (m, 1.5H), 4.40 (d, J = 15.6 Hz, 1H), 4.10 (d, J = 15.6 Hz, 1H, 3.83-3.68 (m, 1H, 2.99-2.84 (m, 1H). | 325.1 0.949 |
| 95 Method 26 | 2-[(S)-[(5S,7S)-7-fluoro-5-(2-fluorophenyl)-6,7-dihydro-5H-pyrrolo[1,2-b][1,2,4]triazol-2-yl]sulfinyl]acetonitrile | 0.190 | Single Unknown Stereoisomer | ¹H NMR (400 MHz, CDCl₃) δ 7.40-7.38 (m, 1H), 7.18-7.13 (m, 2H), 7.10-6.99 (m, 1H), 6.15-6.00 (m, 1H), 5.90-5.88 (m, 1H), 4.34 (d, J = 15.6 Hz, 1H), 4.14 (d, J = 15.6 Hz, 1H), 3.79-3.67 (m, 1H), 3.02-2.91 (m, 1H). | 308.9 0.775 |
| 96 Method 26 | 2-[(R)-[(5S,7S)-7-fluoro-5-(2-fluorophenyl)-6,7-dihydro-5H-pyrrolo[1,2-b][1,2,4]triazol-2-yl]sulfinyl]acetonitrile | 0.003 | Single Unknown Stereoisomer | ¹H NMR (400 MHz, CDCl₃) δ 7.41-7.39 (m, 1H), 7.20-7.14 (m, 2H), 7.01-6.98 (m, 1H), 6.15-6.00 (m, 1H), 5.99-5.89 (m, 1H), 4.40 (d, J = 15.6 Hz, 1H), 4.10 (d, J = 15.6 Hz, 1H), 3.79-3.67 (m, 1H), 3.03-2.93 (m, 1H). | 308.9 0.762 |

TABLE 1-continued

| Example Synthetic Method | Structure | Ki (μM) | Stereo | ¹H NMR | MS (m/z) R.T. (min) |
|---|---|---|---|---|---|
| 97 Method 26 | 2-[(S)-[(5S,7S)-7-fluoro-5-(3-fluorophenyl)-6,7-dihydro-5H-pyrrolo[1,2-b][1,2,4]triazol-2-yl]sulfinyl]acetonitrile | 0.190 | Single Unknown Stereoisomer | ¹H NMR (400 MHz, CDCl₃) δ 7.40-7.35 (m, 1H), 7.16-6.89 (m, 3H), 6.18-5.95 (m, 1H), 5.68-5.58 (m, 1H), 4.31-4.10 (m, 2H), 3.78-3.68 (m, 1H), 3.00-2.88 (m, 1H). | 309.1 0.914 |
| 98 Method 26 | 2-[(R)-[(5S,7S)-7-fluoro-5-(3-fluorophenyl)-6,7-dihydro-5H-pyrrolo[1,2-b][1,2,4]triazol-2-yl]sulfinyl]acetonitrile | 0.003 | Single Unknown Stereoisomer | ¹H NMR (400 MHz, CDCl₃) δ 7.43-7.37 (m, 1H), 7.17-6.92 (m, 3H), 6.18-5.96 (m, 1H), 5.58-5.54 (m, 1H), 4.44-4.03 (m, 2H), 3.81-3.62 (m, 1H), 3.04-2.89 (m, 1H). | 309.1 0.894 |
| 99 Method 26 | 2-[(S)-[(5S,7S)-7-fluoro-5-(4-fluorophenyl)-6,7-dihydro-5H-pyrrolo[1,2-b][1,2,4]triazol-2-yl]sulfinyl]acetonitrile | 0.530 | Single Unknown Stereoisomer | ¹H NMR (400 MHz, CDCl₃) δ 7.37-7.25 (m, 2H), 7.12-7.08 (m, 2H), 6.14-5.98 (m, 1H), 5.62-5.58 (m, 1H), 4.37-4.07 (m, 2H), 3.74-3.68 (m, 1H), 3.00-2.89 (m, 1H). | 309.1 0.907 |
| 100 Method 26 | 2-[(R)-[(5S,7S)-7-fluoro-5-(4-fluorophenyl)-6,7-dihydro-5H-pyrrolo[1,2-b][1,2,4]triazol-2-yl]sulfinyl]acetonitrile | 0.003 | Single Unknown Stereoisomer | ¹H NMR (400 MHz, CDCl₃) δ 7.27-7.22 (m, 2H), 7.14-7.10 (m, 2H), 6.19-5.96 (m, 1H), 5.70-5.55 (m, 1H), 4.39-4.06 (m, 2H), 3.79-3.61 (m, 1H), 3.02-2.92 (m, 1H). | 309.1 0.899 |

TABLE 1-continued

| Example Synthetic Method | Structure | Ki (µM) | Stereo | ¹H NMR | MS (m/z) R.T. (min) |
|---|---|---|---|---|---|
| 101 Method 26 | 2-[(S)-[(5R,7R)-5-(2-chlorophenyl)-7-fluoro-6,7-dihydro-5H-pyrrolo[1,2-b][1,2,4]triazol-2-yl]sulfinyl]acetonitrile | 0.047 | Single Unknown Stereoisomer | ¹H NMR (400 MHz, CD₃OD) δ 7.53 (d, J = 8.4 Hz, 1H), 7.41-7.35 (m, 1H), 7.34-7.28 (m, 1H), 6.89 (d, J = 7.6 Hz, 1H), 6.21 (d, J = 5.2 Hz, 0.5H), 6.12-6.05 (m, 1.5H), 3.90-3.76 (m, 1H), 3.38-3.31 (m, 2H), 2.87-2.72 (m, 1H). | 325.0 0.741 |
| 102 Method 26 | 2-[[(5S,7S)-7-fluoro-5-phenyl-6,7-dihydro-5H-pyrrolo[1,2-b][1,2,4]triazol-2-yl]sulfinyl]acetonitrile | 0.018 | Mixture of Diastereomers | ¹H NMR (400 MHz, CDCl₃) δ 7.43-7.40 (m, 3H), 7.30-7.25 (m, 2H), 6.16-5.99 (m, 1H), 5.63-5.54 (m, 1H), 4.41-4.31 (m, 1H), 4.15-4.06 (m, 1H), 3.72-3.66 (m, 1H), 3.08-2.95 (m, 1H). | 291.1 0.847 |
| 103 Method 27 | 2-methyl-2-[[(5S,7S)-7-fluoro-5-phenyl-6,7-dihydro-5H-pyrrolo[1,2-b][1,2,4]triazol-2-yl]sulfinyl]propanenitrile | 0.150 | Mixture of Diastereomers | ¹H NMR (400 MHz, CDCl₃) δ 7.42-7.38 (m, 3H), 7.27-7.21 (m, 2H), 6.14-6.11 (m, 0.5H), 5.99-5.97 (m, 0.5H), 5.59-5.54 (m, 1H), 3.74-3.62 (m, 1H), 3.03-2.92 (m, 1H), 1.79-1.77 (m, 6H). | 340.9 0.796 |
| 104 Method 27 | 2-(((5S,7S)-7-fluoro-5-phenyl-6,7-dihydro-5H-pyrrolo[1,2-b][1,2,4]triazol-2-yl)sulfonyl)-2-methylpropanenitrile | 0.014 | Single Unknown Stereoisomer | ¹H NMR (400 MHz, CDCl₃) δ 7.43-7.40 (m, 3H), 7.27-7.22 (m, 2H), 6.17-6.00 (m, 1H), 5.64-5.61 (m, 1H), 3.76-3.66 (m, 1H), 3.08-2.97 (m, 1H), 1.89-1.87 (m, 6H). | 335.1 1.794 |

TABLE 1-continued

| Example Synthetic Method | Structure | Ki (μM) | Stereo | ¹H NMR | MS (m/z) R.T. (min) |
|---|---|---|---|---|---|
| 105 Method 26 | (5S,7S)-7-fluoro-2-methyl sulfinyl-5-phenyl-6,7-dihydro-5H-pyrrolo[1,2-b][1,2,4]triazole | 0.046 | Mixture of Diastereomers | ¹H NMR (400 MHz, CDCl₃) δ 7.51-7.34 (m, 3H), 7.27-7.26 (m, 2H), 6.18-5.91 (m, 1H), 5.51-5.50 (m, 1H), 3.79-3.52 (m, 1H), 3.08-3.05 (m, 3H), 3.02-2.90 (m, 1H). | 266.1 1.218 & 1.256 |
| 106 Method 26 | (5S,7S)-7-fluoro-2-methylsulfonyl-5-phenyl-6,7-dihydro-5H-pyrrolo[1,2-b][1,2,4]triazole | 0.022 | Single Unknown Stereoisomer | ¹H NMR (400 MHz, CDCl₃) δ 7.41-7.35 (m, 3H), 7.30-7.27 (m, 2H), 6.16-5.95 (m, 1H), 5.53-5.46 (m, 1H), 3.75-3.63 (m, 1H), 3.28-3.20 (m, 3H), 3.05-2.95 (m, 1H). | 282.1 1.471 |
| 107 Method 26 | (5S,7S)-2-ethylsulfinyl-7-fluoro-5-phenyl-6,7-dihydro-5H-pyrrolo[1,2-b][1,2,4]triazole | 0.034 | Mixture of Diastereomers | ¹H NMR (400 MHz, CDCl₃) δ 7.44-7.35 (m, 3H), 7.26-7.24 (m, 2H), 6.12-5.95 (m, 1H), 5.53-5.48 (m, 1H), 3.73-3.58 (m, 1H), 3.30-3.22 (m, 2H), 3.02-2.92 (m, 1H), 1.33 (t, J = 7.6 Hz, 3H). | 280.1 0.756 |
| 108 Method 26 | (5S,7S)-2-ethylsulfonyl-7-fluoro-5-phenyl-6,7-dihydro-5H-pyrrolo[1,2-b][1,2,4]triazole | 0.011 | Single Unknown Stereoisomer | ¹H NMR (40 MHz, CDCl₃) δ 7.44-7.40 (m, 3H), 7.26-7.24 (m, 2H), 6.14-5.97 (m, 1H), 5.56-5.51 (m, 1H), 3.75-3.60 (m, 1H), 3.43-3.36 (m, 2H), 3.06-2.95 (m, 1H), 1.39 (t, J = 7.6 Hz, 3H). | 295.9 0.799 |

TABLE 1-continued

| Example Synthetic Method | Structure | Ki (μM) | Stereo | ¹H NMR | MS (m/z) R.T. (min) |
|---|---|---|---|---|---|
| 109 Method 26 | (5S,7S)-7-fluoro-2-isopropylsulfinyl-5-phenyl-6,7-dihydro-5H-pyrrolo[1,2-b][1,2,4]triazole | 0.019 | Mixture of Diastereomers | ¹H NMR (400 MHz, CDCl₃) δ 7.28-7.25 (m, 3H), 7.16-7.09 (m, 2H), 6.00-5.84 (m, 1H), 5.41-5.37 (m, 1H), 3.58-3.46 (m, 1H), 3.41-3.21 (m, 1H), 2.96-2.71 (m, 1H), 1.23-1.09 (m, 6H). | 293.9 0.785 |
| 110 Method 26 | (5S,7S)-7-fluoro-2-isopropylsulfonyl-5-phenyl-6,7-dihydro-5H-pyrrolo[1,2-b][1,2,4]triazole | 0.014 | Single Unknown Stereoisomer | ¹H NMR (400 MHz, CDCl₃) δ 7.47-7.30 (m, 3H), 7.28-7.14 (m, 2H), 6.22-5.89 (m, 1H), 5.59-5.53 (m, 1H), 3.75-3.58 (m, 1H), 3.57-3.45 (m, 1H), 3.08-2.90 (m, 1H), 1.40-1.25 (m, 6H). | 309.9 0.826 |
| 111 Method 26 | (5S,7S)-2-(cyclopropylmethylsulfinyl)-7-fluoro-5-phenyl-6,7-dihydro-5H-pyrrolo[1,2-b][1,2,4]triazole | 0.044 | Mixture of Diastereomers | ¹H NMR (400 MHz, CDCl₃) δ 7.38-7.24 (m, 3H), 7.19-7.02 (m, 2H), 5.99-5.85 (m, 1H), 5.41-5.35 (m, 1H), 3.61-3.48 (m, 1H), 3.18-2.83 (m, 3H), 1.05-0.98 (m, 1H), 0.60-0.45 (m, 2H), 0.25-0.16 (m, 2H). | 305.9 0.811 |
| 112 Method 26 | (5S,7S)-2-(cyclopropylmethylsulfonyl)-7-fluoro-5-phenyl-6,7-dihydro-5H-pyrrolo[1,2-b][1,2,4]triazole | 0.060 | Single Unknown Stereoisomer | ¹H NMR (400 MHz, CDCl₃) δ 7.41-7.32 (m, 3H), 7.27-7.16 (m, 2H), 6.14-5.98 (m, 1H), 5.57-5.53 (m, 1H), 3.82-3.58 (m, 1H), 3.35-3.23 (m, 2H), 3.12-2.95 (m, 1H), 1.27-1.13 (m, 1H), 0.69-0.48 (m, 2H), 0.31-0.11 (m, 2H). | 321.9 0.831 |

TABLE 1-continued

| Example Synthetic Method | Structure | Ki (μM) | Stereo | ¹H NMR | MS (m/z) R.T. (min) |
|---|---|---|---|---|---|
| 113 Method 26 | (5S,7S)-7-fluoro-5-phenyl-2-(2,2,2-trifluoroethylsulfinyl)-6,7-dihydro-5H-pyrrolo[1,2-b][1,2,4]triazole | 0.028 | Mixture of Diastereomers | ¹H NMR (400 MHz, CDCl₃) δ 7.46-7.39 (m, 3H), 7.27-7.22 (m, 2H), 6.15-5.97 (m, 1H), 5.55-5.50 (m, 1H), 4.20-4.09 (m, 1H), 4.04-3.95 (m, 1H), 3.76-3.61 (m, 1H), 3.06-2.93 (m, 1H). | 333.9 0.837 |
| 114 Method 26 | (5S,7S)-7-fluoro-5-phenyl-2-(2,2,2-trifluoroethylsulfonyl)-6,7-dihydro-5H-pyrrolo[1,2-b][1,2,4]triazole | 0.071 | Single Unknown Stereoisomer | ¹H NMR (400 MHz, CDCl₃) δ 7.49-7.38 (m, 3H), 7.25-7.18 (m, 2H), 6.19-5.97 (m, 1H), 5.63-5.53 (m, 1H), 4.26-4.19 (m, 2H), 3.75-3.63 (m, 1H), 3.07-3.06 (m, 1H). | 350.1 0.674 |
| 115 Method 26 | (5S,7S)-7-fluoro-2-(methoxymethylsulfinyl)-5-phenyl-6,7-dihydro-5H-pyrrolo[1,2-b][1,2,4]triazole | 0.031 | Mixture of Diastereomers | ¹H NMR (400 MHz, CDCl₃) δ 7.48-7.40 (m, 3H), 7.27-7.22 (m, 2H), 6.16-5.96 (m, 1H), 5.57-5.51 (m, 1H), 5.01-4.85 (m, 2H), 3.70-3.68 (m, 3H), 3.69-3.55 (m, 1H), 3.03-2.82 (m, 1H). | 295.9 0.761 |
| 116 Method 26 | (5S,7S)-7-fluoro-2-(methoxymethylsulfonyl)-5-phenyl-6,7-dihydro-5H-pyrrolo[1,2-b][1,2,4]triazole | 0.170 | Single Unknown Stereoisomer | ¹H NMR (400 MHz, CDCl₃) δ 7.52-7.40 (m, 3H), 7.27-7.19 (m, 2H), 6.15-5.99 (m, 1H), 5.58-5.55 (m, 1H), 4.86-4.77 (m, 2H), 3.79-3.61 (m, 4H), 3.06-2.94 (m, 1H). | 312.1 1.580 |

TABLE 1-continued

| Example Synthetic Method | Structure | Ki (μM) | Stereo | ¹H NMR | MS (m/z) R.T. (min) |
|---|---|---|---|---|---|
| 117 Method 16 | (5S,7S)-2-(2,2-difluorocyclopropyl)sulfinyl-7-fluoro-5-phenyl-6,7-dihydro-5H-pyrrolo[1,2-b][1,2,4]triazole | 0.012 | Mixture of Diastereomers | ¹H NMR (400 MHz, CD₃OD) δ 7.50-7.38 (m, 3H), 7.29-7.25 (m, 2H), 6.21-6.19 (m, 0.5H), 6.07-6.04 (m, 0.5H), 5.69-5.65 (m, 1H), 3.87-3.72 (m, 2H), 2.90-2.82 (m, 1H), 2.45-2.37 (m, 1H), 2.25-2.10 (m, 1H). | 328.1 1.571 & 1.619 |
| 118 Method 28 | (5S,7S)-2-((2,2-difluorocyclopropyl)sulfonyl)-7-fluoro-5-phenyl-6,7-dihydro-5H-pyrrolo[1,2-b][1,2,4]triazole | 0.004 | Mixture of Diastereomers | ¹H NMR (400 MHz, CD₃OD) δ 7.50-7.39 (m, 3H), 7.29-7.25 (m, 2H), 6.22-6.06 (m, 1H), 5.75-5.66 (m, 1H), 3.90-3.22 (m, 2H), 2.91-2.84 (m, 1H), 2.50-2.40 (m, 1H), 2.38-2.25 (m, 1H) s. | 344.1 1.727 & 1.782 |
| 119 Method 28 | (5S,7S)-7-fluoro-5-(2-fluorophenyl)-2-[(1S)-2,2-difluorocyclopropyl]sulfonyl-6,7-dihydro-5H-pyrrolo[1,2-b][1,2,4]triazole | 0.007 | Single Unknown Stereoisomer | ¹H NMR (400 MHz, CD₃OD) δ 7.50-7.41 (m, 1H), 7.27-7.11 (m, 3H), 6.26-6.06 (m, 1H), 5.96-5.87 (m, 1H), 3.92-3.74 (m, 2H), 2.96-2.80 (m, 1H), 2.46-2.41 (m, 1H), 2.30-2.27 (m, 1H). | 362.1 1.010 |
| 120 Method 28 | (5S,7S)-5-(2-chlorophenyl)-7-fluoro-2-[(1S)-2,2-difluorocyclopropyl]sulfonyl-6,7-dihydro-5H-pyrrolo[1,2-b][1,2,4]triazole | <0.005 | Single Unknown Stereoisomer | ¹H NMR (400 MHz, CDCl₃) δ 7.48 (d, J = 8.0 Hz, 1H), 7.38-7.28 (m, 2H), 6.79-6.71 (m, 1H), 6.16-6.10 (m, 0.5H), 6.08-6.01 (m, 1H), 6.00-5.96 (m, 0.5H), 3.80-3.68 (m, 1H), 3.58-3.47 (m, 1H), 2.98-2.87 (m, 1H), 2.65-2.57 (m, 1H), 2.22-2.14 (m, 1H). | 378.1 1.061 |

TABLE 1-continued

| Example Synthetic Method | Structure | Ki (μM) | Stereo | ¹H NMR | MS (m/z) R.T. (min) |
|---|---|---|---|---|---|
| 121 Method 28 | (5S,7S)-2-(2,2-difluorocyclopropyl)sulfonyl-5-(2,3-difluorophenyl)-7-fluoro-6,7-dihydro-5H-pyrrolo[1,2-b][1,2,4]triazole | <0.005 | Mixture of Diastereomers | ¹H NMR (400 MHz, CDCl$_3$) δ 7.27-7.22 (m, 1H), 7.15-7.10 (m, 1H), 6.77-6.70 (m, 1H), 6.16-6.00 (m, 1H), 5.95-5.85 (m, 1H), 3.80-3.68 (m, 1H), 3.52-3.47 (m, 1H), 3.05-2.92 (m, 1H), 2.70-2.52 (m, 1H), 2.20-2.10 (m, 1H). | 380.0 1.823 |
| 122 Method 28 | (5S,7S)-2(2,2-difluorocyclopropyl)sulfonyl-5-(2,5-difluorophenyl)-7-fluoro-6,7-dihydro-5H-pyrrolo[1,2-b][1,2,4]triazole | 0.012 | Single Unknown Stereoisomer | ¹H NMR (400 MHz, CDCl$_3$) δ 7.18-7.09 (m, 2H), 6.75-6.68 (m, 1H), 6.15-5.99 (m, 1H), 5.90-5.85 (m, 1H), 3.79-3.68 (m, 1H), 3.53-3.47 (m, 1H), 3.03-2.92 (m, 1H), 2.65-2.55 (m, 1H), 2.25-2.15 (m, 1H). | 380.1 1.024 |
| 123 Method 28 | (5S,7S)-2-(2,2-difluorocyclopropyl)sulfonyl-5-(2,6-difluorophenyl)-7-fluoro-6,7-dihydro-5H-pyrrolo[1,2-b][1,2,4]triazole | <0.005 | Mixture of Diastereomers | ¹H NMR (400 MHz, CDCl$_3$) δ 7.44-7.38 (m, 1H), 6.99-6.94 (m, 2H), 6.20-6.03 (m, 1H), 5.91-5.87 (m, 1H), 3.84-3.76 (m, 1H), 3.49-3.43 (m, 1H), 3.15-3.00 (m, 1H), 2.70-2.53 (m, 1H), 2.14-2.08 (m, 1H). | 380.1 1.004 |
| 124 Method 28 | (5S,7S)-7-fluoro-5-(2-fluorophenyl)-2-[(1R)-2,2-difluorocyclopropyl]sulfonyl-6,7-dihydro-5H-pyrrolo[1,2-b][1,2,4]triazole | <0.005 | Single Unknown Stereoisomer | ¹H NMR (400 MHz, CD$_3$OD) δ 7.50-7.41 (m, 1H), 7.26-7.10 (m, 3H), 6.26-6.06 (m, 1H), 5.95-5.88 (m, 1H), 3.95-3.72 (m, 2H), 2.99-2.77 (m, 1H), 2.49-2.36 (m, 1H), 2.34-2.22 (m, 1H). | 362.1 1.009 |

TABLE 1-continued

| Example Synthetic Method | Structure | Ki (μM) | Stereo | ¹H NMR | MS (m/z) R.T. (min) |
|---|---|---|---|---|---|
| 125 Method 28 | (5S,7S)-5-(2-chlorophenyl)-7-fluoro-2-[(1R)-2,2-difluorocyclopropyl]sulfonyl-6,7-dihydro-5H-pyrrolo[1,2-b][1,2,4]triazole | <0.005 | Single Unknown Stereoisomer | ¹H NMR (40 MHz, CDCl₃) δ 7.47 (d, J = 7.6 Hz, 1H), 7.38-7.28 (m, 2H), 6.75 (d, J = 7.6 Hz, 1H), 6.13 (d, J = 6.8 Hz, 0.5H), 6.07-6.01 (m, 1H), 5.99 (d, J = 7.2 Hz, 0.5H), 3.84-3.67 (m, 1H), 3.56-3.45 (m, 1H), 3.00-2.85 (m, 1H), 2.69-2.49 (m, 1H), 2.23-2.09 (m, 1H). | 378.1 1.062 |
| 126 Method 28 | (5S,7S)-5-(2,5-difluorophenyl)-7-fluoro-2-[(1S)-2,2-difluorocyclopropyl]sulfonyl-6,7-dihydro-5H-pyrrolo[1,2-b][1,2,4]triazole | <0.005 | Single Unknown Stereoisomer | ¹H NMR (400 MHz, CDCl₃) δ 7.20-7.05 (m, 2H), 6.75-6.68 (m, 1H), 6.16-6.00 (m, 1H), 5.95-5.85 (m, 1H), 3.80-3.68 (m, 1H), 3.60-3.47 (m, 1H), 3.03-2.98 (m, 1H), 2.70-2.52 (m, 1H), 2.20-2.15 (m, 1H). | 380.0 1.808 |
| 127 Method 28 | (5S,7S)-5-(2,5-difluorophenyl)-7-fluoro-2-[(1R)-2,2-difluorocyclopropyl]sulfonyl-6,7-dihydro-5H-pyrrolo[1,2-b][1,2,4]triazole | 0.006 | Single Unknown Stereoisomer | ¹H NMR (400 MHz, CDCl₃) δ 7.20-7.05 (m, 2H), 6.75-6.68 (m, 1H), 6.16-5.95 (m, 1H), 5.90-5.80 (m, 1H), 3.82-3.65 (m, 1H), 3.62-3.40 (m, 1H), 3.07-2.92 (m, 1H), 2.62-2.55 (m, 1H), 2.20-2.12 (m, 1H). | 380.1 1.808 |
| 128 Method 28 | (5S,7S)-5-(2,3-difluorophenyl)-7-fluoro-2-[(1R)-2,2-difluorocyclopropyl]sulfonyl-6,7-dihydro-5H-pyrrolo[1,2-b][1,2,4]triazole | 0.010 | Single Unknown Stereoisomer | ¹H NMR (400 MHz, CDCl₃) δ 7.27-7.22 (m, 1H), 7.20-7.08 (m, 1H), 6.77-6.72 (m, 1H), 6.16-6.00 (m, 1H), 5.98-5.85 (m, 1H), 3.80-3.72 (m, 1H), 3.52-3.44 (m, 1H), 3.05-2.88 (m, 1H), 2.75-2.55 (m, 1H), 2.17-2.13 (m, 1H). | 380.0 1.826 |

TABLE 1-continued

| Example Synthetic Method | Structure | Ki (μM) | Stereo | ¹H NMR | MS (m/z) R.T. (min) |
|---|---|---|---|---|---|
| 129 Method 28 | (5S,7S)-5-(2,3-difluorophenyl)-7-fluoro-2-[(1S)-2,2-difluorocyclopropyl]sulfonyl-6,7-dihydro-5H-pyrrolo[1,2-b][1,2,4]triazole | <0.005 | Single Unknown Stereoisomer | ¹H NMR (400 MHz, CDCl₃) δ 7.27-7.22 (m, 1H), 7.20-7.10 (m, 1H), 6.77-6.72 (m, 1H), 6.16-6.00 (m, 1H), 5.95-5.85 (m, 1H), 3.83-3.73 (m, 1H), 3.55-3.46 (m, 1H), 3.03-2.95 (m, 1H), 2.59-2.54 (m, 1H), 2.16-2.12 (m, 1H). | 380.0 1.830 |
| 130 Method 28 | (5S,7S)-2-(((S)-2,2-difluorocyclopropyl)sulfonyl)-7-fluoro-5-phenyl-6,7-dihydro-5H-pyrrolo[1,2-b][1,2,4]triazole | 0.003 | | ¹H NMR (400 MHz, CD₃OD) δ 7.44-7.37 (m, 3H), 7.29-7.27 (m, 2H), 6.22-6.06 (m, 1H), 5.71-5.66 (m, 1H), 3.89-3.76 (m, 2H), 2.91-2.83 (m, 1H), 2.42-2.38 (m, 1H), 2.29-2.25 (m, 1H). | 344.0 1.771 |
| 131 Method 28 | (5S,7S)-2-(((R)-2,2-difluorocyclopropyl)sulfonyl)-7-fluoro-5-phenyl-6,7-dihydro-5H-pyrrolo[1,2-b][1,2,4]triazole | 0.004 | Single Unknown Stereoisomer | ¹H NMR (400 MHz, CD₃OD) δ 7.45-7.38 (m, 3H), 7.30-7.27 (m, 2H), 6.22-6.06 (m, 1H), 5.71-5.67 (m, 1H), 3.88-3.74 (m, 2H), 2.90-2.82 (m, 1H), 2.42-2.38 (m, 1H), 2.30-2.26 (m, 1H). | 344.1 1.770 min |
| 132 Method 29 | (5S,7S)-7-fluoro-5-phenyl-2-(trifluoromethylsulfinyl)-6,7-dihydro-5H-pyrrolo[1,2-b][1,2,4]triazole | 0.011 | Mixture of Diastereomers | ¹H NMR (400 MHz, CDCl₃) δ 7.44-7.40 (m, 3H), 7.27-7.24 (m, 2H), 6.17-6.13 (m, 0.5H), 6.03-6.00 (m, 0.5H), 5.58-5.55 (m, 1H), 3.75-3.65 (m, 1H), 3.07-2.96 (m, 1H). | 319.9 0.862 |

TABLE 1-continued

| Example Synthetic Method | Structure | Ki (µM) | Stereo | $^1$H NMR | MS (m/z) R.T. (min) |
|---|---|---|---|---|---|
| 133 Method 29 | (5S,7S)-7-fluoro-5-(2-fluorophenyl)-2-(trifluoromethylsulfonyl)-6,7-dihydro-5H-pyrrolo[1,2-b][1,2,4]triazole | 0.004 | Single Unknown Stereoisomer | $^1$H NMR (400 MHz, CDCl$_3$) δ 7.45-7.41 (m, 1H), 7.21-7.14 (m, 2H), 6.99-6.95 (m, 1H), 6.18 (d, J = 7.2 Hz, 0.5H), 6.05 (d, J = 7.2 Hz, 0.5H), 5.96-5.93 (m, 1H), 3.84-3.70 (m, 1H), 3.08-2.92 (m, 1H). | 353.8 0.929 |
| 134 Method 29 | (5S,7S)-5-(2-chlorophenyl)-7-fluoro-2-(trifluoromethylsulfonyl)-6,7-dihydro-5H-pyrrolo[1,2-b][1,2,4]triazole | 0.003 | Single Unknown Stereoisomer | $^1$H NMR (400 MHz, CDCl$_3$) δ 7.49 (d, J = 7.6 Hz, 1H), 7.40-7.27 (m, 2H), 6.70 (d, J = 7.6 Hz, 1H), 6.17 (d, J = 7.2 Hz, 0.5H), 6.13-6.07 (m, 1H), 6.02 (d, J = 5.2 Hz, 0.5H), 3.87-3.71 (m, 1H), 3.03-2.92 (m, 1H). | 370.0 0.900 |
| 135 Method 29 | (5S,7S)-7-fluoro-5-(3-fluorophenyl)-2-(trifluoromethylsulfonyl)-6,7-dihydro-5H-pyrrolo[1,2-b][1,2,4]triazole | 0.004 | Single Unknown Stereoisomer | $^1$H NMR (400 MHz, CD$_3$OD) δ 7.48-7.44 (m, 1H), 7.17-7.06 (m, 3H), 6.26-6.10 (m, 1H), 5.79-5.76 (m, 1H), 3.86-3.75 (m, 1H), 2.96-2.85 (m, 1H). | 354.1 1.135 |
| 136 Method 29 | (5S,7S)-5-(2,3-difluorophenyl)-7-fluoro-2-(trifluoromethylsulfonyl)-6,7-dihydro-5H-pyrrolo[1,2-b][1,2,4]triazole | <0.005 | Single Unknown Stereoisomer | $^1$H NMR (400 MHz, CDCl$_3$) δ 7.27-7.22 (m, 1H), 7.20-7.14 (m, 1H), 6.74-6.70 (m, 1H), 6.20-6.04 (m, 1H), 5.96-5.94 (m, 1H), 3.86-3.72 (m, 1H), 3.09-2.98 (m, 1H). | 372.0 2.022 |

TABLE 1-continued

| Example Synthetic Method | Structure | Ki (µM) | Stereo | ¹H NMR | MS (m/z) R.T. (min) |
|---|---|---|---|---|---|
| 137 Method 29 | (5S,7S)-7-fluoro-5-phenyl-2-(trifluoromethylsulfonyl)-6,7-dihydro-5H-pyrrolo[1,2-b][1,2,4]triazole | 0.004 | Single Unknown Stereoisomer | ¹H NMR (400 MHz, CDCl$_3$) δ 7.44-7.42 (m, 2H), 6.19-6.05 (m, 1H), 5.64-5.60 (m, 1H), 3.79-3.65 (m, 1H), 3.12-3.01 (m, 1H). | 336.1 1.123 |
| 138 Method 29 | (5S,7S)-5-(2,5-difluorophenyl)-7-fluoro-2-(trifluoromethylsulfonyl)-6,7-dihydro-5H-pyrrolo[1,2-b][1,2,4]triazole | <0.005 | Single Unknown Stereoisomer | ¹H NMR (400 MHz, CDCl$_3$) δ 7.17-7.12 (m, 2H), 6.70-6.67 (m, 1H), 6.19-6.03 (m, 1H), 5.90-5.89 (m, 1H), 3.84-3.70 (m, 1H), 3.08-2.97 (m, 1H). | 372.1 1.134 |
| 139 Method 29 | (5S,7S)-5-(2,6-difluorophenyl)-7-fluoro-2-(trifluoromethylsulfonyl)-6,7-dihydro-5H-pyrrolo[1,2-b][1,2,4]triazole | 0.005 | Single Unknown Stereoisomer | ¹H NMR (400 MHz, CD$_3$OD) δ 7.55-7.51 (m, 1H), 7.13-7.08 (m, 2H), 6.29-6.13 (m, 1H), 6.08-6.06 (m, 1H), 3.95-3.83 (m, 1H), 3.04-2.92 (m, 1H). | 372.1 1.124 |
| 140 Method 29 | (5R,7R)-5-(2,3-difluorophenyl)-7-fluoro-2-(trifluoromethylsulfonyl)-6,7-dihydro-5H-pyrrolo[1,2-b][1,2,4]triazole | 0.540 | Single Unknown Stereoisomer | ¹H NMR (400 MHz, CDCl$_3$) δ 7.27-7.24 (m, 1H), 7.23-7.14 (m, 1H), 6.75-6.71 (m, 1H), 6.21-6.05 (m, 1H), 6.02-5.95 (m, 1H), 3.88-3.75 (m, 1H), 3.08-2.97 (m, 1H). | 373.2 2.031 |

TABLE 1-continued

| Example Synthetic Method | Structure | Ki (μM) | Stereo | ¹H NMR | MS (m/z) R.T. (min) |
|---|---|---|---|---|---|
| 141 Method 30 | (5S,7S)-7-fluoro-5-(3-fluorophenyl)-2-[(1S,2S)-2-fluorocyclopropyl]sulfonyl-6,7-dihydro-5H-pyrrolo[1,2-b][1,2,4]triazole | <0.005 | Single Unknown Stereoisomer | ¹H NMR (40 MHz, CDCl$_3$) δ 7.45-7.37 (m, 1H), 7.15-7.09 (m, 1H), 7.08-7.04 (m, 1H), 7.02-6.95 (m, 1H), 6.16-5.98 (m, 1H), 5.58-5.51 (m, 1H), 5.24-5.04 (m, 1H), 3.77-3.62 (m, 1H), 3.23-3.12 (m, 1H), 3.08-2.95 (m, 1H), 1.90-1.75 (m, 2H). | 344.1 0.974 |
| 142 Method 30 | rac-(5S,7S)-7-fluoro-5-(3-fluorophenyl)-2-[rac-(1R,2R)-2-fluorocyclopropyl]sulfonyl-6,7-dihydro-5H-pyrrolo[1,2-b][1,2,4]triazole | <0.005 | Single Unknown Stereoisomer | ¹H NMR (400 MHz, CDCl$_3$) δ 7.45-7.37 (m, 1H), 7.15-7.09 (m, 1H), 7.08-7.04 (m, 1H), 7.02-6.96 (m, 1H), 6.14-5.98 (m, 1H), 5.59-5.49 (m, 1H), 5.22-5.06 (m, 1H), 3.80-3.64 (m, 1H), 3.24-3.10 (m, 1H), 3.08-2.94 (m, 1H), 1.93-1.75 (m, 2H). | 344.1 0.974 |
| 143 Method 29 | (5S,7S)-5-(3,4-difluorophenyl)-7-fluoro-2-[(1S,2S)-2-fluorocyclopropyl]sulfonyl-6,7-dihydro-5H-pyrrolo[1,2-b][1,2,4]triazole | 0.031 | Single Unknown Stereoisomer | ¹H NMR (400 MHz, CDCl$_3$) δ 7.27-7.21 (m, 1H), 7.20-7.10 (m, 1H), 7.06-7.03 (m, 1H), 6.14 (d, J = 8.4 Hz, 0.5H), 6.00 (d, J = 8.0 Hz, 0.5H), 5.53-5.21 (m, 1H), 5.15-5.10 (m, 0.5H), 5.06-3.02 (m, 0.5H), 3.73-3.64 (m, 1H), 3.16-3.12 (m, 1H), 3.03-2.92 (m, 1H), 1.89-1.80 (m, 2H). | 362.1 0.972 |
| 144 Method 29 | (5S,7S)-5-(3,4-difluorophenyl)-7-fluoro-2-[(1R,2R)-2-fluorocyclopropyl]sulfonyl-6,7-dihydro-5H-pyrrolo[1,2-b][1,2,4]triazole | 0.009 | Single Unknown Stereoisomer | ¹H NMR (400 MHz, CDCl$_3$) δ 7.27-7.22 (m, 1H), 7.16-7.10 (m, 1H), 7.07-7.03 (m, 1H), 6.13 (d, J = 6.8 Hz, 0.5H), 6.00 (d, J = 8.4 Hz, 0.5H), 5.54-5.21 (m, 1H), 5.15-5.10 (m, 0.5H), 5.06-5.02 (m, 0.5H), 3.73-3.64 (m, 1H), 3.19-3.12 (m, 1H), 3.04-2.93 (m, 1H), 1.88-1.78 (m, 2H). | 362.1 0.792 |

TABLE 1-continued

| Example Synthetic Method | Structure | Ki (µM) | Stereo | ¹H NMR | MS (m/z) R.T. (min) |
|---|---|---|---|---|---|
| 145 Method 20 | (5S,7S)-7-fluoro-5-phenyl-2-[(1R,2R)-2-fluorocyclopropyl]sulfonyl-6,7-dihydro-5H-pyrrolo[1,2-b][1,2,4]triazole | 0.005 | Single Unknown Stereoisomer | ¹H NMR (400 MHz, CD₃OD) δ 7.47-7.41 (m, 3H), 7.31-7.29 (m, 1H), 5.71-5.69 (m, 1H), 5.22-5.05 (m, 1H), 3.83-3.76 (m, 1H), 3.41-3.33 (m, 1H), 2.95-2.86 (m, 1H), 1.90-1.74 (m, 2H). | 326.1 0.670 |
| 146 Method 20 | (5S,7S)-7-fluoro-5-phenyl-2-[(1S,2S)-2-fluorocyclopropyl]sulfonyl-6,7-dihydro-5H-pyrrolo[1,2-b][1,2,4]triazole | 0.004 | Single Unknown Stereoisomer | ¹H NMR (400 MHz, CD₃OD) δ 7.47-7.41 (m, 3H), 7.32-7.30 (m, 2H), 6.24-6.08 (m, 1H), 5.71-5.69 (m, 1H), 5.22-5.06 (m, 1H), 3.83-3.76 (m, 1H), 3.41-3.32 (m, 1H), 2.95-2.86 (m, 1H), 1.89-1.84 (m, 1H), 1.75-1.70 (m, 1H). | 326.1 0.669 |
| 147 Method 26 | (5S,7S)-7-fluoro-5-phenyl-2-(2-pyridylmethylsulfinyl)-6,7-dihydro-5H-pyrrolo[1,2-b][1,2,4]triazole | 0.140 | Mixture of Diastereomers | ¹H NMR (400 MHz, CD₃OD) δ 8.49-8.46 (m, 1H), 7.77-7.74 (m, 1H), 7.42-7.32 (m, 5H), 7.26-7.25 (m, 1H), 7.18-7.15 (m, 1H), 6.19-6.03 (m, 1H), 5.64-5.60 (m, 1H), 4.76-4.71 (m, 2H), 3.80-3.70 (m, 1H), 2.88-2.74 (m, 1H). | 343.1 1.428 |
| 148 Method 26 | (5S,7S)-2-(2,2-difluoroethylsulfinyl)-7-fluoro-5-phenyl-6,7-dihydro-5H-pyrrolo[1,2-b][1,2,4]triazole | 0.007 | Mixture of Diastereomers | ¹H NMR (400 MHz, CDCl₃) δ 7.45-7.40 (m, 3H), 7.27-7.24 (m, 2H), 6.31-6.15 (m, 1H), 6.13-5.97 (m, 1H), 5.54-5.50 (m, 1H), 3.93-3.75 (m, 1H), 3.73-3.62 (m, 2H), 3.05-2.98 (m, 1H). | 315.9 0.806 |

TABLE 1-continued

| Example Synthetic Method | Structure | Ki (μM) | Stereo | ¹H NMR | MS (m/z) R.T. (min) |
|---|---|---|---|---|---|
| 149 Method 31 | (5S,7S)-2-(1,1-difluoroethylsulfonyl)-7-fluoro-5-phenyl-6,7-dihydro-5H-pyrrolo[1,2-b][1,2,4]triazole | 0.016 | Single Unknown Stereoisomer | ¹H NMR (400 MHz, CD₃OD) δ 7.44-7.41 (m, 3H), 7.28-7.25 (m, 2H), 6.24-6.08 (m, 1H), 5.75-5.70 (m, 1H), 3.86-3.72 (m, 1H), 2.93-2.82 (m, 1H), 2.06 (t, J = 6.8 Hz, 3H). | 332.1 1.081 |
| 150 Method 31 | (5S,7S)-7-fluoro-2-(1-methylcyclopropyl)sulfonyl-5-phenyl-6,7-dihydro-5H-pyrrolo[1,2-b][1,2,4]triazole | 0.021 | Single Unknown Stereoisomer | ¹H NMR (400 MHz, CDCl₃) δ 7.42-7.38 (m, 3H), 7.27-7.23 (m, 2H), 6.13-6.11 (m, 0.5H), 6.00-5.97 (m, 0.5H), 5.56-5.53 (m, 1H), 3.71-3.62 (m, 1H), 3.05-2.94 (m, 1H), 1.75-1.68 (m, 2H), 1.52 (s, 3H), 0.94-0.87 (m, 2H). | 321.9 0.831 |
| 151 Method 26 | (5S,7S)-7-fluoro-5-phenyl-2-(pyrazol-1-ylmethylsulfonyl)-6,7-dihydro-5H-pyrrolo[1,2-b][1,2,4]triazole | 0.730 | Single Unknown Stereoisomer | ¹H NMR (400 MHz, CDCl₃) δ 7.61 (s, 1H), 7.45-7.35 (m, 3H), 7.34-7.30 (m, 1H), 7.21-7.19 (m, 2H), 6.28-6.27 (m, 1H), 6.10-5.96 (m, 1H), 5.75-5.65 (m, 2H), 5.55-5.48 (m, 1H), 3.75-3.60 (m, 1H), 3.05-2.92 (m, 1H). | 348.1 0.905 |
| 152 Method 26 | (5S,7S)-7-fluoro-5-phenyl-2-(pyrazol-1-ylmethylsulfinyl)-6,7-dihydro-5H-pyrrolo[1,2-b][1,2,4]triazole | 0.030 | Mixture of Diastereomers | ¹H NMR (400 MHz, CDCl₃) δ 7.56-7.53 (m, 2H), 7.41-7.39 (m, 3H), 7.26-7.22 (m, 2H), 6.27 (s, 1H), 6.15-5.98 (m, 1H), 5.69-5.55 (m, 2H), 5.53-5.47 (m, 1H), 3.69-3.60 (m, 1H), 3.02-2.92 (m, 1H). | 332.2 0.876 |

TABLE 1-continued

| Example Synthetic Method | Structure | Ki (μM) | Stereo | ¹H NMR | MS (m/z) R.T. (min) |
|---|---|---|---|---|---|
| 153 Method 26 | (5S,7S)-7-fluoro-2-(1,1,2,2,2-pentafluoroethylsulfonyl)-5-phenyl-6,7-dihydro-5H-pyrrolo[1,2-b][1,2,4]triazole | 0.010 | Single Unknown Stereoisomer | ¹H NMR (400 MHz, CD₃OD) δ 7.46-7.41 (m, 3H), 7.29-7.26 (m, 2H), 6.27-6.24 (m, 0.5H), 6.13-6.10 (m, 0.5H), 5.77-5.75 (m, 1H), 3.85-3.75 (m, 1H), 2.95-2.84 (m, 1H). | 386.0 2.113 |
| 154 Method 26 | (5S,7S)-7-fluoro-2-(1,1,2,2,2-pentafluoroethylsulfinyl)-5-phenyl-6,7-dihydro-5H-pyrrolo[1,2-b][1,2,4]triazole | 0.007 | Mixture of Diastereomers | ¹H NMR (400 MHz, CD₃OD) δ 7.43-7.40 (m, 3H), 7.29-7.25 (m, 2H), 6.25-6.22 (m, 0.5H), 6.11-6.08 (m, 0.5H), 5.73-5.70 (m, 1H), 3.85-3.75 (m, 1H), 2.91-2.80 (m, 1H). | 370.0 1.959 |
| 155 Method 32 | (5S,7S)-2-[1-(difluoromethyl)cyclopropyl]sulfonyl-7-fluoro-5-phenyl-6,7-dihydro-5H-pyrrolo[1,2-b][1,2,4]triazole | 0.0048 | Single Unknown Stereoisomer | ¹H NMR (400 MHz, CDCl₃) δ 7.42-7.37 (m, 3H), 7.26-7.18 (m, 2H), 6.57 (t, J = 56.8 Hz, 1H), 6.12-5.96 (m, 1H), 5.56-5.53 (m, 1H), 3.74-3.60 (m, 1H), 3.02-2.92 (m, 1H), 1.90-1.84 (m, 2H), 1.50-1.44 (m, 2H). | 358.1 1.043 |
| 156 Method 33 | 2,2-difluoro-2-[[(5S,7S)-7-fluoro-5-phenyl-6,7-dihydro-5H-pyrrolo[1,2-b][1,2,4]triazol-2-yl]sulfonyl]ethanol | 0.270 | Single Unknown Stereoisomer | ¹H NMR (400 MHz, CD₃OD) δ 7.43-7.40 (m, 3H), 7.28-7.25 (m, 2H), 6.24-6.08 (m, 1H), 5.73-5.71 (m, 1H), 4.19 (t, J = 14.4 Hz, 2H), 3.84-3.73 (m, 1H), 2.91-2.80 (m, 1H). | 348.1 0.972 |

TABLE 1-continued

| Example Synthetic Method | Structure | Ki (μM) | Stereo | ¹H NMR | MS (m/z) R.T. (min) |
|---|---|---|---|---|---|
| 157 Method 34 | 1-[[(5S,7S)-7-fluoro-5-phenyl-6,7-dihydro-5H-pyrrolo[1,2-b][1,2,4]triazol-2-yl]sulfonyl]cyclopropanecarbonitrile | 0.023 | Single Unknown Stereoisomer | ¹H NMR (400 MHz, CDCl$_3$) δ 7.52-7.40 (m, 2H), 7.38-7.25 (m, 3H), 6.16-6.00 (m, 1H), 5.67-5.59 (m, 1H), 3.78-3.64 (m, 1H), 3.08-2.96 (m, 1H), 2.20-2.09 (m, 2H), 1.95-1.80 (m, 2H). | 354.9 [M + Na]$^+$. 0.842 |
| 158 Method 35 | (5S,7S)-7-fluoro-2-(1-fluoroethylsulfonyl)-5-phenyl-6,7-dihydro-5H-pyrrolo[1,2-b][1,2,4]triazole | 0.013 | Mixture of Diastereomers | ¹H NMR (400 MHz, CDCl$_3$) δ 7.43-7.40 (m, 3H), 7.27-7.23 (m, 2H), 6.15-5.98 (m, 1H), 5.74-5.56 (m, 2H), 3.76-3.66 (m, 1H), 3.07-2.96 (m, 1H), 1.88-1.80 (m, 3H). | 314.1 1.692 |
| 159 Method 35 | (5S,7S)-7-fluoro-5-phenyl-2-[(1S)-1-fluoroethyl]sulfonyl-6,7-dihydro-5H-pyrrolo[1,2-b][1,2,4]triazole | 0.015 | Single Unknown Stereoisomer | ¹H NMR (400 MHz, CDCl$_3$) δ 7.45-7.40 (m, 3H), 7.27-7.23 (m, 2H), 6.14-5.98 (m, 1H), 5.74-5.72 (m, 0.5H), 5.62-5.57 (m, 1.5H), 3.74-3.64 (m, 1H), 3.06-2.96 (m, 1H), 1.88-1.80 (m, 3H). | 314.1 1.705 |
| 160 Method 35 | (5S,7S)-7-fluoro-5-phenyl-2-[(1R)-1-fluoroethyl]sulfonyl-6,7-dihydro-5H-pyrrolo[1,2-b][1,2,4]triazole | 0.018 | Single Unknown Stereoisomer | ¹H NMR (400 MHz, CDCl$_3$) δ 7.43-7.40 (m, 3H), 7.27-7.23 (m, 2H), 6.15-5.98 (m, 1H), 5.74-5.71 (m, 0.5H), 5.62-5.56 (m, 1.5H), 3.74-3.63 (m, 1H), 3.07-2.96 (m, 1H), 1.88-1.79 (m, 3H). | 314.1 1.704 |

TABLE 1-continued

| Example Synthetic Method | Structure | Ki (μM) | Stereo | ¹H NMR | MS (m/z) R.T. (min) |
|---|---|---|---|---|---|
| 161 Method 26 | (5S,7S)-7-fluoro-5-phenyl-2-propylsulfonyl-6,7-dihydro-5H-pyrrolo[1,2-b][1,2,4]triazole | 0.026 | Single Unknown Stereoisomer | ¹H NMR (400 MHz, CDCl$_3$) δ 7.44-7.40 (m, 3H), 7.27-7.24 (m, 2H), 6.13-6.11 (m, 0.5H), 5.99-5.97 (m, 0.5H), 5.54-5.52 (m, 1H), 3.71-3.65 (m, 1H), 3.36-3.32 (m, 2H), 3.04-2.94 (m, 1H), 1.92-1.82 (m, 2H), 1.05 (t, J = 7.2 Hz, 3H). | 309.9 0.847 |
| 162 Method 18 | (5S,7S)-7-fluoro-5-phenyl-2-[rac-(1S,2S)-2-methylcyclopropyl]sulfonyl-6,7-dihydro-5H-pyrrolo[1,2-b][1,2,4]triazole | 0.014 | Mixture of Diastereomers | ¹H NMR (400 MHz, CDCl$_3$) δ 7.42-7.40 (m, 3H), 7.25-7.22 (m, 2H), 6.12-6.10 (m, 0.5H), 5.99-5.97 (m, 0.5H), 5.54-5.51 (m, 1H), 3.74-3.63 (m, 1H), 3.05-2.94 (m, 1H), 2.48-2.44 (m, 1H), 1.89-1.86 (m, 1H), 1.63-1.61 (m, 1H), 1.16 (t, J = 5.6 Hz, 3H), 0.97-0.95 (m, 1H). | 322.1 0.689 |
| 163 Method 18 | (5S,7S)-7-fluoro-5-phenyl-2-[rac-(1S,2R)-2-(trifluoromethyl)cyclopropyl]sulfonyl-6,7-dihydro-5H-pyrrolo[1,2-b][1,2,4]triazole | 0.007 | Mixture of Diastereomers | ¹H NMR (400 MHz, CDCl$_3$) δ 7.42-7.40 (m, 3H), 7.27-7.23 (m, 2H), 6.14-6.12 (m, 0.5H), 6.00-5.98 (m, 0.5H), 5.57-5.53 (m, 1H), 3.72-3.66 (m, 1H), 3.13-2.96 (m, 2H), 2.57-2.51 (m, 1H), 1.92-1.88 (m, 1H), 1.60-1.55 (m, 1H). | 376.1 0.846 |
| 164 Method 20a | (5S,7S)-7-fluoro-2-(3-fluorocyclobutyl)sulfonyl-5-phenyl-6,7-dihydro-5H-pyrrolo[1,2-b][1,2,4]triazole | <0.005 | Single Unknown Stereoisomer | ¹H NMR (400 MHz, CDCl$_3$) δ 7.42-7.40 (m, 3H), 7.27-7.23 (m, 2H), 6.12-5.96 (m, 1H), 5.55-5.50 (m, 1H), 5.40-5.24 (m, 1H), 4.15-4.11 (m, 1H), 3.71-3.66 (m, 1H), 3.06-2.99 (m, 3H), 2.67-2.64 (m, 2H). | 340.1 0.980 |

TABLE 1-continued

| Example Synthetic Method | Structure | Ki (µM) | Stereo | ¹H NMR | MS (m/z) R.T. (min) |
|---|---|---|---|---|---|
| 165 Method 35 | (5S,7S)-7-fluoro-2-(1-fluoro-1-methyl-ethyl)sulfonyl-5-phenyl-6,7-dihydro-5H-pyrrolo[1,2-b][1,2,4]triazole | 0.025 | Single Unknown Stereoisomer | ¹H NMR (400 MHz, CD$_3$OD) δ 7.45-7.40 (m, 3H), 7.28-7.26 (m, 2H), 6.24-6.21 (m, 0.5H), 6.09-6.07 (m, 0.5H), 5.72-5.69 (m, 1H), 3.82-3.73 (m, 1H), 2.91-2.81 (m, 1H), 1.87-1.69 (m, 6H). | 328.1 1.745 |
| 166 Method 26 | (5S,7S)-7-fluoro-5-phenyl-2-tetrahydrofuran-3-ylsulfonyl-6,7-dihydro-5H-pyrrolo[1,2-b][1,2,4]triazole | 0.043 | Mixture of Diastereomers | ¹H NMR (400 MHz, CDCl$_3$) δ 7.41-7.39 (m, 3H), 7.26-7.21 (m, 2H), 6.13-5.96 (m, 1H), 5.56-5.53 (m, 1H), 4.33-4.30 (m, 1H), 4.20-4.02 (m, 2H), 4.00-3.77 (m, 2H), 3.75-3.60 (m, 1H), 3.03-2.95 (m, 1H), 2.60-2.54 (m, 1H), 2.30-2.22 (m, 1H). | 338.1 0.905 |
| 167 Method 31 | (5S,7S)-2-(2,2-difluoro-1-methyl-cyclopropyl)sulfonyl-7-fluoro-5-phenyl-6,7-dihydro-5H-pyrrolo[1,2-b][1,2,4]triazole | 0.012 | Mixture of Diastereomers | ¹H NMR (400 MHz, CD$_3$OD) δ 7.45-7.40 (m, 3H), 7.28-7.25 (m, 2H), 6.22-6.06 (m, 1H), 5.77-5.65 (m, 1H), 3.83-3.75 (m, 1H), 2.90-2.83 (m, 1H), 2.62-2.57 (m, 1H), 1.96-1.93 (m, 1H), 1.61-1.57 (m, 3H). | 358.1 0.708 |
| 168 Method 36 | ((1R,3S)-3-(((5S,7S)-fluoro-5-phenyl-6,7-dihydro-5H-pyrrolo[1,2-b][1,2,4]triazol-2-yl)sulfonyl)cyclobutyl)methanol | 0.530 | Single Unknown Stereoisomer | ¹H NMR (400 MHz, CDCl$_3$) δ 7.41-7.38 (m, 3H), 7.26-7.21 (m, 2H), 6.11-5.95 (m, 1H), 5.53-5.49 (m, 1H), 4.10-4.05 (m, 1H), 3.70-3.61 (m, 3H), 2.99-2.95 (m, 1H), 2.60-2.56 (m, 1H), 2.50-2.34 (m, 4H). | 352.1 0.862 |

TABLE 1-continued

| Example Synthetic Method | Structure | Ki (µM) | Stereo | ¹H NMR | MS (m/z) R.T. (min) |
|---|---|---|---|---|---|
| 169 Method 36 | ((1R,3S)-3-(((5S,7S)-7-fluoro-5-phenyl-6,7-dihydro-5H-pyrrolo[1,2-b][1,2,4]triazol-2-yl)sulfonyl)cyclobutyl)methanol | 0.052 | Single Unknown Stereoisomer | ¹H NMR (400 MHz, CDCl₃) δ 7.40-7.38 (m, 3H), 7.26-7.21 (m, 2H), 6.12-5.95 (m, 1H), 5.55-5.50 (m, 1H), 5.43-4.29 (m, 2H), 4.15-4.06 (m, 1H), 3.70-3.64 (m, 1H), 3.01-2.91 (m, 1H), 2.75-2.65 (m, 1H), 2.57-2.47 (m, 2H), 2.46-2.36 (m, 2H). | 354.1 0.976 |
| 170 Method 37 | (5S,7S)-7-fluoro-5-phenyl-2-spiro[2.2]pentan-2-ylsulfonyl-6,7-dihydro-5H-pyrrolo[1,2-b][1,2,4]triazole | <0.005 | Mixture of Diastereomers | ¹H NMR (400 MHz, CDCl₃) δ 7.43-7.40 (m, 3H), 7.27-7.22 (m, 2H), 6.12-5.95 (m, 1H), 5.53-5.50 (m, 1H), 3.75-3.67 (m, 1H), 3.09-2.98 (m, 2H), 1.97-1.94 (m, 1H), 1.61-1.57 (m, 1H), 1.28-1.24 (m, 1H), 1.18-1.12 (m, 1H), 0.98-0.85 (m, 2H). | 334.1 1.768 |
| 171 Method 20 | (5S,7S)-7-fluoro-5-phenyl-2-[(1R)-2,2-difluorocyclobutyl]sulfonyl-6,7-dihydro-5H-pyrrolo[1,2-b][1,2,4]triazole | <0.005 | Single Unknown Stereoisomer | ¹H NMR (400 MHz, CDCl₃) δ 7.42-7.38 (m, 3H), 7.26-7.20 (m, 2H), 6.12-5.96 (m, 1H), 5.55-5.50 (m, 1H), 4.62-4.56 (m, 1H), 3.71-3.62 (m, 1H), 2.99-2.90 (m, 1H), 2.88-2.77 (m, 1H), 2.57-2.50 (m, 2H), 2.30-2.22 (m, 1H). | 358.0 0.918 |
| 172 Method 20 | (5S,7S)-7-fluoro-5-phenyl-2-[(1S)-2,2-difluorocyclobutyl]sulfonyl-6,7-dihydro-5H-pyrrolo[1,2-b][1,2,4]triazole | 0.006 | Single Unknown Stereoisomer | ¹H NMR (400 MHz, CDCl₃) δ 7.41-7.38 (m, 3H), 7.26-7.20 (m, 2H), 6.13-5.96 (m, 1H), 5.56-5.50 (m, 1H), 4.64-4.56 (m, 1H), 3.73-3.64 (m, 1H), 3.03-2.93 (m, 1H), 2.88-2.78 (m, 1H), 2.70-2.55 (m, 2H), 2.30-2.27 (m, 1H). | 357.9 0.915 |

TABLE 1-continued

| Example Synthetic Method | Structure | Ki (µM) | Stereo | ¹H NMR | MS (m/z) R.T. (min) |
|---|---|---|---|---|---|
| 173 Method 43 | (5S)-2-[(R)-difluoromethylsulfinyl]-5-(3,5-difluorophenyl)-6,7-dihydro-5H-pyrrolo[1,2-b][1,2,4]triazole | 0.019 | Single Unknown Stereoisomer | 1H NMR (400 MHz, DMSO-d6) δ 7.52-7.20 (m, 2H), 7.17-7.04 (m, 2H), 5.72 (dd, J = 8.2, 6.3 Hz, 1H), 3.29-3.14 (m, 2H), 3.13-3.02 (m, 1H), 2.70-2.57 (m, 1H). | 320.0 4.26 |
| 174 Method 43 | (5S)-2-[(S)-difluoromethylsulfinyl]-5-(3,5-difluorophenyl)-6,7-dihydro-5H-pyrrolo[1,2-b][1,2,4]triazole | 0.310 | Single Unknown Stereoisomer | 1H NMR (400 MHz, DMSO-d6) δ 7.53-7.19 (m, 2H), 7.15-7.04 (m, 2H), 5.72 (dd, J = 8.2, 6.3 Hz, 1H), 3.27-3.12 (m, 2H), 3.07 (ddd, J = 16.1, 9.7, 6.1 Hz, 1H), 2.70-2.52 (m, 1H). | 320.0 4.30 |
| 175 Method 38 | 2-(difluoromethyl sulfonyl)-5-(3,5-difluorophenyl)-6,7-dihydro-5H-pyrrolo[1,2-b][1,2,4]triazole | 0.220 | Mixture of Enantiomers | 1H NMR (400 MHz, DMSO-d6) δ 7.59-7.24 (m, 2H), 7.22-7.10 (m, 2H), 5.82-5.70 (m, 1H), 3.26-3.01 (m, 3H), 2.71-2.60 (m, 1H). | 336.0 4.73 |
| 176 Method 1 | 2-(difluoromethylsulfinyl)-5-(3,5-difluorophenyl)-6,7-dihydro-5H-pyrrolo[1,2-b][1,2,4]triazole | 0.110 | Mixture of Diastereomers | 1H NMR (400 MHz, DMSO-d6) δ 7.52-7.19 (m, 2H), 7.18-7.00 (m, 2H), 5.77-5.67 (m, 1H), 3.28-3.14 (m, 2H), 3.07 (ddd, J = 16.3, 9.8, 6.2 Hz, 1H), 2.71-2.57 (m, 1H). | 320.0 4.35 |

TABLE 1-continued

| Example Synthetic Method | Structure | Ki (μM) | Stereo | ¹H NMR | MS (m/z) R.T. (min) |
|---|---|---|---|---|---|
| 177 Method 39 | 5-phenyl-2-(2,2,2-trifluoroethylsulfinyl)-6,7-dihydro-5H-pyrrolo[1,2-b][1,2,4]triazole | 0.057 | Mixture of Diastereomers | 1H NMR (400 MHz, DMSO-d6) δ 7.46-7.33 (m, 3H), 7.31-7.20 (m, 2H), 5.66 (q, J = 7.2 Hz, 1H), 4.52-4.38 (m, 2H), 3.29-2.98 (m, 3H), 2.69-2.56 (m, 1H). | 316.0 4.33 |
| 178 Method 40 | (5S,7S)-7-fluoro-2-(1-fluorocyclopropyl)sulfonyl-5-phenyl-6,7-dihydro-5H-pyrrolo[1,2-b][1,2,4]triazole | 0.006 | Single Unknown Stereoisomer | 1H NMR (400 MHz, DMSO-d6) δ 7.52-7.36 (m, 3H), 7.34-7.24 (m, 2H), 6.31 (ddd, J = 56.1, 7.3, 2.2 Hz, 1H), 5.82 (ddd, J = 8.4, 6.5, 3.4 Hz, 1H), 3.79 (dddd, J = 25.0, 15.5, 8.5, 7.3 Hz, 1H), 2.77 (dddd, J = 27.1, 15.1, 3.4, 2.1 Hz, 1H), 1.86-1.63 (m, 4H). | 326.0 4.89 |
| 179 Method 40¹ | rac-(5S,7S)-2-[(S)-difluoromethylsulfinyl]-7-fluoro-5-(3-fluorophenyl)-6,7-dihydro-5H-pyrrolo[1,2-b][1,2,4]triazole | 0.210 | Single Unknown Stereoisomer | 1H NMR (400 MHz, DMSO-d6) δ 7.58-7.12 (m, 5H), 6.31 (ddd, J = 56.0, 7.3, 2.0 Hz, 1H), 5.82 (ddd, J = 8.5, 6.7, 3.2 Hz, 1H), 2.76 (dddd, J = 27.2, 15.3, 3.2, 2.0 Hz, 1H), 2.53 (s, 1H). | 320 4.89 |
| 180 Method 40¹ | rac-(5S,7S)-7-fluoro-5-phenyl-2-[(S)-trifluoromethylsulfinyl]-6,7-dihydro-5H-pyrrolo[1,2-b][1,2,4]triazole | 0.30 | Single Unknown Stereoisomer | 1H NMR (400 MHz, DMSO-d6) δ 7.58-7.12 (m, 5H), 6.31 (ddd, J = 56.0, 7.3, 2.0 Hz, 1H), 5.82 (ddd, J = 8.5, 6.7, 3.2 Hz, 1H), 2.76 (dddd, J = 27.2, 15.3, 3.2, 2.0 Hz, 1H), 2.53 (s, 1H). | 320 4.48 |

TABLE 1-continued

| Example Synthetic Method | Structure | Ki (μM) | Stereo | ¹H NMR | MS (m/z) R.T. (min) |
|---|---|---|---|---|---|
| 181 Method 40[1] | rac-(5S,7S)-7-fluoro-5-phenyl-2-[(R)-trifluoromethylsulfinyl]-6,7-dihydro-5H-pyrrolo[1,2-b][1,2,4]triazole | 0.004 | Single Unknown Stereoisomer | 1H NMR (400 MHz, DMSO-d6) δ 7.65-7.37 (m, 2H), 7.38-7.13 (m, 1H), 7.13 (ddt, J = 21.1, 7.7, 1.6 Hz, 2H), 6.29 (ddd, J = 56.0, 7.2, 2.0 Hz, 1H), 5.83 (ddd, J = 8.7, 6.5, 3.2 Hz, 1H), 2.78 (dddd, J = 26.7, 15.2, 3.3, 2.1 Hz, 1H). | 320 4.41 |
| 182 Method 40[1] | rac-(5S,7S)-2-[(R)-difluoromethylsulfinyl]-7-fluoro-5-(3-fluorophenyl)-6,7-dihydro-5H-pyrrolo[1,2-b][1,2,4]triazole | 0.006 | Single Unknown Stereoisomer | 1H NMR (400 MHz, DMSO-d6) δ 7.58-7.11 (m, 6H), 6.32 (ddd, J = 56.0, 7.3, 2.0 Hz, 1H), 5.82 (ddd, J = 8.4, 6.6, 3.2 Hz, 1H), 2.76 (dddd, J = 27.1, 15.2, 3.2, 2.0 Hz, 1H). | 320 4.85 |
| 183 Method 40[1] | rac-(5S,7S)-7-fluoro-5-phenyl-2-[(S)-2,2,2-trifluoroethylsulfinyl]-6,7-dihydro-5H-pyrrolo[1,2-b][1,2,4]triazole | 0.004 | Single Unknown Stereoisomer | No NMR | 334 4.50 |
| 184 Method 40[1] | rac-(5S,7S)-2-[(R)-cyclopropylmethylsulfinyl]-7-fluoro-5-phenyl-6,7-dihydro-5H-pyrrolo[1,2-b][1,2,4]triazole | 0.130 | Single Unknown Stereoisomer | No NMR | 306.1 3.51 |

TABLE 1-continued

| Example Synthetic Method | Structure | Ki (μM) | Stereo | ¹H NMR | MS (m/z) R.T. (min) |
|---|---|---|---|---|---|
| 185 Method 40[1] | rac-(5S,7S)-7-fluoro-5-phenyl-2-[(R)-2,2,2-trifluoroethylsulfinyl]-6,7-dihydro-5H-pyrrolo[1,2-b][1,2,4]triazole | 0.019 | Single Unknown Stereoisomer | No NMR | 334 4.59 |
| 186 Method 40[1] | rac-(5S,7S)-2-[(S)-cyclopropylmethylsulfinyl]-7-fluoro-5-phenyl-6,7-dihydro-5H-pyrrolo[1,2-b][1,2,4]triazole | 0.020 | Single Unknown Stereoisomer | No NMR | 306.1 4.11 |
| 187 Method 40[1] | rac-(5S,7S)-7-fluoro-2-[(R)-isopropylsulfinyl]-5-phenyl-6,7-dihydro-5H-pyrrolo[1,2-b][1,2,4]triazole | 0.008 | Single Unknown Stereoisomer | 1H NMR (400 MHz, DMSO-d6) δ 7.55-7.26 (m, 3H), 7.38-7.12 (m, 3H), 6.24 (ddd, J = 56.4, 7.2, 2.0 Hz, 1H), 5.72 (ddd, J = 8.4, 6.8, 3.1 Hz, 1H), 3.53-3.28 (m, 2H), 2.71 (dddd, J = 26.9, 15.2, 3.1, 1.9 Hz, 1H), 1.16 (dd, J = 31.2, 6.8 Hz, 6H). | 294.1 3.93 |
| 188 Method 40[1] | rac-(5S,7S)-2-[(R)-ethylsulfinyl]-7-fluoro-5-phenyl-6,7-dihydro-5H-pyrrolo[1,2-b][1,2,4]triazole | 0.510 | Single Unknown Stereoisomer | 1H NMR (400 MHz, DMSO-d6) δ 7.55-7.26 (m, 3H), 7.39-7.13 (m, 2H), 6.24 (ddd, J = 56.4, 7.2, 2.0 Hz, 1H), 5.73 (ddd, J = 8.4, 6.8, 3.1 Hz, 1H), 3.75 (dddd, J = 25.5, 15.5, 8.4, 7.2 Hz, 1H), 3.37-3.03 (m, 2H), 2.87-2.45 (m, 1H), 1.13 (t, J = 7.4 Hz, 3H). | 280.1 3.72 |

TABLE 1-continued

| Example Synthetic Method | Structure | Ki (μM) | Stereo | $^1$H NMR | MS (m/z) R.T. (min) |
|---|---|---|---|---|---|
| 189 Method 40[1] | rac-(5S,7S)-7-fluoro-2-[(S)-isopropylsulfinyl]-5-phenyl-6,7-dihydro-5H-pyrrolo[1,2-b][1,2,4]triazole | 0.760 | Single Unknown Stereoisomer | 1H NMR (400 MHz, DMSO-d6) δ 7.55-7.26 (m, 3H), 7.34-7.08 (m, 2H), 6.24 (ddd, J = 56.4, 7.2, 2.0 Hz, 1H), 5.72 (ddd, J = 8.4, 6.8, 3.1 Hz, 1H), 3.51-3.28 (m, 1H), 2.70 (dddd, J = 27.0, 15.2, 3.2, 2.0 Hz, 1H), 1.16 (dd, J = 32.4, 6.9 Hz, 6H). | 294.1 4.00 |
| 190 Method 40[1] | rac-(5S,7S)-2-[(S)-ethylsulfinyl]-7-fluoro-5-phenyl-6,7-dihydro-5H-pyrrolo[1,2-b][1,2,4]triazole | 0.008 | Single Unknown Stereoisomer | 1H NMR (400 MHz, DMSO-d6) δ 7.55-7.27 (m, 3H), 7.36-7.14 (m, 2H), 6.24 (ddd, J = 56.3, 7.2, 2.0 Hz, 1H), 5.72 (ddd, J = 8.4, 6.8, 3.1 Hz, 1H), 3.75 (dddd, J = 25.7, 15.5, 8.5, 7.2 Hz, 1H), 3.36-3.02 (m, 2H), 2.87-2.56 (m, 1H), 1.12 (t, J = 7.4 Hz, 3H). | 280.1 3.64 |
| 191 Method 40[1] | rac-(5S,7S)-2-[(R)-tert-butylsulfinyl]-7-fluoro-5-phenyl-6,7-dihydro-5H-pyrrolo[1,2-b][1,2,4]triazole | 0.005 | Single Unknown Stereoisomer | 1H NMR (400 MHz, DMSO-d6) δ 7.55-7.26 (m, 3H), 7.33-7.11 (m, 2H), 6.23 (ddd, J = 56.4, 7.2, 1.9 Hz, 1H), 5.71 (ddd, J = 8.4, 6.8, 3.0 Hz, 1H), 2.85-2.53 (m, 1H), 1.19 (s, 9H). | 308.1 4.22 |
| 192 Method 41 | 3-[(5S,7S)-2-(difluoromethylsulfonyl)-7-fluoro-6,7-dihydro-5H-pyrrolo[1,2-b][1,2,4]triazol-5-yl]benzonitrile | 0.350 | Single Unknown Stereoisomer | 1H NMR (40 MHz, CDCl3) δ 7.73 (d, J = 8.0 Hz, 1H), 7.64-7.53 (m, 2H), 7.47 (d, J = 8.0 Hz, 1H), 6.43 (t, J = 53.2 Hz, 1H), 6.21-6.02 (m, 1H), 5.66-5.62 (m, 1H), 3.84-3.67 (m, 1H), 3.10-2.96 (m, 1H). | 343.1 1.058 |

TABLE 1-continued

| Example Synthetic Method | Structure | Ki (μM) | Stereo | ¹H NMR | MS (m/z) R.T. (min) |
|---|---|---|---|---|---|
| 193 Method 42 | (5S,7S)-5-(3,5-difluorophenyl)-7-fluoro-2-trans-(3-fluorocyclobutyl)sulfonyl-6,7-dihydro-5H-pyrrolo[1,2-b][1,2,4]triazole | 0.023 | Single Unknown Stereoisomer | 1H NMR (400 MHz, CDCl3) δ 6.88-6.83 (m, 1H), 6.79-6.77 (m, 2H), 6.12-5.95 (m, 1H), 5.53-5.51 (m, 1H), 5.50-5.25 (m, 1H), 4.17-4.12 (m, 1H), 3.75-3.64 (m, 1H), 3.15-2.98 (m, 3H), 2.75-2.66 (m, 2H). | 376.1 1.142 |
| 195 Method 44 | Cis-3-[[(5S,7S)-7-fluoro-5-(3-fluorophenyl)-6,7-dihydro-5H-pyrrolo[1,2-b][1,2,4]triazol-2-yl]sulfonyl]cyclobutanol | 0.460 | Single Unknown Stereoisomer | 1H NMR (400 MHz, CDCl3) δ 7.43-7.34 (m, 1H), 7.14-7.06 (m, 1H), 7.05-6.99 (m, 1H), 6.98-6.89 (m, 1H), 6.16-5.94 (m, 1H), 5.61-5.50 (m, 1H), 4.33-4.19 (m, 1H), 3.80-3.60 (m, 2H), 3.01-2.88 (m, 1H), 2.77-2.62 (m, 2H), 2.60-2.35 (m, 3H). | 356.1 0.825 |
| 196 Method 30 | (5S,7S)-7-fluoro-5-(4-fluorophenyl)-2-[(1R,2R)-2-fluorocyclopropyl]sulfonyl-6,7-dihydro-5H-pyrrolo[1,2-b][1,2,4]triazole | 0.032 | Single Unknown Stereoisomer | 1H NMR (400 MHz, CDCl3) δ 7.30-7.27 (m, 1H), 7.26-7.23 (m, 1H), 7.14-7.06 (m, 2H), 6.20-5.92 (m, 1H), 5.57-5.49 (m, 1H), 5.27-4.98 (m, 1H), 3.79-3.56 (m, 1H), 3.19-3.08 (m, 1H), 3.05-2.90 (m, 1H), 1.91-1.76 (m, 2H). | 344.1 0.956 |
| 197 Method 30 | (5S,7S)-7-fluoro-5-(4-fluorophenyl)-2-[(1S,2S)-2-fluorocyclopropyl]sulfonyl-6,7-dihydro-5H-pyrrolo[1,2-b][1,2,4]triazole | 0.008 | Single Unknown Stereoisomer | 1H NMR (400 MHz, CDCl3) δ 7.30-7.26 (m, 2H), 7.14-7.07 (m, 2H), 6.17-5.94 (m, 1H), 5.57-5.50 (m, 1H), 5.27-4.98 (m, 1H), 3.79-3.56 (m, 1H), 3.20-3.15 (m, 1H), 3.05-2.91 (m, 1H), 1.90-1.76 (m, 2H). | 344.1 0.952 |

TABLE 1-continued

| Example Synthetic Method | Structure | Ki (μM) | Stereo | ¹H NMR | MS (m/z) R.T. (min) |
|---|---|---|---|---|---|
| 198 Method 45 | (5S,7S)-2-[2-(difluoromethoxy)ethylsulfonyl]-7-fluoro-5-phenyl-6,7-dihydro-5H-pyrrolo[1,2-b][1,2,4]triazole | 0.068 | Single Unknown Stereoisomer | 1H NMR (400 MHz, CD3OD) δ 7.43-7.39 (m, 3H), 7.30-7.27 (m, 2H), 6.22 (t, J = 74.8 Hz, 1H), 6.21-6.03 (m, 1H), 5.68-5.66 (m, 1H), 4.25 (t, J = 5.6 Hz, 2H), 3.82-3.74 (m, 3H), 1.31-1.28 (m, 1H). | 362.1 0.943 |
| 199 Method 30 | (5S,7S)-5-(3-chloro-5-fluoro-phenyl)-7-fluoro-2-[(1R,2R)-2-fluorocyclopropyl]sulfonyl-6,7-dihydro-5H-pyrrolo[1,2-b][1,2,4]triazole | 0.008 | Single Unknown Stereoisomer | 1H NMR (400 MHz, CDCl3) δ 7.17-7.13 (m, 1H), 7.09 (s, 1H), 6.90-6.87 (m, 1H), 6.14-5.98 (m, 1H), 5.52-5.47 (m, 1H), 5.24-5.05 (m, 1H), 3.76-3.61 (m, 1H), 3.22-3.13 (m, 1H), 3.05-2.94 (m, 1H), 1.89-1.75 (m, 2H). | 377.9 0.952 |
| 200 Method 30 | (5S,7S)-5-(3-chloro-5-fluoro-phenyl)-7-fluoro-2-[(1S,2S)-2-fluorocyclopropyl]sulfonyl-6,7-dihydro-5H-pyrrolo[1,2-b][1,2,4]triazole | 0.048 | Single Unknown Stereoisomer | 1H NMR (400 MHz, CDCl3) δ 7.17-7.13 (m, 1H), 7.09 (s, 1H), 6.90-6.87 (m, 1H), 6.14-5.98 (m, 1H), 5.52-5.47 (m, 1H), 5.25-5.05 (m, 1H), 3.76-3.61 (m, 1H), 3.20-3.10 (m, 1H), 3.05-2.94 (m, 1H), 1.93-1.76 (m, 2H). | 378.1 1.030 |
| 201 Method 30 | (5S,7S)-5-(2,5-difluorophenyl)-7-fluoro-2-[(1R,2R)-2-fluorocyclopropyl]sulfonyl-6,7-dihydro-5H-pyrrolo[1,2-b][1,2,4]triazole | 0.025 | Single Unknown Stereoisomer | 1H NMR (400 MHz, CDCl3) δ 7.20-7.05 (m, 2H), 6.76-6.67 (m, 1H), 6.17-5.97 (m, 1H), 5.88-5.80 (m, 1H), 5.29-5.05 (m, 1H), 3.82-3.65 (m, 1H), 3.23-3.11 (m, 1H), 3.05-2.90 (m, 1H), 1.94-1.77 (m, 2H). | 362.1 0.952 |

TABLE 1-continued

| Example Synthetic Method | Structure | Ki (µM) | Stereo | ¹H NMR | MS (m/z) R.T. (min) |
|---|---|---|---|---|---|
| 202 Method 30 | (5S,7S)-5-(2,5-difluorophenyl)-7-fluoro-2-[(1S,2S)-2-fluorocyclopropyl]sulfonyl-6,7-dihydro-5H-pyrrolo[1,2-b][1,2,4]triazole | <0.005 | Single Unknown Stereoisomer | 1H NMR (400 MHz, CDCl3) δ 7.19-7.04 (m, 2H), 6.75-6.65 (m, 1H), 6.18-5.95 (m, 1H), 5.89-5.80 (m, 1H), 5.29-5.01 (m, 1H), 3.83-3.64 (m, 1H), 3.26-3.14 (m, 1H), 3.05-2.89 (m, 1H), 1.92-1.76 (m, 2H). | 362.1 0.955 |
| 203 Method 18 | (5S,7S)-5-(3-chlorophenyl)-2-cyclopropylsulfonyl-7-fluoro-6,7-dihydro-5H-pyrrolo[1,2-b][1,2,4]triazole | 0.039 | Single Unknown Stereoisomer | 1H NMR (400 MHz, CDCl3) δ 7.41-7.31 (m, 2H), 7.26-7.24 (m, 1H), 7.16-7.10 (m, 1H), 6.14-5.95 (m, 1H), 5.56-5.48 (m, 1H), 3.78-3.57 (m, 1H), 3.06-2.87 (m, 1H), 2.80-2.70 (m, 1H), 1.52-1.39 (m, 2H), 1.22-1.07 (m, 2H). | 341.9 0.917 |
| 204 Method 42 | (5S,7S)-5-(2,3-difluorophenyl)-7-fluoro-2-trans-(3-fluorocyclobutyl)sulfonyl-6,7-dihydro-5H-pyrrolo[1,2-b][1,2,4]triazole | 0.016 | Mixture of Diastereomers | 1H NMR (400 MHz, CDCl3) δ 7.27-7.19 (m, 1H), 7.17-7.10 (m, 1H), 6.75-6.72 (m, 1H), 6.17-5.95 (m, 1H), 5.92-5.81 (m, 1H), 5.46-5.19 (m, 1H), 4.24-4.08 (m, 1H), 3.85-3.64 (m, 1H), 3.14-2.91 (m, 3H), 2.79-2.61 (m, 2H). | 376.1 1.845 |
| 205 Method 30 | (5S,7S)-7-fluoro-5-(2-fluorophenyl)-2-[(1R,2R)-2-fluorocyclopropyl]sulfonyl-6,7-dihydro-5H-pyrrolo[1,2-b][1,2,4]triazole | 0.020 | Single Unknown Stereoisomer | 1H NMR (400 MHz, CDCl3) δ 7.44-7.36 (m, 1H), 7.21-7.12 (m, 2H), 6.99 (t, J = 7.2 Hz, 1H), 6.19-5.96 (m, 1H), 5.88-5.85 (m, 1H), 5.28-5.07 (m, 1H), 3.83-3.63 (m, 1H), 3.18-3.16 (m, 1H), 3.06-2.90 (m, 1H), 1.94-1.74 (m, 2H). | 343.9 0.896 |

TABLE 1-continued

| Example Synthetic Method | Structure | Ki (μM) | Stereo | ¹H NMR | MS (m/z) R.T. (min) |
|---|---|---|---|---|---|
| 206 Method 30 | (5S,7S)-7-fluoro-5-(2-fluorophenyl)-2-[(1S,2S)-2-fluorocyclopropyl]sulfonyl-6,7-dihydro-5H-pyrrolo[1,2-b][1,2,4]triazole | 0.010 | Single Unknown Stereoisomer | 1H NMR (400 MHz, CDCl3) δ 7.44-7.37 (m, 1H), 7.21-7.13 (m, 2H), 6.99 (t, J = 6.8 Hz, 1H), 6.16-5.98 (m, 1H), 5.89-5.87 (m, 1H), 5.27-5.04 (m, 1H), 3.81-3.64 (m, 1H), 3.25-3.14 (m, 1H), 3.06-2.90 (m, 1H), 1.91-1.75 (m, 2H). | 343.9 0.897 |
| 207 Method 30 | (5S,7S)-5-(5-chloro-2-fluoro-phenyl)-7-fluoro-2-[(1R,2R)-2-fluorocyclopropyl]sulfonyl-6,7-dihydro-5H-pyrrolo[1,2-b][1,2,4]triazole | 0.037 | Single Unknown Stereoisomer | 1H NMR (400 MHz, CD3OD) δ 7.51-7.44 (m, 1H), 7.30-7.19 (m, 2H), 6.29-6.05 (m, 1H), 5.95-5.80 (m, 1H), 5.30-5.02 (m, 1H), 3.94-3.71 (m, 1H), 3.50-3.38 (m, 1H), 3.01-2.81 (m, 1H), 1.94-1.81 (m, 1H), 1.78-1.67 (m, 1H). | 378.1 1.010 |
| 208 Method 30 | (5S,7S)-5-(3-chloro-2-fluoro-phenyl)-7-fluoro-2-[(1R,2R)-2-fluorocyclopropyl]sulfonyl-6,7-dihydro-5H-pyrrolo[1,2-b][1,2,4]triazole | 0.007 | Single Unknown Stereoisomer | 1H NMR (400 MHz, CDCl3) δ 7.48-7.43 (m, 1H), 7.16-7.10 (m, 1H), 6.89-6.85 (m, 1H), 6.15-5.98 (m, 1H), 5.90-5.85 (m, 1H), 5.24-5.03 (m, 1H), 3.81-3.66 (m, 1H), 3.23-3.14 (m, 1H), 3.03-2.92 (m, 1H), 1.90-1.80 (m, 2H). | 377.9 0.939 |
| 209 Method 46 | (1R,2S)-2-[[(5S,7S)-7-fluoro-5-phenyl-6,7-dihydro-5H-pyrrolo[1,2-b][1,2,4]triazol-2-yl]sulfonyl]cyclopropanecarbonitrile | <0.005 | Single Unknown Stereoisomer | 1H NMR (400 MHz, CD3OD) δ 7.45-7.40 (m, 3H), 7.31-7.29 (m, 2H), 6.23-6.21 (m, 0.5H), 6.09-6.07 (m, 0.5H), 5.70-5.69 (m, 1H), 3.85-3.69 (m, 2H), 2.93-2.82 (m, 1H), 2.54-2.50 (m, 1H), 1.90-1.83 (m, 2H). | 333.1 0.655 |

TABLE 1-continued

| Example Synthetic Method | Structure | Ki (μM) | Stereo | ¹H NMR | MS (m/z) R.T. (min) |
|---|---|---|---|---|---|
| 210 Method 47 | Cis-3-[[(5S,7S)-7-fluoro-5-phenyl-6,7-dihydro-5H-pyrrolo[1,2-b][1,2,4]triazol-2-yl]sulfonyl]cyclobutanecarbonitrile | 0.055 | Mixture of Diastereomers | 1H NMR (400 MHz, DMSO-d6) δ 7.46-7.38 (m, 3H), 7.28-7.26 (m, 2H), 6.35-6.18 (m, 1H), 5.77-5.73 (m, 1H), 4.43-4.35 (m, 1H), 3.83-3.69 (m, 1H), 3.49-3.43 (m, 1H), 2.79-2.74 (m, 1H), 2.72-2.57 (m, 4H). | 347.1 0.908 |
| 211 Method 48 | trans-3-[[(5S,7S)-7-fluoro-5-phenyl-6,7-dihydro-5H-pyrrolo[1,2-b][1,2,4]triazol-2-yl]sulfonyl]cyclobutanecarbonitrile | 0.012 | Mixture of Diastereomers | 1H NMR (400 MHz, DMSO-d6) 7.47-7.38 (m, 3H), 7.30-7.26 (m, 2H), 6.42-6.18 (m, 1H), 5.86-5.67 (m, 1H), 4.45-4.38 (m, 1H), 3.92-3.60 (m, 1H), 3.53-3.43 (m, 1H), 2.83-2.71 (m, 5H). | 347.1 0.923 |
| 212 Method 46 | (1S,2R)-2-[[(5S,7S)-7-fluoro-5-phenyl-6,7-dihydro-5H-pyrrolo[1,2-b][1,2,4]triazol-2-yl]sulfonyl]cyclopropanecarbonitrile | 0.011 | Single Unknown Stereoisomer | 1H NMR (400 MHz, CD3OD) δ 7.45-7.40 (m, 3H), 7.30-7.28 (m, 2H), 6.24-6.21 (m, 0.5H), 6.10-6.07 (m, 0.5H), 5.71-5.68 (m, 1H), 3.86-3.68 (m, 2H), 2.55-2.52 (m, 1H), 2.51-2.50 (m, 1H), 1.91-1.84 (m, 2H). | 333.1 0.655 |
| 213 Method 49 | (5S,7S)-2-trans-[3-(difluoromethoxy)cyclobutyl]sulfonyl-7-fluoro-5-phenyl-6,7-dihydro-5H-pyrrolo[1,2-b][1,2,4]triazole | 0.006 | Mixture of Diastereomers | 1H NMR (400 MHz, DMSO-d6) δ 7.44-7.42 (m, 3H), 7.27-7.26 (m, 2H), 6.68 (t, J = 75.6 Hz, 1H), 6.34-6.18 (m, 1H), 5.80-5.72 (m, 1H), 4.85-4.72 (m, 1H), 4.25-4.17 (m, 1H), 3.80-3.70 (m, 1H), 2.85-2.73 (m, 3H), 2.70-2.61 (m, 2H). | 388.1 1.026 |

TABLE 1-continued

| Example Synthetic Method | Structure | Ki (μM) | Stereo | ¹H NMR | MS (m/z) R.T. (min) |
|---|---|---|---|---|---|
| 214 Method 18 | (5S,7S)-5-(3-chloro-5-fluoro-phenyl)-2-cyclopropylsulfonyl-7-fluoro-6,7-dihydro-5H-pyrrolo[1,2-b][1,2,4]triazole | 0.029 | Single Unknown Stereoisomer | 1H NMR (400 MHz, CDCl3) δ 7.16-7.12 (m, 1H), 7.08 (s, 1H), 6.90-6.86 (m, 1H), 6.13-5.96 (m, 1H), 5.51-5.46 (m, 1H), 3.75-3.60 (m, 1H), 3.02-2.91 (m, 1H), 2.80-2.72 (m, 1H), 1.52-1.46 (m, 2H), 1.20-1.13 (m, 2H). | 359.9 0.926 |
| 215 Method 23 | (5S,7S)-5-(3-chloro-5-fluoro-phenyl)-2-(difluoromethylsulfonyl)-7-fluoro-6,7-dihydro-5H-pyrrolo[1,2-b][1,2,4]triazole | 0.032 | Single Unknown Stereoisomer | 1H NMR (400 MHz, CDCl3) δ 7.18-7.14 (m, 1H), 7.07 (s, 1H), 6.88-6.84 (m, 1H), 6.44 (t, J = 52.8 Hz, 1H), 6.17-6.00 (m, 1H), 5.58-5.53 (m, 1H), 3.79-3.64 (m, 1H), 3.07-2.96 (m, 1H). | 369.9 0.972 |
| 216 Method 30 | (5S,7S)-5-(2,3-difluorophenyl)-7-fluoro-2-[(1R,2R)-2-fluorocyclopropyl]sulfonyl-6,7-dihydro-5H-pyrrolo[1,2-b][1,2,4]triazole | <0.005 | Single Unknown Stereoisomer | 1H NMR (400 MHz, CDCl3) δ 7.26-7.24 (m, 1H), 7.14-7.10 (m, 1H), 6.77-6.75 (m, 1H), 6.21-5.97 (m, 1H), 5.91-5.89 (m, 1H), 5.30-5.01 (m, 1H), 3.80-3.71 (m, 1H), 3.25-3.19 (m, 1H), 3.08-2.78 (m, 1H), 1.94-1.76 (m, 2H). | 362.0 1.825 |
| 217 Method 30 | (5S,7S)-5-(2,3-difluorophenyl)-7-fluoro-2-[(1S,2S)-2-fluorocyclopropyl]sulfonyl-6,7-dihydro-5H-pyrrolo[1,2-b][1,2,4]triazole | 0.006 | Single Unknown Stereoisomer | 1H NMR (400 MHz, CDCl3) δ 7.27-7.19 (m, 1H), 7.18-7.07 (m, 1H), 6.84-6.67 (m, 1H), 6.21-5.97 (m, 1H), 5.90-5.88 (m, 1H), 5.30-5.01 (m, 1H), 3.79-3.73 (m, 1H), 3.25-3.16 (m, 1H), 3.08-2.86 (m, 1H), 2.01-1.75 (m, 2H). | 362.1 1.817 |

TABLE 1-continued

| Example Synthetic Method | Structure | Ki (µM) | Stereo | ¹H NMR | MS (m/z) R.T. (min) |
|---|---|---|---|---|---|
| 218 Method 30 | (5S,7S)-5-(5-chloro-2-fluoro-phenyl)-7-fluoro-2-[(1S,2S)-2-fluorocyclopropyl]sulfonyl-6,7-dihydro-5H-pyrrolo[1,2-b][1,2,4]triazole | 0.140 | Single Unknown Stereoisomer | 1H NMR (400 MHz, CDCl3) δ 7.40-7.32 (m, 1H), 7.12 (t, J = 9.2 Hz, 1H), 7.00-6.95 (m, 1H), 6.17-5.95 (m, 1H), 5.84-5.76 (m, 1H), 5.27-5.06 (m, 1H), 3.80-3.63 (m, 1H), 3.22-3.12 (m, 1H), 3.03-2.91 (m, 1H), 1.93-1.81 (m, 2H). | 378.1 1.018 |
| 219 Method 30 | (5S,7S)-5-(3-chloro-2-fluoro-phenyl)-7-fluoro-2-[(1S,2S)-2-fluorocyclopropyl]sulfonyl-6,7-dihydro-5H-pyrrolo[1,2-b][1,2,4]triazole | 0.025 | Single Unknown Stereoisomer | 1H NMR (400 MHz, CDCl3) δ 7.48-7.44 (m, 1H), 7.15-7.10 (m, 1H), 6.88-6.84 (m, 1H), 6.15-5.98 (m, 1H), 5.90-5.85 (m, 1H), 5.24-5.08 (m, 1H), 3.81-3.66 (m, 1H), 3.23-3.11 (m, 1H), 3.03-2.92 (m, 1H), 1.89-1.84 (m, 2H). | 378.1 1.029 |
| 220 Method 50 | 2-(difluoromethylsulfonyl)-7-phenyl-6,7-dihydro-5H-pyrrolo[1,2-b][1,2,4]triazole | 0.100 | Mixture of Enantiomers | 1H NMR (400 MHz, CDCl3) δ 7.40-7.31 (m, 3H), 7.24-7.21 (m, 2H), 6.42 (t, J = 53.2 Hz, 1H), 4.59-4.55 (m, 1H), 4.52-4.45 (m, 1H), 4.41-4.33 (m, 1H), 3.40-3.30 (m, 1H), 2.89-2.79 (m, 1H). | 299.9 0.896 |
| 221 Method 46 | (1R,2R)-2-[[(5S,7S)-7-fluoro-5-phenyl-6,7-dihydro-5H-pyrrolo[1,2-b][1,2,4]triazol-2-yl]sulfonyl]cyclopropanecarbonitrile | 0.018 | Single Unknown Stereoisomer | 1H NMR (400 MHz, DMSO-d6) δ 7.45-7.40 (m, 3H), 7.30-7.28 (m, 2H), 6.37-6.34 (m, 0.5H), 6.23-6.21 (m, 0.5H), 5.81-5.78 (m, 1H), 3.83-3.75 (m, 1H), 3.63-3.34 (m, 1H), 2.72-2.68 (m, 2H), 1.89-1.81 (m, 2H). | 333.1 0.627 |

TABLE 1-continued

| Example Synthetic Method | Structure | Ki (μM) | Stereo | ¹H NMR | MS (m/z) R.T. (min) |
|---|---|---|---|---|---|
| 222 Method 46 | (1S,2S)-2-[[(5S,7S)-7-fluoro-5-phenyl-6,7-dihydro-5H-pyrrolo[1,2-b][1,2,4]triazol-2-yl]sulfonyl]cyclopropanecarbonitrile | 0.061 | Single Unknown Stereoisomer | 1H NMR (400 MHz, CD3OD) δ 7.44-7.40 (m, 3H), 7.30-7.28 (m, 2H), 6.22-6.20 (m, 0.5H), 6.09-6.06 (m, 0.5H), 5.71-5.68 (m, 1H), 3.81-3.75 (m, 1H), 3.42-3.38 (m, 1H), 2.58-2.57 (m, 1H), 2.46-2.42 (m, 1H), 1.97-1.94 (m, 1H), 1.82-1.78 (m, 1H). | 333.1 0.628 |
| 223 Method 51 | 2-[[(5S,7S)-7-fluoro-5-phenyl-6,7-dihydro-5H-pyrrolo[1,2-b][1,2,4]triazol-2-yl]sulfonyl]ethanol | 0.190 | Single Unknown Stereoisomer | 1H NMR (400 MHz, DMSO-d6) δ 7.45-7.40 (m, 3H), 7.40-7.24 (m, 2H), 6.34-6.17 (m, 1H), 5.77-5.73 (m, 1H), 4.99-4.95 (m, 1H), 3.79-3.72 (m, 3H), 3.63-3.59 (m, 2H), 2.67-2.66 (m, 1H). | 312.1 0.777 |
| 224 Method 25 | (5S,7S)-7-fluoro-2-(2-methoxyethylsulfonyl)-5-phenyl-6,7-dihydro-5H-pyrrolo[1,2-b][1,2,4]triazole | 0.180 | Single Unknown Stereoisomer | 1H NMR (400 MHz, CD3OD) δ 7.44-7.39 (m, 3H), 7.29-7.26 (m, 2H), 6.21-6.04 (m, 1H), 5.70-5.67 (m, 1H), 3.79-3.64 (m, 5H), 3.13 (s, 3H), 2.90-2.82 (m, 1H). | 326.1 0.865 |
| 225 Method 45 | Cis-(3-[[(5S,7S)-7-fluoro-5-phenyl-6,7-dihydro-5H-pyrrolo[1,2-b][1,2,4]triazol-2-yl]sulfonyl]cyclobutanol | 0.300 | Single Unknown Stereoisomer | 1H NMR (400 MHz, CD3OD) δ 7.44-7.39 (m, 3H), 7.27-7.25 (m, 2H), 6.20-6.18 (m, 0.5H), 6.05-6.03 (m, 0.5H), 5.67-5.65 (m, 1H), 4.21-4.15 (m, 1H), 3.77-3.72 (m, 2H), 2.80-2.90 (m, 1H), 2.57-2.51 (m, 2H), 2.38-2.35 (m, 2H). | 338.1 0.585 |

TABLE 1-continued

| Example Synthetic Method | Structure | Ki (μM) | Stereo | ¹H NMR | MS (m/z) R.T. (min) |
|---|---|---|---|---|---|
| 226 Method 42 | (5S,7S)-7-fluoro-2-trans-(3-fluorocyclobutyl)sulfonyl-5-(3-fluorophenyl)-6,7-dihydro-5H-pyrrolo[1,2-b][1,2,4]triazole | 0.0093 | Single Unknown Stereoisomer | 1H NMR (400 MHz, CDCl3) δ 7.45-7.39 (m, 1H), 7.15-7.10 (m, 1H), 7.09-7.03 (m, 1H), 7.02-6.94 (m, 1H), 6.15-5.92 (m, 1H), 5.56-5.49 (m, 1H), 5.44-5.19 (m, 1H), 4.18-4.07 (m, 1H), 3.78-3.57 (m, 1H), 3.11-2.96 (m, 3H), 2.76-2.61 (m, 2H). | 357.9 0.918 |
| 227 Method 26 | (5S,7S)-7-fluoro-5-(3-fluorophenyl)-2-(oxetan-3-ylsulfonyl)-6,7-dihydro-5H-pyrrolo[1,2-b][1,2,4]triazole | | Single Unknown Stereoisomer | 1H NMR (400 MHz, CDCl3) δ 7.46-7.35 (m, 1H), 7.15-7.08 (m, 1H), 7.06-7.01 (m, 1H), 6.99-6.92 (m, 1H), 6.16-5.94 (m, 1H), 5.59-5.50 (m, 1H), 5.12-5.04 (m, 2H), 4.97-4.89 (m, 2H), 4.80-4.70 (m, 1H), 3.79-3.59 (m, 1H), 3.08-2.91 (m, 1H). | 342.1 0.883 |
| 228 Method 26 | (5S,7S)-7-fluoro-2-(oxetan-3-ylsulfonyl)-5-phenyl-6,7-dihydro-5H-pyrrolo[1,2-b][1,2,4]triazole | 0.006 | Single Unknown Stereoisomer | 1H NMR (400 MHz, CDCl3) δ 7.42-7.38 (m, 3H), 7.25-7.12 (m, 2H), 6.14-6.12 (m, 0.5H), 6.00-5.98 (m, 0.5H), 5.54-5.52 (m, 1H), 5.12-5.06 (m, 2H), 4.93-4.89 (m, 2H), 4.77-4.74 (m, 1H), 3.71-3.65 (m, 1H), 3.06-2.95 (m, 1H). | 324.1 0.706 |

¹see Table II for chiral chromatography conditions

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

We claim:

1. A compound of formula I:

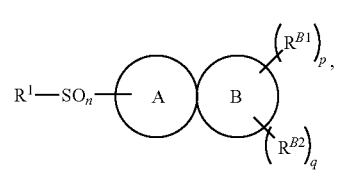

(I)

or a pharmaceutically acceptable salt thereof, wherein:
the A ring and the B ring are fused to form a polycyclic ring system;
p is 2 and q is 1, the A ring and the B ring together are selected from the group consisting of:

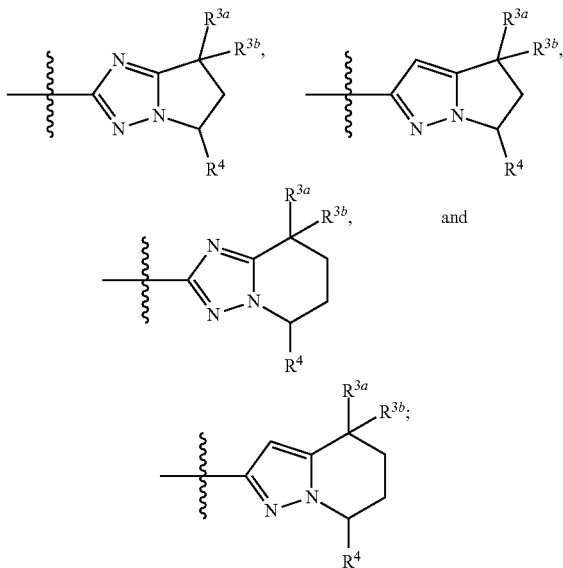

R¹ is selected from the group consisting of $C_1$-$C_6$ alkyl, $C_3$-$C_6$ cycloalkyl, $C_1$-$C_6$ alkoxy, $C_1$-$C_6$ haloalkyl, $C_1$-$C_6$ haloalkoxy, $C_1$-$C_6$ hydroxyalkyl, $C_1$-$C_6$ cyanoalkyl, $C_3$-$C_6$ cycloalkyl-$C_1$-$C_3$ alkyl, $C_1$-$C_6$ alkyl-$N(R^2)_2$, $C_1$-$C_6$ alkoxy-$C_1$-$C_6$ alkyl, $C_1$-$C_6$ haloalkoxy-$C_1$-$C_6$ alkyl, phenyl, benzyl, difluoro(phenyl)methyl, 4 to 6 membered heterocyclyl, 5 to 6 membered heteroaryl, and $CH_2$-(5 to 6 membered heteroaryl); wherein:
  when R¹ is phenyl, benzyl, difluoro(phenyl)methyl, 5 to 6 membered heteroaryl or $CH_2$-(5 to 6 membered heteroaryl), the phenyl or heteroaryl moiety of R¹ is optionally, substituted by one or two substituents independently selected from the group consisting of halogen, $C_1$-$C_6$ alkyl, hydroxyl, hydroxymethyl, methoxymethyl, cyano, trifluoromethyl, difluoromethoxy and trifluoromethoxy; and
  when R¹ is cycloalkyl, the cycloalkyl is optionally substituted by by one, two or three substituents independently selected from the group consisting of fluoro, $C_1$-$C_6$ alkyl, $C_1$-$C_6$ haloalkyl $C_1$-$C_6$ haloalkoxy, hydroxyl, $C_1$-$C_6$ hydroxyalkyl, and cyano;
n is 1 or 2;
each R² is independently selected from the group consisting of $C_1$-$C_6$ alkyl, $C_3$-$C_6$ cycloalkyl, $C_1$-$C_6$ alkoxy, and $C_1$-$C_6$ haloalkyl; or two R² together with the nitrogen atom to which they are both attached form a 4-6 membered heterocyclic ring;
$R^{B1}$ is independently $R^{3a}$ and $R^{3b}$ and each $R^{3a}$ and $R^{3b}$ is independently selected from the group consisting of hydrogen, halogen, deutero, hydroxyl, $C_1$-$C_6$ alkyl, $C_1$-$C_6$ haloalkyl, $C_3$-$C_6$ cycloalkyl $C_1$-$C_6$ alkoxy, $C_1$-$C_6$ haloalkoxy, $C_1$-$C_6$ thioalkyl, $C_1$-$C_6$ alkyl-$N(R^2)_2$, and cyano; and
$R^{B2}$ is R⁴ and R⁴ is selected from the group consisting of $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-$N(R^2)_2$, phenyl, benzyl, $CH_2$-($C_3$-$C_6$ cycloalkyl), $CH_2CH_2$-($C_3$-$C_6$ cycloalkyl), $CH_2$-(4 to 6 membered heterocyclyl), $CH_2CH_2$-(4 to 6 membered heterocyclyl), 5 to 6 membered heteroaryl, and $CH_2$-(5 to 6 membered heteroaryl);
  wherein when R⁴ is phenyl, heteroaryl or benzyl, the phenyl or heteroaryl ring is optionally substituted by 1 to 3 substituents selected from the group consisting of halogen, $C_1$-$C_4$ alkyl, $C_1$-$C_4$ haloalkyl, alkoxy, $C_1$-$C_4$ haloalkoxy, and cyano.

2. The compound of claim 1, or a pharmaceutically acceptable salt thereof, wherein the A ring and the B ring together are:

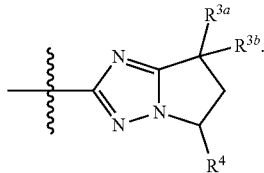

3. The compound of claim 1 wherein:
$R^{3a}$ and $R^{3b}$ are selected as follows:
  one of $R^{3a}$ and $R^{3b}$ is H, and the other is selected from the group consisting of hydrogen, deutero, fluoro, chloro, hydroxyl, cyano, $C_1$-$C_1$ alkyl, $C_1$-$C_4$ haloalkyl, cyclopropyl, $C_1$-$C_4$ alkoxy, and $C_1$-$C_4$ haloalkoxy; or
  each of $R^{3a}$ and $R^{3b}$ is independently selected from the group consisting of deutero, fluoro; chloro, hydroxyl, cyano, and methyl, provided that $R^{3a}$ and $R^{3b}$ cannot both be OH or CN; and
R⁴ is selected from the group consisting of $C_1$-$C_6$ alkyl, $C_1$-$C_6$ haloalkyl, phenyl, and pyridinyl, wherein the phenyl ring or pyridinyl ring is optionally substituted by 1 to 3 substituents selected from the group consisting of halogen, $C_1$-$C_4$ alkyl, $C_1$-$C_4$ haloalkyl, $C_1$-$C_4$ alkoxy; $C_1$-$C_4$ haloalkoxy, and cyano.

4. The compound of claim 1, or a pharmaceutically acceptable salt thereof, wherein $R^{3a}$ and $R^{3b}$ are independently hydrogen or fluorine; and R⁴ is selected from the group consisting of ethyl, isopropyl n-propyl, trifluoromethyl, 1,1-difluoroethyl, 1,1-difluoropropyl, optionally substituted phenyl, and optionally substituted pyridine-2-yl.

5. The compound of claim 1, or a pharmaceutically acceptable salt thereof, wherein the A ring and the B ring together are selected from the group consisting of:

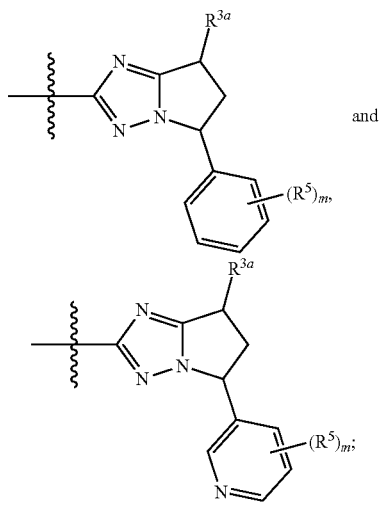

wherein:

R³ᵃ is hydrogen or fluorine;

each R⁵ is selected from the group consisting of hydrogen, fluoro, chloro, $C_1$-$C_6$ alkyl, $C_1$-$C_6$ haloalkyl, $C_1$-$C_6$ alkoxy, and $C_1$-$C_6$ haloalkoxy; and m is 1, 2 or 3.

6. The compound of claim 1, or a pharmaceutically, acceptable salt thereof, wherein the A ring and the B ring together are:

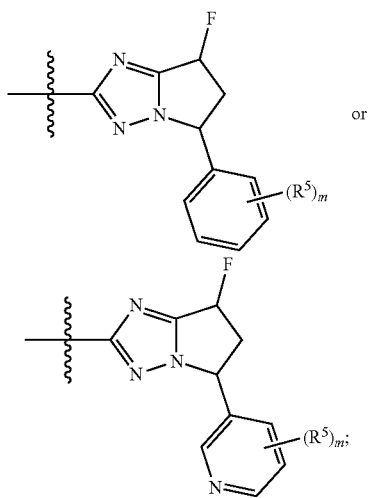

wherein:

each R⁵ is selected from the group consisting of hydrogen, fluoro; chloro, $C_1$-$C_6$ alkyl, $C_1$-$C_6$ haloalkyl, $C_1$-$C_6$ alkoxy, and $C_1$-$C_6$ haloalkoxy; and m is 1, 2 or 3.

7. The compound of claim 1, or a pharmaceutically, acceptable salt thereof, wherein R⁵ is selected from the group consisting of Et, F, Cl, CH₃, CH₂CH₃, OCH₃, CF₃, CF₂H, and OCF₂H.

8. The compound of claim 1, or a pharmaceutically acceptable salt thereof, wherein R⁵ is halo.

9. The compound of claim 1, or a pharmaceutically acceptable salt thereof, wherein the A ring and the B ring together are:

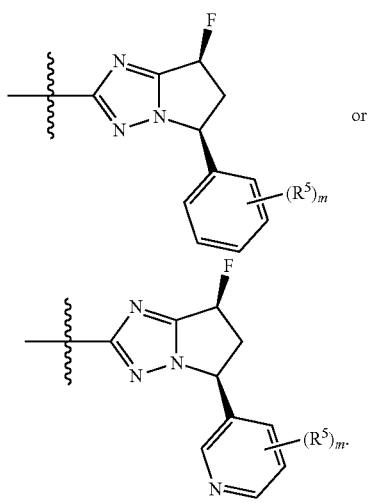

10. The compound of claim 1, or a pharmaceutically, acceptable salt thereof, wherein R¹ is selected from the group consisting of $C_1$-$C_6$ alkyl, optionally substituted $C_3$-$C_6$ cycloalkyl, $C_3$-$C_6$ spirocycloalkyl, $C_1$-$C_6$ haloalkyl, $C_1$-$C_6$ alkoxy-$C_1$-$C_6$ alkyl, $C_1$-$C_6$ cyanoalkyl, $C_1$-$C_6$ hydroxyalkyl, phenyl, benzyl, and difluoro(phenyl)methyl.

11. The compound of claim 1, or a pharmaceutically acceptable salt thereof, wherein R¹ is selected from the group consisting of methyl, ethyl, tert-butyl, difluoromethyl, trifluoromethyl, cyclopropyl, fluorocyclopropyl, difluorocyclopropyl, phenyl, benzyl, and difluoro(phenyl)methyl.

12. The compound of claim 1, or a pharmaceutically, acceptable salt thereof, wherein R¹ is selected from the group consisting of ethyl, difluoromethyl, trifluoromethyl, cyclopropyl, fluorocyclopropyl, and difluorocyclopropyl.

13. The compound of claim 1, or a pharmaceutically acceptable salt thereof, wherein the compound is selected from the group consisting of:
2-(difluoromethylsulfinyl)-5-phenyl-6,7-dihydro-5H-pyrrolo[1,2-b][1,2,4]triazole;
2-ethylsulfonyl-5-phenyl-6,7-dihydro-5H-pyrrolo[1,2-b][1,2,4]triazole;
(5S)-2-[(S)-ethylsulfinyl]-5-phenyl-6,7-dihydro-5H-pyrrolo[1,2-b][1,2,4]triazole;
2-[difluoro(phenyl)methyl]sulfonyl-5-phenyl-6,7-dihydro-5H-pyrrolo[1,2-b][1,2,4]triazole;
2-[difluoro(phenyl)methyl]sulfinyl-5-phenyl-6,7-dihydro-5H-pyrrolo[1,2-b][1,2,4]triazole;
2-(difluoromethylsulfonyl)-5-phenyl-6,7-dihydro-5H-pyrrolo[1,2-b][1,2,4]triazole;
(S)-5-(2-fluorophenyl)-2-methylsulfonyl-6,7-dihydro-5H-pyrrolo[1,2-b][1,2,4]triazole;
(S)-2-ethylsulfonyl-5-(2-fluorophenyl)-6,7-dihydro-5H-pyrrolo[1,2-b][1,2,4]triazole;
2-methylsulfonyl-5-phenyl-6,7-dihydro-5H-pyrrolo[1,2-b][1,2,4]triazole;
5-phenyl-2-(trifluorotnethylsulfinyl)-6,7-dihydro-5H-pyrrolo[1,2-b][1,2,4]triazole;
(5S)-2-[(R)-difluoromethylsulfinyl]-5-phenyl-6,7-dihydro-5H-pyrrolo[1,2-b][1,2,4]triazole;
(5S)-2-[(S-difluoromethylsulfinyl]-5-phenyl-6,7-dihydro-5H-pyrrolo[1,2-b][1,2,4]triazole;
rac-(5S,7S)-2-(difluoromethylsulfinyl)-7-fluoro-5-phenyl-6,7-dihydro-5H-pyrrolo[1,2-b][1,2,4]triazole;
(5R,7R)-2-cyclopropylsulfonyl-7-fluoro-5-phenyl-6,7-dihydro-5H-pyrrolo[1,2-b][1,2,4]triazole;
(5R)-5-(2-chlorophenyl)-2-(difluoromethylsulfonyl)-6,7-dihydro-5H-pyrrolo[1,2-b][1,2,4]triazole
(5S)-5-(2-chlorophenyl)-2-(difluoromethylsulfonyl)-6,7-dihydro-5H-pyrrolo[1,2-b][1,2,4]triazole;
(5S)-5-(2-chlorophenyl)-2-[(S)-difluoromethylsulfinyl]-6,7-dihydro-5H-pyrrolo[1,2-b][1,2,4]triazole;
(5S)-5-(2-chlorophenyl)-2-[(R)-difluoromethylsulfinyl]-6,7-dihydro-5H-pyrrolo[1,2-b][1,2,4]triazole;
(5S,7S)-2-benzylsulfonyl-7-fluoro-5-phenyl-6,7-dihydro-5H-pyrrolo[1,2-b][1,2,4]triazole;
(5S,7S)-2-benzylsulfinyl-7-fluoro-5-phenyl-6,7-dihydro-5H-pyrrolo[1,2-b][1,2,4]triazole;
(5S,7S)-2-[(S)-difluoromethylsulfinyl]-7-fluoro-5-phenyl-6,7-dihydro-5H-pyrrolo[1,2-b][1,2,4]triazole;
(5S,7S)-2-[(R)-difluoromethylsulfinyl]-7-fluoro-5-phenyl-6,7-dihydro-5H-pyrrolo[1,2-b][1,4]triazole;
(5S,7S)-2-(difluoromethylsulfonyl)-7-fluoro-5-phenyl-6,7-dihydro-5H-pyrrol o[1,2-b][1,2,4]triazole;
(5S,7S)-2-tert-butylsulfinyl-7-fluoro-5-phenyl-6,7-dihydro-5H-pyrrolo[1,2-b][1,2,4]triazole;

(5S,7S)-2-tert-butylsulfonyl-7-fluoro-5-phenyl-6,7-dihydro-5H-pyrrolo[1,2-b][1,2,4]triazole;
(5S,7S)-2-cyclopropylsulfinyl-7-fluoro-5-phenyl-6,7-dihydro-5H-pyrrolo[1,2-b][1,2,4]triazole;
(5S,7S)-2-[(R)-cyclopropylsulfinyl]-7-fluoro-5-phenyl-6,7-dihydro-5H-pyrrolo[1,2b][1,2,4]triazole;
(5S,7S)-2-[(S)-cyclopropylsulfinyl]-7-fluoro-5-phenyl-6,7-dihydro-5H-pyrrolo[1,2b][1,2,4]triazole,
(5S,7S)-2-cyclopropylsulfonyl-7-fluoro-5-phenyl-6,7-dihydro-5H-pyrrolo[1,2-b][1,2,4]triazole;
(4S,6S)-2-cyclopropylsulfonyl-4-fluoro-6-phenyl-5,6-dihydro-4H-pyrrolo[1,2-b]pyrazole;
(5S,7S)-5-(2-chlorophenyl)-2-cyclopropylsulfonyl-7-fluoro-6,7-dihydro-5H-pyrrolo[1,2b][1,2,4]triazole,
(5S,7S)-2-cyclopropylsulfonyl-7-fluoro-5-(2-fluorophenyl)-6,7-dihydro-5H-pyrrolo[1,2-b][1,2,4]triazole;
(5S,7S)-2-cyclopropylsulfonyl-7-fluoro-5-((4-fluorophenyl)-6,7-dihydro-5H-pyrrolo[1,2-b][1,2,4]triazole;
(5S,7S)-2-cyclopropylsulfonyl-5-(2,6-difluorophenyl)-7-fluoro-6,7-dihydro-5H-pyrrolo[1,2-b][1,2,4]triazole;
(5R,7R)-2-cyclopropylsulfonyl-5-(2,3-difluorophenyl)-7-fluoro-6,7-dihydro-5H-pyrrolo[1,2-b][1,2,4]triazole;
(5S,7S)-2-cyclopropylsulfonyl-5-(2,5-difluorophenyl)-7-fluoro-6,7-dihydro-5H-pyrrolo[1,2-b][1,2,4]triazole;
(5S,7S)-2-cyclopropylsulfonyl-7-fluoro-5-(2,3,6-trifluorophenyl)-6,7-dihydro-5H-pyrrolo[1,2-b][1,2,4]triazole;
rac-(5S,7S)-2-cyclopropylsulfonyl-7-fluoro-5-(2,3,5-trifluorophenyl)-6,7-dihydro-5H-pyrrolo[1,2-b][1,2,4]triazole;
(5S,7S)-2-cyclopropylsulfonyl-5-(2,3-difluorophenyl)-7-fluoro-6,7-dihydro-5H-pyrrolo[1,2-b][1,2,4]triazole;
(5S,7S)-2-cyclopropylsulfonyl-7-deuterio-5-phenyl-6,7-dihydro-5H-pyrrolo[1,2-b][1,2,4]triazole;
(5S,7S)-2-cyclopropylsulfonyl-5-(3,5-difluorophenyl)-7-fluoro-6,7-dihydro-5H-pyrrolo[1,2-b][1,2,4]triazole;
(5S,7S)-5-(3-chlorophenyl)-2-cyclopropylsulfonyl-7-fluoro-6,7-dihydro-5H-pyrrolo[1,2-b][1,2,4]triazole;
(5S,7S)-2-cyclopropylsulfonyl-5-(3,4-difluorophenyl)-7-fluoro-6,7-dihydro-5H-pyrrolo[1,2-b][1,2,4]triazole;
(5S,7S)-5-(2-chloro-3-fluoro-phenyl)-2-cyclopropylsulfonyl-7-fluoro-6,7-dihydro-5H-pyrrolo[1,2-b][1,2,4]triazole;
(5S,7S)-5-(3-chloro-2-fluoro-phenyl)-2-cyclopropylsulfonyl-7-fluoro-6,7-dihydro-5H-pyrrolo[1,2-b][1,2,4]triazole;
(5S,7S)-5-(5-chloro-2-fluoro-phenyl)-2-cyclopropylsulfonyl-7-fluoro-6,7-dihydro-5H-pyrrolo[1,2-b][1,2,4]triazole;
(5S,7S)-2-cyclopropylsulfonyl-7-fluoro-5-(3-fluorophenyl)-6,7-dihydro-5H-pyrrolo[1,2-b][1,2,4]triazole;
(5S,7S)-2-(3,3-difluorocyclobutyl)sulfinyl-7-fluoro-5-phenyl-6,7-dihydro-5H-pyrrolo[1,2-b][1,2,4]triazole;
(5S,7S)-2-(3,3-difluorocyclobutyl)sulfonyl-7-fluoro-5-phenyl-6,7-dihydro-5H-pyrrolo[1,2-b][1,2,4]triazole;
(5S,7S)-2-[(S)-difluoromethylsulfinyl]-7-fluoro-5-(2-fluorophenyl)-6,7-dihydro-5H-pyrrolo[1,2-b][1,2,4]triazole;
(5S,7S)-2-[(R)-difluoromethylsulfinyl]-7-fluoro-5-(2-fluorophenyl)-6,7-dihydro-5H-pyrrolo[1,2-b][1,2,4]triazole;
(5S,7S)-2-(difluoromethylsulfonyl)-7-fluoro-5-(2-fluorophenyl)-6,7-dihydro-5H-pyrrolo[1,2-b][1,2,4]triazole;
(5S,7S)-2-(difluoromethylsulfinyl)-7-fluoro-5-(3-fluorophenyl)-6,7-dihydro-5H-pyrrolo[1,2-b][1,2,4]triazole;
(5S,7S)-2-(difluoromethylsulfinyl)-7-fluoro-5-(4-fluorophenyl)-6,7-dihydro-5H-pyrrolo[1,2-b][1,2,4]triazole,
(5S,7S)-2-(difluoromethylsulfonyl)-7-fluoro-5-(4-fluorophenyl)-6,7-dihydro-5H-pyrrolo[1,2b][1,2,4]triazole;
(4R,6R)-2-(difluoromethylsulfonyl)-4-fluoro-6-phenyl-5,6-dihydro-4H-pyrrolo[1,2-b]pyrazole;
(5S,7S)-2-(difluoromethylsulfonyl)-5-(2,6-difluorophenyl)-7-fluoro-6,7-dihydro-5H-pyrrolo[1,2-b][1,2,4]triazole,
(5S,7S)-2-(difluoromethylsulfonyl)-7-fluoro-5-(2,3,6-trifluorophenyl)-6,7-dihydro-5H-pyrrolo[1,2-b][1,2,4]triazole;
(5S,7S)-2-(difluoromethylsulfonyl)-7-fluoro-5-(2,3,5-trifluorophenyl)-6,7-dihydro-5H-pyrrolo[1,2-b][1,2,4]triazole;
(5S,7S)-5-(3-chlorophenyl)-2-(difluoromethylsulfonyl)-7-fluoro-6,7-dihydro-5H-pyrrolo[1,2b][1,2,4]triazole;
2-[(5S,7S)-2-(difluoromethylsulfonyl)-7-fluoro-6,7-dihydro-5H-pyrrolo[1,2-b][1,2,4]triazol-5-yl]benzonitrile;
(5S,7S)-2-(difluoromethylsulfonyl)-5-(3,4-difluorophenyl)-7-fluoro-6,7-dihydro-5H-pyrrolo[1,2-b][1,2,4]triazole;
(5S,7S)-5-(2-chloro-3-fluoro-phenyl)-2-(difluoromethylsulfonyl)-7-fluoro-6,7-dihydro-5H-pyrrolo[1,2-b][1,2,4]triazole;
(5S,7S)-5-(3-chloro-2-fluoro-phenyl)-2-(difluoromethylsulfonyl)-7-fluoro-6,7-dihydro-5H-pyrrolo[1,2-b][1,2,4]triazole;
(5S,7S)-5-(5-chloro-2-fluoro-phenyl)-2-(difluoromethylsulfonyl)-7-fluoro-6,7-dihydro-5H-pyrrolo[1,2-b][1,2,4]triazole;
(5S,7S)-2-(difluoromethylsulfonyl)-5-(2,5-difluorophenyl)-7-fluoro-6,7-dihydro-5H-pyrrolo[1,2-b][1,2,4]triazole;
(5S,7S)-2-(difluoromethylsulfonyl)-5-(2,3-difluorophenyl)-7-fluoro-6,7-dihydro-5H-pyrrolo[1,2-b][1,2,4]triazole,
(5S,7S)-2-(difluoromethylsulfonyl)-5-(3,5-difluorophenyl)-7-fluoro-6,7-dihydro-5H-pyrrolo[1,2-b][1,2,4]triazole;
(5S,7S)-2-(difluoromethylsulfonyl)-7-fluoro-5-(3-fluorophenyl)-6,7-dihydro-5H-pyrrolo[1,2b][1,2,4]triazole;
(5S,7S)-7-fluoro-2-[(S)-fluoromethylsulfinyl]-5-phenyl-6,7-dihydro-5H-pyrrolo[1,2b][1,2,4]triazole,
(5S,7S)-7-fluoro-2-(fluoromethylsulfonyl)-5-phenyl-6,7-dihydro-5H-pyrrolo[1,2b][1,2,4]triazole;
(5S,7S)-7-fluoro-2-[(R)-fluoromethylsulfinyl]-5-phenyl-6,7-dihydro-5H-pyrrolo[1,2b][1,2,4]triazole;
(5S,7S)-7-fluoro-2-[(R)-fluoromethylsulfinyl]-5-(2-fluorophenyl)-6,7-dihydro-5H-pyrrolo[1,2-b][1,2,4]triazole;
(5S,7S)-7-fluoro-2-[(S)-fluoromethylsulfinyl]-5-(2-fluorophenyl)-6,7-dihydro-5H-pyrrolo[1,2-b][1,2,4]triazole;
(5S,7S)-5-(2,3-difluorophenyl)-7-fluoro-2-[(R)fluoromethylsulfinyl]-6,7-dihydro-5H-pyrrolo[1,2-b][1,2,4]triazole;
(5S,7S)-5-(2,3-difluorophenyl)-7-fluoro-2-[(S)-fluoromethylsulfinyl]-6,7-dihydro-5H-pyrrolo[1,2-b][1,2,4]triazole;
(5S,7S)-5-(2,5-difluorophenyl)-7-fluoro-2-[(R)-fluoromethylsulfinyl]-6,7-dihydro-5H-pyrrolo[1,2-b][1,2,4]triazole;
(5S,7S)-5-(2,5-difluorophenyl)-7-fluoro-2-[(S)-fluoromethylsulfinyl]-6,7-dihydro-5H-pyrrolo[1,2-b][1,2,4]triazole;

(5S,7S)-5-(2,6-difluorophenyl)-7-fluoro-2-[(R)-fluoromethylsulfinyl]-6,7-dihydro-5H-pyrrolo[1,2-b][1,2,4]triazole;

(5S,7S)-5-(2,6-difluorophenyl)-7-fluoro-2-[(S)-fluoromethylsulfinyl]-6,7-dihydro-5H-pyrrolo[1,2-b][1,2,4]triazole;

(5S,7S)-7-fluoro-2-[(R)-fluoromethylsulfinyl]-5-(3-fluorophenyl)-6,7-dihydro-5H-pyrrolo[1,2b][1,2,4]triazole;

(5S,7S)-7-fluoro-2-[(S)-fluoromethylsulfinyl]-5-(3-fluorophenyl)-6,7-dihydro-5H-pyrrolo[1,2-b][1,2,4]triazole;

(5S,7S)-5-(3,5-difluorophenyl)-7-fluoro-2-[(R)-fluoromethylsulfinyl]-6,7-dihydro-5H-pyrrolo[1,2-b][1,2,4]triazole;

(5S,7S)-5-(3,5-difluorophenyl)-7-fluoro-2-[(S)-fluoromethylsulfinyl]-6,7-dihydro-5H-pyrrolo[1,2-b][1,2,4]triazole;

(5S,7S)-5-(2-chlorophenyl)-7-fluoro-2-[(R)-fluoromethylsulfinyl]-6,7-dihydro-5H-pyrrolo[1,2b][1,2,4]triazole;

(5S,7S)-5-(2-chlorophenyl)-7-fluoro-2-[(S)-fluoromethylsulfinyl]-6,7-dihydro-5H-pyrrolo[1,2b][1,2,4]triazole;

2-[[(5S,7S)-7-fluoro-5-phenyl-6,7-dihydro-5H-pyrrolo[1,2-b][1,2,4]triazol-2-yl]sulfonyl]acetonitrile;

2-[[(5S,7S)-7-fluoro-5-phenyl-6,7-dihydro-5H-pyrrolo[1,2-b][1,2,4]triazol-2-yl]sulfanyl]acetonitrile;

2-2-(((4S,6S)-4-fluoro-6-phenyl-5,6-dihydro-4H-pyrrolo[1,2-b]pyrazol-2-yl)sulfonyl)acetonitrile;

2-2-((R)-((4S,6S)-4-fluoro-6-phenyl-5,6-dihydro-4H-pyrrolo[1,2-b]pyrazol-2-yl)sulfinyl)acetonitrile;

2-2-((S)-((4S,6S)-4-fluoro-6-phenyl-5,6-dihydro-4H-pyrrolo[1,2-b]pyrazol-2-yl)sulfinyl)acetonitrile;

2-[(S)-[(5S,7S)-5-(2-chlorophenyl)-7-fluoro-6,7-dihydro-5H-pyrrolo[1,2-b][1,2,4]triazol-2-yl]sulfinyl]acetonitrile;

2-[(R)-[rac-(5S,7S)-5-(2-chlorophenyl)-7-fluoro-6,7-dihydro-5H-pyrrolo[1,2-b][1,2,4]triazol-2-yl]sulfinyl]acetonitrile;

2-[(S)-[(5S,7S)-7-fluoro-5-(2-fluorophenyl)-6,7-dihydro-5H-pyrrolo[1,2-b][1,2,4]triazol-2-yl]sulfinyl]acetonitrile;

2-[(R)-[(5S,7S)-7-fluoro-5-(2-fluorophenyl)-6,7-dihydro-5H-pyrrolo[1,2-b][1,2,4]triazol-2-yl]sulfinyl]acetonitrile;

2-[(S)-[(5S,7S)-7-fluoro-5-(3-fluorophenyl)-6,7-dihydro-5H-pyrrolo[1,2-b][1,2,4]triazol-2-yl]sulfinyl]acetonitrile;

2-[(R)-[(5S,7S)-7-fluoro-5-(3-fluorophenyl)-6,7-dihydro-5H-pyrrolo[1,2-b][1,2,4]triazol-2-yl]sulfinyl]acetonitrile;

2-[(S)-[(5S,7S)-7-fluoro-5-(4-fluorophenyl)-6,7-dihydro-5H-pyrrolo[1,2-b][1,2,4]triazol-2-yl]sulfinyl]acetonitrile;

2-[(R)-[(5S,7S)-7-fluoro-5-(4-fluorophenyl)-6,7-dihydro-5H-pyrrolo[1,2-b][1,2,4]triazol-2-yl]sulfinyl]acetonitrile;

2-[(S)-[(5R,7R)-5-(2-chlorophenyl)-7-fluoro-6,7-dihydro-5H-pyrrolo[1,2-b][1,2,4]triazol-2-yl]sulfinyl]acetonitrile;

2-[[(5S,7S)-7-fluoro-5-phenyl-6,7-dihydro-5H-pyrrolo[1,2-b][1,2,4]triazol-2-yl]sulfinyl]acetonitrile;

2-methyl-2-[[(5S,7S)-7-fluoro-5-phenyl-6,7-dihydro-5H-pyrrolo[1,2-b][1,2,4]triazol-2-yl]sulfinyl]propanenitrile;

2-(((5S,7S)-7-fluoro-5-phenyl-6,7-dihydro-5H-pyrrolo[1,2-b][1,2,4]triazol-2-yl)sulfonyl)-2-methylpropanenitrile;

(5S,7S)-7-fluoro-2-methyl sulfinyl-5-phenyl-6,7-dihydro-5H-pyrrolo[1,2-b][1,2,4]triazole;

(5S,7S)-7-fluoro-2-methylsulfonyl-5-phenyl-6,7-dihydro-5H-pyrrolo[1,2-b][1,2,4]triazole;

(5S,7S)-2-ethylsulfinyl-7-fluoro-5-phenyl-6,7-dihydro-5H-pyrrolo[1,2-b][1,2,4]triazole;

(5S,7S)-2-ethylsulfonyl-7-fluoro-5-phenyl-6,7-dihydro-5H-pyrrolo[1,2-b][1,2,4]triazole;

(5S,7S)-7-fluoro-2-isopropylsulfinyl-5-phenyl-6,7-dihydro-5H-pyrrolo[1,2-b][1,2,4]triazole;

(5S,7S)-7-fluoro-2-isopropylsulfonyl-5-phenyl-6,7-dihydro-5H-pyrrolo[1,2-b][1,2,4]triazole;

(5S,7S)-2-(cyclopropylmethylsulfinyl)-7-fluoro-5-phenyl-6,7-dihydro-5H-pyrrolo[1,2b][1,2,4]triazole;

(5S,7S)-2-(cyclopropylmethylsulfonyl)-7-fluoro-5-phenyl-6,7-dihydro-5H-pyrrolo[1,2b][1,2,4]triazole, (5S,7S)-7-fluoro-5-phenyl-2-(2,2,2-trifluoroethylsulfinyl)-6,7-dihydro-5H-pyrrolo[1,2b][1,2,4]triazole;

(5S,7S)-7-fluoro-5-phenyl-2-(2,2,2-trifluoroethylsulfonyl)-6,7-dihydro-5H-pyrrolo[1,2b][1,2,4]triazole;

(5S,7S)-7-fluoro-2-(methoxymethyl sulfinyl)-5-phenyl-6,7-dihydro-5H-pyrrolo[1,2b][1,2,4]triazole, (5S,7S)-7-fluoro-2-(methoxymethylsulfonyl)-5-phenyl-6,7-dihydro-5H-pyrrolo[1,2b][1,2,4]triazole;

(5S,7S)-2-(2,2-difluorocyclopropyl)sulfinyl-7-fluoro-5-phenyl-6,7-dihydro-5H-pyrrolo[1,2b][1,2,4]triazole;

(5S,7S)-2-((2,2-difluorocyclopropyl)sulfonyl)-7-fluoro-5-phenyl-6,7-dihydro-5H-pyrrolo[1,2b][1,2,4]triazole;

(5S,7S)-7-fluoro-5-(2-fluorophenyl)-2-[(1S)-2,2-difluorocyclopropyl]sulfonyl-6,7-dihydro-5H-pyrrolo[1,2-b][1,2,4]triazole;

(5S,7S)-5-(2-chlorophenyl)-7-fluoro-2-[(1S)-2,2-difluorocyclopropyl]sulfonyl-6,7-dihydro-5H-pyrrolo[1,2-b][1,2,4]triazole;

(5S,7S)-2-(2,2-difluorocyclopropyl)sulfonyl-5-(2,3-difluorophenyl)-7-fluoro-6,7-dihydro-5H-pyrrolo[1,2-b][1,2,4]triazole;

(5S,7S)-2-(2,2-difluorocyclopropyl)sulfonyl-5-(2,5-difluorophenyl)-7-fluoro-6,7-dihydro-5H-pyrrolo[1,2-b][1,2,4]triazole;

(5S,7S)-2-(2,2-difluorocyclopropyl)sulfonyl-5-(2,6-difluorophenyl)-7-fluoro-6,7-dihydro-5H-pyrrolo[1,2-b][1,2,4]triazole;

(5S,7S)-7-fluoro-5-(2-fluorophenyl)-2-[(1R)-2,2-difluorocyclopropyl]sulfonyl-6,7-dihydro-5H-pyrrolo[1,2-b][1,2,4]triazole;

(5S,7S)-5-(2-chlorophenyl)-7-fluoro-2-[(1R)-2,2-difluorocyclopropyl]sulfonyl-6,7-dihydro-5H-pyrrolo[1,2-b][1,2,4]triazole;

(5S,7S)-5-(2,5-difluorophenyl)-7-fluoro-2-[(1S)-2,2-difluorocyclopropyl]sulfonyl-6,7-dihydro-5H-pyrrolo[1,2-b][1,2,4]triazole;

(5S,7S)-5-(2,5-difluorophenyl)-7-fluoro-2-[(1R)-2,2-difluorocyclopropyl]sulfonyl-6,7-dihydro-5H-pyrrolo[1,2-b][1,2,4]triazole;

(5S,7S)-5-(2,3-difluorophenyl)-7-fluoro-2-[(1R)-2,2-difluorocyclopropyl]sulfonyl-6,7-dihydro-5H-pyrrolo[1,2-b][1,2,4]triazole;

(5S,7S)-5-(2,3-difluorophenyl)-7-fluoro-2-[(1S)-2,2-difluorocyclopropyl]sulfonyl-6,7-dihydro-5H-pyrrolo[1,2-b][1,2,4]triazole;

(5S,7S)-2-(((S)-2,2-difluorocyclopropyl)sulfonyl)-7-fluoro-5-phenyl-6,7-dihydro-5H-pyrrolo[1,2-b][1,2,4]triazole;

(5S,7S)-2-(((R)-2,2-difluorocyclopropyl)sulfonyl)-7-fluoro-5-phenyl-6,7-dihydro-5H-pyrrolo[1,2-b][1,2,4]triazole;
(5S,7S)-7-fluoro-5-phenyl-2-(trifluoromethylsulfinyl)-6,7-dihydro-5H-pyrrolo[1,2-b][1,2,4]triazole;
(5S,7S)-7-fluoro-5-(2-fluorophenyl)-2-(trifluoromethylsulfonyl)-6,7-dihydro-5H-pyrrolo[1,2-b][1,2,4]triazole;
(5S,7S)-5-(2-chlorophenyl)-7-fluoro-2-(trifluoromethylsulfonyl)-6,7-dihydro-5H-pyrrolo[1,2-b][1,2,4]triazole,
(5S,7S)-7-fluoro-5-(3-fluorophenyl)-2-(trifluoromethylsulfonyl)-6,7-dihydro-5H-pyrrolo[1,2-b][1,2,4]triazole;
(5S,7S)-5-(2,3-difluorophenyl)-7-fluoro-2-(trifluoromethyl sulfonyl)-6,7-dihydro-5H-pyrrolo[1,2-b][1,2,4]triazole;
(5S,7S)-7-fluoro-5-phenyl-2-(trifluoromethylsulfonyl)-6,7-dihydro-5H-pyrrolo[1,2-b][1,2,4]triazole,
(5S,7S)-5-(2,5-difluorophenyl)-7-fluoro-2-(trifluoromethylsulfonyl)-6,7-dihydro-5H-pyrrolo[1,2-b][1,2,4]triazole;
(5S,7S)-5-(2,6-difluorophenyl)-7-fluoro-2-(trifluoromethyl sulfonyl)-6,7-dihydro-5H-pyrrolo[1,2-b][1,2,4]triazole;
(5R,7R)-5-(2,3-difluorophenyl)-7-fluoro-2-(trifluoromethylsulfonyl)-6,7-dihydro-5H-pyrrolo[1,2-b][1,2,4]triazole;
(5S,7S)-7-fluoro-5-(3-fluorophenyl)-2-[(1 S,2S)-2-fluorocyclopropyl]sulfonyl-6,7-dihydro-5H-pyrrolo[1,2-b][1,2,4]triazole;
rac-(5S,7S)-7-fluoro-5-(3-fluorophenyl)-2-[rac-(1R,2R)-2-fluorocyclopropyl]sulfonyl-6,7-dihydro-5H-pyrrolo[1,2-b][1,2,4]triazole;
(5S,7S)-5-(3,4-difluorophenyl)-7-fluoro-2-[(1S,2S)-2-fluorocyclopropyl]sulfonyl-6,7-dihydro-5H-pyrrolo[1,2-b][1,2,4]triazole;
(5S,7S)-5-(3,4-difluorophenyl)-7-fluoro-2-[(1R,2R)-2-fluorocyclopropyl]sulfonyl-6,7-dihydro-5H-pyrrolo[1,2-b][1,2,4]triazole;
(5S,7S)-7-fluoro-5-phenyl-2-[(1R,2R)-2-fluorocyclopropyl]sulfonyl-6,7-dihydro-5H-pyrrolo[1,2-b][1,2,4]triazole;
(5S,7S)-7-fluoro-5-phenyl-2-[(1S,2S)-2-fluorocyclopropyl]sulfonyl-6,7-dihydro-5H-pyrrolo[1,2-b][1,2,4]triazole;
(5S,7S)-7-fluoro-5-phenyl-2-(2-pyridylmethylsulfinyl)-6,7-dihydro-5H-pyrrolo[1,2-b][1,2,4]triazole,
(5S,7S)-2-(2,2-difluoroethyl sulfinyl)-7-fluoro-5-phenyl-6,7-dihydro-5H-pyrrolo[1,2-b][1,2,4]triazole;
(5S,7S)-2-(1,1-difluoroethylsulfonyl)-7-fluoro-5-phenyl-6,7-dihydro-5H-pyrrolo[1,2-b][1,2,4]triazole;
(5S,7S)-7-fluoro-2-(1-methylcyclopropyl)sulfonyl-5-phenyl-6,7-dihydro-5H-pyrrolo[1,2-b][1,2,4]triazole,
(5S,7S)-7-fluoro-5-phenyl-2-(pyrazol-1-ylmethylsulfonyl)-6,7-dihydro-5H-pyrrolo[1,2-b][1,2,4]triazole;
(5S,7S)-7-fluoro-5-phenyl-2-(pyrazol-1-ylmethyl sulfinyl)-6,7-dihydro-5H-pyrrolo[1,2-b][1,2,4]triazole;
(5S,7S)-7-fluoro-2-(1,1,2,2,2-pentafluoroethyl sulfonyl)-5-phenyl-6,7-dihydro-5H-pyrrolo[1,2-b][1,2,4]triazole;
(5S,7S)-7-fluoro-2-(1,1,2,2,2-pentafluoroethylsulfinyl)-5-phenyl-6,7-dihydro-5H-pyrrolo[1,2-b][1,2,4]triazole;
(5S,7S)-2-[1-(difluoromethyl)cyclopropyl]sulfonyl-7-fluoro-5-phenyl-6,7-dihydro-5H-pyrrolo[1,2-b][1,2,4]triazole;
2,2-difluoro-2-[[(5S,7S)-7-fluoro-5-phenyl-6,7-dihydro-5H-pyrrolo[1,2-b][1,2,4]triazol-2-yl]sulfonyl]ethanol;
1-[[(5S,7S)-7-fluoro-5-phenyl-6,7-dihydro-5H-pyrrolo[1,2-b][1,2,4]triazol-2-yl]sulfonyl]cyclopropanecarbonitrile;
(5S,7S)-7-fluoro-2-(1-fluoroethyl sulfonyl)-5-phenyl-6,7-dihydro-5H-pyrrolo[1,2b][1,2,4]triazole;
(5S,7S)-7-fluoro-5-phenyl-2-[(1S)-1-fluoroethyl]sulfonyl-6,7-dihydro-5H-pyrrolo[1,2b][1,2,4]triazole;
(5S,7S)-7-fluoro-5-phenyl-2-[(1R)-1-fluoroethyl]sulfonyl-6,7-dihydro-5H-pyrrolo[1,2b][1,2,4]triazole,
(5S,7S)-7-fluoro-5-phenyl-2-propylsulfonyl-6,7-dihydro-5H-pyrrolo[1,2-b][1,2,4]triazole;
(5S,7S)-7-fluoro-5-phenyl-2-[rac-(1S,2S)-2-methylcyclopropyl]sulfonyl-6,7-dihydro-5H-pyrrolo[1,2-b][1,2,4]triazole;
(5S,7S)-7-fluoro-5-phenyl-2-[rac-(1 S,2R)-2-(trifluoromethyl)cyclopropyl]sulfonyl-6,7-dihydro-5H-pyrrolo[1,2-b][1,2,4]triazole;
(5S,7S)-7-fluoro-2-(3-fluorocyclobutyl)sulfonyl-5-phenyl-6,7-dihydro-5H-pyrrolo[1,2-b][1,2,4]triazole;
(5S,7S)-7-fluoro-2-(1-fluoro-1-methyl-ethyl)sulfonyl-5-phenyl-6,7-dihydro-5H-pyrrolo[1,2b][1,2,4]triazole;
(5S,7S)-7-fluoro-5-phenyl-2-tetrahydrofuran-3-yl sulfonyl-6,7-dihydro-5H-pyrrolo[1,2-b][1,2,4]triazole;
(5S,7S)-2-(2,2-difluoro-1-methyl-cyclopropyl)sulfonyl-7-fluoro-5-phenyl-6,7-dihydro-5H-pyrrolo[1,2-b][1,2,4]triazole;
((1R,3S)-3-(((5S,7S)-7-fluoro-5-phenyl-6,7-dihydro-5H-pyrrolo[1,2-b][1,2,4]triazol-2-yl)sulfonyl)cyclobutyl)methanol;
((1R,3S)-3-(((5S,7S)-7-fluoro-5-phenyl-6,7-dihydro-5H-pyrrolo[1,2-b][1,2,4]triazol-2-yl)sulfonyl)cyclobutyl)methanol;
(5S,7S)-7-fluoro-5-phenyl-2-spiro[2.2]pentan-2-ylsulfonyl-6,7-dihydro-5H-pyrrolo[1,2-b][1,2,4]triazole,
(5S,7S)-7-fluoro-5-phenyl-2-[(1R)-2,2-difluorocyclobutyl]sulfonyl-6,7-dihydro-5H-pyrrolo[1,2-b][1,2,4]triazole;
(5S,7S)-7-fluoro-5-phenyl-2-[(1S)-2,2-difluorocyclobutyl]sulfonyl-6,7-dihydro-5H-pyrrolo[1,2-b][1,2,4]triazole;
(5 S)-2-[(R)-difluoromethylsulfinyl]-5-(3,5-difluorophenyl)-6,7-dihydro-5H-pyrrolo[1,2b][1,2,4]triazole,
(5S)-2-[(S)-difluoromethylsulfinyl]-5-(3,5-difluorophenyl)-6,7-dihydro-5H-pyrrolo[1,2b][1,2,4]triazole;
2-(difluoromethylsulfonyl)-5-(3,5-difluorophenyl)-6,7-dihydro-5H-pyrrolo[1,2-b][1,2,4]triazole;
2-(difluoromethylsulfinyl)-5-(3,5-difluorophenyl)-6,7-dihydro-5H-pyrrolo[1,2-b][1,2,4]triazole;
5-phenyl-2-(2,2,2-trifluoroethylsulfinyl)-6,7-dihydro-5H-pyrrolo[1,2-b][1,2,4]triazole;
(5S,7S)-7-fluoro-2-(1-fluorocyclopropyl)sulfonyl-5-phenyl-6,7-dihydro-5H-pyrrolo[1,2b][1,2,4]triazole;
rac-(5S,7S)-2-[(S)-difluoromethylsulfinyl]-7-fluoro-5-(3-fluorophenyl)-6,7-dihydro-5H-pyrrolo[1,2-b][1,2,4]triazole;
rac-(5S,7S)-7-fluoro-5-phenyl-2-[(S)-trifluoromethylsulfinyl]-6,7-dihydro-5H-pyrrolo[1,2b][1,2,4]triazole,
rac-(5S,7S)-7-fluoro-5-phenyl-2-[(R)-trifluoromethylsulfinyl]-6,7-dihydro-5H-pyrrolo[1,2b][1,2,4]triazole;
rac-(5S,7S)-2-[(R)-difluoromethylsulfinyl]-7-fluoro-5-(3-fluorophenyl)-6,7-dihydro-5H-pyrrolo[1,2b][1,2,4]triazole;
rac-(5S,7S)-7-fluoro-5-phenyl-2-[(S)-2,2,2-trifluoroethylsulfinyl]-6,7-dihydro-5H-pyrrolo[1,2b][1,2,4]triazole;
rac-(5S,7S)-2-[(R)-cyclopropylmethylsulfinyl]-7-fluoro-5-phenyl-6,7-dihydro-5H-pyrrolo[1,2b][1,2,4]triazole;
rac-(5S,7S)-7-fluoro-5-phenyl-2-[(R)-2,2,2-trifluoroethylsulfinyl]-6,7-dihydro-5H-pyrrolo[1,2b][1,2,4]triazole;

rac-(5S,7S)-2-[(S)-cyclopropylmethylsulfinyl]-7-fluoro-5-phenyl-6,7-dihydro-5H-pyrrolo[1,2b][1,2,4]triazole;
rac-(5S,7S)-7-fluoro-2-[(R)-isopropylsulfinyl]-5-phenyl-6,7-dihydro-5H-pyrrolo[1,2b][1,2,4]triazole,
rac-(5S,7S)-2-[(R)-ethyl sulfinyl]-7-fluoro-5-phenyl-6,7-dihydro-5H-pyrrolo[1,2b][1,2,4]triazole;
rac-(5S,7S)-7-fluoro-2-[(S)-isopropylsulfinyl]-5-phenyl-6,7-dihydro-5H-pyrrolo[1,2b][1,2,4]triazole;
rac-(5S,7S)-2-[(S)-ethyl sulfinyl]-7-fluoro-5-phenyl-6,7-dihydro-5H-pyrrolo[1,2b][1,2,4]triazole,
rac-(5S,7S)-2-[(R)-tert-butylsulfinyl]-7-fluoro-5-phenyl-6,7-dihydro-5H-pyrrolo[1,2b][1,2,4]triazole;
3-[(5S,7S)-2-(difluoromethylsulfonyl)-7-fluoro-6,7-dihydro-5H-pyrrolo[1,2-b][1,2,4]triazol-5-yl]benzonitrile;
(5S,7S)-5-(3,5-difluorophenyl)-7-fluoro-2-trans-(3-fluorocyclobutyl)sulfonyl-6,7-dihydro-5H-pyrrolo[1,2-b][1,2,4]triazole;
cis-3-[[(5S,7S)-7-fluoro-5-(3-fluorophenyl)-6,7-dihydro-5H-pyrrolo[1,2-b][1,2,4]triazol-2-yl]sulfonyl]cyclobutanol;
(5S,7S)-7-fluoro-5-(4-fluorophenyl)-2-[(1R,2R)-2-fluorocyclopropyl]sulfonyl-6,7-dihydro-5H-pyrrolo[1,2-b][1,2,4]triazole;
(5S,7S)-7-fluoro-5-(4-fluorophenyl)-2-[(1 S,2S)-2-fluorocyclopropyl]sulfonyl-6,7-dihydro-5H-pyrrolo[1,2-b][1,2,4]triazole;
(5S,7S)-2-[2-(difluoromethoxy)ethyl sulfonyl]-7-fluoro-5-phenyl-6,7-dihydro-5H-pyrrolo[1,2-b][1,2,4]triazole;
(5S,7S)-5-(3-chloro-5-fluoro-phenyl)-7-fluoro-2-[(1R,2R)-2-fluorocyclopropyl]sulfonyl-6,7-dihydro-5H-pyrrolo[1,2-b][1,2,4]triazole;
(5S,7S)-5-(3-chloro-5-fluoro-phenyl)-7-fluoro-2-[(1S,2S)-2-fluorocyclopropyl]sulfonyl-6,7-dihydro-5H-pyrrolo[1,2-b][1,2,4]triazole;
(5S,7S)-5-(2,5-difluorophenyl)-7-fluoro-2-[(1R,2R)-2-fluorocyclopropyl]sulfonyl-6,7-dihydro-5H-pyrrolo[1,2-b][1,2,4]triazole;
(5S,7S)-5-(2,5-difluorophenyl)-7-fluoro-2-[(1S,2S)-2-fluorocyclopropyl]sulfonyl-6,7-dihydro-5H-pyrrolo[1,2-b][1,2,4]triazole;
(5S,7S)-5-(3-chlorophenyl)-2-cyclopropylsulfonyl-7-fluoro-6,7-dihydro-5H-pyrrolo[1,2-b][1,2,4]triazole;
(5S,7S)-5-(2,3-difluorophenyl)-7-fluoro-2-trans-(3-fluorocyclobutyl)sulfonyl-6,7-dihydro-5H-pyrrolo[1,2-b][1,2,4]triazole;
(5S,7S)-7-fluoro-5-(2-fluorophenyl)-2-[(1R,2R)-2-fluorocyclopropyl]sulfonyl-6,7-dihydro-5H-pyrrolo[1,2-b][1,2,4]triazole;
(5S,7S)-7-fluoro-5-(2-fluorophenyl)-2-[(1S,2S)-2-fluorocyclopropyl]sulfonyl-6,7-dihydro-5H-pyrrolo[1,2-b][1,2,4]triazole;
(5S,7S)-5-(5-chloro-2-fluoro-phenyl)-7-fluoro-2-[(1R,2R)-2-fluorocyclopropyl]sulfonyl-6,7-dihydro-5H-pyrrolo[1,2-b][1,2,4]triazole;
(5S,7S)-5-(3-chloro-2-fluoro-phenyl)-7-fluoro-2-[(1R,2R)-2-fluorocyclopropyl]sulfonyl-6,7-dihydro-5H-pyrrolo[1,2-b][1,2,4]triazole;
(1R,2S)-2-[[(5S,7S)-7-fluoro-5-phenyl-6,7-dihydro-5H-pyrrolo[1,2-b][1,2,4]triazol-2-yl]sulfonyl]cyclopropanecarbonitrile;
cis-3-[[(5S,7S)-7-fluoro-5-phenyl-6,7-dihydro-5H-pyrrolo[1,2-b][1,2,4]triazol-2-yl]sulfonyl]cyclobutanecarbonitrile;
trans-3-[[(5S,7S)-7-fluoro-5-phenyl-6,7-dihydro-5H-pyrrolo[1,2-b][1,2,4]triazol-2-yl]sulfonyl]cyclobutanecarbonitrile;
(1S,2R)-2-[[(5S,7S)-7-fluoro-5-phenyl-6,7-dihydro-5H-pyrrolo[1,2-b][1,2,4]triazol-2-yl]sulfonyl]cyclopropanecarbonitrile;
(5S,7S)-2-trans-[3-(difluoromethoxy)cyclobutyl]sulfonyl-7-fluoro-5-phenyl-6,7-dihydro-5H-pyrrolo[1,2-b][1,2,4]triazole;
(5S,7S)-5-(3-chloro-5-fluoro-phenyl)-2-cyclopropylsulfonyl-7-fluoro-6,7-dihydro-5H-pyrrolo[1,2-b][1,2,4]triazole;
(5S,7S)-5-(3-chloro-5-fluoro-phenyl)-2-(difluoromethylsulfonyl)-7-fluoro-6,7-dihydro-5H-pyrrolo[1,2-b][1,2,4]triazole;
(5S,7S)-5-(2,3-difluorophenyl)-7-fluoro-2-[(1R,2R)-2-fluorocyclopropyl]sulfonyl-6,7-dihydro-5H-pyrrolo[1,2-b][1,2,4]triazole;
(5S,7S)-5-(2,3-difluorophenyl)-7-fluoro-2-[(1 S,2S)-2-fluorocyclopropyl]sulfonyl-6,7-dihydro-5H-pyrrolo[1,2-b][1,2,4]triazole;
(5S,7S)-5-(5-chloro-2-fluoro-phenyl)-7-fluoro-2-[(1S,2S)-2-fluorocyclopropyl]sulfonyl-6,7-dihydro-5H-pyrrolo[1,2-b][1,2,4]triazole;
(5S,7S)-5-(3-chloro-2-fluoro-phenyl)-7-fluoro-2-[(1S,2S)-2-fluorocyclopropyl]sulfonyl-6,7-dihydro-5H-pyrrolo[1,2-b][1,2,4]triazole;
2-(difluoromethylsulfonyl)-7-phenyl-6,7-dihydro-5H-pyrrolo[1,2-b][1,2,4]triazole;
(1R,2R)-2-[[(5S,7S)-7-fluoro-5-phenyl-6,7-dihydro-5H-pyrrolo[1,2-b][1,2,4]triazol-2-yl]sulfonyl]cyclopropanecarbonitrile;
(1 S,2S)-2-[[(5S,7S)-7-fluoro-5-phenyl-6,7-dihydro-5H-pyrrolo[1,2-b][1,2,4]triazol-2-yl]sulfonyl]cyclopropanecarbonitrile;
2-[[(5S,7S)-7-fluoro-5-phenyl-6,7-dihydro-5H-pyrrolo[1,2-b][1,2,4]triazol-2-yl]sulfonyl]ethanol;
(5S,7S)-7-fluoro-2-(2-ethoxyethylsulfonyl)-5-phenyl-6,7-dihydro-5H-pyrrolo[1,2b][1,2,4]triazole;
cis-3-[[(5S,7S)-7-fluoro-5-phenyl-6,7-dihydro-5H-pyrrolo[1,2-b][1,2,4]triazol-2-yl]sulfonyl]cyclobutanol;
(5S,7S)-7-fluoro-2-trans-(3-fluorocyclobutyl)sulfonyl-5-(3-fluorophenyl)-6,7-dihydro-5H-pyrrolo[1,2-b][1,2,4]triazole;
(5S,7S)-7-fluoro-5-(3-fluorophenyl)-2-(oxetan-3-ylsulfonyl)-6,7-dihydro-5H-pyrrolo[1,2b][1,2,4]triazole; and
(5S,7S)-7-fluoro-2-(oxetan-3-ylsulfonyl)-5-phenyl-6,7-dihydro-5H-pyrrolo[1,2-b][1,2,4]triazole.

14. The compound of claim 1, or a pharamceutically acceptable salt thereof, having a RIP1 kinase inhibitory activity $K_i$ of less than 100 nM.

15. A pharmaceutical composition comprising a compound of claim 1, or a pharmaceutically acceptable salt thereof, and a pharmaceutically acceptable carrier.

16. The compound of claim 1, or a pharmaceutically acceptable salt thereof, wherein the compound is (5S,7S)-2-cyclopropylsulfonyl-7-fluoro-5-(2-fluorophenyl)-6,7-dihydro-5H-pyrrolo[1,2-b][1,2,4]triazole.

17. The compound of claim 1, or a pharmaceutically acceptable salt thereof, wherein the compound is (5S,7S)-2-cyclopropylsulfonyl-5-(2,3-difluorophenyl)-7-fluoro-6,7-dihydro-5H-pyrrol[1,2-b][1,2,4]triazol.

18. The compound of claim 1, or a pharmaceutically acceptable salt thereof, wherein the compound is (5S,7S)-2-(difluoromethylsulfonyl)-5-(2,3-difluorophenyl)-7-fluoro-6,7-dihydro-5H-pyrrolo[1,2-b][1,2,4]triazole.

19. The compound of claim 1, or a pharmaceutically acceptable salt thereof, wherein the compound is (5S,7S)-7-fluoro-5-(3-fluorophenyl)-2-[(1S,2S)-2-fluorocyclopropyl]sulfonyl-6,7-dihydro-5H-pyrrolo[1,2-b][1,2,4]triazole.

20. The compound of claim 1, or a pharmaceutically acceptable salt thereof, wherein the compound is rac-(5S,7S)-7-fluoro-5-(3-fluorophenyl)-2-[rac-(1R,2R)-2-fluorocyclopropyl]sulfonyl-6,7-dihydro-5H-pyrrolo[1,2-b][1,2,4]triazole.

21. The compound of claim 1, or a pharmaceutically acceptable salt thereof, wherein the compound is (5S,7S)-7-fluoro-5-(4-fluorophenyl)-2-[(1S,2S)-2-fluorocyclopropyl]sulfonyl-6,7-dihydro-5H-pyrrolo[1,2-b][1,2,4]triazole.

22. The compound of claim 1, or a pharmaceutically acceptable salt thereof, wherein the compound is (5S,7S)-7-fluoro-5-(2-fluorophenyl)-2-[(1R,2R)-2-fluorocyclopropyl]sulfonyl-6,7-dihydro-5H-pyrrolo[1,2-b][1,2,4]triazole.

23. The compound of claim 1, or a pharmaceutically acceptable salt thereof, wherein the compound is (5S,7S)-7-fluoro-5-(2-fluorophenyl)-2-[(1S,2S)-2-fluorocyclopropyl]sulfonyl-6,7-dihydro-5H-pyrrolo[1,2-b][1,2,4]triazole.

24. The compound of claim 1, or a pharmaceutically acceptable salt thereof, wherein the compound is (5S,7S)-5-(2,3-difluorophenyl)-7-fluoro-2-[(1R,2R)-2-fluorocyclopropyl]sulfonyl-6,7-dihydro-5H-pyrrolo[1,2-b][1,2,4]triazole.

25. The compound of claim 1, or a pharmaceutically acceptable salt thereof, wherein the compound is (5S,7S)-5-(2,3-difluorophenyl)-7-fluoro-24(1S,2S)-2-fluorocyclopropyl]sulfonyl-6,7-dihydro-5H-pyrrolo[1,2-b][1,2,4]triazole.

26. The pharmaceutical composition of claim 15, wherein the compound is (5S,7S)-2-cyclopropylsulfonyl-7-fluoro-5-(2-fluorophenyl)-6,7-dihydro-5H-pyrrolo[1,2-b][1,2,4]triazole, or a pharmaceutically acceptable salt thereof.

27. The pharmaceutical composition of claim 15, wherein the compound is (5S, 7S)-2-cyclopropylsulfonyl-5-(2,3-difluorophenyl)-7-fluoro-6,7-dihydro-5H-pyrrolo[1,2-b][1,2,4]triazole, or a pharmaceutically acceptable salt thereof.

28. The pharmaceutical composition of claim 15, wherein the compound is (5S, 7S)-2-(difluoromethylsulfonyl)-5-(2,3-difluorophenyl)-7-fluoro-6,7-dihydro-5H-pyrrolo[1,2-b][1,2,4]triazole, or a pharmaceutically acceptable salt thereof.

29. The pharmaceutical composition of claim 15, wherein the compound is (5S, 7S)-7-fluoro-5-(3-fluorophenyl)-2-[(1S,2S)-2-fluorocyclopropyl]sulfonyl-6,7-dihydro-5H-pyrrolo[1,2-b][1,2,4]triazole, or a pharmaceutically acceptable salt thereof.

30. The pharmaceutical composition of claim 15, wherein the compound is rac-(5S,7S)-7-fluoro-5-(3-fluorophenyl)-2-[rac-(1R,2R)-2-fluorocyclopropyl]sulfonyl-6,7-dihydro-5H-pyrrolo[1,2-b][1,2,4]triazole, or a pharmaceutically acceptable salt thereof.

31. The pharmaceutical composition of claim 15, wherein the compound is (5S, 7S)-7-fluoro-5-(4-fluorophenyl)-2-[(1S,2S)-2-fluorocyclopropyl]sulfonyl-6,7-dihydro-5H-pyrrolo[1,2-b][1,2,4]triazole, or a pharmaceutically acceptable salt thereof.

32. The pharmaceutical composition of claim 15, wherein the compound is (5S, 7S)-7-fluoro-5-(2-fluorophenyl)-2-[(1R,2R)-2-fluorocyclopropyl]sulfonyl-6,7-dihydro-5H-pyrrolo[1,2-b][1,2,4]triazole, or a pharmaceutically acceptable salt thereof.

33. The pharmaceutical composition of claim 15, wherein the compound is (5S, 7S)-7-fluoro-5-(2-fluorophenyl)-2-[(1S,2S)-2-fluorocyclopropyl]sulfonyl-6,7-dihydro-5H-pyrrolo[1,2-b][1,2,4]triazole, or a pharmaceutically acceptable salt thereof.

34. The pharmaceutical composition of claim 15, wherein the compound is (5S, 7S)-5-(2,3-difluorophenyl)-7-fluoro-2-[(1R,2R)-2-fluorocyclopropyl]sulfonyl-6,7-dihydro-5H-pyrrolo[1,2-b][1,2,4]triazole, or a pharmaceutically acceptable salt thereof.

35. The pharmaceutical composition of claim 15, wherein the compound is (5S, 7S)-5-(2,3-difluorophenyl)-7-fluoro-2-[(1S,2S)-2-fluorocyclopropyl]sulfonyl-6,7-dihydro-5H-pyrrolo[1,2-b][1,2,4]triazole, or a pharmaceutically acceptable salt thereof.

\* \* \* \* \*